United States Patent
Vandyck et al.

(10) Patent No.: US 11,198,699 B2
(45) Date of Patent: Dec. 14, 2021

(54) COMPOUNDS TARGETING PRMT5

(71) Applicant: ALIGOS THERAPEUTICS, INC., South San Francisco, CA (US)

(72) Inventors: Koen Vandyck, Paal (BE); Pierre Jean-Marie Bernard Raboisson, Wavre (BE); Jerome Deval, Pacifica, CA (US); Leonid Beigelman, San Mateo, CA (US); David McGowan, Brussels (BE); Yannick Debing, Bilzen (BE)

(73) Assignee: Aligos Therapeutics, Inc., South San Francisco, CA (US)

(*) Notice: Subject to any disclaimer, the term of this patent is extended or adjusted under 35 U.S.C. 154(b) by 0 days.

(21) Appl. No.: 16/836,132

(22) Filed: Mar. 31, 2020

(65) Prior Publication Data

US 2020/0317686 A1    Oct. 8, 2020

Related U.S. Application Data

(60) Provisional application No. 62/946,649, filed on Dec. 11, 2019, provisional application No. 62/877,411, filed on Jul. 23, 2019, provisional application No. 62/828,282, filed on Apr. 2, 2019.

(51) Int. Cl.

| | |
|---|---|
| *C07D 495/04* | (2006.01) |
| *C07D 513/04* | (2006.01) |
| *C07D 519/00* | (2006.01) |
| *C07D 487/04* | (2006.01) |
| *C07D 473/34* | (2006.01) |
| *A61K 31/53* | (2006.01) |
| *A61K 31/52* | (2006.01) |
| *A61K 31/519* | (2006.01) |
| *A61K 31/522* | (2006.01) |
| *C07D 473/30* | (2006.01) |
| *A61K 31/437* | (2006.01) |
| *A61P 35/00* | (2006.01) |
| *C07D 473/26* | (2006.01) |
| *C07D 471/04* | (2006.01) |
| *C07K 16/22* | (2006.01) |

(52) U.S. Cl.
CPC .......... *C07D 495/04* (2013.01); *A61K 31/437* (2013.01); *A61K 31/519* (2013.01); *A61K 31/52* (2013.01); *A61K 31/522* (2013.01); *A61K 31/53* (2013.01); *A61P 35/00* (2018.01); *C07D 471/04* (2013.01); *C07D 473/26* (2013.01); *C07D 473/30* (2013.01); *C07D 473/34* (2013.01); *C07D 487/04* (2013.01); *C07D 513/04* (2013.01); *C07D 519/00* (2013.01); *C07K 16/22* (2013.01)

(58) Field of Classification Search
None
See application file for complete search history.

(56) References Cited

U.S. PATENT DOCUMENTS

| | | | |
|---|---|---|---|
| 5,514,505 | A | 5/1996 | Limburg et al. |
| 5,861,404 | A | 1/1999 | Niewoehner et al. |
| 5,900,415 | A | 5/1999 | Peterson et al. |
| 5,985,873 | A | 11/1999 | Blum et al. |
| 6,268,372 | B1 | 7/2001 | Pamukcu et al. |
| 6,472,389 | B1 | 10/2002 | Ohtani et al. |
| 6,787,545 | B1 | 9/2004 | Ohtani et al. |
| 2002/0035077 | A1* | 3/2002 | Tam ................. A61P 29/00 514/43 |
| 2003/0175950 | A1 | 9/2003 | McSwiggen et al. |
| 2004/0048802 | A1 | 3/2004 | Ripka et al. |
| 2005/0018383 | A1 | 1/2005 | Ebel |
| 2005/0234046 | A1 | 10/2005 | Zhao et al. |
| 2005/0288329 | A1 | 12/2005 | Yao et al. |
| 2006/0223829 | A1 | 10/2006 | Aertgeerts et al. |
| 2007/0078120 | A1 | 4/2007 | Asano et al. |
| 2007/0142369 | A1 | 6/2007 | Van Heek et al. |
| 2007/0249581 | A1 | 10/2007 | Chen et al. |
| 2007/0249596 | A1 | 10/2007 | Chen et al. |
| 2008/0096922 | A1 | 4/2008 | Asano |
| 2009/0036678 | A1 | 2/2009 | Armitage et al. |
| 2009/0137592 | A1 | 5/2009 | Mehta et al. |
| 2009/0258843 | A1 | 10/2009 | Cantrell et al. |

(Continued)

FOREIGN PATENT DOCUMENTS

| | | |
|---|---|---|
| AU | 9851819 | 6/1998 |
| CA | 2899888 | 2/2016 |

(Continued)

OTHER PUBLICATIONS

Hai et al., "Species- or Isozyme-Specific Enzyme Inhibitors. 7. Selective Effects in Inhibitions of Rat Adenylate Kinase Isozymes by Adenosine 5'-Phosphate Derivatives" J Med Chem vol. 25 pp. 806-812 (Year: 1982).*

(Continued)

*Primary Examiner* — Eric Olson
(74) *Attorney, Agent, or Firm* — Knobbe Martens Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

26 Claims, No Drawings

(56) References Cited

U.S. PATENT DOCUMENTS

| | | | |
|---|---|---|---|
| 2009/0270394 A1 | 10/2009 | Galemmo et al. | |
| 2010/0004127 A1 | 1/2010 | Fischer et al. | |
| 2010/0022544 A1 | 1/2010 | Nell et al. | |
| 2010/0331397 A1 | 12/2010 | Beigelman et al. | |
| 2012/0058999 A1 | 3/2012 | Reich et al. | |
| 2012/0070411 A1 | 3/2012 | Beigelman et al. | |
| 2012/0071434 A1 | 3/2012 | Smith et al. | |
| 2012/0196994 A1 | 8/2012 | Jeon et al. | |
| 2013/0072646 A1 | 3/2013 | Noh et al. | |
| 2013/0079324 A1 | 3/2013 | Cheng et al. | |
| 2013/0165624 A1 | 6/2013 | Geysen | |
| 2014/0163024 A1 | 6/2014 | Fauber et al. | |
| 2014/0288045 A1 | 9/2014 | Ren et al. | |
| 2015/0164901 A1 | 6/2015 | Rubin | |
| 2015/0366887 A1* | 12/2015 | Blatt ................ | A61K 31/7076 514/48 |
| 2016/0031879 A1 | 2/2016 | Karra et al. | |
| 2016/0176773 A1 | 6/2016 | Stoltz et al. | |
| 2017/0100369 A1 | 4/2017 | Manoukian et al. | |
| 2017/0101379 A1 | 4/2017 | Sullivan et al. | |
| 2017/0210701 A1 | 7/2017 | Dittgen et al. | |
| 2017/0313939 A1 | 11/2017 | Jiang et al. | |
| 2017/0348313 A1 | 12/2017 | Tatlock et al. | |
| 2018/0030032 A1 | 2/2018 | Brubaker et al. | |

FOREIGN PATENT DOCUMENTS

| | | |
|---|---|---|
| CN | 102924457 | 2/2013 |
| CN | 103102345 | 5/2013 |
| CN | 104059674 | 9/2014 |
| CN | 104087312 | 10/2014 |
| CN | 104804748 | 7/2015 |
| CN | 104926808 | 9/2015 |
| CN | 107674029 | 2/2018 |
| CN | 107793409 | 3/2018 |
| CN | 108276463 | 7/2018 |
| CN | 110386954 | 10/2019 |
| CN | 110423265 | 11/2019 |
| DE | 102005059892 | 6/2007 |
| EP | 445749 | 9/1991 |
| EP | 722944 | 7/1996 |
| EP | 1479669 | 11/2004 |
| EP | 1616874 | 1/2006 |
| EP | 2508511 | 10/2012 |
| GB | 2291872 | 2/1996 |
| HK | 1055058 | 12/2003 |
| JP | 2006124326 | 5/2006 |
| JP | 2006241090 | 9/2006 |
| JP | 2018070512 | 5/2018 |
| KR | 2019076339 | 7/2019 |
| WO | WO 91/10671 | 7/1991 |
| WO | WO 93/21145 | 10/1993 |
| WO | WO 94/24084 | 10/1994 |
| WO | WO 96/14307 | 5/1996 |
| WO | WO 96/14329 | 5/1996 |
| WO | WO 98/03492 | 1/1998 |
| WO | WO 98/03493 | 1/1998 |
| WO | WO 98/03494 | 1/1998 |
| WO | WO 98/16184 | 4/1998 |
| WO | WO 99/32443 | 7/1999 |
| WO | WO 99/32445 | 7/1999 |
| WO | WO 99/32479 | 7/1999 |
| WO | WO 99/32481 | 7/1999 |
| WO | WO 99/32486 | 7/1999 |
| WO | WO 99/32489 | 7/1999 |
| WO | WO 99/54290 | 10/1999 |
| WO | WO 99/59999 | 11/1999 |
| WO | WO 2001/010846 | 2/2001 |
| WO | WO 2001/014378 | 3/2001 |
| WO | WO 2001/027114 | 4/2001 |
| WO | WO 2001/028979 | 4/2001 |
| WO | WO 2002/003997 | 1/2002 |
| WO | WO 2003/028051 | 4/2003 |
| WO | WO 2003/039523 | 5/2003 |
| WO | WO 2003/072757 | 9/2003 |
| WO | WO 2003/088967 | 10/2003 |
| WO | WO 2003/103669 | 12/2003 |
| WO | WO 2004/014312 | 2/2004 |
| WO | WO 2004/033460 | 4/2004 |
| WO | WO 2004/050024 | 6/2004 |
| WO | WO 2004/058735 | 7/2004 |
| WO | WO 2004/087142 | 10/2004 |
| WO | WO 2004/106356 | 12/2004 |
| WO | WO 2005/021568 | 3/2005 |
| WO | WO 2005/034878 | 4/2005 |
| WO | WO 2005/037269 | 4/2005 |
| WO | WO 2005/060665 | 7/2005 |
| WO | WO 2005/063766 | 7/2005 |
| WO | WO 2005/097738 | 10/2005 |
| WO | WO 2006/081264 | 8/2006 |
| WO | WO 2006/084281 | 8/2006 |
| WO | WO 2006/094347 | 9/2006 |
| WO | WO 2007/001975 | 1/2007 |
| WO | WO 2007/002057 | 1/2007 |
| WO | WO 2007/073856 | 7/2007 |
| WO | WO 2007/075525 | 7/2007 |
| WO | WO 2008/019124 | 2/2008 |
| WO | WO 2008/064788 | 6/2008 |
| WO | WO 2008/067280 | 6/2008 |
| WO | WO 2008/067713 | 6/2008 |
| WO | WO 2008/077597 | 7/2008 |
| WO | WO 2008/138843 | 11/2008 |
| WO | WO 2009/124103 | 10/2009 |
| WO | WO 2010/030858 | 3/2010 |
| WO | WO 2010/051085 | 5/2010 |
| WO | WO 2010/054384 | 5/2010 |
| WO | WO 2010/058512 | 5/2010 |
| WO | WO 2010/091386 | 8/2010 |
| WO | WO 2010/108140 | 9/2010 |
| WO | WO 2010/145778 | 12/2010 |
| WO | WO 2011/005860 | 1/2011 |
| WO | WO 2011/010891 | 1/2011 |
| WO | WO 2011/017561 | 2/2011 |
| WO | WO 2011/018495 | 2/2011 |
| WO | WO 2011/029842 | 3/2011 |
| WO | WO 2011/057204 | 5/2011 |
| WO | WO 2011/061590 | 5/2011 |
| WO | WO 2011/066482 | 6/2011 |
| WO | WO 2011/073376 | 6/2011 |
| WO | WO 2011/103441 | 8/2011 |
| WO | WO 2011/133005 | 10/2011 |
| WO | WO 2011/133871 | 10/2011 |
| WO | WO 2011/136307 | 11/2011 |
| WO | WO 2011/139107 | 11/2011 |
| WO | WO 2011/153197 | 12/2011 |
| WO | WO 2012/025857 | 3/2012 |
| WO | WO 2012/041872 | 4/2012 |
| WO | WO 2012/075381 | 6/2012 |
| WO | WO 2012/114223 | 8/2012 |
| WO | WO 2013/013068 | 1/2013 |
| WO | WO 2013/120040 | 8/2013 |
| WO | WO 2013/151975 | 10/2013 |
| WO | WO 2013/188881 | 12/2013 |
| WO | WO 2014/009447 | 1/2014 |
| WO | WO 2014/026198 | 2/2014 |
| WO | WO 2014/070771 | 5/2014 |
| WO | WO 2014/144584 | 9/2014 |
| WO | WO 2014/152588 | 9/2014 |
| WO | WO 2014/153001 | 9/2014 |
| WO | WO 2014/159224 | 10/2014 |
| WO | WO 2015/077360 | 5/2015 |
| WO | WO 2015/177325 | 11/2015 |
| WO | WO 2015/192441 | 12/2015 |
| WO | WO 2016/012362 | 1/2016 |
| WO | WO 2016/043874 | 3/2016 |
| WO | WO 2016/044772 | 3/2016 |
| WO | WO 2016/049524 | 3/2016 |
| WO | WO 2016/049565 | 3/2016 |
| WO | WO 2016/066582 | 5/2016 |
| WO | WO 2016/115416 | 7/2016 |
| WO | WO 2016/145142 | 9/2016 |
| WO | WO 2016/162644 | 10/2016 |
| WO | WO 2017/027582 | 2/2017 |

(56) References Cited

FOREIGN PATENT DOCUMENTS

| WO | WO 2017/032840 | 3/2017 |
|---|---|---|
| WO | WO 2017/066781 | 4/2017 |
| WO | WO 2017/066782 | 4/2017 |
| WO | WO 2017/066791 | 4/2017 |
| WO | WO 2017/066793 | 4/2017 |
| WO | WO 2017/066797 | 4/2017 |
| WO | WO 2017066789 | 4/2017 |
| WO | WO 2017/099969 | 6/2017 |
| WO | WO 2017/117439 | 7/2017 |
| WO | WO 2017/153186 | 9/2017 |
| WO | WO 2017/211307 | 12/2017 |
| WO | WO 2017/212385 | 12/2017 |
| WO | WO 2018/024188 | 2/2018 |
| WO | WO 2018/160824 | 3/2018 |
| WO | WO 2018/065354 | 4/2018 |
| WO | WO 2018/065365 | 4/2018 |
| WO | WO 2018/081863 | 5/2018 |
| WO | WO 2018/085818 | 5/2018 |
| WO | WO 2018/152501 | 8/2018 |
| WO | WO 2018/152548 | 8/2018 |
| WO | WO 2018/154104 | 8/2018 |
| WO | WO 2018/162607 | 9/2018 |
| WO | WO 2018/213258 | 11/2018 |
| WO | WO 2018/227061 | 12/2018 |
| WO | WO 2019/112719 | 6/2019 |
| WO | WO 2019/116302 | 6/2019 |
| WO | WO 2019/177873 | 9/2019 |
| WO | WO 2019/213174 | 11/2019 |
| WO | WO 2020/033282 | 2/2020 |
| WO | WO 2020/033284 | 2/2020 |
| WO | WO 2020/033285 | 2/2020 |
| WO | WO 2020/033288 | 2/2020 |
| WO | WO 2020/060915 | 3/2020 |

OTHER PUBLICATIONS

Alexandrova, L. A. "4'-C-Nucleoside Derivatives: Synthesis and Antiviral Properties" Russian Journal of Bioorganic Chemistry vol. 37 No. 6 pp. 651-671 (Year: 2011).*

Second Written Opinion dated Feb. 18, 2021 for PCT Application No. PCT/US2020/025966, filed Mar. 31, 2021.

Bezzi et al., "Regulation of constitutive and alternative splicing by PRMT5 reveals a role for Mdm4 pre-mRNA in sensing defects in the spliceosomal machinery" Genes & Development (2013) 27:1903-1916.

CAS Registry No. 1350206-01-7; STN Entry Date: Dec. 7, 2011.

Chan-Penebre et al., "A selective Inhibitor of PRMT5 with in vivo and in vitro potency in MCL models" Nature Chemical Biology (2015) 11:432-437.

Cho et al., "Arginine methylation controls growth regulation by E2F-1" The EMBO Journal (2012) 31:1785-1797.

Chung et al., "Protein Arginine Methyltransferase 5 (PRMT5) Inhibition Induces Lymphoma Cell Death through Reactivation of the Retinoblastoma Tumor Suppressor Pathway and Polycomb Repressor Complex 2 (PRC2) Silencing" J. Biol. Chem. (2013) 288(49):35534-35547.

Friesen et al., "The Methylosome, a 20S Complex Containing JBP1 and plCln, Produces Dimethylarginine-Modified Sm Proteins" Molecular and Cellular Biology (2001) 21(24):8289-8300.

"IUPAC-IUB Commission on Biochemical Nomenclature Abbreviated Nomenclature of Synthetic Polypeptides (Polymerized Amino Acids)* Revised Recommendations (1971)" *Biochem*istry. (1972) 11(5):942-944.

Jiang et al., "PRMT5 promotes cell proliferation by inhibiting BTG2 expression via the ERK signaling pathway in hepatocellular carcinoma" Cancer Medicine (2018) 7(3):869-882.

Kaushik et al., "Genetic deletion or small molecule inhibition of the arginine methyltransferase PRMT5 exhibit anti-tumoral activity in mouse models of MLL-rearranged AML" Leukemia (2018) 32:499-509.

Koh et al., "MYC regulates the core pre-mRNA splicing machinery as an essential step in lymphomagenesis" Nature (2015) 523:96-100.

Kryukov et al., "MTAP deletion confers enhanced dependency on the PRMT5 arginine methyltransferase in cancer cells" Science (2016) 351(6278):1214-1218.

Liu et al., "Arginine methyltransferase PRMT5 is essential for sustaining normal adult hematopoiesis" J. Clin. Invest. (2015) 125(9):3532-3544.

Marjon et al., "MTAP Deletions in Cancer Create Vulnerability to Targeting of the MAT2A/PRMT5/RIOK1 Axis" Cell Report (2016) 15(3):574-587.

Matera et al., "A day in the life of the spliceosome" Nature Reviews Molecular Cell Biology (2014) 14:108-121.

Mavrakis et al., "Disordered methionine metabolism in MTAP/CDKN2A-deleted cancers leads to dependence on PRMT5" Science (2016) 351(6278):1208-1213.

Meister et al., "Methylation of Sm proteins by a complex containing PRMT5 and the putative U snRNP assembly factor plC" Current Biology (2001) 11(24):1990-1994).

Powers et al., "Protein Arginine Methyltransferase 5 Accelerates Tumor Growth by Arginine Methylation of the Tumor Suppressor Programmed Cell Death 4" Cancer Research (2011) 71(16):5579-5587.

Tarighat et al., "The dual epigenetic role of PRMT5 in acute myeloid leukemia:gene activation and repression via histone arginine methylation" Leukemia (2016) 30:789-799 (provided as Tarighat et al., "The dual epigenetic role of PRMT5 in acute myeloid leukemia:gene activation and repression via histone arginine methylation" Leukemia (2015):1-11.

Wei et al., "Protein arginine methyltransferase 5 is a potential oncoprotein that upregulates G1 cyclins/cyclin-dependent kinases and the phosphoinositide 3-kinase/AKT signaling cascade" Cancer Science (2012) 103(9): 1640-1650.

Yang et al., "Protein arginine methyltransferases and cancer" Nature Reviews Cancer (2013) 13:37-50.

International Search Report and Written Opinion dated May 22, 2020 for PCT Application No. PCT/US2020/025966, dated Mar. 31, 2020.

International Preliminary Report on Patentability dated Aug. 2, 2021 for PCT Application No. PCT/US2020/025966, filed Mar. 31, 2021.

* cited by examiner

COMPOUNDS TARGETING PRMT5

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application Nos. 62/828,282, filed Apr. 2, 2019, 62/877,411, filed Jul. 23, 2019 and 62/946,649, filed Dec. 11, 2019.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

In mammals, there are nine enzymes in the seven-β-strand family of protein arginine methyltransferases (PRMTs), designated PRMT1-9. These PRMTs are further divided into three types based on the different methylarginine derivatives they produce: Type I PRMTs (PRMT1-4, 6, and 8) catalyze the production of monomethylarginine (MMA) and asymmetric dimethylarginine (ADMA); Type II PRMTs (PRMT5 and 9) catalyze MMA and symmetric dimethylarginine (SDMA) production; and Type III enzymes (PRMT7) catalyze only the production of MMA residues.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

These are other embodiments are described in greater detail below.

DETAILED DESCRIPTION

PRMT5 is a Type II protein arginine methyltransferase that catalyzes SDMA modification in histones and non-histone substrates, including three subunits of the Survival of Motor Neuron (SMN) complex (SmB, SmD1 and SmD3). These proteins are essential components of the spliceosome machinery (See Friesen et al., Molecular and Cellular Biology (2001) 21(24):8289-8300; Matera et al., Nature Reviews Molecular Cell Biology (2014) 14:108-121; and Meister et al., Current Biology (2001) 11(24):1990-1994), and PRMT5 depletion triggers aberrant splicing in the adult hematopoietic compartment (Bezzi et al., Genes & Development (2013) 27:1903-1916; Koh et al., Nature (2015) 523:96-100; and Liu et al., J. Clin. Invest. (2015) 125(9): 3532-3544).

PRMT5 is overexpressed in a variety of human cancers, including several hematological malignancies such as lymphoma and leukemia (Yang et al., Nature Reviews Cancer (2013) 13:37-50 and Chung et al., J. Biol. Chem. (2013) 288(49):35534-35547), as well as liver cancer (Jiang et al., Cancer Medicine (2018) 7(3):869-882), lung cancer (Wei et al., Cancer Science (2012) 103(9): 1640-1650), breast cancer (Powers et al., Cancer Research (2011) 71(16):5579-5587), and colorectal cancer (Cho et al., The EMBO Journal (2012) 31:1785-1797). Enhanced PRMT5 expression correlates with reduced overall survival and higher recurrence rates for patients with hepatocellular carcinoma (HCC) (Jiang et al., Cancer Medicine (2018) 7(3):869-882). Knocking down PRMT5 expression with shRNA can prevent cell proliferation and colony formation in Huh-7 and SK-Hep1 HCC cells. In a mouse xenograph model for HCC, this approach can result in tumor regression.

Inhibition of PRMT5 has been shown to result in anti-tumor activity in lymphomas (Chan-Penebre et al., Nature Chemical Biology (2015) 11:432-437), MLL-rearranged acute leukemia models (Kaushik et al., Leukemia (2018) 32:499-509), and several other types of leukemia in vitro (Tarighat et al., Leukemia (2016) 30:789-799). In addition, cells lacking MTAP, a critical enzyme in the methionine salvage pathway that is deleted in approximately 15% of all human cancers, can be more sensitive to PRMT5 depletion than MTAP wild type cells (Kryukov et al., Science (2016) 351(6278):1214-1218; Marjon et al., Cell Report (2016) 15(3):574-587; and Mavrakis et al., Science (2016) 351 (6278):1208-1213). Small molecule inhibitors of PRMT5 have shown preferential impairment of cell viability for MTAP-null cancer cell lines compared with isogenic MTAP-expressing counterparts, making PRMT5 a potential vulnerability across multiple cancer lineages.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from deuterium, alkyl, alkenyl, alkynyl, cycloalkyl, cycloalkenyl, aryl, heteroaryl, heterocyclyl, aryl (alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiomorpholine, thiomorpholine sulfoxide, thiomorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl) and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl and acryl. An acyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N ($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N ($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N ($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N($R_A R_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

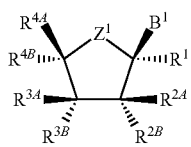
(I)

wherein: B¹ can be an optionally substituted

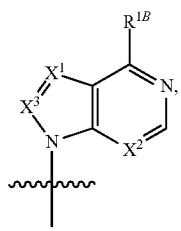

an optionally substituted

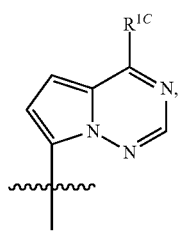

an optionally substituted

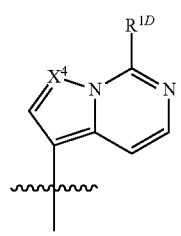

or an optionally substituted

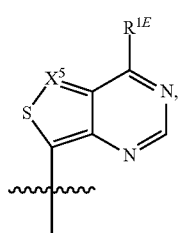

wherein $X^1$ can be N (nitrogen) or $CR^{C1}$; $X^2$ can be N (nitrogen) or $CR^{C2}$; $X^3$ can be N (nitrogen) or $CR^{C3}$; $X^4$ can be N (nitrogen) or $CR^{C4}$; $X^5$ can be N (nitrogen) or $CR^{C5}$; and $R^{C1}$, $R^{C2}$, $R^{C3}$, $R^{C4}$ and $R^{C5}$ can be independently hydrogen or halogen; $R^{1B}$, $R^{1C}$, $R^{1D}$ and $R^{1E}$ can be independently hydrogen, halogen, hydroxy, an unsubstituted $C_{1-4}$ alkyl, an unsubstituted $C_{2-4}$ alkenyl, an unsubstituted $C_3$-$C_6$ cycloalkyl, an unsubstituted $C_{1-4}$ alkoxy or $NR^{A1}R^{A2}$; and $R^{A1}$ and $R^{A2}$ can be independently selected from hydrogen, hydroxy, an unsubstituted $C_{1-4}$ alkyl, an unsubstituted $C_{1-4}$ alkoxy and —C(=O)$R^{C6}$, wherein $R^{C6}$ can be hydrogen, an unsubstituted $C_{1-4}$ alkyl or an unsubstituted $C_{1-4}$ monocyclic cycloalkyl; $R^1$ can be hydrogen or an unsubstituted $C_{1-4}$ alkyl; $R^{2A}$ can be hydrogen or an unsubstituted $C_{1-4}$ alkyl; $R^{2B}$ can be halogen, OH, —O—C(=O)—$C_{1-4}$ alkyl or —O—C(=O)—CH($R^{1''}$)—$NH_2$, wherein $R^{1'}$ can be H, —$CH_3$, —CH($CH_3$)$_2$, —$CH_2$—CH($CH_3$)$_2$ or —CH($CH_3$)—CH($CH_3$)$_2$; $R^{3A}$ can be hydrogen, an unsubstituted or a substituted $C_{1-4}$ alkyl, an unsubstituted or a substituted $C_{2-4}$ alkenyl or an unsubstituted or a substituted $C_{2-4}$ alkynyl, wherein when the $C_{1-4}$ alkyl, the $C_{2-4}$ alkenyl and the $C_{1-4}$ alkynyl are substituted, each can be independently substituted with 1 or more fluoros; $R^{3B}$ can be halogen, OH, —O—C(=O)—$C_{1-4}$ alkyl or —O—C(=O)—CH($R^{1'''}$)—$NH_2$, wherein $R^{1'''}$ is H, —$CH_3$, —CH($CH_3$)$_2$, —$CH_2$—CH($CH_3$)$_2$ or —CH($CH_3$)—CH($CH_3$)$_2$; $R^{4A}$ can be —($CR^{D1}R^{E1}$)($CR^{D2}R^{E2}$)n-$R^{F1}$, —($CR^{G1}R^{H1}$)—O—$R^{J1}$, —O—($CR^{K1}R^{L1}$)—$R^{M1}$ or —($CR^{N1}R^{O1}$)p-$R^{P1}$; wherein $R^{D1}$, $R^{E1}$, $R^{D2}$ and $R^{E2}$ can be independently selected from hydrogen, halogen, hydroxy and an unsubstituted $C_{1-3}$ alkyl; n can be 0 or 1; and $R^{F1}$ can be an unsubstituted or a substituted aryl, an unsubstituted or a substituted heteroaryl or an unsubstituted or a substituted heterocyclyl; or $R^{D1}$ and $R^{E1}$ can be taken together with the carbon to which $R^{D1}$ and $R^{E1}$ are attached to form an unsubstituted cyclopropyl ring; and $R^{D2}$ and $R^{E2}$ can be independently selected from hydrogen, halogen, hydroxy and an unsubstituted $C_{1-3}$ alkyl; n can be 1; and $R^{F1}$ can be an unsubstituted or a substituted aryl, an unsubstituted or a substituted heteroaryl or an unsubstituted or a substituted heterocyclyl; or $R^{D1}$ and $R^{E2}$ can be independently selected from hydrogen, halogen, hydroxy and an unsubstituted $C_{1-3}$ alkyl; $R^{E1}$ and $R^{D2}$ can be taken together with the carbon to which $R^{E1}$ and $R^{D1}$ are attached to form an unsubstituted cyclopropyl ring; n can be 1; and $R^{F1}$ can be an unsubstituted or a substituted aryl, an unsubstituted or a substituted heteroaryl or an unsubstituted or a substituted heterocyclyl; or $R^{D1}$ and $R^{E2}$ can be independently selected from hydrogen, halogen, hydroxy and an unsubstituted $C_{1-3}$ alkyl; $R^{E1}$ and $R^{D2}$ together form a double bond; n can be 1; and $R^{F1}$ can be an unsubstituted or a substituted aryl, an unsubstituted or a substituted heteroaryl or an unsubstituted or a substituted heterocyclyl; $R^{G1}$, $R^{H1}$, $R^{K1}$, $R^{L1}$, $R^{N1}$ and $R^{O1}$ can be independently selected from hydrogen, halogen, hydroxy and an unsubstituted $C_{1-3}$ alkyl; $R^{J1}$ and $R^{M1}$ can be independently an unsubstituted or a substituted aryl, an unsubstituted or a substituted heteroaryl or an unsubstituted or a substituted heterocyclyl; $R^{P1}$ can be an unsubstituted or a substituted heteroaryl; and p can be 3 or 4; $R^{4B}$ can be halogen, cyano, azido, —C(=O)$NH_2$, an unsubstituted or a substituted $C_{1-4}$ alkyl, an unsubstituted or a substituted $C_{2-4}$ alkenyl, an unsubstituted or a substituted $C_{2-4}$ alkynyl or an unsubstituted or a substituted $C_3$-$C_4$ cycloalkyl, wherein when the $C_{1-4}$ alkyl is substituted, the $C_{1-4}$ alkyl can be substituted with 1 or more substituents independently selected from halogen, OH and cyano, and wherein when the $C_{2-4}$ alkenyl is substituted, the $C_{2-4}$ alkenyl can be substituted independently with 1 or more halogens; $Z^1$ can be $CR^{5A}R^{5B}$, O (oxygen), S (sulfur) or N (an unsubstituted $C_{1-4}$ alkyl); $R^{5A}$ and $R^{5B}$ can be independently hydrogen, halogen, cyano or an unsubstituted or a substituted $C_{1-4}$ alkyl, wherein when the $C_{1-4}$ alkyl is substituted, the $C_{1-4}$ alkyl can be substituted with 1 or more substituents independently selected from fluoro and hydroxy; or $R^{5A}$ and $R^{5B}$ together with the carbon $R^{5A}$ and $R^{5B}$ are attached can form a double bond optionally substituted with one or two halogen, $R^{5A}$ and $R^{5B}$ together with the carbon $R^{5A}$ and $R^{5B}$ are attached can form an unsubstituted cyclopropyl or $R^{5A}$ and $R^{5B}$ together with the carbon $R^{5A}$ and $R^{5B}$ are attached can form an unsubstituted or a substituted oxetane, wherein when the oxetane is substituted, the oxetane can be substituted independently with 1 or 2 halogens; or $R^{2A}$ and $R^{2B}$ together with the carbon $R^{2A}$ and $R^{2B}$ are attached can form a 3, 4 or 5 membered monocyclic cycloalkyl or a 3, 4 or 5 membered monocyclic heterocyclyl; or $R^{3A}$ and $R^{3B}$ together with the carbon $R^{3A}$ and $R^{3B}$ are attached can form a 3, 4 or 5 membered monocyclic cycloalkyl or a 3, 4 or 5 membered monocyclic heterocyclyl; or $R^{4B}$ and $R^{3B}$ together with the carbon $R^{4B}$ and $R^{3B}$ are attached can form an unsubstituted oxetane; or $R^{4B}$ and $R^{5B}$ together with the carbon $R^{4B}$ and $R^{5B}$ are attached can form an unsubstituted cyclopropyl; or $R^1$ and $R^{5B}$ together with the carbon $R^1$ and $R^{5B}$ are attached can form an unsubstituted cyclopropyl; or when $Z^1$ is O, then $R^{2B}$ and $R^{4B}$ can be connected via —$(CH_2)y$-O—, wherein y can be 1 or 2,

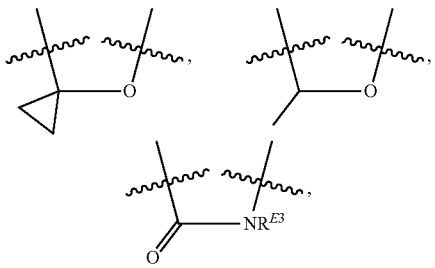

wherein $NR^{E3}$ can be $R^{E3}$ can be hydrogen or an unsubstituted $C_{1-7}$ alkyl or

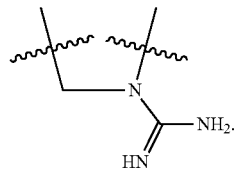 [SMILES: *CN(*)C(=N)N]

The 5-membered ring of Formula (I) can be a carbocyclyl or a heterocyclyl. In some embodiments, the 5-membered ring of Formula (I) can be a carbocyclyl when $Z^1$ is $CR^{5A}R^{5B}$. Various substituents can be present at $R^{5A}$ and $R^{5B}$. In some embodiments, $R^{5A}$ and $R^{5B}$ can be each hydrogen such that $Z^1$ is $CH_2$. In some embodiments, at least one of $R^{5A}$ and $R^{5B}$ can be halogen, for example F. In some embodiments, $R^{5A}$ and $R^{5B}$ can be each halogen. When $R^{5A}$ and $R^{5B}$ are each halogen, the halogens can be the same or different. An example of $R^{5A}$ and $R^{5B}$ each being halogen is $CF_2$. In some embodiments, at least one of $R^{5A}$ and $R^{5B}$ can be cyano. In some embodiments, at least one of $R^{5A}$ and $R^{5B}$ can be an unsubstituted $C_{1-4}$ alkyl. Examples of unsubstituted $C_{1-4}$ alkyls include methyl, ethyl, n-propyl, isopropyl, n-butyl, isobutyl and tert-butyl. In some embodiments, one of $R^{5A}$ and $R^{5B}$ can be an unsubstituted $C_{1-4}$ alkyl (such as those described herein); and the other $R^{5A}$ and $R^{5B}$ can be hydrogen. In some embodiments, at least one of $R^{5A}$ and $R^{5B}$ can be a substituted $C_{1-4}$ alkyl (such as those $C_{1-4}$ alkyls described herein) substituted with 1 or more substituents independently selected from fluoro and hydroxy. Those skilled in the art understand that when $Z^1$ is $CR^{5A}R^{5B}$, the carbon to which $R^{5A}$ and $R^{5B}$ are attached can be a stereocenter. In some embodiments, the carbon to which $R^{5A}$ and $R^{5B}$ are attached can be in the R-configuration

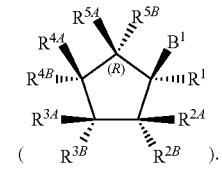

In other embodiments, the carbon to which $R^{5A}$ and $R^{5B}$ are attached can be in the S-configuration

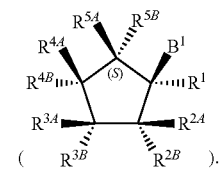

In some embodiments, $Z^1$ can be $CR^{5A}R^{5B}$, wherein $R^{5A}$ and $R^{5B}$ together with the carbon $R^{5A}$ and $R^{5B}$ are attached form a double bond optionally substituted with one or two halogen. For example, $Z^1$ can be $C=CH_2$, $C=CCl_2$ or $C=CF_2$. In other embodiments, when $Z^1$ is $CR^{5A}R^{5B}$, $R^{5A}$ and $R^{5B}$ together with the carbon $R^{5A}$ and $R^{5B}$ are attached form an unsubstituted cyclopropyl. In still other embodiments, when $Z^1$ is $CR^{5A}R^{5B}$, $R^{5A}$ and $R^{5B}$ together with the carbon $R^{5A}$ and $R^{5B}$ are attached form an unsubstituted or a substituted oxetane, wherein when the oxetane is substituted, the oxetane is substituted independently with 1 or 2 halogens (for example, fluoro or chloro). When $R^{5A}$ and $R^{5B}$ together with the carbon $R^{5A}$ and $R^{5B}$ are attached form an unsubstituted cyclopropyl or an unsubstituted or a substituted oxetane, the 5-membered ring of Formula (I) and the unsubstituted cyclopropyl or an unsubstituted or a substituted oxetane are connected in a spiro-manner.

As described herein, the 5-membered ring of Formula (I) can be a heterocyclyl. In some embodiments, $Z^1$ can be S (sulfur). In other embodiments, $Z^1$ can be N (an unsubstituted $C_{1-4}$ alkyl). Exemplary $C_{1-4}$ alkyls are described herein, for example, methyl, ethyl, n-propyl, isopropyl, n-butyl, iso-butyl and tert-butyl.

The 2'-position of the 5-membered ring of Formula (I) can have present various substituents. The positions of the 5-membered ring as referred to herein are as follows:

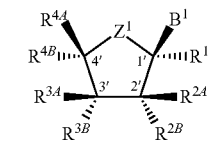

In some embodiments, $R^{2A}$ can be hydrogen. In other embodiments, $R^{2A}$ can be an unsubstituted $C_{1-4}$ alkyl. Suitable examples of $C_{1-4}$ alkyls are provided herein and include methyl, ethyl, n-propyl, isopropyl, n-butyl, isobutyl and tert-butyl. In some embodiments, $R^{2B}$ can be OH. In other embodiments, $R^{2B}$ can be —O—C(=O)—$C_{1-4}$ alkyl, such as —O—C(=O)—$CH_3$, —O—C(=O)—$CH_2CH_3$, —O—C(=O)—CH$_2$CH$_2$CH$_3$, —O—C(=O)—CH$_2$CH$_2$CH$_2$CH$_3$, —O—C(=O)—CH(CH$_3$)$_2$ and —O—C(=O)—C(CH$_3$)$_3$. In still other embodiments, R$^{2B}$ can be an alpha-amino acid linked via its carboxy group. Alpha-amino acids are known to those skilled in the art, and include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. In yet still other embodiments, R$^{2B}$ can be —O—C(=O)—CH(R$^{1'}$)—NH$_2$, wherein R$^{1'}$ can be H, —CH$_3$, —CH(CH$_3$)$_2$, —CH$_2$—CH(CH$_3$)$_2$ or —CH(CH$_3$)—CH(CH$_3$)$_2$. In some embodiments, R$^{2A}$ can be halogen. Examples of halogens include F, Cl, Br and I. In yet still other embodiments, R$^{2A}$ and R$^{2B}$ together with the carbon R$^{2A}$ and R$^{2B}$ are attached form a 3, 4 or 5 membered monocyclic cycloalkyl or a 3, 4 or 5 membered monocyclic heterocyclyl. The 3, 4 or 5 membered monocyclic heterocyclyl formed from R$^{2A}$ and R$^{2B}$ being taken together with the carbon to which R$^{2A}$ and R$^{2B}$ are attached include, but are not limited to, oxetane and thietane. As described herein, R$^{2B}$ can be —O—C(=O)—C$_{1-4}$ alkyl, an alpha-amino acid linked via its carboxy group or —O—C(=O)—CH(R$^{1'''}$)—NH$_2$, and those skilled in the art understand that when R$^{2B}$ is one of the aforementioned substituents, that compound of Formula (I) can be considered a prodrug of the corresponding a compound of Formula (I) where R$^{2B}$ is OH. In some embodiments, In other embodiments, R$^{2B}$ can be halogen, —O—C(=O)—C$_{1-4}$ alkyl or —O—C(=O)—CH(R$^{1'}$)—NH$_2$ and/or R$^{3B}$ can be halogen, —O—C(=O)—C$_{1-4}$ alkyl or —O—C(=O)—CH(R$^{1'''}$)—NH$_2$.

A variety of substituents can also be present at the 3'-position of the 5-membered ring of Formula (I). In some embodiments, R$^{3A}$ can be hydrogen. In other embodiments, R$^{3A}$ can be an unsubstituted C$_{1-4}$ alkyl, such as methyl, ethyl, n-propyl, isopropyl, n-butyl, isobutyl and tert-butyl. In still other embodiments, R$^{3A}$ can be a substituted C$_{1-4}$ alkyl (such as those described herein) substituted with 1 or more fluoros. In some embodiments, R$^{3A}$ can be an unsubstituted C$_{1-4}$ alkenyl. In other embodiments, R$^{3A}$ can be a substituted C$_{2-4}$ alkenyl substituted with 1 or more fluoros. In still other embodiments, R$^{3A}$ can be an unsubstituted C$_{2-4}$ alkynyl. In yet still other embodiments, R$^{3A}$ can be a substituted C$_{2-4}$ alkynyl substituted with 1 or more fluoros.

Further groups can be present at the 3'-position of the 5-membered ring of Formula (I). In some embodiments, R$^{3B}$ can be OH. In other embodiments, R$^{3B}$ can be —O—C(=O)—C$_{1-4}$ alkyl. Exemplary C$_{1-4}$ alkyls are described herein. In still other embodiments, R$^{3B}$ can be an alpha-amino acid linked via its carboxy group. Several alpha-amino acids are known to those skilled in the art, and described herein. In yet still other embodiments, R$^{3B}$ can be —O—C(=O)—CH(R$^{1'''}$)—NH$_2$, wherein R$^{1'''}$ can be H, —CH$_3$, —CH(CH$_3$)$_2$, —CH$_2$—CH(CH$_3$)$_2$ or —CH(CH$_3$)—CH(CH$_3$)$_2$. In some embodiments, R$^{3B}$ can be halogen. For example, R$^{3B}$ can be fluoro. In some embodiments, R$^{3A}$ and R$^{3B}$ together with the carbon R$^{3A}$ and R$^{3B}$ are attached form a 3, 4 or 5 membered monocyclic cycloalkyl or a 3, 4 or 5 membered monocyclic heterocyclyl. When R$^{3B}$ is —O—C(=O)—C$_{1-4}$ alkyl, an alpha-amino acid linked via its carboxy group or —O—C(=O)—CH(R$^{1'''}$)—NH$_2$, the compound of Formula (I) can be considered a prodrug of the corresponding a compound of Formula (I) where R$^{3B}$ is OH. For example, when R$^{2B}$ and R$^{3B}$ are each —O—C(=O)—C$_{1-4}$ alkyl, that compound of Formula (I) can be considered a prodrug a compound of Formula (I) where R$^{2B}$ and R$^{3B}$ are each —OH. An example of this type of prodrug is Compound 26, wherein Compound 26 being considered a prodrug of Compound 12. The structure of Compounds 12 and 26 are provided herein.

As with the other positions on the 5-membered ring, the substituents present at the 4'-position can vary. In some embodiments, R$^{4A}$ can be —(CR$^{D1}$R$^{E1}$)(CR$^{D2}$R$^{E2}$)n-R$^{F1}$. Further, the substituents for R$^{D1}$, R$^{E1}$, R$^{D2}$ and R$^{E2}$ can also vary. In some embodiments, n can be 0. In other embodiments, n can be 1. In some embodiments, R$^{D1}$, R$^{E1}$, R$^{D2}$ and R$^{E2}$ can be each hydrogen, such that —(CR$^{D1}$R$^{E1}$)(CR$^{D2}$R$^{E2}$)n-R$^{F1}$ can be —CH$_2$—R$^{F1}$ or —CH$_2$CH$_2$—R$^{F1}$. In some embodiments, at least one of R$^{D1}$ and R$^{E1}$ can be hydrogen; and the other of R$^{D1}$ and R$^{E1}$ can be a non-hydrogen moiety as described herein. For example, one of R$^{D1}$ and R$^{E1}$ can be hydrogen; and the other of R$^{D1}$ and R$^{E1}$ can be halogen, or one of R$^{D1}$ and R$^{E1}$ can be hydrogen; the other of R$^{D1}$ and R$^{E1}$ can be hydroxy; and one of R$^{D1}$ and R$^{E1}$ can be hydrogen; the other of R$^{D1}$ and R$^{E1}$ can be an unsubstituted C$_{1-3}$ alkyl. In other embodiments, R$^{D1}$ and R$^{E1}$ can be each halogen, for example, fluoro. In some embodiments, at least one of R$^{D1}$ and R$^{E2}$ can be hydrogen; and the other of R$^{D2}$ and R$^{E2}$ can be a non-hydrogen moiety as described herein. For example, one of R$^{D2}$ and R$^{E2}$ can be hydrogen; and the other of R$^{D2}$ and R$^{E2}$ can be halogen, or one of R$^{D2}$ and R$^{E2}$ can be hydrogen; the other of R$^{D2}$ and R$^{E2}$ can be hydroxy; and one of R$^{D2}$ and R$^{E2}$ can be hydrogen; the other of R$^{D2}$ and R$^{E2}$ can be an unsubstituted C$_{1-3}$ alkyl. In other embodiments, R$^{D2}$ and R$^{E2}$ can be each halogen, for example, fluoro.

As described herein the substituents, R$^{D1}$, R$^{E1}$, R$^{D2}$ and R$^{E2}$ can vary. In some embodiments, R$^{4A}$ can be —(CR$^{D1}$R$^{E1}$)(CR$^{D2}$R$^{E2}$)n-R$^{F1}$, wherein two of R$^{D1}$, R$^{E1}$, R$^{D2}$ and R$^{E2}$ can be taken together to form an unsubstituted cyclopropyl or a double bond. Examples of when two of R$^{D1}$, R$^{E1}$, R$^{D2}$ and R$^{E2}$ can be taken together to form an unsubstituted cyclopropyl include the embodiments described in this paragraph. In some embodiments, R$^{D1}$ and R$^{E1}$ can be taken together with the carbon to which R$^{D1}$ and R$^{E1}$ are attached to form an unsubstituted cyclopropyl ring; and R$^{D2}$ and R$^{E2}$ can be independently selected from hydrogen, halogen, hydroxy and an unsubstituted C$_{1-3}$ alkyl; and R$^{F1}$ can be an unsubstituted or a substituted aryl, an unsubstituted or a substituted heteroaryl or an unsubstituted or a substituted heterocyclyl. In other embodiments, R$^{D1}$ and R$^{E2}$ can be independently selected from hydrogen, halogen, hydroxy and an unsubstituted C$_{1-3}$ alkyl; R$^{E1}$ and R$^{D2}$ can be taken together with the carbon to which R$^{E1}$ and R$^{D2}$ are attached to form an unsubstituted cyclopropyl ring; and R$^{F1}$ can be an unsubstituted or a substituted aryl, an unsubstituted or a substituted heteroaryl or an unsubstituted or a substituted heterocyclyl.

In some embodiments, R$^{D1}$ and R$^{E2}$ can be independently selected from hydrogen, halogen, hydroxy and an unsubstituted C$_{1-3}$ alkyl; R$^{E1}$ and R$^{D2}$ together form a double bond; and R$^{F1}$ can be an unsubstituted or a substituted aryl, an unsubstituted or a substituted heteroaryl or an unsubstituted or a substituted heterocyclyl. Examples of R$^{4A}$ include, but are not limited to, —CH$_2$—R$^{F1}$, —CH$_2$CH$_2$—R$^{F1}$, —CF$_2$—R$^{F1}$, —CH(OH)—R$^{F1}$,

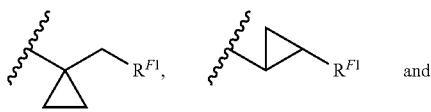

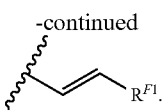

As described herein, $R^{F1}$ can be various ring structures. In some embodiments, $R^{F1}$ can be an unsubstituted aryl. In other embodiments, $R^{F1}$ can be a substituted aryl. When the aryl is monocyclic, $R^{F1}$ can be an unsubstituted or a substituted phenyl. Multicyclic aryl groups can also be present at $R^{F1}$, such as naphthyl and anthracenyl. In some embodiments, $R^{F1}$ can be an unsubstituted heteroaryl. In other embodiments, $R^{F1}$ can be a substituted heteroaryl. The heteroaryl for $R^{F1}$ can be also monocyclic (such as a 5- or 6-membered monocyclic) or multicyclic (for example, bicyclic). In some embodiments, $R^{F1}$ can be 9- or 10-membered bicyclic heteroaryl. Examples of suitable heteroaryls for $R^{F1}$ include quinolinyl and imidazo[1,2-a]pyridinyl. In still other embodiments, $R^{F1}$ can be an unsubstituted heterocyclyl. In yet still other embodiments, $R^{F1}$ can be a substituted heterocyclyl. The heterocyclyls for $R^{F1}$ can be monocyclic or multicyclic. For example, $R^{F1}$ can be a bicyclic heterocyclyl, such as a 9- or 10-membered bicyclic heterocyclyl. Exemplary further $R^{F1}$ groups include quinazoline, quinazolin-4-one, quinoxaline, isoquinoline, cinnoline, naphthyridine, benzimidazole and benzothiazole.

In other embodiments, $R^{4A}$ can be $-(CR^{G1}R^{H1})-O-R^{J1}$. As described herein, $R^{G1}$ and $R^{H1}$ can be independently hydrogen, halogen or hydroxy. In some embodiments, $R^{G1}$ and $R^{H1}$ can be each hydrogen, such that $R^{4A}$ can be $-CH_2-O-R^{J1}$. In some embodiments, at least one of $R^{G1}$ and $R^{H1}$ can be halogen, such as fluoro; and the other of $R^{G1}$ and $R^{H1}$ can be hydrogen. In other embodiments, $R^{G1}$ and $R^{H1}$ can be each halogen. As example of when $R^{G1}$ and $R^{H1}$ are each halogen is $-CF_2-O-R^{J1}$. In some embodiments, at least one of $R^{G1}$ and $R^{H1}$ can be hydroxy. In some embodiments, at least one of $R^{G1}$ and $R^{H1}$ can be hydrogen. When at least one of $R^{G1}$ and $R^{H1}$ can be hydrogen, $-(CR^{G1}R^{H1})-O-R^{J1}$ can be $-CH(CH_3)-O-R^{J1}$.

As with $R^{F1}$, $R^{J1}$ can be various cyclic moieties. In some embodiments, $R^{J1}$ can be an unsubstituted aryl, such as an unsubstituted phenyl or an unsubstituted naphthyl. In other embodiments, $R^{J1}$ can be a substituted aryl, for example, a substituted phenyl or a substituted naphthyl. In some embodiments, $R^{J1}$ is an unsubstituted heteroaryl. In other embodiments, $R^{J1}$ is a substituted heteroaryl. In still other embodiments, $R^{J1}$ is an unsubstituted heterocyclyl. In yet still other embodiments, $R^{J1}$ is a substituted heterocyclyl. The heteroaryl and heterocyclyl for $R^{J1}$ can be monocyclic or bicyclic, for example, $R^{J1}$ can be a 5-membered monocyclic heteroaryl, 6-membered monocyclic heteroaryl, 9-membered bicyclic heteroaryl, 10-membered bicyclic heteroaryl, 5-membered monocyclic heterocyclyl, 6-membered monocyclic heterocyclyl, 9-membered bicyclic heterocyclyl or 10-membered bicyclic heterocyclyl. Examples of cyclic moieties that can be $R^{J1}$ include, but are not limited to, quinolinyl, imidazo[1,2-a]pyridinyl, quinazoline, quinazolin-4-one, quinoxaline, isoquinoline, cinnoline, naphthyridine, benzimidazole and benzothiazole.

In still other embodiments, $R^{4A}$ can be $-O-(CR^{K1}R^{L1})-R^{M1}$. In some embodiments, $R^{K1}$ and $R^{L1}$ can be each hydrogen, such that $R^{4A}$ can be $-O-CH_2-R^{M1}$. In some embodiments, at least one of $R^{K1}$ and $R^{L1}$ can be halogen, such as fluoro; and the other of $R^{K1}$ and $R^{L1}$ can be hydrogen. In other embodiments, $R^{K1}$ and $R^{H1}$ can be each halogen, for example, $-O-CF_2-R^{M1}$. In some embodiments, at least one of $R^{K1}$ and $R^{L1}$ can be hydroxy. In some embodiments, at least one of $R^{K1}$ and $R^{J1}$ can be hydrogen. When at least one of $R^{K1}$ and $R^{L1}$ can be hydrogen, $-O-(CR^{K1}R^{L1})-R^{M1}$ can be $-O-CH(CH_3)-R^{M1}$.

In some embodiments, $R^{M1}$ can be an unsubstituted aryl, such as an unsubstituted phenyl or an unsubstituted naphthyl. In other embodiments, $R^{M1}$ can be a substituted aryl, for example, a substituted phenyl or a substituted naphthyl. In some embodiments, $R^{M1}$ is an unsubstituted heteroaryl. In other embodiments, $R^{M1}$ is a substituted heteroaryl. The heteroaryl can be a monocyclic heteroaryl (such as a 5- or 6-membered monocyclic heteroaryl) or a bicyclic heteroaryl (such as a 9- or 10-membered bicyclic heteroaryl). In still other embodiments, $R^{M1}$ is an unsubstituted heterocyclyl. In yet still other embodiments, $R^{M1}$ is a substituted heterocyclyl. As with the heteroaryl, the heterocyclyl can be a monocyclic heterocyclyl (such as a 5- or 6-membered monocyclic heterocyclyl) or a bicyclic heterocyclyl (such as a 9- or 10-membered bicyclic heterocyclyl). Examples of $R^{M1}$ group include, but are not limited to, quinolinyl, imidazo[1,2-a]pyridinyl, quinazoline, quinazolin-4-one, quinoxaline, isoquinoline, cinnoline, naphthyridine, benzimidazole and benzothiazole.

In some embodiments, $R^{4A}$ can be $-(CR^{N1}R^{O1})p-R^{P1}$. As described herein, in some embodiments, p can be 3. In other embodiments, p can be 4. In some embodiments, each $R^{N1}$ and each $R^{O1}$ can be hydrogen. In some embodiments, at least one $R^{N1}$ and/or at least one $R^{O1}$ can be halogen, such as fluoro; and the remaining $R^{N1}$'s and $R^{O1}$'s can be hydrogen. In other embodiments, at least one $R^{N1}$ and/or at least one $R^{O1}$ can be hydroxy; and the remaining $R^{N1}$'s and $R^{O1}$'s can be hydrogen. In still other embodiments, at least one $R^{N1}$ and/or at least one $R^{O1}$ can be an unsubstituted $C_{1-3}$ alkyl; and the remaining $R^{N1}$'s and $R^{O1}$'s can be hydrogen. As provided herein, $R^{P1}$ can be an unsubstituted or a substituted heteroaryl. In some embodiments, $R^{P1}$ can be an unsubstituted heteroaryl. In other embodiments, $R^{P1}$ can be an unsubstituted heteroaryl. The heteroaryl for $R^{P1}$ can be a monocyclic of a bicyclic heteroaryl. In some embodiments, $R^{P1}$ can be an unsubstituted monocyclic heteroaryl, such as a nitrogen-containing an unsubstituted monocyclic heteroaryl. In other embodiments, $R^{P1}$ can be a substituted monocyclic heteroaryl, for example, a nitrogen-containing a substituted monocyclic heteroaryl.

When substituted, $R^{F1}$, $R^{J1}$, $R^{M1}$ and $R^{P1}$ can be substituted 1, 2, 3 or more than 3 times with a variety of groups. When more than one group is present, one or more of the groups can be the same. The groups on $R^{F1}$, $R^{J1}$, $R^{M1}$ and $R^{P1}$, when substituted, can be different from each other. Examples of groups that can be present on a substituted $R^{F1}$, $R^{J1}$ and/or $R^{M1}$ include, but are not limited to, halogen (for example, F, Cl and Br), cyano, an unsubstituted $C_{1-4}$ alkyl, an unsubstituted $C_{1-4}$ haloalkyl (such as $CH_2F$, $CHF_2$, $CF_3$, $CH_2Cl$, $CHCl_2$ and $Cl_3$), an unsubstituted monocyclic $C_{3-6}$ cycloalkyl, an optionally substituted C-carboxy, an optionally substituted N-amido, amino, a mono-substituted amine, a di-substituted amine, $-NH-C(=O)$-unsubstituted $C_{1-8}$ alkyl, $-NH-C(=O)-O$-unsubstituted $C_{1-4}$ alkyl, $-NH-C(=O)$-unsubstituted $C_{3-6}$ cycloalkyl and $-NH-C(=O)-O$-unsubstituted $C_{3-6}$ cycloalkyl. Further examples that can be present on a substituted $R^{F1}$, $R^{J1}$, $R^{M1}$ and/or $R^{P1}$ include, but are not limited to, an unsubstituted $C_{1-4}$ alkoxy, an unsubstituted or a substituted phenyl and an unsubstituted or a substituted monocyclic heteroaryl (such as an unsubstituted or a substituted 5- or 6-membered heteroaryl). Prodrugs of compounds of Formula (I) can be obtained by substituting $R^{F1}$, $R^{J1}$, $R^{M1}$ and/or $R^{P1}$ with an appropriate group. As an example, when $R^{F1}$, $R^{J1}$, $R^{D11}$ and/or $R^{P1}$ is substituted with —NH—C(=O)-unsubstituted $C_{1-4}$ alkyl, —NH—C(=O)—O-unsubstituted $C_{1-4}$ alkyl, —NH—C(=O)-unsubstituted $C_{3-6}$ cycloalkyl and —NH—C(=O)—O-unsubstituted $C_{3-6}$ cycloalkyl, that compound of Formula (I) can be considered a prodrug of a compound of Formula (I) where an $NH_2$ group replaces the —NH—C(=O)-unsubstituted $C_{1-4}$ alkyl, —NH—C(=O)—O-unsubstituted $C_{1-4}$ alkyl, —NH—C(=O)-unsubstituted $C_{3-6}$ cycloalkyl or —NH—C(=O)—O-unsubstituted $C_{3-6}$ cycloalkyl group. A specific example is Compound 20 as described herein can be considered a prodrug of Compound 12. The specific structure of each of Compound 12 and Compound 20 are provided herein.

Exemplary $R^{F1}$, $R^{J1}$ and $R^{M1}$ groups include, but are not limited to, the following:

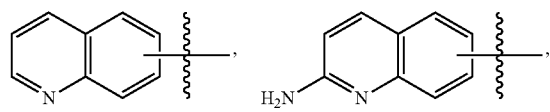

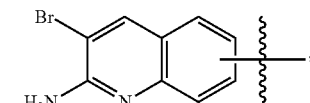

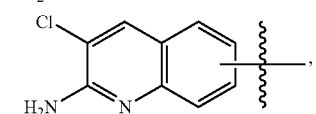

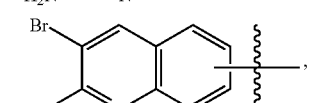

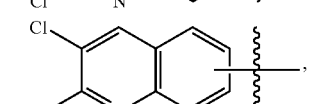

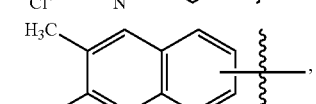

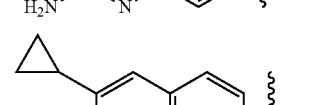


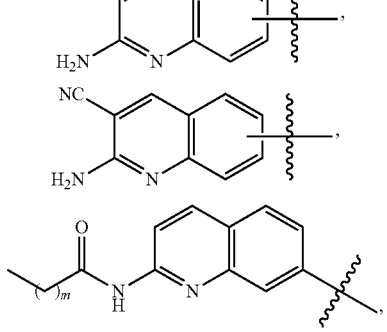

m = 1, 2, 3, 4, 5 or 6

-continued

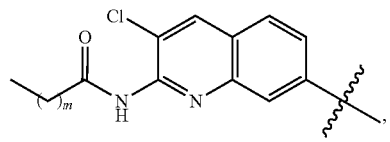

m = 1, 2, 3, 4, 5 or 6

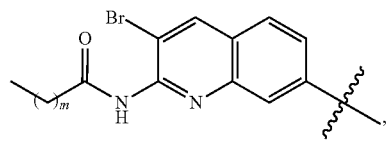

m = 1, 2, 3, 4, 5 or 6

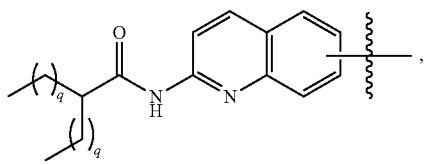

each q = 1, 2, or 3

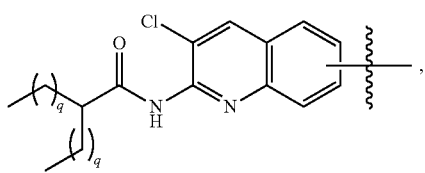

each q = 1, 2, or 3

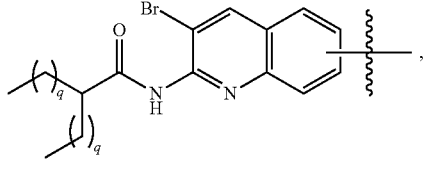

each q = 1, 2, or 3

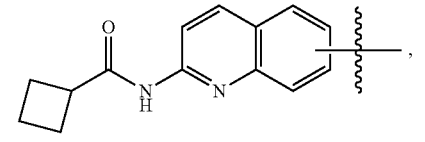

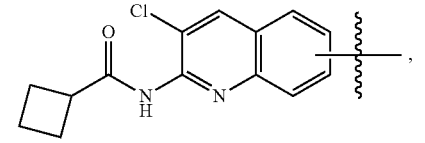

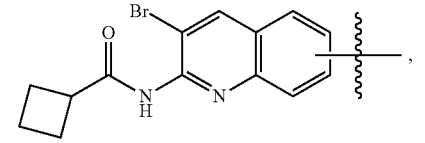

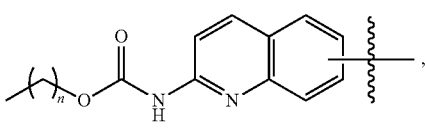

n = 1, 2, 3, 4, 5 or 6

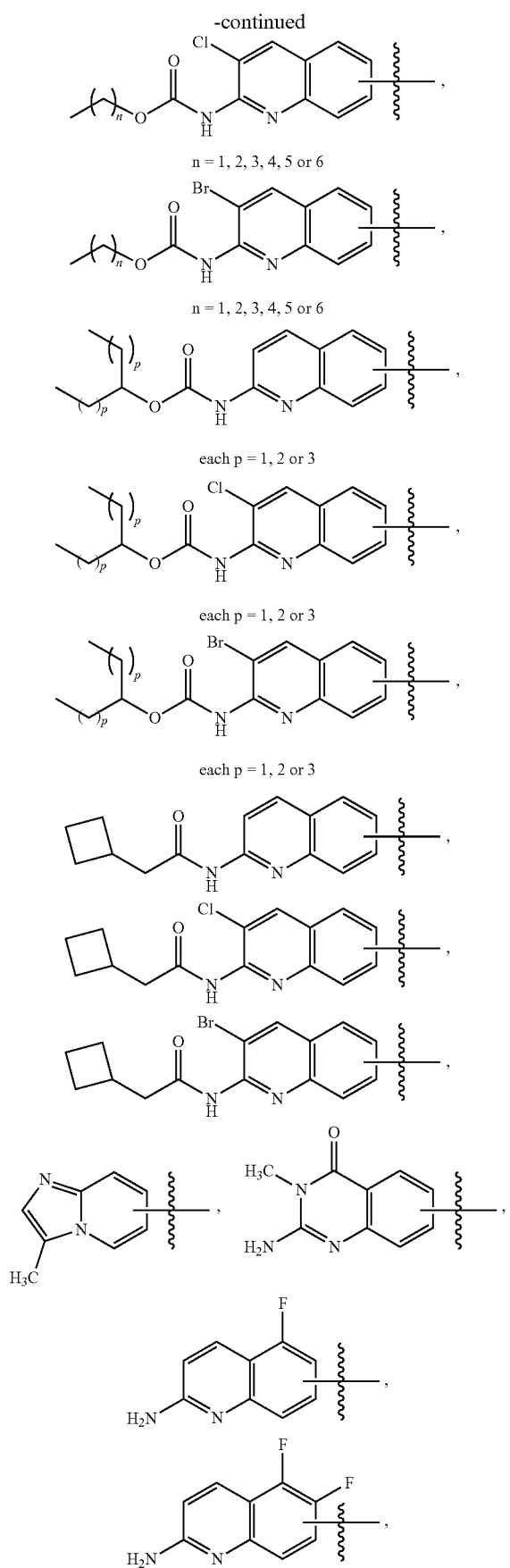
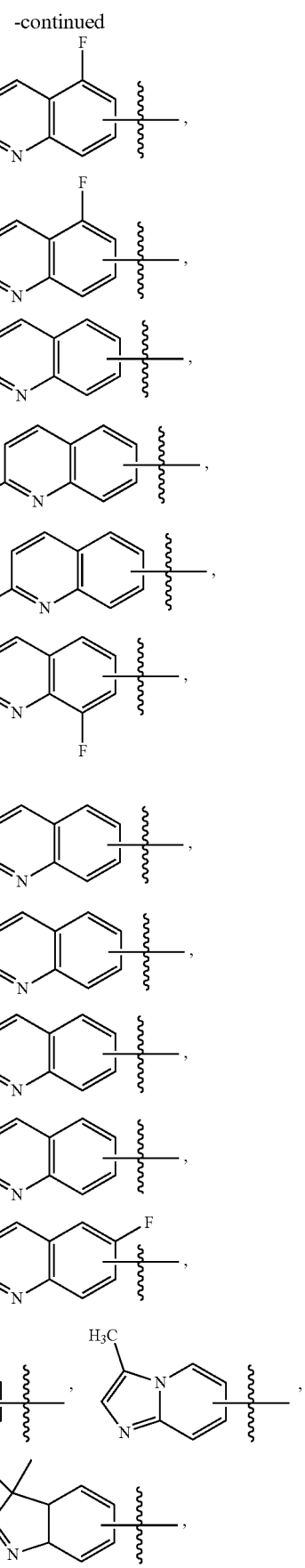

-continued
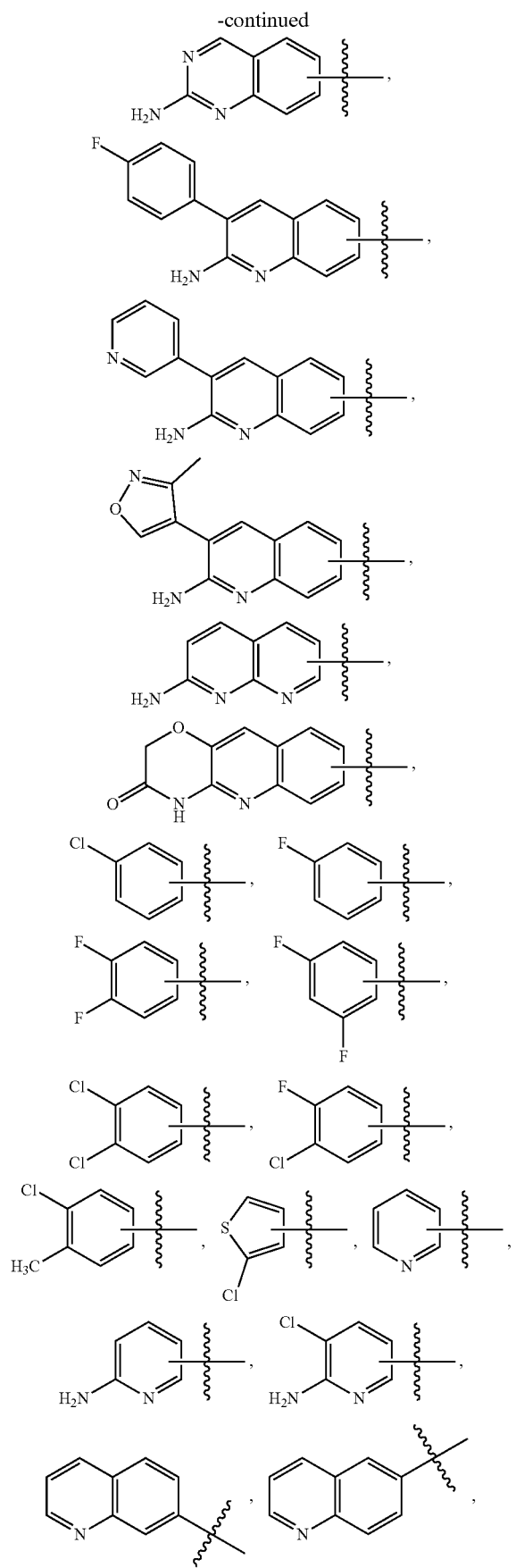
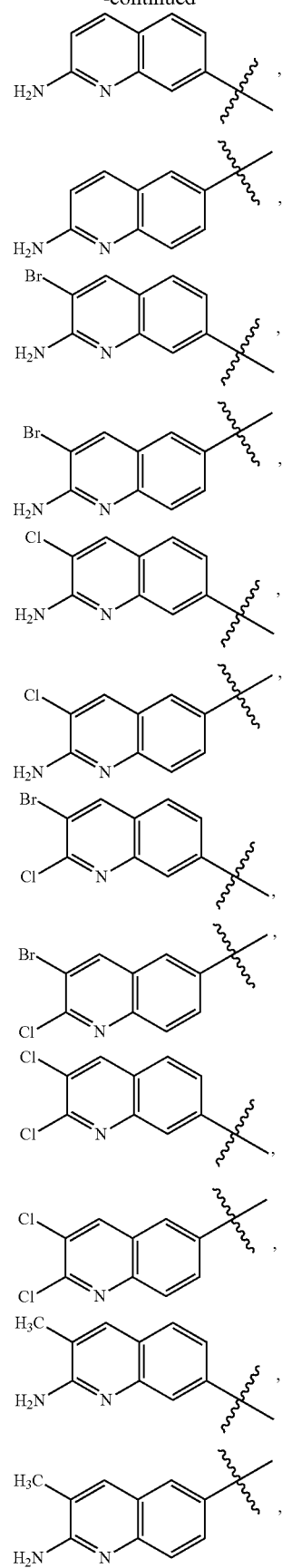

-continued
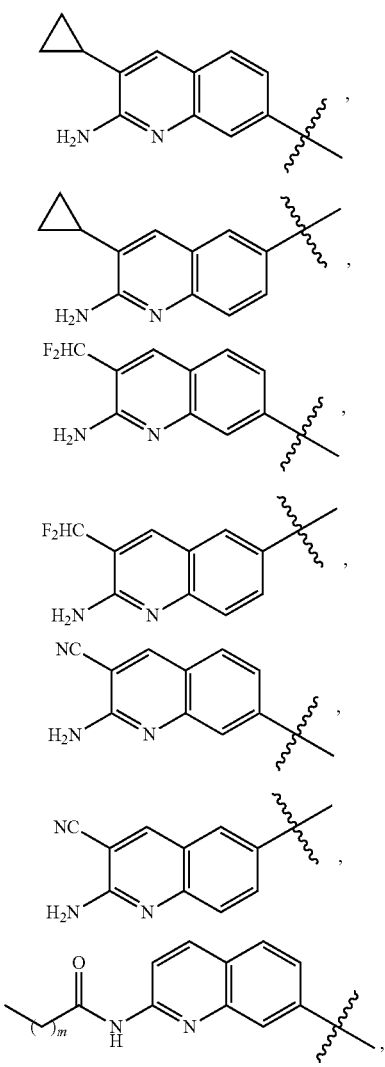
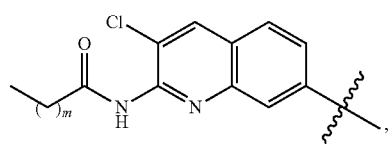
m = 1, 2, 3, 4, 5 or 6
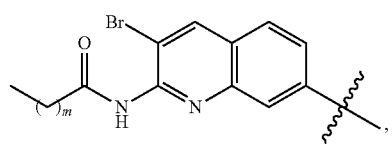
m = 1, 2, 3, 4, 5 or 6
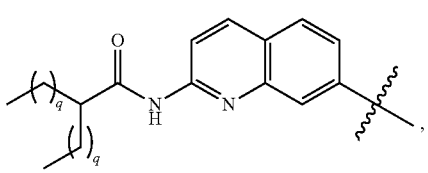
m = 1, 2, 3, 4, 5 or 6
-continued
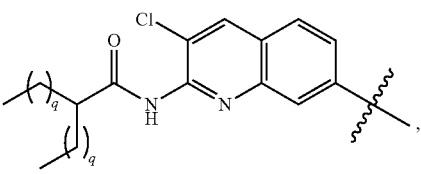
each q = 1, 2, or 3
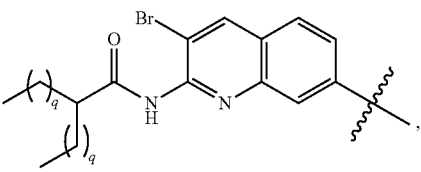
each q = 1, 2, or 3
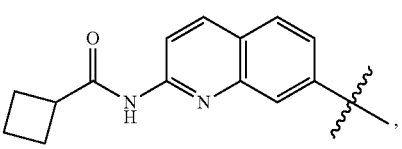
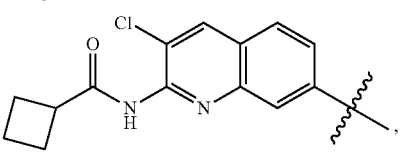
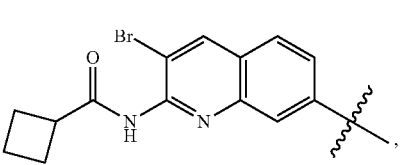
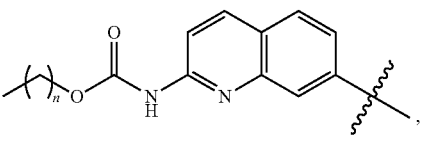
n = 1, 2, 3, 4, 5 or 6
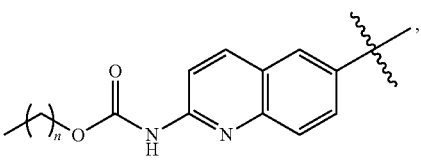
n = 1, 2, 3, 4, 5 or 6
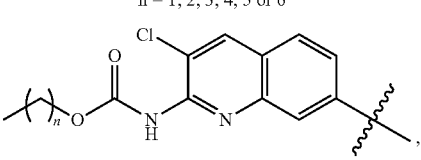
n = 1, 2, 3, 4, 5 or 6
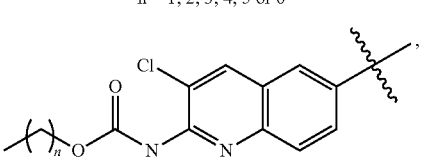
n = 1, 2, 3, 4, 5 or 6
each q = 1, 2, or 3

-continued
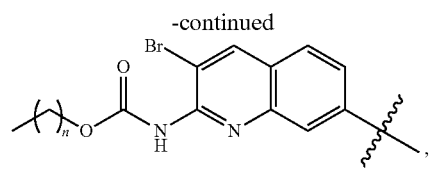
n = 1, 2, 3, 4, 5 or 6
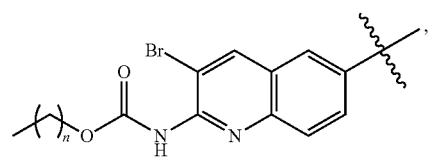
n = 1, 2, 3, 4, 5 or 6
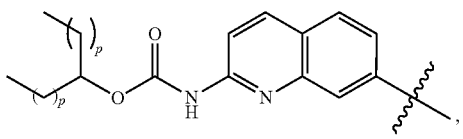
each p = 1, 2 or 3
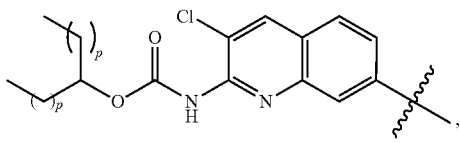
each p = 1, 2 or 3
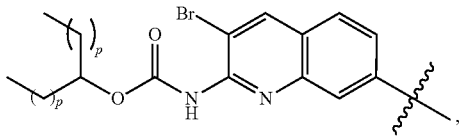
each p = 1, 2 or 3
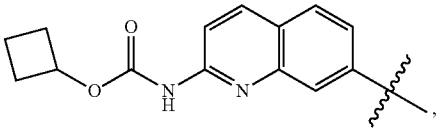
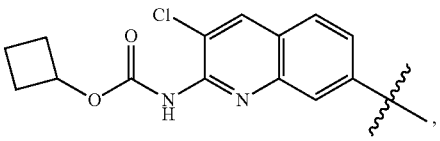
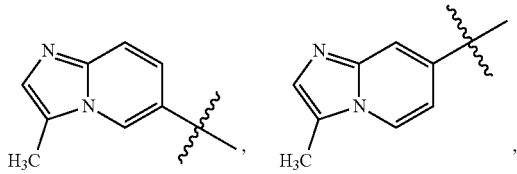
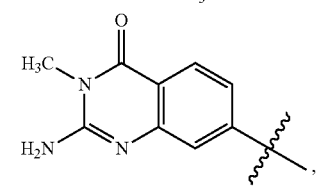
-continued
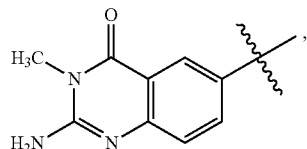
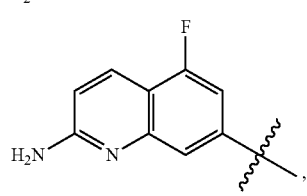
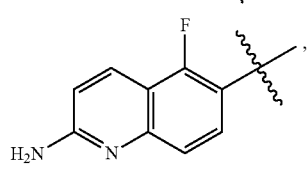
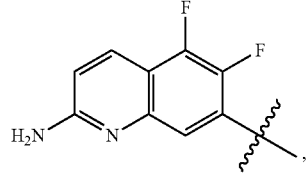
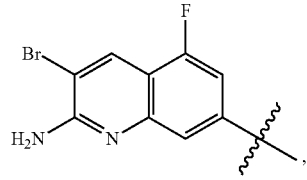
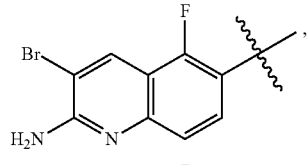
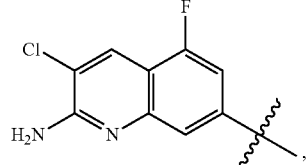
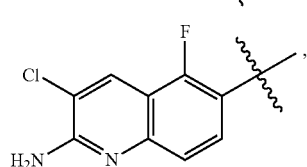
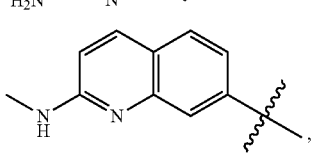
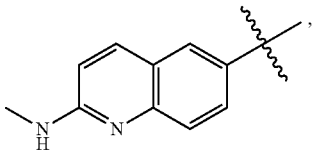

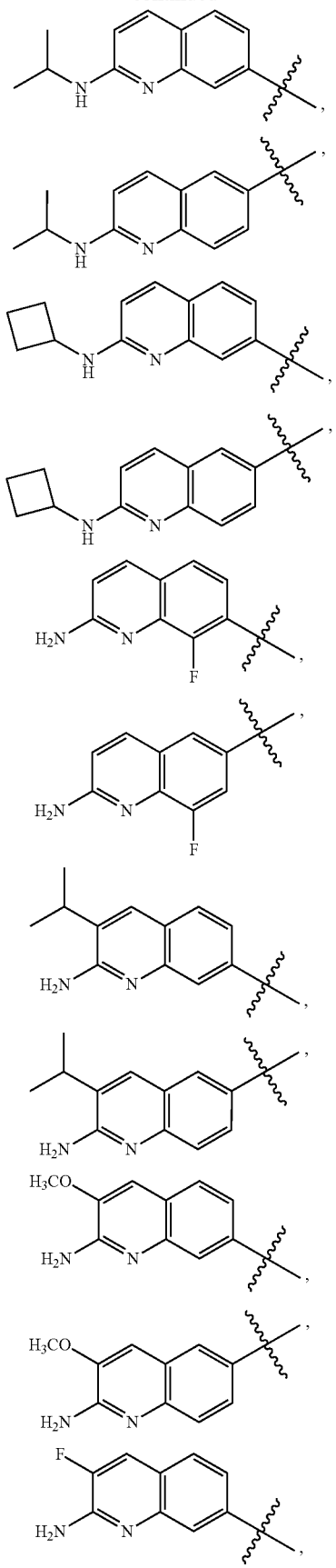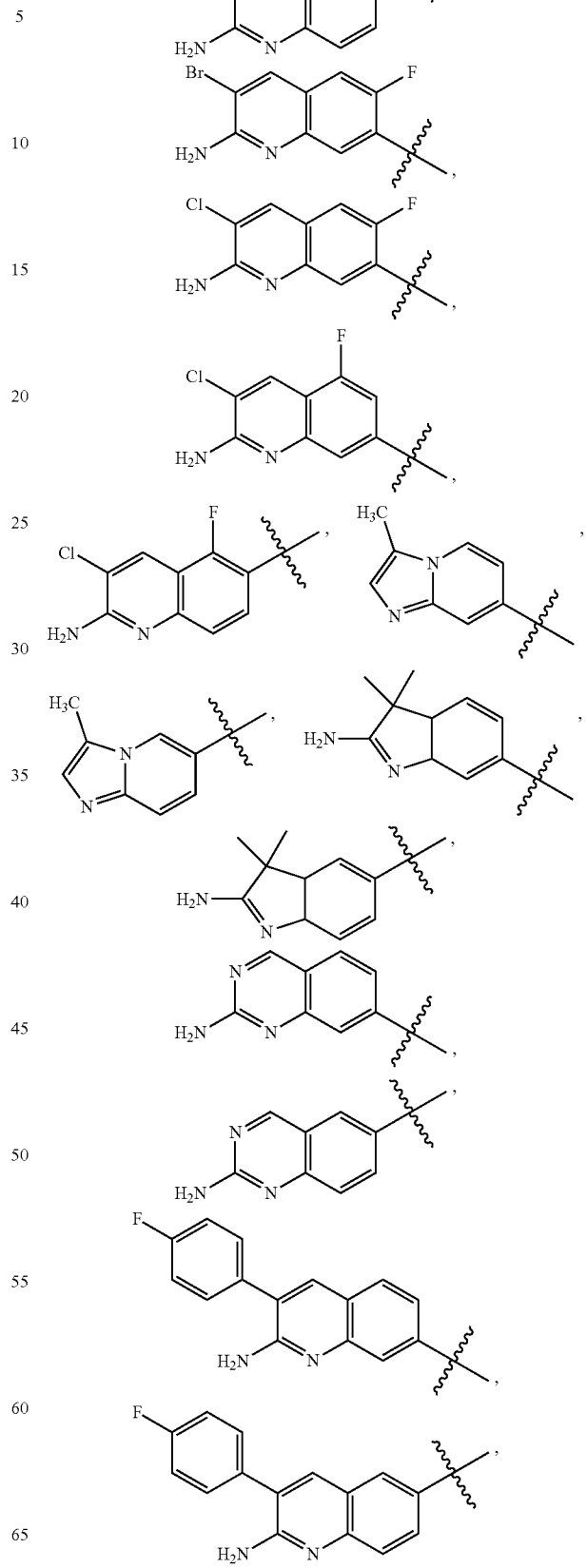

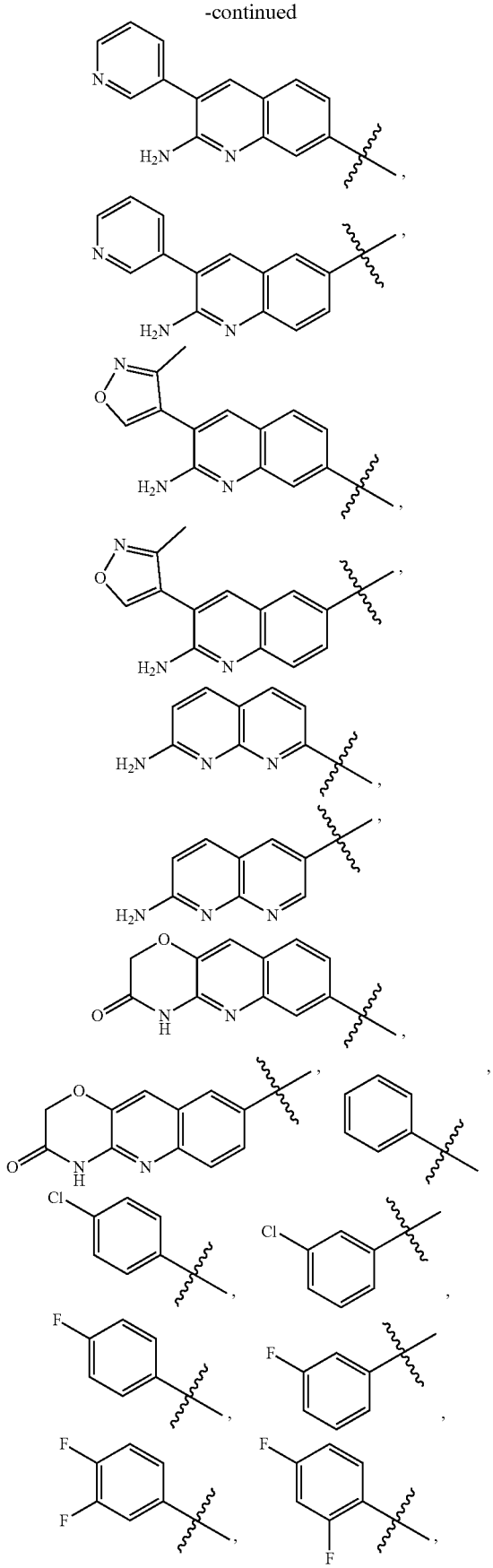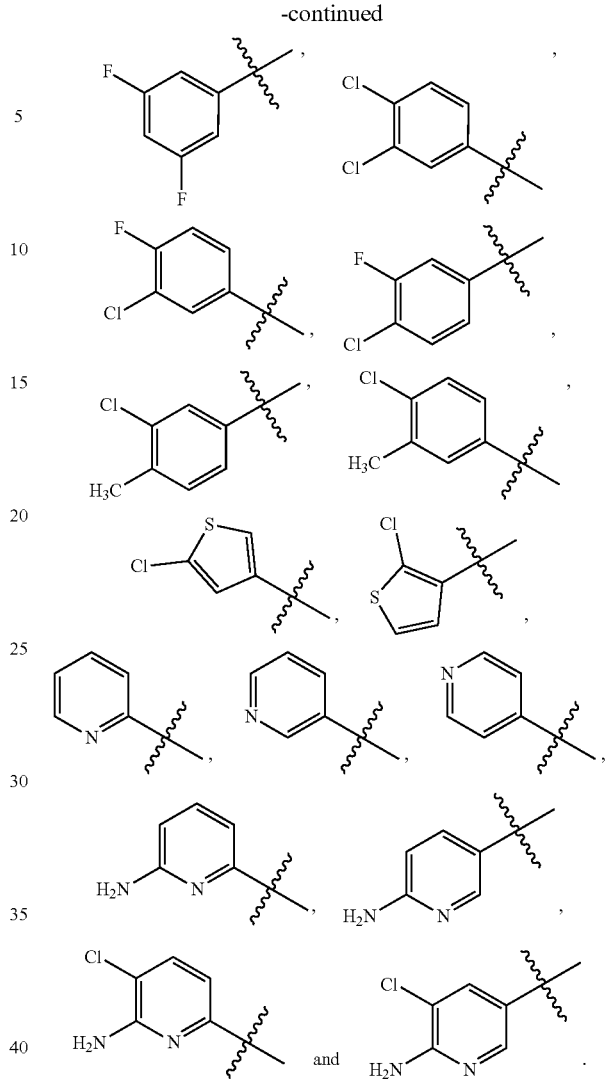
A non-limiting list of $R^{P1}$ groups include the following:
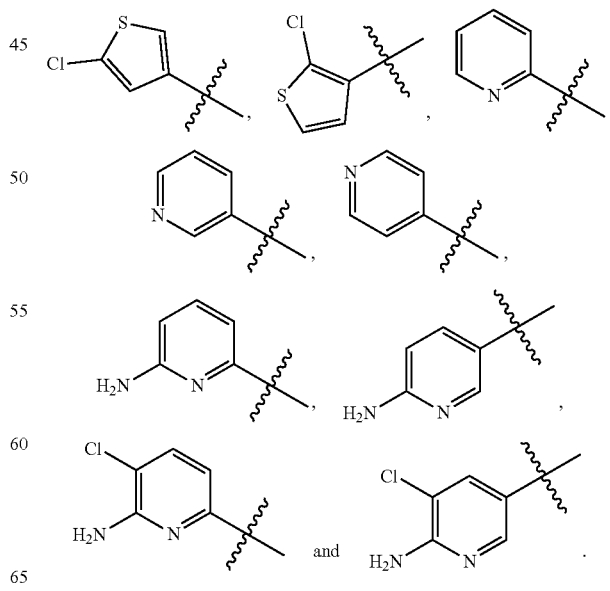

Various other groups can be present at the 4'-position of the 5-membered ring of Formula (I). In some embodiments, $R^{4B}$ can be hydrogen. In other embodiments, $R^{4B}$ can be halogen, such as F. In still other embodiments, $R^{4B}$ can be cyano. In yet still other embodiments, $R^{4B}$ can be azido. In some embodiments, $R^{4B}$ can be —C(=O)NH$_2$. In other embodiments, $R^{4B}$ can be an unsubstituted $C_{1-4}$ alkyl, such as methyl, ethyl, n-propyl, isopropyl, n-butyl, isobutyl and tert-butyl. In still other embodiments, $R^{4B}$ can be a substituted $C_{1-4}$ alkyl substituted with 1 or more substituents independently selected from the halogen (such as F and/or Cl), OH, OCH$_3$ and cyano. Examples of substituted $C_{1-4}$ alkyl for $R^{4B}$ include —CH$_2$F, —CHF$_2$, —CF$_3$, —CH$_2$Cl, —CHCl$_2$, —CCl$_3$, —CH$_2$OH and —CH$_2$CN. In yet still other embodiments, $R^{4B}$ can be an unsubstituted $C_{2-4}$ alkenyl. In some embodiments, $R^{4B}$ can be a substituted $C_{2-4}$ alkenyl substituted independently with 1 or more halogens, for example, fluoro and/or chloro. In other embodiments, $R^{4B}$ can be an unsubstituted $C_{2-4}$ alkynyl. In still other embodiments, $R^{4B}$ can be a substituted $C_{2-4}$ alkynyl. Examples of $C_{2-4}$ alkenyl and $C_{2-4}$ alkynyl include, but are not limited to, ethenyl, propenyl (straight-chained and branched), butenyl (straight-chained and branched), ethynyl, propynyl (straight-chained and branched) and butynyl (straight-chained and branched). In some embodiments, $R^{4B}$ can be an unsubstituted $C_3$-$C_4$ cycloalkyl. In other embodiments, $R^{4B}$ can be a substituted $C_3$-$C_4$ cycloalkyl. For example, $R^{4B}$ can be an unsubstituted or a substituted cyclopropyl or an unsubstituted or a substituted cyclobutyl. Alternatively, the 4'-position can be substituted by taking $R^{4B}$ and $R^{3B}$ together with the carbon $R^{4B}$ and $R^{3B}$ are attached form an unsubstituted oxetane. In some embodiments, $R^{4B}$ can be halogen, cyano, azido, —C(=O)NH$_2$, a substituted $C_{1-4}$ alkyl substituted with OH, OCH$_3$ or cyano, an unsubstituted or a substituted $C_{3-4}$ alkenyl, an unsubstituted or a substituted $C_{2-4}$ alkynyl or an unsubstituted or a substituted $C_3$-$C_4$ cycloalkyl.

As provided herein, the 2'-position and the 4'-position can be connected via various moieties. In some embodiments, the 2'-position and the 4'-position can be connected via a —(CH$_2$)y-O— moiety, wherein y can be 1 or 2. In some embodiments, $R^{2B}$ and $R^{4B}$ can be connected via —(CH$_2$)—O—. In other embodiments, $R^{2B}$ and $R^{4B}$ are connected via —CH$_2$CH$_2$—O—. In some embodiments, the 2'-position and the 4'-position can be connected via

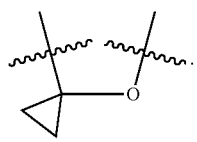 [SMILES: *OC1(*)CC1]

In other embodiments, the 2'-position and the 4'-position can be connected via

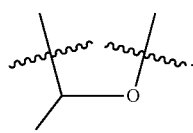 [SMILES: *OC(*)C]

In still other embodiments, the 2'-position and the 4'-position can be connected via

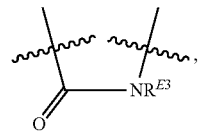

wherein $R^{E3}$ can be hydrogen or an unsubstituted $C_{1-7}$ alkyl, for example,

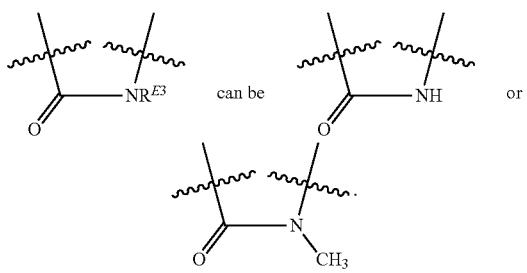

In yet still other embodiments, the 2'-position and the 4'-position can be connected via

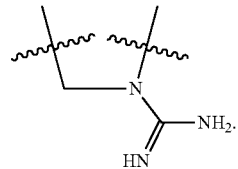 [SMILES: *CN(*)C(=N)N]

In any embodiments of this paragraph, $Z^1$ can be O (oxygen).

The base, $B^1$, can be an optionally substituted, N-linked, 9-membered heteroaryl, such as those described herein. In some embodiments, $B^1$ can be an optionally substituted

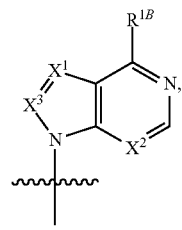

such as an optionally substituted

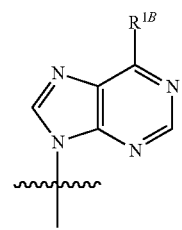

and an optionally substituted

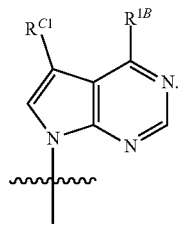

In some embodiments, $X^1$ can be N (nitrogen). In other embodiments, $X^1$ can be $CR^{C1}$. In some embodiments, $X^2$ can be N (nitrogen). In other embodiments, $X^2$ can be $CR^{C2}$. In some embodiments, $X^3$ can be N (nitrogen). In other embodiments, $X^3$ can be $CR^{C3}$. In some embodiments, $X^4$ can be N (nitrogen). In other embodiments, $X^4$ can be $CR^{C4}$. In some embodiments, $R^{C1}$, $R^{C2}$, $R^{C3}$ and/or $R^{C4}$ can be hydrogen. In some embodiments, $R^{C1}$, $R^{C2}$, $R^{C3}$ and/or $R^{C4}$ can be halogen. In some embodiments, $R^{C2}$, $R^{C3}$ and/or $R^{C4}$ can be an unsubstituted $C_{1-4}$ alkyl. In other embodiments, $B^1$ can be

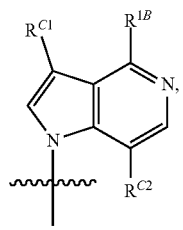

for example, $B^1$ can be

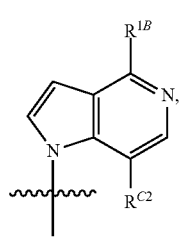

wherein $R^{C2}$ can be halogen (such as F, Cl or Br). In still other embodiments, $B^1$ can be an optionally substituted

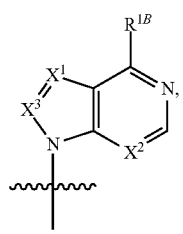

such as

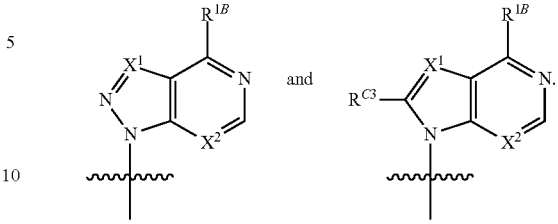

In some embodiments, $R^{1B}$ can be hydrogen, such that $B^1$ can be an optionally substituted

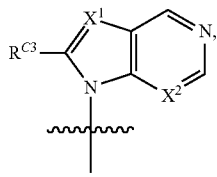

an optionally substituted

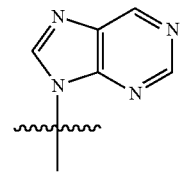

and an optionally substituted

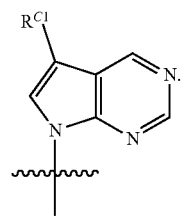

In other embodiments, $R^{1B}$ can be hydroxy or an unsubstituted $C_{1-4}$ alkoxy. In still other embodiments, $R^{1B}$ can be an unsubstituted $C_{1-4}$ alkyl, for example an unsubstituted $C_{1-4}$ alkyl described herein, or an unsubstituted $C_{2-4}$ alkenyl. In yet still other embodiments, $R^{1B}$ can be an unsubstituted $C_3$-$C_6$ cycloalkyl. In some embodiments, $R^{1B}$ can be $NR^{A1}R^{A2}$, such that $B^1$ can be an optionally substituted

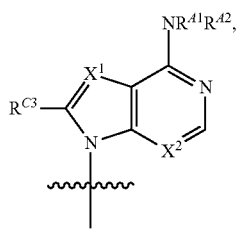

an optionally substituted

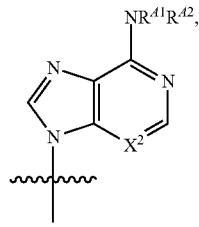

an optionally substituted

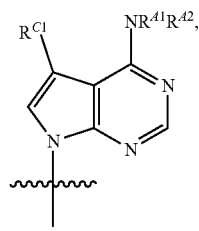

an optionally substituted

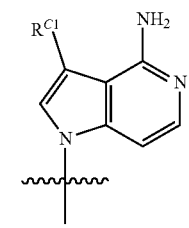

and an optionally substituted

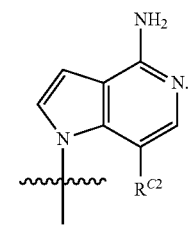

In some embodiments of this paragraph, $R^{C1}$ can be an unsubstituted $C_{1-4}$ alkyl. In other embodiments of this paragraph, $R^{C1}$ can be hydrogen. In still other embodiments of this paragraph, $R^{C1}$ can be halogen, for example, F, Cl or Br. In some embodiments, $B^1$ can be an unsubstituted

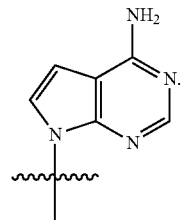 [SMILES: *n1ccc2c(N)ncnc21]

In other embodiments, $B^1$ can be a substituted

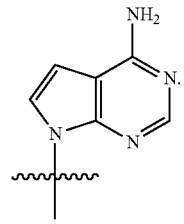 [SMILES: *n1ccc2c(N)ncnc21]

For example,

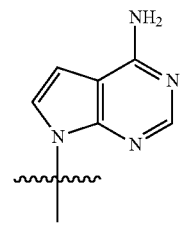

can be substituted with one or more substituents selected from halogen and an unsubstituted $C_{1-4}$ alkyl.

In other embodiments, $B^1$ can be an optionally substituted

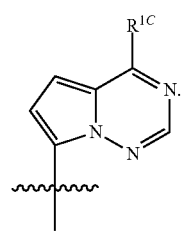

In still other embodiments, $B^1$ can be an optionally substituted

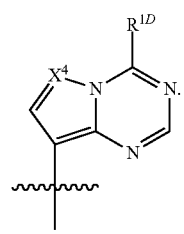

such as an optionally substituted

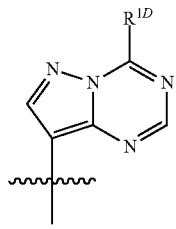

and

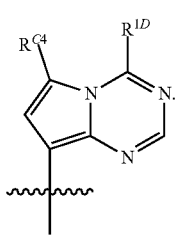

In some embodiments, $R^{C4}$ can be hydrogen. In other embodiments, $R^{C4}$ can be halogen. In still other embodiments, $R^{C4}$ can be an unsubstituted $C_{1-4}$ alkyl. In yet still other embodiments, $B^1$ can be an optionally substituted

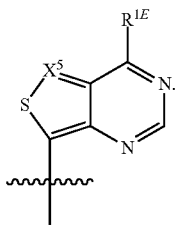

In some embodiments, when $B^1$ is

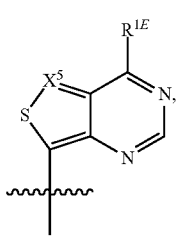

then $X^5$ can be N (nitrogen). In other embodiments, when $B^1$ is

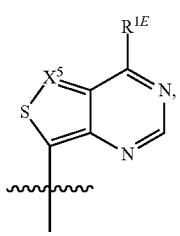

then $X^5$ can be $CR^{C5}$. In some embodiments, $R^{C5}$ can be hydrogen. In other embodiments, $R^{C5}$ can be halogen. In still other embodiments, $R^{C5}$ can be an unsubstituted $C_{1-4}$ alkyl.

In some embodiments, $B^1$ can be an unsubstituted or a substituted

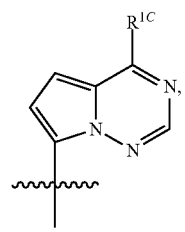

an unsubstituted or a substituted

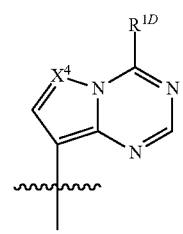

or an unsubstituted or a substituted

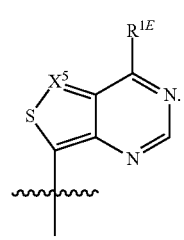

In other embodiments, $B^1$ can be an unsubstituted or a substituted

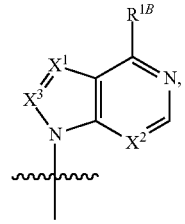

wherein $X^2$ can be $CR^{C2}$. In still other embodiments, $B^1$ can be an unsubstituted or a substituted

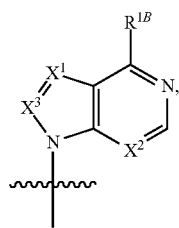

wherein $X^3$ can be N. In yet still other embodiments, $B^1$ can be an unsubstituted or a substituted

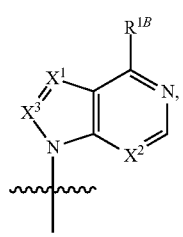

wherein $X^1$ can be $CR^{C1}$; and $R^{C1}$ can be hydroxy, an unsubstituted $C_{2-4}$ alkenyl, an unsubstituted $C_{1-4}$ alkoxy or $NR^{A1}R^{A2}$.

As described herein, $R^{1C}$, $R^{1D}$ and/or $R^{1E}$ can be hydrogen, hydroxy, an unsubstituted $C_{1-4}$ alkyl or $NR^{A1}R^{A2}$. In some embodiments, $R^{1C}$ can be hydrogen. In other embodiments, $R^{1C}$ can be hydroxy. In still other embodiments, $R^{1C}$ can be an unsubstituted $C_{1-4}$ alkyl. In yet still other embodiments, $R^{1C}$ can be an unsubstituted $C_{2-4}$ alkenyl. In some embodiments, $R^{1C}$ can be an unsubstituted $C_{1-4}$ alkoxy. In other embodiments, $R^{1C}$ can be an unsubstituted $C_3$-$C_6$ cycloalkyl. In still other embodiments, $R^{1C}$ can be $NR^{A1}R^{A2}$. In some embodiments, $R^{1D}$ can be hydrogen. In other embodiments, $R^{1D}$ can be hydroxy. In still other embodiments, $R^{1D}$ can be an unsubstituted $C_{1-4}$ alkyl. In yet still other embodiments, $R^{1D}$ can be an unsubstituted $C_{2-4}$ alkenyl. In some embodiments, $R^{1D}$ can be an unsubstituted $C_{1-4}$ alkoxy. In other embodiments, $R^{1D}$ can be an unsubstituted $C_3$-$C_6$ cycloalkyl. In still other embodiments, $R^{1D}$ can be $NR^{A1}R^{A2}$. In some embodiments, $R^{1E}$ can be hydrogen. In other embodiments, $R^{1E}$ can be hydroxy. In still other embodiments, $R^{1E}$ can be an unsubstituted $C_{1-4}$ alkyl. In yet still other embodiments, $R^{1E}$ can be an unsubstituted $C_{2-4}$ alkenyl. In some embodiments, $R^{1E}$ can be an unsubstituted $C_{1-4}$ alkoxy. In other embodiments, $R^{1E}$ can be an unsubstituted $C_3$-$C_6$ cycloalkyl. In still other embodiments, $R^{1E}$ can be $NR^{A1}R^{A2}$.

When $R^{1B}$, $R^{1C}$, $R^{1D}$ and/or $R^{1E}$ are $NR^{A1}R^{A2}$, $R^{A1}$ and $R^{A2}$ can be independently selected from hydrogen, hydroxy, an unsubstituted $C_{1-4}$ alkyl, an unsubstituted $C_{1-4}$ alkoxy and —C(=O)$R^{C6}$, wherein $R^{C6}$ can be hydrogen, an unsubstituted $C_{1-4}$ alkyl or an unsubstituted $C_{3-4}$ monocyclic cycloalkyl. In some embodiments, when $R^{1B}$, $R^{1C}$, $R^{1D}$ and/or $R^{1E}$ is $NR^{A1}R^{A2}$, $R^{A1}$ and $R^{A2}$ can be each hydrogen. For example, $B^1$ can be an optionally substituted

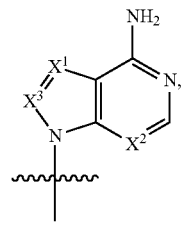

an optionally substituted

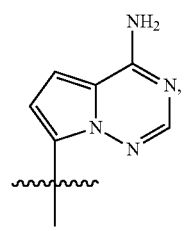

an optionally substituted

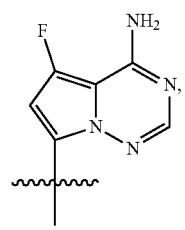

an optionally substituted

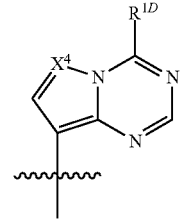

or an optionally substituted

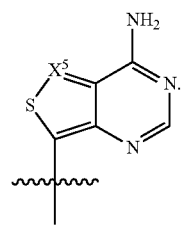

In other embodiments, when $R^{1B}$, $R^{1C}$, $R^{1D}$ and/or $R^{1E}$ is $NR^{A1}R^{A2}$, one of $R^{A1}$ and $R^{A2}$ can be hydrogen, and the other of $R^{A1}$ and $R^{A2}$ can be hydroxy. In still other embodiments, when $R^{1B}$, $R^{1C}$, $R^{1D}$ and/or $R^{1E}$ is $NR^{A1}R^{A2}$, one of $R^{A1}$ and $R^{A2}$ can be hydrogen, and the other of $R^{A1}$ and $R^{A2}$ can be an unsubstituted $C_{1-4}$ alkyl (for example, methyl, ethyl, n-propyl, isopropyl, n-butyl, isobutyl or tert-butyl). In yet still other embodiments, when $R^{1B}$, $R^{1C}$, $R^{1D}$ and/or $R^{1E}$ is $NR^{A1}R^{A2}$, one of $R^{A1}$ and $R^{A2}$ can be hydrogen, and the other of $R^{A1}$ and $R^{A2}$ can be an unsubstituted $C_{1-4}$ alkoxy. In some embodiments, when $R^{1B}$, $R^{1C}$, $R^{1D}$ and/or $R^{1E}$ is $NR^{A1}R^{A2}$, one of $R^{A1}$ and $R^{A2}$ can be hydrogen, and the other of $R^{A1}$ and $R^{A2}$ can be —C(=O)$R^{C6}$, wherein $R^{C6}$ can be hydrogen, an unsubstituted $C_{1-4}$ alkyl or an unsubstituted $C_{3-4}$ monocyclic cycloalkyl. In some embodiments, the $B^1$ groups described herein can be unsubstituted. In some embodiments, the $B^1$ groups described herein can be substituted, for example, substituted one or more times with a variable selected from halogen and an unsubstituted $C_{1-4}$ alkyl.

Provided herein are a variety of $B^1$ groups, including the following:

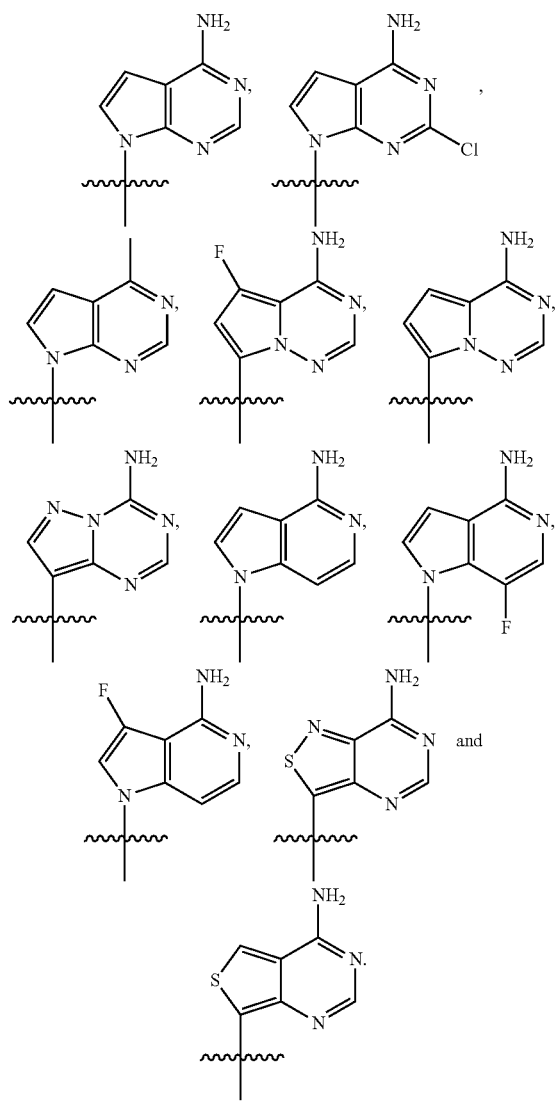

Prodrugs of compounds of Formula (I) can be obtained by substituting $B^1$ with an appropriate group. For example, when $R^{1B}$, $R^{1C}$, $R^{1D}$ and/or $R^{1E}$ is —NH—C(=O)$R^{C6}$, a compound of Formula (I) with the aforementioned group at $R^{1B}$, $R^{1C}$, $R^{1D}$ and/or $R^{1E}$ can be a considered a prodrug of a compound of Formula (I) where $R^{1B}$, $R^{1C}$, $R^{1D}$ and/or $R^{1E}$ is $NH_2$.

The 1'-position of the 5-membered ring of Formula (I) can be unsubstituted or substituted. In some embodiments, $R^1$ can be hydrogen. In other embodiments, $R^1$ can be an unsubstituted $C_{1-4}$ alkyl, such as those described herein.

As provided herein, compounds of Formula (I), or a pharmaceutically acceptable salt thereof, can have various substituents attached to the 5-membered ring of Formula (I). For example, in some embodiments, $R^1$, $R^{2A}$ and $R^{3A}$ can be each hydrogen; $R^{2B}$ and $R^{3B}$ can be each OH; $Z^1$ can be $CH_2$; $R^{4B}$ can be an unsubstituted $C_{1-4}$ alkyl; $B^1$ can be a substituted or an unsubstituted

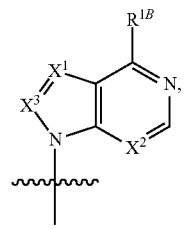

wherein $X^1$ can be N or $CR^{C1}$; $X^2$ can be N or $CR^{C2}$; $X^3$ can be N or $CR^{C3}$; $R^{C1}$, $R^{C2}$ and $R^{C3}$ can be independently hydrogen, halogen or an unsubstituted $C_{1-4}$ alkyl; and $R^{1B}$ can be hydrogen or $NH_2$; and $R^{4A}$—$(CR^{D1}R^{E1})(CR^{D2}R^{E2})$n-$R^{F1}$, wherein $R^{D1}$, $R^{E1}$, $R^{D2}$ and $R^{E2}$ can be independently selected from hydrogen, halogen, hydroxy and an unsubstituted $C_{1-3}$ alkyl; n can be 1; and $R^{F1}$ can be an unsubstituted or a substituted heteroaryl. In other embodiments, $R^1$, $R^{2A}$ and $R^{3A}$ can be each hydrogen; $R^{2B}$ and $R^{3B}$ can be each OH; $Z^1$ can be $CH_2$; $R^{4B}$ can be an unsubstituted $C_{1-4}$ alkyl; $B^1$ can be a substituted or an unsubstituted

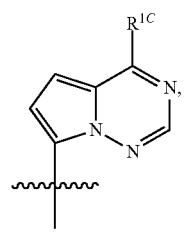

a substituted or an unsubstituted

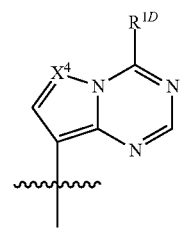

or a substituted or an unsubstituted

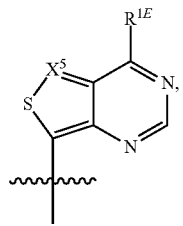

wherein $X^4$ can be N or $CR^{C4}$; $X^5$ can be N or $CR^{C5}$; $R^{C4}$ and $R^{C5}$ can be independently hydrogen, halogen or an unsubstituted $C_{1-4}$ alkyl; and $R^{1C}$, $R^{1D}$ and $R^{1E}$ can be independently hydrogen or $NH_2$; and $R^{4A}$—$(CR^{D1}R^{E1})(CR^{D2}R^{E2})n\text{-}R^{F1}$, wherein $R^{D1}$, $R^{E1}$, $R^{D2}$ and $R^{E2}$ can be independently selected from hydrogen, halogen, hydroxy and an unsubstituted $C_{1-3}$ alkyl; n can be 1; and $R^{F1}$ can be an unsubstituted or a substituted heteroaryl.

In some embodiments, a compound of Formula (I), or a pharmaceutically acceptable salt thereof, can be any one of the following formulae:

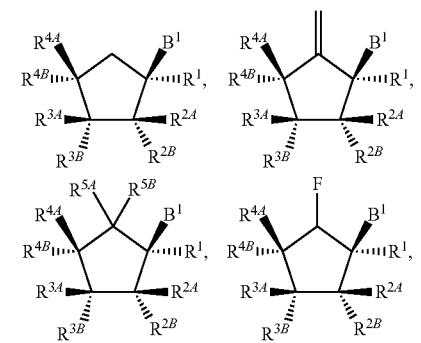

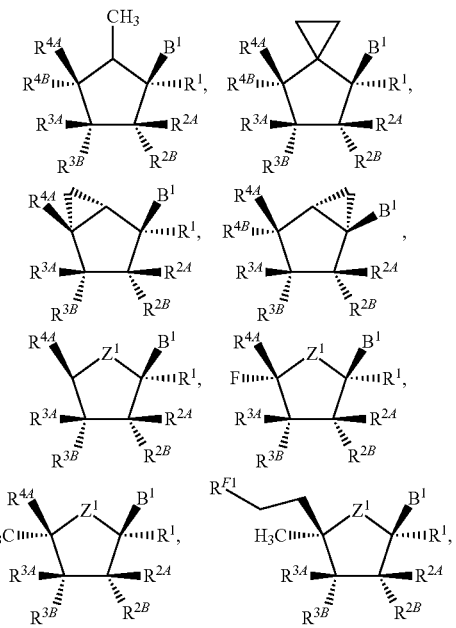

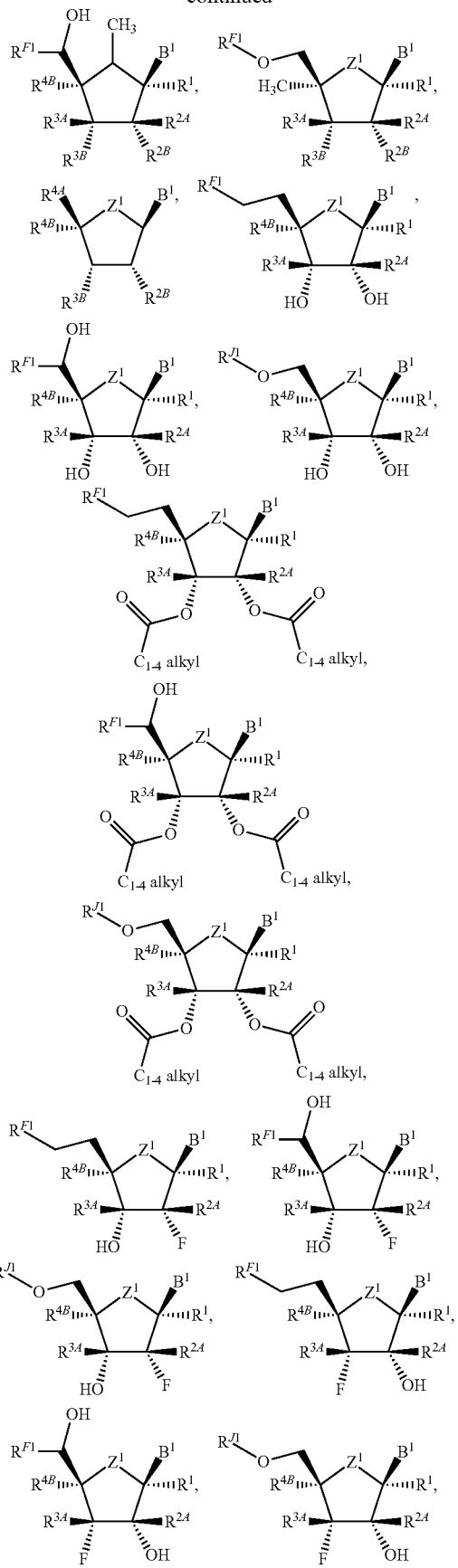

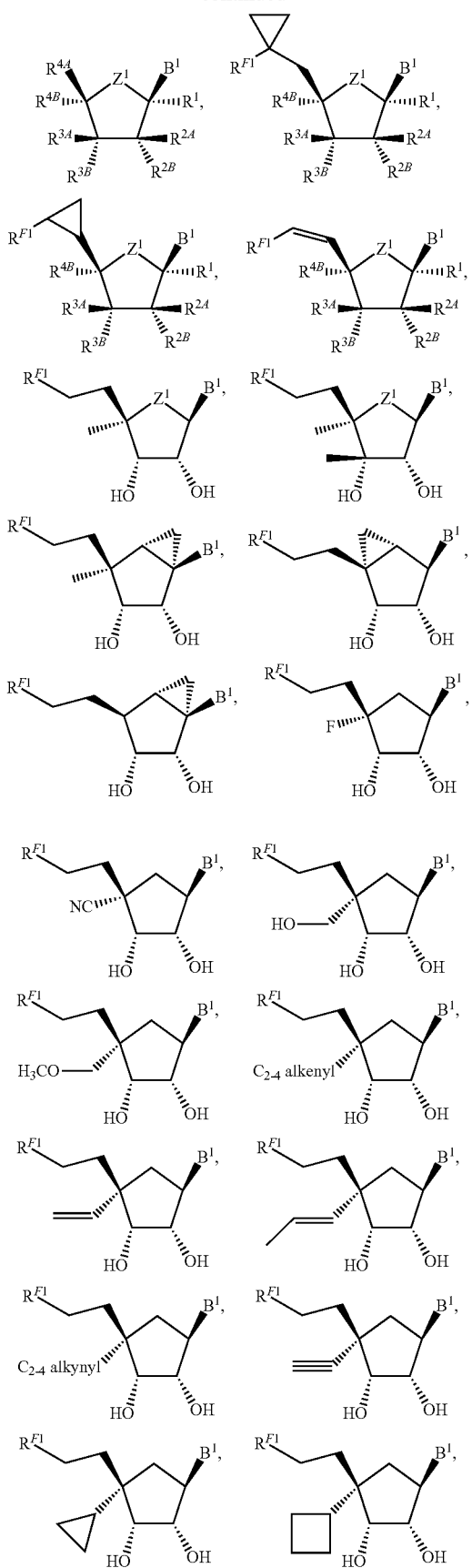
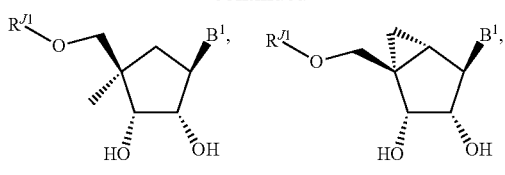
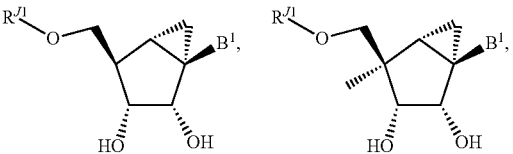
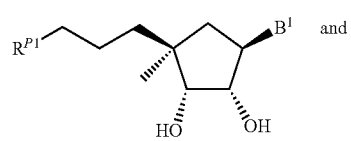
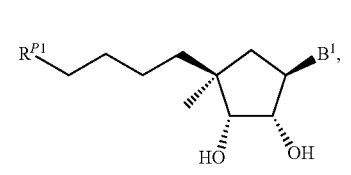

or a pharmaceutically acceptable salt of any of the foregoing. In some embodiments of this paragraph, $R^{4B}$ can be halogen, such as F. In other embodiments of this paragraph, $R^{4B}$ can bean unsubstituted $C_{1-4}$ alkyl, such as those described herein and including methyl. In still other embodiments of this paragraph, $R^{4B}$ can be hydrogen. In some embodiments of this paragraph, $R^{4B}$ and $R^{5B}$ can be together with the carbon $R^{4B}$ and $R^{5B}$ are attached form an unsubstituted cyclopropyl. In some embodiments of this paragraph, $B^1$ can be

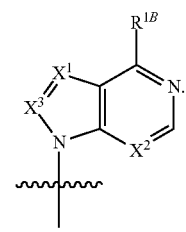

In other embodiments of this paragraph, $B^1$ can be

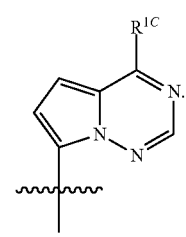

In still other embodiments of this paragraph, B¹ can be

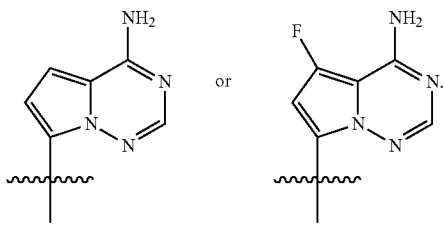 [SMILES: *c1ccc2c(N)ncnn12 ; *c1cc(F)c2c(N)ncnn12]

In yet still other embodiments of this paragraph, B¹ can be

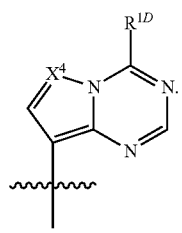

In some embodiments or this paragraph, B¹ can be

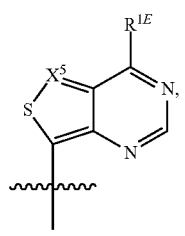

such as

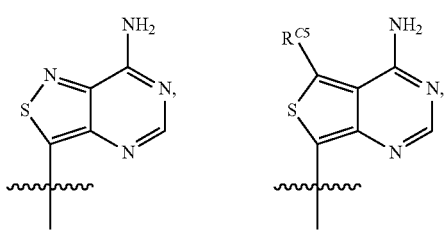

wherein $R^{C5}$ can be halogen or an unsubstituted $C_{1-4}$ alkyl, or

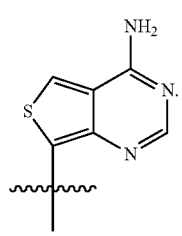 [SMILES: *c1scc2c(N)ncnc12]

In some embodiments of this paragraph, $B^{1B}$ can be

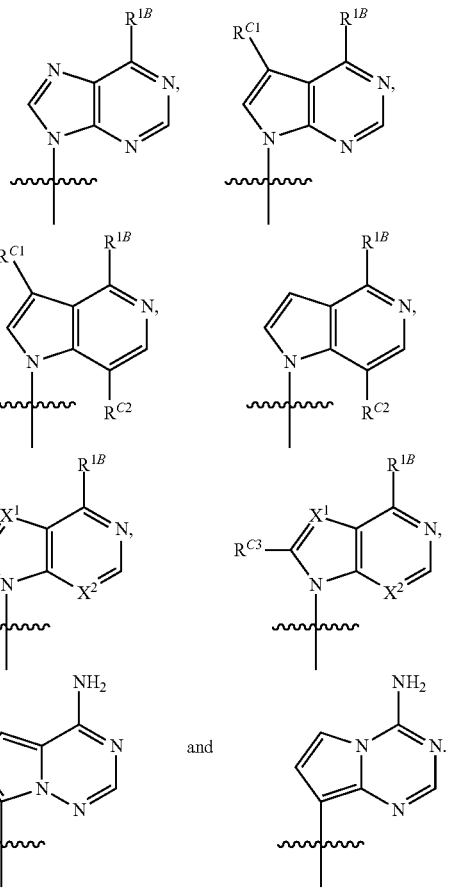

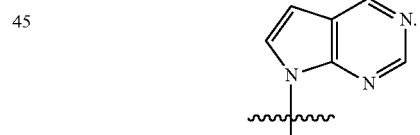

In some embodiments of this paragraph, B¹ can be an unsubstituted

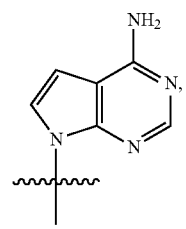

In other embodiments of this paragraph, B¹ can be a substituted

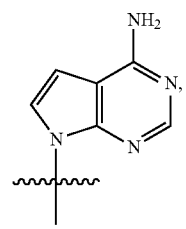

such as those described herein. In some embodiments of this paragraph, B¹ can be an unsubstituted

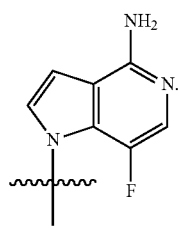 [SMILES: *n1ccc2c(N)ncc(F)c21]

In some embodiments of this paragraph, $R^{4A}$ can be —$(CR^{D1}R^{E1})(CR^{D2}R^{E2})_n$—$R^{F1}$, for example, —$CH_2$—$R^{F1}$, —$CF_2$—$R^{F1}$ and —$CH(OH)$—$R^{F1}$. In some embodiments of this paragraph, $R^{4A}$ can be —$(CR^{G1}R^{H1})$—O—$R^{J1}$, such as —$CH_2$—O—$R^{J1}$. In some embodiments of this paragraph, $R^{4A}$ can be —O—$(CR^{K1}R^{L1})$—$R^{M1}$, such as —O—$CH_2$—$R^{M1}$. In some embodiments of this paragraph, $R^{4A}$ can be —$(CR^{N1}R^{O1})$p-$R^{P1}$. In some embodiments of this paragraph, $R^1$ can be hydrogen. In some embodiments of this paragraph, $R^{2A}$ can be hydrogen. In some embodiments of this paragraph, $R^{3A}$ can be hydrogen. In other embodiments of this paragraph, $R^{3A}$ can be an unsubstituted $C_{1-4}$ alkyl. In some embodiments of this paragraph, $R^{F1}$, $R^{J1}$ and/or $R^{M1}$ can be an unsubstituted or a substituted heteroaryl. In some embodiments of this paragraph, $R^{F1}$, $R^{J1}$ and/or $R^{M1}$ can be a substituted heteroaryl. In some embodiments of this paragraph, $R^{F1}$, $R^{J1}$ and/or $R^{M1}$ can be an unsubstituted or a substituted heterocyclyl. In some embodiments of this paragraph, $R^{F1}$, $R^{J1}$ and/or $R^{M1}$ can be a substituted heterocyclyl. In some embodiments of this paragraph, $R^{F1}$, $R^{J1}$ and/or $R^{M1}$ can be selected from

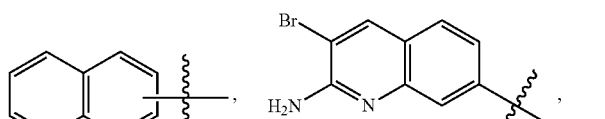

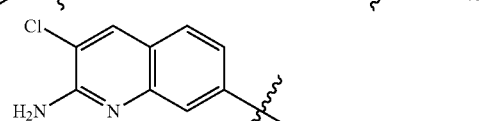

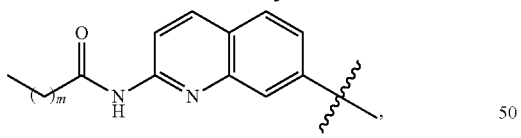

m = 1, 2, 3, 4, 5 or 6


m = 1, 2, 3, 4, 5 or 6 m = 1, 2, 3, 4, 5 or 6

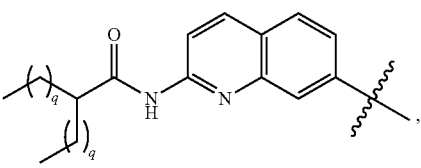

each q = 1, 2, or 3

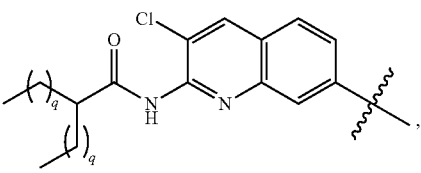

each q = 1, 2, or 3

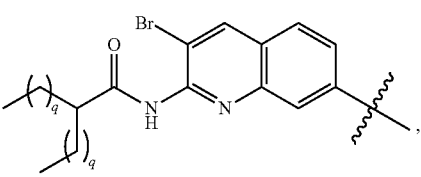

each q = 1, 2, or 3

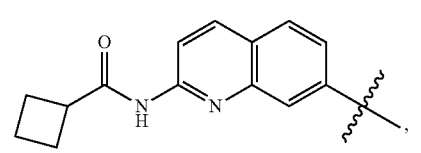

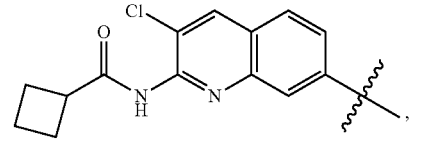

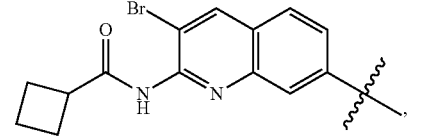

n = 1, 2, 3, 4, 5 or 6

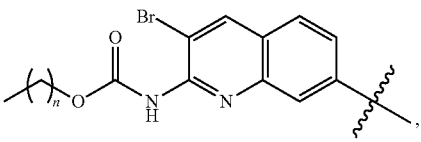

n = 1, 2, 3, 4, 5 or 6

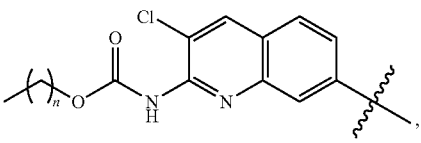

n = 1, 2, 3, 4, 5 or 6

-continued
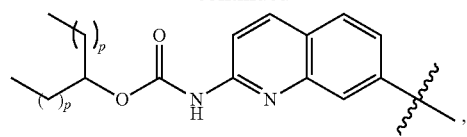
each p = 1, 2, or 3
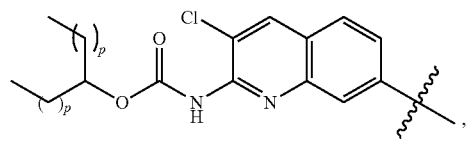
each p = 1, 2, or 3
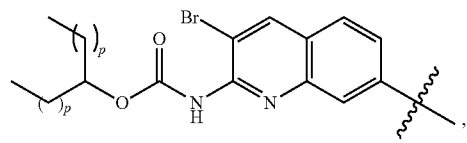
each p = 1, 2, or 3
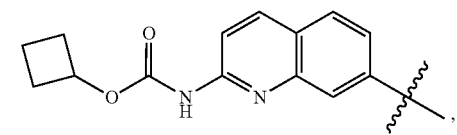
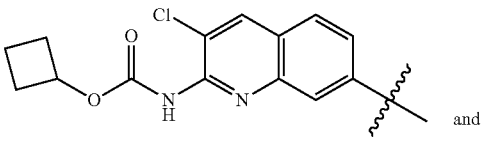
and
In some embodiments, a compound of Formula (I) can have one of the following structures:
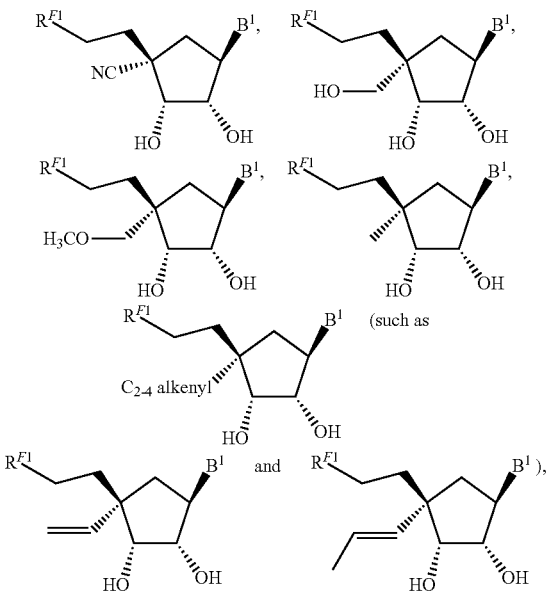
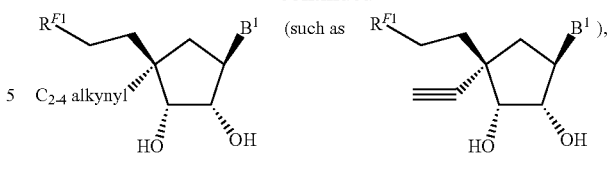
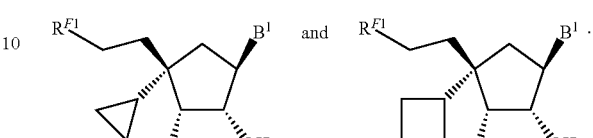
In some embodiments of this paragraph, $B^1$ can be
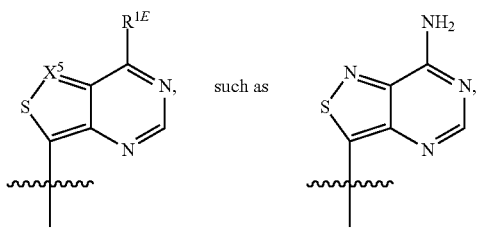
wherein $R^{C5}$ can be halogen or an unsubstituted $C_{1-4}$ alkyl, or
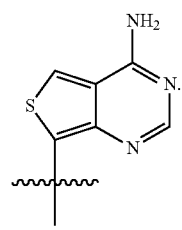 [SMILES: *c1scc2c(N)ncnc12]
In some embodiments of this paragraph, $B^1$ can be
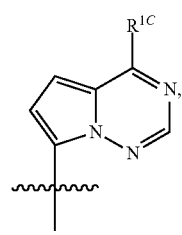

for example,

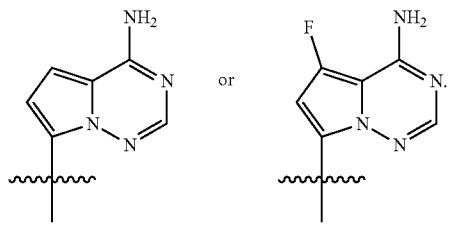 [SMILES: *c1ccc2c(N)ncnn12 ; "or" ; *c1cc(F)c2c(N)ncnn12]

In some embodiments of this paragraph, $B^1$ can be

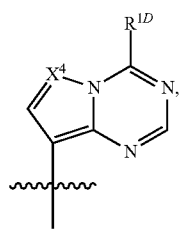

including

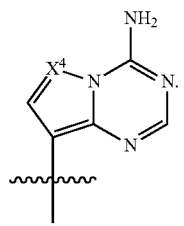

In some embodiments of this paragraph, $B^1$ can be

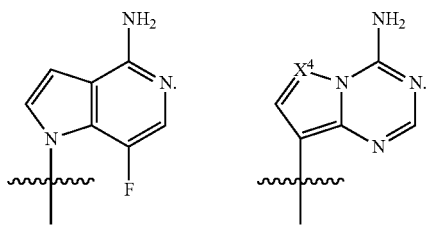

In some embodiments of this paragraph, $B^1$ can be an unsubstituted or a substituted

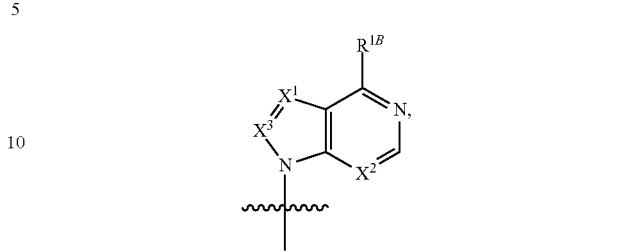

wherein $X^2$ can be $CR^{C2}$; an unsubstituted or a substituted

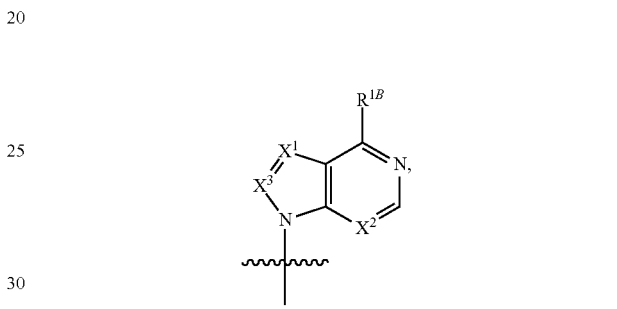

wherein $X^3$ can be N; or an unsubstituted or a substituted

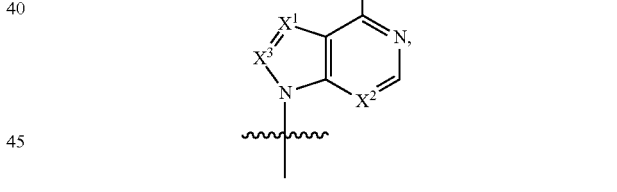

wherein $X^1$ can be $CR^{C1}$, and $R^{C1}$ can be hydroxy, an unsubstituted $C_{2-4}$ alkenyl, an unsubstituted $C_{1-4}$ alkoxy or $NR^{A1}R^{A2}$.

Examples of compounds of Formula (I), or a pharmaceutically acceptable salt thereof, include the following:

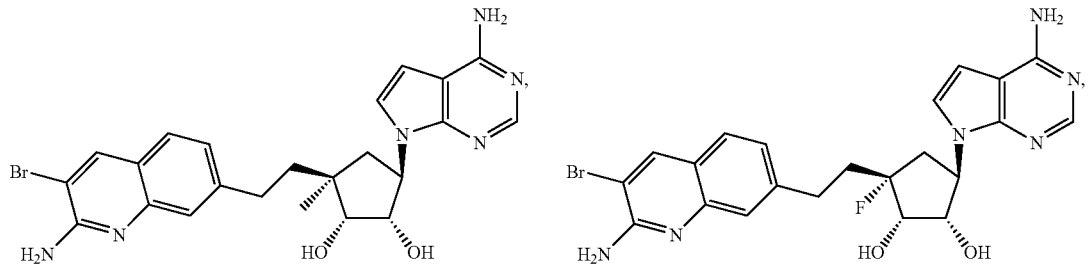

-continued
| 55 | 56 |
|---|---|
| 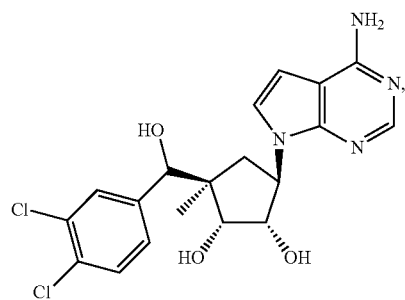 | 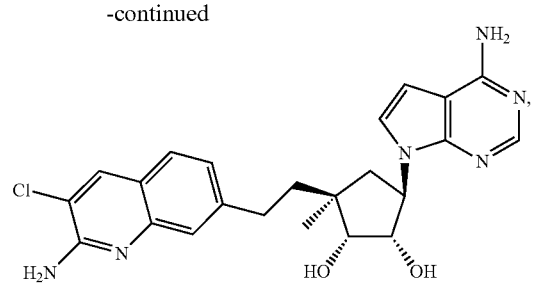 |inued
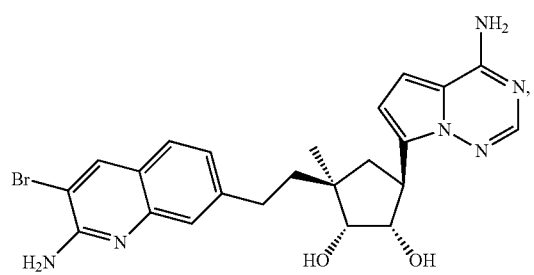 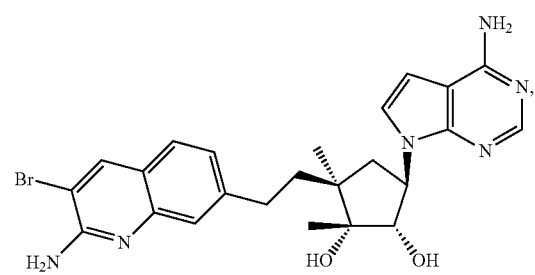
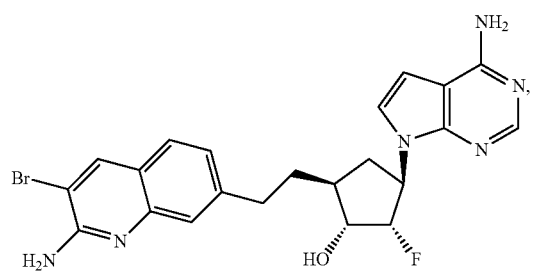 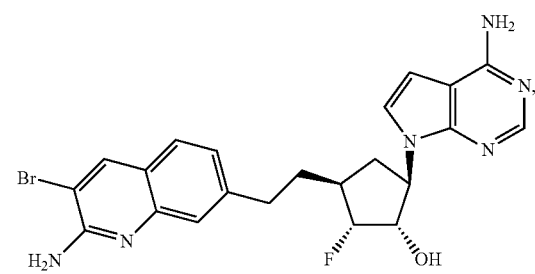
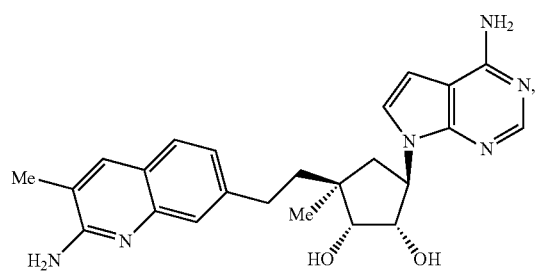 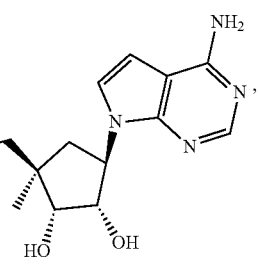
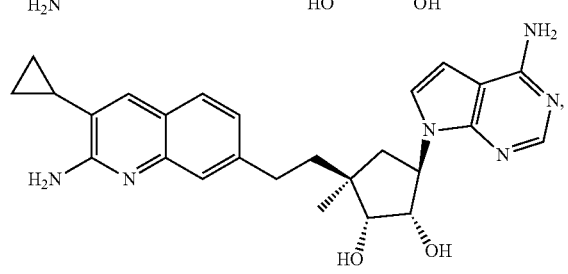
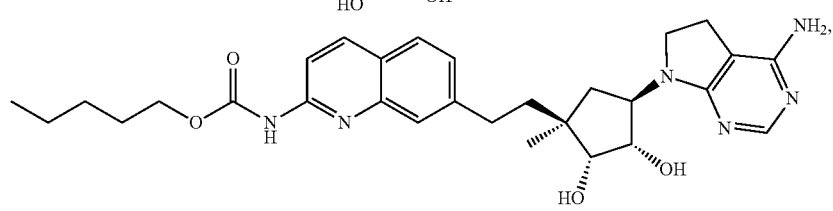

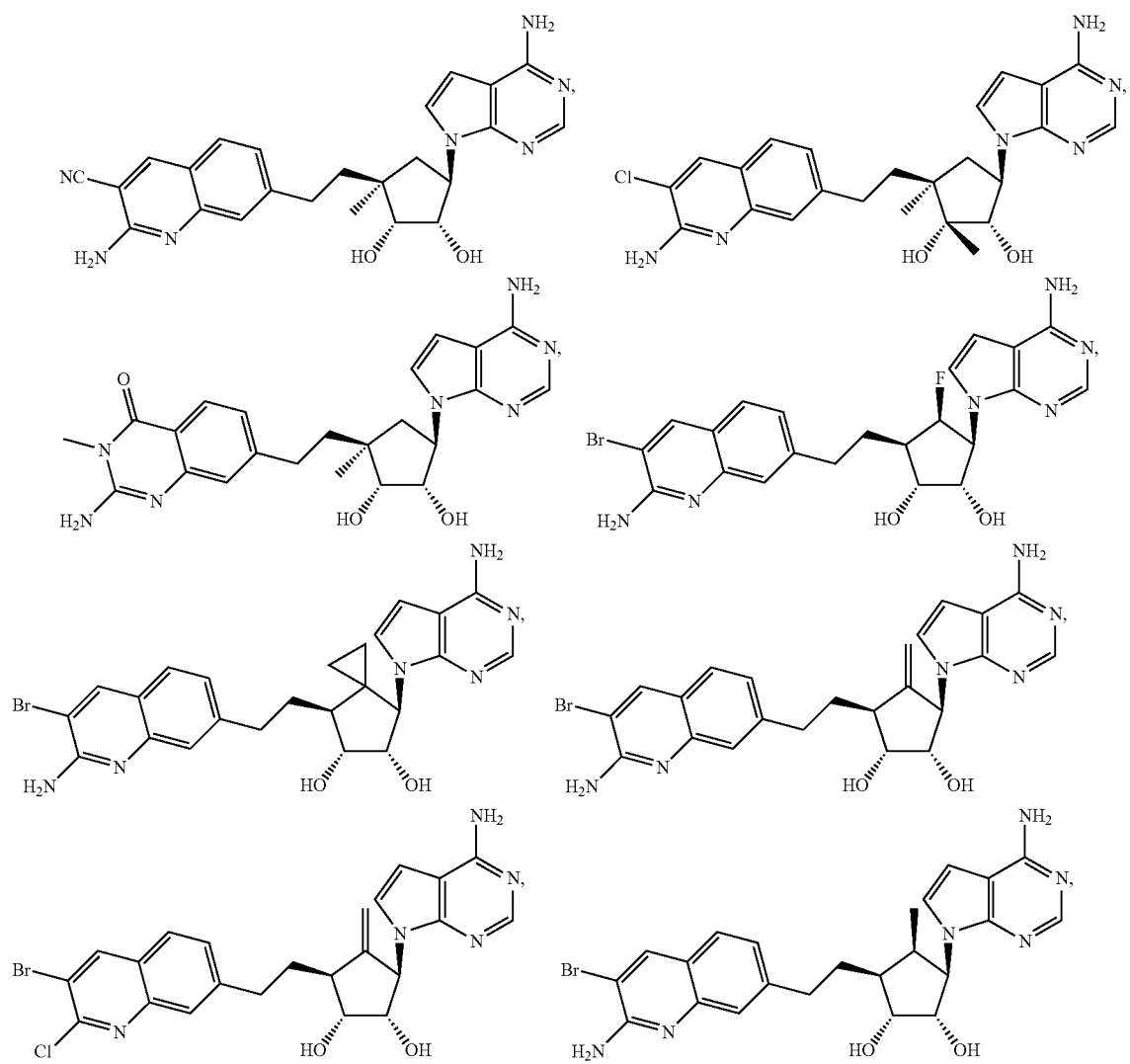

-continued
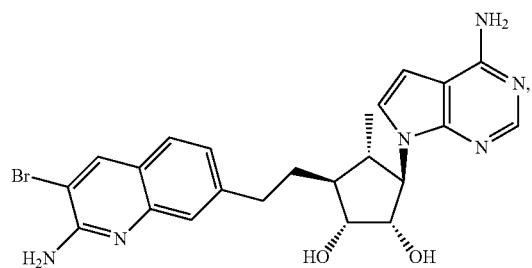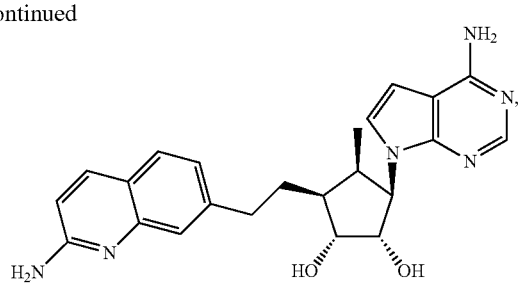
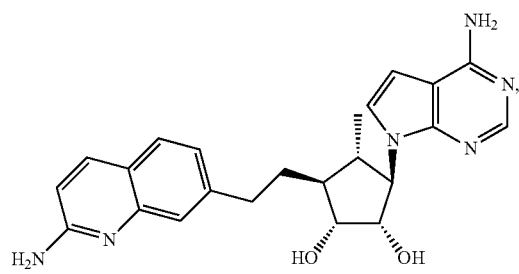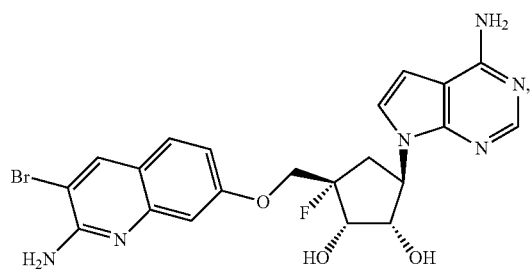
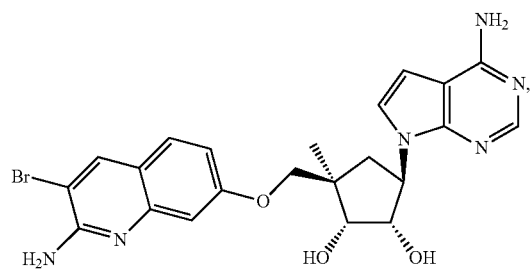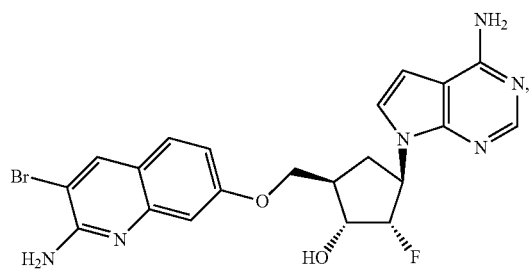
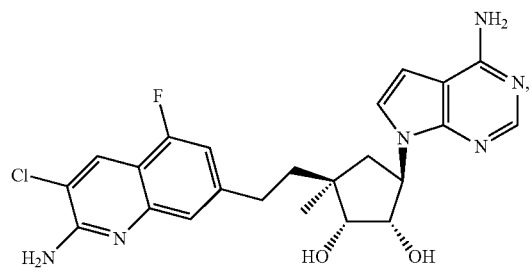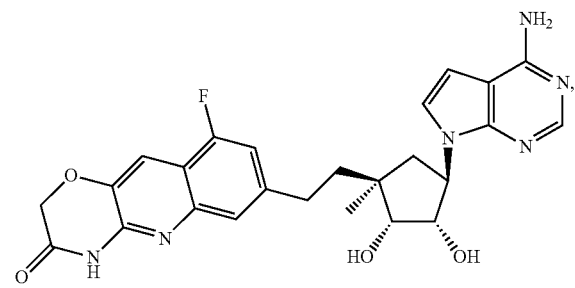
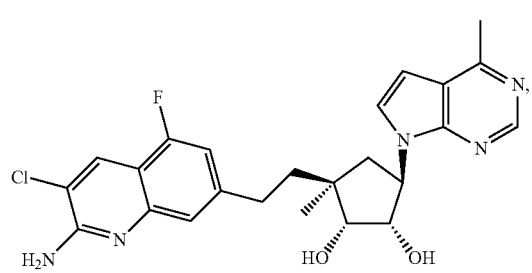
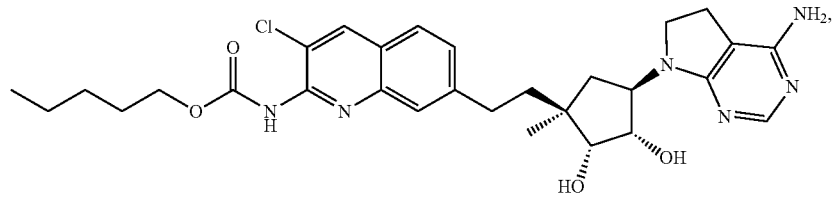

-continued
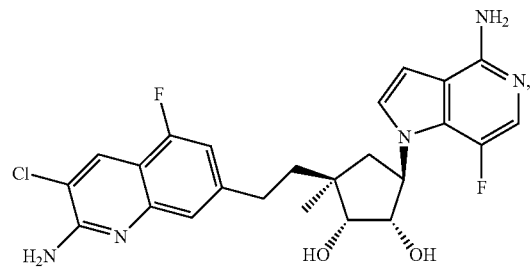
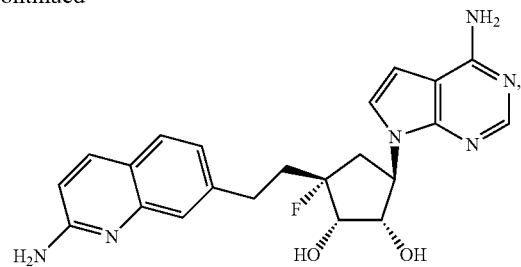
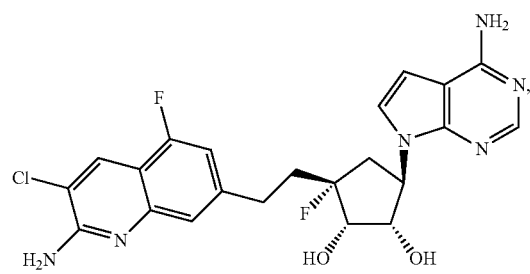
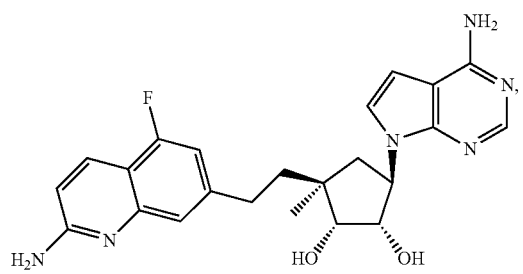
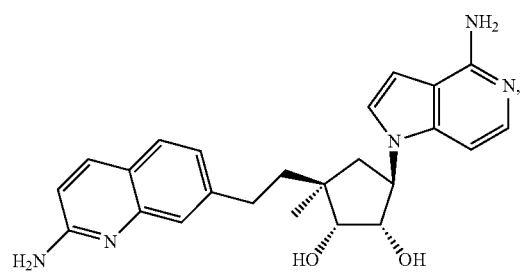
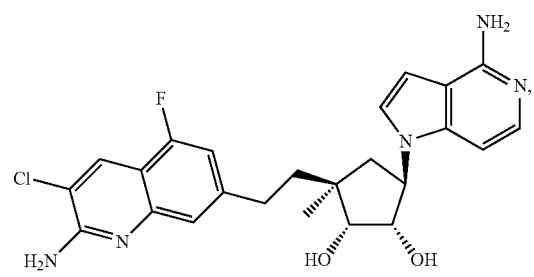
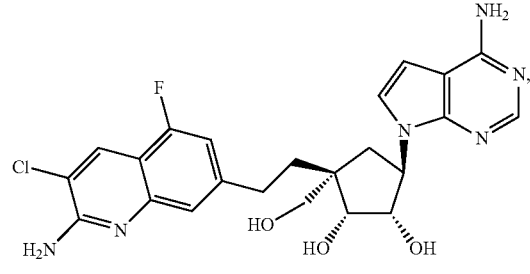
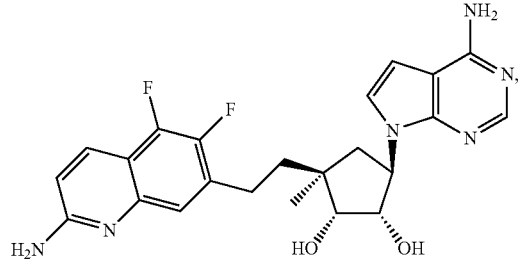
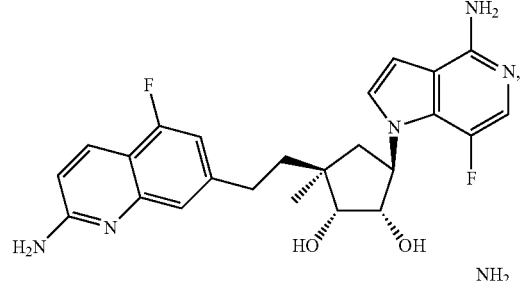
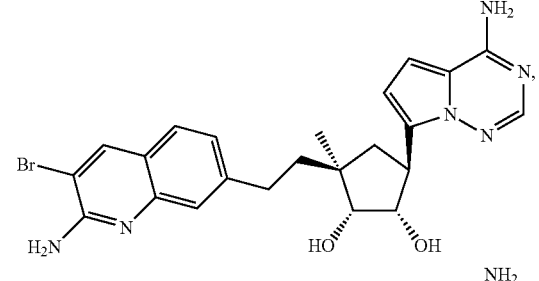
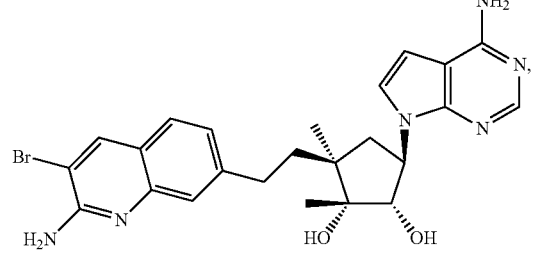
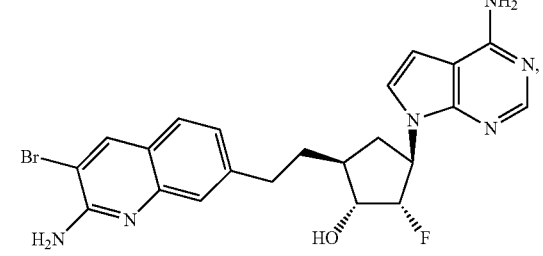

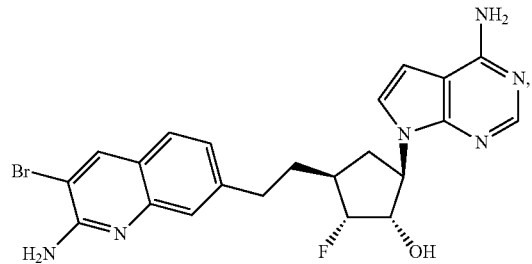
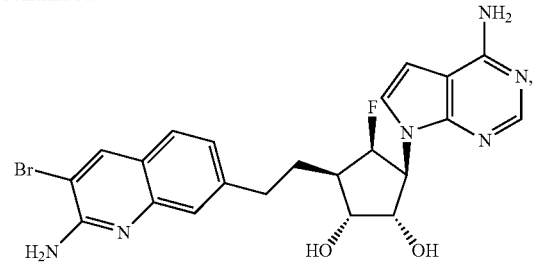
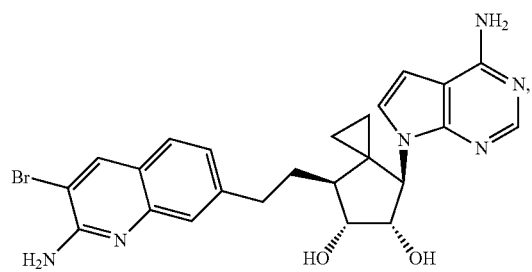
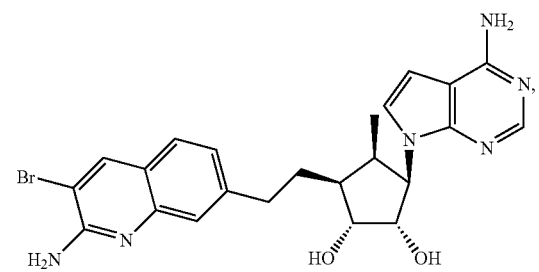
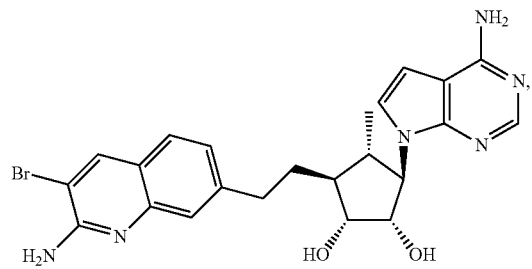
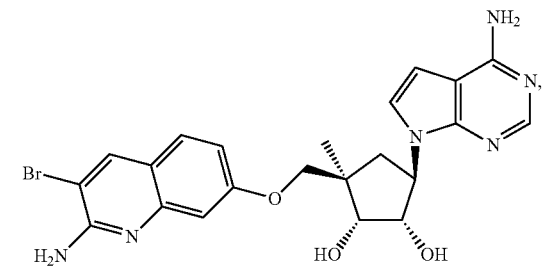
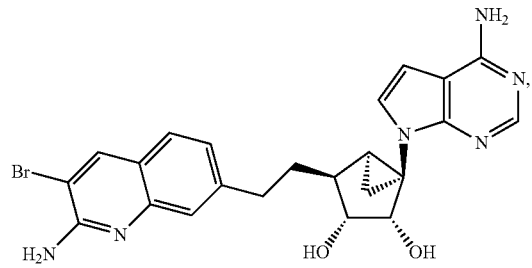
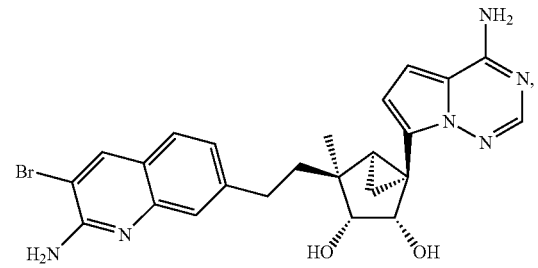
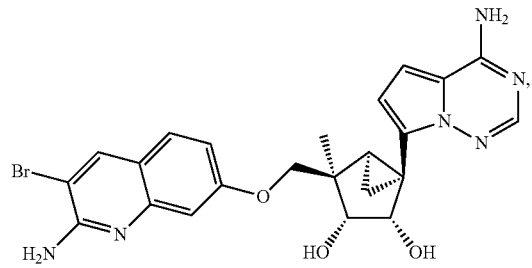
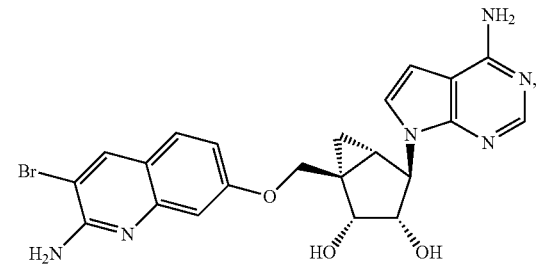
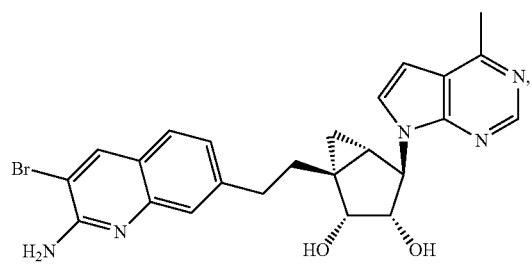
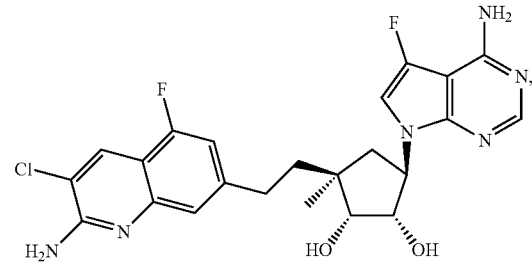

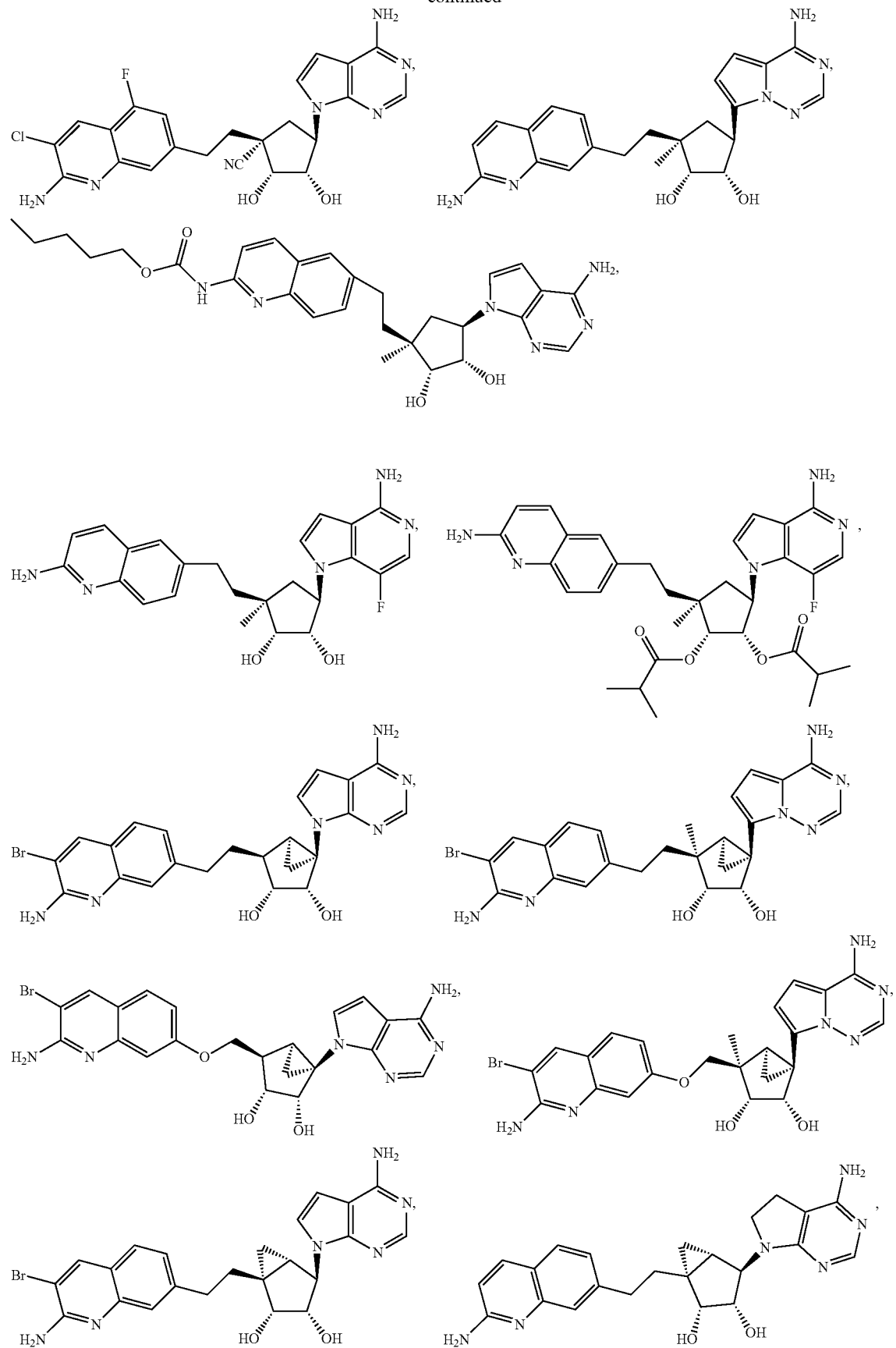

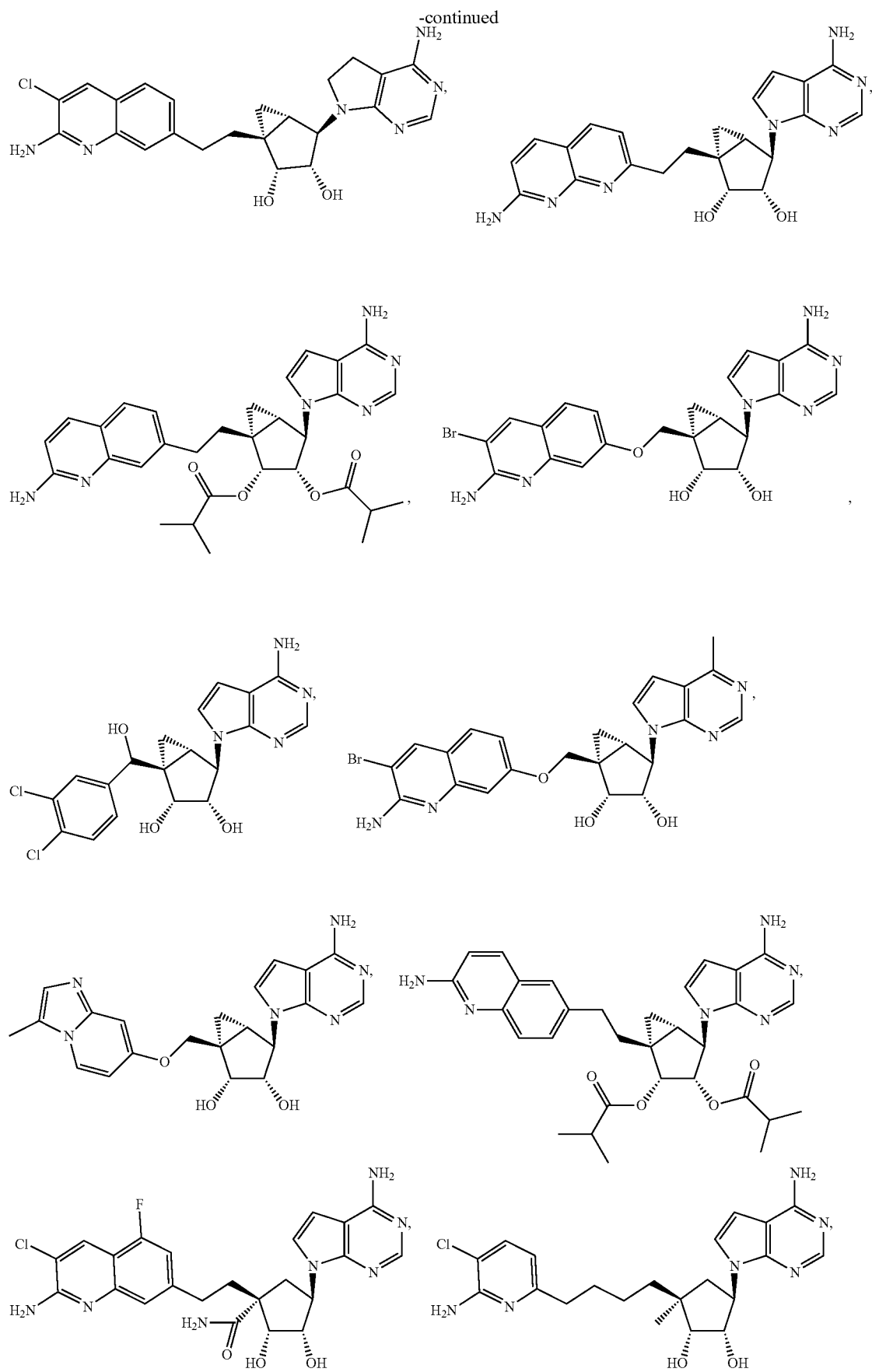

-continued
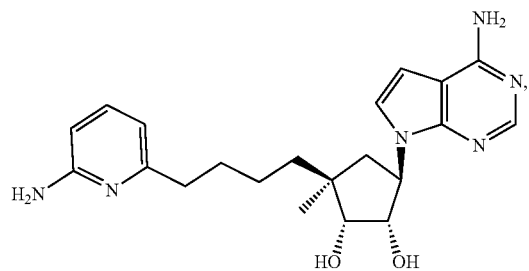
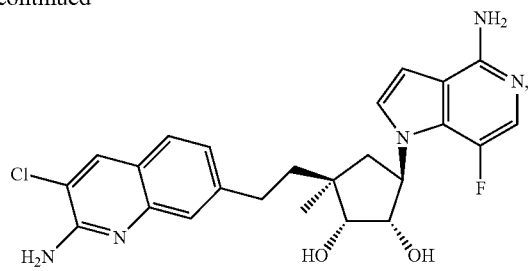
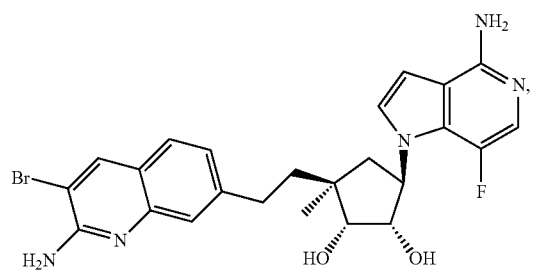
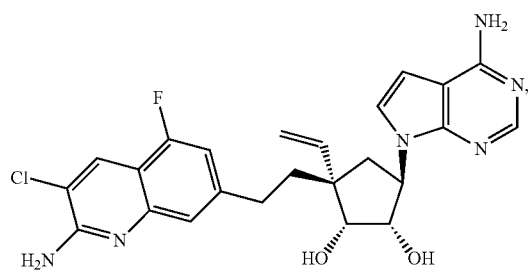
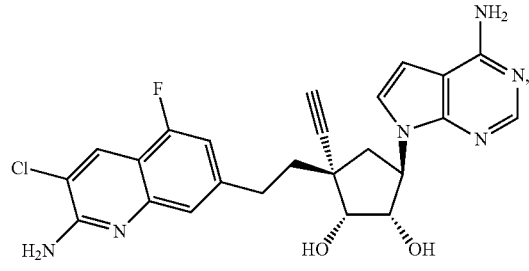
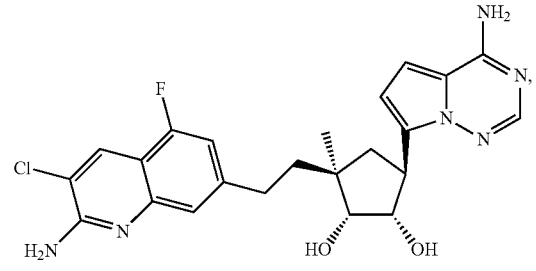
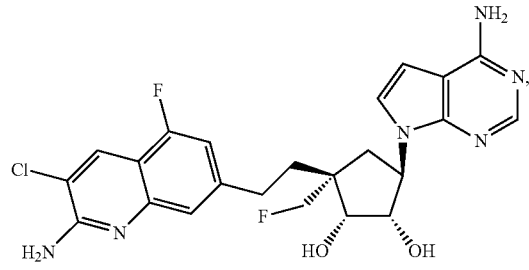
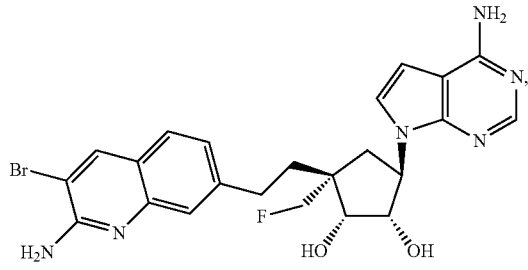
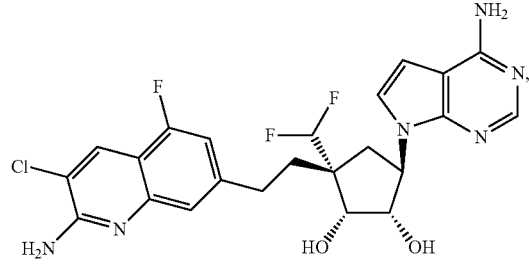
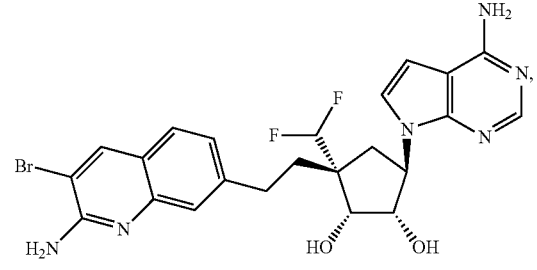
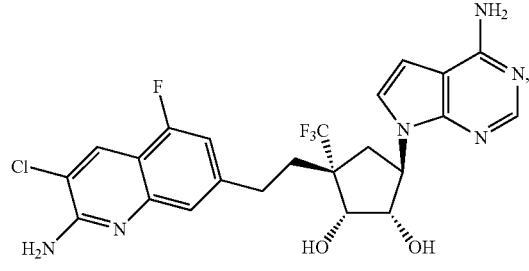
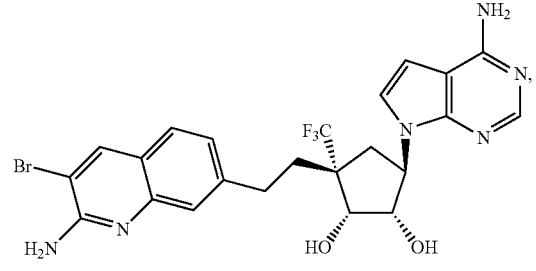

71 72
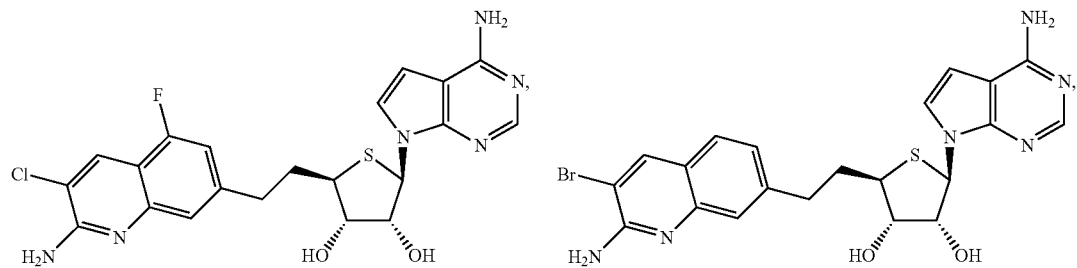
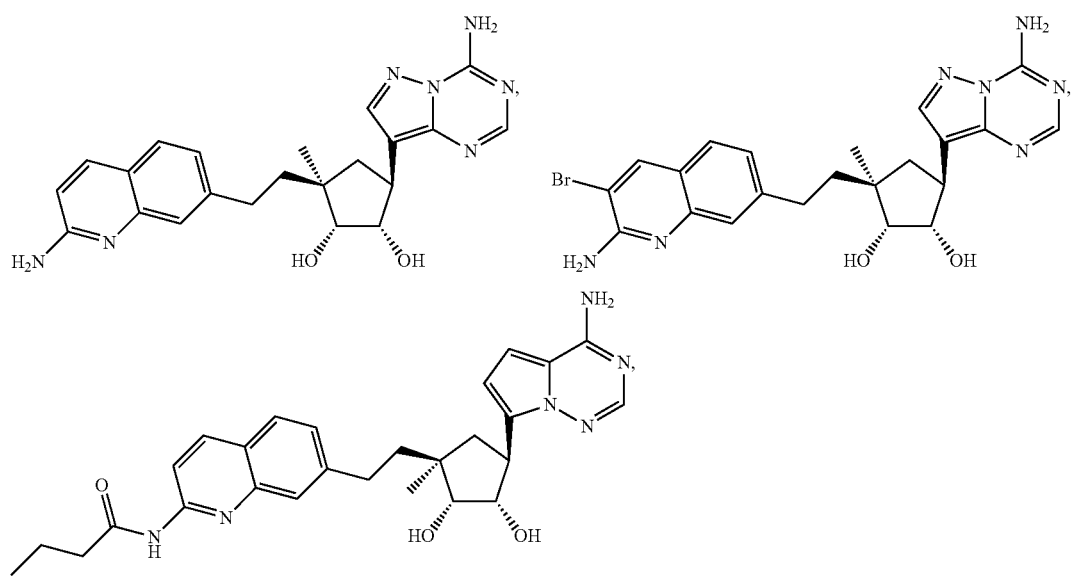
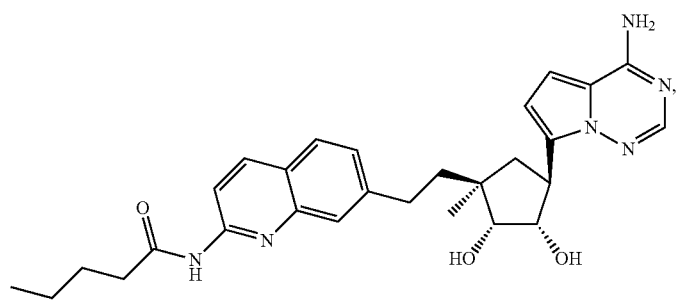
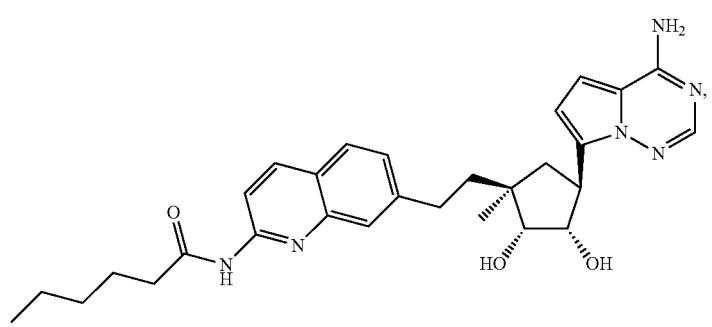

-continued
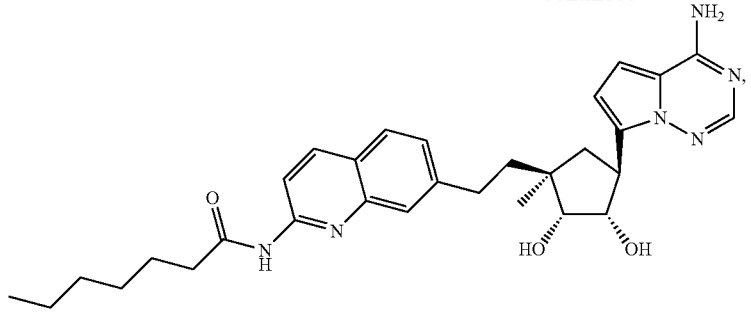
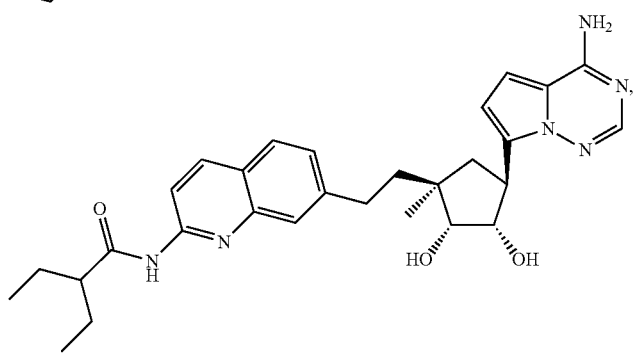
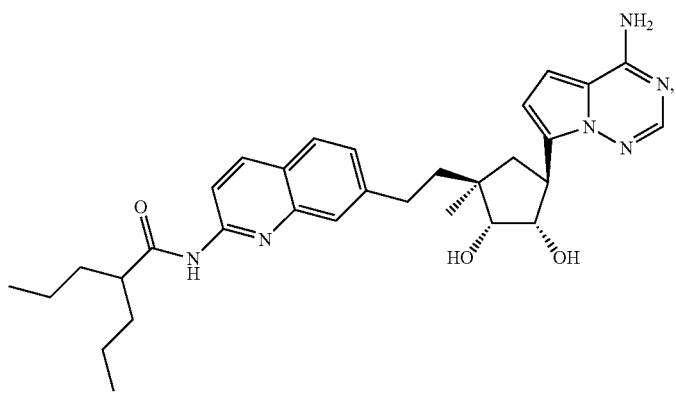
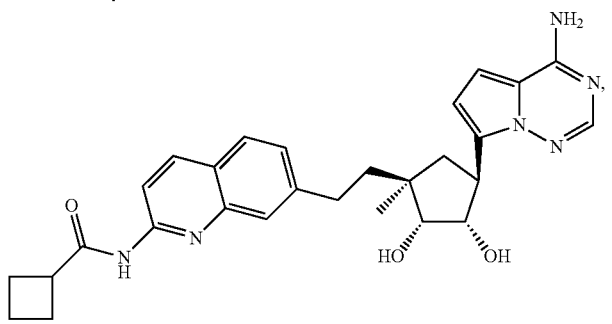
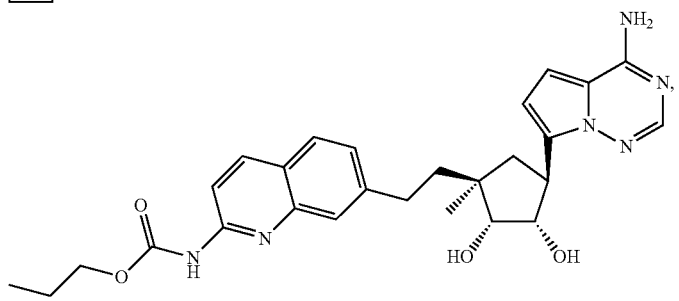

-continued
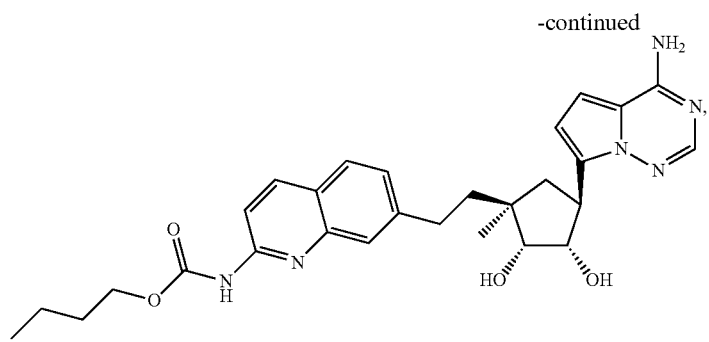
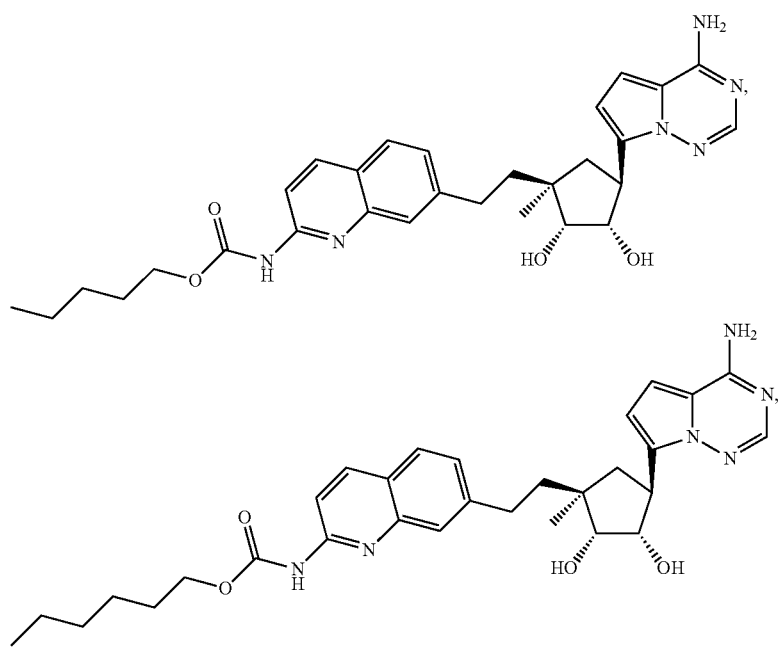
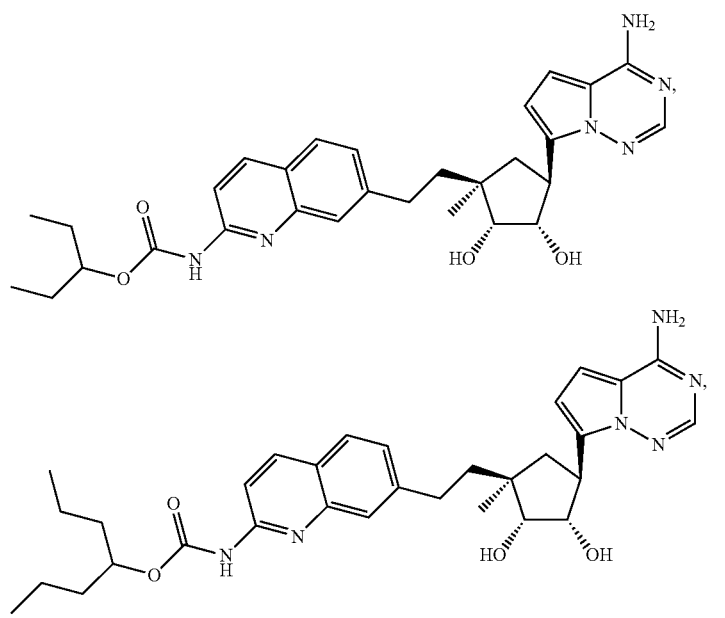

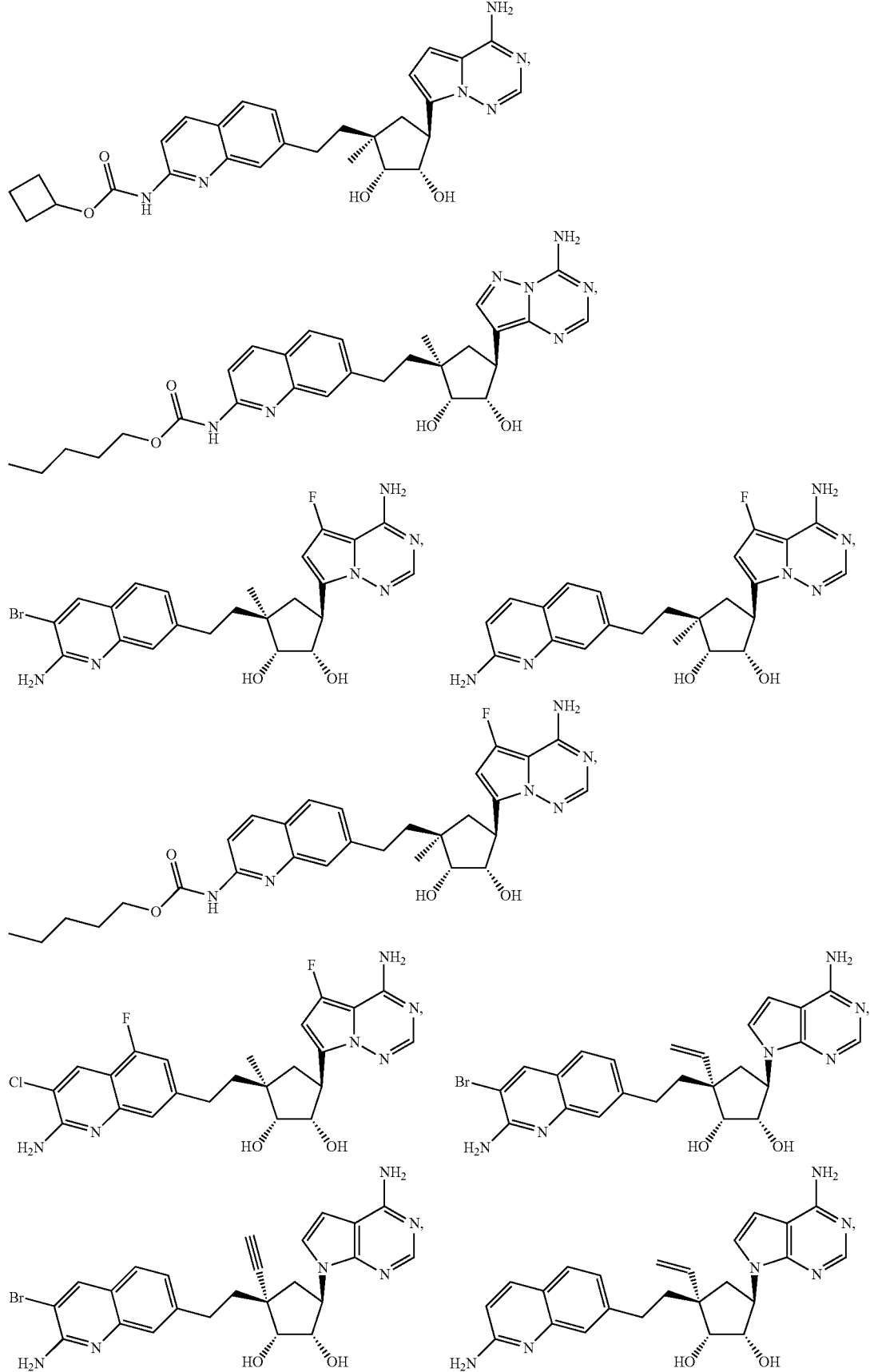

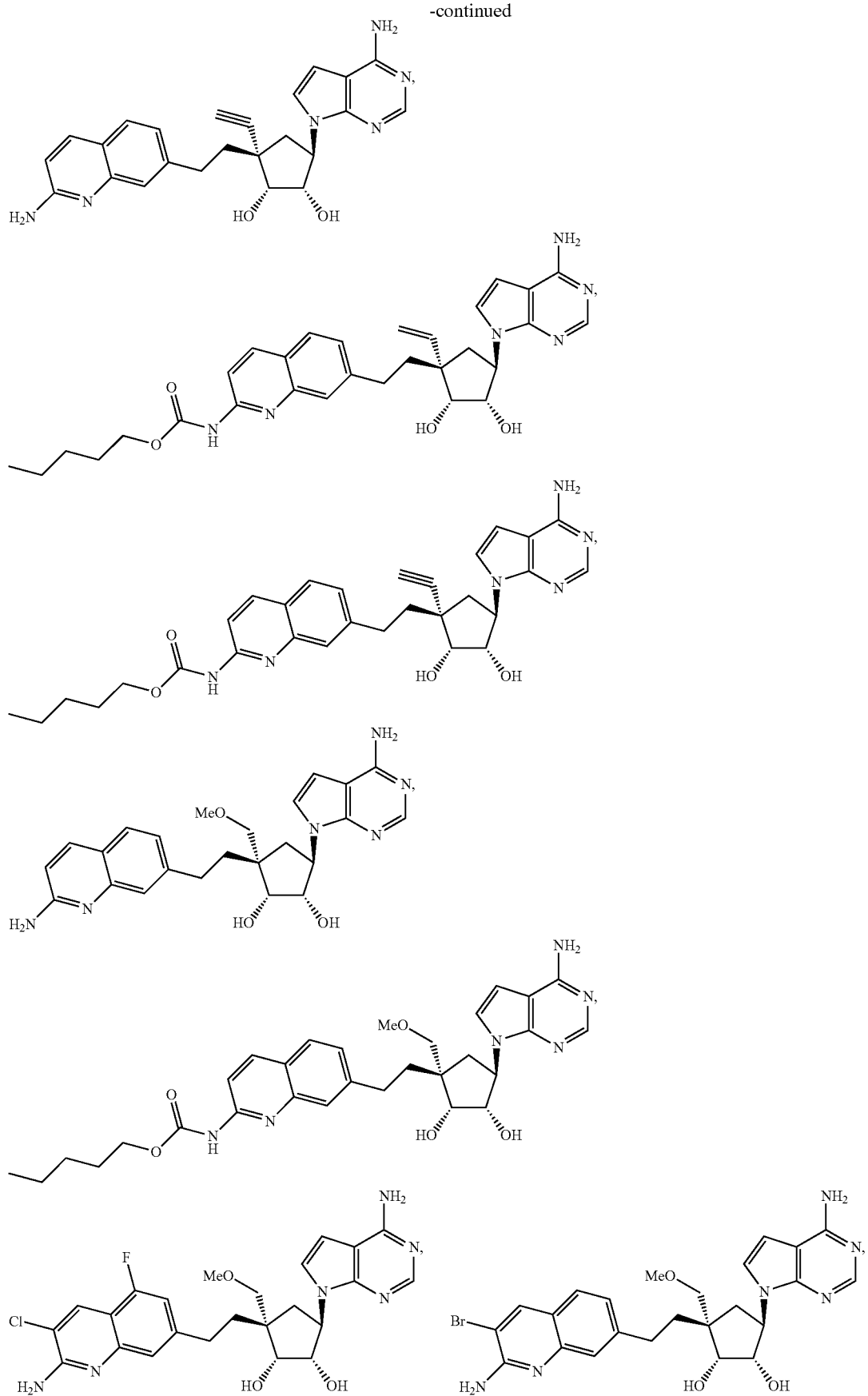

-continued
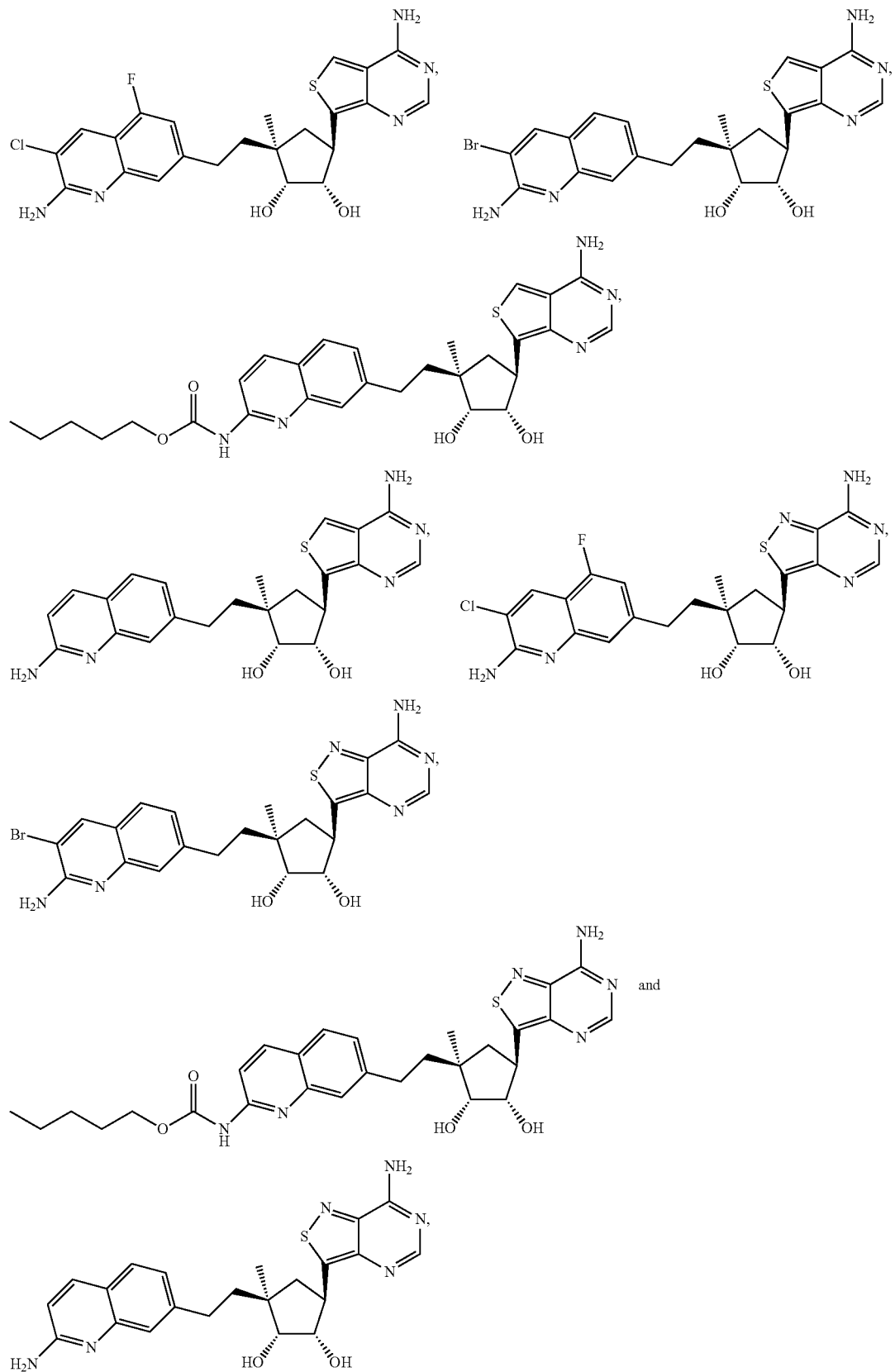

or a pharmaceutically acceptable salt of any of the foregoing.

In some embodiments, $R^{F1}$ cannot be an optionally substituted imidazo[1,2-a]pyridine, an optionally substituted 1H-benzo[d]imidazole, an optionally substituted benzo[d]thiazole, an optionally substituted 1H-pyrrolo[3,2-b]pyridine, an optionally substituted thieno[3,2-b]pyridine, an optionally substituted furo[3,2-b]pyridine, an optionally substituted 1H-pyrrolo[2,3-b]pyridine, an optionally substituted 1H-pyrazole, an optionally substituted pyrimidine, an optionally substituted 1,8a-dihydroimidazo[1,2-a]pyridin-2(3H)-one, an optionally substituted 3,4-dihydro-2H-pyrido[3,2-b][1,4]oxazine, an optionally substituted 2,3-dihydro-1H-pyrrolo[2,3-b]pyridine, an optionally substituted 1H-imidazole and/or an optionally substituted 1H-pyrrolo[2,3-c]pyridine. In some embodiments, when $R^1$, $R^{2A}$, $R^{3A}$, $R^{4B}$, $R^{5A}$ and $R^{5B}$ are each H; $R^{2B}$ and $R^{3B}$ are each OH; and $R^{4A}$ is —CH$_2$—$R^{F1}$ or —(CH$_2$)$_2$—$R^{F1}$, then $R^{F1}$ cannot be an optionally substituted imidazo[1,2-a]pyridine, an optionally substituted 1H-benzo[d]imidazole, an optionally substituted benzo[d]thiazole, an optionally substituted 1H-pyrrolo[3,2-b]pyridine, an optionally substituted thieno[3,2-b]pyridine, an optionally substituted furo[3,2-b]pyridine, an optionally substituted 1H-pyrrolo[2,3-b]pyridine, an optionally substituted 1H-pyrazole, an optionally substituted pyrimidine, an optionally substituted 1,8a-dihydroimidazo[1,2-a]pyridin-2(3H)-one, an optionally substituted 3,4-dihydro-2H-pyrido[3,2-b][1,4]oxazine, an optionally substituted 2,3-dihydro-1H-pyrrolo[2,3-b]pyridine, an optionally substituted 1H-imidazole and/or an optionally substituted 1H-pyrrolo[2,3-c]pyridine. In some embodiments, when $R^1$, $R^{2A}$, $R^{3A}$, $R^{4B}$, $R^{5A}$ and $R^{5B}$ are each H; $R^{2B}$ and $R^{3B}$ are each OH; and $R^{4A}$ is —CH$_2$—O—$R^{J1}$, then $R^{J1}$ cannot be an optionally substituted imidazo[1,2-a]pyridine, an optionally substituted 1H-benzo[d]imidazole, an optionally substituted benzo[d]thiazole, an optionally substituted 1H-pyrrolo[3,2-b]pyridine, an optionally substituted thieno[3,2-b]pyridine, an optionally substituted furo[3,2-b]pyridine, an optionally substituted 1H-pyrrolo[2,3-b]pyridine, an optionally substituted 1H-pyrazole, an optionally substituted pyrimidine, an optionally substituted 1,8a-dihydroimidazo[1,2-a]pyridin-2(3H)-one, an optionally substituted 3,4-dihydro-2H-pyrido[3,2-b][1,4]oxazine, an optionally substituted 2,3-dihydro-1H-pyrrolo[2,3-b]pyridine, an optionally substituted 1H-imidazole and/or an optionally substituted 1H-pyrrolo[2,3-c]pyridine. In some embodiments, when $B^1$ is

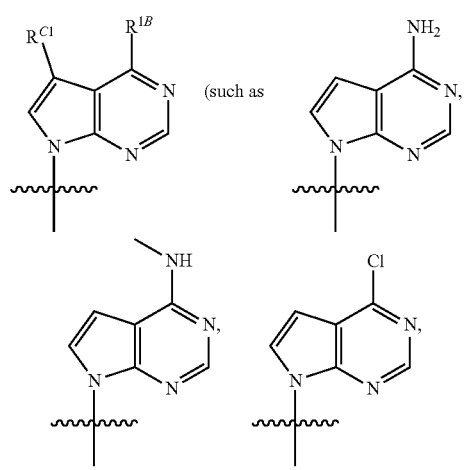

(such as

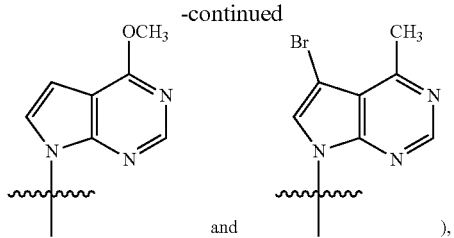

and ), then $R^{F1}$ cannot be an optionally substituted imidazo[1,2-a]pyridine, an optionally substituted 1H-benzo[d]imidazole, an optionally substituted benzo[d]thiazole, an optionally substituted 1H-pyrrolo[3,2-b]pyridine, an optionally substituted thieno[3,2-b]pyridine, an optionally substituted furo[3,2-b]pyridine, an optionally substituted 1H-pyrrolo[2,3-b]pyridine, an optionally substituted 1H-pyrazole, an optionally substituted pyrimidine, an optionally substituted 1,8a-dihydroimidazo[1,2-a]pyridin-2(3H)-one, an optionally substituted 3,4-dihydro-2H-pyrido[3,2-b][1,4]oxazine, an optionally substituted 2,3-dihydro-1H-pyrrolo[2,3-b]pyridine, an optionally substituted 1H-imidazole and/or an optionally substituted 1H-pyrrolo[2,3-c]pyridine. In some embodiments, when $R^1$, $R^{2A}$, $R^{3A}$, $R^{4B}$, $R^{5A}$ and $R^{5B}$ are each H; $R^{2B}$ and $R^{3B}$ are each OH; $R^{4A}$ is —CH$_2$—$R^{F1}$, —(CH$_2$)$_2$—$R^{F1}$ or —CH$_2$-Q-$R^{J1}$; and $B^1$ is

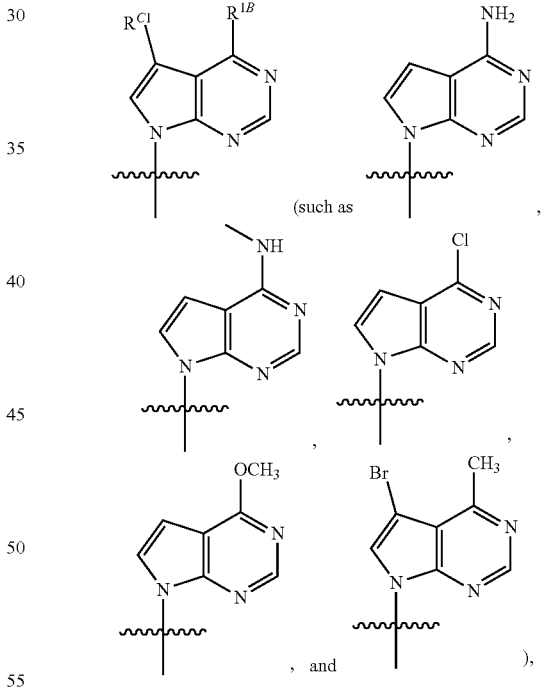

, and ), then $R^{F1}$ and/or $R^{J1}$ cannot be an optionally substituted imidazo[1,2-a]pyridine, an optionally substituted 1H-benzo[d]imidazole, an optionally substituted benzo[d]thiazole, an optionally substituted 1H-pyrrolo[3,2-b]pyridine, an optionally substituted thieno[3,2-b]pyridine, an optionally substituted furo[3,2-b]pyridine, an optionally substituted 1H-pyrrolo[2,3-b]pyridine, an optionally substituted 1H-pyrazole, an optionally substituted pyrimidine, an optionally substituted 1,8a-dihydroimidazo[1,2-a]pyridin-2(3H)-one, an optionally substituted 3,4-dihydro-2H-pyrido[3,2-b][1,4]oxazine, an optionally substituted 2,3-dihydro-1H-pyrrolo

[2,3-b]pyridine, an optionally substituted 1H-imidazole and/or an optionally substituted 1H-pyrrolo[2,3-c]pyridine.

In some embodiments, $R^{F1}$ cannot be an optionally substituted quinoline. In some embodiments, $R^{F1}$ cannot be an optionally substituted quinazoline. In some embodiments, $R^{F1}$ cannot be an optionally substituted quinoxaline. In some embodiments, when $R^1$, $R^{2A}$, $R^{3A}$, $R^{4B}$, $R^{5A}$ and $R^{5B}$ are each H; $R^{2B}$ and $R^{3B}$ are each OH; and $R^{4A}$ is —(CH$_2$)$_2$—$R^{F1}$, then $R^{F1}$ cannot be an optionally substituted quinolone, an optionally substituted quinazoline and/or an optionally substituted quinoxaline. In some embodiments, when $B^1$ is

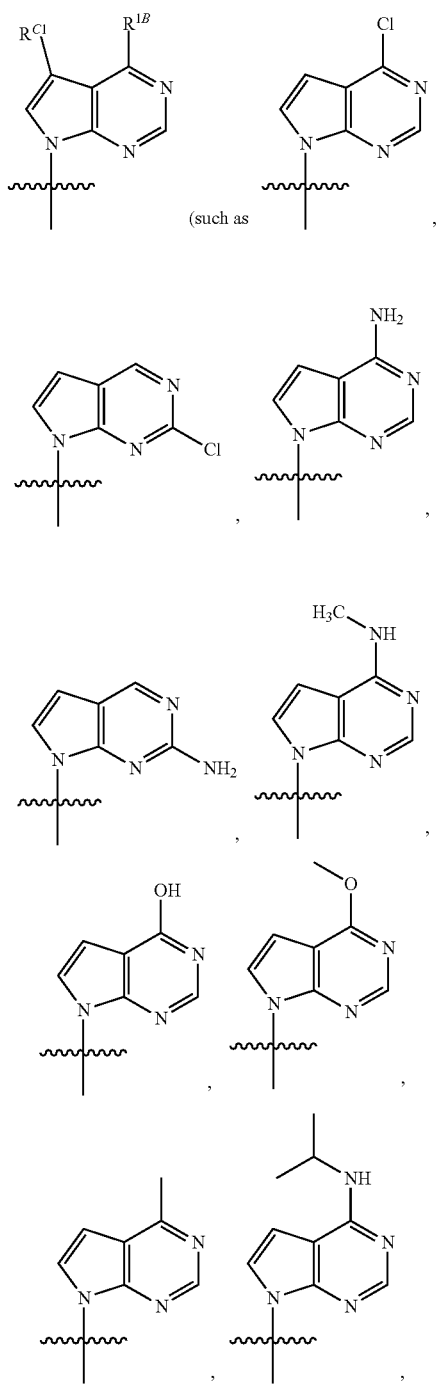

(such as

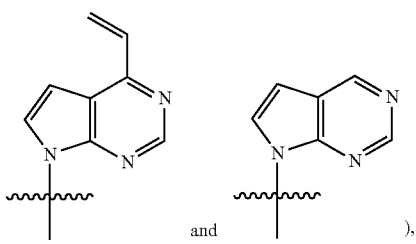

then $R^{F1}$ cannot be an optionally substituted quinolone, an optionally substituted quinazoline and/or an optionally substituted quinoxaline. In some embodiments, when $R^1$, $R^{2A}$, $R^{3A}$, $R^{4B}$, $R^{5A}$ and $R^{5B}$ are each H; $R^{2B}$ and $R^{3B}$ are each OH; $R^{4A}$ is —(CH$_2$)$_2$—$R^{F1}$; and $B^1$ is

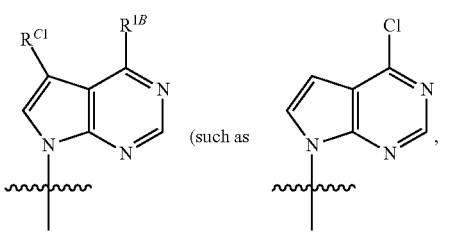

(such as

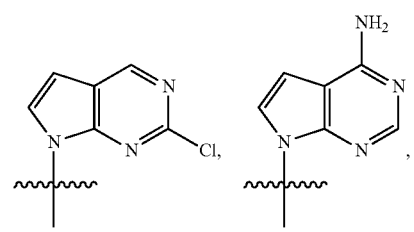

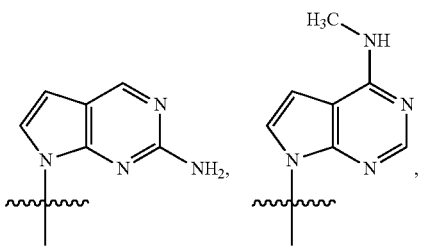

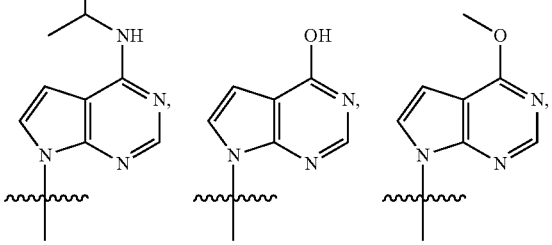

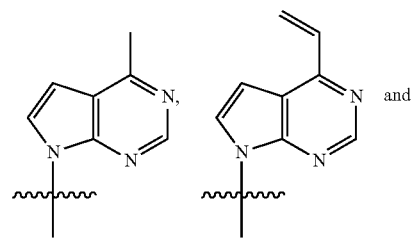

and

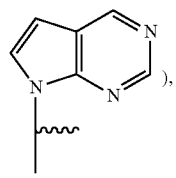

then $R^{F1}$ cannot be an optionally substituted quinoline, an optionally substituted quinazoline and/or an optionally substituted quinoxaline. In some embodiments, when $R^1$, $R^{2A}$, $R^{3A}$, $R^{4A}$, $R^{5A}$ and $R^{5B}$ are each H; $R^{2B}$ and $R^{3B}$ are each OH; $R^{4A}$ is —(CH$_2$)$_2$—$R^{F1}$; and $B^1$ is

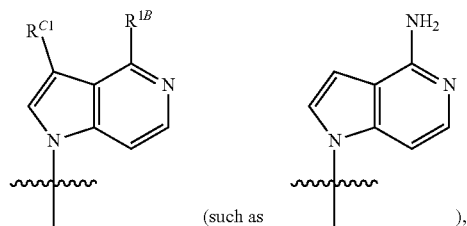

(such as  ), then $R^{F1}$ cannot be an optionally substituted quinolone, an optionally substituted quinazoline and/or an optionally substituted quinoxaline. In some embodiments, when $R^1$, $R^{2A}$, $R^{3A}$, $R^{4B}$, $R^{5A}$ and $R^{5B}$ are each H; $R^{2B}$ and $R^{3B}$ are each OH; $R^{4A}$ is —O—(CH$_2$)—$R^{M1}$; and $B^1$ is

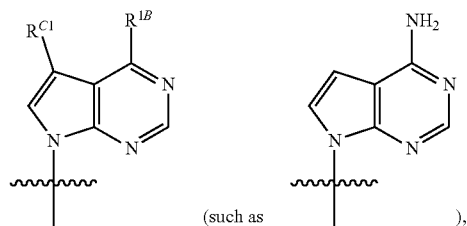

(such as  ), then $R^{M1}$ cannot be an optionally substituted quinolone, an optionally substituted quinazoline and/or an optionally substituted quinoxaline. In some embodiments, when $R^1$, $R^{2A}$, $R^{3A}$, $R^{4B}$, $R^{5A}$ and $R^{5B}$ are each H; $R^{2B}$ and $R^{3B}$ are each OH; $R^{4A}$ is —CH$_2$—$R^{F1}$; and $B^1$ is

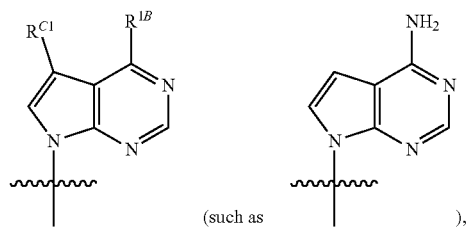

(such as  ), then $R^{F1}$ cannot be an optionally substituted quinolone, an optionally substituted quinazoline and/or an optionally substituted quinoxaline. In some embodiments, when $R^1$, $R^{2A}$, $R^{3A}$, $R^{4B}$, $R^{5A}$ and $R^{5B}$ are each H; $R^{2B}$ and $R^{3B}$ are each OH; $R^{4A}$ is —CH$_2$—$R^{F1}$; and $B^1$ is

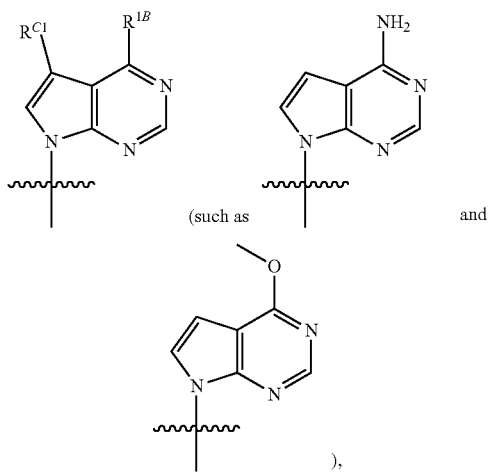

(such as  and  ), then $R^{F1}$ cannot be an optionally substituted naphthalene. In some embodiments, when $R^1$, $R^{2A}$, $R^{3A}$, $R^{4B}$, $R^{5A}$ and $R^{5B}$ are each H; $R^{2B}$ and $R^{3B}$ are each OH; $R^{4A}$ is —CH$_2$—O—$R^{J1}$; and $B^1$ is

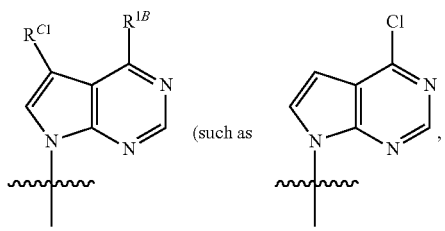

(such as  ,

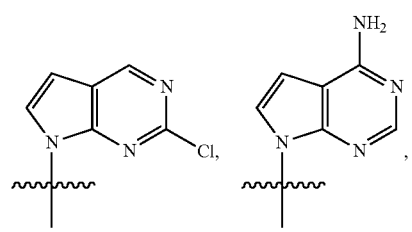

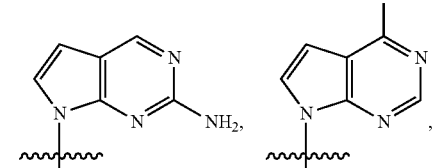

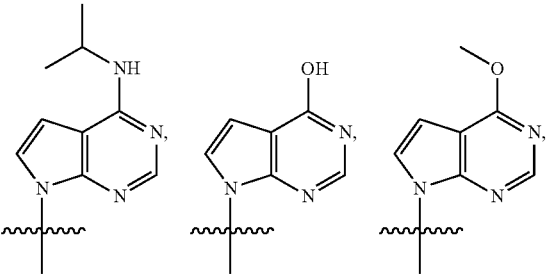

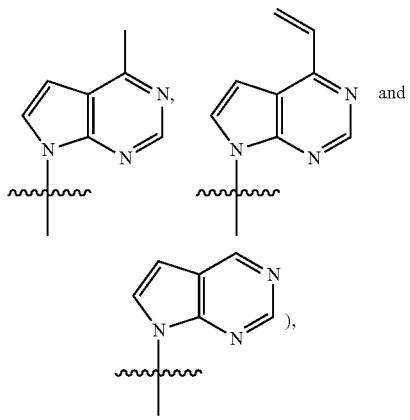

then $R^{J1}$ cannot be an optionally substituted quinolone, an optionally substituted quinazoline and/or an optionally substituted quinoxaline.

In some embodiments, $R^{F1}$ cannot be an optionally substituted phenyl, an optionally substituted thiophene, an optionally substituted pyridine and/or an optionally substituted 1,2,3,4-tetrahydroisoquinoline. In some embodiments, when $R^1$, $R^{2A}$, $R^{3A}$, $R^{4B}$, $R^{5A}$ and $R^{5B}$ are each H; $R^{2B}$ and $R^{3B}$ are each OH; and $R^{4A}$ is —$CH_2$—$R^{F1}$, —CH(OH)—$R^{F1}$, —CH(F)—$R^{F1}$ or —CH(OH)—$CH_2$—$R^{F1}$, then $R^{F1}$ cannot be an optionally substituted phenyl, an optionally substituted thiophene, an optionally substituted pyridine and/or an optionally substituted 1,2,3,4-tetrahydroisoquinoline. In some embodiments, when $R^1$, $R^{2A}$, $R^{3A}$, $R^{4B}$, $R^{5A}$ and $R^{5B}$ are each H; $R^{2B}$ and $R^{3B}$ are each OH; $R^{4A}$ is —$CH_2$—$R^{F1}$, —CH(OH)—$R^{F1}$, —CH(F)—$R^{F1}$ or —CH(OH)—$CH_2$—$R^{F1}$; and $B^1$ is

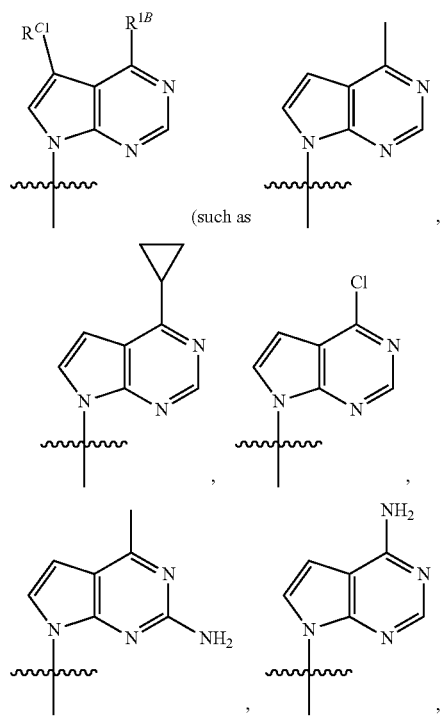

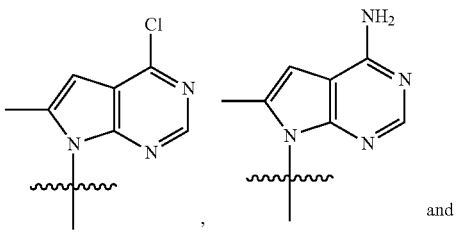

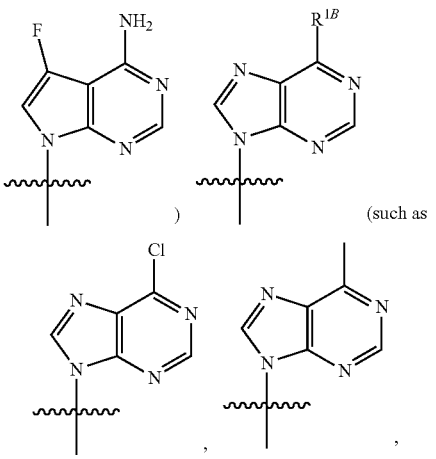

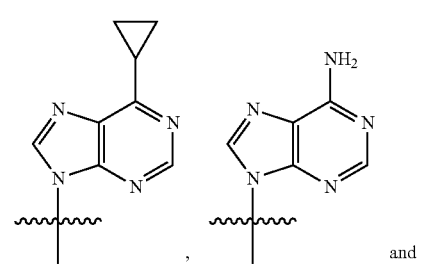

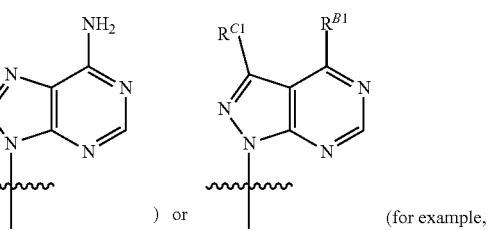

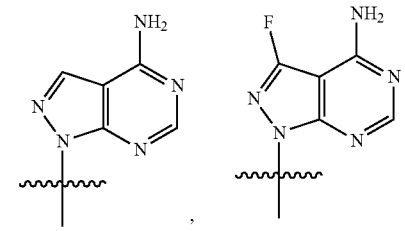

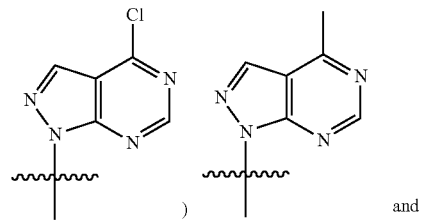

-continued

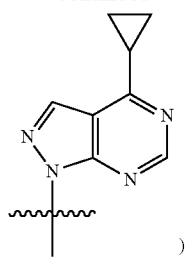), then $R^{F1}$ cannot be an optionally substituted phenyl, an optionally substituted thiophene, an optionally substituted pyridine and/or an optionally substituted 1,2,3,4-tetrahydroisoquinoline. In some embodiments, $R^{4A}$ cannot be —CH(OH)—$R^{F1}$.

In some embodiments, $B^1$ cannot be an optionally substituted

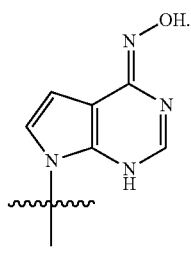 [SMILES: *n1ccc2/c(=N/O)nc[nH]c21]

In some embodiments, $B^1$ cannot be an optionally substituted

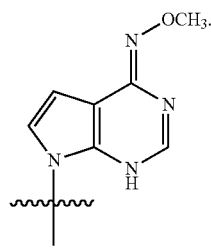 [SMILES: *n1ccc2/c(=N/OC)nc[nH]c21]

In some embodiments, when $R^1$, $R^{2A}$, $R^{3A}$, $R^{4B}$, $R^{5A}$ and $R^{5B}$ are each H; $R^{2B}$ and $R^{3B}$ are each OH; $R^{4A}$ is —CH(OH)—$R^{F1}$; $R^{F1}$ is an optionally substituted phenyl; then $B^1$ cannot be an optionally substituted

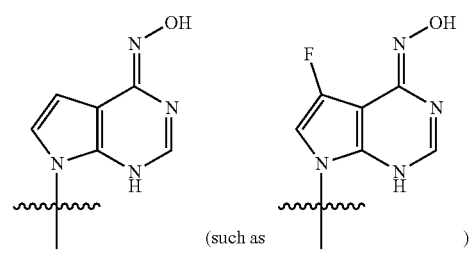 [SMILES: *n1ccc2/c(=N/O)nc[nH]c21 ; *n1cc(F)c2/c(=N/O)nc[nH]c21]

or an optionally substituted

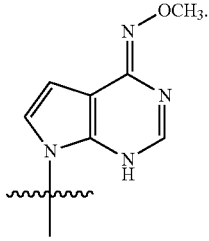 [SMILES: *n1ccc2/c(=N/OC)nc[nH]c21]

In some embodiments, when $R^1$, $R^{2A}$, $R^{3A}$, $R^{4B}$, $R^{5A}$ and $R^{5B}$ are each H; $R^{2B}$ and $R^{3B}$ are each OH; $R^{4A}$ is —(CH$_2$)$_2$—$R^{F1}$ or —CH$_2$—O—$R^{J1}$; $R^{F1}$ and/or $R^{J1}$ is an optionally substituted quinoline; then $B^1$ cannot be an optionally substituted

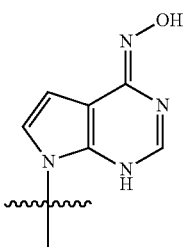 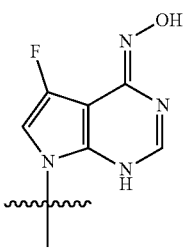

(such as )

or an optionally substituted

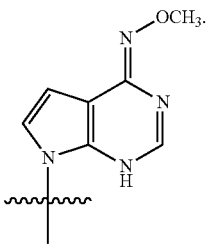 [SMILES: *n1ccc2/c(=N/OC)nc[nH]c21]

In some embodiments, $B^1$ cannot be

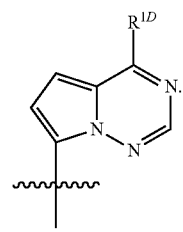

In some embodiments, $B^1$ cannot be one or more of the following:

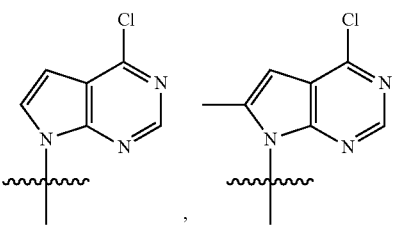

-continued

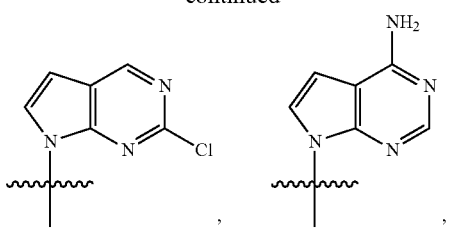
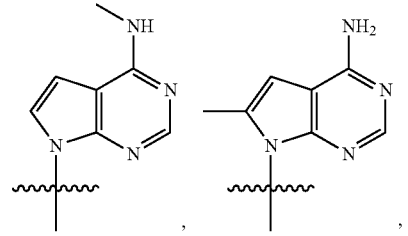
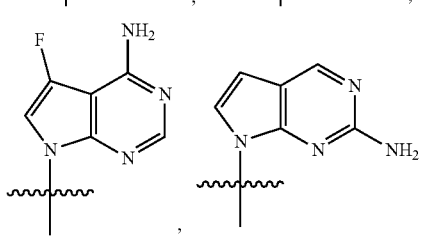
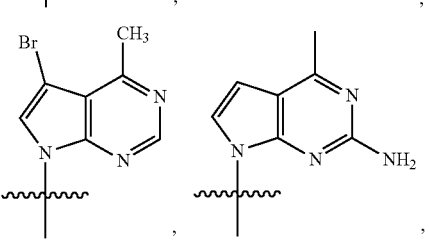
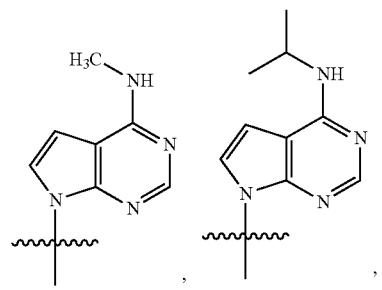
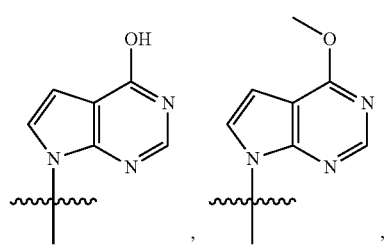
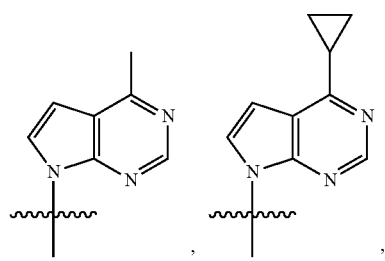

-continued

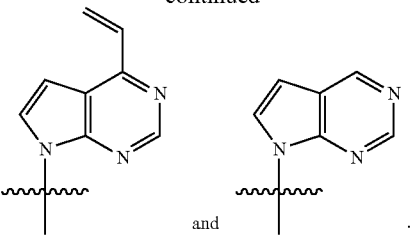

and

In some embodiments, $B^1$ cannot be one or more of the following:

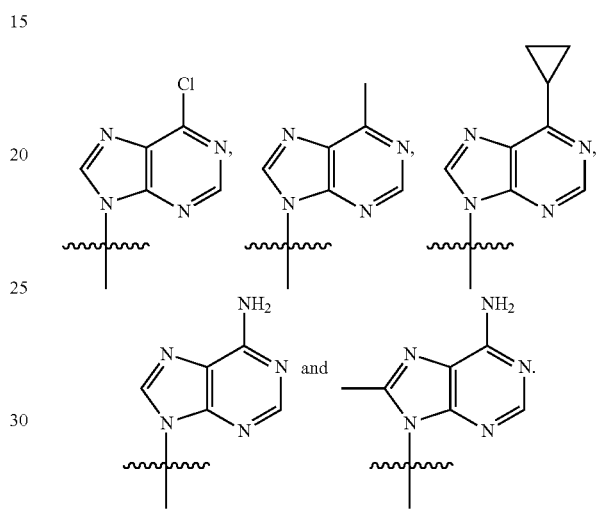

In some embodiments, $B^1$ cannot be one or more of the following:

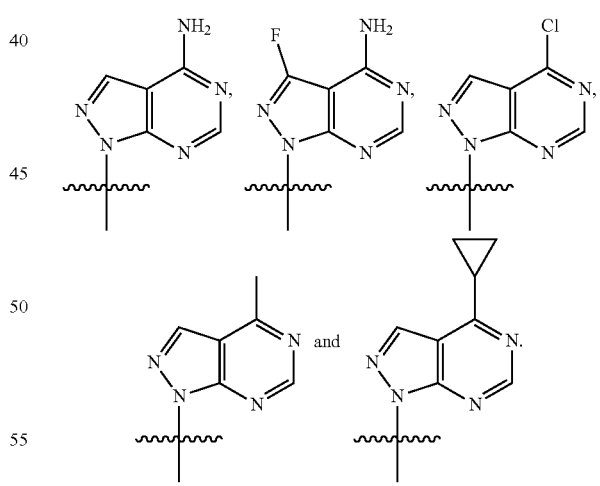

In some embodiments, when $R^1$, $R^{2A}$, $R^{3A}$, $R^{4B}$, $R^{5A}$ and $R^{5B}$ are each H; $R^{2B}$ and $R^{3B}$ are each OH; $R^{4A}$ is —CH(OH)—$R^{F1}$, —(CH$_2$)$_{1-2}$—$R^{F1}$, —CH(F)—$R^{F1}$, —CH(OH)—CH$_2$—$R^{F1}$, —CH$_2$—O—$R^{J1}$ or —O—CH$_2$—$R^{M1}$; then $R^{F1}$, $R^{J1}$ and/or $R^{M1}$ cannot be an optionally substituted phenyl, an optionally substituted naphthalene, an optionally substituted pyridine, an optionally substituted 1,2,3,4-tetrahydroisoquinoline, an optionally substituted quinoline, an optionally substituted quinazoline, an optionally substituted quinoxaline and/or an optionally substituted imidazo[1,2-a]pyridine. In some embodiments, $R^{F1}$, $R^{J1}$ and/or $R^{M1}$ cannot be an optionally substituted phenyl, an optionally substituted naphthalene, an optionally substituted pyridine, an optionally substituted 1,2,3,4-tetrahydroisoquinoline, an optionally substituted quinoline, an optionally substituted quinazoline, an optionally substituted quinoxaline, an optionally substituted imidazo[1,2-a]pyridine, an optionally substituted 1H-benzo[d]imidazole, an optionally substituted benzo[d]thiazole, an optionally substituted 1H-pyrrolo[3,2-b]pyridine, an optionally substituted thieno[3,2-b]pyridine, an optionally substituted furo[3,2-b]pyridine, an optionally substituted 1H-pyrrolo[2,3-b]pyridine, an optionally substituted 1H-pyrazole, an optionally substituted pyrimidine, an optionally substituted 1,8a-dihydroimidazo[1,2-a]pyridin-2(3H)-one, an optionally substituted 3,4-dihydro-2H-pyrido[3,2-b][1,4]oxazine, an optionally substituted 2,3-dihydro-1H-pyrrolo[2,3-b]pyridine, an optionally substituted 1H-imidazole and/or an optionally substituted 1H-pyrrolo[2,3-c]pyridine. In some embodiments, $R^{F1}$ cannot be

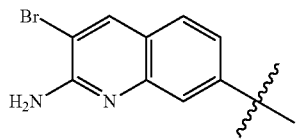

In some embodiments. $R^{J1}$ cannot be

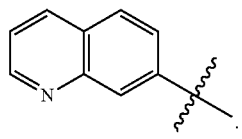 [SMILES: *c1ccc2cccnc2c1]

In some embodiments, $R^{J1}$ cannot be

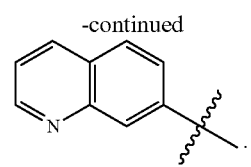

In some embodiments, $R^{J1}$ cannot be

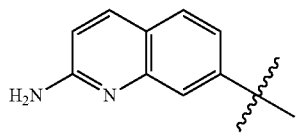

In some embodiments, when $Z^1$ is O, $R^{4B}$ is an unsubstituted $C_{1-4}$ alkyl (such as methyl), then $R^{J1}$ cannot be

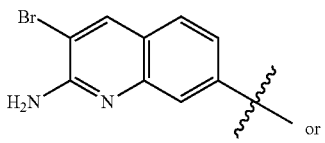

or

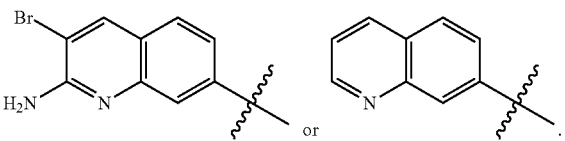 [SMILES: *c1ccc2cc(Br)c(N)nc2c1 ; *c1ccc2cccnc2c1]

In some embodiments, when $Z^1$ is $CH_2$, $R^{4B}$ is an unsubstituted $C_{1-4}$ alkyl (such as methyl), then $R^{F1}$ cannot be

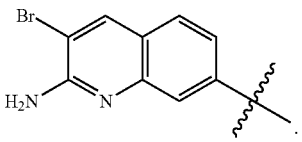 [SMILES: *c1ccc2cc(Br)c(N)nc2c1]

In some embodiments, when $Z^1$ is S, $R^{4B}$ is an unsubstituted $C_{1-4}$ alkyl (such as methyl), then $R^{F1}$ cannot be

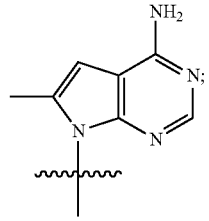

In some embodiments, when $R^1$, $R^{2A}$, $R^{3A}$ and $R^{5A}$ are each H; $R^{4B}$ and $R^{5B}$ together with the carbon $R^{4B}$ and $R^{5B}$ are attached form an unsubstituted cyclopropyl; $R^{2B}$ and $R^{3B}$ are each OH; and $R^{4A}$ is $-CH_2CH_2-R^{F1}$, $-CH_2CH(CH_3)-R^{F1}$, $-CH(CH_3)CH_2-R^{F1}$ or $-CH_2O-R^{J1}$; and $B^1$ is

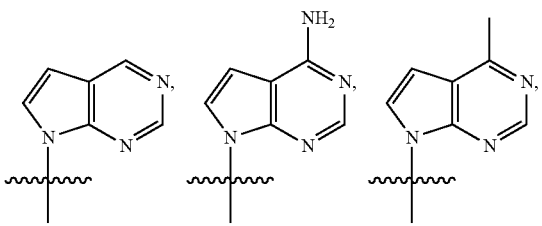

then $R^{F1}$ cannot be

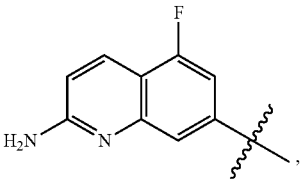

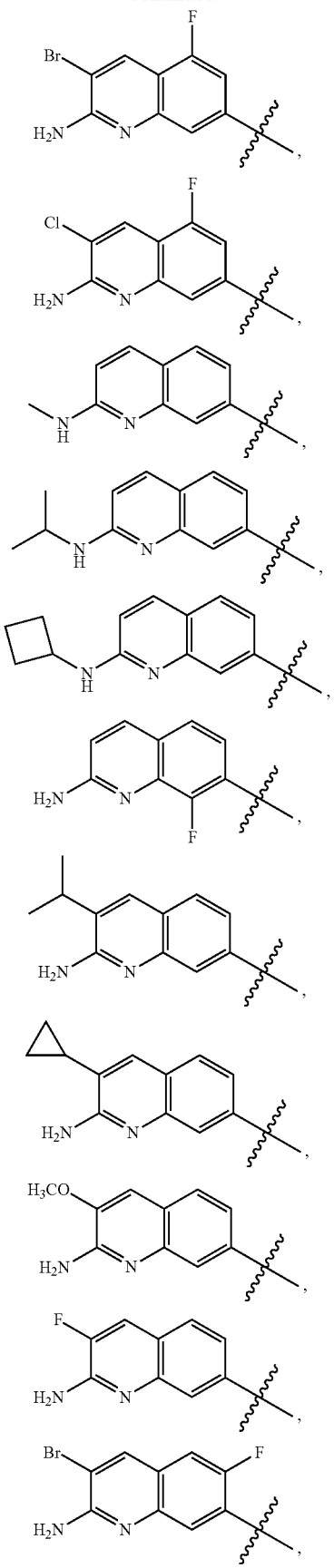
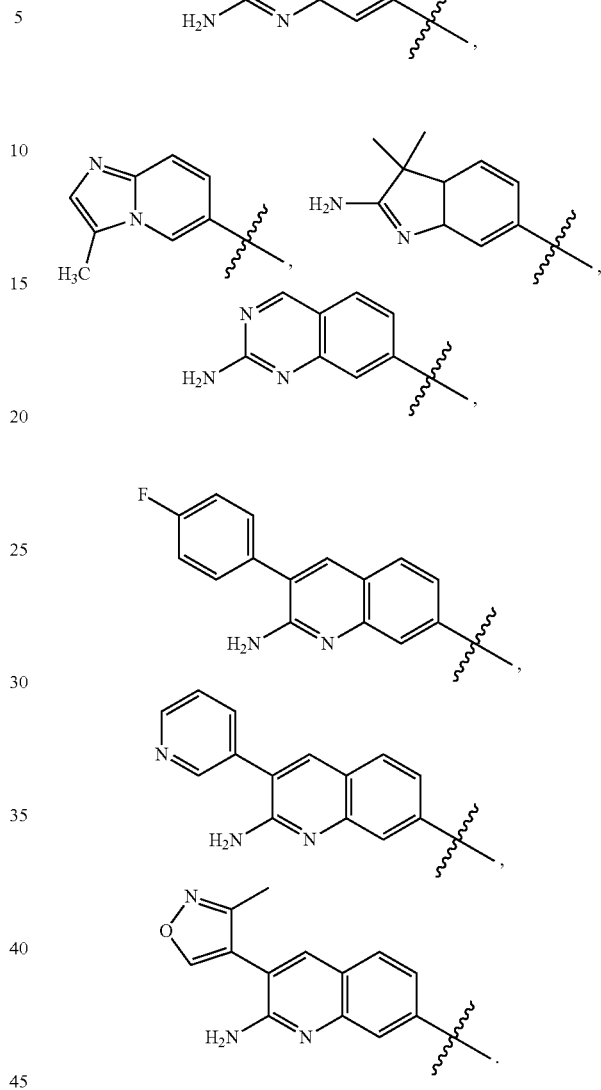

In some embodiments, when $R^1$, $R^{2A}$, $R^{3A}$ and $R^{5A}$ are each H; and $R^{2B}$ and $R^{3B}$ are each OH; then $R^{4B}$ and $R^{5B}$ together with the carbon $R^{4B}$ and $R^{5B}$ are attached form an unsubstituted cyclopropyl. In some embodiments, when $R^1$, $R^{2A}$, $R^{3A}$ and $R^{5A}$ are each H; $R^{4B}$ and $R^{5B}$ together with the carbon $R^{4B}$ and $R^{5B}$ are attached form an unsubstituted cyclopropyl; $R^{2B}$ and $R^{3B}$ are each OH; and $R^{4A}$ is —CH$_2$CH$_2$—R$^{F1}$, —CH$_2$CH(CH$_3$)—R$^{F1}$, —CH(CH$_3$)CH$_2$—R$^{F1}$ or —CH$_2$O—R$^{J1}$; and B$^1$ is

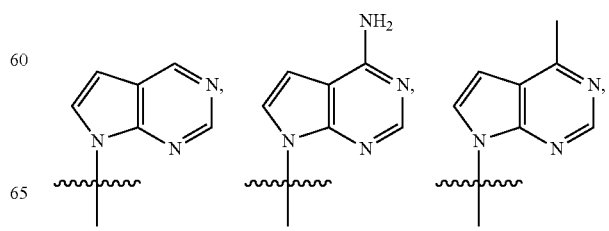

-continued

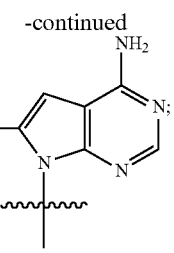

then $R^{F1}$ cannot be an optionally substituted heteroaryl. In some embodiments, $R^{4B}$ and $R^{5B}$ cannot be together with the carbon $R^{4B}$ and $R^{5B}$ are attached form an unsubstituted cyclopropyl.

In some embodiments, $R^{4A}$ cannot be —$(CR^{D1}R^{E1})(CR^{D1}R^{E1})_n$—$R^{F1}$. In some embodiments, $R^{4A}$ cannot be —$CH_2$—$R^{F1}$. In some embodiments, $R^{4A}$ cannot be —$(CH_2)_2$—$R^{F1}$. In some embodiments, $R^{4A}$ cannot be —$CH(OH)$—$R^{F1}$. In other embodiments, $R^{4A}$ cannot be —$(CR^{G1}R^{H1})$—O—$R^{J1}$. In some embodiments, $R^{4A}$ cannot be —$CH_2$—O—$R^{J1}$. In still other embodiments, $R^{4A}$ cannot be —O—$(CR^{K1}R^{L1})$—$R^{M1}$. In some embodiments, $R^{4A}$ cannot be —O—$CH_2$—$R^{M1}$. In some embodiments, $R^{4A}$ cannot be —$(CR^{N1}R^{O1})p$-$R^{P1}$. In some embodiments, $R^1$, $R^{2A}$, $R^{3A}$, $R^{4B}$, $R^{5A}$ and $R^{5B}$ cannot be each hydrogen.

In some embodiments, $R^{F1}$ cannot be an optionally substituted bicyclic heteroaryl. In other embodiments, $R^{F1}$ cannot be an optionally substituted bicyclic heterocyclyl. In still other embodiments, $R^{F1}$ cannot be an optionally substituted phenyl. In some embodiments, $R^{J1}$ cannot be an optionally substituted bicyclic heteroaryl. In other embodiments, $R^{J1}$ cannot be an optionally substituted bicyclic heterocyclyl. In still other embodiments, $R^{J1}$ cannot be an optionally substituted phenyl. In some embodiments, $R^{M1}$ cannot be an optionally substituted bicyclic heteroaryl. In other embodiments, $R^{M1}$ cannot be an optionally substituted bicyclic heterocyclyl. In still other embodiments, $R^{M1}$ cannot be an optionally substituted phenyl. In some embodiments, $R^{F1}$, $R^{J1}$ and/or $R^{M1}$ cannot be an optionally substituted

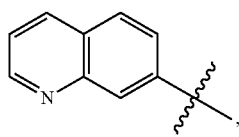

an optionally substituted

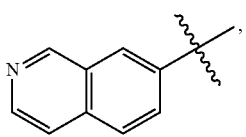 [SMILES: *c1ccc2ccncc2c1]

an optionally substituted an optionally substituted

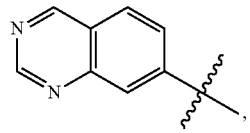

an optionally substituted

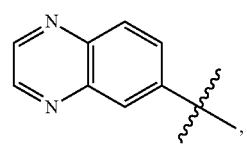 [SMILES: *c1ccc2nccnc2c1]

an optionally substituted

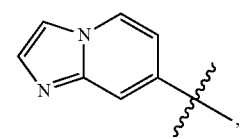 [SMILES: *c1ccn2ccnc2c1]

an optionally substituted phenyl, an optionally substituted pyridinyl (such as an optionally substituted

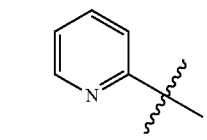 [SMILES: *c1ccccn1]

and/or an optionally substituted

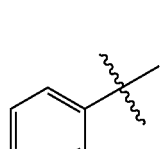

an optionally substituted

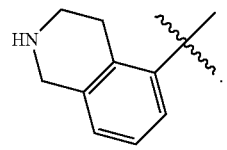 [SMILES: *c1cccc2c1CCNC2]

an optionally substituted

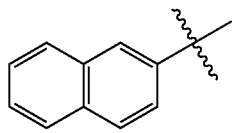 [SMILES: *c1ccc2ccccc2c1]

and/or an optionally substituted

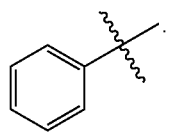 [SMILES: *c1ccccc1]

In some embodiments, $R^{4B}$ can be an unsubstituted $C_{1-4}$ alkyl (such as methyl); and $B^1$ can be an unsubstituted or a substituted

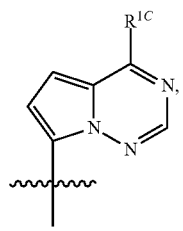

an unsubstituted or a substituted

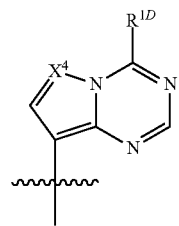

or an unsubstituted or a substituted

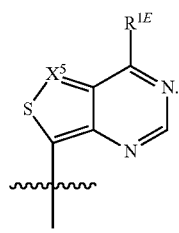

In some embodiments, $R^{4B}$ can be an unsubstituted $C_{1-4}$ alkyl (such as methyl); and $B^1$ can be an unsubstituted or a substituted

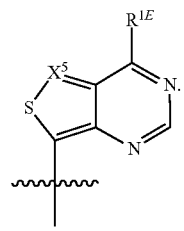

In some embodiments, $R^{4B}$ can be an unsubstituted $C_{1-4}$ alkyl (such as methyl); and $B^1$ can be an unsubstituted or a substituted

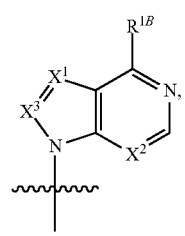

wherein $X^2$ can be $CR^{C2}$. In some embodiments, $R^{4B}$ can be an unsubstituted $C_{1-4}$ alkyl (such as methyl); and $B^1$ can be an unsubstituted or a substituted

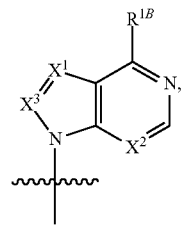

wherein $X^3$ can be N, or an unsubstituted or a substituted

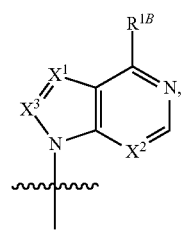

wherein $X^1$ can be $CR^{C1}$; and $R^{C1}$ can be hydroxy, an unsubstituted $C_{2-4}$ alkenyl, an unsubstituted $C_{1-4}$ alkoxy or $NR^{A1}R^{A2}$.

In some embodiments, a compound of Formula (I), or a pharmaceutically acceptable salt thereof, cannot be a compound as provided in WO 2018/065354, WO 2018/154104, WO 2018/152548, WO 2018/160824, WO 2017/212385, WO 2017/032840, WO 2019/116302, WO 2020/033282, WO 2020/033285 and/or WO 2020/033288.

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

synthesis scheme, functional group conversions can be performed on the compound of General Formula VI, for example conversion of $R^{4B}$ from —$CH_2$—OH via —C(=O)—H to —CN (as described in example 40), —(C=O)$NH_2$ (as described in example 40), vinyl (as described in example 46) or alkyne (as described in example 47).

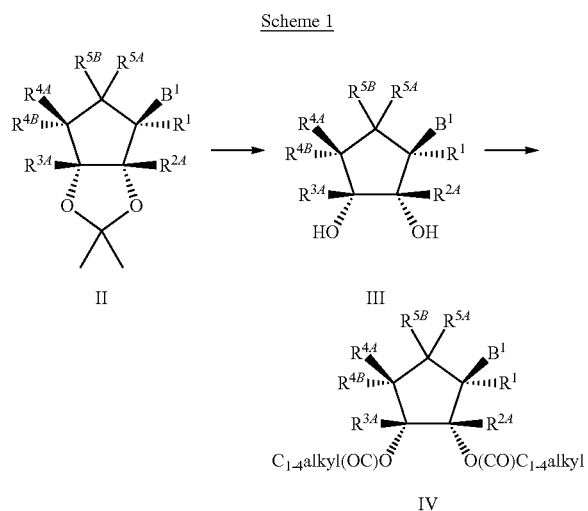

Scheme 1

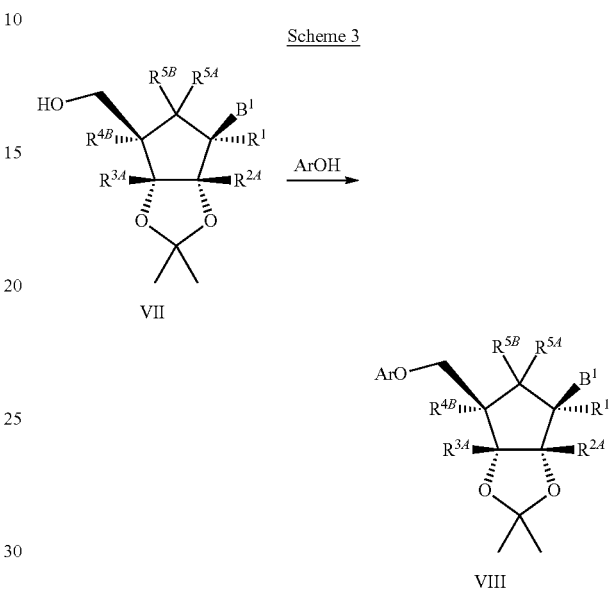

Scheme 3

Deprotection of the acetonide of General Formula II can be performed in the presence of a suitable acid, for example HCl in MeOH, at a suitable temperature (such as room temperature), resulting in the formation of the compound of General Formula III. Optionally, compound of General Formula III can be converted to its corresponding ester of General Formula IV, by reaction with a suitable $C_{1-4}$ alkyl acid anhydride or $C_{1-4}$ alkyl acid chloride.

As depicted in scheme 3, Mitsunobu reaction of a compound of General Formula VII with ArOH (or in extension, if applicable, $R^{J1}$OH), results in the formation of a compound of General Formula VIII (where in extension ArO—, can be $R^{J1}$O—), for example, by using $PPh_3$ and DIAD in a solvent like THF, or cyanomethylenetributylphosphorane (CMBP) in a suitable solvent (for example, toluene).

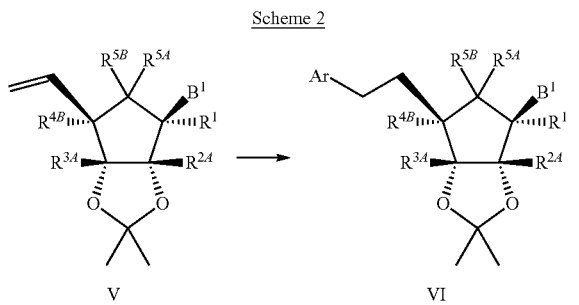

Scheme 2

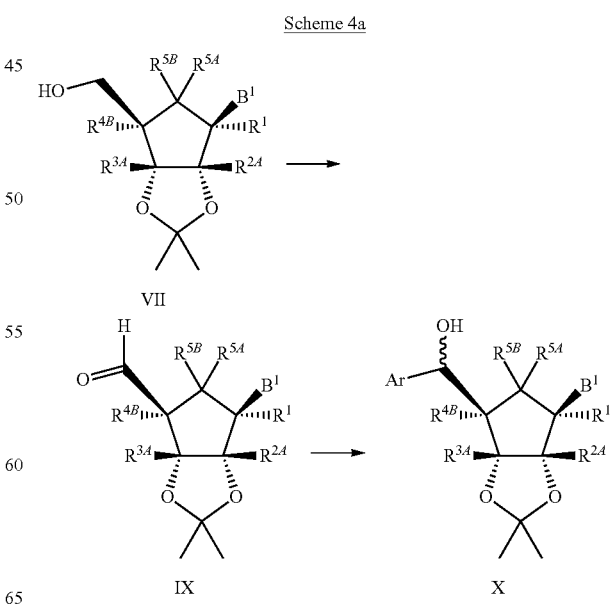

Scheme 4a

As depicted in Scheme 2, introduction of an aryl group (Ar) or in extension, if applicable, $R^{F1}$, on the vinyl side chain on a compound of General Formula V, is performed by a reaction of the double bond with 9-BBN under an inert atmosphere, for example in a suitable solvent under appropriate conditions. An example of a suitable solvent and temperature is THF, at 50° C. The carbon-carbon bond can then be formed with a suitable Ar—Br or Ar—I (or in extension, if applicable $R^{F1}$—Br or $R^{F1}$—I) using a suitable catalyst (such as Pd(dppf)$Cl_2$) in the presence of a base (for example, $K_3PO_4$), resulting in the formation of a compound of General Formula VI. In the context of the generic A compound of General Formula VII can be oxidized to the corresponding aldehyde of General Formula IX, followed by addition of an organometallic reagent like ArylMg (halide), or in extension, if applicable, $R^{F1}$—Mg(halide), resulting in the formation of a compound of General Formula X (wherein, in extension Ar— can be $R^{F1}$—). Alternatively, a compound of General Formula IX can be formed by oxidation of the vinyl functionality of compound of General Formula V, for example, by dihydroxylation with $OsO_4$, followed by oxidation with $NaIO_4$. A compound of General Formula V can be formed by a Wittig reaction of the aldehyde of General Formula IX.

Scheme 4b

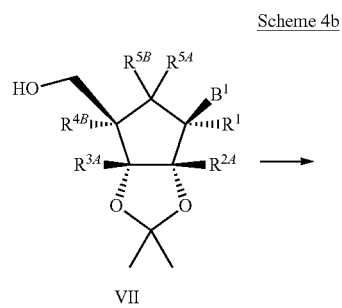

VII

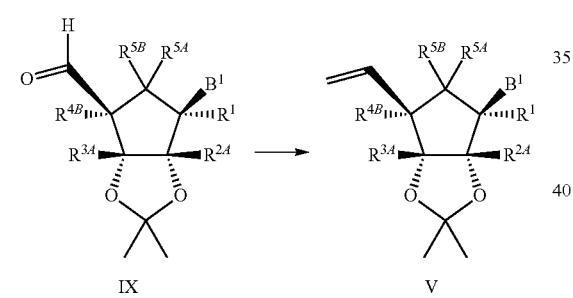

IX V

As known to those skilled in the art, the compounds of Scheme 1 to 3 can be suitably protected when required. Compounds of General Formulae VII and V can be commercially available or can be obtained by methods known to those skilled in the art. An example of a compound of General Formula VII is

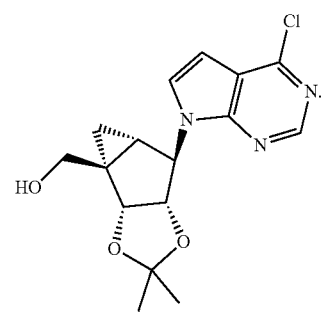

An example of a compound of General Formula V is

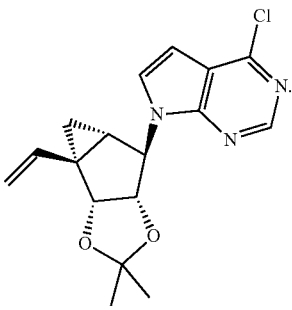

Another example of General Formulae VII and V are

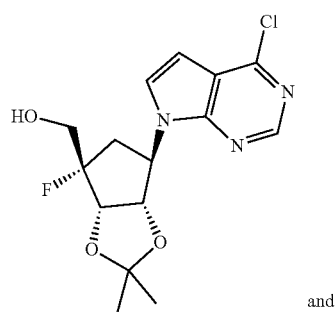

and

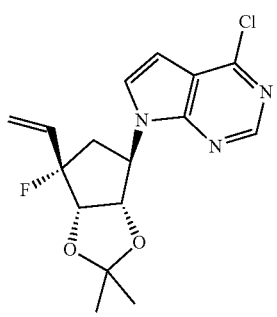

respectively, for which the synthesis is described in example 31.

Scheme 5a

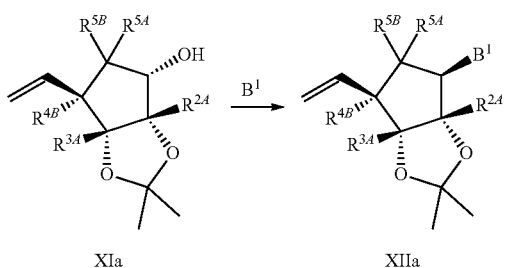

XIa XIIa

-continued

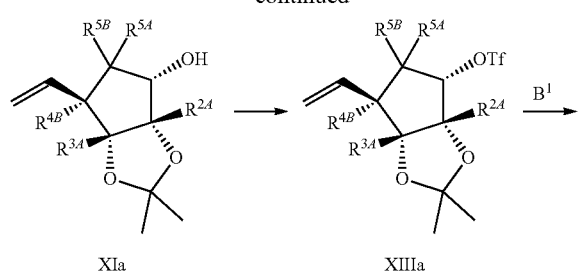

XIa → XIIIa

Scheme 5b

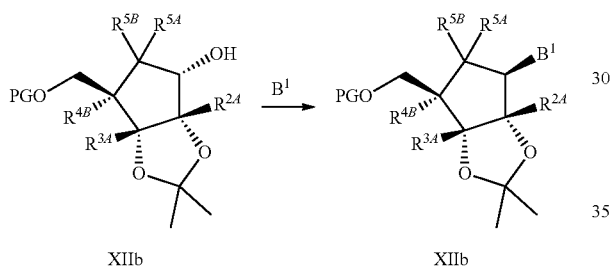

XIIb → XIIb

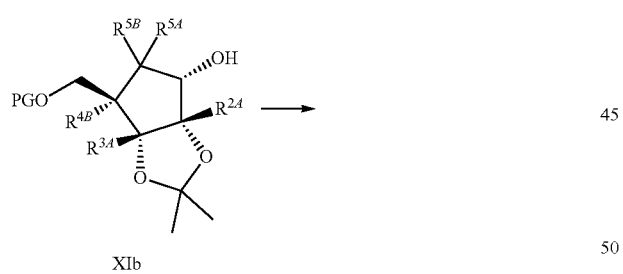

XIb

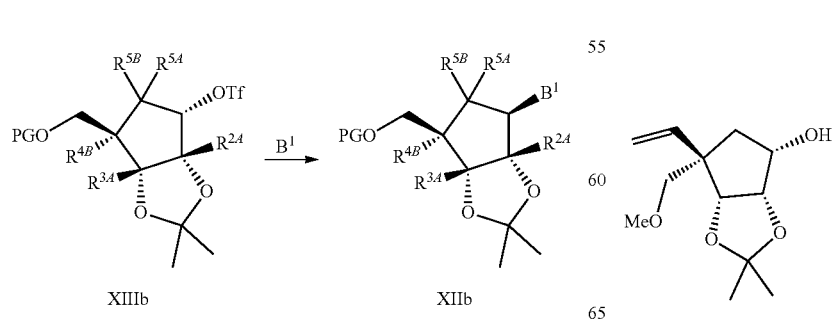

XIIIb → XIIb

Introduction of a nucleobase described herein (denoted as B$^1$) can be performed as exemplified in Scheme 5a and 5b, either using Mitsunobu-like conditions, for example using DIAD and PPh$_3$, in THF at room temperature, and then converting the compound of General Formula XIa or XIb to a compound of General Formula XIIa or XIIb, respectively. Alternatively, General Formula XIa or XIb can be converted to a triflate of General Formula XIIIa or XIIIb, respectively. Following substitution, a compound of General Formula XIIa or XIIb, respectively, can be obtained. An example of a compound of General Formula XIB is:

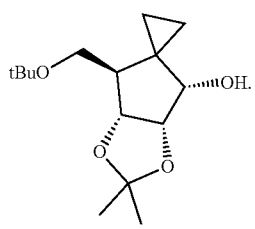

An example of a compound of General Formulae XIa and XIIa, within the context of the generic synthesis scheme, are

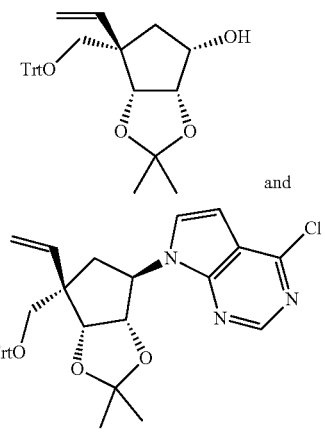

and respectively, prepared as described in example 36. Trt or Trityl is a protecting group that can be removed in the course of the synthetic route. Another example of compounds of General Formulae XIa and XIIa are

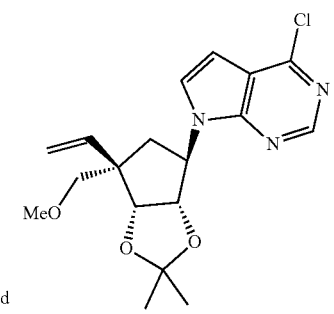

respectively, prepared as described in example 53.

Scheme 6

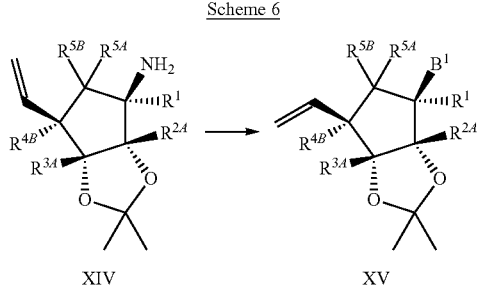

XIV → XV

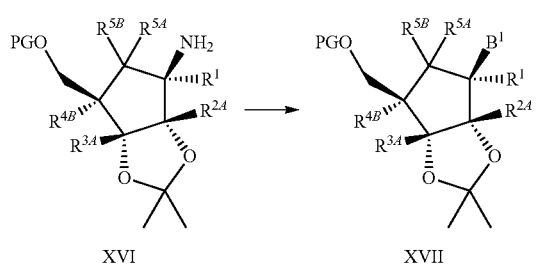

XVI → XVII

As shown in Scheme 6, when $B^1$ is connect to the rest of the scaffold via a nitrogen, amines of General Formulae XIV and XVI (PG represents a protection group) can be converted to compounds of General Formulae XV and XVII, respectively, using methods know to those skilled in the art. Amines of General Formulae XIV and XVI can be obtained utilizing methods known to those skilled in the art. An example of a compound of General Formula XVI is

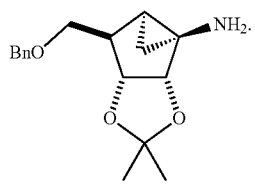

Where desired, functional group transformations can be performed on the compounds of general formulae depicted in Scheme 1 to 6, containing a $B^1$ group. For example, conversion of the $R^{1B}$, substituent from chloro to $NH_2$, via displacement with ammonia, such as described in example 1 for conversion of 8A to 9A. Or for example, conversion of the $R^{1B}$, substituent from chloro to $NH_2$, by palladium catalyzed coupling, such as with diphenylmethanimine, followed by removal of the protecting group as exemplified in example 17. Another example can be the conversion of $R^{1B}$ from chloride to methyl, as exemplified in example 28.

Scheme 7

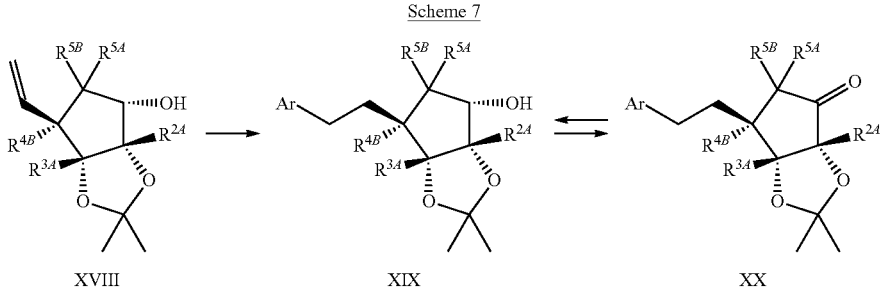

XVIII → XIX ⇌ XX

As exemplified in Scheme 7, a compound of the General Formula XVIII can be converted to a compound of General Formula XIX, using methods similar to those described for the conversion of a compound of General Formula V to a compound of General Formula VI. Oxidation of the alcohol to the ketone, for example, using IBX (2-Iodoxybenzoic acid) in acetonitrile at a temperature of 60° C., can provide a compound of General Formula XX. Functional group modification on $R^{5B}/R^{5A}$, or introduction of $R^{5B}/R^{5A}$ can be performed utilizing a compound of General Formula XX. For example if $R^{5B}$ and $R^{5A}$ are each hydrogen, introduction of an exocyclic vinyl can be performed by using an Eschenmoser's salt, followed by amine methylation under the influence of MeI and subsequent elimination. The formed ketone of General Formula XX can be, after functional group modification of $R^{5B}$ and/or $R^{5A}$, reduced back to the alcohol of General Formula XIX. An example of such a ketone of General Formula XX, formed by functional group modification at the stage of a compound of General Formula XX, is:

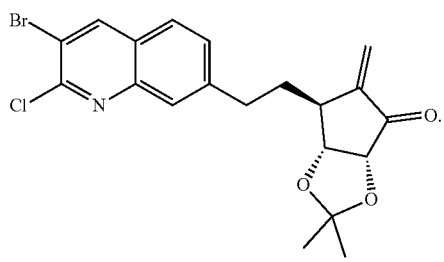

Scheme 8

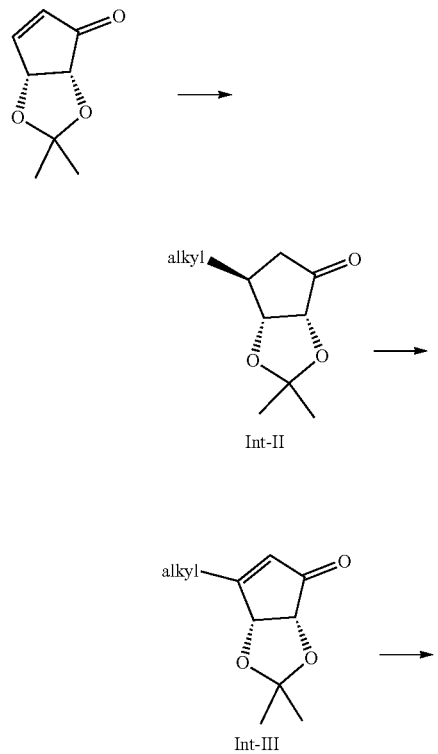

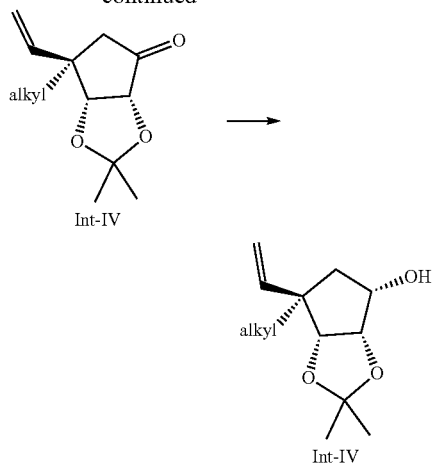

As described in Scheme 8, addition of an alkyl group as described herein to the 4'-position of the 5-membered ring of a compound of Formula (I) can be accomplished with an enone (3aR,6aR)-2,2-dimethyl-3a,6a-dihydrocyclopenta[d][1,3]dioxol-4-one. For example, using a cupper reagent, made from alkyl lithium in the presence of CuI in THF at 0° C., followed by addition to the enone at −78° C., can result in the formation of an intermediate of General Formula Int-II. Oxidation of the intermediate of General Formula Int-II to General Formula Int-III can be performed by forming the TES-enol, followed by oxidation in the presence of Pd(OAc)$_2$ and oxygen in DMSO at a suitable temperature (such as 60° C.). Stereoselective addition of a vinyl group to the enone of General Formula Int-III, can be performed, for example, by treating a mixture of LiCl and CuI in THF with a mixture of TMSCl and General Formula Int-III, followed by addition of vinylmagnesium bromide at 0° C. This can be followed by the deprotection of any formed silyl enolate. Treatment with an acid, like HCl, in acetone/MeOH at a suitable temperature (for example, room temperature) can provide a compound of General Formula Int-IV. The ketone can be reduced to the alcohol of General Formula Int-IV, for example, by treatment with NaBH$_4$ in MeOH at 0° C.

Scheme 9

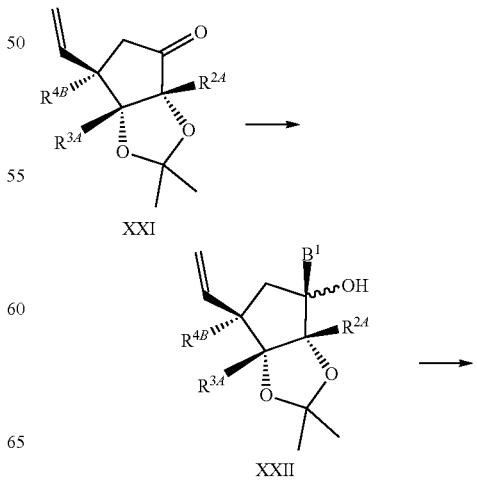

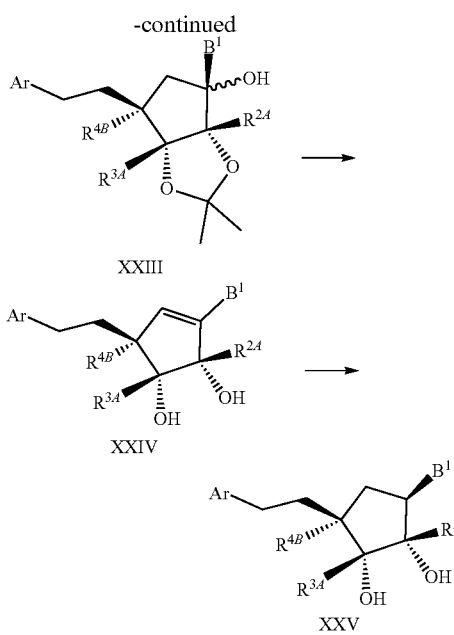

XXIII

XXIV

XXV

Scheme 9 describes a generic synthesis of the compounds which has $B^1$ connected to the five-membered ring via a carbon-carbon bond. A compound of General Formula XXII can be formed by addition of an organometallic reagent to the ketone of General Formula XXI. An example of such organometallic reagent can be generated from reacting

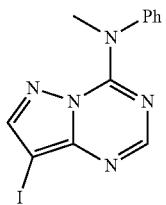

with i-PrMgCl.LiCl, as described in example 51. Another example of such organometallic reagent, can be prepared by reaction of

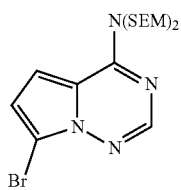

with i-PrMgCl.LiCl, as described in example 43. Further transformations involve introduction of —Ar from General Formula XXII to General Formula XXIII, similar as described for the conversion of a compound of General Formula V to a compound of General Formula VI. Elimination of the —OH of General Formula XXIII to the alkene of General Formula XXIV, can be performed under acidic conditions, or, for example, by treating with DAST. The acetonide protecting group can be removed under acidic conditions, for example, by the treatment with aqueous HCl. Reduction of the double bond in General Formula XXIV, can be accomplished by hydrogenation using a heterogeneous catalyst like $PtO_2$ in a suitable solvent (such as THF) under a hydrogen atmosphere. Alternatively, depending on the substituents on General Formula XXIV, Crabtree's catalyst can be used for the hydrogenation, for example, in MeOH under hydrogen atmosphere. In case diastereoisomers are obtained after the reduction, the desired isomer of General Formula XXV can be isolated out.

During the synthesis of compounds of Formula (I), such as those shown in Schemes 1-9, one or more moieties can be protected with one or more suitable protecting groups. Those skilled in the art know and can select the suitable protecting group(s) and the conditions to add and remove the suitable protecting group(s). The protecting group(s) may be chosen in such a way, that they are stable to certain reaction conditions and readily removed at a convenient stage using methodology known from the art.

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Pharmaceutical compositions may be formulated in a variety forms, such as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a cancer that can include administering to a subject identified as suffering from a cancer an effective amount of a compound described herein, or a pharmaceutically acceptable salt thereof, or a pharmaceutical composition that includes an effective amount of a compound described herein, or a pharmaceutically acceptable salt thereof. Other embodiments described herein relate to using a compound described herein, or a pharmaceutically acceptable salt thereof, in the manufacture of a medicament for treating a cancer. Still other embodiments described herein relate to the use of a compound described herein, or a pharmaceutically acceptable salt thereof, or a pharmaceutical composition that includes a compound described herein, or a pharmaceutically acceptable salt thereof, for treating a cancer. Examples of suitable cancers include lymphomas, leukemias, liver cancers, lung cancers, breast cancers and/or colorectal cancers.

Some embodiments described herein relate to a method of treating a liver cancer (for example, hepatocellular carcinoma (HCC)) that can include administering to a subject identified as suffering from the liver cancer an effective amount of a compound described herein, or a pharmaceutically acceptable salt thereof, or a pharmaceutical composition that includes an effective amount of a compound described herein, or a pharmaceutically acceptable salt thereof. Other embodiments described herein relate to using a compound described herein, or a pharmaceutically acceptable salt thereof, in the manufacture of a medicament for treating a liver cancer (such as HCC). Still other embodiments described herein relate to the use of a compound described herein, or a pharmaceutically acceptable salt thereof, or a pharmaceutical composition that includes a compound described herein, or a pharmaceutically acceptable salt thereof, for treating a liver cancer (for example, HCC).

Some embodiments described herein relate to a method for inhibiting replication of a cancer cell that can include contacting the cancer cell or administering to a subject identified as suffering from HCC with an effective amount of a compound described herein, or a pharmaceutically acceptable salt thereof, or a pharmaceutical composition that includes of a compound described herein, or a pharmaceutically acceptable salt thereof. Other embodiments described herein relate to the use of an effective amount of a compound described herein, or a pharmaceutically acceptable salt thereof, or a pharmaceutical composition that includes of a compound described herein, or a pharmaceutically acceptable salt thereof, in the manufacture of a medicament for inhibiting replication of a cancer cell. Still other embodiments described herein relate to an effective amount of a compound described herein, or a pharmaceutically acceptable salt thereof, or a pharmaceutical composition that includes of a compound described herein, or a pharmaceutically acceptable salt thereof, for inhibiting replication of a cancer cell.

Some embodiments described herein relate to a method for inhibiting cell proliferation, such as inhibiting cell proliferation of cancer cells, that can include administering to a subject identified as suffering from a disease wherein inhibiting cell proliferation is desirable with an effective amount of a compound described herein, or a pharmaceutically acceptable salt thereof, or a pharmaceutical composition that includes of a compound described herein, or a pharmaceutically acceptable salt thereof. Other embodiments described herein relate to the use of an effective amount of a compound described herein, or a pharmaceutically acceptable salt thereof, or a pharmaceutical composition that includes of a compound described herein, or a pharmaceutically acceptable salt thereof, in the manufacture of a medicament for inhibiting cell proliferation, such as inhibiting cell proliferation of cancer cells. Still other embodiments described herein relate to an effective amount of a compound described herein, or a pharmaceutically acceptable salt thereof, or a pharmaceutical composition that includes of a compound described herein, or a pharmaceutically acceptable salt thereof, for inhibiting cell proliferation, such as inhibiting cell proliferation of cancer cells.

Some embodiments described herein relate to a method of modulating a PRMT5 enzyme that can include contacting a cell (for example, a cancer cell described herein) with an effective amount of a compound described herein, or a pharmaceutically acceptable salt thereof, or a pharmaceutical composition that includes an effective amount of a compound described herein, or a pharmaceutically acceptable salt thereof. Other embodiments described herein relate to using a compound described herein, or a pharmaceutically acceptable salt thereof, in the manufacture of a medicament for modulating a PRMT5 enzyme. Still other embodiments described herein relate to the use of a compound described herein, or a pharmaceutically acceptable salt thereof, or a pharmaceutical composition that includes a compound described herein, or a pharmaceutically acceptable salt thereof, for modulating a PRMT5 enzyme.

Some embodiments described herein relate to a method of inhibiting the activity of a PRMT5 enzyme that can include contacting a cell (for example, a cancer cell described herein) with an effective amount of a compound described herein, or a pharmaceutically acceptable salt thereof, or a pharmaceutical composition that includes an effective amount of a compound described herein, or a pharmaceutically acceptable salt thereof. Other embodiments described herein relate to using a compound described herein, or a pharmaceutically acceptable salt thereof, in the manufacture of a medicament for inhibiting the activity of a PRMT5 enzyme. Still other embodiments described herein relate to the use of a compound described herein, or a pharmaceutically acceptable salt thereof, or a pharmaceutical composition that includes a compound described herein, or a pharmaceutically acceptable salt thereof, for inhibiting the activity of a PRMT5 enzyme.

Some embodiments described herein relate to a method of inducing apoptosis of a cell (for example, a cancer cell described herein) that can include contacting the cell with an effective amount of a compound described herein, or a pharmaceutically acceptable salt thereof, or a pharmaceutical composition that includes an effective amount of a compound described herein, or a pharmaceutically acceptable salt thereof. Other embodiments described herein relate to using a compound described herein, or a pharmaceutically acceptable salt thereof, in the manufacture of a medicament for inducing apoptosis of a cell, such as a cancer cell described herein. Still other embodiments described herein relate to the use of a compound described herein, or a pharmaceutically acceptable salt thereof, or a pharmaceutical composition that includes a compound described herein, or a pharmaceutically acceptable salt thereof, for inducing apoptosis of a cell, such as a cancer cell described herein.

Some embodiments described herein relate to a method of decreasing the viability of a cell (for example, a cancer cell described herein) that can include contacting the cell with an effective amount of a compound described herein, or a pharmaceutically acceptable salt thereof, or a pharmaceutical composition that includes an effective amount of a compound described herein, or a pharmaceutically acceptable salt thereof. Other embodiments described herein relate to using a compound described herein, or a pharmaceutically acceptable salt thereof, in the manufacture of a medicament for decreasing the viability of a cell, such as a cancer cell described herein. Still other embodiments described herein relate to the use of a compound described herein, or a pharmaceutically acceptable salt thereof, or a pharmaceutical composition that includes a compound described herein, or a pharmaceutically acceptable salt thereof, for decreasing the viability of a cell, such as a cancer cell described herein. Exemplary cancer cells include lymphoma cells, leukemia cells, liver cancer cells, lung cancer cells, breast cancer cells and/or colorectal cancer cells. In some embodiments, the cancer cell can be a liver cancer cell.

For treatment of liver cancer, a high liver to plasma ratio can be useful. Accordingly, compounds that with a high liver to plasma ratio are of interest. In some embodiments, a compound described herein (for example, a compound of Formula (I), or a pharmaceutically acceptable salt thereof) can have a liver to plasma ratio of >5. In some embodiments, a compound described herein (for example, a compound of Formula (I), or a pharmaceutically acceptable salt thereof) can have a liver to plasma ratio of >10.

Compounds disclosed herein can be evaluated for efficacy and toxicity using known methods. A non-limiting list of potential advantages of compounds described herein (such as a compound of Formula (I), and pharmaceutically acceptable salts thereof) include improved stability, increased safety profile, increased efficacy, increased binding to the target, increased specificity for the target (for example, a cancer cell).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, including a human cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, a compound described herein, or a pharmaceutically acceptable salt thereof, can be used in combination with one or more additional agent(s) for treating and/or inhibiting replication HCC. Additional agents include, but are not limited to, a kinase inhibitor (such as Sorafenib, Lenvatinib and Apatinib), a checkpoint inhibitor/modulator (such as a PD1/PDL1 inhibitor, an anti-PD1 antibody, for example, Nivolumab, Keytruda® and cemiplimab, an anti-PDL1 antibody, such as atezolizumab, avelumab and durvalumab, and an anti-CTLA4 antibody, such as Tremelimumab and Ipilimumab) and an anti-VEGF antibody (such as Bevacizumab).

In some embodiments, a compound described herein, or a pharmaceutically acceptable salt thereof, can be administered with one or more additional agent(s) together in a single pharmaceutical composition. In some embodiments, a compound described herein, or a pharmaceutically acceptable salt thereof, can be administered with one or more additional agent(s) as two or more separate pharmaceutical compositions. Further, the order of administration of a compound described herein, or a pharmaceutically acceptable salt thereof, with one or more additional agent(s) can vary.

EXAMPLES

Table of Abbreviations

The following abbreviations may appear in the present disclosure:

| Abbreviation | Name |
|---|---|
| Ac | Acetate |
| ACN | Acetonitrile |
| anhyd. | Anhydrous |
| aq. | Aqueous |

-continued

| Abbreviation | Name |
|---|---|
| BPO | Benzoylperoxide |
| Bu | Butyl |
| CAN | Ceric ammonium nitrate |
| conc. | Concentrated |
| DCM | Dichloromethane |
| DIPEA | N,N-Diisopropylethylamine |
| DMA | N,N-dimethylacetamide |
| DMF | N,N-Dimethylformamide |
| DMSO | Dimethyl sulfoxide |
| DPPA | Diphenylphosphoryl azide |
| Dppf | 1,1'-Bis(diphenylphosphino)ferrocene |
| EA = EtOAc | Ethyl acetate |
| ECF | Ethyl chloroformate |
| Et | Ethyl |
| FA | Formic acid |
| G | Gram(s) |
| H | Hour(s) |
| IBX | 2-Iodoxybenzoic acid |
| Me | Methyl |
| MeOH | Methanol |
| Min | Minute(s) |
| NBS | N-Bromosuccinimide |
| NIS | N-Iodosuccinimide |
| PE | Petroleum ether |
| rt | Room temperature |
| sat. | Saturated |
| TBAF | Tetra-n-butylammonium fluoride |
| TBSCL | t-Butyldimethylsilyl chloride |
| TFA | Trifluoroacetic acid |
| THF | Tetrahydrofuran |

Additional embodiments are disclosed in further detail in the following examples, which are not in any way intended to limit the scope of the claims.

Example 1

Compound 1

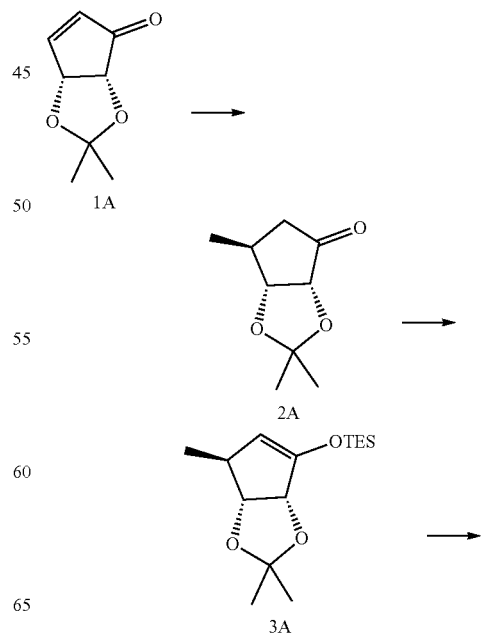

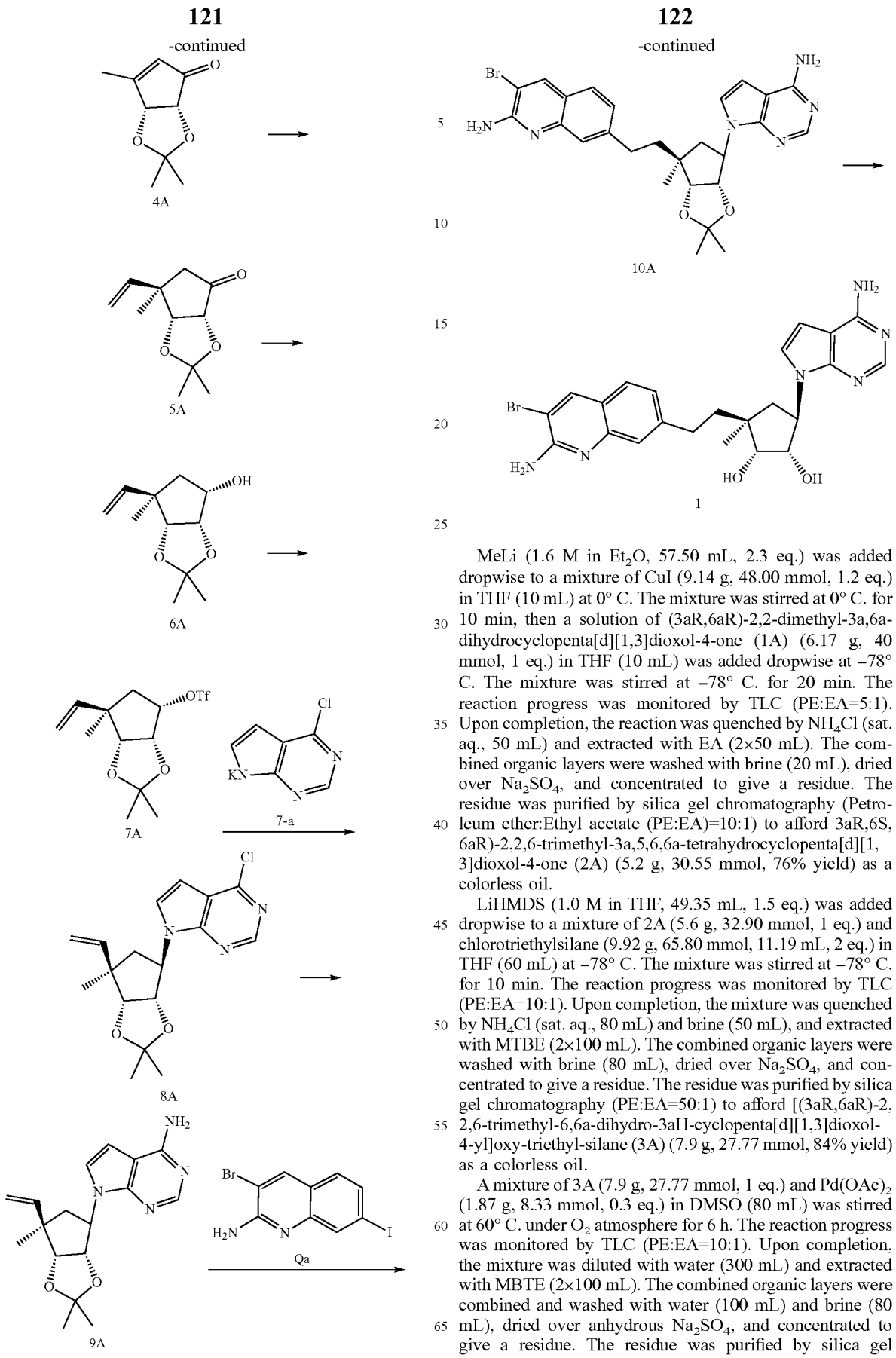

MeLi (1.6 M in Et$_2$O, 57.50 mL, 2.3 eq.) was added dropwise to a mixture of CuI (9.14 g, 48.00 mmol, 1.2 eq.) in THF (10 mL) at 0° C. The mixture was stirred at 0° C. for 10 min, then a solution of (3aR,6aR)-2,2-dimethyl-3a,6a-dihydrocyclopenta[d][1,3]dioxol-4-one (1A) (6.17 g, 40 mmol, 1 eq.) in THF (10 mL) was added dropwise at −78° C. The mixture was stirred at −78° C. for 20 min. The reaction progress was monitored by TLC (PE:EA=5:1). Upon completion, the reaction was quenched by NH$_4$Cl (sat. aq., 50 mL) and extracted with EA (2×50 mL). The combined organic layers were washed with brine (20 mL), dried over Na$_2$SO$_4$, and concentrated to give a residue. The residue was purified by silica gel chromatography (Petroleum ether:Ethyl acetate (PE:EA)=10:1) to afford 3aR,6S,6aR)-2,2,6-trimethyl-3a,5,6,6a-tetrahydrocyclopenta[d][1,3]dioxol-4-one (2A) (5.2 g, 30.55 mmol, 76% yield) as a colorless oil.

LiHMDS (1.0 M in THF, 49.35 mL, 1.5 eq.) was added dropwise to a mixture of 2A (5.6 g, 32.90 mmol, 1 eq.) and chlorotriethylsilane (9.92 g, 65.80 mmol, 11.19 mL, 2 eq.) in THF (60 mL) at −78° C. The mixture was stirred at −78° C. for 10 min. The reaction progress was monitored by TLC (PE:EA=10:1). Upon completion, the mixture was quenched by NH$_4$Cl (sat. aq., 80 mL) and brine (50 mL), and extracted with MTBE (2×100 mL). The combined organic layers were washed with brine (80 mL), dried over Na$_2$SO$_4$, and concentrated to give a residue. The residue was purified by silica gel chromatography (PE:EA=50:1) to afford [(3aR,6aR)-2,2,6-trimethyl-6,6a-dihydro-3aH-cyclopenta[d][1,3]dioxol-4-yl]oxy-triethyl-silane (3A) (7.9 g, 27.77 mmol, 84% yield) as a colorless oil.

A mixture of 3A (7.9 g, 27.77 mmol, 1 eq.) and Pd(OAc)$_2$ (1.87 g, 8.33 mmol, 0.3 eq.) in DMSO (80 mL) was stirred at 60° C. under O$_2$ atmosphere for 6 h. The reaction progress was monitored by TLC (PE:EA=10:1). Upon completion, the mixture was diluted with water (300 mL) and extracted with MBTE (2×100 mL). The combined organic layers were combined and washed with water (100 mL) and brine (80 mL), dried over anhydrous Na$_2$SO$_4$, and concentrated to give a residue. The residue was purified by silica gel chromatography (PE:EA=5:1) to afford (3aR, 6aR)-2,2,6- trimethyl-3a,6a-dihydrocyclopenta[d][1,3]dioxol-4-one (4A) (3.7 g, 22.00 mmol, 79% yield) as a colorless oil.

A mixture of LiCl (8.48 mg, 200.00 µmol, 4.10 µL, 0.2 eq.), CuI (19.04 mg, 100.00 µmol, 0.1 eq.) in THF (2 mL) was stirred at 0° C. for 10 min. Then a mixture of TMSCl (130.37 mg, 1.20 mmol, 152.30 µL, 1.2 eq.) and 4A (168.19 mg, 1 mmol, 1 eq.) in THF (1 mL) was added dropwise at 0° C., and string was continued at 0° C. for 20 min. Vinylmagnesium bromide (1 M in THF, 1.60 mL, 1.6 eq.) was added dropwise at 0° C., and the mixture was stirred at 0° C. for 30 min. The reaction progress was monitored by TLC (PE:EA=5:1). Upon completion, the mixture was quenched by $NH_4Cl$ (sat. aq., 10 mL) and extracted with EA (2×20 mL). The combined organic layers were washed with brine (20 mL), dried over anhydrous $Na_2SO_4$, and concentrated to give a mixture of 5A and silyl enolate. The mixture was dissolved in acetone (2 mL) and MeOH (2 mL), conc. HCl (0.05 mL) was added, and the mixture was stirred at room temperature (rt) for 10 min. TEA (1 mL) was added to the mixture to quench the reaction. The solvent was removed under reduced pressure to give a residue. The residue was purified by silica gel chromatography (PE/EA=10:1) to afford (3aR,4R,6aR)-2,2,4-trimethyl-4-vinyl-5,6a-dihydro-3aH-cyclopenta[d][1,3]dioxol-6-one (5A) (97 mg, 494.29 µmol, 49% yield) as a colorless oil.

$NaBH_4$ (35.5 mg, 937.62 µmol, 2 eq.) was added to a mixture of 5A (92 mg, 468.81 µmol, 1 eq.) and THF (1 mL) at 0° C. The mixture was stirred at 0° C. for 0.5 h. The reaction progress was monitored by TLC (PE:EA=10:1). Upon completion, the mixture was quenched by acetone (0.5 mL) and then concentrated to give a residue. The residue was diluted with aqueous potassium sodium tartrate (sat. aq., 20 mL) and then extracted with EA (2×20 mL). The combined organic layers were washed with brine (10 mL), dried over anhydrous $Na_2SO_4$, and concentrated to give a residue. The residue was purified by silica gel chromatography (PE:EA=20:1) to afford (3aR,4R,6S,6aS)-2,2,4-trimethyl-4-vinyl-3a,5,6,6a-tetrahydrocyclopenta[d][1,3]dioxol-6-ol (6A) (67 mg, 337.54 µmol, 72% yield) as a colorless oil.

Trifluoromethanesulfonic anhydride (423.21 mg, 1.50 mmol, 247.49 µL, 1.5 eq.) was added to a mixture of 6A (198.26 mg, 1 mmol, 1 eq.) and pyridine (316.40 mg, 4.00 mmol, 322.86 µL, 4 eq.) in DCM (5 mL) at 0° C. The mixture was stirred at 0° C. for 1 h. The reaction progress was monitored by TLC (PE:EA=10:1). The mixture was quenched by ice-water (10 mL) and extracted with DCM (2×15 mL). The combined organic layers were washed with brine (10 mL), dried over anhydrous $Na_2SO_4$, and concentrated to give crude (7A) (330 mg) as a yellow oil, which was used for next step without further purification.

A solution of (4-chloropyrrolo[2,3-d]pyrimidin-7-yl)potassium (7-a) (191.47 mg, 999.03 µmol, 1 eq.) in DMF (1 mL) was added dropwise to a solution of crude 7A (330 mg) in DMF (3 mL) at 0° C. The mixture was stirred at rt for 36 h. The reaction progress was monitored by TLC (PE:EA=5:1). The mixture was diluted with water (20 mL) and extracted with EA (2×20 mL). The combined organic layers were washed with water (20 mL) and brine (30 mL), dried over anhydrous $Na_2SO_4$, and concentrated to give a residue. The residue was purified by silica gel chromatography (PE:EA=10:1) to afford 7-[(3aR,4R,6R,6aS)-2,2,4-trimethyl-4-vinyl-3a,5,6,6a-tetrahydrocyclopenta[d][1,3]dioxol-6-yl]-4-chloro-pyrrolo[2,3-d]pyrimidine (8A) (134 mg, 397.41 µmol, 40% yield) as a colorless gum.

A mixture of 8A (700 mg, 2.10 mmol, 1 eq.) and $NH_3 \cdot H_2O$ (28.00 g, 199.74 mmol, 30.77 mL, 95.25 eq.) in dioxane (16 mL) was stirred at 100° C. for 60 h. The reaction progress was monitored by LCMS. Upon completion, the mixture was concentrated under reduced pressure to give a residue. The residue was purified by silica gel chromatography (PE:EA=6:1, 200 mL, DCM:MeOH=20:1, 200 mL) to give 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (490 mg, 1.56 mmol, 74% yield) as a yellow foam.

To a solution of 9A (314.38 mg, 1 mmol, 1 eq.) in THF (5 mL) was added 9-BBN dimer (532.44 mg, 2.20 mmol, 2.2 eq.). The mixture was stirred at 50° C. for 2 h and then cooled to 20° C. $K_3PO_4$ (1.06 g, 5.00 mmol, 5 eq.). To the mixture was added $H_2O$ (0.5 mL), and the mixture was stirred at rt for 0.5 h. 3-bromo-7-iodo-quinolin-2-amine (Qa) (488.55 mg, 1.40 mmol, 1.4 eq.) and Pd(dppf)Cl₂ (73.17 mg, 100.00 µmol, 0.1 eq.) were added to the mixture. The mixture was stirred at 60° C. for 12 h. The reaction progress was monitored by LCMS. Upon completion, the mixture was diluted with brine (20 mL) and extracted with EA (3×30 mL). The combined organic layers were dried over anhydrous $Na_2SO_4$ and concentrated to give a residue. The residue was purified by silica gel chromatography (EA=100%, 200 mL; DCM:MeOH=20:1, 500 mL) to afford the crude product, which was further purified by prep-HPLC (column: Phenomenex Gemini-NX 150*30 mm*5 um; mobile phase: [water (0.04% $NH_3H_2O$*10 mM $NH_4HCO_3$)-ACN]; B %: 42%-72%, 8 min) to afford 7-[(E)-2-[(3aR,4R,6R,6aS)-6-(4-aminopyrrolo[2,3-d]pyrimidin-7-yl)-2,2,4-trimethyl-3a,5,6,6a-tetrahydrocyclopenta[d][1,3]dioxol-4-yl]vinyl]-3-bromo-quinolin-2-amine (10A) (350 mg, 653.67 µmol, 65% yield) as a yellow foam.

A mixture of 10A (150 mg, 280.15 µmol, 1 eq.) in MeOH (15 mL) and HCl (4 M, 4 mL, 57.11 eq.) was stirred at rt for 12 h. The reaction progress was monitored by LCMS. Upon completion, the mixture was concentrated under reduced pressure to afford a residue. The residue was suspended in MeOH (4 mL) and neutralized by $NH_4OH$ (aq., 25%) to reach pH 8.0. The solid was dissolved first and then precipitated again. The resulting suspension was filtered and the collected solid was washed with water to afford (1S,2R,3R,5R)-3-[(E)-2-(2-amino-3-bromo-7-quinolyl)vinyl]-5-(4-aminopyrrolo[2,3-d]pyrimidin-7-yl)-3-methyl-cyclopentane-1,2-diol (1) (130 mg, 262.43 µmol, 94% yield) as an off-white solid. LCMS: (ESI): m/z calcd. for $C_{23}H_{26}BrN_6O_2$ 497.13 [M+H]⁺, found 497.1. ¹H NMR (400 MHz, DMSO-$d_6$) δ: 8.32 (s, 1H), 8.03 (s, 1H), 7.58 (d, J=8.2 Hz, 1H), 7.33 (s, 1H), 7.27 (d, J=3.5 Hz, 1H), 7.12 (hr d, J=8.4 Hz, 1H), 6.91 (hr s, 2H), 6.56 (hr s, 2H), 6.53 (d, J=3.3 Hz, 1H), 4.94-4.83 (m, 2H), 4.60 (d, J=5.5 Hz, 1H), 4.39 (q, J=6.4 Hz, 1H), 3.77 (t, J=5.7 Hz, 1H), 2.83-2.59 (m, 2H), 1.96-1.66 (m, 4H), 1.10 (s, 3H).

Example 2

Compound 2

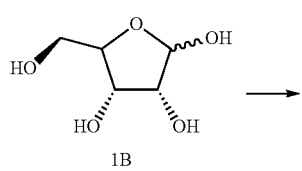

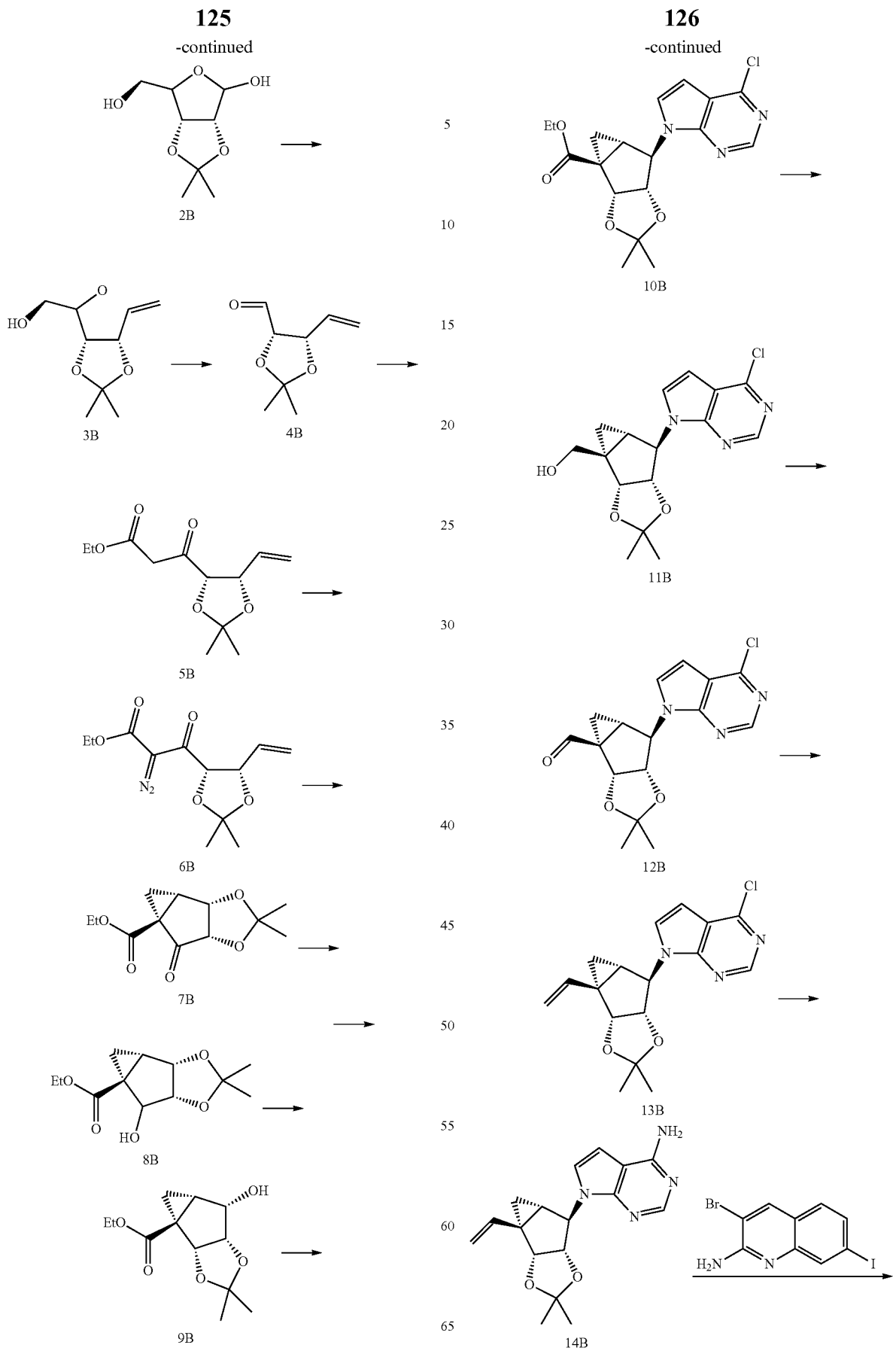

-continued

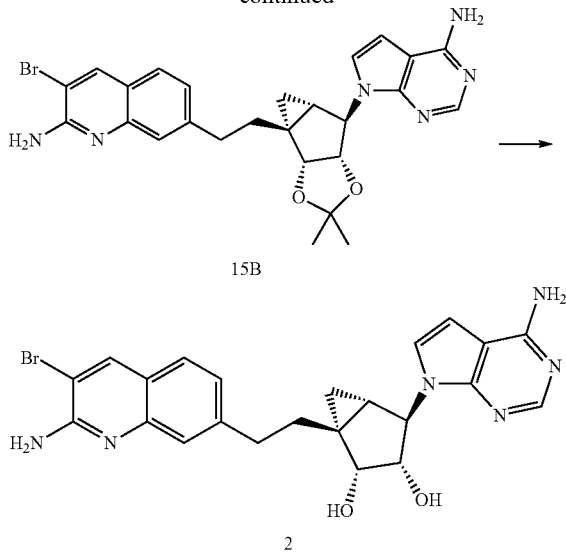

15B

2

To a solution of 1B (50 g, 333.04 mmol, 1 eq.) in acetone (500 mL) was added 2,2-dimethoxypropane (36.42 g, 349.70 mmol, 42.85 mL, 1.05 eq.) and TsOH.H$_2$O (633.51 mg, 3.33 mmol, 0.01 eq.) in one portion at 25° C. under N$_2$. The mixture was stirred at 25° C. for 12 h. The mixture was neutralized by solid NaHCO$_3$ to reach PH 8.0 and then filtrated. The filtrate was concentrated to give a residue as brown oil. The residue was purified by column chromatography (SiO$_2$, PE:EA=5:1 to 1:1) to give 2B (55 g, 274.72 mmol, 82.49% yield, 95% purity) as a brown oil.

To a solution of Ph$_3$PMeBr (88.32 g, 247.25 mmol, 2.85 eq.) in THF (800 mL) was added t-BuOK (32.79 g, 277.61 mmol, 95% purity, 3.2 eq.) at 0° C. The mixture was stirred at 0° C. for 0.5 h and then at 20° C. for 1 h. A solution of 2B in THF (200 mL) was added dropwise to the mixture at 0° C. during a period of 0.5 h, and the mixture was stirred at 20° C. for an additional 12 h. Upon completion, the mixture was diluted with H$_2$O (400 mL) and EA (500 mL). The mixture was extracted with EA (2×200 mL). The combined organic phase was washed with brine (100 mL), dried over anhydrous Na$_2$SO$_4$, filtered and concentrated in vacuum to give a residue. The residue was purified by column chromatography (SiO$_2$, PE:EA=5:1 to 1:1) to give 3B (25 g, crude) as a brown oil.

To a mixture of 3B in DCM (30 mL) was added a solution of NaIO$_4$ (3.41 g, 15.94 mmol, 883.20 µL, 1 eq.) in H$_2$O (20 mL) at 25° C., and the mixture was stirred at 25° C. for 1 h. Upon completion, the mixture was diluted with DCM (60 mL) and water (50 mL). The aqueous phase was extracted with DCM (2×20 mL). The combined organic phase was washed with brine (50 mL), dried over anhydrous Na$_2$SO$_4$, filtered and concentrated in vacuum. The residue was purified by column chromatography (SiO$_2$, PE:EA=15:1 to 5:1) to give 4B (2 g, 12.81 mmol, 80.34% yield) as a brown oil.

To a mixture of 4B (1.2 g, 7.68 mmol, 1 eq.) in anhydrous DCM (8 mL) was added SnCl$_2$ (174.83 mg, 922.02 µmol, 23.92 µL, 0.12 eq.) and a solution of ethyl 2-azidoacetate (1.09 g, 8.45 mmol, 1.19 mL, 1.1 eq.) in DCM (5 mL) at 0° C. The reaction was stirred at 25° C. for 1 h and then filtrated through a pad of Celite. The filtrate was concentrated to give a residue as a brown oil. The residue was purified by column chromatography (SiO$_2$, PE:EA=50:1 to 15:1) to give 5B (1.2 g, 4.46 mmol, 58.02% yield, 90% purity) as a brown oil.

To a solution of 5B (1.2 g, 4.95 mmol, 1 eq.) and N-diazo-4-methyl-benzenesulfonamide (976.84 mg, 4.95 mmol, 1 eq.) in CH$_3$CN (10 mL) was added TEA (1.00 g, 9.91 mmol, 1.38 mL, 2 eq.) dropwise at 0° C. The reaction was stirred at 0° C. for 0.5 h and then at 25° C. for another 1.5 h. The mixture was diluted with EA (20 mL) and water (10 mL). The organic layer was separated and concentrated under reduce pressure to give a residue as a brown oil. The residue was purified by column chromatography (SiO$_2$, PE:EA=50:1 to 20:1) to give 6B (1 g, 3.35 mmol, 67.73% yield, 90% purity) as a brown oil.

To a solution of 6B (400.00 mg, 1.49 mmol, 1 eq.) in toluene (4 mL) was added CuI (14.20 mg, 74.55 µmol, 0.05 eq.) at 25° C. The reaction was stirred at 110° C. for 12 h and then diluted with EA (60 mL) and water (40 mL). The aqueous phase was extracted with EA (2×20 mL). The combined organic phase was washed with brine (15 mL), dried over anhydrous Na$_2$SO$_4$, filtered and concentrated in vacuum. The residue was purified by column chromatography (SiO$_2$, PE:EA=60:1 to 10:1) to give 7B (200 mg, 832.46 µmol, 27.92% yield) as a brown oil.

To a solution of 7B (0.22 g, 915.71 µmol, 1 eq.) in MeOH (6 mL) was added NaBH$_4$ (34.64 mg, 915.71 µmol, 1 eq.) at 25° C. The reaction was stirred at 25° C. for 1 h. Acetone (1 mL) was added, and the mixture was stirred for 5 min. The reaction was concentrated in vacuum to give a residue. The residue was purified by column chromatography (SiO$_2$, PE:EA=8:1 to 2:1) to give 8B (200 mg, 825.53 µmol, 90.15% yield) as a brown oil.

To a solution of 8B (0.2 g, 832.46 µmol, 1 eq.) in acetone (8 mL) was added TsOH.H$_2$O (79.17 mg, 416.23 µmol, 0.5 eq.) at 25° C. The reaction was stirred at 80° C. for 8 h. TEA (0.5 mL) was added to the mixture. The mixture was diluted with EA (60 mL) and water (40 mL). The aqueous phase was extracted with EA (2×20 mL). The combined organic phase was washed with brine (15 mL), dried over anhydrous Na$_2$SO$_4$, filtered and concentrated in vacuum. The residue was purified by column chromatography (SiO$_2$, PE:EA=6:1 to 2:1) to give 9B (160 mg, crude) as a brown oil.

To a solution of triphenyl phosphine (2.60 g, 9.91 mmol, 2 eq.) and 4-chloro-7H-pyrrolo[2,3-d]pyrimidine (1.52 g, 9.91 mmol, 2 eq.) in THF (20 mL) was added diisopropylazodicarboxylate (2.00 g, 9.91 mmol, 1.93 mL, 2 eq.) at 20° C. The mixture was stirred at 20° C. for 0.5 h. The mixture was added to a solution of 9B (1.2 g, 4.95 mmol, 1 eq.) in THF (20 mL) dropwise at 20° C. The reaction was stirred at 20° C. for 2 h, and then concentrated in vacuum to give a residue. The residue was purified by column chromatography (SiO$_2$, PE:EA=8:1 to 2:1) to give 10A (1.5 g, crude), which was then purified by prep-HPLC (Neutral condition) (column: Xtimate C18 150*25 mm*5 um; mobile phase: [water (10 mM NH$_4$HCO$_3$)-ACN]; B %: 63%-63%, 10 min) to give 10A (0.8 g, 2.08 mmol, 41.89% yield, 98% purity) as a brown solid.

To a solution of 10A (0.93 g, 2.46 mmol, 1 eq.) in DCM (20 mL) was added DIBAL-H (1 M in toluene, 6.15 mL, 2.5 eq.) at −78° C. The reaction was stirred at −78° C. for 1.5 h. The reaction was treated sequentially with H$_2$O (1 mL) and NaOH (aq. 2M, 1 mL) and stirred for 5 min. Additional H$_2$O (1 mL) was added, and the mixture was stirred for another 5 min. The mixture was filtrated through a pad of Celite and concentrated in vacuum to give 11A (830 mg, crude) as a brown oil, which was used for the next step without further purification.

To a solution of 11B (100 mg, 297.81 µmol, 1 eq.) in CH$_3$CN (3 mL) was added IBX (125.09 mg, 446.71 µmol, 1.5 eq.) at 25° C. The reaction was stirred at 80° C. for 1.5 h and then concentrated in vacuum to give 12B (100 mg, crude) as a brown oil. The residue was used for the next step without further purification.

To a solution of Ph₃PMeBr (267.57 mg, 749.02 µmol, 2.5 eq.) in THF (2 mL) was added t-BuOK (84.05 mg, 749.02 µmol, 2.5 eq.) at 0° C. The reaction was stirred at 0° C. for 10 min, and then at 20° C. for 20 min. A solution of 12B (100 mg, 299.61 µmol, 1 eq.) in THF (1.5 mL) was added dropwise at 0° C., and the reaction was stirred at 20° C. for another 0.5 h. Upon completion, the reaction was diluted with H₂O (20 mL) and EA (50 mL). The aqueous phase was extracted with EA (60 mL). The combined organic phase was washed with brine (10 mL), dried over anhydrous Na₂SO₄, filtered and concentrated in vacuum. The residue was purified by column chromatography (SiO₂, PE:EA=12:1 to 5:1) to give 13B (90 mg, 271.25 µmol, 90.54% yield, 100% purity) as a brown oil.

A mixture of 13B (220 mg, 663.06 µmol, 1 eq.) and NH₃·H₂O (24.38 g, 194.75 mmol, 26.79 mL, 28% purity, 293.71 eq.) in dioxane (10 mL) was stirred at 100° C. for 72 h in a steel sealed tube. The mixture was concentrated in vacuum to give a residue as a brown oil. The residue was purified by column chromatography (SiO₂, DCM:MeOH=200:1 to 100:2) to give 13B (350 mg, 1.09 mmol, 81.96% yield, 97% purity, from parallel 2 batches) as a brown oil.

To a solution of 14B (350 mg, 1.12 mmol, 1 eq.) in THF (12 mL) was added 9-BBN (solid, dimer, 542.35 mg, 2.24 mmol, 2 eq.) at 20° C. The mixture was degassed and then stirred at 50° C. for 2 h. The reaction was cooled to 20° C. and treated with a solution of K₃PO₄ (1.19 g, 5.60 mmol, 5 eq.) in H₂O (1.2 mL). Stirring was continued for another 30 min. To the mixture were added 3-bromo-7-iodo-quinolin-2-amine (586.51 mg, 1.68 mmol, 1.5 eq.) and Pd(dppf)Cl₂ (81.99 mg, 112.05 µmol, 0.1 eq.). The mixture was degassed, stirred at 60° C. for another 15 h, and diluted with EA (50 mL) and water (30 mL). The aqueous phase was extracted with EA (50 mL). The combined organic phase was washed with brine (30 mL), dried over anhydrous Na₂SO₄, filtered and concentrated in vacuum to give a residue as a brown oil. The residue was purified by column chromatography (SiO₂, DCM:MeOH=200:1 to 20:1) to give 15B (360 mg, 611.84 µmol, 54.61% yield, 91% purity) as a brown solid. The product was then purified by reversed-phase HPLC (Neutral condition) (column: Xtimate C18 150*25 mm*5 um; mobile phase: [water (10 mM NH₄HCO₃)-ACN]; B %: 46%-76%, 11 min) to give 15B (350 mg, 647.14 µmol, 80.58% yield, 99% purity) as a white solid.

To a solution of 15B (350 mg, 653.67 µmol, 1 eq.) in THF (10 mL) was added HCl (aq., 4 M, 5 mL, 30.60 eq.) at 20° C. The reaction was stirred at 20° C. for 5 h and then concentrated in vacuum to give crude product (315 mg, HCl salt) as a brown oil. The crude product (280 mg) was purified by reversed-phase HPLC (column: Agela DuraShell 150 mm_25 mm_5 um; mobile phase: [water (0.05% HCl)-ACN]; B %: 0%-30%, 8 min) to give 2 (160 mg, 322.99 µmol, 61.35% yield) as a white solid. MS: (ESI): m/z calcd. for $C_{23}H_{24}BrN_6O_2$ 495.11 [M+H]⁺, found 495.3. ¹H NMR (400 MHz, CD₃OD) δ: 8.79 (s, 1H), 8.27 (s, 1H), 7.81 (d, J=8.3 Hz, 1H), 7.65 (s, 1H), 7.51 (dd, J=1.4, 8.2 Hz, 1H), 7.38 (d, J=3.8 Hz, 1H), 6.94 (d, J=3.8 Hz, 1H), 5.05 (s, 1H), 4.67 (d, J=6.8 Hz, 1H), 3.96 (d, J=6.8 Hz, 1H), 3.20-2.96 (m, 2H), 2.41-2.26 (m, 1H), 1.88 (ddd, J=6.3, 11.0, 13.9 Hz, 1H), 1.46-1.33 (m, 2H), 0.74-0.55 (m, 1H).

Example 2

Compounds 3 and 4

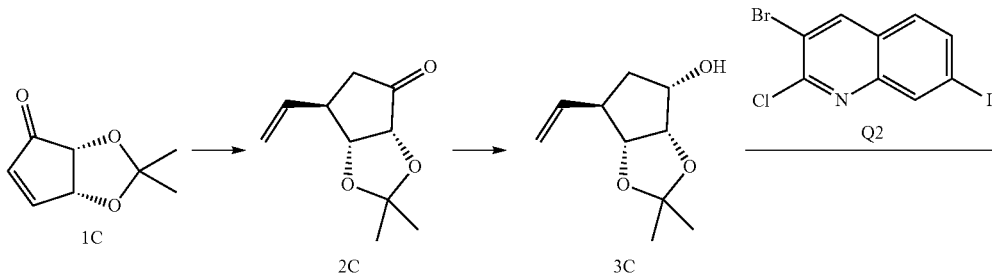

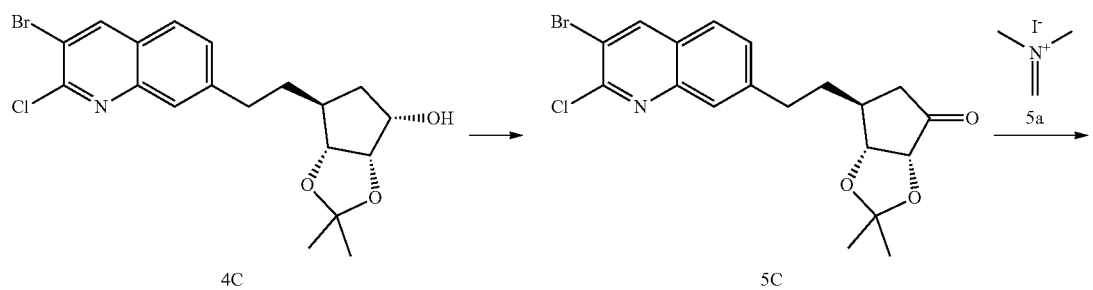

-continued
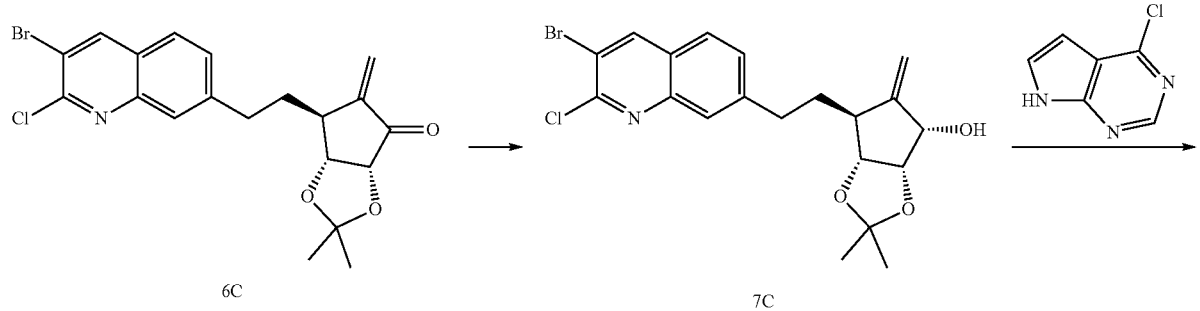
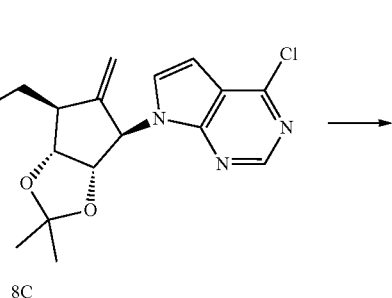
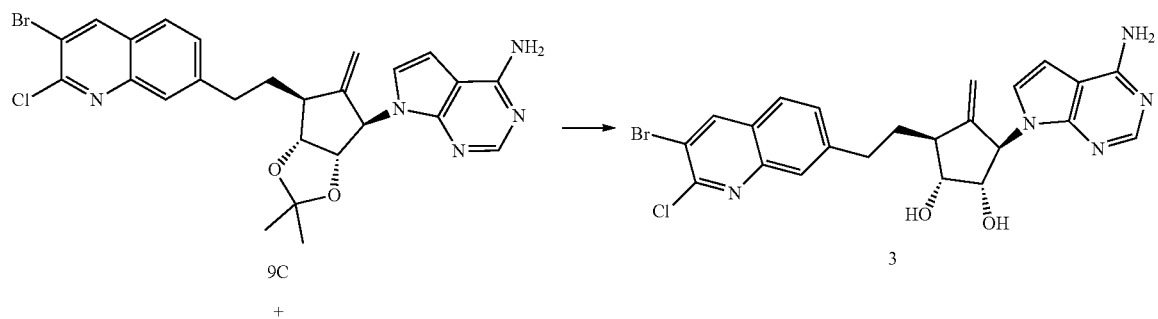
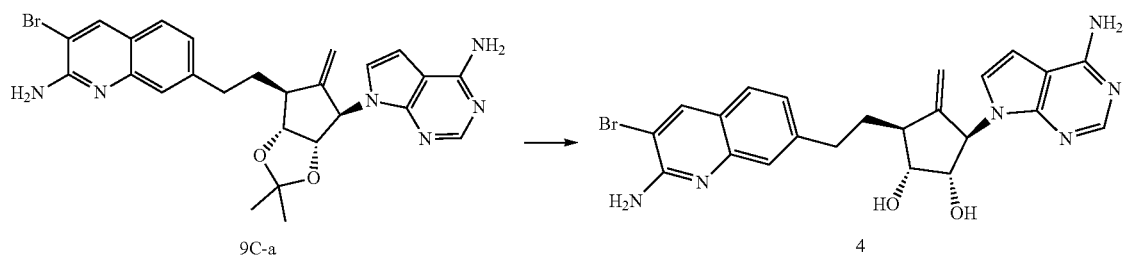
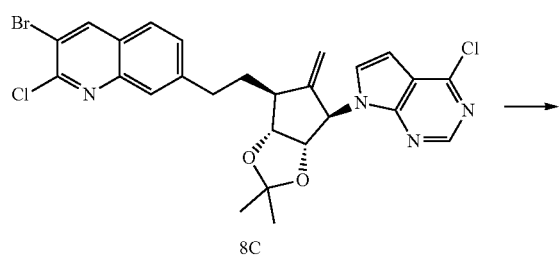

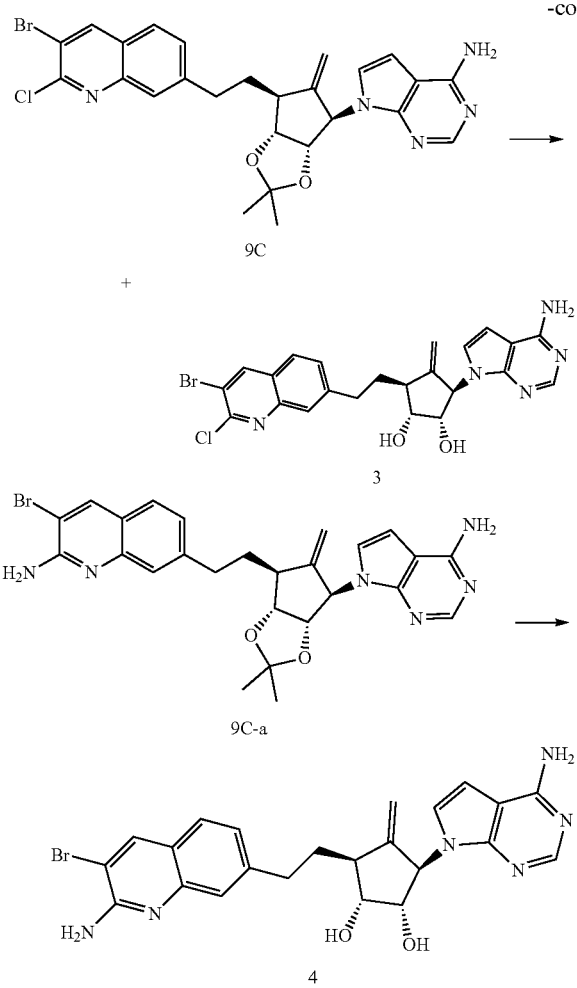

TMEDA (5.65 g, 48.65 mmol, 7.34 mL, 1.5 eq.) was added to a mixture of CuI (339.73 mg, 1.78 mmol, 0.055 eq.) in THF (125 mL) at 0° C. The mixture was stirred at 0° C. for 5 min, and then cooled to −78° C. A solution of vinylmagnesium bromide (1 M in THF, 48.65 mL, 1.5 eq.) was added, and the mixture was stirred at −78° C. for 20 min. TMSCl (4.23 g, 38.92 mmol, 4.94 mL, 1.2 eq.) was added, followed by a solution of 1C (5 g, 32.43 mmol, 1 eq.) in THF (35 mL). The mixture was stirred at −78° C. for 3 h. The reaction progress was monitored by TLC (PE:EA=5:1). Upon completion, the reaction was quenched by NH$_4$Cl (sat., aq., 50 mL), and the mixture was extracted with EA (2×100 mL). The combined organic layers were washed with brine (2×100 mL), dried over Na$_2$SO$_4$, filtered and concentrated to give a residue. The residue was purified by column chromatography (SiO$_2$, PE:EA=20:1 to 10:1) to afford 2C (3.8 g, 18.77 mmol, 57% yield) as a yellow oil.

NaBH$_4$ (151.3 mg, 4.00 mmol, 2 eq.) was added to a mixture of 2C (364.4 mg, 2 mmol, 1 eq.) in MeOH (30 mL) at 0° C. The mixture was stirred at 0° C. for 0.5 h. The reaction progress was monitored by TLC (PE:EA=5:1). Upon completion, the mixture was quenched by acetone (5 mL) and then concentrated under reduced pressure to afford a residue. The residue was diluted with brine (50 mL) and then extracted with EA (2×50 mL). The combined organic layers were dried over anhydrous Na$_2$SO$_4$, filtered and concentrated to afford a crude product. The crude product was purified by silica gel chromatography (PE:EA=20:1) to afford 3C (260.0 mg, 1.41 mmol, 71% yield) as a colorless oil.

9-BBN dimer (181.5 mg, 750.00 μmol, 1.5 eq.) was added to a mixture of 3C (92.1 mg, 0.5 mmol, 1 eq.) in THF (5 mL). The mixture was stirred at 50° C. under Ar atmosphere for 1 h. The mixture was cooled to it, and then a solution of K$_3$PO$_4$ (530.7 mg, 2.50 mmol, 5 eq.) in H$_2$O (0.5 mL) was added. After stirring at rt for 0.5 h, 3-bromo-2-chloro-7-iodo-quinoline (Q2, 221.0 mg, 600.00 μmol, 1.2 eq.) and Pd(dppf)Cl$_2$ (36.6 mg, 50.00 μmol, 0.1 eq.) were added. The flask was degassed for several times and then stirred at 50° C. under Ar atmosphere for 11.5 h. The reaction progress was monitored by TLC (PE:EA=5:1). Upon completion, the mixture was diluted with brine (10 mL) and extracted with EA (2×20 mL). The combined organic layers were dried over anhydrous Na$_2$SO$_4$, filtered and concentrated to afford a residue. The residue was purified by silica gel chromatography (PE:EA=3:1) to afford 4C (146 mg, 342.14 μmol, 68% yield) as a yellow gum.

To a solution of 4C (0.2 g, 468.68 μmol, 1 eq.) in ACN (4 mL) was added IBX (196.86 mg, 703.02 μmol, 1.5 eq.) at 20° C., and the reaction was stirred at 60° C. for 2 h. The mixture was then cooled to 20° C. and filtered. The collected solid was washed with acetonitrile. The filtrate was concentrated under reduced pressure to afford a residue. The residue was purified by column chromatography (SiO$_2$, PE:EA=10:1 to 2:1) to give 5C (0.17 g, 400.27 μmol, 85.40% yield) as a white solid.

To a solution of 5C (200 mg, 470.90 μmol, 1 eq.) in THF (4 mL) was added LDA (2 M in THF, 0.3 mL, 1.27 eq.) at −78° C. The reaction was stirred at −78° C. for 0.5 h, and then dimethyl(methylene)ammonium iodide (5a) (348.48 mg, 1.88 mmol, 4 eq.) was added. The mixture was stirred at −78° C. for 0.5 h and then warmed to rt and stirred for 11.5 h. Then CH$_3$I (0.89 g, 6.27 mmol, 390.35 μL, 13.32 eq.) was added at rt, and the mixture was stirred for another 3 h. The reaction progress was monitored by TLC (PE:EA=3:1). Upon completion, the mixture was quenched by 10% NaHCO$_3$ (aq., 5 mL) and stirred for 0.5 h. The mixture was extracted with EA (2×50 mL). The combined organic layers were washed with 10% NaHCO$_3$ (aq., 20 mL), brine (20 mL), dried with anhydrous Na$_2$SO$_4$, filtered and concentrated in vacuum. The residue was purified by vacuum silica gel column chromatography (SiO$_2$, PE:EA=15:1 to 5:1) to give 6C (120 mg, 219.82 μmol, 46.68% yield, 80% purity) as a white solid.

To a solution of 6C (854 mg, 1.96 mmol, 1 eq.) in MeOH (10 mL) and THF (10 mL) was added CeCl$_3$.7 H$_2$O (801.43 mg, 2.15 mmol, 204.45 μL, 1.1 eq.) at −78° C. The mixture was stirred at the same temperature for 10 min, then NaBH$_4$ (81.38 mg, 2.15 mmol, 1.1 eq.) was added. The mixture was stirred at −78° C. and stirred for another 10 min. The mixture was warmed to 0° C. and stirred at 0° C. for 10 min. The reaction was quenched with NH$_4$Cl (sat., aq., 5 mL), and the mixture was extracted with EA (2×50 mL). The combined organic layers were washed with brine (20 mL), dried with anhydrous Na$_2$SO$_4$, filtered and concentrated in vacuum to give a residue. The residue was purified by column chromatography (SiO$_2$, PE:EA=8:1 to 3:1) to give 7C (654 mg, 894.38 μmol, 45.7% yield, 60% purity) as a brown solid.

To a solution of triphenyl phosphine (896.73 mg, 3.42 mmol, 2.5 eq.), 4-chloro-7H-pyrrolo[2,3-d]pyrimidine (315.02 mg, 2.05 mmol, 1.5 eq.), and 7C (600 mg, 1.37 mmol, 1 eq.) in THF (12 mL) was added DIAD (636.02 mg, 3.15 mmol, 611.56 μL, 2.3 eq.) at 20° C. After stirring at rt for 5 h, the mixture was concentrated in vacuum to give a residue. The residue was purified by column chromatography (SiO$_2$, PE:EA=20:1 to 8:1) to give 8C (600 mg, 1.02 mmol, 74.8% yield, 98% purity) as a brown solid.

8C (500 mg, 870.63 μmol, 1 eq.) was dissolved in NH$_3$.H$_2$O (10 mL) and dioxane (10 mL) at 20° C. in an autoclave. The mixture was stirred at 140° C. for 48 h and then concentrated to give a brown residue. The residue was purified by column chromatography (SiO$_2$, DCM: MeOH=40:1 to 10:1) to give 9C (70 mg, 14.49% yield) and 9C-a (280 mg, 449.73 μmol, 51.6% yield, 86% purity).

To a solution of 9C (60 mg, 108.13 μmol, 1 eq.) in THF (3 mL) was added HCl (4 M, 1.50 mL eq.) at 20° C. The mixture was stirred at 20° C. for 4 h and then concentrated. The residue was neutralized by NH$_3$.H$_2$O to reach pH ~8 and then purified by prep-HPLC (basic condition, column: Phenomenex Gemini-NX 150*30 mm*5 um; mobile phase: [water (0.04% NH$_3$H$_2$O+10 mM NH$_4$HCO$_3$)-ACN]; B %: 31%-71%, 8 min) to give 3 (35 mg, 67.72 μmol, 62.6% yield, 99.6% purity) as a white solid. LCMS: (ESI): m/z calcd. for C$_{23}$H$_{22}$BrClN$_5$O$_2$, 516.1 [M+H]$^+$, found 516.1. $^1$H NMR (400 MHz, DMSO) δ: 8.92 (s, 1H), 8.03 (s, 1H), 7.98 (d, J=8.3 Hz, 1H), 7.88 (s, 1H), 7.68 (dd, J=1.5, 8.5 Hz, 1H), 7.12 (d, J=3.5 Hz, 1H), 6.95 (br s, 2H), 6.58 (d, J=3.5 Hz, 1H), 5.44 (br d, J=9.3 Hz, 1H), 5.03 (d, J=6.8 Hz, 1H), 4.98 (br s, 1H), 4.91 (d, J=3.5 Hz, 1H), 4.44-4.34 (m, 1H), 4.31 (br s, 1H), 3.96 (br s, 1H), 3.31-3.24 (m, 1H), 3.07-2.85 (m, 2H), 2.07-1.77 (m, 2H).

To a solution of 9C-a (80 mg, 149.41 μmol, 1 eq.) in THF (4.5 mL) was added HCl (4 M, 2.25 mL, 55.49 eq.) at 20° C. The mixture was stirred at 20° C. for 4 h and then concentrated. The residue was neutralized by NH$_3$.H$_2$O to reach pH ~8 and then purified by prep-HPLC (basic condition, column: Phenomenex Gemini-NX 150*30 mm*5 um; mobile phase: [water (0.04% NH$_3$H$_2$O+10 mM NH$_4$HCO$_3$)-ACN]; B %: 25%-55%, 8 min) to give 4 (45 mg, 89.48 μmol, 60% yield, 98.5% purity) as white solid. LCMS: (ESI): m/z calcd. for C$_{23}$H$_{24}$BrN$_6$O$_2$, 495.1, 497.1 [M+H]$^+$, found 495.2, 497.2. $^1$H NMR (400 MHz, CD$_3$OD) δ: 8.28 (s, 1H), 8.06 (s, 1H), 7.59 (d, J=8.3 Hz, 1H), 7.45 (s, 1H), 7.24 (d, J=8.0 Hz, 1H), 7.09 (d, J=3.5 Hz, 1H), 6.64 (d, J=3.8 Hz, 1H), 5.57 (br d, J=9.3 Hz, 1H), 5.10 (br s, 1H), 4.54 (s, 1H), 4.44 (dd, J=4.9, 9.2 Hz, 1H), 4.08 (br d, J=2.8 Hz, 1H), 3.07-2.85 (m, 2H), 2.69 (br s, 1H), 2.15-1.84 (m, 2H).

Example 3

Compounds 5 and 6

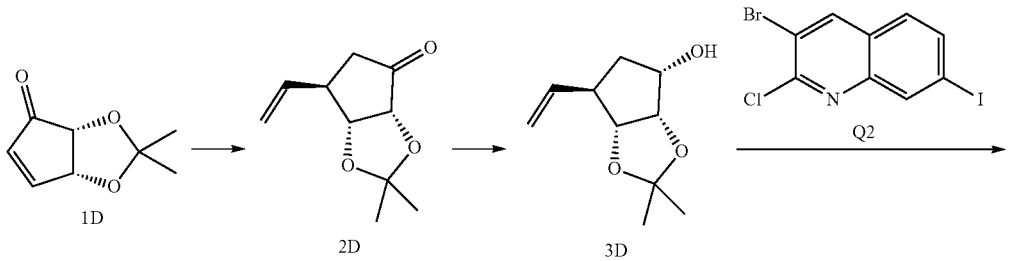

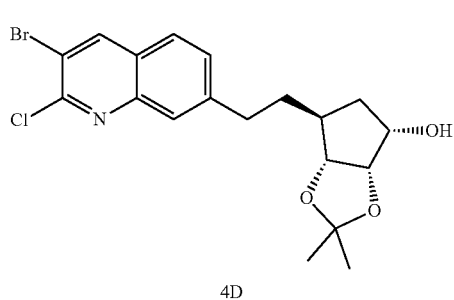
4D
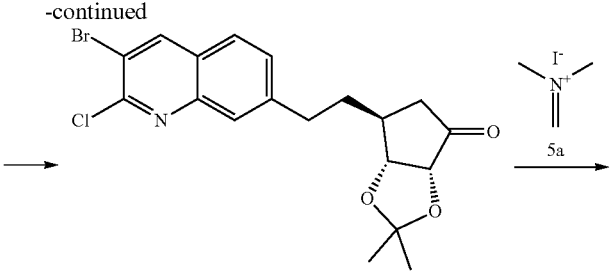
5D
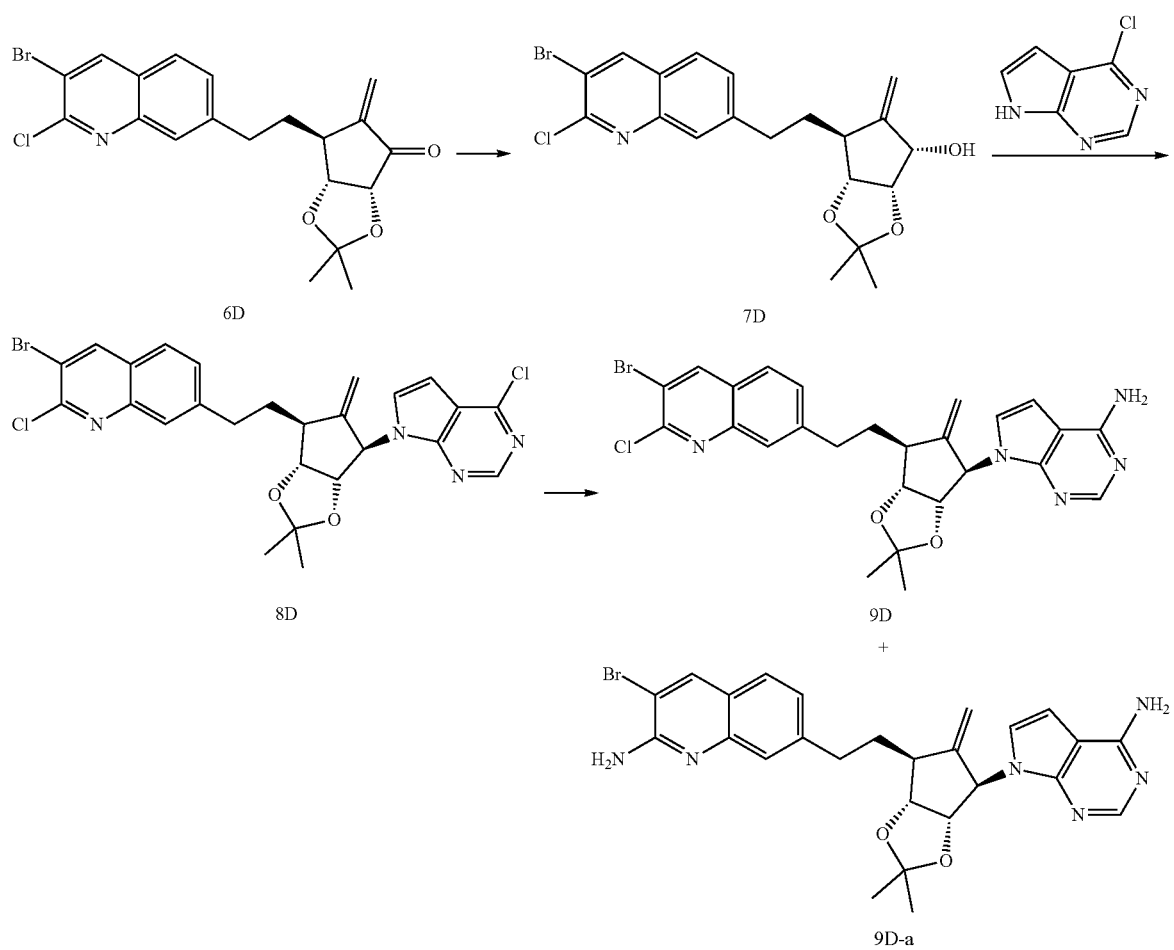
6D
7D
8D
9D
+
9D-a
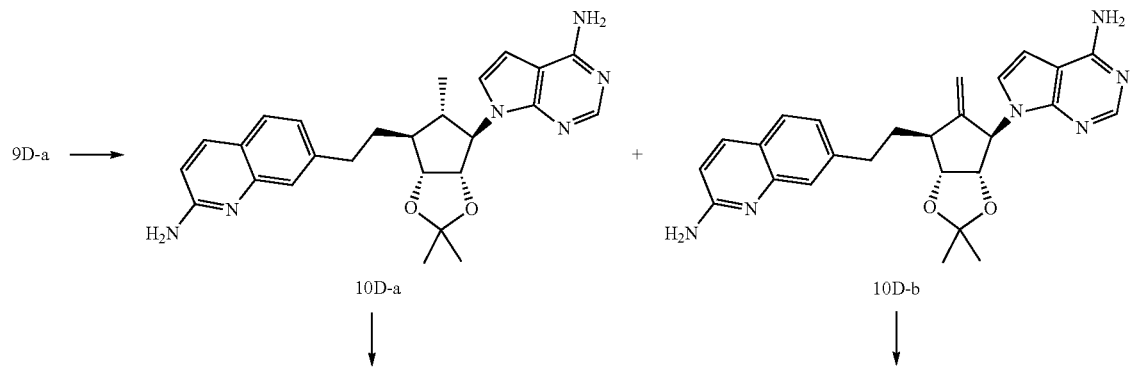
9D-a →
10D-a
10D-b -continued

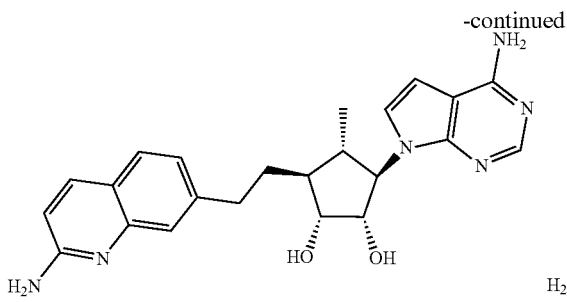

5

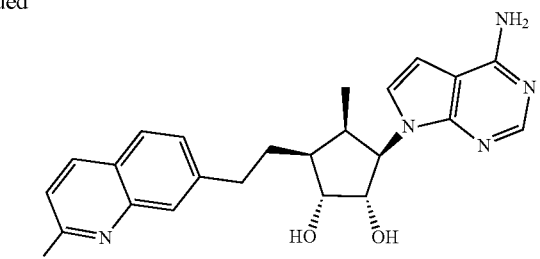

6

TMEDA (5.65 g, 48.65 mmol, 7.34 mL, 1.5 eq.) was added to a mixture of CuI (339.73 mg, 1.78 mmol, 0.055 eq.) in THF (125 mL) at 0° C. The mixture was stirred at 0° C. for 5 min and then cooled to −78° C. A solution of vinylmagnesium bromide (1 M in THF, 48.65 mL, 1.5 eq.) was added, and the mixture was stirred at −78° C. for 20 min. TMSCl (4.23 g, 38.92 mmol, 4.94 mL, 1.2 eq.) was added, followed by a solution of ID (5 g, 32.43 mmol, 1 eq.) in THF (35 mL). The mixture was stirred at −78° C. for 3 h. The reaction progress was monitored by TLC (PE:EA=5:1). Upon completion, the reaction was quenched by NH$_4$Cl (sat., aq., 50 mL), and the mixture was extracted with EA (2×100 mL). The combined organic layers were washed with brine (2×100 mL), dried over Na$_2$SO$_4$, filtered and concentrated to give a residue. The residue was purified by column chromatography (SiO$_2$, PE:EA=20:1 to 10:1) to afford 2D (3.8 g, 18.77 mmol, 57% yield) as a yellow oil.

NaBH$_4$ (151.3 mg, 4.00 mmol, 2 eq.) was added to a mixture of 2D (364.4 mg, 2 mmol, 1 eq.) in MeOH (30 mL) at 0° C. The mixture was stirred at 0° C. for 0.5 h. The reaction progress was monitored by TLC (PE:EA=5:1). Upon completion, the mixture was quenched by acetone (5 mL) and then concentrated under reduced pressure to afford a residue. The residue was diluted with brine (50 mL) and then extracted with EA (2×50 mL). The combined organic layers were dried over anhydrous Na$_2$SO$_4$, filtered and concentrated to afford a crude product. The crude product was purified by silica gel chromatography (PE:EA=20:1) to afford 3D (260.0 mg, 1.41 mmol, 71% yield) as a colorless oil.

9-BBN dimer (181.5 mg, 750.00 µmol, 1.5 eq.) was added to a mixture of 3D (92.1 mg, 0.5 mmol, 1 eq.) in THF (5 mL). The mixture was stirred at 50° C. under Ar for 1 h. The mixture was cooled to rt, and then a solution of K$_3$PO$_4$ (530.7 mg, 2.50 mmol, 5 eq.) in H$_2$O (0.5 mL) was added. After stirring at rt for 0.5 h, Q2 (221.0 mg, 600.00 µmol, 1.2 eq.) and Pd(dppf)Cl$_2$ (36.6 mg, 50.00 µmol, 0.1 eq.) were added. The flask was degassed for several times and then stirred at 50° C. under Ar for 11.5 h. The reaction progress was monitored by TLC (PE:EA=5:1). Upon completion, the mixture was diluted with brine (10 mL) and extracted with EA (2×20 mL). The combined organic layers were dried over anhydrous Na$_2$SO$_4$, filtered and concentrated to afford a residue. The residue was purified by silica gel chromatography (PE:EA=3:1) to afford 4D (146 mg, 342.14 µmol, 68% yield) as a yellow gum.

To a solution of 4D (0.2 g, 468.68 µmol, 1 eq.) in ACN (4 mL) was added IBX (196.86 mg, 703.02 µmol, 1.5 eq.) at 20° C., and the mixture was stirred at 60° C. for 2 h. The mixture was then cooled to 20° C. and filtered. The collected solid was washed with ACN. The filtrate was concentrated under reduced pressure to afford a residue. The residue was purified by column chromatography (SiO$_2$, PE:EA=10:1 to 2:1) to give 5D (0.17 g, 400.27 µmol, 85.40% yield) as a white solid.

To a solution of 5D (200 mg, 470.90 µmol, 1 eq.) in THF (4 mL) was added LDA (2 M in THF, 0.3 mL, 1.27 eq.) at −78° C. The mixture was stirred at −78° C. for 0.5 h, and then dimethyl(methylene)ammonium iodide (5a) (348.48 mg, 1.88 mmol, 4 eq.) was added. The mixture was stirred at −78° C. for 0.5 h. The mixture was then warmed to rt and stirred for 11.5 h. CH$_3$I (0.89 g, 6.27 mmol, 390.35 µL, 13.32 eq.) was added at rt, and the mixture was stirred for another 3 h. The reaction progress was monitored by TLC (PE:EA=3:1). Upon completion, the reaction was quenched by 10% NaHCO$_3$ (aq., 5 mL) and stirred for 0.5 h. The mixture was extracted with EA (2×50 mL). The combined organic layers were washed with 10% NaHCO$_3$ (aq., 20 mL) and brine (20 mL), dried with anhydrous Na$_2$SO$_4$, filtered and concentrated in vacuum. The residue was purified by vacuum silica gel column chromatography (SiO$_2$, PE:EA=15:1 to 5:1) to give 6D (120 mg, 219.82 µmol, 46.7% yield, 80% purity) as a white solid.

To a solution of 6D (854 mg, 1.96 mmol, 1 eq.) in MeOH (10 mL) and THF (10 mL) was added CeCl$_3$.7H$_2$O (801.43 mg, 2.15 mmol, 204.45 µL, 1.1 eq.) at −78° C. The mixture was stirred at the same temperature for 10 min. NaBH$_4$ (81.38 mg, 2.15 mmol, 1.1 eq.) was added at −78° C., and the mixture was stirred for 10 min. The mixture was warmed to 0° C. and then stirred at 0° C. for 10 min. The reaction was quenched with NH$_4$Cl (sat., aq., 5 mL), and the mixture was extracted with EA (2×50 mL). The combined organic layers were washed with brine (20 mL), dried with anhydrous Na$_2$SO$_4$, filtered and concentrated in vacuum to give a residue. The residue was purified by column chromatography (SiO$_2$, PE:EA=8:1 to 3:1) to give 7D (654 mg, 894.38 µmol, 45.7% yield, 60% purity) as a brown solid.

To a solution of triphenyl phosphine (896.73 mg, 3.42 mmol, 2.5 eq.), 4-chloro-7H-pyrrolo[2,3-d]pyrimidine (315.02 mg, 2.05 mmol, 1.5 eq.), and 7D (600 mg, 1.37 mmol, 1 eq.) in THF (12 mL) was added DIAD (636.02 mg, 3.15 mmol, 611.56 µL, 2.3 eq.) at 20° C. After stirring at rt for 5 h, the mixture was concentrated in vacuum to give a residue. The residue was purified by column chromatography (SiO$_2$, PE:EA=20:1 to 8:1) to give 8D (600 mg, 1.02 mmol, 74.8% yield, 98% purity) as a brown solid.

8D (500 mg, 870.63 µmol, 1 eq.) was dissolved in NH$_3$.H$_2$O (10 mL) and dioxane (10 mL) at 20° C. in an autoclave. The mixture was stirred at 140° C. for 48 h and then concentrated to give a brown residue. The residue was purified by column chromatography (SiO$_2$, DCM: MeOH=40:1 to 10:1) to give 9D (70 mg, 14.5% yield) and 9D-a (280 mg, 449.73 µmol, 51.6% yield, 86% purity).

To a solution of 9D-a (45 mg, 84.04 μmol) in EtOH (4 mL) was added PtO$_2$ (3.82 mg, 16.81 μmol, 0.2 eq.) at rt. The mixture was degassed under vacuum and purged with H$_2$ (15 psi) several times. The mixture was stirred under H$_2$ (15 psi) at rt for 6 h and then filtered over a pad of Celite. The filtrate was concentrated to give a residue. The residue was purified by column chromatography (SiO$_2$, DCM:MeOH=20:1 to 7:1) to give a mixture of 10D-a and 10D-b (35 mg) as a white solid. The ratio of isomers was approximately 2:1 based on SFC analysis. The mixture was purified by SFC separation (column: DAICEL CHIRALCEL OD (250 mm*30 mm, 10 um); mobile phase: [0.1% NH$_3$H$_2$O ETOH]; B %: 45%) to give 10D-a (retention time: 3.471 min) (20 mg, 43.62 μmol, 57.1% yield) as a white solid and 10D-b (retention time: 2.779 min) (14 mg, 30.53 μmol, 40.0% yield) as a white solid. 10D-a: $^1$H NMR (400 MHz, CD$_3$OD) δ: 8.04 (s, 1H), 7.87 (d, J=9.0 Hz, 1H), 7.55 (d, J=8.1 Hz, 1H), 7.41 (s, 1H), 7.27-7.13 (m, 2H), 6.75 (d, J=8.8 Hz, 1H), 6.62 (d, J=3.4 Hz, 1H), 4.94-4.89 (m, 1H), 4.61-4.46 (m, 2H), 3.14-2.92 (m, 1H), 2.83 (br dd, J=8.8, 14.2 Hz, 1H), 2.26 (dt, J=6.6, 11.4 Hz, 1H), 2.09-1.97 (m, 2H), 1.54 (s, 3H), 1.57-1.51 (m, 1H), 1.30 (s, 3H), 0.81 (br d, J=6.6 Hz, 3H). LCMS: (ESI): m/z calcd. for C$_{26}$H$_{31}$N$_6$O$_2$, 459.2 [M+H]$^+$, found 459.2. 10D-b: $^1$H NMR (400 MHz, CD$_3$OD) δ: 8.04 (s, 1H), 7.86 (d, J=8.8 Hz, 1H), 7.54 (d, J=8.3 Hz, 1H), 7.37 (s, 2H), 7.14 (dd, J=1.5, 8.1 Hz, 1H), 6.74 (d, J=8.8 Hz, 1H), 6.60 (d, J=3.7 Hz, 1H), 5.38 (t, J=7.5 Hz, 1H), 4.99 (t, J=6.7 Hz, 1H), 4.59 (t, J=7.1 Hz, 1H), 2.90-2.66 (m, 3H), 2.39-2.22 (m, 1H), 1.94-1.80 (m, 2H), 1.49 (s, 3H), 1.35 (s, 3H), 0.65 (d, J=7.6 Hz, 3H). LCMS: (ESI): m/z calcd. for C$_{26}$H$_{31}$N$_6$O$_2$, 459.2 [M+H]$^+$, found 459.2.

To a solution of 10D-a (20 mg, 43.62 μmol, 1 eq.) in THF (3 mL) was added HCl (4 M, 1.5 mL in H$_2$O) at rt. The mixture was stirred at rt for 12 h. The mixture was then concentrated in vacuum to give a residue. The mixture was neutralized with NH$_3$.H$_2$O to pH 9. The residue was purified by prep-HPLC (basic condition; column: Phenomenex Gemini-NX 150*30 mm*5 um; mobile phase: [water (0.04% NH$_3$H$_2$O+10 mM NH$_4$HCO$_3$-ACN]; B %: 20%-50%, 8 min) to give 5 (12 mg, 28.53 μmol, 65.4% yield, 99.5% purity) as a white solid. $^1$H NMR (400 MHz, CD$_3$OD) δ: 8.04 (s, 1H), 7.88 (d, J=8.8 Hz, 1H), 7.56 (d, J=8.0 Hz, 1H), 7.40 (s, 1H), 7.27-7.13 (m, 2H), 6.75 (d, J=9.0 Hz, 1H), 6.61 (d, J=3.5 Hz, 1H), 4.58-4.45 (m, 1H), 4.36 (dd, J=6.3, 9.0 Hz, 1H), 3.97 (dd, J=3.9, 6.1 Hz, 1H), 3.04-2.77 (m, 2H), 2.06-1.77 (m, 3H), 1.71-1.60 (m, 1H), 0.93 (d, J=6.5 Hz, 3H). LCMS: (ESI): m/z calcd. for C$_{23}$H$_{27}$N$_6$O$_2$, 419.5 [M+H]$^+$, found 419.2.

To a solution of 10D-b (14 mg, 30.53 μmol, 1 eq.) in THF (3 mL) was added HCl (4 M, 1.5 mL in water) at 20° C. The mixture was stirred at 20° C. for 12 h. The mixture was concentrated in vacuum to give a residue. The residue was neutralized with NH$_3$.H$_2$O to pH 9. The residue was purified by prep-HPLC (basic condition; column: Phenomenex Gemini-NX 150*30 mm*5 um; mobile phase: [water (0.04% NH$_3$H$_2$O+10 mM NH$_4$HCO$_3$)-ACN]; B %: 20%-50%, 8 min) to give 6 (7 mg, 16.54 μmol, 54.17% yield, 98.88% purity) as a white solid. $^1$H NMR (400 MHz, CD$_3$OD) δ: 8.06 (s, 1H), 7.87 (d, J=8.8 Hz, 1H), 7.56 (d, J=7.8 Hz, 1H), 7.38 (s, 1H), 7.32 (d, J=3.8 Hz, 1H), 7.20-7.09 (m, 1H), 6.75 (d, J=8.8 Hz, 1H), 6.60 (d, J=3.8 Hz, 1H), 4.86 (br s, 1H), 4.76-4.68 (m, 1H), 3.95 (t, J=7.3 Hz, 1H), 2.84 (t, J=8.2 Hz, 1H), 2.71-2.57 (m, 1H), 2.24-2.09 (m, 1H), 2.08-1.78 (m, 2H), 0.58 (d, J=7.5 Hz, 3H). LCMS: (ESI): m/z calcd. for C$_{23}$H$_{27}$N$_6$O$_2$, 419.5 [M+H]$^+$, found 419.2.

Example 4

Compounds 7 and 8

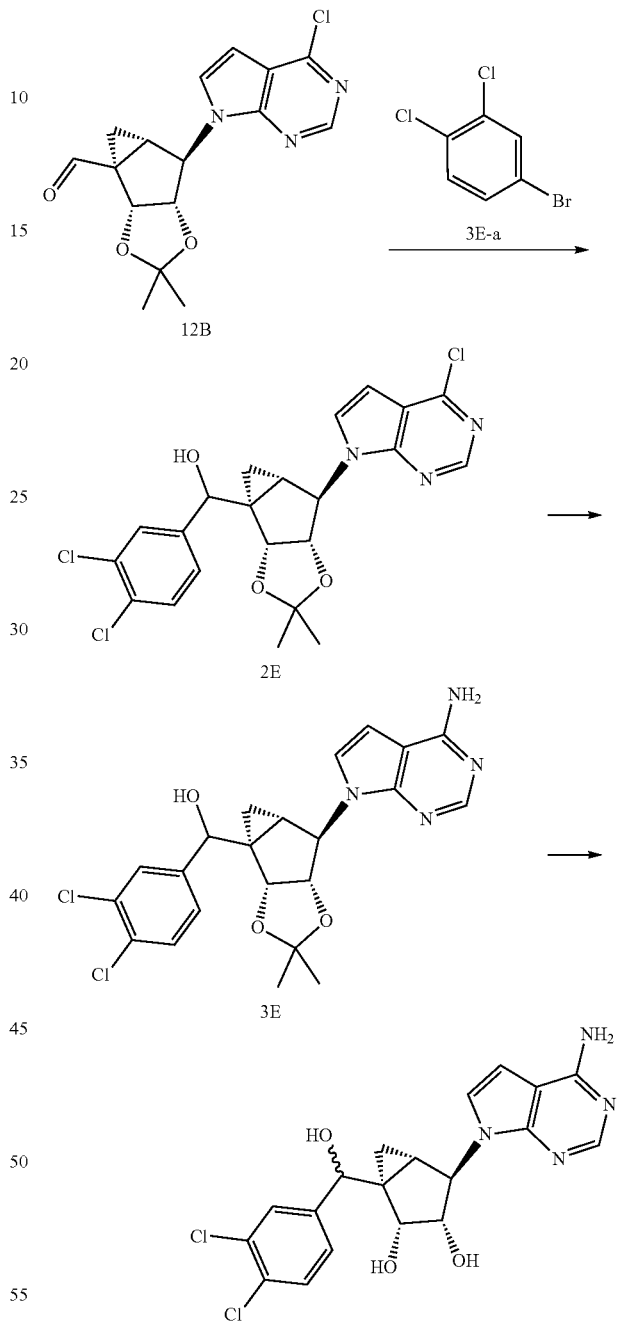

Chloro(isopropyl)magnesium (2 M, 449.41 μL, 2 eq.) was added dropwise to a solution of 4-bromo-1,2-dichloro-benzene (203.04 mg, 898.83 μmol, 2 eq.) in THF (1 mL) at −15° C. The mixture was stirred at −15° C. for 10 min, and then warmed to 0° C. The mixture was stirred at 0° C. for 1 h. A solution of 12B (150 mg, 449.41 μmol, 1 eq.) in THF (1.5 mL) was added at −20° C., and the mixture was stirred at 0° C. for 20 min. The reaction progress was monitored by TLC (PE:EA=2:1). Upon completion, the reaction was quenched with NH$_4$Cl (sat. aq., 2 mL) and extracted with EA (2×3 mL). The combined organic layers were washed with brine (2×3 mL), dried over Na$_2$SO$_4$, and concentrated to give a residue. The residue was purified by column chromatography (SiO$_2$, PE:EA=20:1 to 6:1) to afford two isomers, (R or S)-[(15S,16R,17S,18R,21R)-16-(4-chloropyrrolo[2,3-d]pyrimidin-7-yl)-20,20-dimethyl-26,27-dioxatricyclononan-21-yl]-(3,4-dichlorophenyl)methanol (2E-a) (60 mg, 92.35 μmol, 20% yield) as a white solid, and (S or R)-[(15S,16R,17S,18R,21R)-16-(4-chloropyrrolo[2,3-d]pyrimidin-7-yl)-20,20-dimethyl-26,27-dioxatricyclononan-21-yl]-(3,4-dichlorophenyl)methanol (2E-b) (70 mg, 110.66 μmol, 24% yield) as a white solid.

Compound 2E-a: LCMS: (ESI): m/z calcd. for C$_{22}$H$_{21}$Cl$_3$N$_3$O$_3$ 482.05 [M+H]$^+$, found 481.7. $^1$H NMR (400 MHz, CDCl$_3$) δ: 8.70 (s, 1H), 7.70 (s, 1H), 7.48-7.35 (m, 2H), 7.30 (d, J=3.5 Hz, 1H), 6.66 (d, J=3.3 Hz, 1H), 5.84 (s, 1H), 5.49 (d, J=7.3 Hz, 1H), 4.74 (s, 1H), 4.68 (d, J=7.5 Hz, 1H), 4.44 (s, 1H), 1.94 (br dd, J=4.7, 9.2 Hz, 1H), 1.46 (s, 3H), 1.32-1.28 (m, 2H), 1.15 (s, 3H). Compound 2E-b: LCMS: (ESI): m/z calcd. for C$_{22}$H$_{21}$Cl$_3$N$_3$O$_3$ 482.05 [M+H]$^+$, found 481.9. $^1$H NMR (400 MHz, CDCl$_3$) δ: 8.72 (s, 1H), 7.39-7.32 (m, 2H), 7.26 (br s, 1H), 7.09 (dd, J=1.5, 8.2 Hz, 1H), 6.66 (d, J=3.5 Hz, 1H), 5.68 (d, J=7.3 Hz, 1H), 5.59 (d, J=6.2 Hz, 1H), 5.35 (d, J=6.2 Hz, 1H), 4.81 (s, 1H), 4.67 (d, J=7.5 Hz, 1H), 1.66 (br dd, J=4.4, 9.3 Hz, 2H), 1.59-1.57 (m, 6H), 1.10 (s, 1H), 0.56 (br dd, J=6.5, 8.5 Hz, 1H).

NH$_3$·H$_2$O (728.00 mg, 5.82 mmol, 0.8 mL, 28% purity, 46.61 eq.) was added to a solution of (2E-a) (60 mg, 124.80 μmol, 1 eq.) in dioxane (1.2 mL). The mixture was stirred at 100° C. for 16 h. The reaction progress was monitored by TLC (PE:EA=1:1). Upon completion, the mixture was extracted with EA (3×5 mL). The combined organic layers were washed with brine (3×5 mL), dried over Na$_2$SO$_4$, and concentrated to give a residue that afforded (R or S)-[(15S,16R,17S,18R,21R)-16-(4-aminopyrrolo[2,3-d]pyrimidin-7-yl)-20,20-dimethyl-27,28-dioxatricyclononan-21-yl]-(3,4-dichlorophenyl)methanol (3E-a) (68 mg, crude) as a pale yellow solid. LCMS: (ESI): m/z calcd. for C$_{22}$H$_{23}$Cl$_2$N$_4$O$_3$ 461.11 [M+H]$^+$, found 461.0.

(S or R)-[(15S,16R,17S,18R,21R)-16-(4-aminopyrrolo[2,3-d]pyrimidin-7-yl)-20,20-dimethyl-27,28-dioxatricyclononan-21-yl]-(3,4-dichlorophenyl)methanol (3E-b) (67 mg, crude) was obtained as a pale yellow solid by the same procedure from (S or R)-[(15S,16R,17S,18R,21R)-16-(4-chloropyrrolo[2,3-d]pyrimidin-7-yl)-20,20-dimethyl-26,27-dioxatricyclononan-21-yl]-(3,4-dichlorophenyl)methanol (2E-b) (70 mg, 145.60 μmol, 1 eq.). LCMS: (ESI): m/z calcd. for C$_{22}$H$_{23}$Cl$_2$N$_4$O$_3$ 461.11 [M+H]$^+$, found 461.1.

HCl (4 M, aq., 0.75 mL, 20.35 eq.) was added to a solution of (3E-a) (68 mg, 147.40 μmol, 1 eq.) in THF (1.5 mL). The mixture was stirred at 25° C. for 16 h. The reaction progress was monitored by TLC (DCM:MeOH=10:1). Upon completion, the reaction mixture was quenched by NH$_4$OH (25% wt, 1 mL) and then concentrated to give a residue. The residue was purified by prep-HPLC (column: Phenomenex Gemini-NX 150*30 mm*5 um; mobile phase: [water (0.04% NH$_3$H$_2$O+10 mM NH$_4$HCO$_3$)-ACN]; B %: 24%-54%, 8 min) and SFC (column: DAICEL CHIRALPAK AD (250 mm*30 mm, 10 um); mobile phase: [0.1% NH$_3$H$_2$O ETOH]; B %: 45%) to afford (1R,2R,3S,4R,5S)-4-(4-aminopyrrolo[2,3-d]pyrimidin-7-yl)-1-[(R or S)-(3,4-dichlorophenyl)-hydroxy-methyl]bicyclo[3.1.0]hexane-2,3-diol (7) (15 mg, 35.29 μmol, 99% purity) as a white solid. LCMS: (ESI): m/z calcd. for C$_{19}$H$_{19}$Cl$_2$N$_4$O$_3$ 421.08 [M+H]$^+$, found 421.0. $^1$H NMR (400 MHz, MeOD) δ: 8.09 (s, 1H), 7.69 (s, 1H), 7.46 (q, J=8.4 Hz, 2H), 7.24 (d, J=3.3 Hz, 1H), 6.57 (d, J=3.3 Hz, 1H), 4.83 (br s, 1H), 4.74 (br d, J=6.5 Hz, 1H), 4.58 (s, 1H), 3.88 (br d, J=6.5 Hz, 1H), 1.62 (brd, J=9.3 Hz, 1H), 1.48 (br s, 1H), 1.16-1.08 (m, 1H).

(1R, 2R, 3S, 4R, 5S)-4-(4-aminopyrrolo[2,3-d]pyrimidin-7-yl)-1-[(S or R)-(3,4-dichlorophenyl)-hydroxy-methyl]bicyclo[3.1.0]hexane-2,3-diol (8) (19 mg, 44.65 μmol, 99% purity) was obtained as a white solid by the same procedure and purified by prep-HPLC (column: Phenomenex Gemini-NX 150*30 mm*5 um; mobile phase: [water (0.04% NH$_3$H$_2$O+10 mM NH$_4$HCO$_3$)-ACN]; B %: 24%-54%, 8 min) and SFC (column: DAICEL CHIRALPAK AD (250 mm*30 mm, 10 um); mobile phase: [0.1% NH$_3$H$_2$O ETOH]; B %: 45%) from (S or R)-[(15S,16R,17S,18R,21R)-16-(4-aminopyrrolo[2,3-d]pyrimidin-7-yl)-20,20-dimethyl-27,28-dioxatricyclononan-21-yl]-(3,4-dichlorophenyl)methanol (3E-b) (67 mg, crude). Compound 8: LCMS: (ESI): m/z calcd. for C$_{19}$H$_{19}$Cl$_2$N$_4$O$_3$ 421.08 [M+H]$^+$, found 421.1. $^1$H NMR (400 MHz, CD$_3$OD) (signals under solvent peak not listed) δ: 8.08 (br s, 1H), 7.54-7.45 (m, 2H), 7.42 (br s, 1H), 7.31 (br s, 1H), 6.58 (br s, 1H), 5.17 (br s, 1H), 3.78 (br s, 1H), 1.52-1.39 (m, 2H), 0.38 (br s, 1H).

Example 5

Compound 9

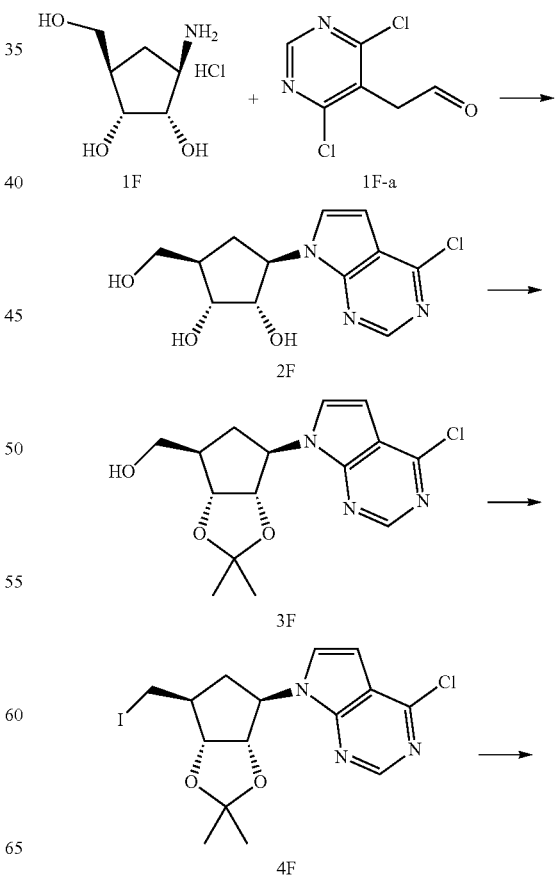

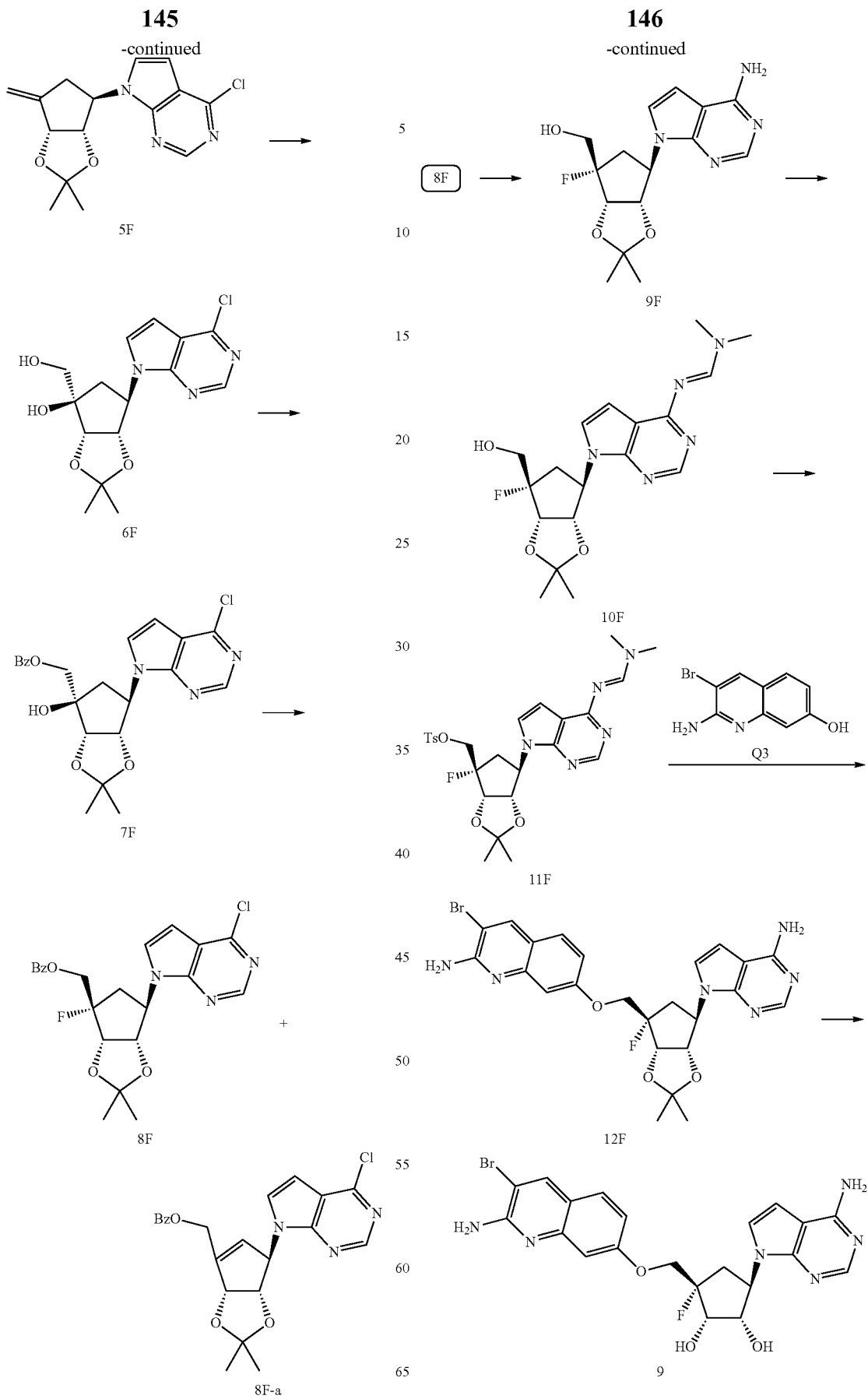
-continued

To a solution of (1R,2S,3R,5R)-3-amino-5-(hydroxymethyl)cyclopentane-1,2-diol (1F) (3.67 g, 20.0 mmol, 1 eq., HCl salt) and 2-(4,6-dichloropyrimidin-5-yl)acetaldehyde (1F-a) (3.82 g, 20.0 mmol, 1 eq.) in EtOH (80 mL) was added TEA (6.07 g, 60 mmol, 8.4 mL, 3 eq.). The mixture was refluxed for 24 h. The reaction progress was monitored by LCMS. Upon completion, the mixture was concentrated under vacuum to give a residue. The residue was dissolved in sat. NaHCO$_3$ solution (50 mL), and then extracted with EtOAc (9×50 mL). The combined organic layer were washed with brine (300 mL), dried over Na$_2$SO$_4$, and then filtered. The filtrate was concentrated under reduced pressure to afford the crude 2F (5.8 g) as a yellow gum, which was used for next step without further purification.

To a solution of 2F (5.8 g, crude) and 2,2-dimethoxypropane (4.26 g, 40.8 mmol, 5.0 mL, 2 eq.) in acetone (60 mL) was added 4-methylbenzenesulfonic acid hydrate (388.9 mg, 2.0 mmol, 0.1 eq.). The mixture was stirred at rt for 2 h and then refluxed for 24 h. The reaction progress was monitored by LCMS. Upon completion, the reaction was quenched by Et$_3$N (0.7 mL), and then concentrated under reduced pressure to give a residue. The residue was treated with sat. NaHCO$_3$ solution (20 mL) and brine (20 mL). The resulting mixture was extracted with EtOAc (3×40 mL). The combined organic layers were washed with brine (100 mL), dried over Na$_2$SO$_4$, and then filtered. The filtrate was concentrated under reduced pressure to give a residue. The residue was purified by column chromatography (PE:EA=5:1 to 1:1) to afford [(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]methanol (3F) (4.25 g, 65% yield, 2 steps from 1F) as a yellow solid. LCMS: (ESI): m/z calcd. for C$_{15}$H$_{19}$ClN$_3$O$_3$ 324.11 [M+H]$^+$, found 324.2.

To a solution of PPh$_3$ (6.72 g, 25.6 mmol, 2 eq.) and imidazole (1.83 g, 26.9 mmol, 2.1 eq.) in THF (60 mL) was added I$_2$ (6.51 g, 25.6 mmol, 2 eq.). The mixture was stirred at rt for 15 min under N$_2$, and then a solution of 3F (4.15 g, 12.8 mmol, 1 eq.) in THF (40 mL) was added. The mixture was stirred at rt for 1.5 h under N$_2$. The reaction progress was monitored by TLC (PE:E=5:1). Upon completion, the reaction was quenched with sat. Na$_2$S$_2$O$_3$ solution (100 mL), and then extracted with DCM (3×100 mL). The combined organic layers were washed with brine (300 mL), dried over Na$_2$SO$_4$, and then filtered. The filtrate was concentrated in vacuum to give a residue. The residue was purified by column chromatography (PE:EA=20:1 to 5:1) to afford 7-[(3aS,4R,6S,6aR)-6-(iodomethyl)-2,2-dimethyl-4,5,6,6a-tetrahydro-3aH-cyclopenta[d][1,3]dioxol-4-yl]-4-chloropyrrolo[2,3-d]pyrimidine (4F) (4.16 g, 70% yield) as a yellow solid. LCMS: (ESI): m/z calcd. for C$_{15}$H$_{18}$ClIN$_3$O$_2$ 434.01 [M+H]$^+$, found 434.0.

tBuOK (697.0 mg, 6.2 mmol, 1 eq.) in THF (8 mL) was added dropwise to a mixture of 4F (2.69 g, 6.2 mmol, 1 eq.) and THF (30 mL) at 0° C. The mixture was stirred at 0° C. for 0.5 h. The reaction progress was monitored by TLC (PE:EA=5:1). Upon completion, the reaction was quenched with sat. aq. NH$_4$Cl (50 mL). The mixture was extracted with EA (2×50 mL). The separated organic layers were combined and washed with brine (30 mL), dried over anhydrous Na$_2$SO$_4$ and concentrated to afford a residue. The residue was purified by silica gel chromatography (EA:PE=8:1) to afford 7-[(3aR,6R,6aS)-2,2-dimethyl-4-methylene-3a,5,6,6a-tetrahydro[d][1,3]dioxol-6-yl]-4-chloro-pyrrolo[2,3-d]pyrimidine (5F) (1.9 g, 94% yield) as colorless foam. LCMS: (ESI): m/z calcd. for C$_{15}$H$_{17}$ClN$_3$O$_2$ 306.10 [M+H]$^+$, found 306.1.

K$_2$OsO$_4$.2H$_2$O (75.32 mg, 204.41 μmol, 0.025 eq.) was added to a mixture of 5F (2.5 g, 8.2 mmol, 1 eq.) and NMO (1.9 g, 16.4 mmol, 2 eq.) in a mixed solvent of acetone (40 mL) and H$_2$O (8 mL). The mixture was stirred at it for 20 h. The reaction progress was monitored by TLC (PE:EA=5:1). Upon completion, the mixture was concentrated under reduced pressure to afford a residue. The residue was purified by silica gel chromatography (PE:EA:EtOH=30:10:1) to afford (3aS,4R,6R,6aS)-6-(4-chloropyrrolo[2,3-d]pyrimidin-7-yl)-4-(hydroxymethyl)-2,2-dimethyl-3a,5,6,6a tetrahydrocyclopenta[d][1,3]dioxol-4-ol (6F) (2.51 g, 90% yield) as a light yellow foam. LCMS: (ESI): m/z calcd. for C$_{15}$H$_{19}$ClN$_3$O$_4$ 340.11 [M+H]$^+$, found 340.0.

Benzoyl chloride (297.87 mg, 2.12 mmol, 246.17 μL, 1.2 eq.) was added dropwise to a mixture of 6F (600 mg, 1.77 mmol, 1 eq.), DMAP (21.6 mg, 176.6 μmol, 0.1 eq.), and Et$_3$N (536.1 mg, 5.3 mmol, 737.4 μL, 3 eq.) in DCM (10 mL) at rt. The mixture was stirred at rt for 3 h. The reaction progress was monitored by LCMS. Upon completion, the mixture was concentrated under reduced pressure to afford a residue. The residue was purified by silica gel chromatography (EA:PE=3:1) to afford [(3aS,4R,6R,6aS)-6-(4-chloropyrrolo[2,3-d]pyrimidin-7-yl)-4-hydroxy-2,2-dimethyl-3a,5,6,6a-tetrahydrocyclopenta[d][1,3]dioxol-4-yl]methyl benzoate (7F) (743 mg, 94% yield) as a white foam. LCMS: (ESI): m/z calcd. for C$_{22}$H$_{23}$ClN$_3$O$_5$ 444.13 [M+H]$^+$, found 444.1.

DAST (435.76 mg, 2.70 mmol, 357.18 μL, 2 eq.) was added to a solution of 7F (600 mg, 1.35 mmol, 1 eq.) in DCM (10 mL) at 0° C. The mixture was stirred at 0° C. for 1 h. The reaction progress was monitored by LCMS. Upon completion, the reaction was quenched with sat. NaHCO$_3$ (aq., 10 mL). The mixture was extracted with DCM (2×20 mL). The separated organic layers were combined and washed with brine (10 mL), dried over anhydrous Na$_2$SO$_4$ and concentrated to afford a residue. The residue was purified by chromatography on silica gel (PE:EA=8:1) to afford a mixture of 8F and 8F-a (200 mg, 8:8a=1:2) as a white foam. 8F: LCMS (ESI): m/z calcd. for C$_{22}$H$_{22}$ClFN$_3$O$_4$ 446.13 [M+H]$^+$, found 446.2; and 8F-a: LCMS (ESI): m/z calcd. for C$_{22}$H$_{21}$ClN$_3$O$_4$ 426.12 [M+H]$^+$, found 426.2.

A mixture of 8F:8a-F (=1:2, 50.00 mg) and NH$_3$—H$_2$O (1.7 mL, 25% wt) in dioxane (10 mL) was heated at 100° C. for 16 h. The mixture was concentrated under reduced pressure to afford a residue. The residue was purified by silica gel chromatography (DCM:MeOH=20:1) to afford the crude 9F as colorless gum (crude, 32 mg). LCMS: (ESI): m/z calcd. for C$_{15}$H$_{20}$FN$_4$O$_3$ 323.15 [M+H]$^+$, found 323.2.

A mixture of 9F (crude 90 mg), DMF-DMA (133.1 mg, 1.1 mmol, 148.4 μL, 4 eq.) and THF (2 mL) was stirred at 60° C. for 48 h. The reaction progress was monitored by LCMS. Upon completion, the mixture was concentrated to afford crude 10F (crude, 90 mg) as a yellow gum, which was used for next step without further purification.

p-TsCl (159.12 mg, 834.63 μmol, 3 eq.) was added to a mixture of 10F (105 mg, 278.2 μmol, 1 eq.), TEA (140.8 mg, 1.4 mmol, 194 μL, 5 eq.), DMAP (3.4 mg, 27.8 μmol, 0.1 eq.) and DCM (1 mL). The mixture was stirred at 15° C. for 2 h. The reaction progress was monitored by TLC (DCM:MeOH=10:1). Upon completion, the residue was concentrated to afford a residue. The residue was purified by silica gel chromatography (DCM:MeOH=30:1) to afford [(3aS, 4S,6R,6aS)-6-[4-[(E)-dimethylaminomethyleneamino]pyrrolo[2,3-d]pyrimidin-7-yl]-4-fluoro-2,2-dimethyl-3a,5,6,6a-tetrahydrocyclopenta[d][1,3]dioxol-4-yl]methyl 4-methylbenzenesulfonate (11F) (58 mg) as a yellow foam. LCMS: (ESI): m/z calcd. for $C_{25}H_{31}FN_5O_5S$ 532.20 [M+H]$^+$, found 532.1.

A mixture of 11F (58 mg, 109.10 μmol, 1 eq.), 2-amino-3-bromo-quinolin-7-ol (Q3) (39.1 mg, 163.7 μmol, 1.5 eq.) and $Cs_2CO_3$ (106.7 mg, 327.3 μmol, 3 eq.) in DMF (1 mL) was stirred at 70° C. for 16 h. The reaction progress was monitored by LCMS. Upon completion, the mixture was diluted with water (10 mL). The resulting mixture was extracted with EA (2×20 m). The separated organic layers were combined and washed with brine (10 mL), dried over anhydrous $Na_2SO_4$, and concentrated to afford a residue. The residue was purified by silica gel chromatography (DCM:MeOH:Et$_3$N=30:1:0.3) to afford the crude product (30 mg). The crude product was further purified by chiral-SFC (column: DAICEL CHIRALCEL OD-H (250 mm*30 mm, 5 um); mobile phase: [0.1% $NH_3H_2O$ ETOH]; B %: 45%) to afford 7-[[(3aS,4S,6R,6aS)-6-(4-aminopyrrolo[2,3-d]pyrimidin-7-yl)-4-fluoro-2,2-dimethyl-3a,5,6,6a-tetrahydrocyclopenta[d][1,3]dioxol-4-yl]methoxy]-3-bromo-quinolin-2-amine (12F) (18 mg, 26% yield) as a white solid. LCMS: (ESI): m/z calcd. for $C_{24}H_{25}BrFN_6O_3$ 543.12 [M+H]$^+$, found 543.2.

HCl (4 M, 1 mL, 120.75 eq.) was added to the mixture of 12F (18 mg, 33.1 μmol, 1 eq.) and THF (2 mL) at rt. The mixture was stirred at rt, and the reaction progress was monitored by LCMS. Upon completion, the mixture was concentrated under reduced pressure to afford a residue. $NH_3.H_2O$ (0.1 mL) was added to neutralize the residue. The resultant mixture was dissolved in MeCN:H$_2$O=1:1 (3 mL) and then purified by prep-HPLC (column: Phenomenex Gemini-NX 150*30 mm*5 um; mobile phase: [water (0.04% $NH_3H_2O$+10 mM $NH_4HCO_3$)-ACN]; B %: 27%-57%, 8 min) to afford (1S,2S,3S,5R)-3-[(2-amino-3-bromo-7-quinolyl)oxymethyl]-5-(4-aminopyrrolo[2,3-d]pyrimidin-7-yl)-3-fluoro-cyclopentane-1,2-diol (9) (9 mg, 54% yield) as white solid. LCMS: (ESI): m/z calcd. for $C_{21}H_{21}BrFN_6O_3$ 503.08 [M+H]$^+$, found 503.1. $^1$H NMR (400 MHz, CD$_3$OD) δ: 8.22 (s, 1H), 8.04 (s, 1H), 7.56 (d, J=9.0 Hz, 1H), 7.24 (d, J=3.7 Hz, 1H), 7.07 (d, J=2.2 Hz, 1H), 7.00 (dd, J=2.4, 8.8 Hz, 1H), 6.59 (d, J=3.7 Hz, 1H), 5.19-5.06 (m, 1H), 4.60-4.56 (m, 1H), 4.53-4.35 (m, 3H), 2.76-2.45 (m, 2H).

Example 6

Compound 10

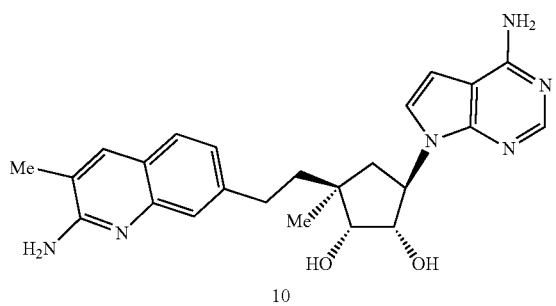

A mixture of 1 (20.1 mg, 40.4 μmol, 1 eq.), 2,4,6-trimethyl-1,3,5,2,4,6-trioxatriborinane (15.2 mg, 121.1 μmol, 16.9 μL, 3 eq.), $K_3PO_4$ (25.7 mg, 121.1 μmol, 3 eq.) and Pd(dppf)Cl$_2$ (2.9 mg, 4.0 μmol, 0.1 eq.) in a mixed solvent of dioxane (1 mL) and water (0.2 mL) was stirred at 90° C. under Ar for 16 h. The reaction progress was monitored by LCMS. Upon completion, the mixture was filtered through a filter element. The filtrate was purified by acid pre-HPLC (column: Venusil ASB Phenyl 150*30 mm*5 um; mobile phase: [water (0.05% HCl)-ACN]; B %: 15%-45%, 10 min) and then by basic pre-HPLC (column: Phenomenex Gemini-NX 150*30 mm*5 um; mobile phase: [water (0.04% $NH_3H_2O$+10 mM $NH_4HCO_3$)-ACN]; B %: 25%-55%, 8 min) to afford (1S,2R,3S,5R)-3-[2-(2-amino-3-methyl-7-quinolyl)ethyl]-5-(4-aminopyrrolo[2,3-d]pyrimidin-7-yl)-3-methyl-cyclopentane-1,2-diol (10) (5.4 mg, 31% yield) as a white solid. LCMS: (ESI): m/z calcd. for $C_{24}H_{29}N_6O_2$ 433.23 [M+H]$^+$, found 433.3. $^1$H NMR (400 MHz, CD$_3$OD) δ: 8.08 (s, 1H), 7.74 (s, 1H), 7.54 (d, J=8.1 Hz, 1H), 7.38 (s, 1H), 7.24 (d, J=3.7 Hz, 1H), 7.14 (dd, J=1.3, 8.2 Hz, 1H), 6.60 (d, J=3.7 Hz, 1H), 5.07-4.98 (m, 1H), 4.52 (t, J=7.0 Hz, 1H), 3.94 (d, J=6.4 Hz, 1H), 2.92-2.71 (m, 2H), 2.29 (s, 3H), 2.12-2.04 (m, 1H), 1.99-1.80 (m, 3H), 1.25 (s, 3H).

Example 7

Compound 11

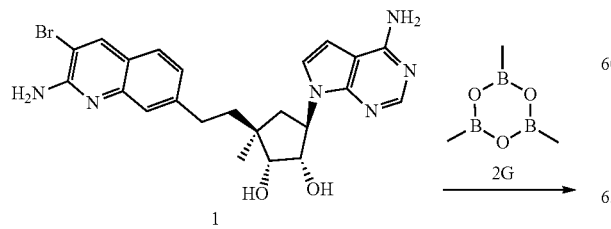

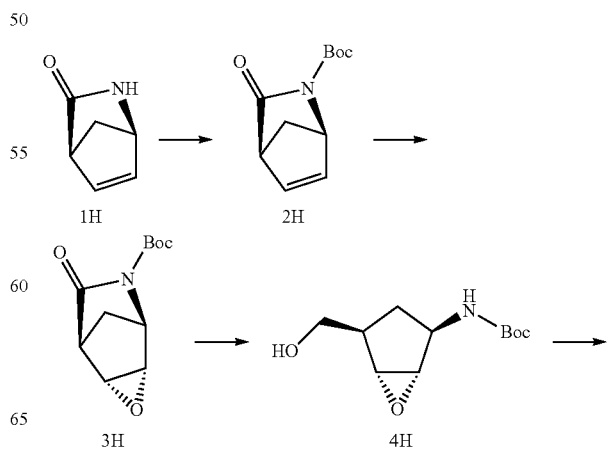

-continued
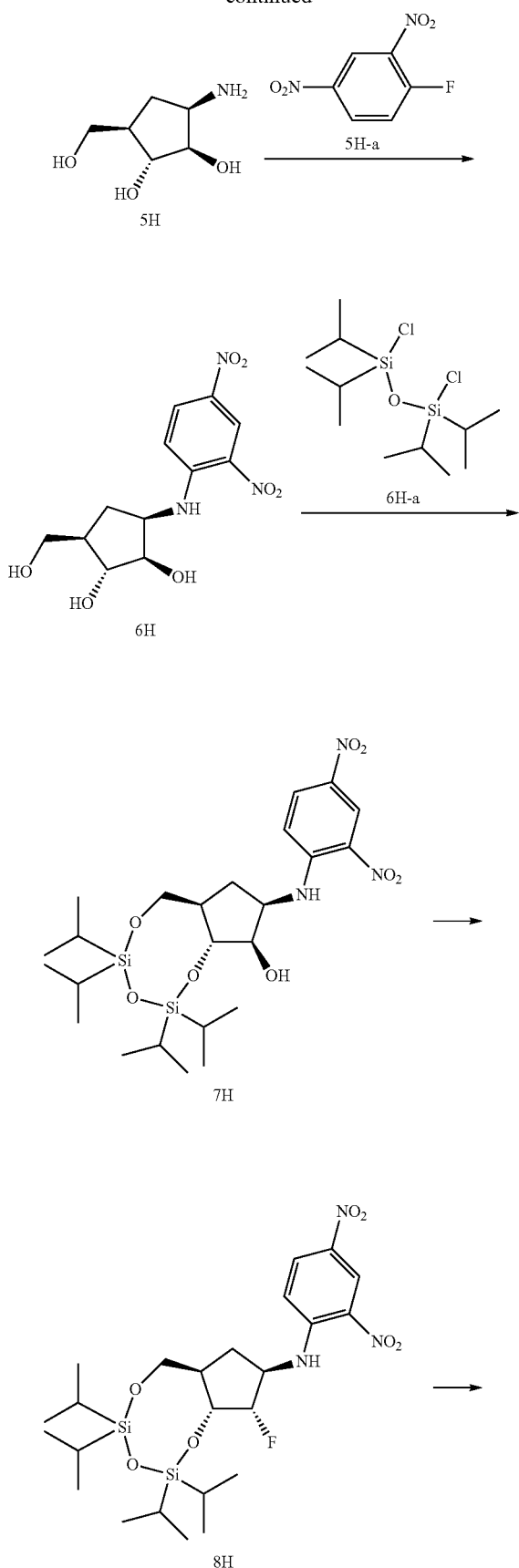
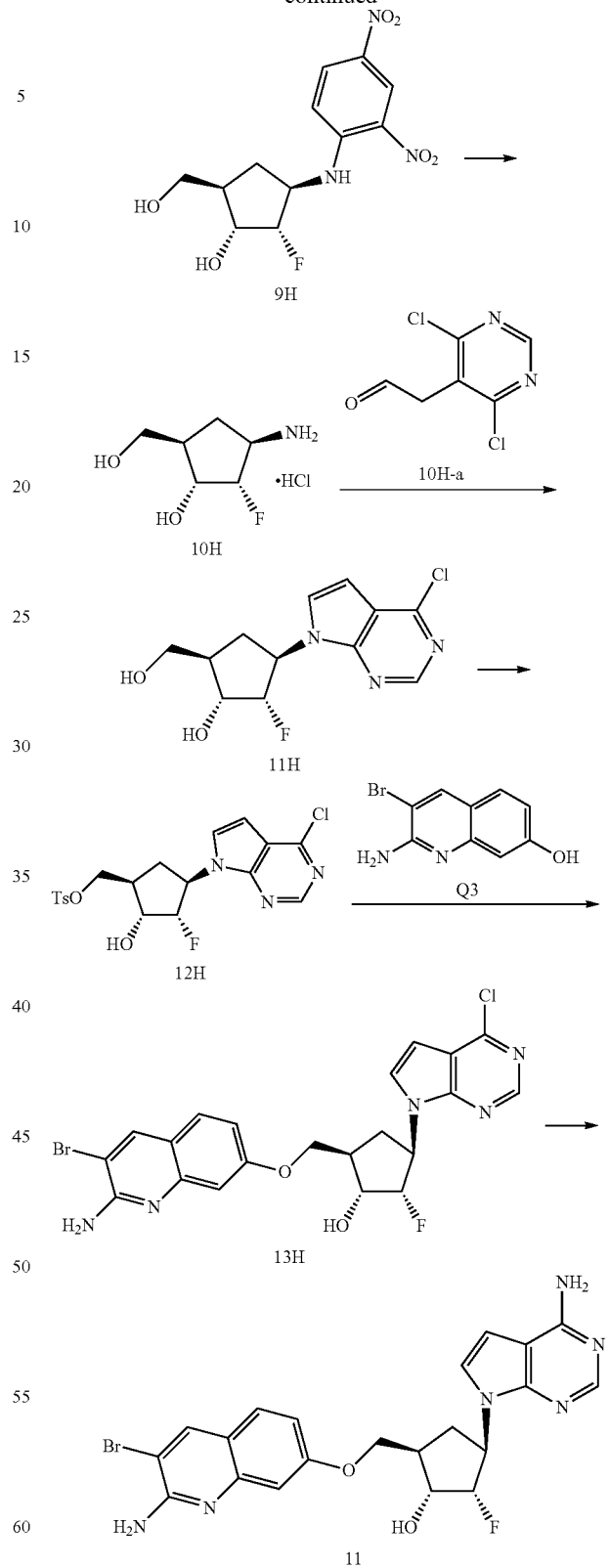
Tert-butoxycarbonyl tert-butyl carbonate (30.00 g, 137.46 mmol, 31.58 mL, 1.5 eq.) was added dropwise to a mixture of (1S,4R)-3-azabicyclo[2.2.1]hept-5-en-2-one (1H) (10 g, 91.64 mmol, 1 eq.), DMAP (1.12 g, 9.16 mmol, 0.1 eq.) and TEA (18.55 g, 183.27 mmol, 25.51 mL, 2 eq.) in DCM (150 mL) at 0° C. The mixture was stirred at 25° C. for 12 h. The reaction progress was monitored by TLC (PE:EA=3:1). Upon completion, the reaction was quenched by NaHCO$_3$ (sat. aq., 20 mL) and extracted with DCM (2×20 mL). The combined organic layers were washed with brine (2×20 mL), dried over MgSO$_4$ and concentrated to give a residue. The residue was purified by column chromatography (SiO$_2$, PE:EA=15:1 to 5:1) to afford tert-butyl (1S, 4R)-2-oxo-3-azabicyclo[2.2.1]hept-5-ene-3-carboxylate (2H) (16.5 g, 78.86 mmol, 86% yield) as a white solid. LCMS: (ESI): m/z calcd. for C$_{11}$H$_{15}$NNaO$_3$ 232.09 [M+Na]$^+$, found 232.0.

m-CPBA (19.41 g, 95.58 mmol, 85% purity, 4 eq.) was added to a solution of 2H (5 g, 23.90 mmol, 1 eq.) in DCE (150 mL). The mixture was stirred at 25° C. for 96 h. The mixture was stirred at 25° C. for 12 h. The reaction progress was monitored by TLC (PE:EA=3:1). Upon completion, the reaction was quenched by Na$_2$S$_2$O$_3$ (sat. aq., 10 mL) and extracted with DCM (2×30 mL). The combined organic layers were washed with brine (2×30 mL), dried over MgSO$_4$ and concentrated to give a residue. The residue was purified by column chromatography (SiO$_2$, PE:EA=30:1 to 5:1) to afford tert-butyl (4S, 5R, 6R, 7S)-8-oxo-14-oxa-11-azatricyclooctane-11-carboxylate (3H) (4.6 g, 14.30 mmol, 60% yield) as a white solid. LCMS: (ESI): m/z calcd. for C$_{11}$H$_{15}$NNaO$_4$ 248.09 [M+Na]$^+$, found 247.9.

NaBH$_4$ (2.65 g, 69.93 mmol, 5 eq.) was added in portions to a solution of 3H (4.5 g, 13.99 mmol, 1 eq.) in MeOH (120 mL) at 0° C. The mixture was stirred at 0° C. for 1 h. The reaction progress was monitored by TLC (PE:EA=1:1). Upon completion, the mixture was neutralized by a solution of 10% acetic acid in MeOH, and then extracted with DCM (3×50 mL). The combined organic layers were washed with brine (2×50 mL), dried over Na$_2$SO$_4$, and concentrated to give a residue. The residue was purified by column chromatography (SiO$_2$, PE:EA=15:1 to 3:1) to afford tert-butyl N-[(1S, 2R, 4R, 5R)-4-(hydroxymethyl)-6-oxabicyclo[3.1.0]hexan-2-yl]carbamate (4H) (2.35 g, 10.25 mmol, 71% yield) as a white solid. $^1$H NMR (400 MHz, CDCl$_3$) δ: 5.79 (br d, J=7.5 Hz, 1H), 4.29 (br s, 1H), 3.93 (br d, J=10.3 Hz, 1H), 3.69 (td, J=3.5, 10.1 Hz, 1H), 3.44 (s, 2H), 2.42 (br d, J=9.0 Hz, 1H), 2.19-2.06 (m, 1H), 1.78 (br s, 1H), 1.46 (s, 9H), 1.43 (br s, 1H).

To a solution of NaOH (1 M, 88 mL, 9.17 eq.) in H$_2$O was added 4H (2.2 g, 9.60 mmol, 1 eq.). The mixture was stirred at 75° C. for 2 h. The mixture was stirred at 0° C. for 1 h. The reaction progress was monitored by TLC (DCM:MeOH=20:1). Upon completion, the reaction mixture was quenched by H-form ion-exchange resin (pH to ~8) and then filtered. The filtrate was concentrated under reduced pressure to give a residue to afford (1R,2R,3R,5R)-3-amino-5-(hydroxymethyl)cyclopentane-1,2-diol (5H) (2.13 g, crude) as a yellow solid.

1-fluoro-2,4-dinitro-benzene (5H-a) (1.61 g, 8.66 mmol, 1.09 mL, 1 eq.) and Na$_2$CO$_3$ (917.36 mg, 8.66 mmol, 1 eq.) were added to a solution of 5H (1.93 g, 8.66 mmol, 1 eq., crude) in DMF (20 mL). The mixture was stirred at 25° C. for 2 h. The reaction progress was monitored by TLC (DCM:MeOH=20:1). Upon completion, the mixture was extracted with DCM (2×30 mL). The combined organic layers were washed with brine (2×30 mL), dried over Na$_2$SO$_4$, and concentrated to give a residue. The residue was purified by column chromatography (SiO$_2$, DCM:MeOH=100:1 to 20:1) to afford (1R,2R,3R,5R)-3-(2,4-dinitroanilino)-5-(hydroxymethyl)cyclopentane-1,2-diol (6H) (1.3 g, 4.07 mmol, 47% yield) as a yellow solid. LCMS: (ESI): m/z calcd. for C$_{12}$H$_{16}$N$_3$O$_7$ 314.09 [M+H]$^+$, found 313.9.

Chloro-[chloro(diisopropyl)silyl]oxy-diisopropyl-silane (6H-a) (1.44 g, 4.56 mmol, 1.46 mL, 1.1 eq.) was added dropwise to a solution of 6H (1.3 g, 4.15 mmol, 1 eq.) in pyridine (15 mL). The mixture was stirred at 25° C. for 12 h. The reaction progress was monitored by TLC (PE:EA=3:1). Upon completion, the mixture was concentrated to give a residue. The residue was purified by column chromatography (SiO$_2$, PE:EA=20:1 to 5:1) to afford (6aR,8R,9R,9aR)-8-(2,4-dinitroanilino)-2,2,4,4-tetraisopropyl-6,6a,7,8,9,9a-hexahydrocyclopenta[f][1,3,5,2,4]trioxadisilocin-9-ol (7H) (1.62 g, 2.91 mmol, 70% yield) as a yellow solid. LCMS: (ESI): m/z calcd. for C$_{24}$H$_{42}$N$_3$O$_8$Si$_2$ 556.24 [M+H]$^+$, found 556.1.

DAST (555.89 mg, 3.10 mmol, 455.65 μL, 90% purity, 1.5 eq.) was added to a solution of 7H (1.15 g, 2.07 mmol, 1 eq.) in DCM (25 mL) at 0° C. The mixture was stirred at 0° C. for 1 h. The reaction progress was monitored by TLC (PE:EA=3:1). Upon completion, the mixture was filtered and concentrated under reduced pressure to give a residue. The residue was purified by column chromatography (SiO$_2$, PE:EA=40:1 to 15:1) to afford (6aR,8R,9S,9aR)—N-(2,4-dinitrophenyl)-9-fluoro-2,2,4,4-tetraisopropyl-6,6a,7,8,9,9a-hexahydrocyclopenta[f][1,3,5,2,4]trioxadisilocin-8-amine (8H) (630 mg, 508.28 μmol, 24% yield) as a yellow solid. LCMS: (ESI): m/z calcd. for C$_{24}$H$_{41}$FN$_3$O$_7$Si$_2$ 558.24 [M+H]$^+$, found 558.3.

NH$_4$F (470.63 mg, 12.71 mmol, 25 eq.) was added to a solution of 8H (630 mg, 508.28 μmol, 1 eq.) in MeOH (23 mL). The mixture was stirred at 25° C. for 12 h. The reaction progress was monitored by TLC (DCM:MeOH=20:1). Upon completion, the mixture was filtered and concentrated under reduced pressure to give a residue. The residue was purified by column chromatography (SiO$_2$, DCM:MeOH=200:1 to 100:1) to afford (1R, 2S, 3R, 5R)-3-(2,4-dinitroanilino)-2-fluoro-5-(hydroxymethyl)cyclopentanol (9H) (135 mg, 398.25 μmol, 78% yield) as a yellow solid. LCMS: (ESI): m/z calcd. for C$_{12}$H$_{15}$FN$_3$O$_6$ 316.09 [M+H]$^+$, found 315.9.

Amberlite IRA 400 (OH—) resin (2.2 g) was added to a solution of 9H (135 mg, 428.23 μmol, 1 eq.) in acetone (3.8 mL) and H$_2$O (1.9 mL). The mixture was stirred at 25° C. for 12 h. The reaction progress was monitored by TLC (DCM:MeOH=10:1). Upon completion, the mixture was filtered and washed with water (2 mL). HCl (1 N, 0.8 mL) was added, and the solution was washed with EA (3×5 mL). The mixture was concentrated under reduced pressure to give (1R, 2S, 3R, 5R)-3-amino-2-fluoro-5 (hydroxymethyl)cyclopentanol (10H) (97 mg, crude, HCl salt) as a pale yellow solid. $^1$H NMR (400 MHz, DMSO-d$_6$) δ: 8.59 (br s, 3H), 4.91-4.68 (m, 1H), 3.61-3.49 (m, 1H), 3.49-3.30 (m, 2H), 2.15 (td, J=8.4, 13.2 Hz, 1H), 1.95 (br d, J=5.3 Hz, 1H), 1.33 (td, J=9.3, 13.2 Hz, 1H).

Et$_3$N (181.53 mg, 1.79 mmol, 249.70 μL, 3 eq.) and 2-(4,6-dichloropyrimidin-5-yl) acetaldehyde (10H-a) (114.22 mg, 597.98 μmol, 1 eq.) was added to a solution of 10H (185 mg, 597.98 μmol, 1 eq., HCl) in EtOH (3 mL). The mixture was stirred at 80° C. for 2 h. The reaction progress was monitored by TLC (DCM:MeOH=10:1). Upon completion, the mixture was filtered and concentrated under reduced pressure to give a residue. The residue was purified by column chromatography (SiO$_2$, DCM:MeOH=200:1 to 50:1) to afford (1R, 2S, 3R, 5R)-3-(4-chloropyrrolo[2, 3-d]pyrimidin-7-yl)-2-fluoro-5-(hydroxymethyl)cyclopentanol (11H) (144 mg, 504.02 µmol, 84% yield) as a yellow oil. LCMS: (ESI): m/z calcd. for $C_{12}H_{14}ClFN_3O_2$ 286.07 [M+H]$^+$, found 285.9.

4-methylbenzenesulfonyl chloride (80.08 mg, 420.02 µmol, 1.2 eq.) was added to a solution of 11H (100 mg, 350.02 µmol, 1 eq.) in pyridine (0.5 mL) at 0° C. The mixture was stirred at 25° C. for 2 h. The reaction progress was monitored by TLC (DCM:MeOH=20:1). The mixture was filtered and concentrated under reduced pressure to give a residue. The residue was purified by column chromatography (SiO$_2$, PE:EA=20:1 to 1:2) to afford [(1R,2R,3S,4R)-4-(4-chloropyrrolo[2,3-d]pyrimidin-7-yl)-3-fluoro-2-hydroxy-cyclopentyl]methyl 4-methylbenzenesulfonate (12H) (57 mg, 129.58 µmol, 37% yield) as a yellow solid. LCMS: (ESI): m/z calcd. for $C_{19}H_{20}ClFN_3O_4S$ 440.08 [M+H]$^+$, found 440.0.

Cs$_2$CO$_3$ (148.88 mg, 456.94 µmol, 3 eq.) was added to a mixture of 12H (67 mg, 152.31 µmol, 1 eq.) and 2-amino-3-bromo-quinolin-7-ol (36.41 mg, 152.31 µmol, 1 eq.) (Q3) in DMF (0.5 mL). The mixture was stirred at 25° C. for 15 h. The reaction progress was monitored by TLC (DCM:MeOH=20:1). Upon completion, the mixture was diluted with water (5 mL) and extracted with EA (3×3 mL). The combined organic layers were washed with brine (2×5 mL), dried over Na$_2$SO$_4$, and concentrated to give a residue. The residue was purified by prep-TLC (SiO$_2$, DCM:MeOH=20:1) to afford (1R, 2S, 3R, 5R)-5-[(2-amino-3-bromo-7-quinolyl)oxymethyl]-3-(4-chloropyrrolo[2,3-d]pyrimidin-7-yl)-2-fluoro-cyclopentanol (13H) (41 mg, 79.94 µmol, 52% yield) as a white solid. LCMS: (ESI): m/z calcd. for $C_{21}H_{19}BrClFN_5O_2$ 508.03 [M+H]$^+$, found 508.0.

NH$_3$.H$_2$O (4.55 g, 36.35 mmol, 5 mL, 28% purity, 526.34 eq.) was added to a solution of 13H (35 mg, 69.07 µmol, 1 eq.) in dioxane (5 mL). The mixture was stirred at 100° C. for 48 h. The reaction progress was monitored by TLC (DCM:MeOH=10:1). Upon completion, the mixture was filtered and concentrated under reduced pressure to give a residue. The residue was purified by prep-HPLC (column: Phenomenex Gemini-NX 150*30 mm*5 um; mobile phase: [water (0.04% NH$_3$H$_2$O*10 mM NH$_4$HCO$_3$)-ACN]; B %: 26%-56%, 8 min) to afford (1R,2S,3R,5R)-5-[(2-amino-3-bromo-7-quinolyl)oxymethyl]-3-(4-aminopyrrolo[2,3-d]pyrimidin-7-yl)-2-fluoro-cyclopentanol (11) (12 mg, 24.25 µmol, 35% yield) as a white solid. LCMS: (ESI): m/z calcd. for $C_{21}H_{21}BrFN_6O_2$ 487.08 [M+H]$^+$, found 487.1. $^1$H NMR (400 MHz, CD$_3$OD) δ: 8.21 (s, 1H), 8.10 (s, 1H), 7.55 (d, J=9.0 Hz, 1H), 7.31 (d, J=3.5 Hz, 1H), 7.04 (d, J=2.3 Hz, 1H), 7.00 (d, J=8.8 Hz, 1H), 6.66 (d, J=3.5 Hz, 1H), 5.37-5.11 (m, 2H), 4.40 (td, J=5.6, 13.2 Hz, 1H), 4.28 (br dd, J=4.6, 8.4 Hz, 2H), 2.62 (br d, J=7.8 Hz, 2H), 2.08-1.96 (m, 1H).

Example 8

Compound 12

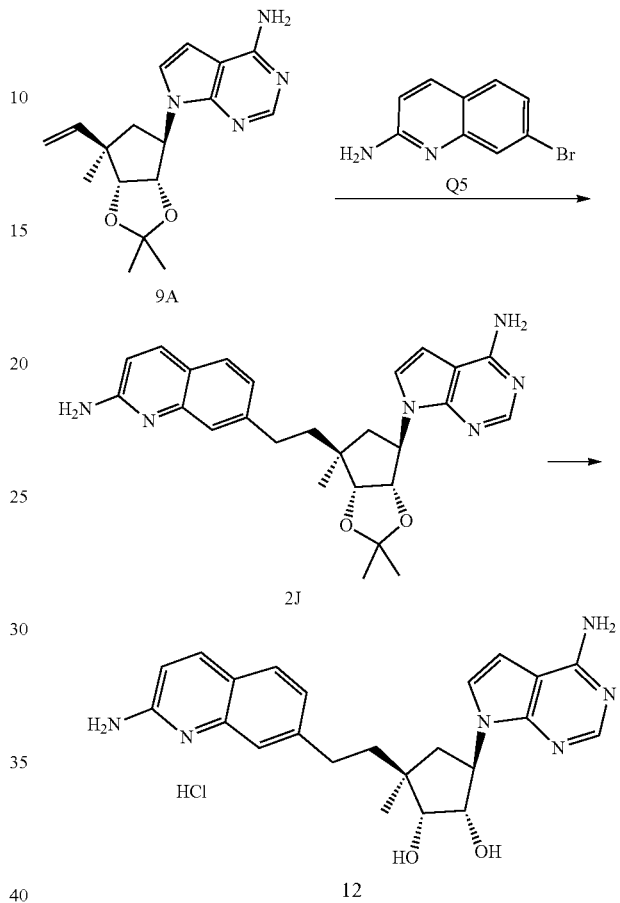

To a solution of 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (180 mg, 572.6 µmol, 1 eq.) in THF (6 mL) was added 9-BBN dimer (304.9 mg, 1.3 mmol, 2.2 eq.). The mixture was stirred at 50° C. for 2 h and cooled to 20° C. K$_3$PO$_4$ (607.7 mg, 2.9 mmol, 5 eq.) and H$_2$O (0.6 mL) were added. The mixture was stirred at 20° C. for 0.5 h. Then 7-bromoquinolin-2-amine (153.3 mg, 687.1 µmol, 1.2 eq.) and Pd(dppf)Cl$_2$ (41.9 mg, 57.3 µmol, 0.1 eq.) were added. The mixture was stirred at 70° C. for 12 h. The reaction progress was monitored by LCMS. Upon completion, the mixture was diluted with brine (10 mL). The mixture was extracted with EA (3×20 mL). The organic layers were combined, dried over anhydrous Na$_2$SO$_4$, and concentrated to afford a residue. The residue was purified by reversed-phase HPLC (0.1% NH$_3$.H$_2$O) to afford 7-[2-[(3aR,4S,6R,6aS)-6-(4-aminopyrrolo[2,3-d]pyrimidin-7-yl)-2,2,4-trimethyl-3a,5,6,6a-tetrahydrocyclopenta[d][1,3]dioxol-4-yl]ethyl]quinolin-2-amine (2J) (175 mg, 64.5% yield) as white solid. LCMS: (ESI): m/z calcd. for $C_{26}H_{31}N_6O_2$ 459.25 [M+H]$^+$, found 459.4.

A mixture of 2J (230 mg, 501.58 µmol, 1 eq.), HCl (4 M, 3 mL) and THF (6 mL) was stirred at rt for 6 h. The reaction progress was monitored by LCMS. Upon completion, the mixture was concentrated under reduced pressure to afford a solid. The solid was washed with MeCN:H₂O (10:1.6 mL) to afford (1S,2R,3S,5R)-5-(4-amino-7H-pyrrolo[2,3-d]pyrimidin-7-yl)-3-(2-(2-aminoquinolin-7-yl)ethyl)-3-methylcyclopentane-1,2-diol (12) as a hydrochloride salt (white solid, 180 mg, 72% yield). LCMS: (ESI): m/z calcd. for 419.22 [M+H]⁺, found 419.3. ¹H NMR (CD₃OD) δ: 8.31 (d, J=9.3 Hz, 1H), 8.25 (s, 1H), 7.82 (d, J=8.2 Hz, 1H), 7.58 (d, J=3.7 Hz, 1H), 7.53 (s, 1H), 7.45 (dd, J=1.3, 8.2 Hz, 1H), 7.01 (d, J=9.5 Hz, 1H), 6.92 (d, J=3.5 Hz, 1H), 5.19-5.07 (m, 1H), 4.61-4.49 (m, 1H), 3.96 (d, J=6.4 Hz, 1H), 3.02-2.78 (m, 2H), 2.17-1.80 (m, 4H), 1.25 (s, 3H).

Example 9

Compound 13

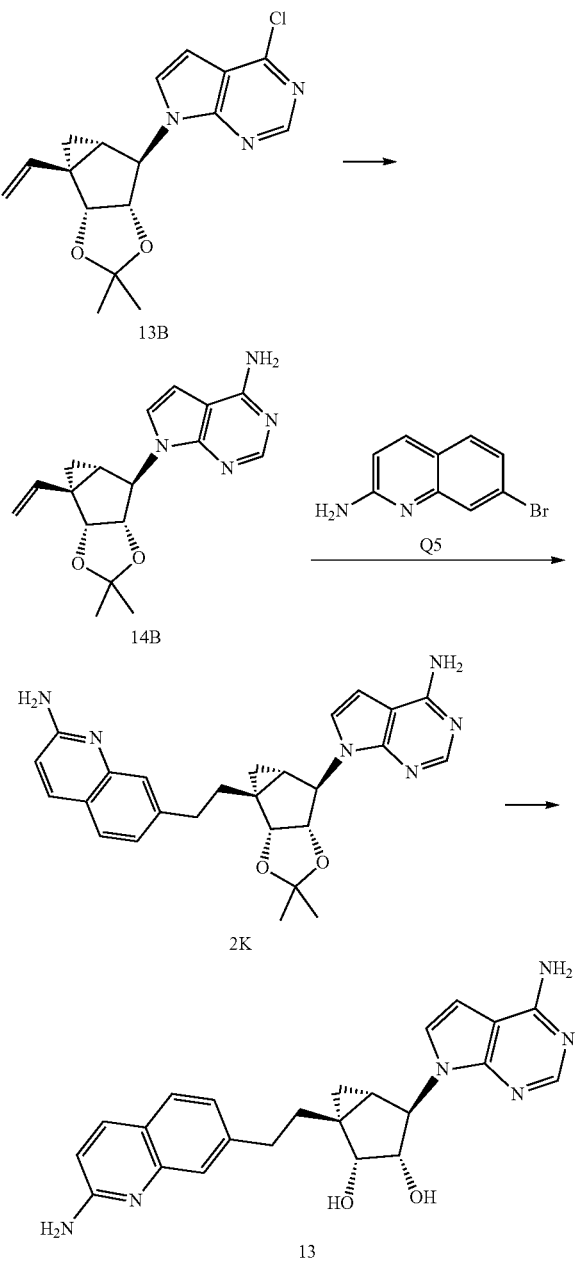

NH₃·H₂O (20 mL, 28% wt) was added to a solution of 4-chloro-7-[(11S,12R,13S,14R,16S)-15,15-dimethyl-16-vinyl-20,21-dioxatricyclononan-12-yl]pyrrolo[2,3-d]pyrimidine (13B) (788 mg, 2.37 mmol, 1 eq.) in dioxane (20 mL). The mixture was stirred at 100° C. for 48 h. The reaction progress was monitored by TLC (DCM:MeOH=20:1). Upon completion, the mixture was filtered and concentrated under reduced pressure to give a residue. The residue was purified by flash silica gel chromatography (ISCO®; 12 g Sepa Flash® Silica Flash Column, Eluent of 0~8% DCM/MeOH @ 30 mL/min) to afford 7-[(11S,12R,13S,14R,16S)-15,15-dimethyl-16-vinyl-21,22-dioxatricyclononan-12-yl]pyrrolo[2,3-d]pyrimidin-4-amine (14B) (773 mg, 2.03 mmol, 85% yield) as a white solid. LCMS: (ESI): m/z calcd. for C₁₇H₂₁N₄O₂ 313.16 [M+H]⁺, found 312.9.

9-BBN dimer (1.05 g, 4.32 mmol, 2.7 eq.) was added to a solution of 14B (500 mg, 1.60 mmol, 1 eq.) in THF (10 mL), and the mixture was stirred at 50° C. for 3.5 h under Ar atmosphere. The mixture was cooled to rt, and then K₃PO₄ (1.70 g, 8.00 mmol, 5 eq.) in H₂O (1 mL) were added. The resulting mixture was stirred at 25° C. for 0.5 h, and then 7-bromoquinolin-2-amine (Q5) (357.06 mg, 1.60 mmol, 1 eq.) and Pd(dppf)Cl₂ (117.12 mg, 160.07 µmol, 0.1 eq.) were added. The mixture was purged with Ar (3×), and then stirred at 72° C. for 12 h. The reaction progress was monitored by TLC (DCM:MeOH=10:1). Upon completion, the mixture was extracted with EA (3×10 mL). The combined organic layers were washed with brine (3×20 mL), dried over Na₂SO₄ and concentrated to give a residue. The residue was purified by prep-HPLC Combi-flash reversed-phase C-18 column chromatography (10%~60% CH₃CN/water (1 mL/3 L NH₃·H₂O in water)® 75 mL/min) to afford 7-[2-[(20S,21R,22S,23R,25R)-21-(4-aminopyrrolo[2,3-d]pyrimidin-7-yl)-24,24-dimethyl-32,33-dioxatricyclononan-25-yl]ethyl]quinolin-2-amine (2K) (446 mg, 976.92 µmol, 19% yield) as a yellow solid. LCMS: (ESI): m/z calcd. for C₂₆H₂₉N₆O₂ 457.23 [M+H]⁺, found 457.1.

To a solution of 2K (446 mg, 976.92 µmol, 1 eq.) in THF (10 mL) was added HCl (4 M, 5 mL). The mixture was stirred at 25° C. for 12 h. The reaction progress was monitored by TLC (DCM:MeOH=5:1). Upon completion, the mixture was filtered and concentrated under reduced pressure to give a residue (400 mg, crude, HCl salt) as a brown solid. This residue (200 mg) was purified by prep-HPLC (column: Phenomenex Gemini-NX 150*30 mm*5 um; mobile phase: [water (0.04% NH₃H₂O+10 mM NH₄HCO₃)-ACN]; B %: 20%-50%, 8 min) to afford (1R,2R,3S,4R,5S)-4-(4-aminopyrrolo[2,3-d]pyrimidin-7-yl)-1-[2-(2-amino-7-quinolyl)ethyl]bicyclo[3.1.0]hexane-2,3-diol (13) (115 mg, 274.39 µmol, 58% yield) as a white solid. LCMS: (ESI): m/z calcd. for C₂₃H₂₅N₆O₂ 417.2 [M+H]⁺, found 417.2. ¹H NMR (400 MHz, CD₃OD) δ: 8.09 (s, 1H), 7.90 (d, J=8.8 Hz, 1H), 7.57 (d, J=8.3 Hz, 1H), 7.41 (s, 1H), 7.18 (dd, J=1.4, 8.2 Hz, 1H), 7.01 (d, J=3.8 Hz, 1H), 6.77 (d, J=9.0 Hz, 1H), 6.57 (d, J=3.8 Hz, 1H), 4.95 (s, 1H), 4.60 (br d, J=6.5 Hz, 1H), 3.86 (d, J=6.8 Hz, 1H), 3.12-2.87 (m, 2H), 2.30-2.18 (m, 1H), 2.05-1.93 (m, 1H), 1.47 (t, J=4.3 Hz, 1H), 1.39 (dd, J=3.3, 8.5 Hz, 1H), 0.68 (dd, J=5.3, 7.0 Hz, 1H).

Example 10

Compound 14

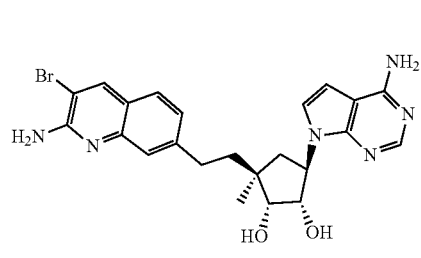

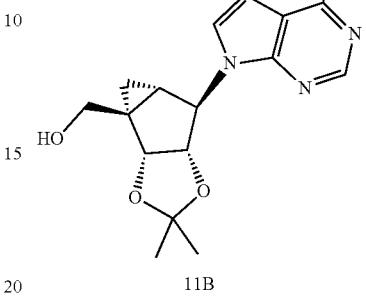

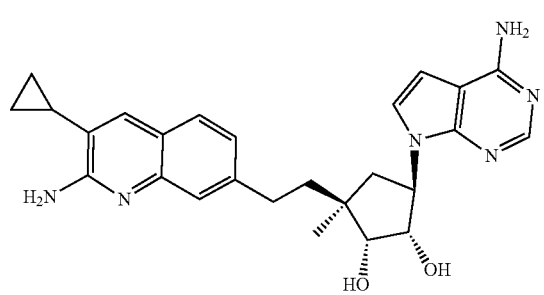

To a solution of 1 (40 mg, 80.4 μmol, 1 eq.) in dioxane (1 mL) and H$_2$O (0.2 mL) were added K$_2$CO$_3$ (27.8 mg, 201.05 μmol, 2.5 eq.), cyclopropyl boronic acid (17.3 mg, 201.1 μmol, 2.5 eq.), and Pd(dppf)Cl$_2$ (5.9 mg, 8.0 μmol, 0.1 eq.). The mixture was stirred at 100° C. for 16 h under Ar atmosphere. The reaction was monitored by LC-MS. Upon completion, the mixture was filtrated. The filter cake was washed with dioxane/water (5:1) (4 mL). The residue was purified by prep-HPLC (HCl condition; water (0.05% HCl)-ACN, column: Phenomenex Gemini-NX 150*30 mm*5 um, begin: 10, end: 30, Gradient Time (min): 7 min, 100% B Hold Time (min): 0, FlowRate (ml/min): 35) to give (1S, 2R,3S,5R)-3-[2-(2-amino-3-cyclopropyl-7-quinolyl)ethyl]-5-(4-aminopyrrolo[2,3-d]pyrimidin-7-yl)-3-methylcyclopentane-1,2-diol (14) (24 mg, 45.05 μmol, 56.0% yield, 99.8% purity, 2 HCl) as a white solid. LCMS: (ESI): m/z calcd. for C$_{26}$H$_{31}$N$_6$O$_2$ 459.24 [M+H]$^+$, found 459.2. $^1$HNMR (400 MHz, CD$_3$OD) δ: 8.25 (s, 1H), 8.12 (s, 1H), 7.79 (d, J=8.3 Hz, 1H), 7.56 (d, J=3.4 Hz, 1H), 7.53 (s, 1H), 7.40-7.44 (m, 1H), 6.90-6.93 (m, 1H), 5.08-5.16 (m, 1H), 4.52-4.58 (m, 1H), 3.96 (d, J=6.4 Hz, 1H), 2.81-3.00 (m, 2H), 1.97-2.14 (m, 2H), 1.81-1.96 (m, 3H), 1.25 (s, 3H), 1.11-1.17 (m, 2H), 0.80-0.85 (m, 2H).

Example 11

Compound 15

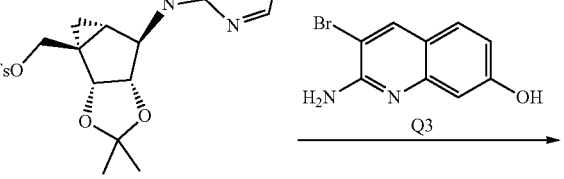

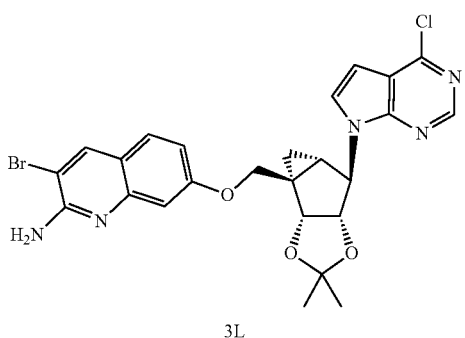

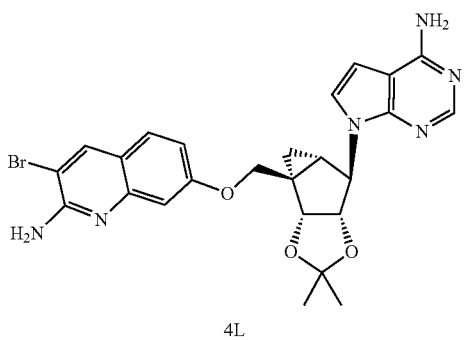

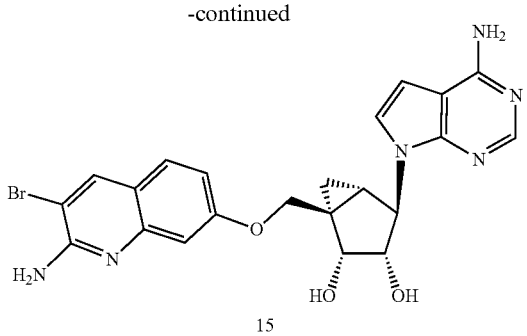

To a solution of [(10S,11R,12S,13R,15R)-11-(4-chloropyrrolo[2,3-d]pyrimidin-7-yl)-14,14-dimethyl-20,21-dioxatricyclononan-15-yl]methanol (11B) (500 mg, 1.49 mmol, 1 eq.) in DCM (10 mL) were added Et$_3$N (1.51 g, 14.90 mmol, 2.1 mL, 10 eq.), DMAP (36.4 mg, 298.0 µmol, 0.2 eq.), and 4-methylbenzenesulfonyl chloride (852.2 mg, 4.47 mmol, 3 eq.). The mixture was stirred at 25° C. for 16 h. The mixture was concentrated under reduced pressure to give a residue. The residue was purified by flash silica gel chromatography (ISCO®; 12 g SepaFlash® Silica Flash Column, Eluent of 0~32% EA:PE gradient @ 36 mL/min) to give 2L (420 mg, 831.5 µmol, 55.8% yield) as a white solid. LCMS: (ESI): m/z calcd. for C$_{23}$H$_{25}$ClN$_3$O$_5$S 490.11 [M+H]$^+$, found 490.1.

To a mixture of 2L (345 mg, 704.12 µmol, 1 eq.) and 2-amino-3-bromo-quinolin-7-ol (Q3) (168.33 mg, 704.12 µmol, 1.0 eq.) in DMF (3 mL) was added Cs$_2$CO$_3$ (688.25 mg, 2.11 mmol, 3.0 eq.). The mixture was stirred at 20° C. for 16 h. The reaction progress was monitored by TLC. The mixture was then diluted with H$_2$O (30 mL) and extracted with EtOAc (3×10 mL). The combined organic layers were washed with brine (2×20 mL), dried over Na$_2$SO$_4$, filtered and concentrated under reduced pressure to give a residue. The residue was purified by flash silica gel chromatography (ISCO®; 12 g SepaFlash® Silica Flash Column, Eluent of 0~80% EA:PE gradient @ 30 mL/min). 3-bromo-7-[[(19S, 20R,21S,22R,24R)-20-(4-chloropyrrolo[2,3-d]pyrimidin-7-yl)-23,23-dimethyl-30,31-dioxatriyclononan-24-yl]methoxy]quinolin-2-amine (3L) (280 mg, 482.7 µmol, 68% yield, 96% purity) was obtained as a light yellow solid. LCMS: (ESI): m/z calcd. for C$_{25}$H$_{25}$BrClN$_5$O$_3$ 558.07 [M+H]$^+$, found 557.9.

A mixture of 3L (280 mg, 502.84 µmol, 1 eq.) and NH$_3$.H$_2$O (5 mL, 25% wt) in dioxane (5 mL) was heated in a sealed tube at 100° C. for 48 h. The reaction progress was monitored by LCMS. The mixture was then extracted with DCM (3×10 mL). The combined organic phase was washed with brine (20 mL), dried over Na$_2$SO$_4$, filtered and concentrated to give a residue. The residue was purified by prep-HPLC (column: Phenomenex Gemini-NX 150*30 mm*5 µm; mobile phase: [water (0.04% NH$_3$H$_2$O+10 mM NH$_4$HCO$_3$)-ACN]; B %: 42%-72%, 8 min). 7-[[(19S,20R, 21S,22R,24R)-20-(4-aminopyrrolo[2,3-d]pyrimidin-7-yl)-23,23-dimethyl-31,32-dioxatricyclononan-24-yl]methoxy]-3-bromo-quinolin-2-amine (4L) (140 mg, 247.48 µmol, 49.22% yield, 95% purity) was obtained as a light yellow solid. LCMS: (ESI): m/z calcd. for C$_{25}$H$_{26}$BrN$_6$O$_3$ 539.12 [M+H]$^+$, found 539.2.

To a mixture of 4L (140 mg, 260.5 µmol, 1.0 eq.) in THF (6 mL) was added HCl (4 M, 2.6 mL). The mixture was then stirred at 20° C. for 16 h. The reaction progress was monitored by LCMS. Upon completion the solution was adjusted to pH=8 with NH$_3$.H$_2$O and concentrated under reduced pressure to give a residue. The residue was purified by prep-HPLC (column: Phenomenex Gemini-NX 150*30 mm*5 µm; mobile phase: [water (0.04% NH$_3$H$_2$O+10 mM NH$_4$HCO$_3$)-ACN]; B %: 25%-55%, 8 min). (1R,2R,3S,4R, 5S)-1-[(2-amino-3-bromo-7-quinolyl)oxymethyl]-4-(4-aminopyrrolo[2,3-d]pyrimidin-7-yl)bicyclo[3.1.0]hexane-2,3-diol (15) (74 mg, 146.2 µmol, 56% yield) was obtained as a white solid. LCMS: (ESI): m/z calcd. for C$_{22}$H$_{22}$BrN$_6$O$_3$ 497.09 [M+H]$^+$, found 497.1. $^1$H NMR (400 MHz, CD$_3$OD) δ: 8.22 (s, 1H), 8.11 (s, 1H), 7.71 (d, J=3.7 Hz, 1H), 7.59 (d, J=8.8 Hz, 1H), 7.08-7.01 (m, 2H), 6.66 (d, J=3.4 Hz, 1H), 5.10 (s, 1H), 4.84-4.79 (m, 1H), 4.61 (s, 1H), 3.87 (d, J=10.3 Hz, 1H), 3.78 (d, J=6.8 Hz, 1H), 1.77-1.71 (m, 2H), 0.92 (br s, 1H).

Example 12

Compound 16

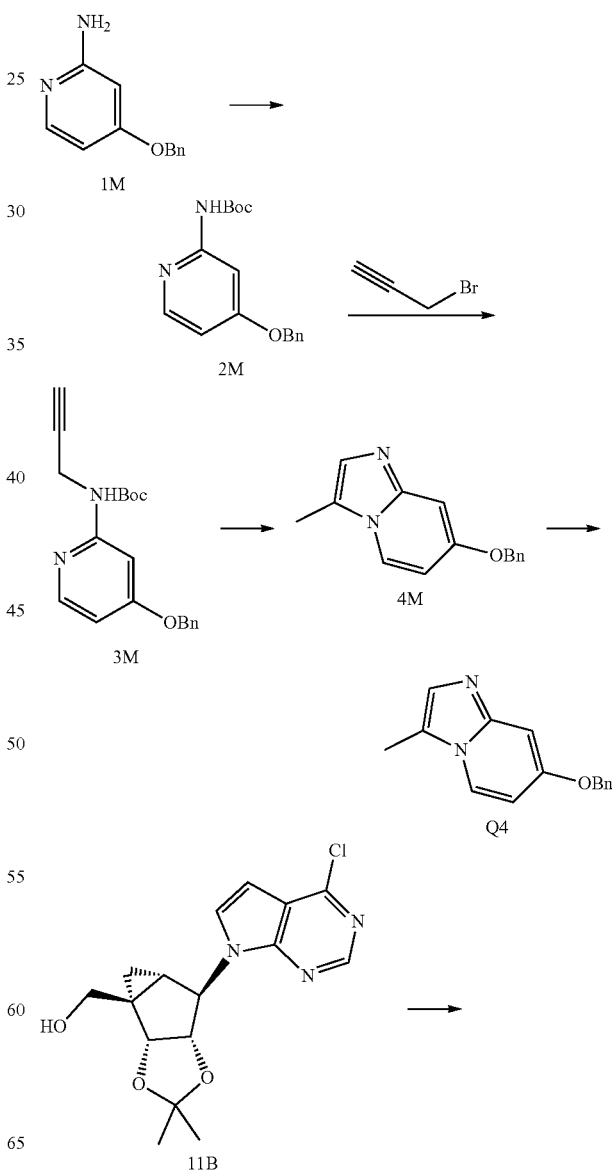

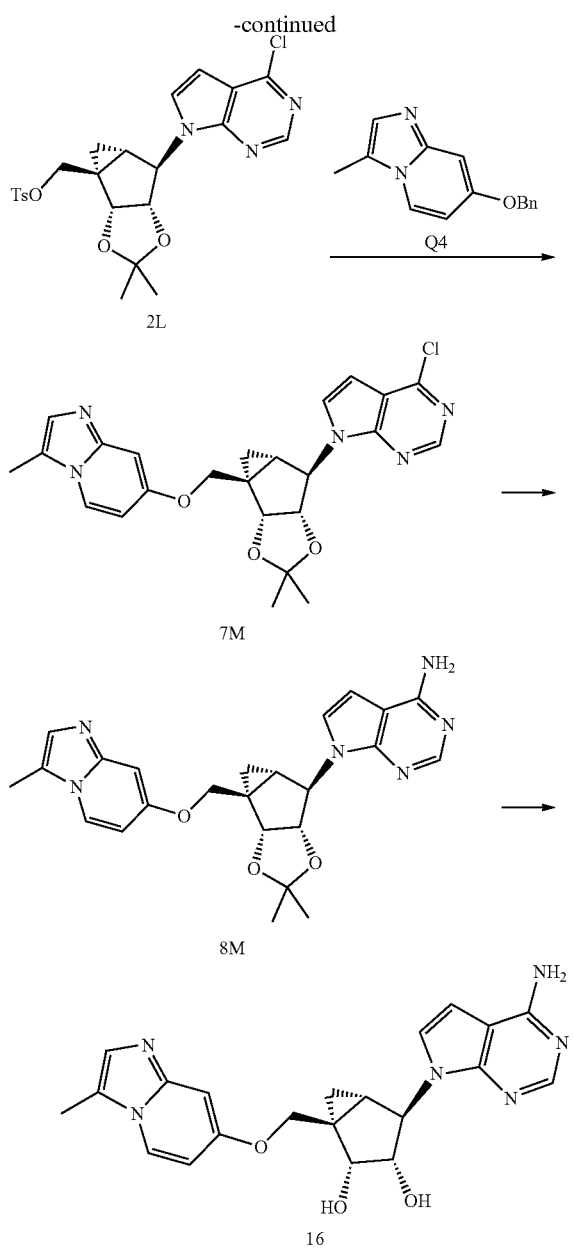

A mixture of 4-benzyloxypyridin-2-amine (11B) (100 mg, 499.4 μmol, 1 eq.) and Boc₂O (119.9 mg, 549.4 μmol, 1.1 eq.) in t-BuOH (1.5 mL) was stirred at 50° C. for 1 h. The reaction progress was monitored by LCMS. Upon completion, the mixture was cooled to rt and diluted with EtOH (5 mL). The precipitate was filtered and dried under high vacuum to give crude 2L (116 mg, 363.1 μmol, 72.7% yield) as a white solid. LCMS: (ESI): m/z calcd. for $C_{17}H_{21}N_2O_3$ 301.15 $[M+H]^+$, found 301.0.

To a solution of 2L (116 mg, 386.2 μmol, 1 eq.) in DMF (2 mL) was added NaH (23.2 mg, 579.3 μmol, 60% purity, 1.5 eq.) in portions at 17° C. under a N₂ atmosphere. Upon completion of the addition, the mixture was stirred for 10 min. 3-bromoprop-1-yne (68.9 mg, 579.3 μmol, 49.9 μL, 1.5 eq.) was then added, and the mixture was stirred at 17° C. for 1 h. The reaction progress was monitored by LCMS. Upon completion, the reaction was quenched by addition H₂O (3 mL) and extracted with EA (2×3 mL). The combined organic layers were washed with H₂O (2×3 mL), dried over Na₂SO₄, filtered and concentrated under reduced pressure to give a residue. The residue was purified by flash silica gel chromatography (ISCO®; 12 g SepaFlash® Silica Flash Column, Eluent of 0~22% EA:PE gradient @ 36 mL/min) to give 3M (110 mg, 312.1 μmol, 80.8% yield) as a light yellow oil. LCMS: (ESI): m/z calcd. for $C_{20}H_{23}N_2O_3$ 339.16 $[M+H]^+$, found 339.0.

To a solution of 3M (110 mg, 325.1 μmol, 1 eq.) in THF (3 mL) was added t-BuOK (43.8 mg, 390.1 μmol, 1.2 eq.). The mixture was stirred at 15° C. for 30 min. The reaction progress was monitored by LCMS. Upon completion, the mixture was diluted with H₂O (3 mL) and extracted with EA (2×3 mL). The combined organic layers were dried over Na₂SO₄, filtered and concentrated under reduced pressure to give a residue. The residue was purified by flash silica gel chromatography (ISCO®; 4 g SepaFlash® Silica Flash Column, Eluent of 0~5% Methanol/Dichloromethane @ 36 mL/min) to give 4M (39 mg, 148.9 μmol, 45.8% yield) as a yellow solid. LCMS: (ESI): m/z calcd. for $C_{15}H_{15}N_2O$ 239.11 $[M+H]^+$, found 238.9.

To a solution of 4M (2.3 g, 9.65 mmol, 1 eq.) in MeOH (60 mL) was added Pd/C (10%, 1 g) under N₂ atmosphere. The mixture was stirred under H₂ (15 Psi) at 15° C. for 1 h. The reaction progress was monitored by LCMS. Upon completion, the mixture was filtered and concentrated under reduced pressure to give a crude Q4 (1.48 g, crude, 85% purity) as a black solid. LCMS: (ESI): m/z calcd. for $C_8H_9N_2O$ 149.06 $[M+H]^+$, found 149.2.

To a solution of [(10S,11R,12S,13R,15R)-11-(4-chloropyrrolo[2,3-d]pyrimidin-7-yl)-14,14-dimethyl-20,21-dioxatricyclononan-15-yl]methanol (11B) (500 mg, 1.49 mmol, 1 eq.) in DCM (10 mL) was added Et₃N (1.51 g, 14.90 mmol, 2.1 mL, 10 eq.), DMAP (36.4 mg, 298.0 μmol, 0.2 eq.) and 4-methylbenzenesulfonyl chloride (852.2 mg, 4.47 mmol, 3 eq.). The mixture was stirred at 25° C. for 16 h. The mixture was concentrated under reduced pressure to give a residue. The residue was purified by flash silica gel chromatography (ISCO®; 12 g SepaFlash® Silica Flash Column, Eluent of 0~32% EA:PE gradient @ 36 mL/min) to give 2 L (420 mg, 831.5 μmol, 55.8% yield) as a white solid. LCMS: (ESI): m/z calcd. for $C_{23}H_{25}ClN_3O_5S$ 490.11 $[M+H]^+$, found 490.1.

To a mixture of 2L (500 mg, 1.02 mmol, 1 eq.) and Q4 (181.4 mg, 1.22 mmol, 1.2 eq.) in DMF (5 mL) was added Cs₂CO₃ (997.5 mg, 3.06 mmol, 3 eq.). The mixture was stirred at 20° C. for 16 h. The reaction progress was monitored by LCMS. Upon completion, the mixture was diluted with H₂O (30 mL) and extracted with EA (3×10 mL). The combined organic layers were washed with brine (2×20 mL), dried over Na₂SO₄, filtered and concentrated under reduced pressure to give a residue. The residue was purified by flash silica gel chromatography (ISCO®; 12 g SepaFlash® Silica Flash Column, Eluent of 0~5% MeOH/DCM gradient @ 30 mL/min) to give 7M (350 mg, 721.14 μmol, 70.67% yield, 96% purity) as a slightly yellow solid. LCMS: (ESI): m/z calcd. for $C_{24}H_{25}ClN_5O_3$ 466.16 $[M+H]^+$, found 466.3.

To a solution of NH₃.H₂O (10 mL, 25% wt) and dioxane (10 mL) was added 7M (350 mg, 751.2 μmol, 1 eq.). The mixture was heated in a sealed tube at 100° C. and stirred for 40 h. The mixture was extracted with EA (2×10 mL). The combined organic layers were dried over Na₂SO₄, filtered and concentrated under reduced pressure to give a residue. The residue was purified by prep-HPLC (basic condition: column: Phenomenex Gemini-NX 150*30 mm*5 μm; mobile phase: [water (0.04% NH₃.H₂O+10 mM NH₄HCO₃)-ACN]; B %: 28%-58%, 8 min) to give 8M (226 mg, 491 μmol, 65.4% yield) as a light yellow solid. LCMS: (ESI): m/z calcd. for C₂₄H₂₇N₆O₃ 447.21 [M+H]⁺, found 447.3.

To a solution of 8M (226 mg, 506.16 μmol, 1 eq.) in THF (6 mL) was added HCl (4 M, 3 mL, 23.71 eq.). The mixture was stirred at 25° C. for 12 h. The reaction progress was monitored by LCMS. Upon completion, the mixture was concentrated under reduced pressure to give a residue. The residue was diluted with H₂O (10 mL) and lyophilized to give 16 (2 HCl, 245 mg, 505.5 μmol, 99.9% yield) as a white solid. LCMS: (ESI): m/z calcd. for C₂₁H₂₃N₆O₃ 407.18 [M+H]⁺, found 407.2. ¹H NMR (400 MHz, CD₃OD) δ: 8.55 (d, J=7.5 Hz, 1H), 8.30 (s, 1H), 7.76 (d, J=3.8 Hz, 1H), 7.63 (d, J=1.0 Hz, 1H), 7.37-7.25 (m, 2H), 7.02 (d, J=3.8 Hz, 1H), 5.24 (s, 1H), 4.85-4.80 (m, 2H), 4.16 (d, J=10.3 Hz, 1H), 3.93 (d, J=6.5 Hz, 1H), 2.59 (d, J=1.0 Hz, 3H), 1.84-1.72 (m, 2H), 1.06-0.96 (m, 1H).

Example 13

Compound 17

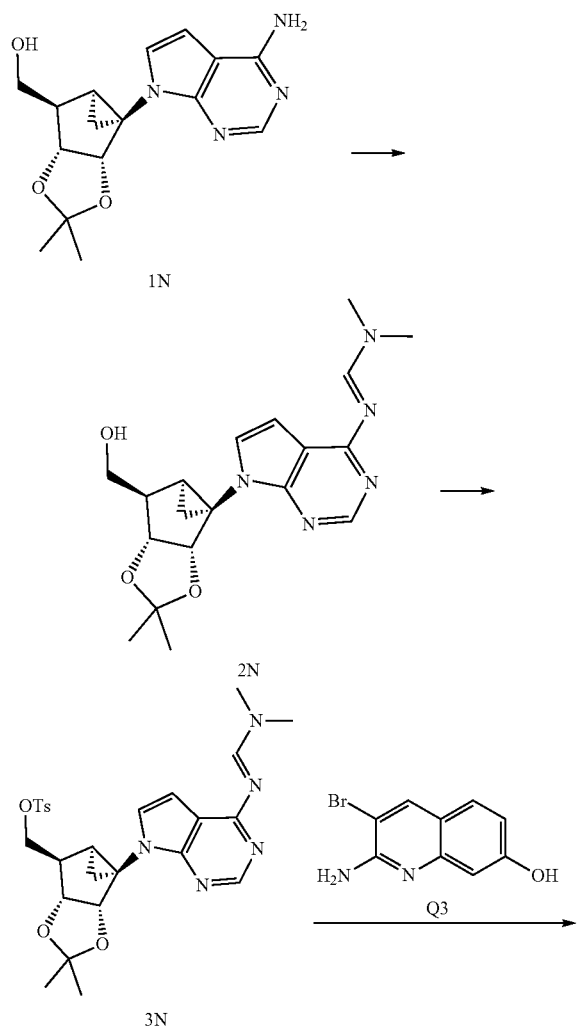

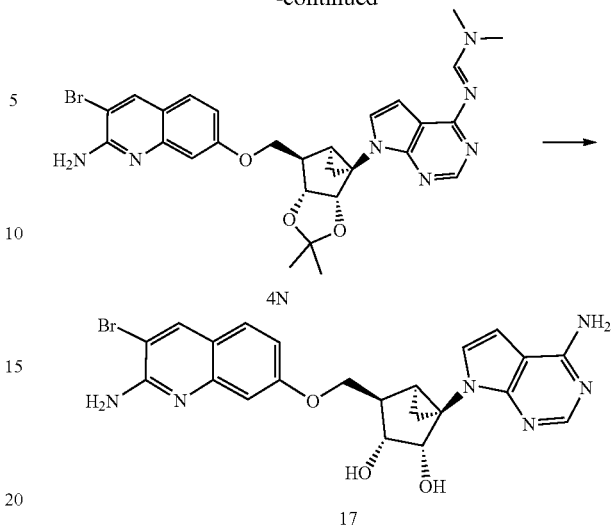

A mixture of Rac-[(10S,11R,12R,13S)-15-(4-aminopyrrolo[2,3-d]pyrimidin-7-yl)-14,14-dimethyl-21,22-dioxatricyclononan-11-yl]methanol (25 mg, 79.03 μmol, 1 eq.) in THF (2 mL) was added 1,1-dimethoxy-N,N-dimethyl-methanamine (188.4 mg, 1.58 mmol, 210.0 μL, 20 eq.), and the mixture was then stirred at 60° C. for 24 h. The reaction progress was monitored by LCMS. Upon completion, the mixture was concentrated to afford a residue. The residue was purified by pre-TLC (DCM:MeOH=10:1) to afford Compound rac-N'-[7-[(13S,14R,15R,16S)-14-(hydroxymethyl)-17,17-dimethyl-25,26-dioxatricyclononan-18-yl] pyrrolo[2,3 d]pyrimidin-11-yl]-N,N-dimethyl-formamidine (2N) (26 mg, 70.0 μmol, 88.6% yield) as a brown gum. LCMS: (ESI): m/z calcd, for C₁₉H₂₆N₅O₃ 372.20 [M+H]⁺, found 372.1.

4-methylbenzenesulfonyl chloride (40.1 mg, 210.0 μmol, 3 eq.) was added to the mixture of 2N (26 mg, 70.0 μmol, 1 eq.), TEA (35.4 mg, 350.0 μmol, 49 μL, 5 eq.) and DMAP (1.7 mg, 14.0 μmol, 0.2 eq.) in DCM (1 mL). After being stirred at 25° C. for 2 h, the mixture was concentrated and purified by pre-TLC (EA) to afford rac-[(20S,21R,22R, 23S)-25-[4-[(E)-dimethylaminomethyleneamino]pyrrolo[2, 3-d]pyrimidin-7-yl]-24,24-dimethyl-33,34-dioxatricyclononan-21-yl]methyl 15-methylbenzenesulfonate (3N) (15 mg, 28.5 μmol, 40.8% yield) as a brown gum. LCMS: (ESI): m/z calcd, for C₂₆H₃₂N₅O₅S 526.21 [M+H]⁺, found 526.1.

To a solution of 3N (15 mg, 28.54 μmol, 1 eq.) and 2-amino-3-bromo-quinolin-7-ol (6.8 mg, 28.5 μmol, 1 eq.) in DMF (1 mL) was added Cs₂CO₃ (27.9 mg, 85.6 μmol, 3 eq.). The mixture was stirred at 20° C. for 12 h. The reaction progress was monitored by LCMS. Upon completion, the mixture was concentrated to afford a residue. The residue was purified by pre-TLC (EA, 100%) to afford rac-N'-[7-[(22S,23R,24R,25S)-23-[(2-amino-3-bromo-7-quinolyl)oxymethyl]-26,26-dimethyl-35,36-dioxatricyclononan-27-yl]pyrrolo[2,3-d]pyrimidin-20-yl]-N,N-dimethyl-formamidine (4N) (7 mg, 8.1 μmol, 28.5% yield, 68.8% purity) was obtained as a white solid. LCMS: (ESI): m/z calcd, for C₂₈H₃₁BrN₇O₃ 594.16 [M+H]⁺, found 594.2.

To a solution of 4N (7 mg, 8.1 μmol, 68.8% purity, 1 eq.) in THF (0.6 mL) was added HCl (4 M, 0.3 mL). The mixture was stirred at 20° C. for 12 h. The reaction progress was monitored by LCMS. Upon completion, the mixture was concentrated under reduced pressure to give a residue. The residue was neutralized by NH₄OH (0.1 mL), and then purified by prep-HPLC (Column: Boston Prime C18 150*30 mm*5 um, Condition: water (0.04% NH₃H₂O+10 mM NH₄HCO₃)-ACN, begin B: 30%, end B: 60%, Gradient Time (min): 8, 100% B Hold Time (min): 2, FlowRate (ml/min): 25) to give rac-(2S,3R,4R,5S)-4-[(2-amino-3-bromo-7-quinolyl)oxymethyl]-1-(4-aminopyrrolo[2,3-d]pyrimidin-7-yl)bicyclo[3.1.0]hexane-2,3-diol (17) (2.6 mg, 5.1 μmol, 43.4% yield, 98.08% purity) as a white solid. LCMS: (ESI): m/z calcd. for $C_{22}H_{22}BrN_6O_3$ 499.09 [M+H]⁺, found 499.1. ¹H NMR (400 MHz, CD₃OD) δ: ppm 8.21 (s, 1H), 8.03 (s, 1H), 7.56 (d, J=8.8 Hz, 1H), 7.15 (d, J=3.7 Hz, 1H), 7.11 (d, J=2.2 Hz, 1H), 6.98 (dd, J=8.8, 2.4 Hz, 1H), 6.51 (d, J=3.7 Hz, 1H), 4.78 (br d, J=6.4 Hz, 1H), 4.43-4.52 (m, 2H), 4.11 (d, J=6.4 Hz, 1H), 2.60 (t, J=6.1 Hz, 1H), 1.94-1.98 (m, 2H), 1.22-1.29 (m, 1H).

Example 14

Compound 18

To a solution of 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (200 mg, 636.17 μmol, 1 eq.) in THF (10 mL) was added 9-BBN dimer (338.7 mg, 1.40 mmol, 2.2 eq.) at 20° C. The reaction was stirred at 50° C. for 1 h. The mixture was cooled to 20° C., and a solution of K₃PO₄ (675.2 mg, 3.18 mmol, 5 eq.) in H₂O (2 mL) was added. The mixture stirred for 30 min, and then 7-bromo-3-chloroquinolin-2-amine (Q8) (213 mg, 827.0 μmol, 1.3 eq.) and Pd(dppf)Cl₂ (46.6 mg, 63.6 μmol, 0.1 eq.) were added at 20° C. The mixture was stirred at 70° C. for 15 h. The reaction progress was monitored by LCMS. Upon completion the mixture was filtered, diluted with brine (10 mL) and extracted with DCM (2×10 mL). The combined organic layers were dried over Na₂SO₄, filtered and concentrated under reduced pressure to give a residue. The residue was purified by column chromatography (SiO₂, DCM:MeOH=50:1 to 20:1) to give 2O (280 mg, 482.8 μmol, 75.9% yield, 85% purity) as a white solid. LCMS: (ESI): m/z calcd. for $C_{26}H_{30}ClN_6O_2$ 493.20 [M+H]⁺, found 493.3.

To a solution of 2O (280 mg, 567.95 μmol, 1 eq.) in THF (5 mL) was added HCl (4 M, 2.5 mL, 17.61 eq.). The mixture was stirred at 20° C. for 12 h. The mixture was concentrated under reduced pressure to give a residue. The crude product was triturated with CH₃CN:H₂O=10:1 (2×11 mL) at 25° C. for 30 min to give 18 (2 HCl, 218 mg, 406.3 μmol, 71.5% yield, 98% purity, 2 HCl) as a white solid. LCMS: (ESI): m/z calcd. for $C_{23}H_{26}C_1N_6O_2$ 453.17 [M+H]⁺, found 453.3. ¹H NMR (400 MHz, CD₃OD) δ: 8.59 (s, 1H), 8.25 (s, 1H), 7.83 (d, J=8.3 Hz, 1H), 7.63-7.55 (m, 2H), 7.49 (d, J=8.3 Hz, 1H), 6.92 (d, J=3.7 Hz, 1H), 5.19-5.05 (m, 1H), 4.61-4.50 (m, 1H), 3.96 (d, J=6.1 Hz, 1H), 3.02-2.82 (m, 2H), 2.15-2.07 (m, 1H), 2.06-1.98 (m, 1H), 1.97-1.83 (m, 2H), 1.25 (s, 3H).

Example 15

Compound 19

-continued

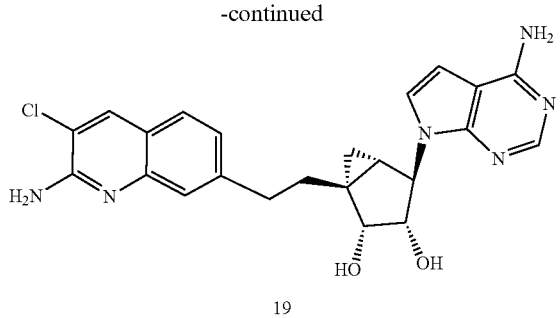

19

9-BBN dimer (193.7 mg, 800.3 µmol, 2.5 eq.) was added to a solution of 7-[(11S,12R,13S,14R,16S)-15,15-dimethyl-16-vinyl-21,22-dioxatricyclononan-12-yl]pyrrolo[2,3-d]pyrimidin-4-amine (14B) (100 mg, 320.1 µmol, 1 eq.) in THF (4 mL). The mixture was stirred at 50° C. for 2 h under $N_2$, and then cooled to 25° C. A solution of $K_3PO_4$ (339.8 mg, 1.60 mmol, 5 eq.) in $H_2O$ (0.4 mL) were added. The mixture was stirred at rt for 0.5 h. 7-bromo-3-chloro-quinolin-2-amine (123.7 mg, 480.2 µmol, 1.5 eq.) and Pd(dppf)Cl$_2$ (23.4 mg, 32.0 µmol, 0.1 eq.) were added. The mixture was stirred at 70° C. for 12 h under $N_2$. The reaction progress was monitored by TLC (DCM:MeOH=10:1). Upon completion, the mixture was diluted with water (10 mL) and extracted with EA (2×10 mL). The combined organic layers were washed with brine (2×10 mL), dried over $Na_2SO_4$ and concentrated to give a crude product (600 mg). An additional reaction (100 mg of 14B) was performed using the above procedure, and 700 mg of crude product was obtained.

The crude products from two batches were combined and purified by column chromatography (SiO$_2$, DCM:MeOH=50:1 to 30:1) to afford 7-[2-[(20S,21R,22S,23R,25R)-21-(4-aminopyrrolo[2,3-d]pyrimidin-7-yl)-24,24-dimethyl-32,33-dioxatricyclononan-25-yl]ethyl]-3-chloro-quinolin-2-amine (2P) (240 mg, 87% purity, 427.2 µmol, 66% yield, average of 2 batches) as a yellow solid. LCMS: (ESI): m/z calcd. for $C_{26}H_{28}ClN_6O_2$ 491.19 [M+H]$^+$, found 491.2.

To a solution of 2P (240 mg, 87% purity, 427.2 µmol, 1 eq.) in THF (5 mL) was added HCl (4 M, 2.5 mL). The mixture was stirred at 25° C. for 12 h. The reaction progress was monitored by TLC (DCM:MeOH=5:1). Upon completion, the mixture was filtered and concentrated under reduced pressure to give a residue. The residue was purified by prep-HPLC (column: Phenomenex Gemini-NX 150*30 mm*5 um; mobile phase: [water (0.04% NH$_3$H$_2$O+10 mM NH$_4$HCO$_3$)-ACN]; B %: 26%-56%, 8 min) to afford (1R, 2R,3S,4R,5S)-1-[2-(2-amino-3-chloro-7-quinolyl)ethyl]-4-(4-aminopyrrolo[2,3-d]pyrimidin-7-yl)bicyclo[3.1.0]hexane-2,3-diol (19) (110 mg, 241.8 µmol, 57% yield) as a white solid. LCMS: (ESI): m/z calcd. for $C_{23}H_{24}ClN_6O_2$ 451.16 [M+H]$^+$, found 451.2. $^1$H NMR (400 MHz, CD$_3$OD) δ: 8.08 (d, J=11.5 Hz, 2H), 7.56 (d, J=8.3 Hz, 1H), 7.45 (s, 1H), 7.21 (dd, J=1.3, 8.3 Hz, 1H), 7.02 (d, J=3.5 Hz, 1H), 6.57 (d, J=3.8 Hz, 1H), 4.94 (s, 1H), 4.59 (s, 1H), 3.86 (d, J=6.5 Hz, 1H), 3.10-2.90 (m, 2H), 2.29-2.19 (m, 1H), 2.02-1.93 (m, 1H), 1.48-1.35 (m, 2H), 0.68 (br dd, J=5.4, 7.2 Hz, 1H).

Example 16

Compounds 20 and 20-A

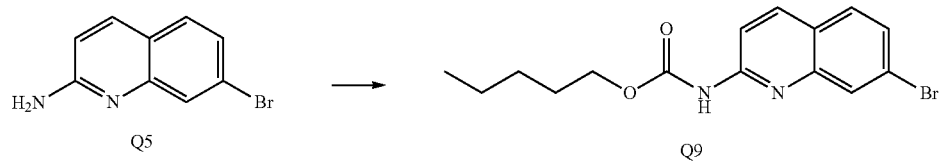

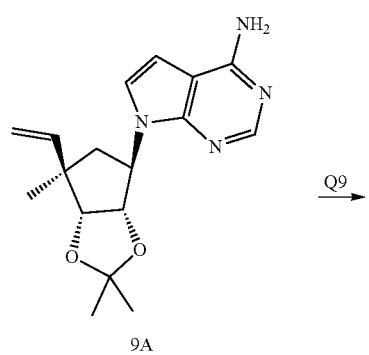

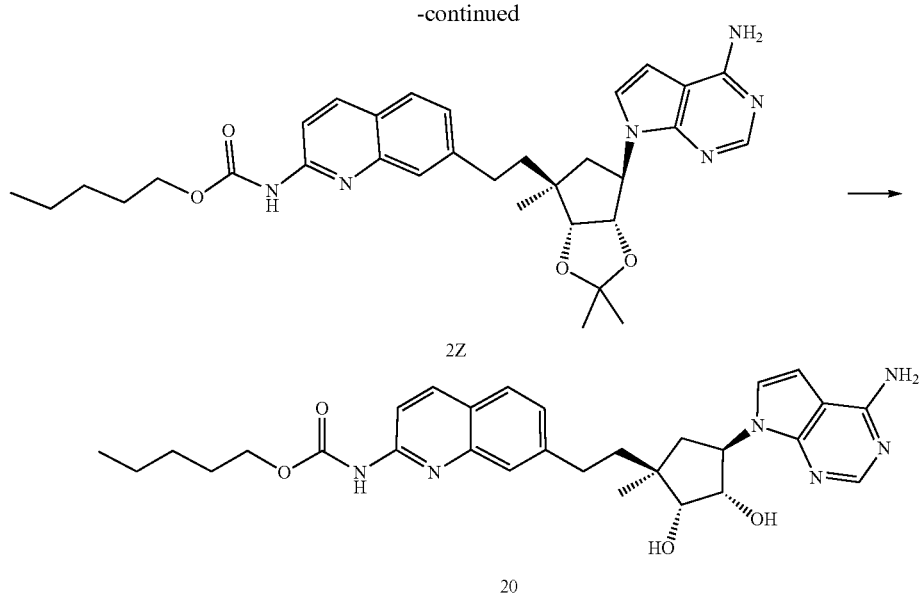

To a solution of 7-bromoquinolin-2-amine (Q5) (4.2 g, 16.03 mmol) in DCM (50 mL) were added N-methylimidazole (7.90 g, 96.20 mmol, 7.67 mL) and pentyl carbonochloridate (7.24 g, 48.10 mmol) at 0° C. The mixture was stirred at 20° C. for 12 h. The mixture was partitioned between DCM (30 mL) and brine (30 mL). The organic phase was separated, and the aqueous phase extracted with DCM (3×30 mL). The organic layers were combined and dried over $Na_2SO_4$. The solids were removed by filtration, and the filtrate was concentrated under reduced pressure. The crude was purified by column chromatography ($SiO_2$, PE:EA=0:1 to 20:1) to afford pentyl N-(7-bromo-2-quinolyl) carbamate (Q9) (3.2 g, 9.49 mmol, 59% yield, 100% purity) was obtained as a white solid. LCMS: (ESI): m/z calcd. for $C_{15}H_{18}BrN_2O_2$ 337.05 $[M+H]^+$, found 337.1.

A mixture of 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (1 g, 3.18 mmol) and 9-BBN dimer (1.92 g, 7.95 mmol) in THF (30 mL) was stirred at 50° C. for 1.5 h under Ar and then cooled to 20° C. A solution of $K_3PO_4$ (3.38 g, 15.90 mmol) in $H_2O$ (8 mL) was added. The mixture was stirred at 20° C. for 0.5 h. Pentyl N-(7-bromo-2-quinolyl)carbamate (1.29 g, 3.82 mmol) (Q9) and Pd(dppf)Cl$_2$ (232.75 mg, 318.09 μmol) were added. The mixture was stirred at 60° C. for 12 h under Ar. The mixture was partitioned between EA (30 mL) and water (30 mL). The organic phase was separated, and the aqueous phase washed with EA (3×30 mL). The organic layers were combined, washed with brine (30 mL) and dried over $Na_2SO_4$. The solids were removed by filtration, and the filtrate was concentrated under reduced pressure. The crude was purified by column chromatography ($SiO_2$, PE:EA=1:1 then DCM:MeOH=20:1) to afford pentyl (7-(2-((3aR,4S,6R,6aS)-6-(4-amino-7H-pyrrolo[2,3-d]pyrimidin-7-yl)-2,2,4-trimethyltetrahydro-4H-cyclopenta[d][1,3]dioxol-4-yl) ethyl)quinolin-2-yl)carbamate (2Z) (2.01 g, 3.14 mmol, 98% yield, 89% purity) as a yellow solid. LCMS: (ESI): m/z calcd. for $C_{32}H_{41}N_6O_4$ 573.31 $[M+H]^+$, found 573.5.

To a solution of pentyl N-[7-[2-[(3aR,4S,6R,6aS)-6-(4-aminopyrrolo[2,3-d]pyrimidin-7-yl)-2,2,4-trimethyl-3a,5,6,6a-tetrahydrocyclopenta[d][1,3]dioxol-4-yl]ethyl]-2-quinolyl]carbamate (2Z) (2.01 g, 3.14 mmol, 89% purity) in THF (10 mL) was added HCl (4 M, 8.96 mL). The mixture was stirred at 20° C. for 1 h. The mixture was concentrated under reduced pressure to afford a residue. The residue was purified by prep-HPLC (HCl condition, column: YMC-Triart Prep C18 150×40 mm×7 um; mobile phase: [water (0.225% HCl)-ACN]; B %: 22%-52%, 7.7 min) to afford pentyl N-[7-[2-[(1S,2R,3S,4R)-4-(4-aminopyrrolo[2,3-d]pyrimidin-7-yl)-2,3-dihydroxy-1-methyl-cyclopentyl] ethyl]-2-quinolyl]carbamate (20) (1.2 g, 1.98 mmol, 63% yield, 99% purity, 2 HCl) as an off-white solid. LCMS: (ESI): m/z calcd. for $C_{29}H_{37}N_6O_4$ 533.28 $[M+H]^+$, found 533.5. $^1$H NMR (400 MHz, CD$_3$OD) δ: 8.78 (d, J=9.0 Hz, 1H), 8.25 (s, 1H), 8.06 (d, J=8.4 Hz, 1H), 8.02 (s, 1H), 7.71 (d, J=8.2 Hz, 1H), 7.59 (d, J=3.5 Hz, 1H), 7.42 (d, J=9.3 Hz, 1H), 6.93 (d, J=3.5 Hz, 1H), 5.08-5.20 (m, 1H), 4.52-4.59 (m, 1H), 4.41 (t, J=6.6 Hz, 2H), 3.98 (d, J=6.2 Hz, 1H), 2.89-3.10 (m, 2H), 1.87-2.17 (m, 4H), 1.76-1.86 (m, 2H), 1.37-1.52 (m, 4H), 1.27 (s, 3H), 0.92-1.03 (m, 3H).

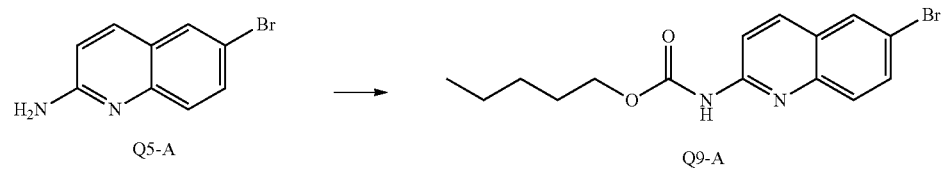

-continued

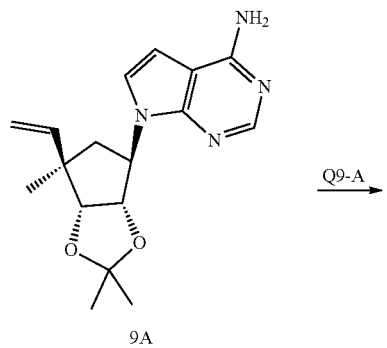

9A

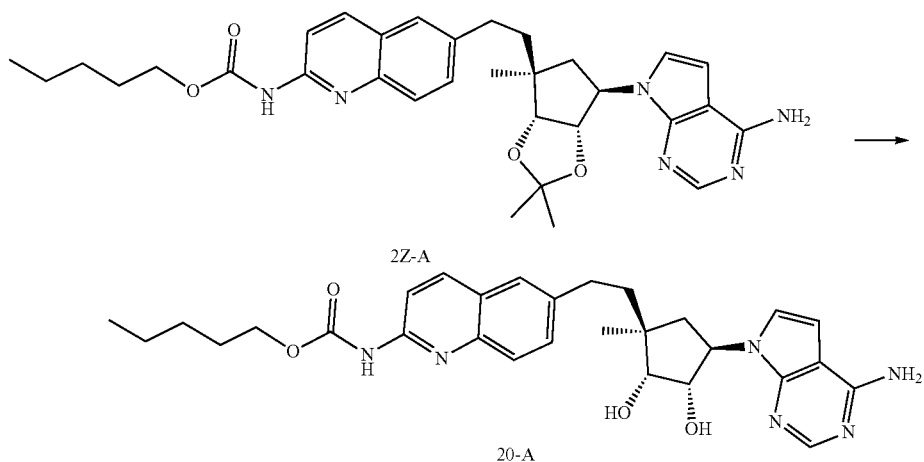

Pentyl carbonochloridate (202.54 mg, 1.34 mmol, 3 eq.) was added dropwise to a solution of 6-bromoquinolin-2-amine (Q5-A) (100 mg, 448.3 μmol, 1 eq.) and 1-methylimidazole (220.8 mg, 2.69 mmol, 214 μL) in DCM (2.5 mL) at 0° C. The mixture was stirred at 25° C. for 12 h. The reaction progress was monitored by TLC (PE:EA=1:1). Upon completion, the mixture was extracted with EA (2×5 mL). The combined organic layers were washed with brine (2×5 mL), dried over $Na_2SO_4$, filtered and concentrated under reduced pressure to give a residue. The residue was purified by flash silica gel chromatography (ISCO®; 4 g SepaFlash® Silica Flash Column, Eluent of 0~10% EA:PE gradient @18 mL/min) to afford pentyl N-(6-bromo-2-quinolyl) carbamate (Q9-A) (130 mg, 380.9 μmol, 84% yield) as a white solid. LCMS: (ESI): m/z calcd. for $C_{15}H_{18}BrN_2O_2$ 339.05 [M+H]$^+$, found 338.8.

9-BBN dimer (192.45 mg, 795.21 μmol, 2.5 eq.) was added to a solution of 9A (100 mg, 318.09 μmol, 1 eq.) in THF (4 mL), and the mixture was stirred at 50° C. for 2 h under Ar. The mixture was cooled to rt, and then a solution of $K_3PO_4$ (337.59 mg, 1.59 mmol, 5 eq.) in $H_2O$ (0.4 mL) were added. The mixture was stirred for 0.5 h, and then Q9-A (128.71 mg, 381.70 μmol, 1.2 eq.) and Pd(dppf)Cl$_2$ (23.27 mg, 31.81 μmol, 0.1 eq.) were added. The mixture was stirred at 70° C. for 12 h. The reaction progress was monitored by TLC (DCM:MeOH=10:1). Upon completion, the reaction mixture was extracted with EA (2×5 mL). The combined organic layers were washed with brine (2×5 mL), dried over $Na_2SO_4$, filtered and concentrated under reduced pressure to give a residue. The residue was purified by flash silica gel chromatography (ISCO®; 12 g SepaFlash® Silica Flash Column, Eluent of 0-5% DCM/MeOH @ 30 mL/min) to afford pentyl N-[7-[2-[(3aR,4S,6R,6aS)-6-(4-aminopyrrolo[2,3-d]pyrimidin-7-yl)-2,2,4-trimethyl-3a,5,6,6a-tetrahydrocyclopenta[d][1,3]dioxol-4-yl]ethyl]-2-quinolyl]carbamate (2Z-A) (110 mg, 79% purity, 151.7 μmol, 47% yield) as a yellow oil. LCMS: (ESI): m/z calcd. for $C_{32}H_{41}N_6O_2$ 573.31 [M+H]$^+$, found 573.3.

To a solution of 2Z-A (110 mg, 79% purity, 151.7 μmol, 1 eq.) in THF (4 mL) was added HCl (4 M, 2 mL). The mixture was stirred at 25° C. for 12 h. The reaction progress was monitored by TLC (DCM:MeOH=5:1). Upon completion, the mixture was filtered and concentrated under reduced pressure to give a residue. The residue was purified by prep-HPLC (column: Phenomenex Gemini-NX 150*30 mm*5 um; mobile phase: [water (0.05% HCl)-ACN]; B %: 20%-42%, 5 min) to afford pentyl N-[7-[2-[(1S,2R,3S,4R)-4-(4-aminopyrrolo[2,3-d]pyrimidin-7-yl)-2,3-dihydroxy-1-methyl-cyclopentyl]ethyl]-2-quinolyl]carbamate (20-A) (68 mg, 111.6 μmol, 73% yield, 99.4% purity, 2 HCl salt) as a white solid. LCMS: (ESI): m/z calcd. for $C_{29}H_{37}N_6O_4$ 533.28 [M+H]$^+$, found 533.3. $^1$H NMR (400 MHz, CD$_3$OD) δ: 8.81 (d, J=9.0 Hz, 1H), 8.24 (s, 1H), 8.12 (d, J=8.6 Hz, 1H), 8.03-7.94 (m, 2H), 7.59 (d, J=3.7 Hz, 1H), 7.43 (d, J=9.3 Hz, 1H), 6.93 (d, J=3.7 Hz, 1H), 5.14 (td, J=8.3, 10.7 Hz, 1H), 4.58-4.52 (m, 1H), 4.42 (t, J=6.6 Hz, 2H), 3.98 (d, J=6.4 Hz, 1H), 3.05-2.87 (m, 2H), 2.15-1.98 (m, 2H), 1.92 (dt, J=5.4, 11.5 Hz, 2H), 1.86-1.77 (m, 2H), 1.52-1.38 (m, 4H), 1.26 (s, 3H), 1.00-0.94 (m, 3H).

Example 17

Compounds 21 and 21-A

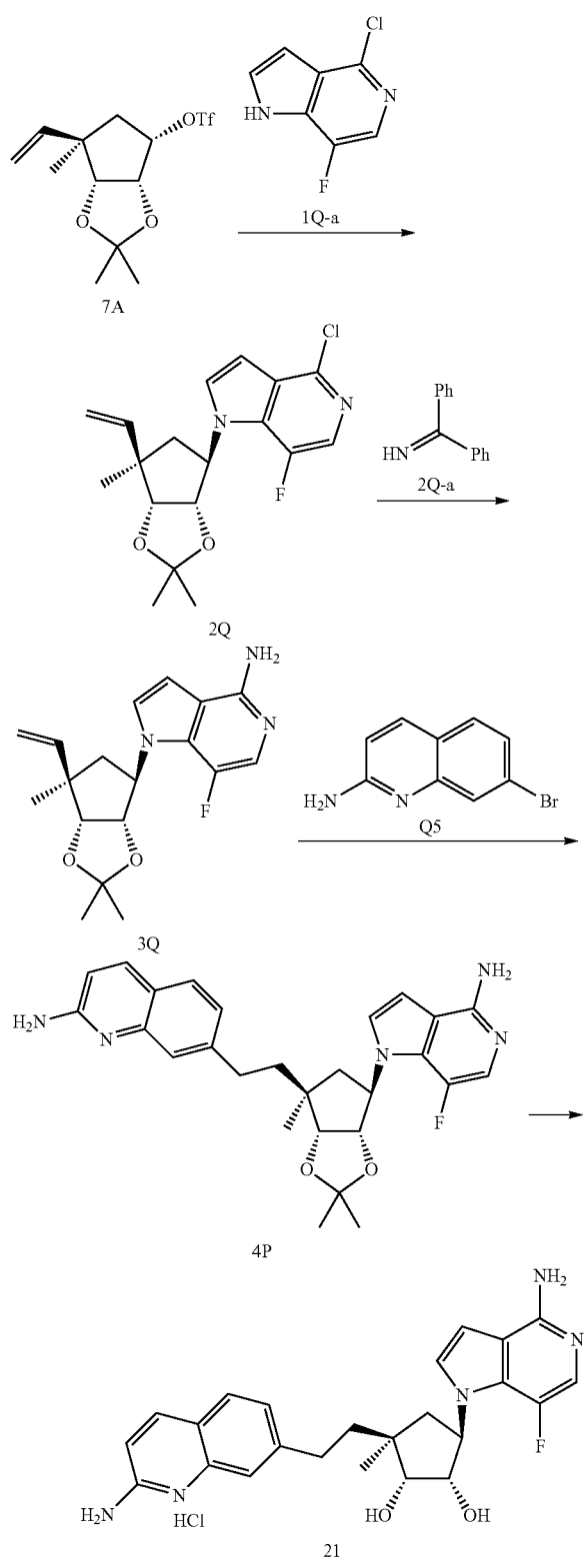

t-BuOK (951 mg, 8.48 mmol) was added to a mixture of 4-chloro-7-fluoro-1H-pyrrolo[3,2-c]pyridine (1Q-a) (1.55 g, 9.08 mmol) and DMF (15 mL). The mixture was stirred at rt for 30 min. Then [(3aR,4R,6S,6aR)-2,2,4-trimethyl-4-vinyl-3a,5,6,6a-tetrahydrocyclopenta[d][1,3]dioxol-6-yl] trifluoromethanesulfonate (7A) (2.0 g, 6.05 mmol) was added. The mixture was stirred at rt for 19 h. The mixture was diluted with water (20 mL) and then extracted with EA (2×20 mL). The organic layers were combined, washed with brine (10 mL) and dried over anhydrous $Na_2SO_4$. The solids were removed by filtration, and the filtrate was concentrated to afford a residue. The residue was purified by reversed-phase HPLC (A: 0.04% $NH_3.H_2O$, B: $CH_3OH$) to afford 4-chloro-7-fluoro-1-((3aS,4R,6R,6aR)-2,2,6-trimethyl-6-vinyltetrahydro-4H-cyclopenta[d][1,3]dioxol-4-yl)-1H-pyrrolo[3,2-c]pyridine (2Q) (710 mg, 33% yield) as a yellow gum. LCMS: (ESI): m/z calcd. for $C_{18}H_{21}ClFN_2O_2$ 351.13 [M+H]$^+$, found 351.1.

A mixture of 2Q (70.2 mg, 0.2 mmol), diphenylmethanimine (54.4 mg, 0.300 mmol, 0.050 mL), BINAP (24.9 mg, 40.0 μmol), $Pd_2(dba)_3$ (18.3 mg, 0.020 mmol) and t-BuONa (38.4 mg, 0.400 mmol) in toluene (2 mL) was degassed under vacuum and purged with Ar. The mixture was stirred at 110° C. for 18 h. The reaction was quenched with $NH_4Cl$ (sat., aq., 1 mL). The mixture was diluted with EA (20 mL) and washed with brine (10 mL). The organic layer was dried over anhydrous $Na_2SO_4$ and concentrated to afford a crude inline intermediate. The crude intermediate was dissolved in $CH_3OH$ (3 mL). Hydroxylamine (64 mg, 50% solution in water) was added at rt. The mixture was stirred at rt for 1 h. The mixture was concentrated under reduced pressure. The residue was purified by silica gel chromatography (PA: EA=2:1, 200 mL; then DCM:MeOH=20:1) to afford 1-[(3aR,4R,6R,6aS)-2,2,4-trimethyl-4-vinyl-3a,5,6,6a-tetrahydrocyclopenta[d][1,3]dioxol-6-yl]-7-fluoro-pyrrolo[3,2-c]pyridin-4-amine (3Q) (40 mg, 60% yield over 2 steps) as a yellow gum. LCMS: (ESI): m/z calcd. for $C_{18}H_{23}FN_3O_2$ 332.18 [M+H]$^+$, found 332.1.

9-BBN dimer (255.61 mg, 1.06 mmol) was added to a solution of 3Q (140 mg, 422.47 μmol) in THF (4 mL). The mixture was stirred at 50° C. for 2 h under Ar. The mixture was cooled to 25° C., and then a solution of $K_3PO_4$ (448.38 mg, 2.11 mmol) in $H_2O$ (0.4 mL) were added. The mixture was stirred for 0.5 h. 7-bromoquinolin-2-amine (Q5) (122.51 mg, 549.21 μmol) and Pd (dppf)$Cl_2$ (30.91 mg, 42.25 μmol) were added. The mixture was stirred at 70° C. for 12 h under Ar. The mixture was filtered and concentrated under reduced pressure. The residue was purified by reverse-phase column (C18: 0%~70% water (0.5 mL $NH_3.H_2O$ in 1 L $H_2O$)/$CH_3CN$ at 40 mL/min) to afford 7-[2-[(3aR,4S,6R,6aS)-6-(4-amino-7-fluoro-pyrrolo[3,2-c]pyridin-1-yl)-2,2,4-trimethyl-3a,5,6,6a-tetrahydrocyclopenta[d][1,3]dioxol-4-yl]ethyl]quinolin-2-amine (4P) (110 mg, 0.212 mmol, 50% yield, 92% purity) as a yellow solid. LCMS: (ESI): m/z calcd. for $C_{27}H_{31}FN_5O_2$ 476.24 [M+H]$^+$, found 476.2.

HCl (4 M, 2 mL) was added to a solution of 4P (110 mg, 212.80 μmol) in THF (4 mL). The mixture was stirred at 25° C. for 12 h. The mixture was filtered and then concentrated under reduced pressure. The residue was purified by prep-HPLC (column: Phenomenex Gemini-NX 150×30 mm×5 um; mobile phase: [water (0.05% HCl)-ACN]; B %: 5%-35%, 7 min) to afford (1S,2R,3S,5R)-5-(4-amino-7-fluoro-pyrrolo[3,2-c]pyridin-1-yl)-3-[2-(2-amino-7-quinolyl)ethyl]-3-methyl-cyclopentane-1,2-diol (21) as a hydrochloride salt (white solid, 62 mg, 120.46 μmol, 56% yield, 98.78% purity). LCMS: (ESI): m/z calcd. for $C_{24}H_{27}FN_5O_2$. 436.21 [M+H]$^+$, found 436.2. $^1$H NMR (400

MHz, CDCl₃) δ: 8.31 (d, J=9.3 Hz, 1H), 7.82 (d, J=8.2 Hz, 1H), 7.73 (d, J=3.5 Hz, 1H), 7.60 (d, J=6.4 Hz, 1H), 7.53 (s, 1H), 7.45 (dd, J=1.3, 8.1 Hz, 1H), 7.13 (dd, J=2.0, 3.2 Hz, 1H), 7.01 (d, J=9.3 Hz, 1H), 5.19-5.11 (m, 1H), 4.45-4.40 (m, 1H), 3.93 (d, J=6.4 Hz, 1H), 2.98-2.82 (m, 2H), 2.17 (dd, J=8.2, 12.9 Hz, 1H), 1.95-1.80 (m, 3H), 1.24 (s, 3H).

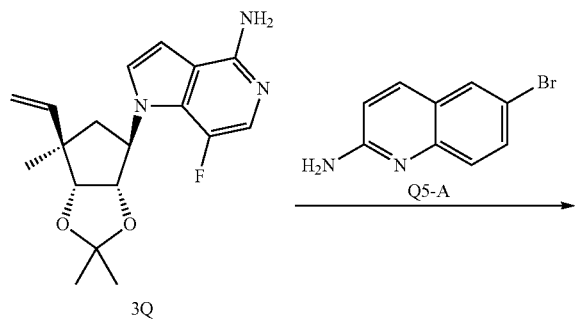

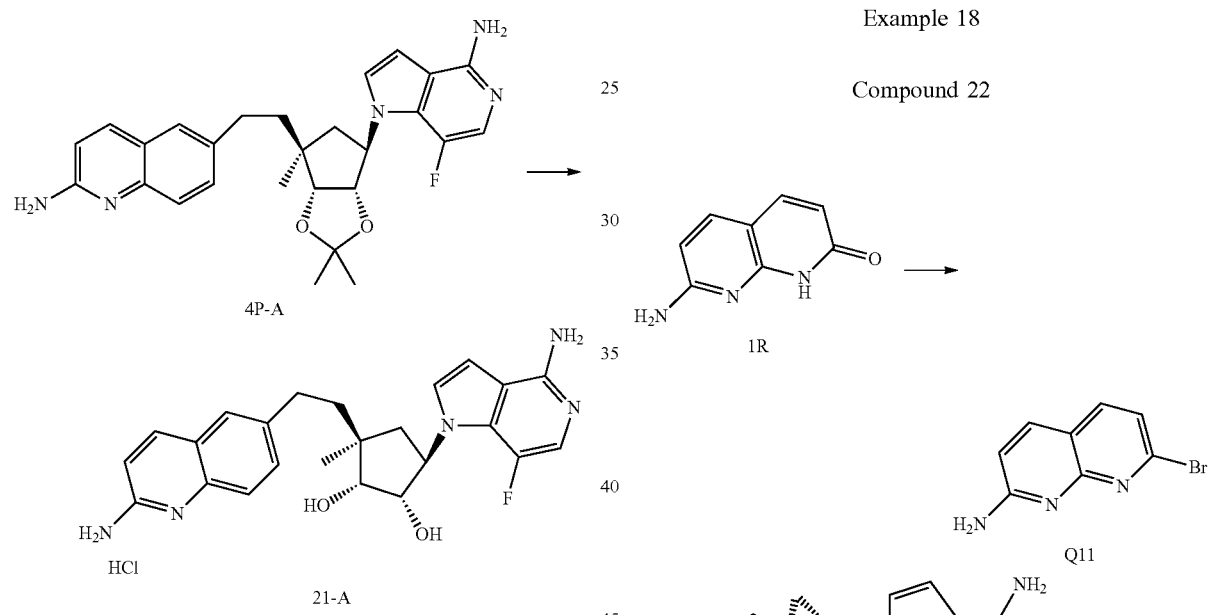

9-BBN dimer (182.6 mg, 754.4 μmol, 2.5 eq.) was added to a solution of 3Q (100 mg, 301.8 μmol, 1 eq.) in THF (4 mL), and the mixture was stirred at 50° C. for 2 h under Ar. The mixture was cooled to 25° C., and then a solution of K₃PO₄ (320.3 mg, 1.51 mmol, 5 eq.) in H₂O (0.4 mL) were added. The mixture was stirred for 0.5 h. 7-bromoquinolin-2-amine (Q5-A) (87.5 mg, 392.3 μmol, 1.3 eq.) and Pd(dppf)Cl₂ (22.1 mg, 30.2 μmol, 0.1 eq.) were added. The mixture was stirred at 70° C. for 12 h under Ar. The reaction progress was monitored by TLC (DCM:MeOH=10:1). Upon completion, the mixture was filtered and concentrated under reduced pressure to give a residue. The residue was purified by reversed-phase HPLC (40 g C-18 column: chromatography (10%~70% water (0.5 mL NH₃.H₂O in 1 L H₂O)/CH₃CN @ 40 mL/min) to afford 7-[2-[(3aR,4S,6R,6aS)-6-(4-amino-7-fluoro-pyrrolo[3,2-c]pyridin-1-yl)-2,2,4-trimethyl-3a,5,6,6a-tetrahydrocyclopenta[d][1,3]dioxol-4-yl]ethyl]quinolin-2-amine (4P-A) (100 mg, 92.8% purity, 193.5 μmol, 64% yield) as a yellow solid. LCMS: (ESI): m/z calcd. for $C_{27}H_{31}FN_5O_2$ 476.24 [M+H]⁺, found 476.3.

HCl (4 M, 2 mL) was added to a solution of 4P-A (100 mg, 92.8% purity, 193.5 μmol, 1 eq.) in THF (4 mL). The mixture was stirred at 25° C. for 12 h. The reaction progress was monitored by TLC (DCM:MeOH=10:1). Upon completion, the mixture was filtered and concentrated under reduced pressure to give a residue. The residue was purified by prep-HPLC (column: Phenomenex Gemini-NX 150*30 mm*5 um; mobile phase: [water (0.05% HCl)-ACN]; B %: 0%-30%, 7 min) to afford (1S,2R,3S,5R)-5-(4-amino-7-fluoro-pyrrolo[3,2-c]pyridin-1-yl)-3-[2-(2-amino-7-quinolyl)ethyl]-3-methyl-cyclopentane-1,2-diol (21-A) as a hydrochloride salt (white solid, 62 mg, 0.122 mmol, 63% yield, 100% purity). LCMS: (ESI): m/z calcd. for $C_{24}H_{27}FN_5O_2$ 436.21 [M+H]⁺, found 436.3. ¹H NMR (400 MHz, CDCl₃) δ: 8.31 (d, J=9.3 Hz, 1H), 7.76 (s, 1H), 7.75-7.69 (m, 2H), 7.62-7.58 (m, 2H), 7.14-7.12 (m, 1H), 7.06 (d, J=9.3 Hz, 1H), 5.19-5.11 (m, 1H), 4.45-4.40 (m, 1H), 3.93 (d, J=6.3 Hz, 1H), 2.94-2.78 (m, 2H), 2.16 (dd, J=8.3, 13.1 Hz, 1H), 1.93-1.78 (m, 3H), 1.23 (s, 3H).

Example 18

Compound 22

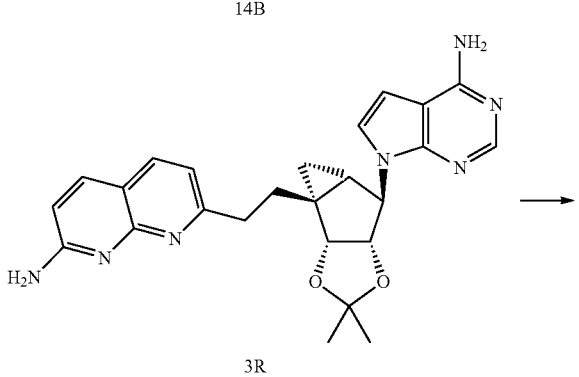

-continued

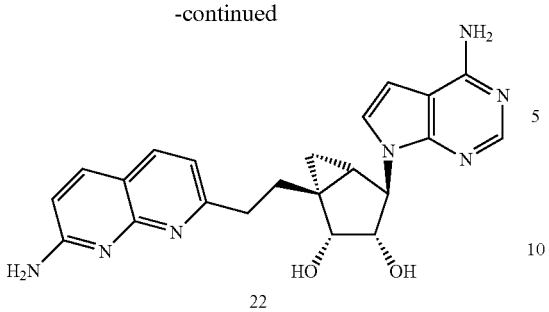

22

A mixture of 7-amino-1H-1,8-naphthyridin-2-one (1R) (1 g, 6.20 mmol, 1 eq.) and POBr₃ (5.34 g, 18.61 mmol, 1.89 mL, 3 eq.) in MeCN (10 mL) was refluxed for 3 h under Ar atmosphere. The reaction progress was monitored by LCMS. Upon completion, the mixture was cooled to rt, and the reaction quenched by ice-water (20 mL). The mixture was neutralized by NH₄OH to pH>8. The precipitated solid was filtered and washed with water. The filter cake was triturated with MeOH (50 mL) at rt for 30 min. The insoluble solid was filtered off. The filtrate was concentrated under reduced pressure to give a residue. The residue was purified by column chromatography (SiO₂, DCM:MeOH=50:1 to 20:1). 7-bromo-1,8-naphthyridin-2-amine (Q11) (90 mg, 5.6% yield, 89% purity) was obtained as a yellow solid. LCMS: (ESI): m/z calcd. for $C_8H_7BrN_3$ 225.97 [M+H]⁺, found 226.1.

7-[(12R,13S,14R,16S)-15,15-dimethyl-16-vinyl-21,22-dioxatricyclononan-12-yl]pyrrolo[2,3-d]pyrimidin-4-amine (14B) (100 mg, 320.1 μmol, 1 eq.) in THF (5 mL) was added 9-BBN dimer (170.5 mg, 704.3 μmol, 2.2 eq.) at 20° C. The mixture was stirred at 50° C. for 60 min, and then cooled to 20° C. K₃PO₄ (339.8 mg, 1.60 mmol, 5 eq.) in H₂O (1 mL) was added, and the mixture and stirred for 30 min. Q11 (86.1 mg, 384.17 μmol, 1.2 eq.) and Pd(dppf)Cl₂ (23.4 mg, 32.01 μmol, 0.1 eq.) were added. The reaction was degassed for 3 times and then stirred at 70° C. for 15 h. The reaction progress was monitored by LCMS. Upon completion, the mixture was diluted with brine (10 mL) and extracted with EA (3×20 mL). The combined organic layers were dried over Na₂SO₄, filtered and concentrated under reduced pressure to give a residue. The residue was purified by reversed-phase HPLC (0.05% NH₃.H₂O condition) to give 7-[2-[(20R,21S,22R,24R)-20-(4-aminopyrrolo[2,3-d]pyrimidin-7-yl)-23,23-dimethyl-32,33-dioxatricyclononan-24-yl]ethyl]-1,8-naphthyridin-2-amine (3R) (81 mg, 173.4 μmol, 54.2% yield, 97.9% purity) as a yellow solid. LCMS: (ESI): m/z calcd. for $C_{25}H_{28}N_7O_2$ 458.22 [M+H]⁺, found 458.2.

To a solution of 3R (81 mg, 173.4 μmol, 97.9% purity, 1 eq.) in THF (6 mL) was added HCl (4 M, 3 mL). The mixture was stirred at 20° C. for 4 h. The reaction progress was monitored by LCMS. Upon completion, the mixture was concentrated under reduced pressure to afford a residue. The residue was neutralized by NH₄OH to pH>8 and then purified by prep-HPLC (column: YMC Triart C18 150*25 mm*5 um; mobile phase: [water (10 mM NH₄HCO₃-ACN]; B %: 21%-51%) to afford (1R,2R,3S,4R)-1-[2-(7-amino-1,8-naphthyridin-2-yl)ethyl]-4-(4-aminopyrrolo[2,3-d]pyrimidin-7-yl)bicyclo[3.1.0]hexane-2,3-diol (22) (37 mg, 88.5 μmol, 51% yield, 99.87% purity) as a white solid. LCMS: (ESI): m/z calcd. for $C_{22}H_{24}N_7O_2$ 418.19 [M+H]⁺, found 418.2. ¹H NMR (400 MHz, CD₃OD) δ: 8.08 (s, 1H), 8.00 (d, J=7.8 Hz, 1H), 7.92 (d, J=8.8 Hz, 1H), 7.22 (d, J=7.8 Hz, 1H), 7.06 (d, J=3.4 Hz, 1H), 6.85 (d, J=8.8 Hz, 1H), 6.58 (d, J=3.7 Hz, 1H), 4.94 (s, 1H), 4.63 (br d, J=6.8 Hz, 1H), 3.87 (d, J=6.6 Hz, 1H), 3.06-3.23 (m, 2H), 2.40 (ddd, J=14.2, 9.2, 5.4 Hz, 1H), 2.04 (ddd, J=13.9, 9.7, 7.0 Hz, 1H), 1.34-1.45 (m, 2H), 0.58 (br dd, J=7.0, 5.3 Hz, 1H).

Example 19

Compound 23

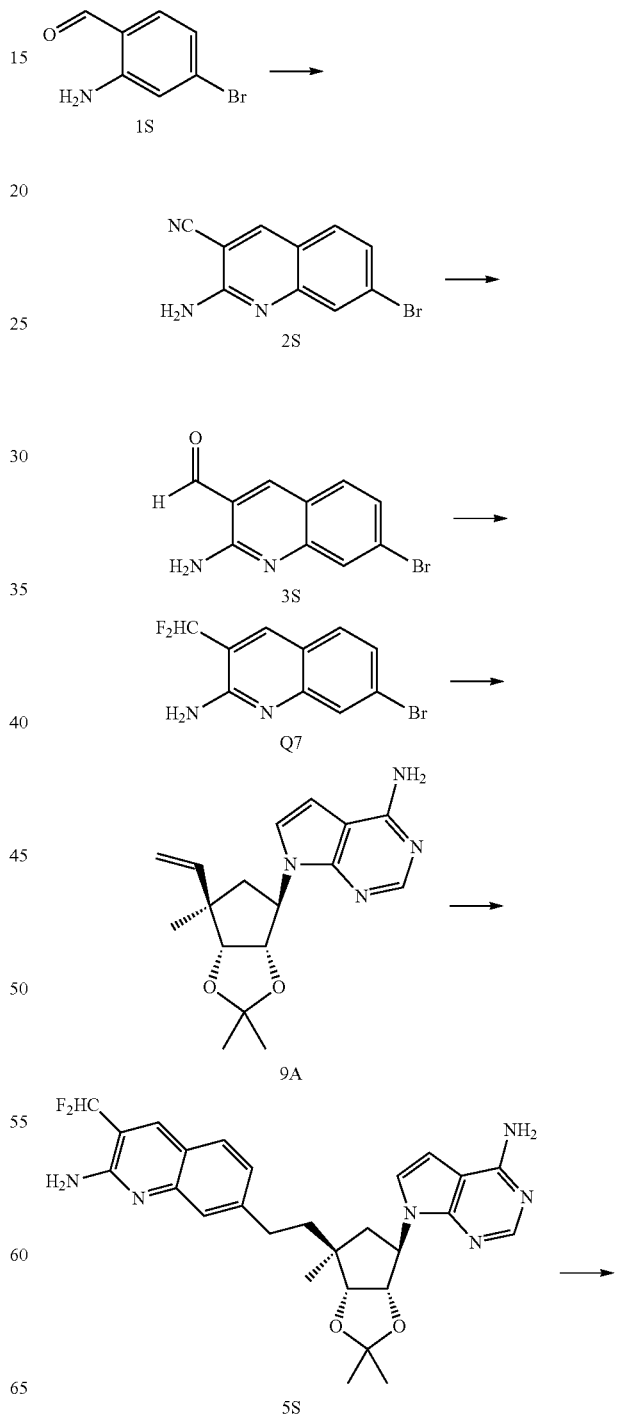

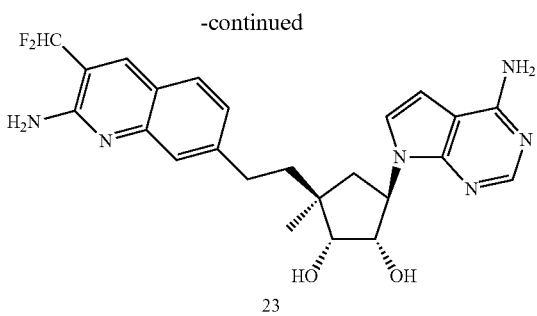

23

Piperidine (42.6 mg, 0.5 mmol, 50 μL, 0.1 eq.) was added to a mixture of 2-amino-4-bromo-benzaldehyde (1.0 g, 5.00 mmol, 1 eq.) and malononitrile (396.3 mg, 6.0 mmol, 1.2 eq.) in EtOH (20 mL). The mixture was refluxed for 4 h, and the product precipitated as a yellow solid. The reaction progress was monitored by LCMS. Upon completion, the solid was filtered. The collected solid was washed successively with EtOH (5 mL), MeOH (10 mL) and MTBE (10 mL). The mixture was dried under high vacuum to afford 2-amino-7-bromo-quinoline-3-carbonitrile (2S) (1.2 g, 4.84 mmol, 96.8% yield) as a yellow solid, which was used in the next step without further purification. LCMS: (ESI): m/z calcd. for $C_{10}H_7BrN_3$ 249.98 [M+H]$^+$, found 250.1.

A solution of DIBAL-H (1 M in toluene, 3.30 mL, 3.3 eq.) was added dropwise to a mixture of 2S (248.1 mg, 1.0 mmol, 1 eq.) in DCM (10 mL) at −78° C. under N$_2$. After completion of the addition, the mixture was stirred at −78° C. for 4 h. The flask was then transformed to an ice-water bath, and the mixture was stirred at 0° C. for 30 min. The reaction was quenched by 2 M HCl to pH=3. The mixture was extracted with DCM:MeOH (10:1, 6×30 mL). The separated organic layers were combined, washed with brine (10 mL), dried over anhydrous Na$_2$SO$_4$, and concentrated to afford crude 2-amino-7-bromo-quinoline-3-carbaldehyde (3S) (146 mg, 44% purity) as a yellow solid, which was used in the next step without further purification.

To a solution of 3S (146 mg) in DCM (6 mL) was added DAST (562.4 mg, 3.49 mmol, 461 μL, 6 eq.) at 0° C. The mixture was stirred at rt for 16 h. The reaction progress was monitored by LCMS. Upon completion, the reaction was quenched by sat. aq. solution of NaHCO$_3$ (10 mL). The mixture was diluted with water (10 mL) and then extracted with EA (2×20 mL). The separated organic layers were combined, washed with brine (10 mL), dried over anhydrous Na$_2$SO$_4$, and concentrated to afford a brown residue. The residue was purified by reversed pre-HPLC (0.05% NH$_3$.H$_2$O condition) to afford 7-bromo-3-(difluoromethyl)quinolin-2-amine (Q7) (34 mg, 12% yield over two steps) as a yellow solid. LCMS: (ESI): m/z calcd. for $C_{10}H_8BrF_2N_2$ 274.98 [M+H]$^+$, found 274.9.

A mixture of 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (150 mg, 477.1 μmol, 1 eq.) and 9-BBN dimer (254.0 mg, 1.05 mmol, 2.2 eq.) in dry THF (5 mL) was stirred at 50° C. for 2 h under Ar. The mixture was cooled to rt. A solution of K$_3$PO$_4$ (506.40 mg, 2.39 mmol, 5 eq.) in H$_2$O (0.5 mL) was added. The mixture was stirred at rt for 0.5 h. 7-bromo-3-(difluoromethyl)quinolin-2-amine (Q7) (169.4 mg, 620 μmol, 1.3 eq.) and Pd(dppf)Cl$_2$ (34.9 mg, 47.7 μmol, 0.1 eq.) were added. The mixture was stirred at 70° C. for 12 h under Ar. The reaction progress was monitored by LCMS. Upon completion, the mixture was diluted with brine (15 mL) and extracted with EA (4×20 mL). The separated organic layers were combined, dried over anhydrous Na$_2$SO$_4$, and concentrated to afford a residue. The residue was purified by silica gel chromatography (PE:EA=1:0 to 1:1, and then DCM:MeOH=10:0 to 10:1) to afford 5S (190 mg, 367.6 μmol, 77% yield, 98.4% purity) as light yellow solid. LCMS: (ESI): m/z calcd. for $C_{27}H_{31}F_2N_6O_2$ 509.25 [M+H]$^+$, found 509.4.

A mixture of 5S (185 mg, 363.8 μmol, 1 eq.), HCl (4 M, 2 mL), and THF (4 mL) was stirred at 20° C. for 16 h. The mixture was concentrated under high vacuum to afford a residue. The residue was dissolved in MeCN:H$_2$O (1:1.1 mL). MeCN (4 mL) was added dropwise to the mixture. The precipitated light yellow solid was collected by filtration and washed with MeCN:H$_2$O (10:1.3 mL) to afford Compound 23 as a hydrochloride salt (light yellow solid, 126 mg, 63.6% yield, 99.3% purity). LCMS: (ESI): m/z calcd. for $C_{24}H_{27}F_2N_6O_2$ 469.22 [M+H]$^+$, found 469.2. $^1$H NMR (400 MHz, CD$_3$OD) δ: 8.66 (s, 1H), 8.25 (s, 1H), 7.94 (d, J=8.3 Hz, 1H), 7.61 (s, 1H), 7.57 (d, J=3.5 Hz, 1H), 7.51 (d, J=8.3 Hz, 1H), 7.21-6.89 (m, 2H), 5.17-5.06 (m, 1H), 4.59-4.52 (m, 1H), 3.96 (d, J=6.3 Hz, 1H), 3.05-2.82 (m, 2H), 2.14-1.98 (m, 2H), 1.98-1.83 (m, 2H), 1.25 (s, 3H). $^{19}$F NMR (376 MHz, CD$_3$OD) δ: 120.5.

Example 20

Compound 24

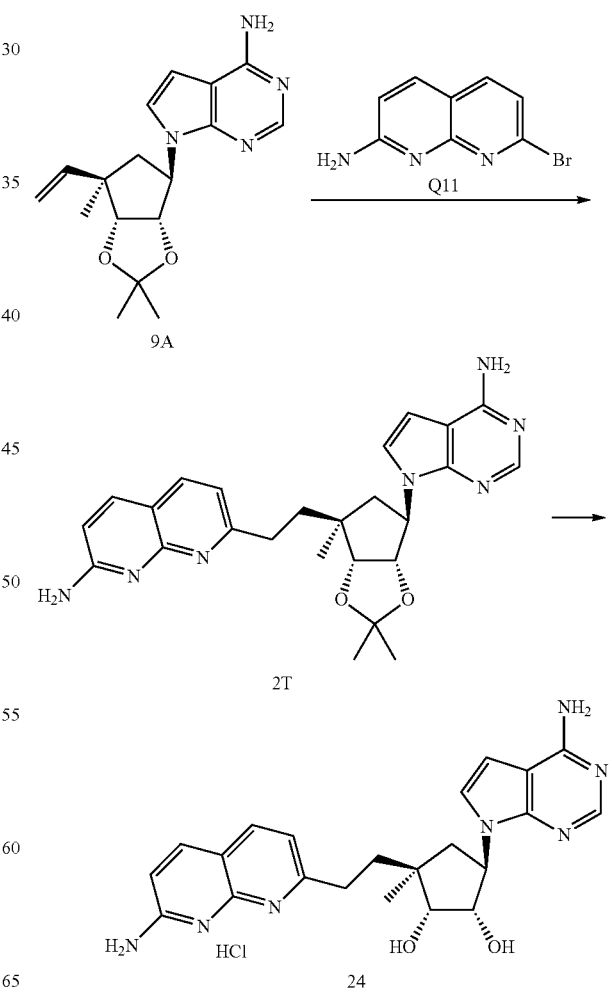

A mixture of 7-[(3 aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (150 mg, 477.1 µmol, 1 eq.) and 9-BBN dimer (288.7 mg, 1.19 mmol, 2.5 eq.) in THF (5 mL) was stirred at 50° C. for 2 h under Ar. The mixture was then cooled to rt. A solution of $K_3PO_4$ (506.4 mg, 2.39 mmol, 5 eq.) in $H_2O$ (1 mL) was added. The mixture was stirred at rt for 30 min. 7-bromo-1, 8-naphthyridin-2-amine (Q11) (139.0 mg, 620.3 µmol, 1.3 eq.) and Pd(dppf)$Cl_2$ (34.9 mg, 47.7 µmol, 0.1 eq.) were added. The mixture was stirred at 70° C. for 16 h under Ar. The reaction progress was monitored by LCMS. Upon completion, the mixture was diluted with $H_2O$ (10 mL) and extracted with EA (3×20 mL). The combined organic layers were washed with brine (10 mL), dried over anhydrous $Na_2SO_4$, filtered and concentrated under reduced pressure to give a residue. The residue was purified by prep-HPLC (0.05% $NH_3.H_2O$ condition) to afford 2T (122 mg, 259.3 µmol, 54.4% yield, 97.7% purity) as a yellow gum. LCMS: (ESI): m/z calcd. for $C_{25}H_{30}N_7O_2$ 460.24 [M+H]$^+$, found 460.3.

To a mixture of 2T (122 mg, 259.3 µmol, 54.4% yield, 97.7% purity) in THF (6 mL) was added HCl (4 M, 3 mL). The mixture was stirred at rt for 12 h. The reaction progress was monitored by LCMS. Upon completion, the mixture was concentrated under reduced pressure to afford a residue. The residue was triturated with MeCN:water (10:1, 10 mL) at 20° C. for 30 min. The solid was collected by filtration and then suspended in MeCN:water (1:1, 1 mL). MeCN:water (10:1, 5 mL) was added dropwise. The solid was filtered and washed with MeCN:water (10:1, 5 mL) to afford Compound 24 as a hydrochloride salt (white solid, 83 mg, 167 µmol, 64.4% yield, and 99.1% purity). LCMS: (ESI): m/z calcd. for $C_{22}H_{26}N_7O_2$ 420.21 [M+H]$^+$, found 420.3. $^1$H NMR (400 MHz, $CD_3OD$) δ: 8.37 (d, J=8.1 Hz, 1H), 8.21-8.27 (m, 2H), 7.56 (d, J=3.7 Hz, 1H), 7.50 (d, J=8.1 Hz, 1H), 7.07 (d, J=9.0 Hz, 1H), 6.91 (d, J=3.7 Hz, 1H), 5.06-5.19 (m, 1H), 4.54 (t, J=7.0 Hz, 1H), 3.97 (d, J=6.4 Hz, 1H), 2.97-3.20 (m, 2H), 1.93-2.15 (m, 4H), 1.24 (s, 3H).

Example 21

Compound 25-A

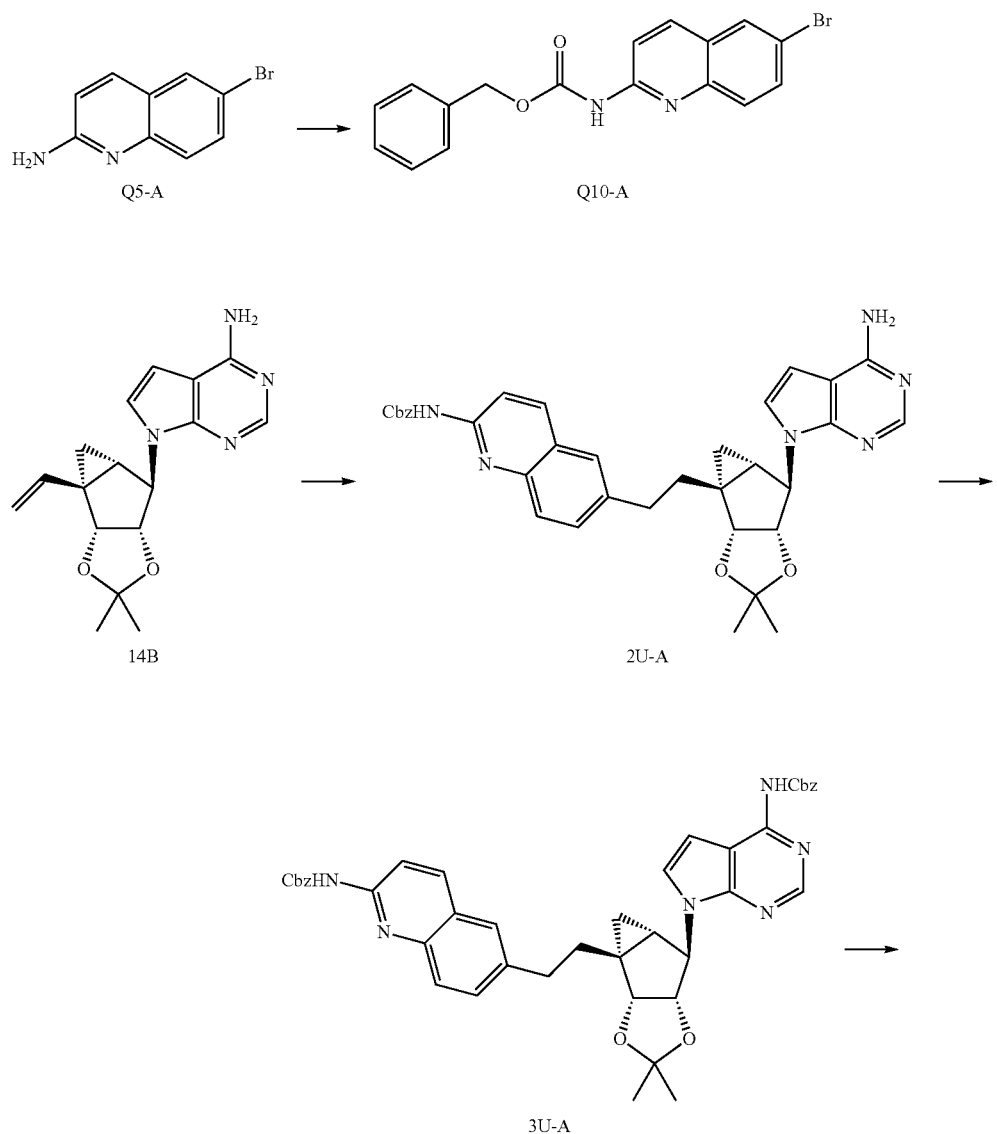

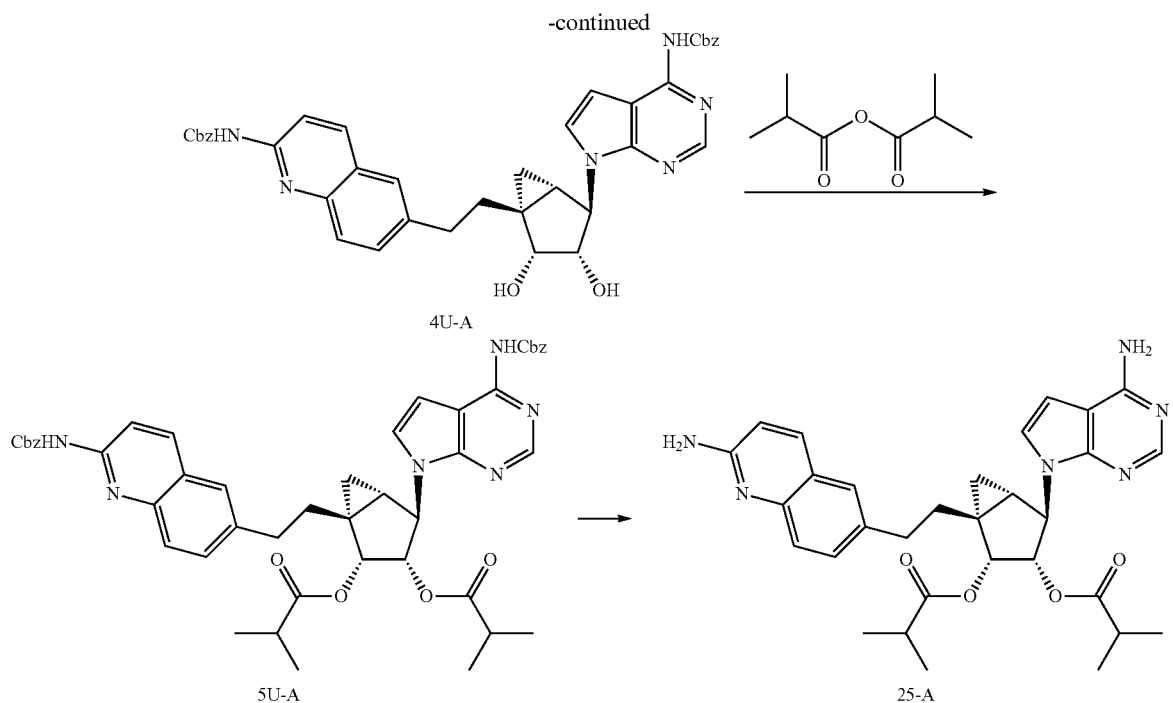

CbzCl (1.84 g, 10.76 mmol, 1.53 mL) was added dropwise to a solution of 1 (600 mg, 2.69 mmol) and 1-methylimidazole (1.77 g, 21.52 mmol, 1.72 mL) in DCM (15 mL) at 0° C. The mixture was stirred at 25° C. for 12 h. The reaction was quenched with NaHCO$_3$ (sat., aq., 10 mL) and extracted with EA (2×10 mL). The combined organic layers were washed with brine (10 mL×2), dried over Na$_2$SO$_4$. The solids were removed by filtration, and the filtrate was concentrated under reduced pressure. The residue was purified by silica column chromatography (PE:EA=20:1 to 10:1) to afford benzyl W-(6-bromo-2-quinolyl)carbamate (Q10-A) (780 mg, 2.14 mmol, 76% yield) as a white solid. LCMS: (ESI): m/z calcd. for C$_{17}$H$_{14}$BrN$_2$O$_2$ 357.02 [M+H]$^+$, found 357.0.

A mixture of 7-[(11S,12R,13S,14R,16S)-15,15-dimethyl-16-vinyl-21,22-dioxatriclononan-12-yl]pyrrolo[2,3-d]pyrimidin-4-amine (14B) (200 mg, 0.640 mmol) and 9-BBN dimer (387.4 mg, 1.60 mmol) in THF (8 mL) was stirred at 50° C. for 2 h under Ar and then cooled to rt. A solution of K$_3$PO$_4$ (679.54 mg, 3.20 mmol) in H$_2$O (0.8 mL) was added. The mixture was stirred at rt for 0.5 h. Compound Q10-A (297.3 mg, 0.832 mol) and Pd(dppf)Cl$_2$ (46.9 mg, 0.064 mmol) were added. The mixture was stirred at 70° C. for 12 h under Ar. The mixture was filtered and concentrated under reduced pressure. The residue was purified by silica column chromatography (PE:EA=3:1 to 1:1 and DCM: MeOH=100:1 to 20:1) to afford benzyl (6-(2-((3aR,3bR,4aS,5R,5aS)-5-(4-amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)quinolin-2-yl)carbamate (2U-A) (273 mg, 0.374 mmol, 58%) as a yellow solid. LCMS: (ESI): m/z calcd. for C$_{34}$H$_{35}$N$_6$O$_4$ 591.26 [M+H]$^+$, found 591.2.

CbzCl (369.68 mg, 2.17 mmol, 0.308 mL) was added dropwise to a solution of 2U-A (320 mg, 0.542 mmol) and 1-methylimidazole (355.84 mg, 4.33 mmol, 0.345 mL) in DCM (8 mL) at 0° C. The mixture was stirred at rt for 12 h, and then quenched by addition of NaHCO$_3$ (sat., aq., 5 mL). The mixture was extracted with DCM (3×5 mL). The combined organic layers were washed with brine, dried over Na$_2$SO$_4$. The solids were removed by filtration, and the filtrate was concentrated under reduced pressure. The residue was purified by silica column chromatography (PE: EA=1:1 to DCM:MeOH=50:1 to 20:1) to afford benzyl (7-((3aR,3bR,4aS,5R,5aS)-3b-(2-(2-(((benzyloxy)carbonyl)amino)quinolin-6-yl)ethyl)-2,2-dimethylhexahydrocyclopropa[3,4]cyclopenta[1,2-d][1,3]dioxol-5-yl)-7H-pyrrolo[2,3-d]pyrimidin-4-yl)carbamate (3U-A) (158 mg, 0.202 mmol, 37% yield) as a white oil. LCMS: (ESI): m/z calcd. for C$_{42}$H$_{41}$N$_6$O$_6$ 725.3 [M+H]$^+$, found 725.4.

To a solution of 3U-A (158 mg, 0.202 mmol) in THF (2 mL) was added HCl (4 M, 0.929 mL). The mixture was stirred at 25° C. for 3 h. The reaction was quenched by NH$_3$.H$_2$O (1 mL) and extracted with EA (2×5 mL). The combined organic layers were washed with brine (2×5 mL), dried over Na$_2$SO$_4$, filtered and concentrated under reduced pressure to give benzyl (7-((1S,2R,3S,4R,5R)-5-(2-(2-(((benzyloxy)carbonyl)amino)quinolin-6-yl)ethyl)-3,4-dihydroxybicyclo[3.1.0]hexan-2-yl)-7H-pyrrolo[2,3-d]pyrimidin-4-yl)carbamate (4U-A) (143 mg, crude) as a colorless solid. LCMS: (ESI): m/z calcd. for C$_{39}$H$_{37}$N$_6$O$_6$ 685.27 [M+H]$^+$, found 685.3.

Isobutyric anhydride (160.8 mg, 1.02 mmol, 169 μL) was added to a solution of 4U-A (232 mg, 0.339 mmol), TEA (205.7 mg, 2.03 mmol, 0.283 mL) and DMAP (4.1 mg, 0.034 mmol) in DMF (5 mL). The mixture was stirred at 60° C. for 3 h, and then quenched with NaHCO$_3$ (sat., aq., 5 mL) and extracted with EA (3×5 mL). The combined organic layers were washed with brine (2×5 mL), dried over Na$_2$SO$_4$. The solids were removed by filtration, and the filtrate was concentrated under reduced pressure. The residue was purified by silica gel chromatography (0~50% EA:PE gradient) to afford (1R,2R,3S,4R,5S)-4-(4-(((benzyloxy)carbonyl)amino)-7H-pyrrolo[2,3-d]pyrimidin-7-yl)-1-(2-(2-(((benzyloxy)carbonyl)amino)quinolin-6-yl)ethyl)bicyclo[3.1.0]hexane-2,3-diyl bis(2-methylpropanoate) (5U-

A) (157 mg, 0.169 mmol, 49%) as a white solid. LCMS: (ESI): m/z calcd. for $C_{47}H_{49}N_6O_8$ 825.35 [M+H]$^+$, found 825.4.

To a solution of 5U-A (187 mg, 0.226 mmol) in EtOH (5 mL) and THF (2 mL) was added Pd/C (100 mg, 10% wt). The mixture was degassed under reduced pressure, purged with H$_2$ and then stirred under H$_2$ atmosphere (15 psi) at 25° C. for 20 h. The mixture was filtered through a Celite pad to remove the Pd/C. The filtrate was concentrated under reduced pressure to afford the residue. The residue was purified by prep-HPLC (column: YMC Triart C18 150×25 mm×5 μm; mobile phase: [water (10 mM NH$_4$HCO$_3$)-ACN]; B %: 42%-72%, 9.5 min) to afford (1R,2R,3S,4R,5S)-4-(4-amino-7H-pyrrolo[2,3-d]pyrimidin-7-yl)-1-(2-(2-aminoquinolin-6-yl)ethyl)bicyclo[3.1.0]hexane-2,3-diyl bis (2-methylpropanoate) (25-A) (82 mg, 0.147 mmol, 65%) as a white solid. LCMS: (ESI): m/z calcd. for $C_{31}H_{37}N_6O_4$ 557.28 [M+H]$^+$, found 557.3. $^1$H NMR (400 MHz, CD$_3$OD) δ: 8.08 (s, 1H), 7.86 (d, J=8.8 Hz, 1H), 7.48-7.41 (m, 3H), 7.01 (d, J=3.8 Hz, 1H), 6.80 (d, J=8.8 Hz, 1H), 6.60 (d, J=3.8 Hz, 1H), 5.88 (d, J=6.3 Hz, 1H), 5.23 (brd, J=7.3 Hz, 1H), 4.98 (d, J=1.8 Hz, 1H), 2.95-2.83 (m, 2H), 2.58 (quin, J=7.0, 11.3 Hz, 2H), 2.23-2.15 (m, 1H), 2.01-1.93 (m, 1H), 1.50 (dd, J=3.9, 8.4 Hz, 1H), 1.37-1.33 (m, 1H), 1.22 (d, J=7.0 Hz, 3H), 1.19-1.13 (m, 9H), 0.94-0.89 (m, 1H).

Example 22

Compounds 26 and 26-A

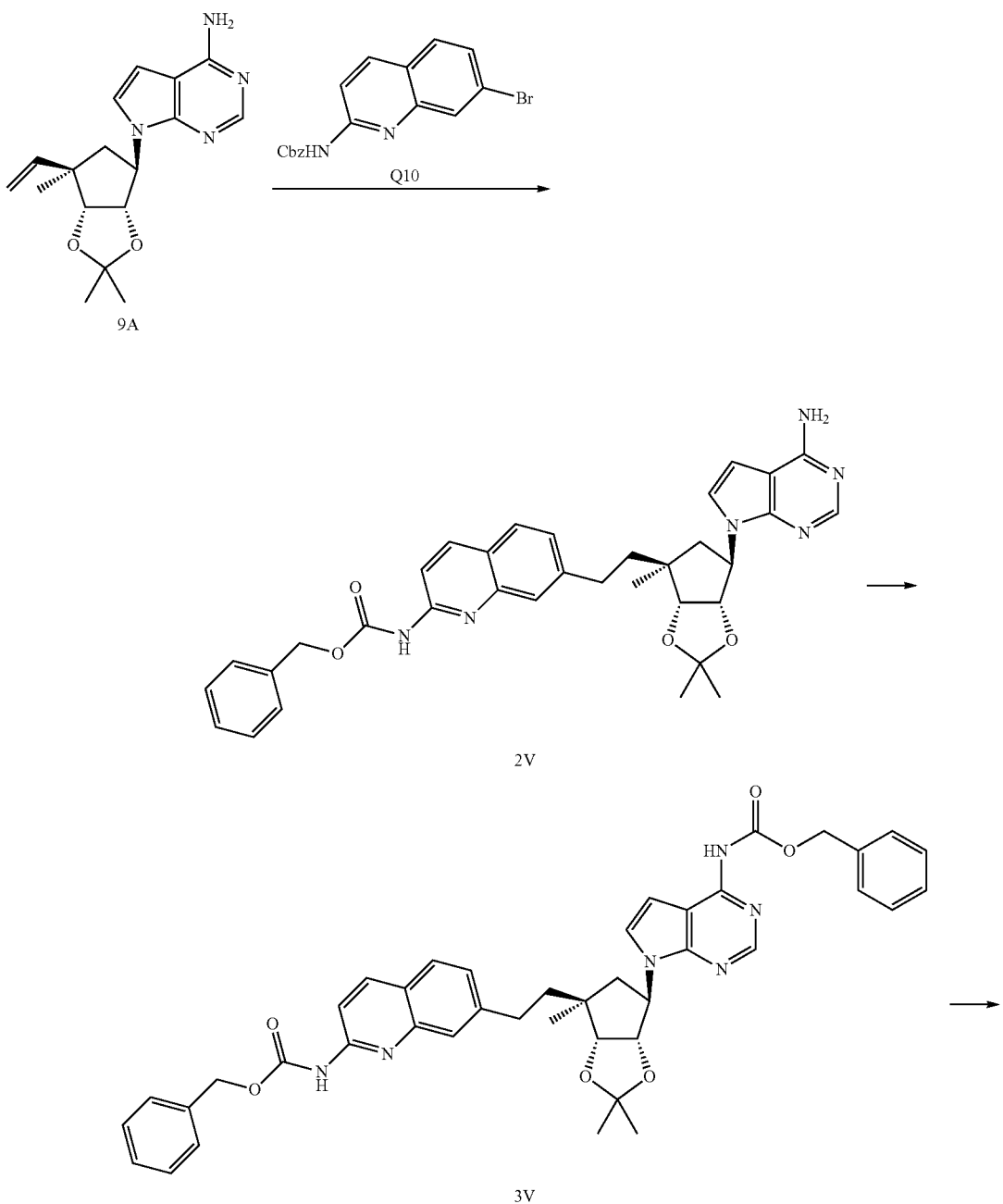

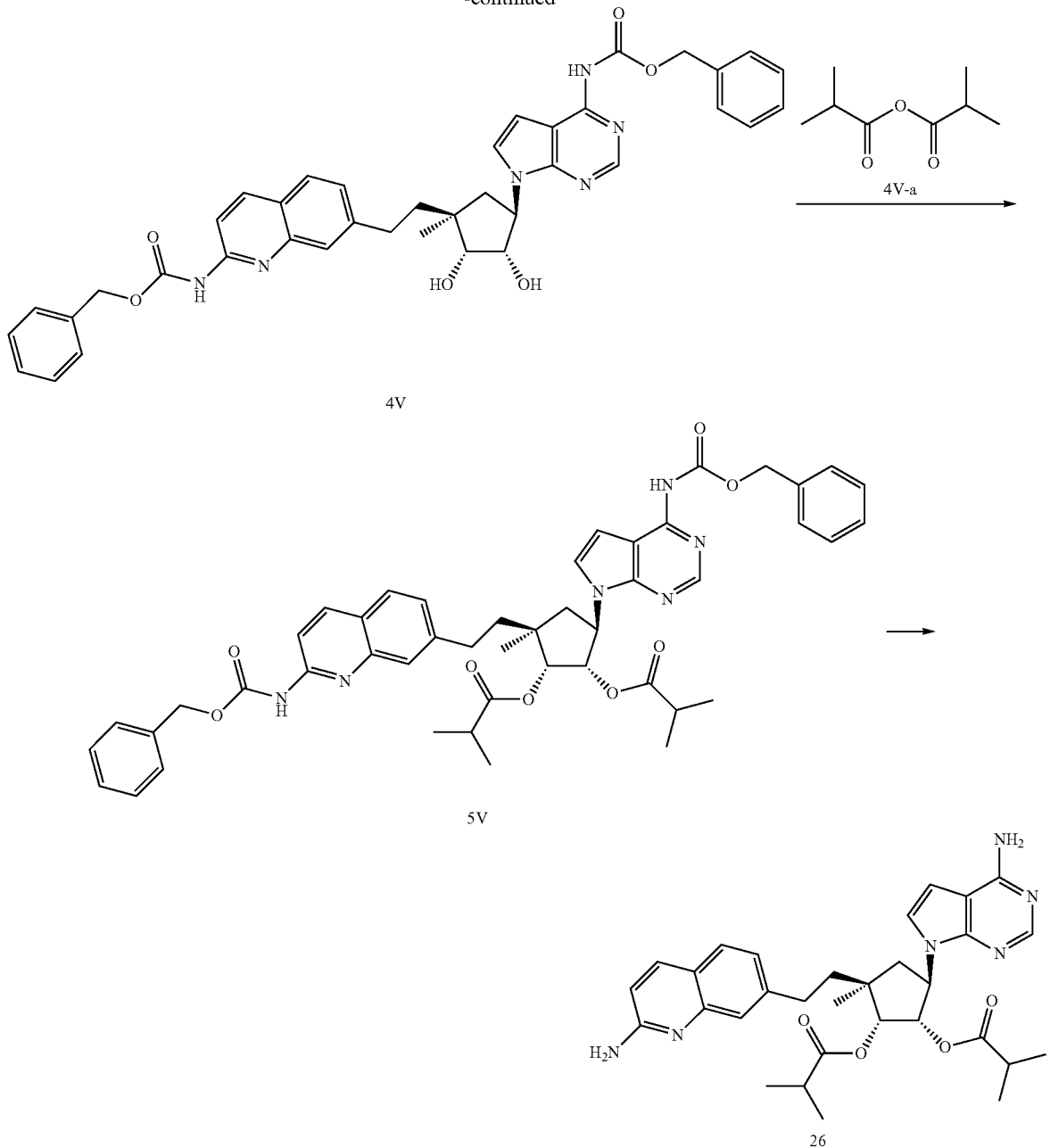

A mixture of 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (400 mg, 1.27 mmol) and 9-BBN dimer (769.82 mg, 3.18 mmol) in THF (8 mL) was stirred at 50° C. for 2 h under Ar and then cooled to rt. A solution of $K_3PO_4$ (1.35 g, 6.36 mmol) in $H_2O$ (0.8 mL) was added. The mixture was stirred for 0.5 h. Benzyl N-(7-bromo-2-quinolyl)carbamate (Q10) (545.38 mg, 1.53 mmol) and Pd(dppf)Cl$_2$ (93.10 mg, 0.127 mmol) were added. The mixture was stirred at 70° C. for 12 h under Ar. The mixture was extracted with EA (2×10 mL). The combined organic layers were washed with brine (2×10 mL) and dried over $Na_2SO_4$. The solids were removed by filtration, and the filtrate was concentrated under reduced pressure. The residue was purified by silica gel chromatography (20%~50% EA/PE gradient to 0%~12% DCM/CH$_3$OH) to afford benzyl (7-(2-((3aR,4S,6R,6aS)-6-(4-amino-7H-pyrrolo[2,3-d]pyrimidin-7-yl)-2,2,4-trimethyltetrahydro-4H-cyclopenta[d][1,3]dioxol-4-yl)ethyl)quinolin-2-yl)carbamate (2V) (584 mg, 0.871 mmol, 68% yield) as a yellow solid. LCMS: (ESI): m/z calcd. for $C_{34}H_{37}N_6O_4$ 593.28 [M+H]$^+$, found 593.4.

Intermediate 3V was prepared similarly as described for 3U-A starting from 2V with the change that the reaction was stirred for 16 h to afford benzyl (7-((3aS,4R,6S,6aR)-6-(2-(2-(((benzyloxy)carbonyl)amino)quinolin-7-yl)ethyl)-2,2,6-trimethyltetrahydro-4H-cyclopenta[d][1,3]dioxol-4-yl)-7H-pyrrolo[2,3-d]pyrimidin-4-yl)carbamate (3V) (360 mg, 0.492 mmol, 56%) as a white solid. LCMS: (ESI): m/z calcd. for $C_{42}H_{43}N_6O_6$ 727.32 [M+H]$^+$, found 727.4.

To a solution of 3V (360 mg, 492.34 µmol) in THF (4 mL) was added HCl (4 M, 2 mL). The mixture was stirred at 25° C. for 12 h. The reaction was quenched by $NH_3 \cdot H_2O$ (1 mL) and extracted with EA (2×5 mL). The combined organic layers were washed with brine (5 mL), dried over $Na_2SO_4$, filtered and concentrated under reduced pressure to give benzyl (7-((1R,2S,3R,4S)-4-(2-(2-(((benzyloxy)carbonyl)amino)quinolin-7-yl)ethyl)-2,3-dihydroxy-4-methylcyclopentyl)-7H-pyrrolo[2,3-d]pyrimidin-4-yl)carbamate (4V) (328 mg, crude) as a white solid. LCMS: (ESI): m/z calcd. for $C_{39}H_{39}N_6O_6$ 687.29 [M+H]$^+$, found 687.3.

To a mixture of 4V (328 mg, 0.478 mmol), TEA (289.98 mg, 2.87 mmol, 0.399 mL), and DMAP (5.83 mg, 0.048 mmol) in DMF (5 mL) was added 2-methylpropanoyl 2-methylpropanoate (4V-a) (226.67 mg, 1.43 mmol, 0.238 mL). The mixture was stirred at 60° C. for 3 h. The reaction was quenched by $NaHCO_3$ (sat., aq., 5 mL) and extracted with EA (2×5 mL). The combined organic layers were washed with brine (5 mL) and dried over $Na_2SO_4$. The solids were removed by filtration, and the filtrate was concentrated under reduced pressure. The residue was purified by silica gel chromatography (0~50% EA/PE gradient) to afford (1S,2R,3S,5R)-5-(4-(((benzyloxy)carbonyl)amino)-7H-pyrrolo[2,3-d]pyrimidin-7-yl)-3-(2-(2-(((benzyloxy)carbonyl)amino)quinolin-7-yl)ethyl)-3-methylcyclopentane-1,2-diyl bis(2-methylpropanoate) (5V) (295 mg, 0.320 mmol, 67% yield) as a white solid. LCMS: (ESI): m/z calcd. for $C_{47}H_{51}N_6O_8$ 827.37 [M+H]$^+$, found 827.4. $^1$H NMR (400 MHz, CDCl$_3$) δ: 8.50 (s, 1H), 8.20-8.10 (m, 2H), 7.81 (br s, 2H), 7.70 (d, J=7.8 Hz, 1H), 7.62 (s, 1H), 7.44-7.34 (m, 10H), 7.30 (br dd, J=1.5, 8.3 Hz, 1H), 7.14 (d, J=3.7 Hz, 1H), 7.05 (d, J=3.7 Hz, 1H), 5.77 (dd, J=6.0, 7.8 Hz, 1H), 5.40-5.31 (m, 2H), 5.26 (s, 4H), 2.93-2.78 (m, 2H), 2.65 (quin, J=7.0 Hz, 1H), 2.41 (td, J=7.0, 14.0 Hz, 1H), 2.29-2.20 (m, 1H), 2.18-2.11 (m, 1H), 1.99 (br t, J=8.6 Hz, 2H), 1.29-1.25 (m, 9H), 1.04 (d, J=7.0 Hz, 3H), 0.99 (d, J=7.0 Hz, 3H).

Cbz deprotection was prepared similarly as described for 5U-A, starting from 5V, to afford (1S,2R,3S,5R)-5-(4-amino-7H-pyrrolo[2,3-d]pyrimidin-7-yl)-3-(2-(2-aminoquinolin-7-yl)ethyl)-3-methylcyclopentane-1,2-diyl bis(2-methylpropanoate) (26) (105 mg, 187.46 µmol, 58%) as a white solid. LCMS: (ESI): m/z calcd. for $C_{31}H_{39}N_6O_4$ 559.30 [M+H]$^+$, found 559.5. $^1$H NMR (400 MHz, CD$_3$OD) δ: 8.08 (s, 1H), 7.88 (d, J=9.0 Hz, 1H), 7.56 (d, J=8.0 Hz, 1H), 7.39 (s, 1H), 7.26 (d, J=3.5 Hz, 1H), 7.15 (dd, J=1.4, 8.2 Hz, 1H), 6.76 (d, J=8.8 Hz, 1H), 6.60 (d, J=3.8 Hz, 1H), 5.69 (dd, J=6.4, 7.7 Hz, 1H), 5.36 (d, J=6.5 Hz, 1H), 5.34-5.28 (m, 1H), 2.89-2.76 (m, 2H), 2.71-2.61 (m, 1H), 2.46-2.37 (m, 1H), 2.19 (d, J=9.3 Hz, 2H), 1.97 (t, J=8.5 Hz, 2H), 1.29 (s, 3H), 1.23 (dd, J=7.0, 8.8 Hz, 6H), 1.02 (d, J=6.8 Hz, 3H), 0.97 (d, J=6.8 Hz, 3H).

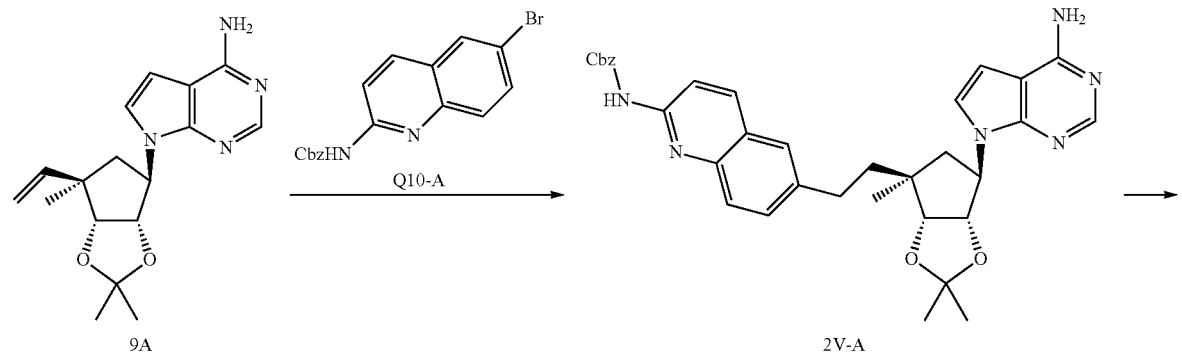

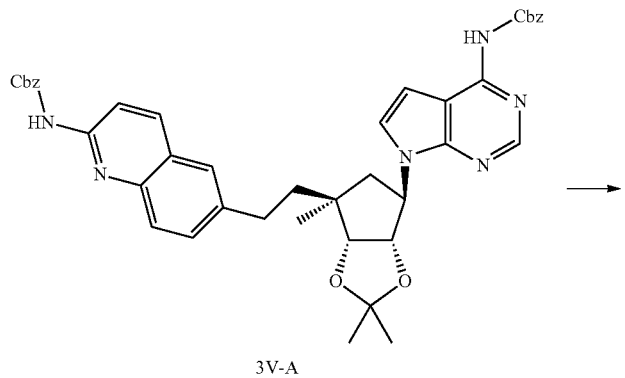

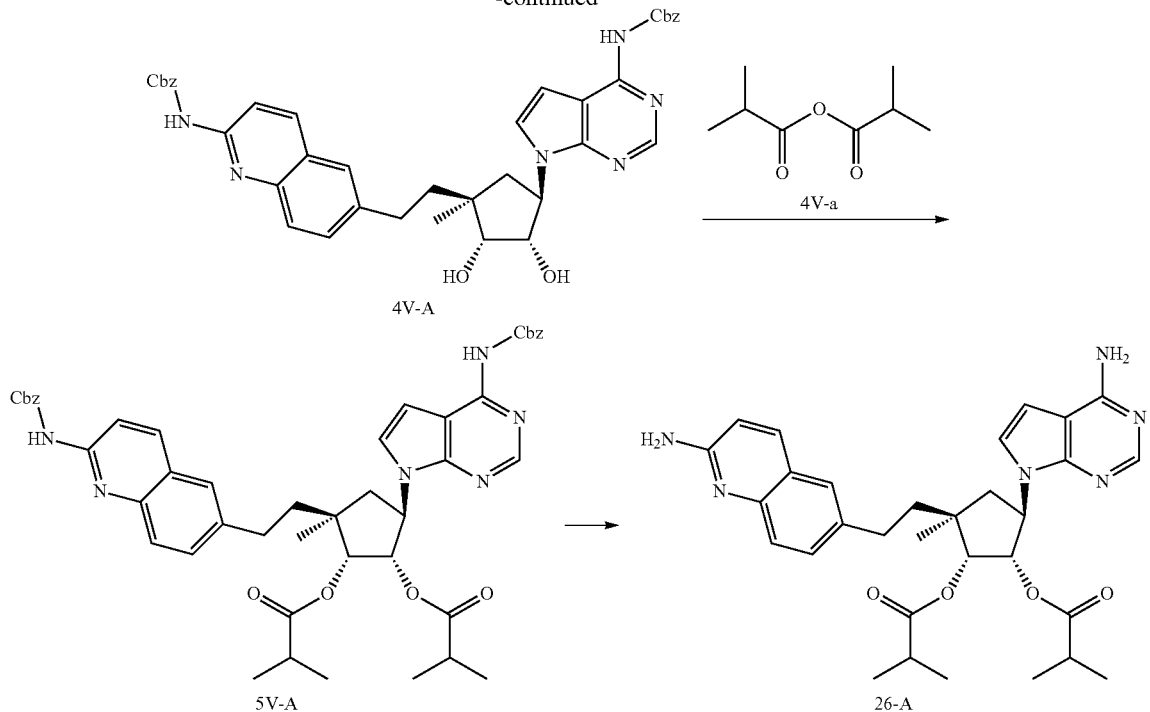

A mixture of 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (300 mg, 954.3 µmol, 1 eq.) and 9-BBN dimer (577.4 mg, 2.39 mmol, 2.5 eq.) in THF (8 mL) was stirred at 50° C. for 2 h under Ar and then cooled to rt. A solution of $K_3PO_4$ (1.01 g, 4.77 mmol, 5 eq.) in $H_2O$ (0.8 mL) was added. The mixture was stirred for 0.5 h. Benzyl N-(6-bromo-2-quinolyl)carbamate (Q10-a) (409.0 mg, 1.15 mmol, 1.2 eq.) and Pd(dppf)Cl$_2$ (69.8 mg, 95.4 µmol, 0.1 eq.) were added. The mixture was stirred at 70° C. for 12 h under Ar. The reaction progress was monitored by TLC (DCM:MeOH=20:1). Upon completion, the mixture was extracted with EA (2×5 mL). The combined organic layers were washed with brine (2×5 mL), dried over $Na_2SO_4$, filtered and concentrated under reduced pressure to give a residue. The residue was purified by flash silica gel chromatography (ISCO®; 20 g SepaFlash® Silica Flash Column, Eluent of 10%~50% EA:PE gradient to 0%~10% DCM/MeOH @ 35 mL/min) to afford 2V-A (312 mg, 431.7 µmol, 45% yield) as a yellow solid. LCMS: (ESI): m/z calcd. for $C_{34}H_{37}N_6O_4$ 593.28 $[M+H]^+$, found 593.3.

To a solution of 2V-A (312 mg, 431.7 µmol, 1 eq.) in DCM (8 mL) were added 1-methylimidazole (283.5 mg, 3.45 mmol, 275, 8 eq.) and CbzCl (294.6 mg, 1.73 mmol, 245 µL, 4 eq.) at 0° C. The mixture was stirred at 25° C. for 16 h. The reaction was quenched by addition of sat. NaHCO$_3$ solution (5 mL) and then extracted with DCM (3×5 mL). The combined organic layers were washed with brine, dried over Na$_2$SO$_4$, filtered and concentrated under reduced pressure to give a residue. The residue was purified by flash silica gel chromatography (ISCO®; 20 g SepaFlash® Silica Flash Column, Eluent of 10%~50% EA:PE gradient to 0%~15% DCM/MeOH @ 35 mL/min) to afford 3V-A (178 mg, 233.9 µmol, 54% yield) as a white solid. LCMS: (ESI): m/z calcd. for $C_{42}H_{43}N_6O_6$ 727.32 $[M+H]^+$, found 727.3.

To a solution of 3V-A (178 mg, 233.88 µmol, 1 eq.) in THF (2 mL) was added HCl (4 M, 1 mL). The mixture was stirred at 25° C. for 12 h. The reaction progress was monitored by TLC (DCM:MeOH=20:1). Upon completion, the reaction was quenched by NH$_3$.H$_2$O solution (1 mL) and extracted with EA (2×5 mL). The combined organic layers were washed with brine (2×5 mL), dried over Na$_2$SO$_4$, filtered and concentrated under reduced pressure to give 4V-A (161 mg, crude) as a white solid. LCMS: (ESI): m/z calcd. for $C_{39}H_{39}N_6O_6$ 687.29 $[M+H]^+$, found 687.3.

To a mixture of 4V-A (200 mg, 291.2 µmol, 1 eq.), TEA (176.8 mg, 1.75 mmol, 243 µL, 6 eq.) and DMAP (3.6 mg, 29.1 µmol, 0.1 eq.) in DMF (5 mL) was added 2-methylpropanoyl 2-methylpropanoate (4V-a) (138.2 mg, 873.7 µmol, 145 µL, 3 eq.). The mixture was stirred at 60° C. for 3 h. The reaction progress was monitored by TLC (PE:EA=1:1). Upon completion, the reaction was quenched by sat.NaHCO$_3$ solution (5 mL) and extracted with EA (2×5 mL). The combined organic layers were washed with brine (2×5 mL), dried over Na$_2$SO$_4$, filtered and concentrated under reduced pressure to give a residue. The residue was purified by flash silica gel chromatography (ISCO®; 12 g SepaFlash® Silica Flash Column, Eluent of 0~50% EA:PE gradient @ 30 mL/min) to afford 5V-A (196 mg, 208.6 µmol, 71% yield) as a white solid. LCMS: (ESI): m/z calcd. for $C_{47}H_{51}N_6O_8$ 827.37 $[M+H]^+$, found 827.6.

To a solution of 5V-A (213 mg, 257.6 µmol, 1 eq.) in EtOH (5 mL) and THF (2 mL) was added Pd/C (100 mg, 10% wt). The mixture was degassed under reduced pressure and purged with H$_2$ (3×). The mixture was then stirred under H$_2$ atmosphere (15 psi) at 25° C. for 20 h. The reaction progress was monitored by TLC (DCM:MeOH=10:1). Upon completion, the mixture was filtered through a Celite pad to remove the Pd/C. The filtrate was concentrated under reduced pressure to afford a residue. The residue was purified by prep-HPLC (column: Welch Xtimate C18 150*25 mm*5 um; mobile phase: [water (10 mM NH$_4$HCO$_3$)-ACN]; B %: 45%-75%, 8.5 min) to afford Compound 26-A (73 mg, 130.5 µmol, 50.7% yield, 99.9% purity) as a white solid. LCMS: (ESI): m/z calcd. for $C_{31}H_{39}N_6O_4$ 558.30 [M+H]$^+$, found 558.3. $^1$H NMR (400 MHz, CD$_3$OD) δ: 8.07 (s, 1H), 7.89 (d, J=8.8 Hz, 1H), 7.51-7.43 (m, 3H), 7.25 (d, J=3.8 Hz, 1H), 6.80 (d, J=8.8 Hz, 1H), 6.60 (d, J=3.8 Hz, 1H), 5.70 (dd, J=6.4, 7.9 Hz, 1H), 5.38-5.28 (m, 2H), 2.88-2.74 (m, 2H), 2.67 (spt, J=7.0 Hz, 1H), 2.48-2.36 (m, 1H), 2.25-2.13 (m, 2H), 1.96 (dd, J=7.8, 9.3 Hz, 2H), 1.29 (s, 3H), 1.23 (dd, J=7.0, 8.3 Hz, 6H), 1.02 (d, J=6.8 Hz, 3H), 0.97 (d, J=7.0 Hz, 3H).

Example 23

Compound 27

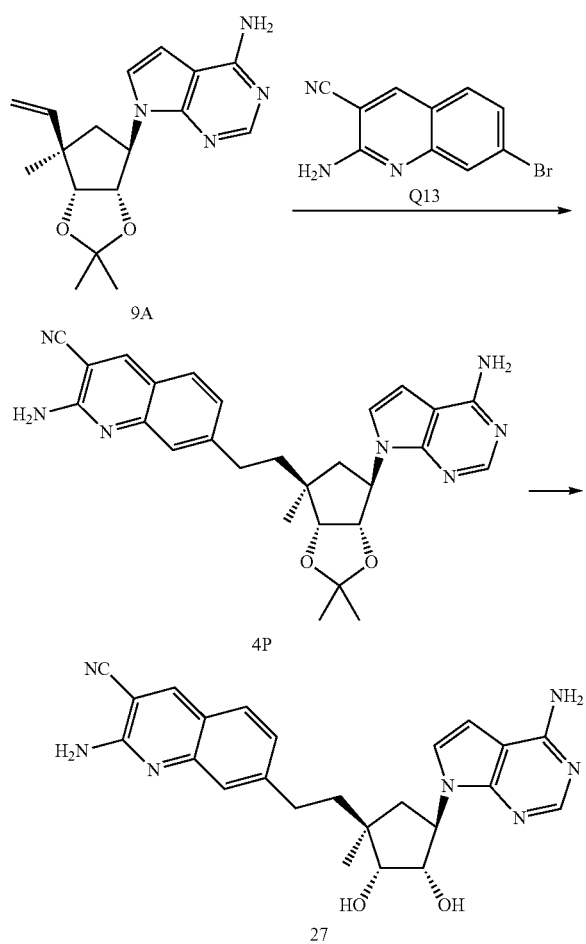

To a mixture of 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (150 mg, 477.1 µmol, 1 eq.) in THF (5 mL) was added 9-BBN dimer (254.0 mg, 1.05 mmol, 2.2 eq.) at 20° C. The mixture was stirred at 50° C. for 1.5 h under Ar, and then cooled to 20° C. A solution of K$_3$PO$_4$ (506.4 mg, 2.39 mmol, 5 eq.) in H$_2$O (1 mL) was added, and the mixture was stirred for 30 min. 2-amino-7-bromo-quinoline-3-carbonitrile (142.0 mg, 572.6 µmol, 1.2 eq.) and Pd(dppf)Cl$_2$ (34.9 mg, 47.7 µmol, 0.1 eq.) were added to the mixture at 20° C., and the mixture was degassed for several times. The mixture was then stirred at 70° C. for 16 h under Ar. The reaction progress was monitored by LCMS. Upon completion, the mixture was partitioned between EA (20 mL) and brine (10 mL). The organic phase was separated, and the aqueous phase was extracted with EA (3×20 mL). The organics were combined and dried over Na$_2$SO$_4$, filtered and concentrated under reduced pressure to give a residue. The residue was purified by column chromatography (SiO$_2$, PE:EA:EtOH=20:20:1 to 30:70:3) to provide 2W (105 mg, 209.1 µmol, 43.8% yield, 96.3% purity) as a yellow solid. LCMS: (ESI): m/z calcd. for $C_{27}H_{30}N_7O_2$ 484.25 [M+H]$^+$, found 484.2.

To a solution of 2W (105 mg, 209.1 µmol, 43.8% yield, 96.3% purity, 1 eq.) in THF (6 mL) was added HCl (4 M, 3 mL), and the mixture was stirred at 20° C. for 12 h. The mixture was concentrated under reduced pressure give a residue. The residue was purified by prep-HPLC (HCl condition, column: Phenomenex Gemini-NX 150*30 mm*5 um; mobile phase: [water (0.05% HCl)-ACN]; B %: 3%-30%) followed by prep-HPLC (basic condition, Column: YMC Triart C18 150*25 mm*5 um, Condition: water (10 mM NH$_4$HCO$_3$)-ACN, B %: 24%-54%) to afford Compound 27 (54 mg, 120.8 µmol, 57.7% yield, 99.2% purity) as a white solid. LCMS: (ESI): m/z calcd. for 444.21 [M+H]$^+$, found 444.3. $^1$H NMR (400 MHz, CD$_3$OD) δ: 8.46 (s, 1H), 8.08 (s, 1H), 7.65 (d, J=8.3 Hz, 1H), 7.43 (s, 1H), 7.18-7.28 (m, 2H), 6.60 (d, J=3.4 Hz, 1H), 4.95-5.06 (m, 1H), 4.53 (t, J=6.8 Hz, 1H), 3.93 (d, J=6.4 Hz, 1H), 2.72-2.95 (m, 2H), 2.03-2.13 (m, 1H), 1.81-2.00 (m, 3H), 1.24 (s, 3H).

Example 24

Compound 28

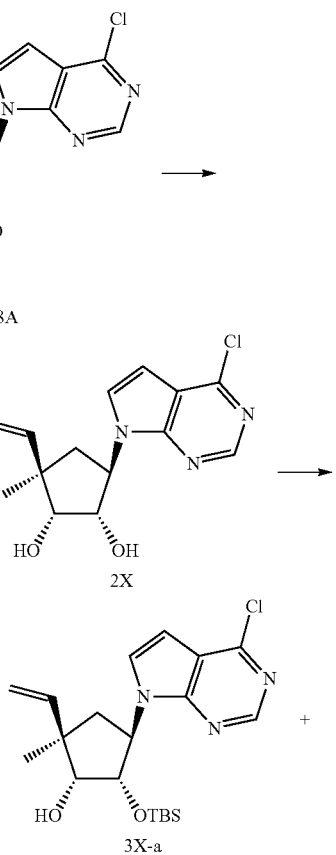

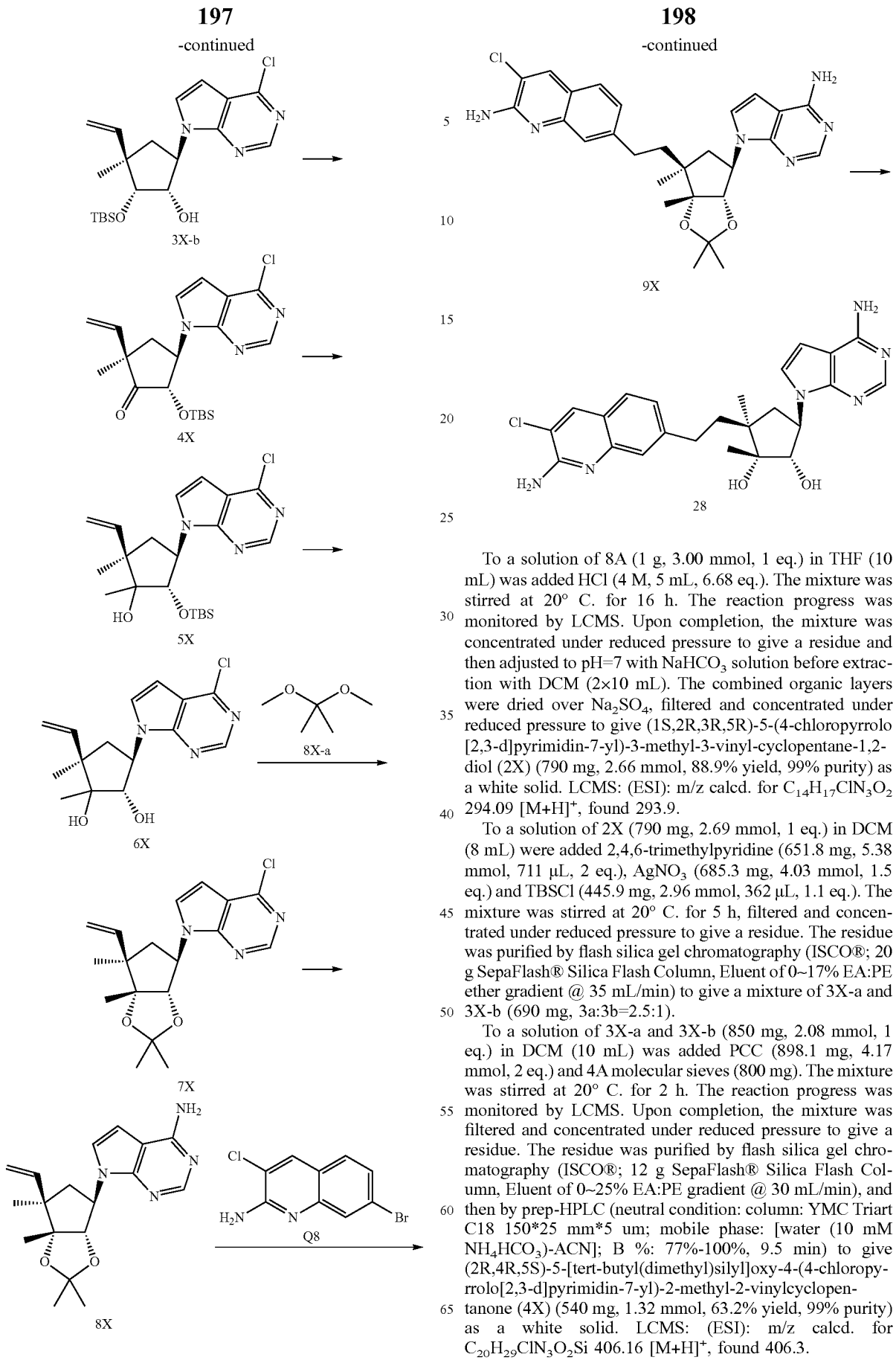

To a solution of 8A (1 g, 3.00 mmol, 1 eq.) in THF (10 mL) was added HCl (4 M, 5 mL, 6.68 eq.). The mixture was stirred at 20° C. for 16 h. The reaction progress was monitored by LCMS. Upon completion, the mixture was concentrated under reduced pressure to give a residue and then adjusted to pH=7 with NaHCO$_3$ solution before extraction with DCM (2×10 mL). The combined organic layers were dried over Na$_2$SO$_4$, filtered and concentrated under reduced pressure to give (1S,2R,3R,5R)-5-(4-chloropyrrolo [2,3-d]pyrimidin-7-yl)-3-methyl-3-vinyl-cyclopentane-1,2-diol (2X) (790 mg, 2.66 mmol, 88.9% yield, 99% purity) as a white solid. LCMS: (ESI): m/z calcd. for C$_{14}$H$_{17}$ClN$_3$O$_2$ 294.09 [M+H]$^+$, found 293.9.

To a solution of 2X (790 mg, 2.69 mmol, 1 eq.) in DCM (8 mL) were added 2,4,6-trimethylpyridine (651.8 mg, 5.38 mmol, 711 µL, 2 eq.), AgNO$_3$ (685.3 mg, 4.03 mmol, 1.5 eq.) and TBSCl (445.9 mg, 2.96 mmol, 362 µL, 1.1 eq.). The mixture was stirred at 20° C. for 5 h, filtered and concentrated under reduced pressure to give a residue. The residue was purified by flash silica gel chromatography (ISCO®; 20 g SepaFlash® Silica Flash Column, Eluent of 0~17% EA:PE ether gradient @ 35 mL/min) to give a mixture of 3X-a and 3X-b (690 mg, 3a:3b=2.5:1).

To a solution of 3X-a and 3X-b (850 mg, 2.08 mmol, 1 eq.) in DCM (10 mL) was added PCC (898.1 mg, 4.17 mmol, 2 eq.) and 4A molecular sieves (800 mg). The mixture was stirred at 20° C. for 2 h. The reaction progress was monitored by LCMS. Upon completion, the mixture was filtered and concentrated under reduced pressure to give a residue. The residue was purified by flash silica gel chromatography (ISCO®; 12 g SepaFlash® Silica Flash Column, Eluent of 0~25% EA:PE gradient @ 30 mL/min), and then by prep-HPLC (neutral condition: column: YMC Triart C18 150*25 mm*5 um; mobile phase: [water (10 mM NH$_4$HCO$_3$)-ACN]; B %: 77%-100%, 9.5 min) to give (2R,4R,5S)-5-[tert-butyl(dimethyl)silyl]oxy-4-(4-chloropyrrolo[2,3-d]pyrimidin-7-yl)-2-methyl-2-vinylcyclopentanone (4X) (540 mg, 1.32 mmol, 63.2% yield, 99% purity) as a white solid. LCMS: (ESI): m/z calcd. for C$_{20}$H$_{29}$ClN$_3$O$_2$Si 406.16 [M+H]$^+$, found 406.3.

To a solution of 4X (540 mg, 1.33 mmol, 1 eq.) in THF (6 mL) was added bromo(methyl)magnesium (3 M, 1.33 mL, 3 eq.) at −78° C. The mixture was stirred at 0° C. for 6 h. The reaction progress was monitored by LCMS. Upon completion, the reaction was quenched by NH$_4$Cl solution (5 mL), diluted with water (5 mL) and extracted with DCM (2×5 mL). The combined organic layers were washed with brine (2×5 mL), dried over Na$_2$SO$_4$, filtered and concentrated under reduced pressure to give (1R,2R,4R,5S)-5-[tert-butyl(dimethyl)silyl]oxy-4-(4-chloropyrrolo[2,3-d]pyrimidin-7-yl)-1,2-dimethyl-2-vinylcyclopentanol (5X) (480 mg, crude) as a colorless oil.

To a solution of 5X (480 mg, crude, 1 eq.) in THF (10 mL) was added HCl (4 M, 5 mL). The mixture was stirred at 20° C. for 36 h. The reaction progress was monitored by LCMS. Upon completion, the mixture was concentrated under reduced pressure to give a residue. The residue was then adjusted to pH=7 with NaHCO$_3$ solution and extracted with DCM (2×10 mL). The combined organic layers were dried over Na$_2$SO$_4$, filtered and concentrated under reduced pressure to give (1R,2S,3R,5R)-3-(4-chloropyrrolo[2,3-d]pyrimidin-7-yl)-1,5-dimethyl-5-vinyl-cyclopentane-1,2-diol (6X) (380 mg, crude) as a purple solid.

To a solution of 6X (380 mg, crude, 1 eq.) and 2,2-dimethoxypropane (385.76 mg, 3.70 mmol, 454 µL, 3 eq.) in acetone (10 mL) was added TsOH.H$_2$O (7.0 mg, 37.0 µmol, 0.03 eq.) at 0° C. The mixture was stirred at 25° C. for 2 h. The reaction progress was monitored by LCMS. Upon completion, the reaction was quenched by the addition NaHCO$_3$ solution (10 mL) and extracted with DCM (2×10 mL). The combined organic layers were dried over Na$_2$SO$_4$, filtered and concentrated under reduced pressure to give a residue. The residue was purified by flash silica gel chromatography (ISCO®; 12 g SepaFlash® Silica Flash Column, Eluent of 0~8% EA:PE gradient @ 30 mL/min) to give 7X (280 mg, 780.8 µmol, 63% yield, 97% purity) as a colorless oil. LCMS: (ESI): m/z calcd. for C$_{18}$H$_{23}$ClN$_3$O$_2$ 348.14 [M+H]$^+$, found 348.1.

To a mixture of NH$_3$.H$_2$O (4.55 g, 32.46 mmol, 5 mL, 25%, 45.16 eq.) and dioxane (5 mL) was added 7X (250 mg, 718.7 µmol, 1 eq.). The mixture was heated in a sealed tube at 100° C. and stirred for 48 h. The reaction progress was monitored by LCMS. Upon completion, the mixture was extracted with DCM (2×5 mL). The combined organic layers were washed with brine (2×5 mL), dried over Na$_2$SO$_4$, filtered and concentrated under reduced pressure to give a residue. The residue was purified by flash silica gel chromatography (ISCO®; 12 g SepaFlash® Silica Flash Column, Eluent of 0~75% EA/PE @ 30 mL/min) to give 7-[(3aR,4R,6R,6aS)-2,2,3a,4-tetramethyl-4-vinyl-6,6a-dihydro-5H-cyclopenta[d][1,3]dioxol-6-yl]pyrrolo[2,3-d]pyrimidin-4-amine (8X) (158 mg, 476.3 µmol, 66.3% yield, 99% purity) as a colorless oil. LCMS: (ESI): m/z calcd. for C$_{18}$H$_{25}$N$_4$O$_2$ 329.19 [M+H]$^+$, found 329.3.

To a solution of 8X (158 mg, 481.1 µmol, 1 eq.) in THF (10 mL) was added 9-BBN dimer (465.8 mg, 1.92 mmol, 4 eq.) at 25° C. The mixture was stirred at 50° C. for 1 h. The mixture was then cooled to 25° C. and a solution of K$_3$PO$_4$ (1.02 g, 4.81 mmol, 10 eq.) in H$_2$O (4 mL) was added. The mixture was stirred for 30 min, and then 7-bromo-3-chloro-quinolin-2-amine (161.1 mg, 625.4 µmol, 1.3 eq.) and Pd(dppf)Cl$_2$ (35.2 mg, 48.1 µmol, 0.1 eq.) were added at 25° C. The mixture was stirred at 70° C. for 15 h. The reaction progress was monitored by LCMS. Upon completion, the reaction mixture was filtered. The filtrate was diluted with brine (10 mL) and extracted with DCM (2×10 mL). The combined organic layers dried over Na$_2$SO$_4$, filtered and concentrated under reduced pressure to give a residue. The residue was purified by column chromatography (SiO$_2$, PE:EA=100:1 to 0:1, DCM:MeOH=50:1 to 10:1) to give 7-[2-[(3aR,4S,6R,6aS)-6-(4-aminopyrrolo[2,3-d]pyrimidin-7-yl)-2,2,3a,4-tetramethyl-6,6a-dihydro-5Hcyclopenta[d][1,3]dioxol-4-yl]ethyl]-3-chloro-quinolin-2-amine (9X) (180 mg, 284.0 µmol, 59.0% yield, 80% purity) as a yellow solid. LCMS: (ESI): m/z calcd. for C$_{27}$H$_{32}$ClN$_6$O$_2$ 507.22 [M+H]$^+$, found 507.2.

To a solution of 9X (180 mg, 284.01 µmol, 80% purity, 1 eq.) in THF (5 mL) was added HCl (4 M, 2.00 mL). The mixture was stirred at 20° C. for 12 h. The reaction progress was monitored by LCMS. Upon completion, the mixture was concentrated under reduced pressure to give a residue. The residue was purified by prep-HPLC (basic condition: column: Phenomenex Gemini-NX C18 75*30 mm*3 um; mobile phase: [water (0.04% NH$_3$H$_2$O+10 mM NH$_4$HCO$_3$)-ACN]; B %: 30%-60%, 7 min) to give Compound 28 (63 mg, 132.2 µmol, 46.6% yield, 98% purity) as a white solid. LCMS: (ESI): m/z calcd. for C$_{24}$H$_{28}$ClN$_6$O$_2$ 467.19 [M+H]$^+$, found 467.2. $^1$H NMR (400 MHz, CD$_3$OD) δ: 8.07 (d, J=2.4 Hz, 2H), 7.58 (d, J=8.3 Hz, 1H), 7.45 (s, 1H), 7.20 (dd, J=1.2, 8.3 Hz, 1H), 7.17 (d, J=3.7 Hz, 1H), 6.59 (d, J=3.4 Hz, 1H), 4.96 (q, J=8.9 Hz, 1H), 4.48 (d, J=9.0 Hz, 1H), 2.87-2.71 (m, 2H), 2.23-2.13 (m, 2H), 2.00 (dt, J=4.9, 12.2 Hz, 1H), 1.79 (dt, J=5.6, 12.3 Hz, 1H), 1.23 (s, 3H), 1.20 (s, 3H).

Example 25

Compound 29

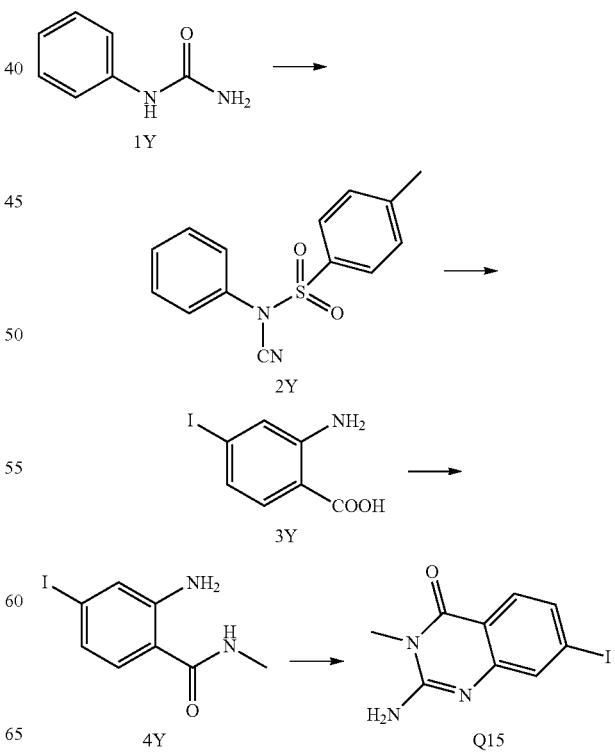

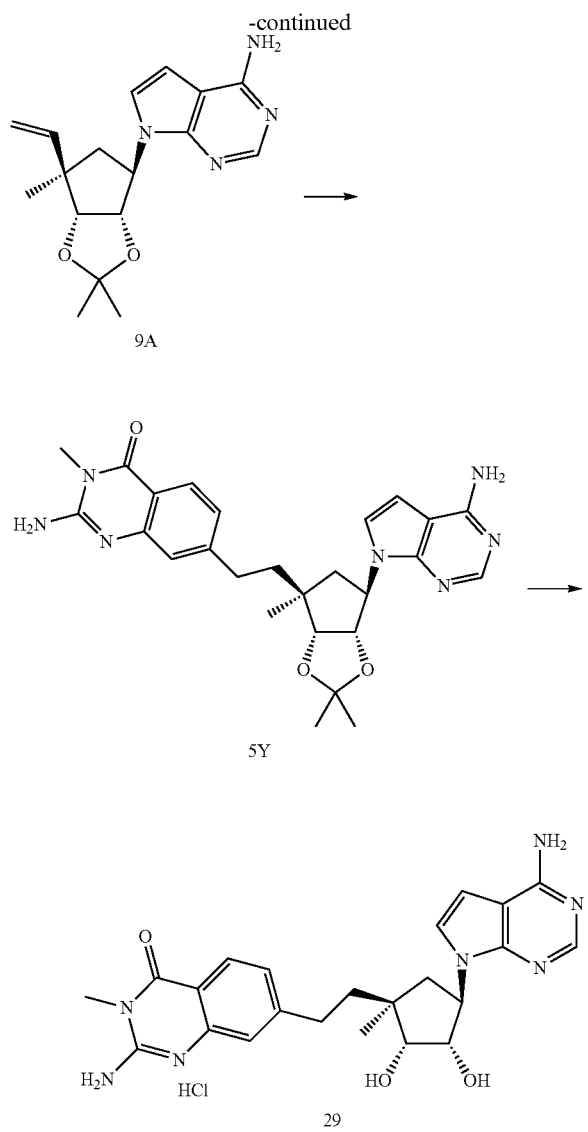

To a solution of phenylurea (1Y) (1 g, 7.3 mmol, 1 eq.) in pyridine (5 mL) was added dropwise toluenesulfonyl chloride (4.90 g, 25.7 mmol, 3.71 mL, 3.5 eq.) at 20° C. After addition, the mixture was stirred at 20° C. for 15 min. The reaction progress was monitored by TLC (PE:EA=1:1). Upon completion, the reaction was quenched by addition of ice-cooled water (30 mL) at 20° C. The precipitate formed during stirring was filtered and washed with water. The solid was collected by filtration to give a crude product. The crude product was triturated with EtOH (5 mL) at 20° C. for 30 min and then filtered to give 2Y (800 mg, 2.9 mmol, 40% yield) as a white solid. $^1$H NMR (400 MHz, CDCl$_3$) δ: 7.64 (d, J=8.3 Hz, 2H), 7.33-7.45 (m, 5H), 7.20 (d, J=7.5 Hz, 2H), 2.48 (s, 3H).

To a solution of 2-amino-4-iodo-benzoic acid (3Y) (1 g, 3.8 mmol, 1 eq.), methanamine hydrochloride (308 mg, 4.6 mmol, 1.20 eq.) and DIEA (1.47 g, 11.4 mmol, 1.99 mL, 3 eq.) in DCM (12 mL) were added EDCI (729 mg, 3.8 mmol, 1 eq.) and HOBt (616 mg, 4.7 mmol, 1.2 eq.). The mixture was stirred at 20° C. for 3.5 h. The reaction progress was monitored by LCMS. Upon completion, the reaction was quenched by addition of water (15 mL). The mixture was then partitioned between EA (20 mL) and a sat. Na$_2$CO$_3$ solution (30 mL). The organic phase was separated, and the aqueous phase washed with EA (3×20 mL). The combined organic layers were combined, dried over Na$_2$SO$_4$, filtered and concentrated under reduced pressure to give a residue. The residue was purified by flash silica gel chromatography (ISCO®; 20 g SepaFlash® Silica Flash Column, Eluent of 0~50% EA:PE gradient @ 30 mL/min) to give 2-amino-4-iodo-N-methyl-benzamide (4Y) (1 g, 3.6 mmol, 95% yield, 100% purity) as a white solid. LCMS: (ESI): m/z calcd. for C$_8$H$_{10}$IN$_2$O 276.98 [M+H]$^+$, found 276.9.

To a solution of 4Y (300 mg, 1.1 mmol, 1 eq.) in dioxane (8 mL) were added N-cyano-4-methyl-N-phenyl-benzene-sulfonamide (296 mg, 1.1 mmol, 1 eq.) and LiHMDS (1 M, 3.3 mL, 3 eq.) at 20° C. The mixture was stirred at 100° C. for 1 h. The reaction progress was monitored by LCMS. Upon completion, the reaction was quenched by water (10 mL). The aqueous phase washed with EA (3×20 mL). The organic layers were combined, washed with brine (20 mL), dried over Na$_2$SO$_4$, filtered and concentrated under reduced pressure to give a residue. The residue was purified by flash silica gel chromatography (ISCO®; 20 g SepaFlash® Silica Flash Column, Eluent of 0~100% EA:PE gradient @ 35 mL/min). Q15 (225 mg, 729 μmol, 67% yield, 98% purity) was obtained as a white solid. LCMS: (ESI): m/z calcd. for C$_9$H$_9$IN$_3$O 301.97 [M+H]$^+$, found 301.9.

A mixture of 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (150 mg, 477 μmol, 1 eq.) and 9-BBN dimer (289 mg, 1.2 mmol, 2.5 eq.) in THF (5 mL) was stirred at 50° C. for 2 h under Ar. The mixture was cooled to 20° C. and then a solution of K$_3$PO$_4$ (506 mg, 2.4 mmol, 5 eq.) in H$_2$O (1 mL) was added. The mixture was then stirred for 30 min. Compound Q15 (172 mg, 573 μmol, 98% purity, 1.2 eq.) and Pd(dppf)Cl$_2$ (35 mg, 48 μmol, 0.1 eq.) were added. The mixture was stirred at 70° C. for 16 h under Ar. The reaction progress was monitored by LCMS. Upon completion, the mixture was partitioned between EA (20 mL) and brine (10 mL). The organic phase was separated, and the aqueous phase was extracted with EA (3×20 mL). The separated organic layers were combined, dried over Na$_2$SO$_4$, filtered and concentrated under reduced pressure to give a residue. The residue was purified by column chromatography (SiO$_2$, DCM:MeOH=20:1 to 100:7). Compound 5Y (145 mg, 277 μmol, 58% yield, 93% purity) was obtained as a yellow gum. LCMS: (ESI): m/z calcd. for C$_{26}$H$_{32}$N$_7$O$_3$ 490.25 [M+H]$^+$, found 490.2.

To a solution of 5Y (145 mg, 277 μmol, 93% purity, 1 eq.) in THF (6 mL) was added HCl (4 M, 3 mL). The mixture was stirred at 20° C. for 12 h. The reaction progress was monitored by LCMS. Upon completion, the mixture was concentrated under reduced pressure to remove solvent to give a residue. The residue was purified by prep-HPLC (HCl condition: Column: Venusil ASB Phenyl 150*30 mm*5 um, Condition: water (0.05% HCl)-ACN, B %: 10%-40%) to give Compound 29 as a hydrochloride salt (white solid, 110 mg, 207 μmol, 75% yield, 98% purity). LCMS: (ESI): m/z calcd. for C$_{23}$H$_{28}$N$_7$O$_3$ 450.22 [M+H]$^+$, found 450.2. $^1$H NMR (400 MHz, CD$_3$OD) δ: 8.25 (s, 1H), 8.09 (d, J=8.1 Hz, 1H), 7.57 (d, J=3.7 Hz, 1H), 7.37 (d, J=8.1 Hz, 1H), 7.33 (s, 1H), 6.92 (d, J=3.4 Hz, 1H), 5.06-5.16 (m, 1H), 4.55 (dd, J=7.5, 6.5 Hz, 1H), 3.95 (d, J=6.1 Hz, 1H), 3.55 (s, 3H), 2.75-2.97 (m, 2H), 1.96-2.13 (m, 2H), 1.79-1.95 (m, 2H), 1.23 (s, 3H).

Example 26

Compound 30

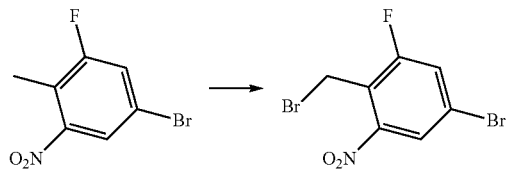

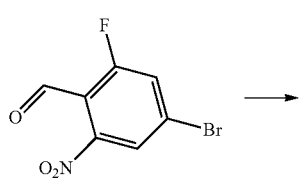

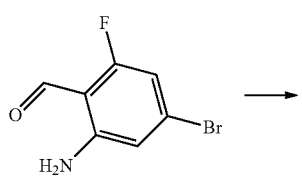

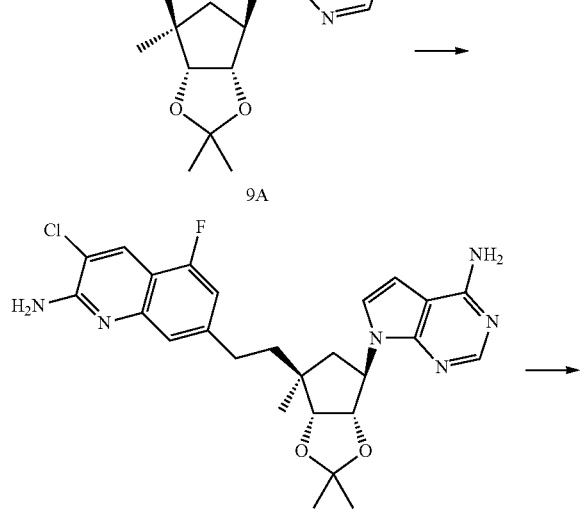

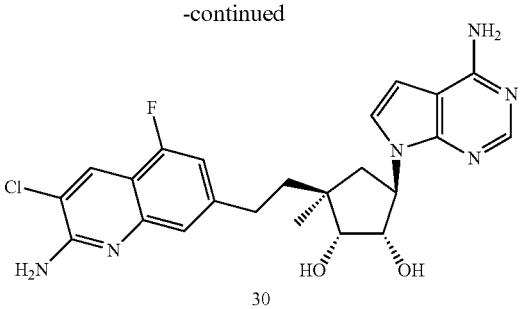

NBS (8.03 g, 45.12 mmol) and BPO (1.30 g, 3.76 mmol, 70% purity) were added to a solution of 5-bromo-1-fluoro-2-methyl-3-nitrobenzene (8.8 g, 37.60 mmol) in $CCl_3$ (130 mL) at 80° C. The mixture was stirred at 80° C. for 12 h. The mixture was extracted with EA (3×100 mL). The combined organic layers were washed with brine (2×100 mL) and dried over $Na_2SO_4$. The solids were removed by filtration, and the filtrate was concentrated under reduced pressure. The residue was purified by silica gel chromatography (0~2% PE/EA gradient) to afford 5-bromo-2-(bromomethyl)-1-fluoro-3-nitro-benzene (12.4 g, 31.70 mmol, 84% yield) as a colorless oil. $^1$H NMR (400 MHz, $CDCl_3$) δ 8.02 (s, 1H), 7.58 (dd, J=1.7, 8.6 Hz, 1H), 4.76 (d, J=1.5 Hz, 2H).

4-methyl-4-oxido-morpholin-4-ium (8.91 g, 76.08 mmol, 8.0 mL) was added to a mixture of 5-bromo-2-(bromomethyl)-1-fluoro-3-nitro-benzene (12.4 g, 31.7 mmol) and 4 Å molecular sieves (20 g) in MeCN (130 mL). The mixture was stirred at 25° C. for 3 h. The mixture was extracted with EA (3×50 mL). The combined organic layers were washed with water, 1M HCl and brine (2×50 mL) and dried over $Na_2SO_4$. The solids were removed by filtration, and the filtrate was concentrated under reduced pressure. The residue was purified by silica gel chromatography (0~7% PE/EA gradient) to afford 4-bromo-2-fluoro-6-nitro-benzaldehyde (6.49 g, 26.17 mmol, 82%) as a white solid. $^1$H NMR (400 MHz, $CDCl_3$) δ 10.24 (s, 1H), 8.02-7.98 (m, 1H), 7.68 (dd, J=1.8, 8.6 Hz, 1H).

Fe powder (14.61 g, 261.69 mmol) was added to a solution of 4-bromo-2-fluoro-6-nitro-benzaldehyde (6.49 g, 26.17 mmol) in EtOH (30 mL) and AcOH (30 mL) at 0° C. The mixture was stirred at 25° C. for 3 h, then diluted with EA (100 mL). The reaction was neutralized with $NaHCO_3$ (sat., aq., 300 mL). The mixture was filtered through a Celite pad. The separated organic layer was washed with brine (3×100 mL) and dried over $Na_2SO_4$. The solids were removed by filtration, and the filtrate was concentrated under reduced pressure to afford 2-amino-4-bromo-6-fluoro-benzaldehyde (5.67 g, crude) as a light green solid. LCMS: (ESI): m/z calcd. for $C_7H_6BrFNO$ 217.95 [M+H]$^+$, found 217.8.

To a solution of 2-amino-4-bromo-6-fluoro-benzaldehyde (3 g, 13.76 mmol) and 2,2,2-trichloroacetonitrile (2.19 g, 15.14 mmol, 1.52 mL) in THF (40 mL) was added Fe (7.68 g, 137.60 mmol). The mixture was diluted with EA (20 mL) and filtered to give a filtrate. The mixture was then extracted with EA (3×30 mL). The combined organic layers were washed with brine (3×50 mL), dried over $Na_2SO_4$, filtered and concentrated under reduced pressure. The residue was purified by silica gel chromatography (0~12% EA/PE gradient) to give a solid, that was suspended in PE:EA (10:1.20 mL) and stirred at 25° C. for 1 h. The solid was collected by filtration and dried under reduced pressure to afford 7-bromo-3-chloro-5-fluoro-quinolin-2-amine (Q16) (1.9 g, 6.90 mmol, 45% yield) as a yellow solid. LCMS: (ESI): m/z calcd. for C$_9$H$_6$BrClFN$_2$, 276.93 [M+H]$^+$, found 276.7.

A mixture of 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (150 mg, 0.477 mmol) and 9-BBN dimer (288.68 mg, 1.19 mmol) in THF (5 mL) was stirred at 50° C. for 2 h under Ar and then cooled to it. A solution of K$_3$PO$_4$ (506.39 mg, 2.39 mmol) in H$_2$O (0.5 mL) was added. The mixture was stirred for 0.5 h. Compound Q16 (197.18 mg, 715.69 μmol) and Pd(dppf)Cl$_2$ (34.91 mg, 47.71 μmol) were added. The mixture was stirred at 70° C. for 12 h under Ar. The mixture was diluted with EA (2 mL) and extracted with EA (2×5 mL). The combined organic layers were washed with brine (3×5 mL), dried over Na$_2$SO$_4$, filtered and concentrated under reduced pressure. The residue was purified by silica column chromatography (PE:EA=50:1 to 1:2 to DCM:MeOH=100:1 to 20:1) to afford 7-(2-((3aR,4S,6R,6aS)-6-(4-amino-7H-pyrrolo[2,3-d]pyrimidin-7-yl)-2,2,4-trimethyltetrahydro-4H-cyclopenta[d][1,3]dioxol-4-yl)ethyl)-3-chloro-5-fluoroquinolin-2-amine (193 mg, 339.9 μmol, 71%) as a yellow solid. LCMS: (ESI): m/z calcd. for C$_{26}$H$_{29}$ClFN$_6$O$_2$ 511.19 [M+H]$^+$, found 511.3.

To a solution of 7-(2-((3aR,4S,6R,6aS)-6-(4-amino-7H-pyrrolo[2,3-d]pyrimidin-7-yl)-2,2,4-trimethyltetrahydro-4H-cyclopenta[d][1,3]dioxol-4-yl)ethyl)-3-chloro-5-fluoroquinolin-2-amine (193 mg, 0.340 mmol) in THF (4 mL) was added HCl (4 M, 2 mL). The mixture was stirred at 25° C. for 12 h. The mixture was filtered and concentrated under reduced pressure. The solid was added to MeCN:H$_2$O (10:1, 3×10 mL) and stirred at 60° C. for 1 h. The mixture was filtered, and the collected solid was dried under reduced pressure to afford (1S,2R,3S,5R)-3-(2-(2-amino-3-chloro-5-fluoroquinolin-7-yl)ethyl)-5-(4-amino-7H-pyrrolo[2,3-d]pyrimidin-7-yl)-3-methylcyclopentane-1,2-diol (30) as a hydrochloride salt (white solid, 140 mg, 0.253 mmol, 74%). LCMS: (ESI): m/z calcd. for C$_{23}$H$_{25}$ClFN$_6$O$_2$ 471.16 [M+H]$^+$, found 471.2. $^1$H NMR (400 MHz, CD$_3$OD) δ: 8.68 (s, 1H), 8.25 (s, 1H), 7.59 (d, J=3.7 Hz, 1H), 7.43 (s, 1H), 7.28 (d, J=10.9 Hz, 1H), 6.92 (d, J=3.5 Hz, 1H), 5.16-5.07 (m, 1H), 4.55 (dd, J=6.4, 7.5 Hz, 1H), 3.95 (d, J=6.4 Hz, 1H), 3.02-2.80 (m, 2H), 2.13-1.97 (m, 2H), 1.96-1.82 (m, 2H), 1.24 (s, 3H).

Example 27

Compound 31

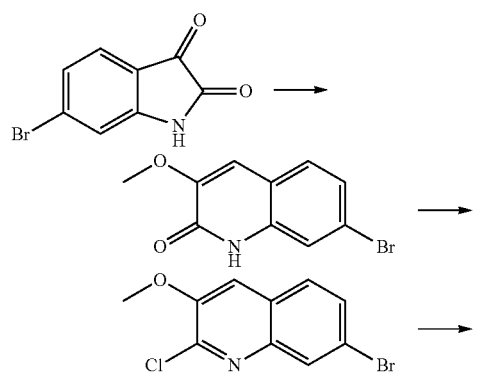

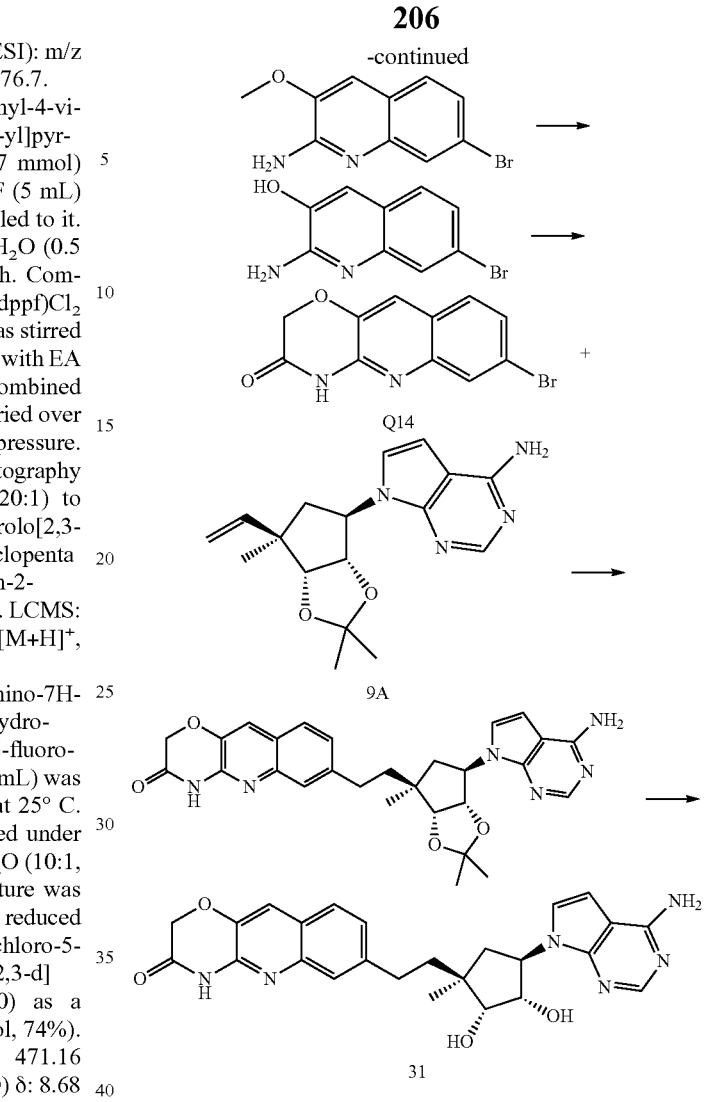

To a solution of 6-bromoindoline-2,3-dione (5 g, 22.1 mmol) in EtOH (30 mL) was added diazomethyl(trimethyl)silane (5.1 g, 44.2 mmol) then followed by TEA (4.5 g, 44.2 mmol, 6.2 mL). The mixture was stirred at 20° C. for 18 h. The mixture was filtered, and the filter cake was washed with EtOH (30 mL) to afford 7-bromo-3-methoxy-1H-quinolin-2-one (3.1 g, 11.5 mmol, 52% yield, 94% purity) as a white solid. LCMS: (ESI): m/z calcd. for C$_{10}$H$_9$BrNO$_2$ 253.97 [M+H]$^+$, found 253.9.

To a solution of 7-bromo-3-methoxy-1H-quinolin-2-one (1 g, 3.9 mmol) in toluene (20 mL) were added SOCl$_2$ (37.5 g, 314.9 mmol, 22.8 mL) and DMF (28.8 mg, 0.394 mmol, 0.030 mL) at 20° C. under N$_2$. The mixture was stirred at 80° C. for 2 h. The mixture was concentrated under reduced pressure to afford 7-bromo-2-chloro-3-methoxy-quinoline (1.05 g, 3.8 mmol, 96%) as a yellow solid, which was used for next step without further purification. LCMS: (ESI): m/z calcd. for C$_{10}$H$_8$BrClNO 273.94 [M+H]$^+$, found 273.8.

A solution of 7-bromo-2-chloro-3-methoxy-quinoline (1.05 g, 3.8 mmol) in dioxane (20 mL) and NH$_3$.H$_2$O (20 mL, 25% wt) was stirred at 110° C. for 18 h in a 100 mL of sealed tube. The mixture was partitioned between brine (30 mL) and EA (30 mL). The organic phase was separated, washed with EA mL (3×30 mL), dried over Na$_2$SO$_4$, filtered and concentrated under reduced pressure. The residue was purified by silica gel chromatography (EA/PE gradient).

7-bromo-3-methoxy-quinolin-2-amine (590 mg, 2.1 mmol, 54% yield, 89% purity) was obtained as a yellow solid. LCMS: (ESI): m/z calcd. for $C_{10}H_{10}BrN_2O$ 252.99 [M+H]$^+$, found 253.0.

To a solution of 7-bromo-3-methoxy-quinolin-2-amine (590 mg, 2.1 mmol, 89% purity) in DCM (5 mL) was added BBr$_3$ (1.57 g, 6.3 mmol, 0.602 mL). The mixture was stirred at 20° C. for 2 h. The mixture was diluted with DCM (30 mL) and then quenched by addition of MeOH at 0° C. The mixture was concentrated under reduced pressure to give 2-amino-7-bromo-quinolin-3-ol hydrobromide (785 mg, crude) as a brown solid, which was used for the next step without further purification. LCMS: (ESI): m/z calcd. for $C_9H_8BrN_2O$ 238.97 [M+H]$^+$, found 240.9.

To a solution of 2-amino-7-bromo-quinolin-3-ol hydrobromide (685 mg, 2.1 mmol) in THF (34 mL) were added TEA (630.2 mg, 6.2 mmol, 0.867 mL) and 2-chloroacetyl chloride (304.8 mg, 2.7 mmol, 0.215 mL) at 0° C. The mixture was stirred at 20° C. for 2 h, then K$_2$CO$_3$ (573.8 mg, 4.2 mmol) was added. The mixture was stirred at 50° C. for 1 h. The reaction was quenched by addition of H$_2$O (20 mL) at 20° C., and then extracted with EA (3×40 mL). The combined organic layers were washed with NaCl (aq., 30 mL), dried over Na$_2$SO$_4$, filtered and concentrated under reduced pressure. The crude product was triturated with EA (50 mL) at 20° C. for 30 min. The solid was filtered, and the filter cake was dried under reduced pressure to afford 7-bromo-2H-[1,4]oxazino[3,2-b]quinolin-3(4H)-one (Q14) (426 mg, 1.5 mmol, 72%) as a yellow solid. LCMS: (ESI): m/z calcd. for $C_{11}H_8BrN_2O_2$ 278.97 [M+H]$^+$, found 280.9.

A mixture of 7-[(3aR,4R,6R,6aS)-2,2,4-trimethyl-4-vinyl-3a,5,6,6a-tetrahydrocyclopenta[d][1,3]dioxol-6-yl]pyrrolo[2,3-d]pyrimidin-4-amine (9A) (150 mg, 472 µmol) and 9-BBN dimer (285.8 mg, 1.2 mmol) in THF (5 mL) was stirred at 50° C. for 1.5 h under Ar and then cooled to 20° C. K$_3$PO$_4$ (501.3 mg, 2.4 mmol) in water (1 mL) was added. The mixture was stirred at 20° C. for 0.5 h. Compound Q14 (173.3 mg, 614 µmol) and Pd(dppf)Cl$_2$ (34.6 mg, 0.047 mmol) were added. The mixture was stirred at 70° C. for 12 h under Ar. The mixture was partitioned between EA (20 mL) and water (20 mL). The organic phase was separated, and the aqueous phase was extracted with EA (3×30 mL). The organic phases were combined and washed with brine (30 mL), dried over anhydrous Na$_2$SO$_4$, filtered and concentrated under reduced pressure. The residue was purified by silica column chromatography (DCM/MeOH=100/1 to 100/3) to afford 7-(2-((3aR,4S,6R,6aS)-6-(4-amino-7H-pyrrolo[2,3-d]pyrimidin-7-yl)-2,2,4-trimethyltetrahydro-4H-cyclopenta[d][1,3]dioxol-4-yl)ethyl)-2H-[1,4]oxazino[3,2-d]quinolin-3(4H)-one (144 mg, 277 µmol, 58%) as a yellow solid. LCMS: (ESI): m/z calcd. for $C_{28}H_{31}N_6O_4$ 515.23 [M+H]$^+$, found 515.2.

To a solution of 7-(2-((3aR,4S,6R,6aS)-6-(4-amino-7H-pyrrolo[2,3-d]pyrimidin-7-yl)-2,2,4-trimethyltetrahydro-4H-cyclopenta[d][1,3]dioxol-4-yl)ethyl)-2H-[1,4]oxazino[3,2-b]quinolin-3(4H)-one (144 mg, 0.277 mmol) in THF (6 mL) was added HCl (4 M, 3 mL). The mixture was stirred at 20° C. for 12 h. The mixture was concentrated under reduced pressure. The residue was triturated with water/MeCN (10/1) at 20° C. for 1 h and then filtered to afford 7-(2-((1S,2R,3S,4R)-4-(4-amino-7H-pyrrolo[2,3-d]pyrimidin-7-yl)-2,3-dihydroxy-1-methylcyclopentyl)ethyl)-2H-[1,4]oxazino[3,2-b]quinolin-3(4H)-one as a hydrochloride salt (31) (white solid, 117 mg, 0.209 mmol, 76%). LCMS: (ESI): m/z calcd. for $C_{25}H_{27}N_6O_4$ 475.20 [M+H]$^+$, found 475.2. $^1$H NMR (400 MHz, CD$_3$OD) δ: 8.25 (s, 1H), 7.66-7.76 (m, 3H), 7.55 (d, J=3.4 Hz, 1H), 7.39 (br d, J=8.1 Hz, 1H), 6.91 (d, J=3.7 Hz, 1H), 5.11 (q, J=8.8 Hz, 1H), 4.76 (s, 2H), 4.58 (t, J=7.0 Hz, 1H), 3.95 (d, J=5.9 Hz, 1H), 2.75-2.97 (m, 2H), 1.99-2.13 (m, 2H), 1.91 (dt, J=11.2, 5.5 Hz, 2H), 1.25 (s, 3H).

Example 28

Compound 32

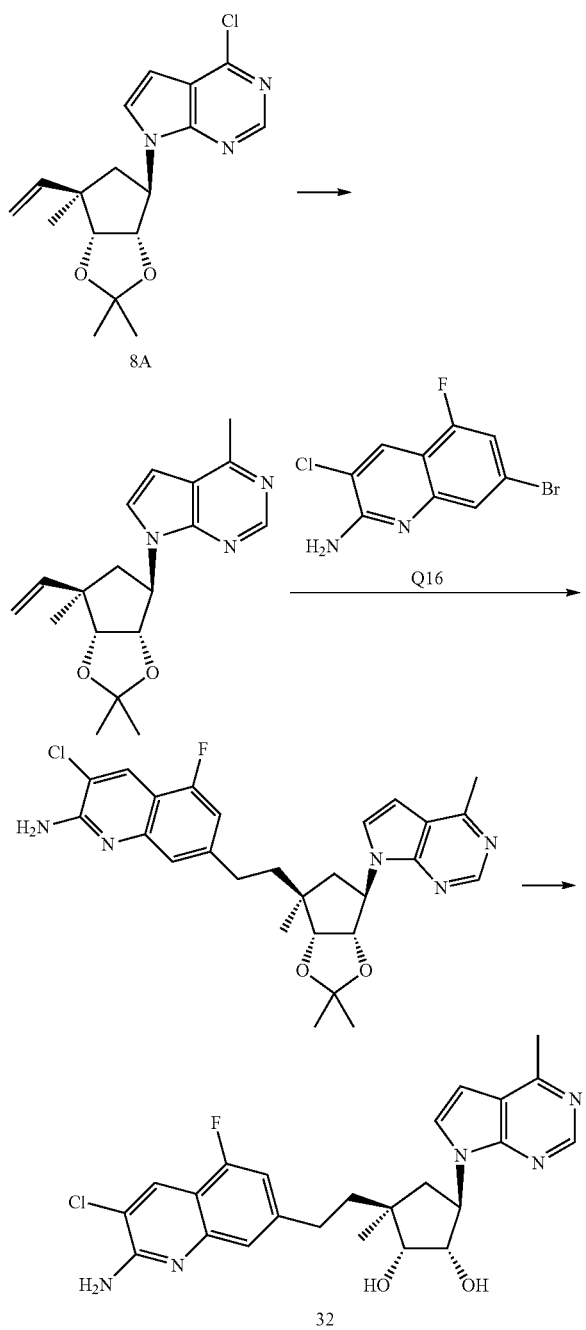

To a solution of 4-chloro-7-((3aS,4R,6R,6aR)-2,2,6-trimethyl-6-vinyltetrahydro-4H-cyclopenta[d][1,3]dioxol-4-yl)-7H-pyrrolo[2,3-d]pyrimidine (300 mg, 0.899 mmol) in dioxane (5 mL) and H$_2$O (1 mL) were added 2,4,6-trimethyl-1,3,5,2,4,6-trioxatriborinane (676.92 mg, 2.70 mmol, 0.754 mL, 50% wt), Pd(dppf)Cl$_2$ (65.76 mg, 0.090 mmol), and K$_3$PO4 (953.83 mg, 4.49 mmol). The mixture was stirred at 90° C. for 12 h. The residue was diluted with water (5 mL) and extracted with EA (2×10 mL). The combined organic layers were washed with brine (10 mL), dried over Na$_2$SO$_4$. The solids were removed by filtration, and the filtrate was concentrated under reduced pressure. The residue was purified by silica gel chromatography (0~25% EA/PE gradient) to afford 4-methyl-7-((3aS,4R,6R,6aR)-2,2,6-trimethyl-6-vinyltetrahydro-4H-cyclopenta[d][1,3]dioxol-4-yl)-7H-pyrrolo[2,3-d]pyrimidine (189 mg, 597.05 μmol, 66%) as colorless oil. LCMS: (ESI): m/z calcd. for C$_{18}$H$_{24}$N$_3$O$_2$ 314.18 [M+H]$^+$, found 314.1.

A mixture of 4-methyl-7-((3aS,4R,6R,6aR)-2,2,6-trimethyl-6-vinyltetrahydro-4H-cyclopenta[d][1,3]dioxol-4-yl)-7H-pyrrolo[2,3-d]pyrimidine (189 mg, 0.597 mmol) and 9-BBN dimer (361.24 mg, 1.49 mmol) in THF (5 mL) was stirred at 50° C. for 2 h under N$_2$. The mixture was cooled to rt, and then a solution of K$_3$PO$_4$ (633.66 mg, 2.99 mmol) in H$_2$O (0.5 mL) was added. After stirring at rt for 0.5 h, 7-bromo-3-chloro-5-fluoro-quinolin-2-amine (246.73 mg, 0.896 mmol) and Pd(dppf)Cl$_2$ (43.69 mg, 0.060 mmol) were added. The mixture was stirred at 70° C. under N$_2$ for 12 h. The mixture was diluted with water (10 mL) and then extracted with EA (2×10 mL). The combined organic layers were washed with brine (10 mL), dried over Na$_2$SO$_4$, filtered and concentrated under reduced pressure. The residue was purified by silica column chromatography (PE:EA=3:1 to 1:1, then DCM:MeOH=100:1 to 20:1) followed by prep-HPLC purification (column: Phenomenex Gemini-NX 150×30 mm×5 μm; mobile phase: [water (0.04% NH$_3$H$_2$O+10 mM NH4HCO3)-ACN]; B %: 53%-83%, 8 min) to afford 3-chloro-5-fluoro-7-(2-((3aR,4S,6R,6aS)-2,2,4-trimethyl-6-(4-methyl-7H-pyrrolo[2,3-d]pyrimidin-7-yl)tetrahydro-4H-cyclopenta[d][1,3]dioxol-4-yl)ethyl)quinolin-2-amine (152 mg, 291.78 μmol, 49%) as an off-white solid. LCMS: (ESI): m/z calcd. for C$_{27}$H$_{30}$ClFN$_5$O$_2$ 510.20 [M+H]$^+$, found 510.3.

To a solution of 3-chloro-5-fluoro-7-(2-((3aR,4S,6R,6aS)-2,2,4-trimethyl-6-(4-methyl-7H-pyrrolo[2,3-d]pyrimidin-7-yl)tetrahydro-4H-cyclopenta[d][1,3]dioxol-4-yl)ethyl)quinolin-2-amine (152 mg, 291.78 μmol) in THF (4 mL) was added HCl (4 M, 2 mL). The mixture was stirred at 25° C. for 7 h. The mixture was concentrated under reduced pressure. The residue was washed with MeCN:H$_2$O (10:1, 10 mL) to afford (1S,2R,3S,5R)-3-(2-(2-amino-3-chloro-5-fluoroquinolin-7-yl)ethyl)-3-methyl-5-(4-methyl-7H-pyrrolo[2,3-d]pyrimidin-7-yl)cyclopentane-1,2-diol (32) as a hydrochloride salt (white solid, 113 mg, 206.93 μmol, 71%). LCMS: (ESI): m/z calcd. for C$_{24}$H$_{26}$ClFN$_5$O$_2$ 470.17 [M+H]$^+$, found 470.3. $^1$H NMR (400 MHz, CD$_3$OD) δ: 8.97 (s, 1H), 8.60 (s, 1H), 8.06 (d, J=4.0 Hz, 1H), 7.43 (s, 1H), 7.24 (d, J=10.3 Hz, 1H), 7.17 (d, J=3.8 Hz, 1H), 5.32-5.24 (m, 1H), 4.62 (dd, J=6.3, 7.8 Hz, 1H), 3.98 (d, J=6.3 Hz, 1H), 2.98 (s, 3H), 2.97-2.82 (m, 2H), 2.16-2.04 (m, 2H), 1.98-1.86 (m, 2H), 1.26 (s, 3H).

Example 29

Compound 33

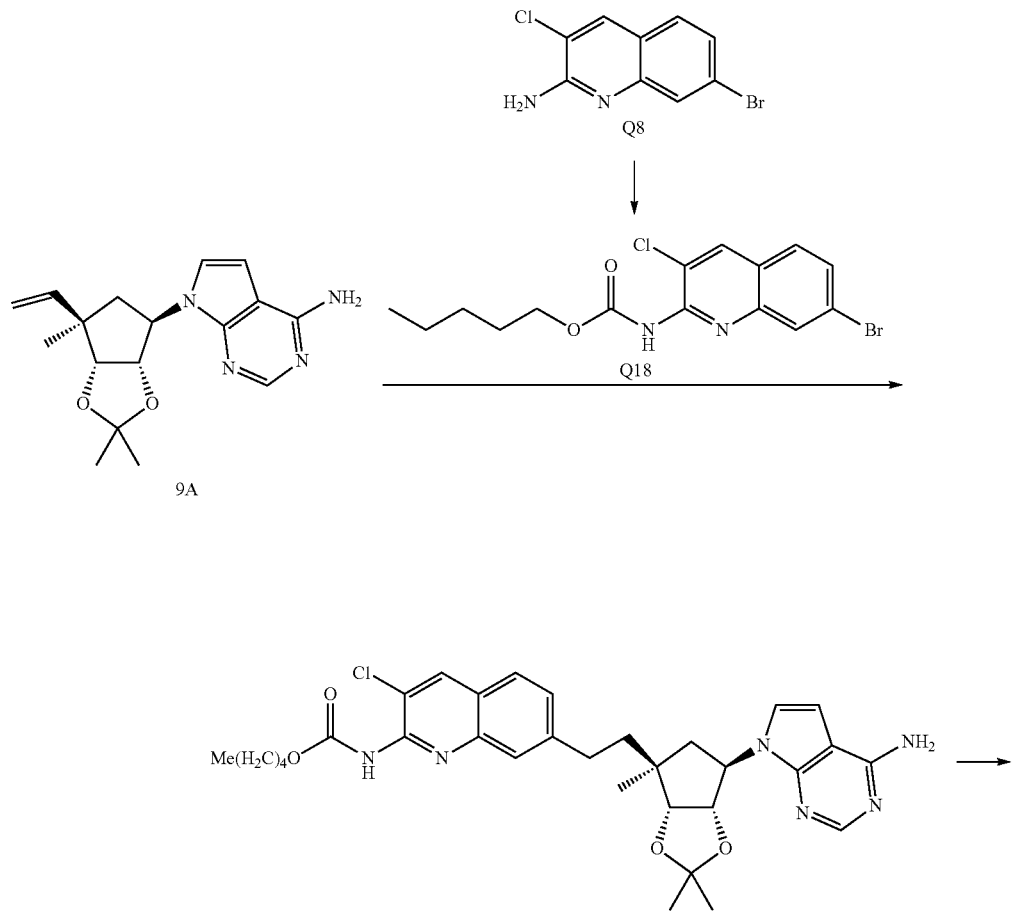

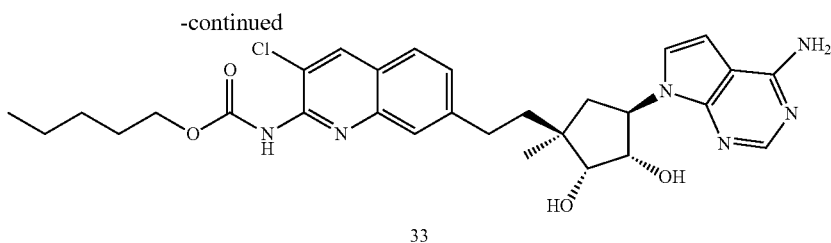

33

To a solution of 7-bromo-3-chloroquinolin-2-amine (Q8) (150 mg, 0.583 mmol) in DCM (3 mL) were added N-methylimidazole (286.95 mg, 3.49 mmol, 0.279 mL) and pentyl carbonochloridate (263.2 mg, 1.75 mmol) at 0° C. The mixture was stirred at rt for 12 h. The mixture was partitioned between EA (5 mL) and water (5 mL). The organic phase was separated, the aqueous phase extracted with EA (5 mL). The organic layers were combined, washed with brine (5 mL) and dried over $Na_2SO_4$, filtered and concentrated under reduced pressure. The residue was purified by silica gel chromatography (5%~9% PE/EA gradient) to afford pentyl (7-bromo-3-chloroquinolin-2-yl)carbamate (Q18) (75 mg, 0.200 mmol, 34% yield, 99.1% purity) as a pale yellow solid. LCMS: (ESI): m/z calcd. for $C_{15}H_{17}BrClN_2O_2$ 373.01 $[M+H]^+$, found 372.9.

A mixture of 7-((3aS,4R,6R,6aR)-2,2,6-trimethyl-6-vinyltetrahydro-4H-cyclopenta[d][1,3]dioxol-4-yl)-7H-pyrrolo[2,3-d]pyrimidin-4-amine (9A) (170 mg, 540.74 μmol) and 9-BBN dimer (327.18 mg, 1.35 mmol) in THF (5 mL) was stirred at 50° C. for 2 h under $N_2$ and then cooled to 20° C. A solution of $K_3PO_4$ (573.9 mg, 2.70 mmol) in water (0.5 mL) was added. The mixture was stirred at 20° C. for 0.5 h. Compound Q18 (241.2 mg, 0.649 mmol) and Pd(dppf)Cl$_2$ (39.57 mg, 54.07 μmol) were added. The mixture was stirred at 60° C. for 2 h under Ar. The mixture was partitioned between EA (5 mL) and water (5 mL). The organic phase was separated, and the aqueous phase washed with EA (5 mL). The organic layers were combined and washed with brine (5 mL), dried over $Na_2SO_4$, filtered and concentrated under reduced pressure. The residue was purified by column chromatography (SiO$_2$, PE:EA=2:1 then DCM:MeOH=100:1 to 30:1) to afford pentyl (7-(2-((3aR,4S,6R,6aS)-6-(4-amino-7H-pyrrolo[2,3-d]pyrimidin-7-yl)-2,2,4-trimethyltetrahydro-4H-cyclopenta[d][1,3]dioxol-4-yl)ethyl)-3-chloroquinolin-2-yl)carbamate (235 mg, 0.327 mmol, 60%, 84% purity) as a yellow solid. LCMS: (ESI): m/z calcd. for $C_{32}H_{40}ClN_6O_4$ 607.27 $[M+H]^+$, found 607.5.

To a solution of pentyl (7-(2-((3aR,4S,6R,6aS)-6-(4-amino-7H-pyrrolo[2,3-d]pyrimidin-7-yl)-2,2,4-trimethyltetrahydro-4H-cyclopenta[d][1,3]dioxol-4-yl)ethyl)-3-chloroquinolin-2-yl)carbamate (185 mg, 257.17 μmol) in THF (4 mL) was added HCl (4 M, 2 mL). The mixture was stirred at rt for 12 h. The mixture was concentrated under reduced pressure. The residue was purified by prep-HPLC (Phenomenex Gemini-NX 80×40 mm×3 μm; mobile phase: [water (0.05% NH3 in H$_2$O+10 mM NH$_4$HCO$_3$)-ACN]; B %: 39%-69%, 8 min) to afford pentyl (7-(2-((1S,2R,3S,4R)-4-(4-amino-7H-pyrrolo[2,3-d]pyrimidin-7-yl)-2,3-dihydroxy-1-methylcyclopentyl)ethyl)-3-chloroquinolin-2-yl)carbamate (33) (76 mg, 0.133 mmol, 52%) as a white solid. LCMS: (ESI): m/z calcd. for $C_{29}H_{36}ClN_6O_4$ 567.24 $[M+H]^+$, found 567.2. $^1$H NMR (400 MHz, CD$_3$OD) δ: 8.38 (s, 1H), 8.07 (s, 1H), 7.82 (s, 1H), 7.78 (d, J=8.3 Hz, 1H), 7.49 (d, J=7.0 Hz, 1H), 7.24 (d, J=3.8 Hz, 1H), 6.60 (d, J=3.5 Hz, 1H), 5.07-4.97 (m, 1H), 4.53 (t, J=6.9 Hz, 1H), 4.23 (t, J=6.7 Hz, 2H), 3.95 (d, J=6.3 Hz, 1H), 3.00-2.80 (m, 2H), 2.13-2.05 (m, 1H), 2.00-1.84 (m, 3H), 1.74 (quin, J=6.9 Hz, 2H), 1.48-1.34 (m, 4H), 1.26 (s, 3H), 0.98-0.91 (m, 3H).

Example 30

Compound 34

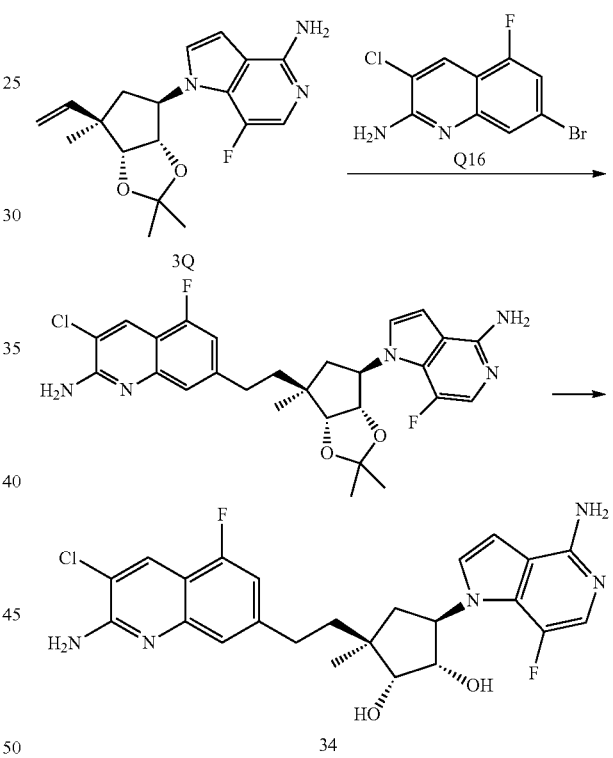

34

A mixture of 1-[(3aR,4R,6R,6aS)-2,2,4-trimethyl-4-vinyl-3a,5,6,6a-tetrahydrocyclopenta[d][1,3]dioxol-6-yl]-7-fluoro-pyrrolo[3,2-c]pyridin-4-amine (3Q) (140 mg, 0.422 mmol) and 9-BBN dimer (255.6 mg, 1.06 mmol) in THF (5 mL) was stirred at 50° C. for 1.5 h under Ar and then cooled to 20° C. A solution of $K_3PO_4$ (448.4 mg, 2.11 mmol) in H$_2$O (1 mL) was added. The mixture was stirred at 20° C. for 0.5 h. 7-bromo-3-chloro-5-fluoro-quinolin-2-amine (168.1 mg, 0.549 mmol) and Pd(dppf)Cl$_2$ (30.9 mg, 0.042 mmol) were added. The mixture was stirred at 70° C. for 12 h under Ar. The mixture was partitioned between EA (10 mL) and water (10 mL). The organic phase was separated, the aqueous phase washed with EA (3×10 mL). The organic layers were combined and washed with brine (10 mL), dried over $Na_2SO_4$, filtered and concentrated under reduced pressure.

The residue was purified by silica column chromatography (PE:EA=1:1 then DCM:MeOH=20:1) to afford 7-[2-[(3aR,4S,6R,6aS)-6-(4-amino-7-fluoro-pyrrolo[3,2-c]pyridin-1-yl)-2,2,4-trimethyl-3a,5,6,6a-tetrahydrocyclopenta[d][1,3]dioxol-4-yl]ethyl]-3-chloro-5-fluoro-quinolin-2-amine (174 mg, 264.68 μmol, 63% yield, 80% purity) as a yellow solid. LCMS: (ESI): m/z calcd. for $C_{27}H_{29}ClF_2N_5O_2$ 528.19 $[M+H]^+$, found 528.2.

To a solution of 7-[2-[(3aR,4S,6R,6aS)-6-(4-amino-7-fluoro-pyrrolo[3,2-c]pyridin-1-yl)-2,2,4-trimethyl-3a,5,6,6a-tetrahydrocyclopenta[d][1,3]dioxol-4-yl]ethyl]-3-chloro-5-fluoro-quinolin-2-amine (174 mg, 0.265 mmol, 80% purity) in THF (4 mL) was added HCl (4 M, 2 mL). The mixture was stirred at 20° C. for 2 h. The mixture was concentrated under reduced pressure to remove the solvent. The residue was purified by prep-HPLC (HCl conditions, column: Venusil ASB Phenyl 150×30 mm×5 μm; mobile phase: [water (0.05% HCl)-ACN]; B %: 17%-47%, 9 min) to afford (1S,2R,3S,5R)-3-[2-(2-amino-3-chloro-5-fluoro-7-quinolyl)ethyl]-5-(4-amino-7-fluoro-pyrrolo[3,2-c]pyridin-1-yl)-3-methyl-cyclopentane-1,2-diol (34) as a hydrochloride salt (off-white solid, 88 mg, 0.157 mmol, 59%). LCMS: (ESI): m/z calcd. for $C_{24}H_{25}ClF_2N_5O_2$ 488.16 $[M+H]^+$, found 488.4. $^1$H NMR (400 MHz, $CD_3OD$) δ: 8.68 (s, 1H), 7.74 (d, J=3.5 Hz, 1H), 7.60 (d, J=6.4 Hz, 1H), 7.44 (s, 1H), 7.29 (d, J=9.7 Hz, 1H), 7.13 (dd, J=3.1, 2.0 Hz, 1H), 5.09-5.20 (m, 1H), 4.40-4.46 (m, 1H), 3.92 (d, J=6.4 Hz, 1H), 2.82-2.99 (m, 2H), 2.16 (dd, J=12.9, 8.3 Hz, 1H), 1.79-1.95 (m, 3H), 1.23 (s, 3H).

Example 31

Compound 35

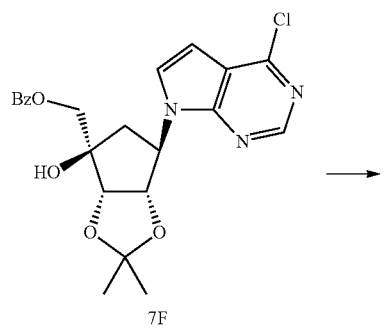

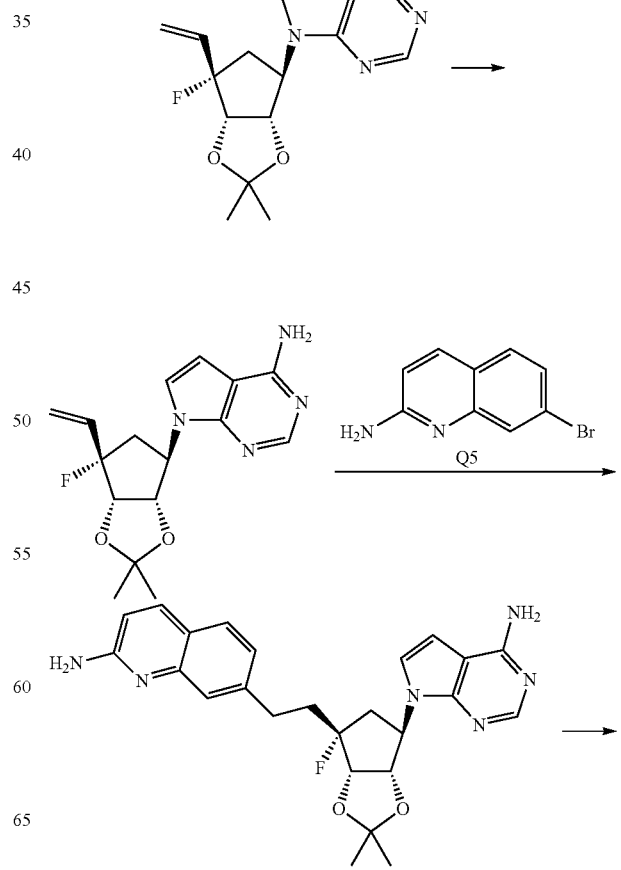

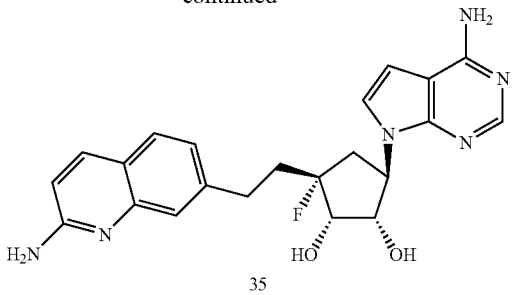
35

DAST (6.54 g, 40.55 mmol, 5.4 mL) was added dropwise to a solution of [(3aS,4R,6R,6aS)-6-(4-chloropyrrolo[2,3-d]pyrimidin-7-yl)-4-hydroxy-2,2-dimethyl-3a,5,6,6a-tetrahydrocyclopenta[d][1,3]dioxol-4-yl]methyl benzoate (4.5 g, 10.14 mmol) in DCM (50 mL) at 0° C. The mixture was stirred at 0° C. for 1 h, and then the reaction was quenched by NaHCO₃ (sat., aq., 100 mL). The mixture was extracted with DCM (2×50 mL). The separated organic layers were combined and washed with brine (20 mL) and dried over anhydrous Na₂SO₄. The solids were removed by filtration, and the filtrate was concentrated under reduced pressure. The residue was purified by silica gel column (PE/EA=8/1) to afford ((3aS,4S,6R,6aS)-6-(4-chloro-7H-pyrrolo[2,3-d]pyrimidin-7-yl)-4-fluoro-2,2-dimethyltetrahydro-4H-cyclopenta[d][1,3]dioxol-4-yl)methyl benzoate (880 mg, 60% pure) as a white foam. LCMS: (ESI): m/z calcd. for $C_{22}H_{22}ClFN_3O_4$ 446.12 [M+H]⁺, found 446.2.

K₂CO₃ (53.5 mg, 386.8 μmol) was added to a solution of ((3aS,4S,6R,6aS)-6-(4-chloro-7H-pyrrolo[2,3-d]pyrimidin-7-yl)-4-fluoro-2,2-dimethyltetrahydro-4H-cyclopenta[d][1,3]dioxol-4-yl)methyl benzoate (880 mg, 60% pure) in MeOH (15 mL) at 25° C. The mixture was stirred at 25° C. for 1 h, and then the reaction was quenched with AcOH (60 mg) and diluted with brine (10 mL). The mixture was extracted with EA (2×50 mL). The separated organic layers were combined and dried over anhydrous Na₂SO₄. The solids were removed by filtration, and the filtrate was concentrated under reduced pressure. The residue was purified by silica gel chromatography (PE:EA:EtOH=30:10:1) to afford ((3aS,4S,6R,6aS)-6-(4-chloro-7H-pyrrolo[2,3-d]pyrimidin-7-yl)-4-fluoro-2,2-dimethyltetrahydro-4H-cyclopenta[d][1,3]dioxol-4-yl)methanol (570 mg, 60% pure) as a white foam. LCMS: (ESI): m/z calcd. for $C_{15}H_{18}ClFN_3O_3$ 342.09 [M+H]⁺, found 342.1.

To a solution of ((3aS,4S,6R,6aS)-6-(4-chloro-7H-pyrrolo[2,3-d]pyrimidin-7-yl)-4-fluoro-2,2-dimethyltetrahydro-4H-cyclopenta[d][1,3]dioxol-4-yl)methanol (200 mg, 60% pure) in MeCN (5 mL) was added IBX (186.8 mg, 667.1 μmol). The mixture was stirred at 70° C. for 6 h. The mixture was cooled to rt and filtered. The filtrate was concentrated to afford (3aS,4R,6R,6aS)-6-(4-chloro-7H-pyrrolo[2,3-d]pyrimidin-7-yl)-4-fluoro-2,2-dimethyltetrahydro-4H-cyclopenta[d][1,3]dioxole-4-carbaldehyde (210 mg, 46% pure) as a white foam, which was used in the next step without further purification. LCMS: (ESI): m/z calcd. for $C_{15}H_{18}ClFN_3O_4$ 358.09 [M+H₃O]⁺, found 358.2.

A solution of tBuOK (123.1 mg, 1.10 mmol) in THF (2 mL) was added dropwise to a mixture of methyl(triphenyl)phosphonium bromide (420.0 mg, 1.18 mmol) in toluene (6 mL) at 25° C. The mixture was stirred at 25° C. for 1 h. (3aS,4R,6R,6aS)-6-(4-chloro-7H-pyrrolo[2,3-d]pyrimidin-7-yl)-4-fluoro-2,2-dimethyltetrahydro-4H-cyclopenta[d][1,3]dioxole-4-carbaldehyde (170 mg, 46% pure) in toluene (2 mL) was added dropwise at 0° C. After addition, the mixture was stirred at 25° C. for 16 h. NH₄Cl (aq., 5 mL) was added to quench the reaction. The mixture was extracted with EA (2×20 mL). The separated organic layers were combined, washed with brine (30 mL) and dried over anhydrous Na₂SO₄. The solids were removed by filtration, and the filtrate was concentrated under reduced pressure. The residue was purified by silica gel chromatography (PE:EA=100:0 to 85:15) to afford 4-chloro-7-((3aS,4R,6S,6aS)-6-fluoro-2,2-dimethyl-6-vinyltetrahydro-4H-cyclopenta[d][1,3]dioxol-4-yl)-7H-pyrrolo[2,3-d]pyrimidine (51 mg, 0.147 mmol) as a colorless gum. LCMS: (ESI): m/z calcd. for $C_{16}H_{18}ClFN_3O_2$ 338.10 [M+H]⁺, found 338.1.

A mixture of 4-chloro-7-((3aS,4R,6S,6aS)-6-fluoro-2,2-dimethyl-6-vinyltetrahydro-4H-cyclopenta[d][1,3]dioxol-4-yl)-7H-pyrrolo[2,3-d]pyrimidine (100 mg, 0.296 mmol) and NH₄OH (6.7 mL, aq., 25% wt) in dioxane (10 mL) was sealed in a tube and stirred at 100° C. for 36 h. The mixture was concentrated under reduced pressure, diluted with brine (10 mL) and then extracted with EA (2×20 mL). The separated organic layers were combined and dried over anhydrous Na₂SO₄. The solids were removed by filtration, and the filtrate was concentrated. The residue was purified by silica gel chromatography (PE:EA=3:1, 160 mL; then DCM:MeOH=20:1, 300 mL) to afford 7-((3aS,4R,6S,6aS)-6-fluoro-2,2-dimethyl-6-vinyltetrahydro-4H-cyclopenta[d][1,3]dioxol-4-yl)-7H-pyrrolo[2,3-d]pyrimidin-4-amine (68 mg, 0.207 mmol, 70%) as a white solid. LCMS: (ESI): m/z calcd. for $C_{16}H_{20}FN_4O_2$ 319.15 [M+H]⁺, found 319.3.

To a mixture of 7-((3aS,4R,6S,6aS)-6-fluoro-2,2-dimethyl-6-vinyltetrahydro-4H-cyclopenta[d][1,3]dioxol-4-yl)-7H-pyrrolo[2,3-d]pyrimidin-4-amine (62 mg, 195 μmol) in THF (3 mL) was added 9-BBN dimer (122.7 mg, 0.507 mmol). The mixture was stirred at 50° C. for 1 h and cooled to 20° C. A solution of K₃PO₄ (206.7 mg, 0.974 mmol) in H₂O (0.3 mL) was added. The mixture was stirred at 20° C. for 0.5 h, and then 7-bromoquinolin-2-amine (Q5) (60.8 mg, 273 μmol) and Pd(dppf)Cl₂ (14.2 mg, 0.019 mmol) were added. The mixture was stirred at 65° C. for 19 h. The mixture was diluted with brine (20 mL) and extracted with EA (6×30 mL). The separated organic layers were combined and dried over anhydrous Na₂SO₄. The solids were removed by filtration, and the filtrate was concentrated. The residue was purified by prep-HPLC (column: C18; mobile phase: [water (0.05% NH₃H₂O)-ACN]; B %: 5%-60%, 15 min) to afford 7-(2-((3aS,4R,6R,6aS)-6-(4-amino-7H-pyrrolo[2,3-d]pyrimidin-7-yl)-4-fluoro-2,2-dimethyltetrahydro-4H-cyclopenta[d][1,3]dioxol-4-yl)ethyl)quinolin-2-amine (35 mg, 0.053 mmol, 27% yield, 70% purity) as white solid. LCMS: (ESI): m/z calcd. for $C_{25}H_{28}FN_6O_2$ 463.22 [M+H]⁺, found 463.4.

To a solution of 7-(2-((3aS,4R,6R,6aS)-6-(4-amino-7H-pyrrolo[2,3-d]pyrimidin-7-yl)-4-fluoro-2,2-dimethyltetrahydro-4H-cyclopenta[d][1,3]dioxol-4-yl)ethyl)quinolin-2-amine (32.2 mg, 69.5% purity, 48.39 μmol) in THF (4.6 mL) was added HCl (4 M, 2.30 mL) at 25° C. The mixture was stirred at 25° C. for 16 h. The mixture was concentrated under reduced pressure. The residue was purified by pre-HPLC (column: Phenomenex Gemini-NX 150×30 mm×5 μm; mobile phase: [water (0.05% HCl)-ACN]; B %: 3%-30%, 7 min) to afford (1S,2S,3R,5R)-5-(4-amino-7H-pyrrolo[2,3-d]pyrimidin-7-yl)-3-(2-(2-aminoquinolin-7-yl)ethyl)-3-fluorocyclopentane-1,2-diol (35) as a hydrochloride salt (light yellow solid, 14 mg, 0.028 mmol, 58%). LCMS: (ESI): m/z calcd. for $C_{22}H_{24}FN_6O_2$ 423.19 [M+H]⁺, found 423.2. ¹H NMR (400 MHz, CD₃OD) δ: 8.31 (d, J=9.3 Hz, 1H), 8.26 (s, 1H), 7.83 (d, J=8.2 Hz, 1H), 7.58 (d, J=3.7 Hz, 1H), 7.55 (s, 1H), 7.47 (dd, J=1.4, 8.2 Hz, 1H), 7.01 (d, J=9.3 Hz, 1H), 6.93 (d, J=3.7 Hz, 1H), 5.20 (ddd, J=6.1, 8.6, 11.0 Hz, 1H), 4.47 (t, J=6.6 Hz, 1H), 4.29-4.17 (m, 1H), 3.17-2.95 (m, 2H), 2.67-2.52 (m, 1H), 2.46-2.10 (m, 3H). $^{19}$F NMR (376 MHz, CDCl$_3$) δ: 169.91.

Example 32

Compound 36

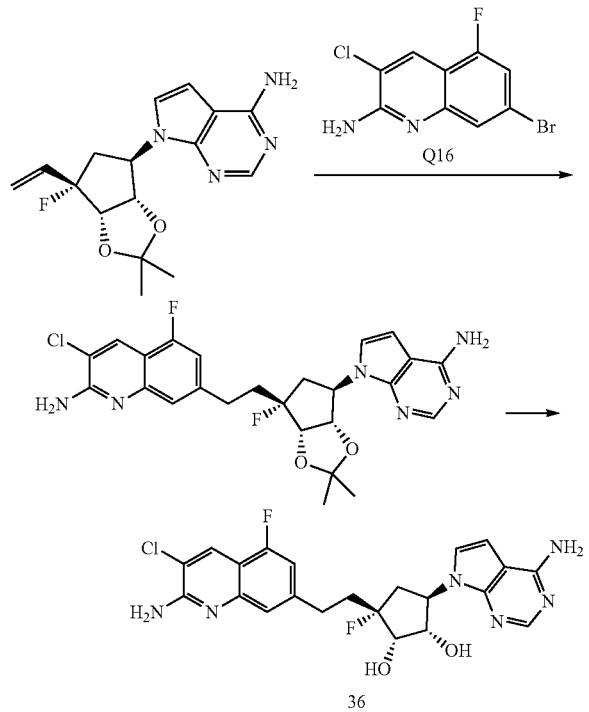

A mixture of 7-((3aS,4R,6S,6aS)-6-fluoro-2,2-dimethyl-6-vinyltetrahydro-4H-cyclopenta[d][1,3]dioxol-4-yl)-7H-pyrrolo[2,3-d]pyrimidin-4-amine (100 mg, 0.307 mmol) and 9-BBN dimer (185.8 mg, 767.88 μmol) in THF (5 mL) was stirred at 50° C. for 1.5 h under Ar and then cooled to 20° C. A solution of K$_3$PO$_4$ (326.0 mg, 1.54 mmol) in H$_2$O (1 mL) was added. The mixture was stirred at 20° C. for 0.5 h. 7-bromo-3-chloro-5-fluoro-quinolin-2-amine (Q16) (101.6 mg, 0.369 mmol) and Pd(dppf)Cl$_2$ (22.5 mg, 30.72 μmol) were added. The mixture was stirred at 60° C. for 12 h under Ar. The mixture was partitioned between EA (10 mL) and water (10 mL). The organic phase was separated, and the aqueous phase washed with EA (3×10 mL). The organic layers were combined, washed with brine (10 mL), dried over Na$_2$SO$_4$, filtered and concentrated under reduced pressure. The residue was purified by silica column chromatography (PE:EA=1:1 then DCM:MeOH=20:1) to afford 7-(2-((3aS,4R,6R,6aS)-6-(4-amino-7H-pyrrolo[2,3-d]pyrimidin-7-yl)-4-fluoro-2,2-dimethyltetrahydro-4H-cyclopenta[d][1,3]dioxol-4-yl)ethyl)-3-chloro-5-fluoroquinolin-2-amine (134 mg, 0.234 mmol, 76%, 90% purity) as yellow gum. LCMS: (ESI): m/z calcd. for C$_{25}$H$_{26}$ClF$_2$N$_6$O$_2$ 515.17 [M+H]$^+$, found 515.3.

To a solution of 7-(2-((3aS,4R,6R,6aS)-6-(4-amino-7H-pyrrolo[2,3-d]pyrimidin-7-yl)-4-fluoro-2,2-dimethyltetrahydro-4H-cyclopenta[d][1,3]dioxol-4-yl)ethyl)-3-chloro-5-fluoroquinolin-2-amine (134 mg, 90% purity, 0.235 mmol) in THF (4 mL) was added HCl (4 M, 2 mL). The mixture was stirred at 25° C. for 12 h. The mixture was concentrated under reduced pressure. The residue was purified by prep-HPLC (Venusil ASB Phenyl 150×30 mm×5 μm; mobile phase: [water (0.05% HCl)-ACN]; B %: 10%-40%, 9 min) to afford (1S,2S,3R,5R)-3-(2-(2-amino-3-chloro-5-fluoroquinolin-7-yl)ethyl)-5-(4-amino-7H-pyrrolo[2,3-d]pyrimidin-7-yl)-3-fluorocyclopentane-1,2-diol (36) as a hydrochloride salt (off-white solid, 75 mg, 0.135 mmol, 62%). LCMS: (ESI): m/z calcd. for C$_{22}$H$_{22}$ClF$_2$N$_6$O$_2$ 475.14 [M+H]$^+$, found 475.1. $^1$H NMR (400 MHz, CD$_3$OD) δ: 8.69 (s, 1H), 8.27 (s, 1H), 7.59 (d, J=3.5 Hz, 1H), 7.46 (s, 1H), 7.31 (d, J=9.7 Hz, 1H), 6.93 (d, J=3.7 Hz, 1H), 5.19 (ddd, J=10.9, 8.4, 6.1 Hz, 1H), 4.47 (t, J=6.5 Hz, 1H), 4.18-4.29 (m, 1H), 2.97-3.16 (m, 2H), 2.59 (td, J=14.9, 8.6 Hz, 1H), 2.09-2.46 (m, 3H). $^{19}$F NMR (376 MHz, CD$_3$OD) δ: −121.36 (brd, J=10.3 Hz, 1 F), −172.93--167.03 (m, 1 F).

Example 33

Compound 37

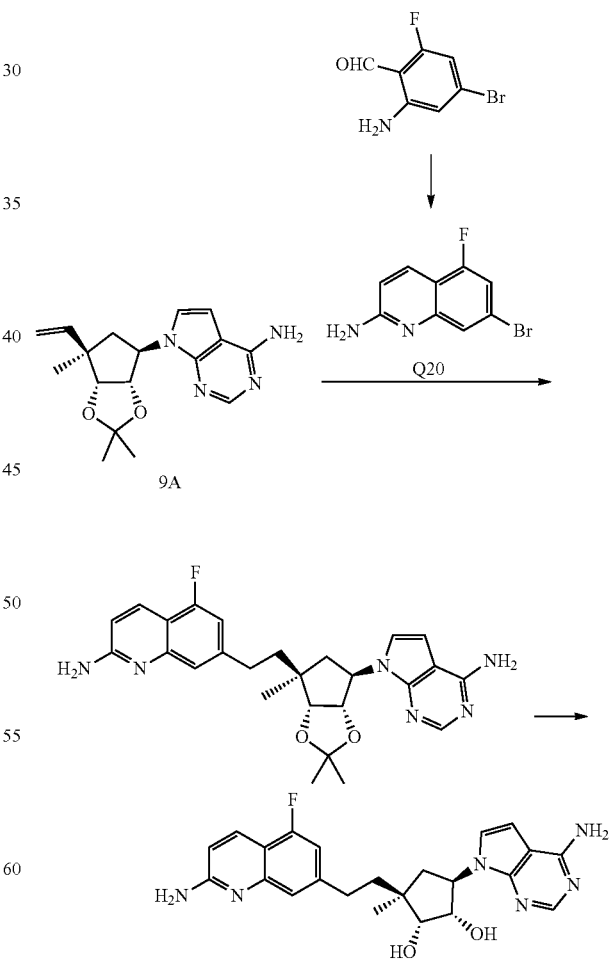

To a solution of 2-amino-4-bromo-6-fluoro-benzaldehyde (1 g, 4.59 mmol) and acetonitrile (376.58 mg, 9.17 mmol, 0.483 mL) in DMSO (20 mL) was added t-BuOK (1.03 g, 9.17 mmol) at 0° C. The mixture was stirred at rt for 15 min. The mixture was partitioned between EA (30 mL) and water (30 mL). The organic phase was separated, and the aqueous phase extracted with EA (30 mL). The organic layers were combined, washed with brine (50 mL) and dried over $Na_2SO_4$. The solids were removed by filtration, and the filtrate was concentrated under reduced pressure. The residue was purified by silica gel chromatography (0%~35% PE/EA gradient) to afford 7-bromo-5-fluoroquinolin-2-amine (Q20) (715 mg, 2.97 mmol, 64%) as a yellow solid. LCMS: (ESI): m/z calcd. for $C_9H_7BrFN_2$ 242.97 $[M+H]^+$, found 242.8.

A mixture of 7-((3aS,4R,6R,6aR)-2,2,6-trimethyl-6-vinyltetrahydro-4H-cyclopenta[d][1,3]dioxol-4-yl)-7H-pyrrolo[2,3-d]pyrimidin-4-amine (9A) (100 mg, 0.318 mmol) and 9-BBN dimer (192.45 mg, 0.795 mmol) in THF (3 mL) was stirred at 50° C. for 2 h under $N_2$ and then cooled to 20° C. A solution of $K_3PO_4$ (337.59 mg, 1.59 mmol) in water (0.4 mL) was added. The mixture was stirred at 20° C. for 0.5 h. Compound Q20 (92.01 mg, 0.382 mmol) and Pd(dppf)$Cl_2$ (23.27 mg, 0.032 mmol) were added. The mixture was stirred at 60° C. for 12 h under Ar. The mixture was partitioned between EA (10 mL) and water (5 mL). The organic phase was separated, and the aqueous phase washed with EA (10 mL). The organic layers were combined, washed with brine (5 mL), dried over $Na_2SO_4$, filtered and concentrated under reduced pressure. The residue was purified by silica column chromatography (PE:EA=2:1 to 1:1 then DCM:MeOH=50:1 to 10:1) to afford 7-(2-((3aR,4S,6R,6aS)-6-(4-amino-7H-pyrrolo[2,3-d]pyrimidin-7-yl)-2,2,4-trimethyltetrahydro-4H-cyclopenta[d][1,3]dioxol-4-yl)ethyl)-5-fluoroquinolin-2-amine (149 mg, 0.300 mmol, 94% yield, 96% purity) as a white solid. LCMS: (ESI): m/z calcd. for $C_{26}H_{30}FN_6O_2$ 477.23 $[M+H]^+$, found 477.2.

To a solution of 7-(2-((3aR,4S,6R,6aS)-6-(4-amino-7H-pyrrolo[2,3-d]pyrimidin-7-yl)-2,2,4-trimethyltetrahydro-4H-cyclopenta[d][1,3]dioxol-4-yl)ethyl)-5-fluoroquinolin-2-amine (149 mg, 0.300 mmol) in THF (4 mL) was added HCl (4 M, 2 mL). The mixture was stirred at rt for 12 h. The mixture was concentrated under reduced pressure. The residue was triturated with $CH_3CN:H_2O$ (10:1, 20 mL) at rt for 30 min. The crude product was purified by prep-HPLC (column: Phenomenex Gemini-NX 80×40 mm×3 μm; mobile phase: [water (0.05% $NH_3$ in $H_2O$+10 mM $NH_4HCO_3$)-ACN]; B %: 20%-50%, 8 min) to afford (1S,2R,3S,5R)-3-(2-(2-amino-5-fluoroquinolin-7-yl)ethyl)-5-(4-amino-7H-pyrrolo[2,3-d]pyrimidin-7-yl)-3-methylcyclopentane-1,2-diol (37) (73 mg, 0.167 mmol, 56%) as a white solid. LCMS: (ESI): m/z calcd. for $C_{23}H_{26}FN_6O_2$ 437.20 $[M+H]^+$, found 437.2. $^1$H NMR (400 MHz, $CD_3OD$-$d_4$) δ: 8.08 (s, 1H), 8.06 (d, J=9.7 Hz, 1H), 7.24 (s, 1H), 7.19 (s, 1H), 6.87 (d, J=11.0 Hz, 1H), 6.81 (d, J=9.1 Hz, 1H), 6.60 (d, J=3.6 Hz, 1H), 5.05-4.97 (m, 1H), 4.53 (t, J=6.9 Hz, 1H), 3.93 (d, J=6.4 Hz, 1H), 2.88-2.70 (m, 2H), 2.11-2.03 (m, 1H), 1.96 (d, J=10.7 Hz, 1H), 1.93-1.80 (m, 2H), 1.23 (s, 3H). $^{19}$F NMR (376 MHz, $CD_3OD$-$d_4$) δ: -126.40 (1 F).

Example 34

Compound 38

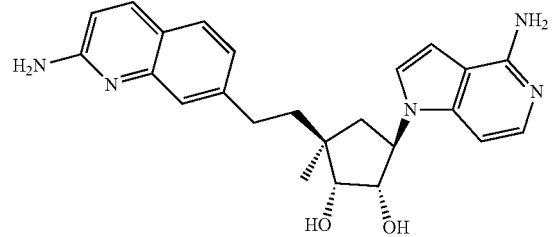 [SMILES: C[C@]1(CCc2ccc3ccc(N)nc3c2)C[C@@H](n2ccc3c(N)nccc32)[C@H](O)[C@@H]1O]

To a solution of 4-chloro-1H-pyrrolo[3,2-c]pyridine (554.30 mg, 3.63 mmol) in DMF (15 mL) was added f-BuOK (380.47 mg, 3.39 mmol). The mixture was stirred at 25° C. for 0.5 h followed by the addition of (3aR,4S,6R,6aR)-2,2,6-trimethyl-6-vinyltetrahydro-4H-cyclopenta[d][1,3]dioxol-4-yl trifluoromethanesulfonate (0.8 g, 2.42 mmol). The mixture was stirred at 25° C. for 12 h. The reaction progress was monitored by TLC (PE:EA=10:1). Upon completion, the mixture was diluted with water (30 mL) and then extracted with EA (2×30 mL). The separated organic layers were combined, washed with brine (60 mL), dried over anhydrous $Na_2SO_4$, and concentrated to afford a residue. The residue was purified by flash silica gel chromatography (eluent of 0~4% Methanol/DCM gradient) to afford 4-chloro-1-((3aS,4R,6R,6aR)-2,2,6-trimethyl-6-vinyltetrahydro-4H-cyclopenta[d][1,3]dioxol-4-yl)-1H-pyrrolo[3,2-c]pyridine (0.29 g, 0.871 mmol, 36%) as white solid. LCMS: (ESI): RT=3.328 min, m/z calcd. for $C_{18}H_{22}N_2O_2Cl$ 333.13, $[M+H]^+$, found 333.1.

To a solution of 4-chloro-1-((3aS,4R,6R,6aR)-2,2,6-trimethyl-6-vinyltetrahydro-4H-cyclopenta[d][1,3]dioxol-4-yl)-1H-pyrrolo[3,2-c]pyridine (0.29 g, 0.871 mmol) and diphenylmethanimine (236.87 mg, 1.31 mmol, 0.219 mL) in toluene (8 mL) were added BINAP (108.51 mg, 0.174 mmol), $Pd_2(dba)_3$ (79.79 mg, 0.087 mmol) and t-BuONa (167.48 mg, 1.74 mmol). The mixture was stirred at 110° C. for 18 h under $N_2$. The reaction was quenched with $NH_4Cl$ (sat., aq., 10 mL). The mixture was extracted with EA (3×10 mL). The separated organic layers were combined, washed with brine (30 mL), dried over anhydrous $Na_2SO_4$, filtered and concentrated to afford a crude inline intermediate. The crude intermediate was dissolved in MeOH (10 mL). Hydroxylamine (276.87 mg, 4.19 mmol, 50% wt in water) was added at 20° C. The mixture was stirred at 20° C. for 1 h. Upon completion of the reaction, the mixture was concentrated to dryness. The residue was purified by flash silica gel chromatography (eluent of 0~5% Methanol/DCM gradient) to afford 1-((3aS,4R,6R,6aR)-2,2,6-trimethyl-6-vinyltetrahydro-4H-cyclopenta[d][1,3]dioxol-4-yl)-1H-pyrrolo[3,2-c]pyridin-4-amine (0.19 g, 69% yield over 2 steps) as a yellow semi-solid. LCMS: (ESI): RT=2.062 min, m/z calcd. for $C_{18}H_{24}O_2N_3$ 314.18, $[M+H]^+$, found 314.1.

To a solution of 1-[(3aR,4R,6R,6aS)-2,2,4-trimethyl-4-vinyl-3a,5,6,6a-tetrahydrocyclopenta[d][1,3]dioxol-6-yl]pyrrolo[3,2-c]pyridin-4-amine (100 mg, 0.319 mmol) in THF (5 mL) was added 9-BBN dimer (115.84 mg, 0.479 mmol). The mixture was stirred at 50° C. for 1h and then cooled to 30° C. A solution of $K_3PO_4$ (338.66 mg, 1.60 mmol) in $H_2O$ (0.5 mL) was added. The mixture was stirred at 30° C. for 0.5 h, followed by addition of 7-bromoquinolin- 2-amine (Q5) (85.41 mg, 0.383 mmol) and Pd(dppf)Cl$_2$ (23.35 mg, 0.032 mmol). The mixture was degassed (3×) and stirred at 60° C. for 10.5 h. Upon completion, the reaction was quenched with brine (20 mL), and then extracted with EA (3×20 mL). The combined organic layers were washed with brine (60 mL) and dried over anhydrous Na$_2$SO$_4$. The solids were removed by filtration, and the filtrate was concentrated under reduced pressure. The residue was purified by prep-HPLC (column: Phenomenex Gemini-NX 80×40 mm×3 um; mobile phase: [water (0.05% NH3H$_2$O+10 mM NH$_4$HCO$_3$)-ACN]; B %: 17%-47%, 8 min) to afford 7-(2-((3aR,4S,6R,6aS)-6-(4-amino-1H-pyrrolo[3,2-c]pyridin-1-yl)-2,2,4-trimethyltetrahydro-4H-cyclopenta[d][1,3]dioxol-4-yl)ethyl)quinolin-2-amine (35 mg, 0.0744 mmol, 23%) as a brown semi-solid. LCMS: (ESI): RT=4.145 min, m/z calcd. for C$_{27}$H$_{32}$O$_2$N$_5$ 458.3, [M+H]$^+$, found 458.4.

To a solution of 7-[2-[(3aR,4S,6R,6aS)-6-(4-aminopyrrolo[3,2-c]pyridin-1-yl)-2,2,4-trimethyl-3a,5,6,6a-tetrahydrocyclopenta[d][1,3]dioxol-4-yl]ethyl]quinolin-2-amine (32 mg, 0.070 mmol) in THF (2 mL) was added HCl (4 M, 1 mL). The mixture was stirred at 20° C. for 4 h. Upon completion, the mixture was filtered and concentrated under reduced pressure to give a residue. The residue was purified by prep-HPLC (column: Phenomenex Gemini-NX 80×40 mm×3 um; mobile phase: [water (0.05% NH$_3$H$_2$O+10 mM NH$_4$HCO$_3$)-ACN]; B %: 19%-49%, 8 min) to afford (1S, 2R,3S,5R)-5-(4-amino-1H-pyrrolo[3,2-c]pyridin-1-yl)-3-(2-(2-aminoquinolin-7-yl)ethyl)-3-methylcyclopentane-1,2-diol (38) (14 mg, 0.0326 mmol, 45%) as a white solid. LCMS: (ESI): RT=2.561 min, m/z calcd. for C$_{24}$H$_{28}$O$_2$N$_5$ 418.22, [M+H]$^+$, found 418.3. $^1$H NMR (400 MHz, CD$_3$OD) δ: 7.88 (d, J=8.8 Hz, 1H), 7.59-7.50 (m, 2H), 7.38 (s, 1H), 7.35 (d, J=3.5 Hz, 1H), 7.14 (dd, J=1.5, 8.2 Hz, 1H), 6.95 (d, J=6.6 Hz, 1H), 6.78-6.72 (m, 2H), 4.82-4.76 (m, 1H), 4.39-4.33 (m, 1H), 3.90 (d, J=6.2 Hz, 1H), 2.91-2.71 (m, 2H), 2.12 (dd, J=8.7, 13.1 Hz, 1H), 1.97-1.77 (m, 3H), 1.25 (s, 3H).

Example 35

Compound 39

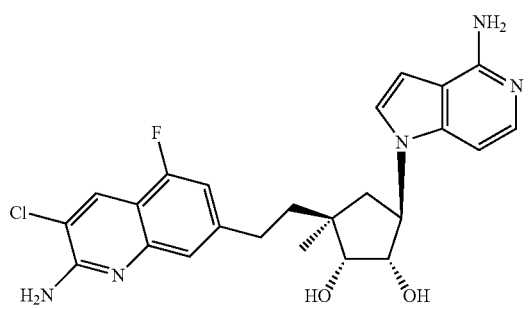 [SMILES: C[C@]1(CCc2cc(F)c3cc(Cl)c(N)nc3c2)C[C@@H](n2ccc3c(N)nccc32)[C@H](O)[C@@H]1O]

(1S,2R,3S,5R)-5-(4-amino-1H-pyrrolo[3,2-c]pyridin-1-yl)-3-(2-(2-amino-3-chloro-5-fluoroquinolin-7-yl)ethyl)-3-methylcyclopentane-1,2-diol was prepared similarly as described for (1S,2R,3S,5R)-5-(4-amino-1H-pyrrolo[3,2-c]pyridin-1-yl)-3-(2-(2-aminoquinolin-7-yl)ethyl)-3-methylcyclopentane-1,2-diol starting from (3aR,4S,6R,6aR)-2,2,6-trimethyl-6-vinyltetrahydro-4H-cyclopenta[d][1,3]dioxol-4-yl trifluoromethanesulfonate in a reaction with 7-bromo-3-chloro-5-fluoro-quinolin-2-amine (Q16). LCMS: (ESI): RT=2.905 min, m/z calcd. for C$_{24}$H$_{26}$O$_2$N$_5$ClF 470.17, [M+H]$^+$, found 470.2. $^1$H NMR (400 MHz, CD$_3$OD) δ=8.18 (s, 1H), 7.54 (d, J=6.2 Hz, 1H), 7.29 (d, J=3.3 Hz, 1H), 7.23 (s, 1H), 6.92 (dd, J=1.0, 10.9 Hz, 1H), 6.88 (d, J=6.3 Hz, 1H), 6.67 (d, J=3.2 Hz, 1H), 4.82-4.73 (m, 1H), 4.35 (t, J=6.9 Hz, 1H), 3.90 (d, J=6.3 Hz, 1H), 2.90-2.70 (m, 2H), 2.10 (dd, J=8.6, 13.1 Hz, 1H), 1.95-1.75 (m, 3H), 1.23 (s, 3H). $^{19}$F NMR (376 MHz, CD$_3$OD) δ: −125.76 (s, 1F).

Example 36

Compound 40

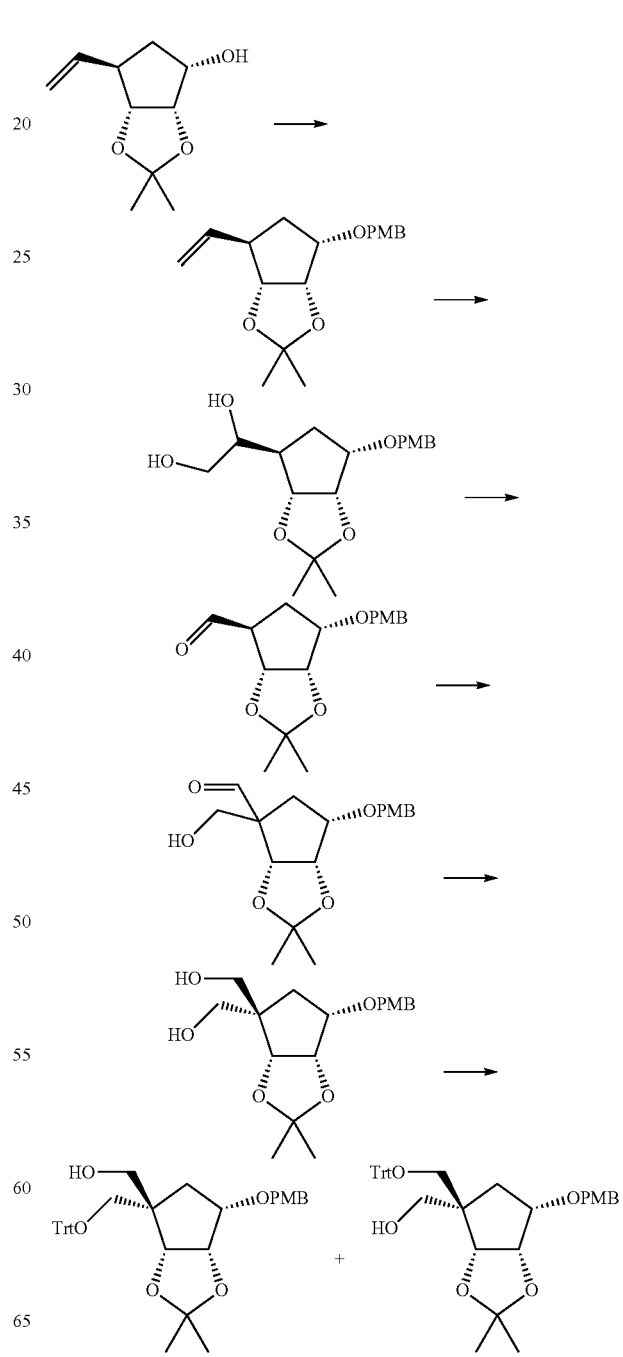

223

-continued

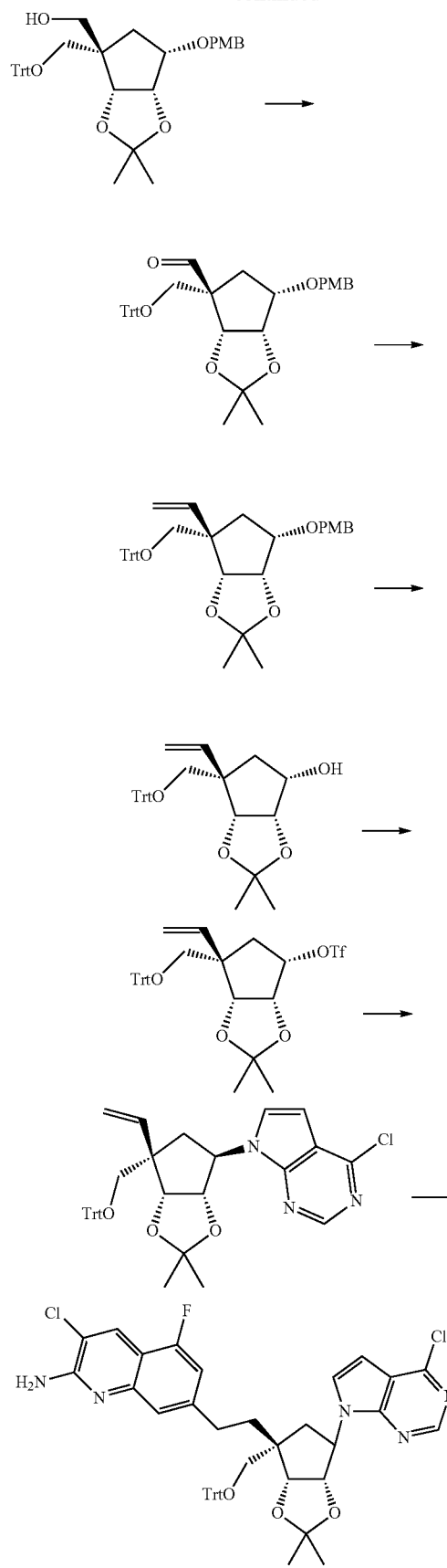

224

-continued

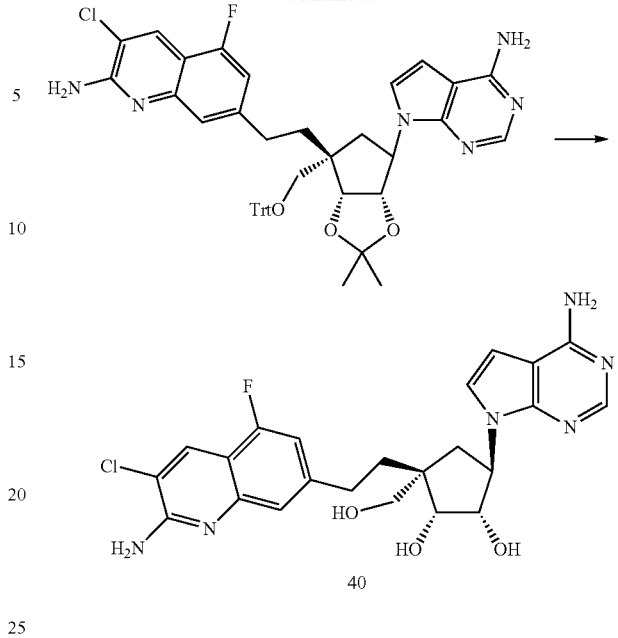

To a solution of (3aS,4S,6R,6aR)-2,2-dimethyl-6-vinyltetrahydro-3 aH-cyclopenta[d][1,3]dioxol-4-ol (7.4 g, 40.17 mmol, 1 eq.) in DMF (40 mL) was added NaH (3.21 g, 80.33 mmol, 60% purity, 2.0 eq.) at 0° C. After stirring at 0° C. for 0.5 h, PMB-Cl (11.32 g, 72.30 mmol, 9.85 mL, 1.8 eq.) was added, and the mixture was stirred at 25° C. for 2 h. The reaction progress was monitored by TLC (PE:EtOAc=5:1). Upon completion, the reaction was quenched by addition of NH$_4$Cl (40 mL), and then extracted with EtOAc (3×100 mL). The combined organic layers was washed with brine 300 mL (3×100 mL), dried over anhydrous Na$_2$SO$_4$, filtered and concentrated under reduced pressure to give a residue. The residue was purified by flash silica gel chromatography (ISCO®; 120 g SepaFlash® Silica Flash Column, Eluent of 0~10% EA/PE gradient @ 45 mL/min) to afford (3aS,4S,6R,6aR)-4-((4-methoxybenzyl)oxy)-2,2-dimethyl-6-vinyltetrahydro-3aH-cyclopenta[d][1,3]dioxole (7.6 g, 24.97 mmol) as a colorless oil.

To a solution of (3aS,4S,6R,6aR)-4-((4-methoxybenzyl)oxy)-2,2-dimethyl-6-vinyltetrahydro-3aH-cyclopenta[d][1,3]dioxole (22.26 g, 73.13 mmol, 1 eq.) in a mixed solvent of THF (150 mL) and H$_2$O (150 mL) were added K$_2$OsO$_4$ (2.09 g, 10.97 mmol, 0.15 eq.) and NMO (17.13 g, 146.26 mmol, 2.0 eq.). The mixture was stirred at 25° C. for 18 h. Upon completion, the reaction was quenched by the addition of sat. aq. Na$_2$S$_2$O$_3$ (100 mL), and then extracted with EtOAc (3×200 mL). The combined organic layers was washed with brine (300 mL), dried over anhydrous Na$_2$SO$_4$, filtered and concentrated under reduced pressure to give a residue. The residue was purified by column chromatography (SiO$_2$, DCM:MeOH=30:1 to 10:1) to afford 1-((3aR,4R,6S,6aS)-6-((4-methoxybenzyl)oxy)-2,2-dimethyltetrahydro-4H-cyclopenta[d][1,3]dioxol-4-yl)ethane-1,2-diol (24.3 g, 71.81 mmol, 98% yield) as a yellow oil. LCMS: (ESI): m/z calcd. for C$_{18}$H$_{26}$O$_6$Na, 361.17 [M+Na]$^+$, found 361.1.

To a mixture of 1-((3aR,4R,6S,6aS)-6-((4-methoxybenzyl)oxy)-2,2-dimethyltetrahydro-4H-cyclopenta[d][1,3]dioxol-4-yl)ethane-1,2-diol (24.3 g, 71.81 mmol, 1 eq.) in THF (50 mL) and H$_2$O (50 mL) was added NaIO$_4$ (15.36 g, 71.81 mmol, 3.98 mL, 1.0 eq.). The mixture was stirred at 25° C. for 1 h. Upon completion, the mixture was diluted by the addition water (50 mL), and then extracted with EtOAc (3×100 mL). The combined organic layers were washed with brine (100 mL), dried over anhydrous $Na_2SO_4$, filtered and concentrated under reduced pressure to give a residue. The residue was concentrated under reduced pressure to give (17.53 g, 57.22 mmol, crude) as a colorless oil. LCMS: (ESI): m/z calcd. for $C_{17}H_{24}O_6Na$, 347.2 $[M+H_2O+Na]^+$, found 347.0.

To a solution of (3aR,4S,6S,6aS)-6-((4-methoxybenzyl) oxy)-2,2-dimethyltetrahydro-3aH-cyclopenta[d][1,3]dioxole-4-carbaldehyde (17.53 g, 57.22 mmol, 1 eq.) in dioxane (20 mL) were added KOH (2 M, 57.22 mL, 2 eq.) and HCHO (37.15 g, 457.77 mmol, 34.08 mL, 37% aq solution, 8 eq.). The mixture was stirred at 25° C. for 2 h. The reaction was quenched with $H_2O$ (30 mL), and then extracted with EtOAc (3×100 mL). The combined organic layers was washed with brine (100 mL), dried over anhydrous $Na_2SO_4$, filtered and concentrated under reduced pressure to give crude (3aR,6S,6aS)-4-(hydroxymethyl)-6-((4-methoxybenzyl)oxy)-2,2-dimethyltetrahydro-4H-cyclopenta[d][1,3]dioxole-4-carbaldehyde.

To a solution of crude (3aR,6S,6aS)-4-(hydroxymethyl)-6-((4-methoxybenzyl)oxy)-2,2-dimethyltetrahydro-4H-cyclopenta[d][1,3]dioxole-4-carbaldehyde in MeOH (20 mL) was added $NaBH_4$ (6.49 g, 171.66 mmol, 3 eq.) at 0° C., and the mixture was stirred at 0° C. for 1 h. The reaction progress was monitored by TLC (PE:EtOAc=0:1). Upon completion, the reaction was quenched by sat. $NH_4Cl$ solution (30 mL), and then extracted with EtOAc (3×100 mL). The combined organic layers was washed with brine (100 mL), dried over anhydrous $Na_2SO_4$, filtered and concentrated under reduced pressure to give a residue. The residue was purified by flash silica gel chromatography (ISCO®; 120 g SepaFlash® Silica Flash Column, Eluent of 0~79% EA/PE ether gradient @ 45 mL/min) to afford ((3aR,6S,6aS)-6-((4-methoxybenzyl)oxy)-2,2-dimethyltetrahydro-3aH-cyclopenta[d][1,3]dioxole-4,4-diyl)dimethanol (16 g, 47.28 mmol, 83% yield) as a colorless oil. LCMS: (ESI): m/z calcd. for $C_{18}H_{26}O_6Na$, 361.17 $[M+Na]^+$, found 361.0.

To a mixture of ((3aR,6S,6aS)-6-((4-methoxybenzyl) oxy)-2,2-dimethyltetrahydro-3aH-cyclopenta[d][1,3]dioxole-4,4-diyl)dimethanol (16 g, 47.28 mmol, 1 eq.) in DCM (100 mL) were added TEA (47.84 g, 472.82 mmol, 65.81 mL, 10 eq.) and TrtCl (15.82 g, 56.74 mmol, 1.2 eq.) at 0° C. The mixture was stirred at 25° C. for 12 h. The reaction progress was monitored by TLC (PE:EtOAc=0:1 and then toluene:EA=5:1). Upon completion, the reaction was quenched by the addition of HCl (4 M, 15 mL), and then extracted with EtOAc (3×200 mL). The combined organic layers were washed with brine (200 mL), dried over anhydrous $Na_2SO_4$, filtered and concentrated under reduced pressure to give a residue. The residue was purified by silica gel flash chromatography (ISCO®; 220 g SepaFlash® Silica Flash Column, Eluent of 0-20% EA/PE gradient @ 65 mL/min), followed by re-purification by silica gel flash chromatography (ISCO®; 120 g SepaFlash® Silica Flash Column, Eluent of 0-7% EA/toluene ether gradient @ 45 mL/min) to afford ((3aR,4R,6S,6aS)-6-((4-methoxybenzyl) oxy)-2,2-dimethyl-4-((trityloxy)methyl)tetrahydro-4H-cyclopenta[d][1,3]dioxol-4-yl)methanol (12.59 g, 21.68 mmol, 46% yield) and ((3aR,4S,6S,6aS)-6-((4-methoxybenzyl) oxy)-2,2-dimethyl-4-((trityloxy)methyl)tetrahydro-4H-cyclopenta[d][1,3]dioxol-4-yl)methanol (2.65 g, 4.56 mmol, 10% yield). ((3aR,4R,6S,6aS)-6-((4-methoxybenzyl)oxy)-2, 2-dimethyl-4-((trityloxy)methyl)tetrahydro-4H-cyclopenta [d][1,3]dioxol-4-yl)methanol: LCMS: (ESI): m/z calcd. for $C_{37}H_{40}O_6Na$, 603.28 $[M+Na]^+$, found 603.3.

To a mixture of ((3aR,4R,6S,6aS)-6-((4-methoxybenzyl) oxy)-2,2-dimethyl-4-((trityloxy)methyl)tetrahydro-4H-cyclopenta[d][1,3]dioxol-4-yl)methanol (6.89 g, 11.86 mmol, 1 eq.) in EtOAc (60 mL) was added IBX (4.98 g, 17.80 mmol, 1.5 eq.). The mixture was stirred at 60° C. for 12 h. The reaction progress was monitored by TLC (toluene: EA=3:1). Upon completion, the mixture was filtered and concentrated under reduced pressure to afford (3aR,4R,6S, 6aS)-6-((4-methoxybenzyl)oxy)-2,2-dimethyl-4-((trityloxy) methyl)tetrahydro-3aH-cyclopenta[d][1,3]dioxole-4-carbaldehyde (7.18 g, crude) as a colorless oil. The crude was used for the next step without further purification.

To a mixture of methyl triphenyl phosphonium bromide (24.27 g, 67.95 mmol, 5.5 eq.) and THF (200 mL) was added t-BuOK (6.93 g, 61.78 mmol, 5 eq.) at 0° C. The mixture was stirred at 0° C. for 0.5 h and then (3aR,4R,6S,6aS)-6-((4-methoxybenzyl)oxy)-2,2-dimethyl-4-((trityloxy) methyl)tetrahydro-3aH-cyclopenta[d][1,3]dioxole-4-carbaldehyde (7.15 g, 12.36 mmol, 1 eq.) was added. The mixture was stirred at 25° C. for 1 h. The reaction progress was monitored by TLC (PE:EtOAc=5:1). Upon completion, the reaction was quenched by the addition of sat. $NH_4Cl$ solution (20 mL), and then extracted with EtOAc (3×100 mL). The combined organic layers were washed with brine (3×100 mL), dried over anhydrous $Na_2SO_4$, filtered and concentrated under reduced pressure to give a residue. The residue was purified by flash silica gel chromatography (ISCO®; 80 g SepaFlash® Silica Flash Column, Eluent of 0-10% EA/PE gradient @ 45 mL/min) to afford (3aR,4R, 6S,6aS)-6-((4-methoxybenzyl)oxy)-2,2-dimethyl-4-((trityloxy)methyl)-4-vinyltetrahydro-3aH-cyclopenta[d][1,3]dioxole (5.54 g, 9.61 mmol, 78% yield) as a colorless oil.

To a mixture of (3aR,4R,6S,6aS)-6-((4-methoxybenzyl) oxy)-2,2-dimethyl-4-((trityloxy)methyl)-4-vinyltetrahydro-3aH-cyclopenta[d][1,3]dioxole (5.54 g, 9.61 mmol, 1 eq.) in a mixed solvent of PBS buffer (pH=7.4, 10 mL) and DCM (10 mL) was added DDQ (6.54 g, 28.82 mmol, 3 eq.). The mixture was stirred at 25° C. for 2 h. The reaction progress was monitored by TLC (PE:EtOAc=5:1). Upon completion, the reaction was quenched by addition of water (20 mL), and then extracted with EtOAc (3×100 mL). The combined organic layers was washed with brine (3×100 mL), dried over anhydrous $Na_2SO_4$, filtered and concentrated under reduced pressure to give a residue. The residue was purified by flash silica gel chromatography (ISCO®; 80 g SepaFlash® Silica Flash Column, Eluent of 0-25% EA/PE gradient @ 45 mL/min) to afford (3aS,4S,6R,6aR)-2,2-dimethyl-6-((trityloxy)methyl)-6-vinyltetrahydro-3aH-cyclopenta[d][1,3]dioxol-4-ol (3.97 g, 7.65 mmol, 80% yield, 88% purity) as a colorless oil.

To a solution of (3aS,4S,6R,6aR)-2,2-dimethyl-6-((trityloxy)methyl)-6-vinyltetrahydro-3aH-cyclopenta[d][1,3]dioxol-4-ol (1.95 g, 4.34 mmol, 1 eq.) in DCM (20 mL) and pyridine (1.37 g, 17.35 mmol, 1.40 mL, 4 eq.) was added dropwise $Tf_2O$ (1.84 g, 6.51 mmol, 1.07 mL, 1.5 eq.) at 0° C. The mixture was stirred at 0° C. for 1 h. The reaction progress was monitored by TLC (PE:EtOAc=5:1). Upon completion, the reaction was quenched by the addition of ice water (20 mL), and then extracted with DCM (3×50 mL). The combined organic layers were washed with brine (150 mL), dried over anhydrous $Na_2SO_4$, filtered and concentrated under reduced pressure to give a residue. The residue was concentrated under reduced pressure to afford (3aR,4S, 6R,6aR)-2,2-dimethyl-6-((trityloxy)methyl)-6-vinyltetrahydro-3aH-cyclopenta[d][1,3]dioxol-4-yl trifluoromethanesulfonate (2.43 g, crude) as a colorless oil.

To a solution of (3aR,4S,6R,6aR)-2,2-dimethyl-6-((trityloxy)methyl)-6-vinyltetrahydro-3aH-cyclopenta[d][1,3]dioxol-4-yl trifluoromethanesulfonate (4.2 g, 7.14 mmol, 1 eq.) in DMF (50 mL) was added the potassium salt of 4-chloro-7H-pyrrolo[2,3-d]pyrimidine (7-a) (2.05 g, 10.70 mmol, 1.5 eq.). The mixture was stirred at 25° C. for 12 h. Upon completion, the mixture was diluted with H$_2$O (50 mL) and extracted with EtOAc (3×50 mL). The combined organic layers was washed with brine (150 mL), dried over Na$_2$SO$_4$, filtered and concentrated under reduced pressure to give a residue. The residue was purified by flash silica gel chromatography (ISCO®; 40 g SepaFlash® Silica Flash Column, Eluent of 0~10% EA/PE gradient @ 35 mL/min) to afford 4-chloro-7-((3aS,4R,6R,6aR)-2,2-dimethyl-6-((trityloxy)methyl)-6-vinyltetrahydro-3aH-cyclopenta[d][1,3]dioxol-4-yl)-7H-pyrrolo[2,3-d]pyrimidine (1.98 g, 3.01 mmol, 44% yield, 90% purity) as a white solid. LCMS: (ESI): m/z calcd. for C$_{36}$H$_{35}$ClN$_3$O$_3$, 592.23 [M+H]$^+$, found 592.2.

To a solution of 4-chloro-7-((3aS,4R,6R,6aR)-2,2-dimethyl-6-((trityloxy)methyl)-6-vinyltetrahydro-3aH-cyclopenta[d][1,3]dioxol-4-yl)-7H-pyrrolo[2,3-d]pyrimidine (500 mg, 0.844 mmol, 1 eq.) in THF (10 mL) was added 9-BBN dimer (226.67 mg, 1.86 mmol, 2.2 eq.). The mixture was stirred at 50° C. for 2 h under AT, and then cooled to 25° C. A solution of K$_3$PO$_4$ (896.20 mg, 4.22 mmol, 5 eq.) in H$_2$O (1 mL) was added, and the mixture was stirred for 0.5 h. 7-bromo-3-chloro-5-fluoro-quinolin-2-amine (Q16) (302.43 mg, 1.10 mmol, 1.3 eq.) and Pd(dppf)Cl$_2$ (61.79 mg, 84.44 µmol, 0.1 eq.) were added, and the mixture was stirred at 60° C. for 12 h. The reaction progress was monitored by TLC (DCM:MeOH=10:1). Upon completion, the reaction was quenched by addition of water (20 mL), and then extracted with EtOAc (3×30 mL). The combined organic layers were washed with brine (60 mL), dried over anhydrous Na$_2$SO$_4$, filtered and concentrated under reduced pressure to give a residue. The residue was purified by flash silica gel chromatography (ISCO®; 24 g SepaFlash® Silica Flash Column, Eluent of 0~48% EA/PE gradient @ 35 mL/min) to afford 3-chloro-7-(2-((3aR,4S,6R,6aS)-6-(4-chloro-7H-pyrrolo[2,3-d]pyrimidin-7-yl)-2,2-dimethyl-4-((trityloxy)methyl)tetrahydro-3aH-cyclopenta[d][1,3]dioxol-4-yl)ethyl)-5-fluoroquinolin-2-amine (349 mg, 0.450 mmol, 50% yield) as a yellow solid. LCMS: m/z calcd. for C$_{45}$H$_{41}$Cl$_2$FN$_5$O$_3$, 788.3 [M+H]$^+$, found 788.3.

To a solution of 3-chloro-7-(2-((3aR,4S,6R,6aS)-6-(4-chloro-7H-pyrrolo[2,3-d]pyrimidin-7-yl)-2,2-dimethyl-4-((trityloxy)methyl)tetrahydro-3aH-cyclopenta[d][1,3]dioxol-4-yl)ethyl)-5-fluoroquinolin-2-amine (340 mg, 0.431 mmol, 1 eq.) in dioxane (4 mL) was added NH$_3$.H$_2$O (3.64 g, 29.08 mmol, 4 mL, 28% purity, 67.46 eq.). The mixture was stirred at 110° C. for 12 h in a 30 mL sealed tube. The reaction progress was monitored by TLC (DCM:MeOH=10:1). Upon completion, the residue was diluted with NH$_4$Cl (10 mL) and extracted with EtOAc (3×50 mL). The combined organic layers were washed with brine (50 mL), dried over anhydrous Na$_2$SO$_4$, filtered and concentrated under reduced pressure to give a residue. The residue was purified by flash silica gel chromatography (ISCO®; 24 g SepaFlash® Silica Flash Column, Eluent of 0~4% MeOH/DCM @ 35 mL/min) to afford 7-(2-((3aR,4S,6R,6aS)-6-(4-amino-7H-pyrrolo[2,3-d]pyrimidin-7-yl)-2,2-dimethyl-4-((trityloxy)methyl)tetrahydro-3aH-cyclopenta[d][1,3]dioxol-4-yl)ethyl)-3-chloro-5-fluoroquinolin-2-amine (200 mg, 0.247 µmol, 57% yield, 95% purity) as a white solid. LCMS: (ESI): m/z calcd. for C$_{45}$H$_{43}$ClFN$_6$O$_3$, 769.3 [M+H]$^+$, found 769.3.

A solution of 7-(2-((3aR,4S,6R,6aS)-6-(4-amino-7H-pyrrolo[2,3-d]pyrimidin-7-yl)-2,2-dimethyl-4-((trityloxy)methyl)tetrahydro-3aH-cyclopenta[d][1,3]dioxol-4-yl)ethyl)-3-chloro-5-fluoroquinolin-2-amine (200 mg, 259.98 µmol, 1 eq.) in HCl (4M, aq., 1 mL) and THF (2 mL) was stirred at 25° C. for 12 h. The reaction progress was monitored by TLC (DCM:MeOH=10:1). Upon completion, the mixture was concentrated under reduced pressure to give a residue. The residue was purified by prep-HPLC (column: Phenomenex Gemini-NX 80*40 mm*3 um; mobile phase: [water (0.05% NH$_3$H$_2$O+10 mM NH$_4$HCO$_3$)-ACN]; B %: 21%-45%, 8 min) to afford (1S,2R,3S,5R)-3-(2-(2-amino-3-chloro-5-fluoroquinolin-7-yl)ethyl)-5-(4-amino-7H-pyrrolo[2,3-d]pyrimidin-7-yl)-3-(hydroxymethyl)cyclopentane-1,2-diol (40) (75 mg, 154.03 µmol, 59% yield, 100% purity) as a white solid. LCMS: (ESI): m/z calcd. for C$_{23}$H$_{25}$ClFN$_6$O$_3$ 487.16. [M+H]$^+$, found 487.3. $^1$H NMR (400 MHz, CD$_3$OD) δ: 8.19 (s, 1H), 8.13-8.00 (m, 1H), 7.28 (s, 1H), 7.24 (d, J=3.5 Hz, 1H), 6.97 (hr d, J=10.6 Hz, 1H), 6.59 (d, J=3.5 Hz, 1H), 5.06-4.99 (m, 1H), 4.67-4.62 (m, 1H), 4.03 (d, J=5.5 Hz, 1H), 3.86 (br d, J=11.2 Hz, 1H), 3.74 (br d, J=11.2 Hz, 1H), 2.87 (dt, J=5.4, 12.6 Hz, 1H), 2.81-2.66 (m, 1H), 2.17 (br dd, J=9.2, 13.3 Hz, 1H), 2.07-1.83 (m, 3H). $^{19}$F NMR (376 MHz, CD$_3$OD) δ: −125.85 (s, 1F).

Example 37

Compound 41

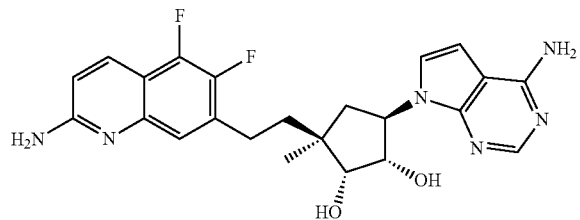 [SMILES: C[C@]1(CCc2cc3nc(N)ccc3c(F)c2F)C[C@@H](n2ccc3c(N)ncnc32)[C@H](O)[C@@H]1O]

(1S,2R,3S,5R)-3-(2-(2-amino-5,6-difluoroquinolin-7-yl)ethyl)-5-(4-amino-7H-pyrrolo[2,3-d]pyrimidin-7-yl)-3-methylcyclopentane-1,2-diol (41) was obtained as a hydrochloride salt and was prepared similarly as described for (1S,2R,3S,5R)-3-(2-(2-amino-5-fluoroquinolin-7-yl)ethyl)-5-(4-amino-7H-pyrrolo[2,3-d]pyrimidin-7-yl)-3-methylcyclopentane-1,2-diol starting from 7-((3aS,4R,6R,6aR)-2,2,6-trimethyl-6-vinyltetrahydro-4H-cyclopenta[d][1,3]dioxol-4-yl)-7H-pyrrolo[2,3-d]pyrimidin-4-amine (9A) in a reaction with 7-bromo-5,6-difluoro-quinolin-2-amine (Q21). LCMS: (ESI): m/z calcd. for C$_{23}$H$_{25}$F$_2$N$_6$O$_2$ 455.19 [M+H]$^+$, found 455.2. $^1$H NMR (400 MHz, CD$_3$OD) δ: 8.45 (d, J=9.5 Hz, 1H), 8.25 (s, 1H), 7.58 (d, J=3.7 Hz, 1H), 7.43 (br d, J=4.4 Hz, 1H), 7.13 (d, J=9.5 Hz, 1H), 6.92 (d, J=3.7 Hz, 1H), 5.06-5.20 (m, 1H), 4.55 (t, J=6.9 Hz, 1H), 3.97 (d, J=6.4 Hz, 1H), 2.85-3.09 (m, 2H), 1.97-2.16 (m, 2H), 1.81-1.96 (m, 2H), 1.26 (s, 3H). $^{19}$F NMR (376 MHz, CDCl$_3$) δ: −147.26 (br d, J=19.1 Hz, 1 F), −148.94 (br d, J=19.8 Hz, 1 F).

Example 38

Compound 42

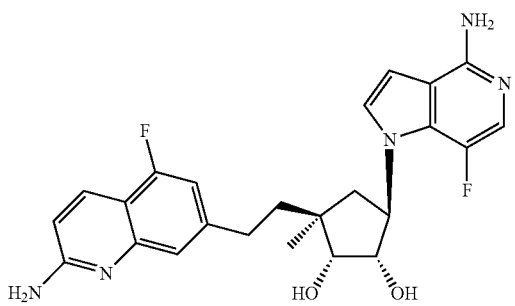 [SMILES: C[C@]1(CCc2cc(F)c3ccc(N)nc3c2)C[C@@H](n2ccc3c(N)ncc(F)c32)[C@H](O)[C@@H]1O]

(1S,2R,3S,5R)-3-(2-(2-amino-5-fluoroquinolin-7-yl)ethyl)-5-(4-amino-7-fluoro-1H-pyrrolo[3,2-c]pyridin-1-yl)-3-methylcyclopentane-1,2-diol (42) was obtained as hydrochloride salt and was prepared similarly as described for (1S,2R,3S,5R)-3-[2-(2-amino-3-chloro-5-fluoro-7-quinolyl)ethyl]-5-(4-amino-7-fluoro-pyrrolo[3,2-c]pyridin-1-yl)-3-methyl-cyclopentane-1,2-diol hydrochloride salt starting from 1-[(3aR,4R,6R,6aS)-2,2,4-trimethyl-4-vinyl-3a,5,6,6a-tetrahydrocyclopenta[d][1,3]dioxol-6-yl]-7-fluoro-pyrrolo[3,2-c]pyridin-4-amine (3Q) in a reaction with 7-bromo-3-chloro-5-fluoro-quinolin-2-amine (Q16) to afford the desired compound (106 mg, 0.199 mmol, 95%) as an off-white solid. LCMS: (ESI): RT=4.523 min, m/z calcd. for $C_{24}H_{26}F_2O_2N_5$ 454.2, [M+H]$^+$, found 454.1. $^1$H NMR (400 MHz, CD$_3$OD) δ: 8.43 (d, J=9.5 Hz, 1H), 7.74 (d, J=3.3 Hz, 1H), 7.60 (d, J=6.4 Hz, 1H), 7.37 (s, 1H), 7.24 (d, J=10.6 Hz, 1H), 7.13 (dd, J=2.0, 3.3 Hz, 1H), 7.06 (d, J=9.5 Hz, 1H), 5.19-5.10 (m, 1H), 4.47-4.39 (m, 1H), 3.93 (d, J=6.4 Hz, 1H), 2.99-2.79 (m, 2H), 2.16 (brdd, J=8.4, 12.8 Hz, 1H), 1.95-1.79 (m, 3H), 1.23 (s, 3H).

Example 39

Compound 43

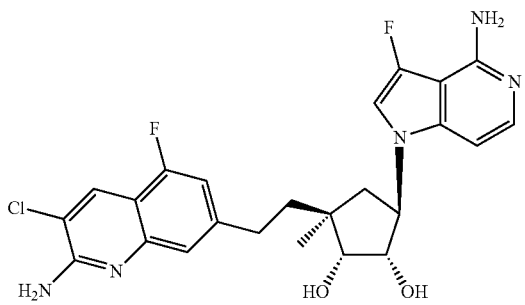 [SMILES: C[C@]1(CCc2cc(F)c3cc(Cl)c(N)nc3c2)C[C@@H](n2cc(F)c3c(N)nccc32)[C@H](O)[C@@H]1O]

(1S,2R,3S,5R)-3-(2-(2-amino-3-chloro-5-fluoroquinolin-7-yl)ethyl)-5-(4-amino-3-fluoro-1H-pyrrolo[3,2-c]pyridin-1-yl)-3-methylcyclopentane-1,2-diol (43) was obtained similar as described for (1S,2R,3S,5R)-5-(4-amino-1H-pyrrolo[3,2-c]pyridin-1-yl)-3-(2-(2-amino-3-chloro-5-fluoroquinolin-7-yl)ethyl)-3-methylcyclopentane-1,2-diol, using 4-chloro-3-fluoro-1H-pyrrolo[3,2-c]pyridine instead of 4-chloro-1H-pyrrolo[3,2-c]pyridine. The obtained residue was purified by prep-HPLC (column: Phenomenex Gemini-NX 80*40 mm*3 um; mobile phase: [water (0.05% NH$_3$H$_2$O+10 mM NH$_4$HCO$_3$)-ACN]; B %: 36%-62%, 8 min) to afford (1S,2R,3S,5R)-3-(2-(2-amino-3-chloro-5-fluoroquinolin-7-yl)ethyl)-5-(4-amino-3-fluoro-1H-pyrrolo[3,2-c]pyridin-1-yl)-3-methylcyclopentane-1,2-diol (65 mg, 0.132 mmol) as an off-white solid. $^1$H NMR (400 MHz, CD$_3$OD) δ=8.19 (s, 1H), 7.54 (d, J=6.3 Hz, 1H), 7.24 (s, 1H), 7.17 (d, J=2.5 Hz, 1H), 6.93 (d, J=10.8 Hz, 1H), 6.82 (dd, J=2.5, 6.5 Hz, 1H), 4.73 (q, J=8.8 Hz, 1H), 4.30-4.23 (m, 1H), 3.86 (d, J=6.3 Hz, 1H), 2.89-2.71 (m, 2H), 2.12-2.02 (m, 1H), 1.93-1.73 (m, 3H), 1.22 (s, 3H). $^{19}$F NMR (376 MHz, CD$_3$OD-d$_4$) δ=−125.79 (s, 1F), −172.16 (s, 1F).

Example 40

Compounds 44 and 45

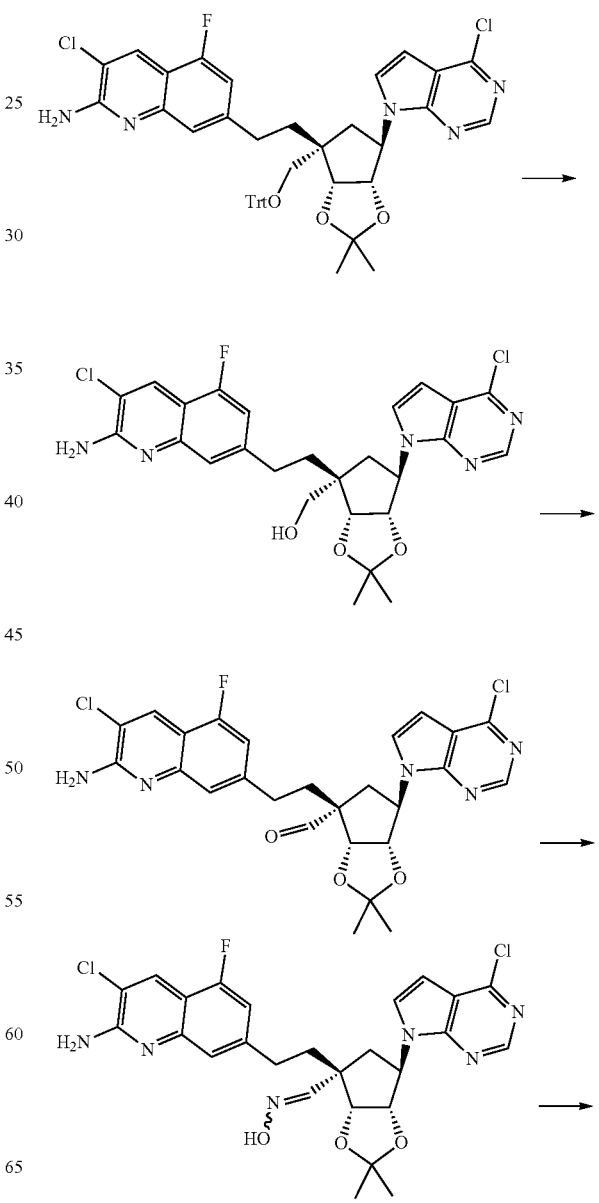

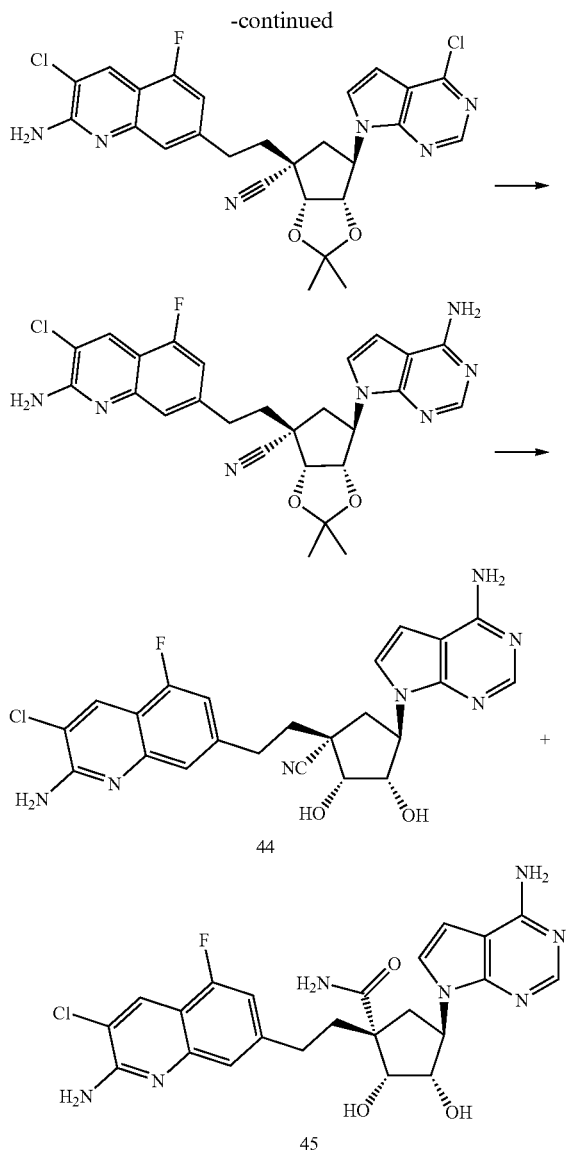

To a solution of 3-chloro-7-(2-((3aR,4S,6R,6aS)-6-(4-chloro-7H-pyrrolo[2,3-d]pyrimidin-7-yl)-2,2-dimethyl-4-((trityloxy)methyl)tetrahydro-3aH-cyclopenta[d][1,3]dioxol-4-yl)ethyl)-5-fluoroquinolin-2-amine (200 mg, 0.254 mmol, 1 eq.) in DCM (25 mL) were added triethylsilane (3.64 g, 31.30 mmol, 5.00 mL, 123.4 eq.) and TFA (770.00 mg, 6.75 mmol, 0.5 mL, 26.63 eq.) in DCM (5 mL) at −20° C. The mixture was stirred at −20° C. for 5 min. Upon completion, the mixture was diluted with NH$_4$Cl (10 mL) and extracted with EtOAc (3×50 mL). The combined organic layers were washed with brine (150 mL), dried over anhydrous Na$_2$SO$_4$, filtered and concentrated under reduced pressure to give a residue, which was purified by flash silica gel chromatography (ISCO®; 24 g SepaFlash® Silica Flash Column, Eluent of 0~4% MeOH/DCM @ 35 mL/min) to give ((3aR,4S,6R,6aS)-4-(2-(2-amino-3-chloro-5-fluoroquinolin-7-yl)ethyl)-6-(4-chloro-7H-pyrrolo[2,3-d]pyrimidin-7-yl)-2,2-dimethyltetrahydro-4H-cyclopenta[d][1,3]dioxol-4-yl)methanol (113 mg, 0.207 mmol, 82% yield) as a yellow solid. LCMS: (ESI): m/z calcd. for C$_{26}$H$_{27}$Cl$_2$FN$_5$O$_3$ 546.1 [M+H]$^+$, found 546.1.

To a solution of ((3aR,4S,6R,6aS)-4-(2-(2-amino-3-chloro-5-fluoroquinolin-7-yl)ethyl)-6-(4-chloro-7H-pyrrolo[2,3-d]pyrimidin-7-yl)-2,2-dimethyltetrahydro-4H-cyclopenta[d][1,3]dioxol-4-yl)methanol (146 mg, 0.267 mmol, 1 eq.) in DMSO (1 mL) was added IBX (149.6 mg, 0.534 mmol, 2 eq.), and the mixture was stirred at 25° C. for 12 h. The reaction progress was monitored by TLC (DCM:MeOH=10:1). Upon completion, the mixture was diluted with H$_2$O (10 mL) and extracted with EtOAc (3×20 mL, and concentrated under reduced pressure to give (3aR,4R,6R,6aS)-4-(2-(2-amino-3-chloro-5-fluoroquinolin-7-yl)ethyl)-6-(4-chloro-7H-pyrrolo[2,3-d]pyrimidin-7-yl)-2,2-dimethyltetrahydro-4H-cyclopenta[d][1,3]dioxole-4-carbaldehyde (150 mg, crude) as a colorless oil, which was used for next step without further purification. LCMS: (ESI): m/z calcd. for C$_{26}$H$_{25}$Cl$_2$FN$_5$O$_3$ 544.1. [M+H]$^+$, found 544.1.

To a solution of (3aR,4R,6R,6aS)-4-(2-(2-amino-3-chloro-5-fluoroquinolin-7-yl)ethyl)-6-(4-chloro-7H-pyrrolo[2,3-d]pyrimidin-7-yl)-2,2-dimethyltetrahydro-4H-cyclopenta[d][1,3]dioxole-4-carbaldehyde (100 mg, 183.69 μmol, 1 eq.) in EtOH (1.6 mL) and H$_2$O (0.2 mL) were added NaOAc (30.14 mg, 367.37 μmol, 2 eq.) and NH$_2$OH.HCl (25.53 mg, 367.37 μmol, 2 eq.). The mixture was stirred at 25° C. for 3 h. The reaction progress was monitored by TLC (DCM:MeOH=10:1). Upon completion, the mixture was diluted with NH$_4$Cl (10 mL) and extracted with EtOAc (3×50 mL). The combined organic layers were washed with brine (50 mL), dried over anhydrous Na$_2$SO$_4$, filtered and concentrated under reduced pressure to afford 4-(2-(2-amino-3-chloro-5-fluoroquinolin-7-yl)ethyl)-6-(4-chloro-7H-pyrrolo[2,3-d]pyrimidin-7-yl)-2,2-dimethyltetrahydro-4H-cyclopenta[d][1,3]dioxole-4-carbaldehyde oxime (93 mg, crude) as a white solid, which was used for next step without further purification. LCMS: (ESI): m/z calcd. for C$_{26}$H$_{26}$Cl$_2$FN$_6$O$_3$ 559.1. [M+H]$^+$, found 559.2.

To a solution of 4-(2-(2-amino-3-chloro-5-fluoroquinolin-7-yl)ethyl)-6-(4-chloro-7H-pyrrolo[2,3-d]pyrimidin-7-yl)-2,2-dimethyltetrahydro-4H-cyclopenta[d][1,3]dioxole-4-carbaldehyde oxime (80 mg, 0.143 mmol, 1 eq.) in CH$_3$CN (4 mL) were added CDI (115.9 mg, 0.715 mmol, 5 eq.) and Et$_3$N (72.4 mg, 0.715 mmol, 5 eq.). The mixture was stirred at 25° C. for 4 h. The reaction progress was monitored by TLC (DCM:MeOH=10:1). Upon completion, the residue was diluted with H$_2$O (20 mL) and extracted with EtOAc (3×30 mL). The combined organic layers were washed with brine (90 mL), dried over anhydrous Na$_2$SO$_4$, filtered and concentrated under reduced pressure to give a residue. The residue was purified by flash silica gel chromatography (ISCO®; 12 g SepaFlash® Silica Flash Column, Eluent of 0~8% EA:PE gradient @ 20 mL/min) to give (3aR,4S,6R,6aS)-4-(2-(2-amino-3-chloro-5-fluoroquinolin-7-yl)ethyl)-6-(4-chloro-7H-pyrrolo[2,3-d]pyrimidin-7-yl)-2,2-dimethyltetrahydro-4H-cyclopenta[d][1,3]dioxole-4-carbonitrile (61.4 mg, 0.110 mmol, 77% yield) as a white solid. LCMS: (ESI): m/z calcd. for C$_{26}$H$_{24}$N$_6$O$_2$Cl$_2$F, 541.1 [M+H]$^+$, found 541.0.

To a solution of (3aR,4S,6R,6aS)-4-(2-(2-amino-3-chloro-5-fluoroquinolin-7-yl)ethyl)-6-(4-chloro-7H-pyrrolo[2,3-d]pyrimidin-7-yl)-2,2-dimethyltetrahydro-4H-cyclopenta[d][1,3]dioxole-4-carbonitrile (85 mg, 0.157 mmol, 1 eq.) in dioxane (5 mL) and NH$_3$.H$_2$O (5 mL, 25% wt) was stirred at 110° C. for 12 h in a 30 mL sealed tube. Upon completion, the mixture was concentrated. The residue was diluted with NaHCO$_3$ (sat. aq., 5 mL) and extracted with EtOAc (3×50 mL). The combined organic layers were washed with brine (150 mL), dried over anhydrous Na$_2$SO$_4$, filtered, and concentrated under reduced pressure to give a residue, which was purified by flash silica gel chromatography (ISCO®; 25 g SepaFlash® Silica Flash Column, Eluent of 04.7% EA:PE gradient @ 35 mL/min) to give (3aR,4S,6R,6aS)-4-(2-(2-amino-3-chloro-5-fluoroquinolin-7-yl)ethyl)-6-(4-amino-7H-pyrrolo[2,3-d]pyrimidin-7-yl)-2,2-dimethyltetrahydro-4H-cyclopenta[d][1,3]dioxole-4-carbonitrile (66 mg, 0.126 mmol, 81% yield) as a white solid. LCMS: (ESI): m/z calcd. for $C_{26}H_{26}ClFN_7O_2$, 522.2 [M+H]$^+$, found 522.1.

To a solution of (3aR,4S,6R,6aS)-4-(2-(2-amino-3-chloro-5-fluoroquinolin-7-yl)ethyl)-6-(4-amino-7H-pyrrolo[2,3-d]pyrimidin-7-yl)-2,2-dimethyltetrahydro-4H-cyclopenta[d][1,3]dioxole-4-carbonitrile (66 mg, 0.126 mmol, 1 eq.) in THF (2 mL) was added 4 M HCl (1 mL). The mixture was stirred at 25° C. for 15 h. Upon completion, the mixture was concentrated under reduced pressure to give a residue. The residue was purified by prep-HPLC (column: Phenomenex Gemini-NX 80*40 mm*3 um; mobile phase: [water (0.05% $NH_3H_2O$+10 mM $NH_4HCO_3$)-ACN]; B %: 21%-45%, 8 min) to give (1S,2R,3S,4R)-1-(2-(2-amino-3-chloro-5-fluoroquinolin-7-yl)ethyl)-4-(4-amino-7H-pyrrolo[2,3-d]pyrimidin-7-yl)-2,3-dihydroxycyclopentane-1-carbonitrile (44) (32 mg, 0.066 μmol, 52% yield, 99% purity) and (1R,2R,3S,4R)-1-(2-(2-amino-3-chloro-5-fluoroquinolin-7-yl)ethyl)-4-(4-amino-7H-pyrrolo[2,3-d]pyrimidin-7-yl)-2,3-dihydroxycyclopentane-1-carboxamide (45) (5 mg, 0.010 μmol, 8% yield, 98% purity).

Compound 44: LCMS: (ESI): m/z calcd. for $C_{23}H_{22}ClFN_7O_2$ 482.1. [M+H]$^+$, found 482.2. $^1$H NMR (400 MHz, CD$_3$OD) δ: 8.20 (s, 1H), 8.09 (s, 1H), 7.30 (s, 1H), 7.21 (d, J=3.6 Hz, 1H), 6.97 (d, J=10.8 Hz, 1H), 6.58 (d, J=3.6 Hz, 1H), 5.07-4.99 (m, 1H), 4.64 (dd, J=6.3, 13.5 Hz, 1H), 4.15 (d, J=5.7 Hz, 1H), 3.10-2.91 (m, 2H), 2.72 (dd, J=9.0, 13.6 Hz, 1H), 2.37 (dd, J=10.3, 13.6 Hz, 1H), 2.32-2.23 (m, 2H). $^{19}$F NMR (376 MHz, CD$_3$OD) δ: −125.35 (s, 1F).

Compound 45: LCMS: (ESI): m/z calcd. for $C_{23}H_{24}ClFN_7O_3$ 500.2. [M+H]$^+$, found 500.2. $^1$H NMR (400 MHz, CD$_3$OD) δ: 8.19 (s, 1H), 8.10 (s, 1H), 7.26 (s, 1H), 7.21 (d, J=3.5 Hz, 1H), 6.93 (d, J=10.8 Hz, 1H), 6.59 (d, J=3.5 Hz, 1H), 4.96-4.92 (m, 1H), 4.72 (dd, J=4.9, 7.5 Hz, 1H), 4.19 (d, J=4.6 Hz, 1H), 3.01 (dd, J=9.9, 13.6 Hz, 1H), 2.81-2.65 (m, 2H), 2.32-2.22 (m, 2H), 2.06 (dd, J=9.3, 13.6 Hz, 1H). $^{19}$F NMR (376 MHz, CD$_3$OD) δ: −125.75 (s, 1F).

Example 41

Compound 46

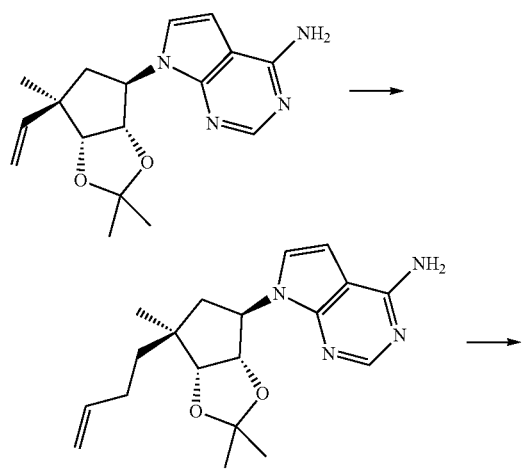

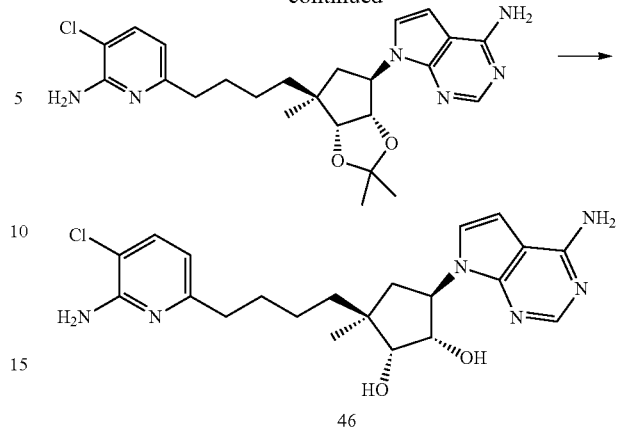

46

To a solution of 7-((3aS,4R,6R,6aR)-2,2,6-trimethyl-6-vinyltetrahydro-4H-cyclopenta[d][1,3]dioxol-4-yl)-7H-pyrrolo[2,3-d]pyrimidin-4-amine (500 mg, 1.59 mmol, 1 eq.) in THF (4 mL) was added 9-BBN dimer (962.3 mg, 3.98 mmol, 2.5 eq.). The mixture was stirred at 50° C. for 2 h under N$_2$, and then cooled to it. A solution of K$_3$PO$_4$ (1.69 g, 7.95 mmol, 5 eq.) in H$_2$O (2 mL) was added. The mixture was stirred at rt for 0.5 h, and then vinyl bromide (1 M, 7 mL, 4.40 eq.) and Pd(dppf)Cl$_2$ (116.37 mg, 0.159 mmol, 0.1 eq.) were added. The mixture was stirred at 40° C. for 16 h under N$_2$. The mixture was then diluted with brine (10 mL) and extracted with EA (2×20 mL). The combined organic layers were combined, dried over Na$_2$SO$_4$, filtered and concentrated to afford a residue, which was purified by prep-HPLC (40 g C-18 column, gradient: 0%~70% CH$_3$CN in water (1 mL NH$_3$.H$_2$O in 2 L H$_2$O) in 15 min@ 40 mL/min to give 7-((3aS,4R,6S,6aR)-6-(but-3-en-1-yl)-2,2,6-trimethyltetrahydro-4H-cyclopenta[d][1,3]dioxol-4-yl)-7H-pyrrolo[2,3-d]pyrimidin-4-amine (142.8 mg, 0.417 mmol, 26% yield) as a brown solid. LCMS: (ESI): RT=5.117 min, m/z calcd. for $C_{19}H_{27}O_2N_4$ 343.2, [M+H]$^+$, found 343.3.

To a solution of 7-((3aS,4R,6S,6aR)-6-(but-3-en-1-yl)-2,2,6-trimethyltetrahydro-4H-cyclopenta[d][1,3]dioxol-4-yl)-7H-pyrrolo[2,3-d]pyrimidin-4-amine (142.8 mg, 0.417 mmol, 1 eq.) in THF (4 mL) was added 9-BBN dimer (252.31 mg, 1.04 mmol, 2.5 eq.). The mixture was stirred at 50° C. for 2 h under N$_2$, and then cooled to 25° C. A solution of K$_3$PO$_4$ (442.59 mg, 2.09 mmol, 5 eq.) in H$_2$O (0.4 mL) was added, and the mixture was then stirred at rt for 0.5 h. 6-bromo-3-chloro-pyridin-2-amine (103.8 mg, 0.500 mmol, 1.2 eq.) and Pd(dppf)Cl$_2$ (30.5 mg, 0.042 mmol, 0.1 eq.) were added, and the mixture was stirred at 60° C. for 16 h. The mixture was diluted with water (5 mL) and extracted with EA (3×10 mL). The combined organic layers were washed with brine (30 mL) (3×10 mL), dried over Na$_2$SO$_4$, filtered and concentrated to give 7-((3aS,4R,6S,6aR)-6-(4-(6-amino-5-chloropyridin-2-yl)butyl)-2,2,6-trimethyltetrahydro-4H-cyclopenta[d][1,3]dioxol-4-yl)-7H-pyrrolo[2,3-d]pyrimidin-4-amine (50.5 mg, 70% purity, 0.075 mmol, 18% yield). LCMS: (ESI): RT=1.757 min, m/z calcd. for $C_{24}H_{32}ClO_2N_6$ 471.22, [M+H]$^+$, found 471.3.

To a solution of 7-((3aS,4R,6S,6aR)-6-(4-(6-amino-5-chloropyridin-2-yl)butyl)-2,2,6-trimethyltetrahydro-4H-cyclopenta[d][1,3]dioxol-4-yl)-7H-pyrrolo[2,3-d]pyrimidin-4-amine (50.5 mg, 70% purity, 0.075 mmol, 1 eq.) in THF (3 mL) was added HCl (4 M, 1.5 mL). The mixture was stirred at 20° C. for 12 h. Upon completion, the mixture was concentrated under reduced pressure to give a residue. The residue was purified by prep-HPLC (column: Phenomenex Gemini-NX 80*40 mm*3 um; mobile phase: [water (0.05% NH$_3$H$_2$O+10 mM NH$_4$HCO$_3$)-ACN]; B %: 20%-50%, 8 min) to give (1S,2R,3S,5R)-3-(4-(6-amino-5-chloropyridin-2-yl)butyl)-5-(4-amino-7H-pyrrolo[2,3-d]pyrimidin-7-yl)-3-methylcyclopentane-1,2-diol (46) (9.0 mg, 0.021 mmol, 28%). $^1$H NMR (400 MHz, CD$_3$OD) δ: 8.05 (s, 1H), 7.45 (d, J=7.8 Hz, 1H), 7.21 (d, J=3.5 Hz, 1H), 6.60 (d, J=3.5 Hz, 1H), 6.51 (d, J=7.8 Hz, 1H), 5.01-4.93 (m, 1H), 4.45 (dd, J=6.3, 7.8 Hz, 1H), 3.80 (d, J=6.0 Hz, 1H), 2.64-2.57 (m, 2H), 1.98 (dd, J=8.8, 12.8 Hz, 1H), 1.77 (dd, J=10.8, 13.1 Hz, 1H), 1.68 (quin, J=7.3 Hz, 2H), 1.60-1.31 (m, 4H), 1.09 (s, 3H).

Example 42

Compound 47

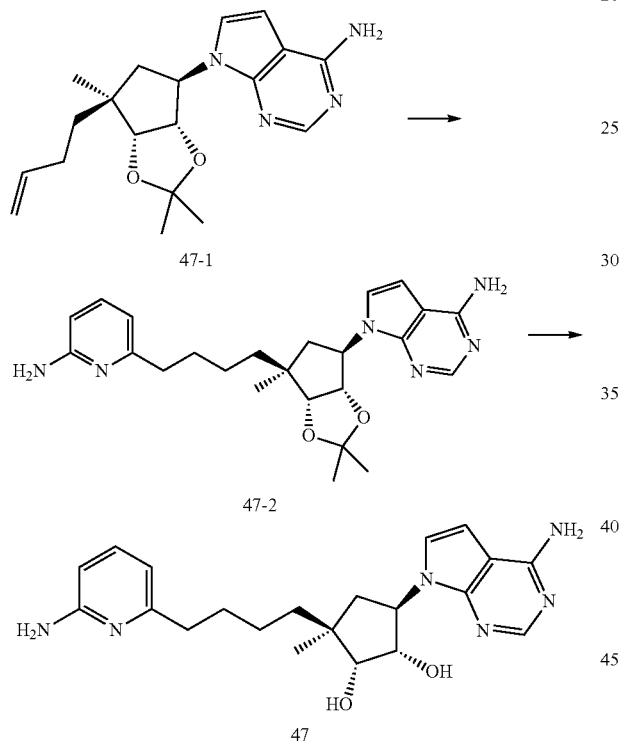

To a solution of 47-1 (177.5 mg, 0.508 mmol, 1 eq.) in THF (4 mL) was added 9-BBN dimer (313.6 mg, 1.30 mmol, 2.5 eq.), and the mixture was stirred at 50° C. for 2 h under N$_2$. The mixture was cooled to rt, and then a solution of K$_3$PO$_4$ (550.1 mg, 2.6 mmol, 5 eq.) in H$_2$O (0.5 mL) was added. After stirring at rt for 0.5 h, 6-bromopyridin-2-amine (107.6 mg, 0.622 mmol, 1.2 eq.) and Pd(dppf)Cl$_2$ (37.9 mg, 0.052 mmol, 0.1 eq.) were added, and the mixture was stirred at 60° C. for 16 h under N$_2$. Upon completion, the mixture was diluted with brine (10 mL) and extracted with EA (2×20 mL). The combined organic layers were combined and dried over NaS$_2$O$_4$, filtered, and concentrated to give a residue. The residue was purified by prep-HPLC (40 g C-18 column, gradient: 0%~70% CH$_3$CN in water (1 mL NH$_3$.H$_2$O in 2 L H$_2$O) in 15 min@ 40 mL/min to afford 47-2 (85.4 mg, 0.196 mmol, 38% yield) as a brown solid. LCMS: (ESI): RT=1.553 min, m/z calcd. for C$_{24}$H$_{33}$O$_2$N$_6$ 437.26, [M+H]$^+$, found 437.2.

To a solution of 47-2 (85.4 mg, 0.196 mmol, 1 eq.) in THF (3 mL) was added HCl (aq., 4 M, 1.5 mL), and the mixture was stirred at 20° C. for 12 h. Upon completion, the mixture was concentrated under reduced pressure to give a residue, which was purified by prep-HPLC (column: Venusil ASB Phenyl 150*30 mm*5 um; mobile phase: [water (0.05% HCl)-ACN]; B %: 9%-39%, 9 min) to afford 47 as a hydrochloride salt (54.4 mg, 0.115 mmol, 59% yield). LCMS: (ESI): RT=3.688 min, m/z calcd. for C$_{21}$H$_{29}$N$_6$O$_2$ 397.23, [M+H]$^+$, found 397.3. $^1$H NMR (400 MHz, CD$_3$OD) δ: 8.25 (s, 1H), 7.84 (dd, J=7.3, 8.8 Hz, 1H), 7.57 (d, J=3.5 Hz, 1H), 6.92 (d, J=3.5 Hz, 1H), 6.84 (d, J=8.8 Hz, 1H), 6.76 (d, J=7.3 Hz, 1H), 5.14-5.05 (m, 1H), 4.55-4.48 (m, 1H), 3.84 (d, J=6.0 Hz, 1H), 2.80 (br t, J=7.8 Hz, 2H), 2.04-1.96 (m, 1H), 1.92-1.83 (m, 1H), 1.81-1.72 (m, 2H), 1.66-1.38 (m, 4H), 1.11 (s, 3H).

Example 43

Compound 48

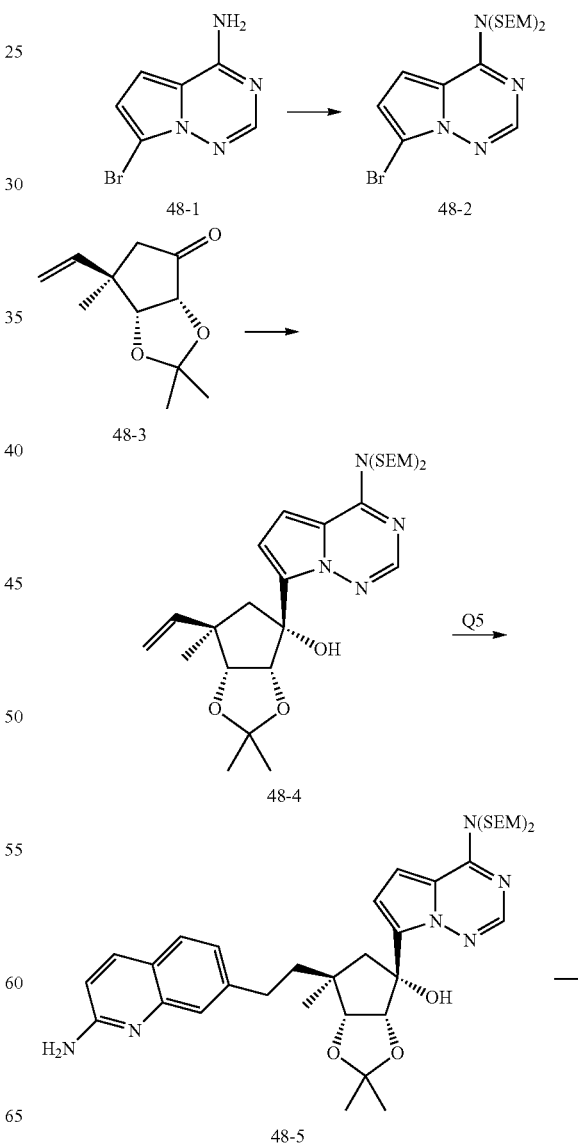

-continued

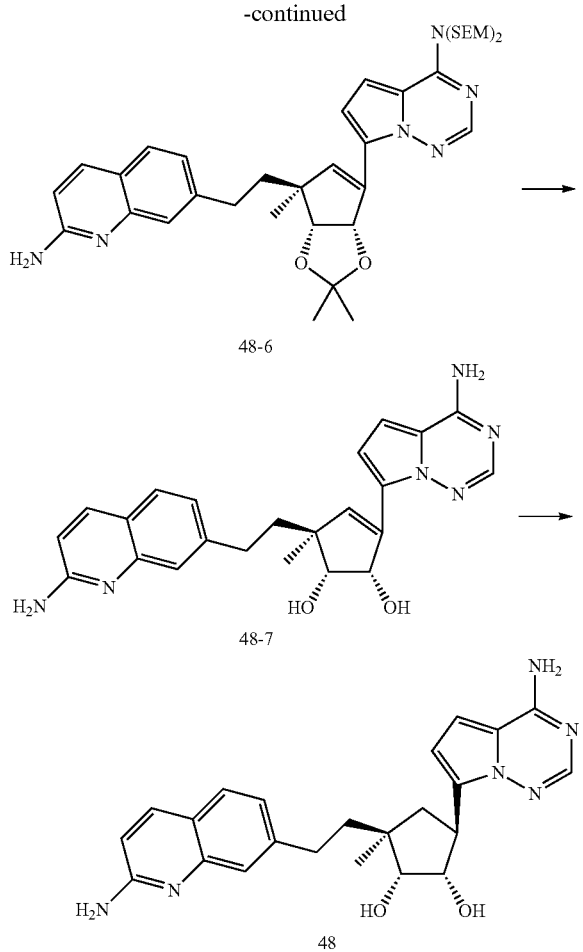

48-6

48-7

48

To a solution of 7-bromopyrrolo[2,1-f][1,2,4]triazin-4-amine (48-1) (5.5 g, 25.82 mmol, 1 eq.) in DMF (50 mL) was added NaH (2.58 g, 64.54 mmol, 60% purity, 2.5 eq.) at 0° C., and the mixture was stirred at 0° C. for 0.5 h. 2-(chloromethoxy)ethyl-trimethyl-silane (9.04 g, 54.22 mmol, 9.60 mL, 2.1 eq.) was added, and the mixture was stirred at 25° C. for 5 h. Upon completion, the reaction was quenched by sat. aq. NH$_4$Cl (50 mL) and extracted with EA (2×50 mL). The combined organic layers were washed with brine (50 mL), dried over Na$_2$SO$_4$, filtered, and concentrated under reduced pressure to give a residue, which was purified by flash silica gel chromatography (ISCO®; 40 g SepaFlash® Silica Flash Column, Eluent of 0~2% EA/PE gradient @ 40 mL/min) to afford 48-2 (7.6 g, 15.90 mmol, 61% yield) as a colorless oil. LCMS: (ESI): m/z calcd. for C$_{18}$H$_{34}$BrN$_4$O$_2$Si$_2$ 473.13 [M+H]$^+$, found 473.2. $^1$H NMR (400 MHz, CDCl$_3$) δ: 8.09 (s, 1H), 7.08 (d, J=4.8 Hz, 1H), 6.77 (d, J=4.8 Hz, 1H), 5.22 (s, 4H), 3.70-3.65 (m, 4H), 1.02-0.95 (m, 4H), 0.02-0.00 (m, 18H).

Chloro(isopropyl)magnesium lithium chloride (1.3 M, 5.88 mL in THF, 3 eq.) was added dropwise to a solution of 48-2 (3.62 g, 7.64 mmol, 3 eq.) in THF (5 mL) at −20° C. The mixture was stirred at −20° C. for 10 min, then warmed to 0° C. The mixture was stirred at 0° C. for 1 h, and a solution of 48-3 (500 mg, 2.55 mmol, 1 eq.) in THF (7 mL) was added dropwise at −20° C. The mixture was stirred at 0° C. for 1 h. Upon completion, the reaction was quenched by sat. NH$_4$Cl solution (15 mL) and extracted with EA (2×20 mL). The combined organic layers were washed with water and brine (20 mL), dried over Na$_2$SO$_4$, filtered and concentrated under reduced pressure to give a residue, which was purified by flash silica gel chromatography (ISCO®; 40 g SepaFlash® Silica Flash Column, Eluent of 0~10% EA/PE gradient @ 30 mL/min) to give 48-4 (967 mg, 94% purity, 1.54 mmol, 60% yield) as a yellow oil. LCMS: (ESI): m/z calcd. for C$_{29}$H$_{51}$N$_4$O$_5$Si$_2$ 591.33 [M+H]$^+$, found 591.4.

A mixture of 48-4 (470 mg, 0.795 mmol, 1 eq.) and 9-BBN dimer (481.2 mg, 1.99 mmol, 2.5 eq.) in THF (10 mL) was stirred at 50° C. for 2 h under N$_2$. The mixture was cooled to rt, and a solution of K$_3$PO$_4$ (844.2 mg, 3.98 mmol, 5 eq.) in H$_2$O (1 mL) was added. The mixture was stirred for 0.5 h. Q5 (212.9 mg, 0.954 mmol, 1.2 eq.) and Pd(dppf)Cl$_2$ (58.20 mg, 0.080 mmol, 0.1 eq.) were added. The mixture was stirred at 70° C. under N$_2$ for 12 h. The mixture was diluted with brine (10 mL) and extracted with EA (2×10 mL). The combined organic layers were dried over Na$_2$SO$_4$, filtered and concentrated under reduced pressure to give a residue. The residue was purified by column chromatography (SiO$_2$, PE:EA (3:1 to 1:1) to (DCM:MeOH 30:1 to 20:1)) to afford 48-5 (508 mg, 0.580 mmol, 72% yield) as a yellow solid. LCMS: (ESI): m/z calcd. for C$_{38}$H$_{59}$N$_6$O$_5$Si$_2$ 735.4 [M+H]$^+$, found 735.5.

To a solution of 48-5 (350 mg, 0.476 mmol, 1 eq.) in DCM (8.5 mL) was added DAST (383.8 mg, 2.38 mmol, 314 µL, 5 eq.) at 0° C. The mixture was stirred at 0° C. for 1 h. The mixture was filtered and concentrated under reduced pressure to give a residue. The residue was purified by column chromatography (SiO$_2$, DCM:MeOH (50:1 to 20:1)) to afford 48-6 (313 mg, 0.393 mmol, 82% yield) as a white solid. LCMS: (ESI): m/z calcd. for C$_{38}$H$_{57}$N$_6$O$_4$Si$_2$ 717.39 [M+H]$^+$, found 717.4.

To a solution of 48-6 (313 mg, 0.393 mmol, 1 eq.) in THF (8.5 mL) was added HCl (aq., 4 M, 4 mL). The mixture was stirred at 25° C. for 3.5 h. The mixture was filtered and concentrated under reduced pressure to give a residue. To a solution of the residue in a mixed a solvent of t-BuOH (7 mL) and H$_2$O (3 mL) was added PPTS (700.71 mg, 2.79 mmol, 5 eq.). The mixture was stirred at 50° C. for 12 h, and then concentrated under reduced pressure to give a residue. The residue was purified by prep-HPLC (column: Phenomenex Gemini-NX 80*40 mm*3 um; mobile phase: [water (0.05% NH$_3$H$_2$O+10 mM NH$_4$HCO$_3$)-ACN]; B %: 17%-47%, 8 min) to afford 48-7 (57 mg, 0.133 mmol, 34% yield) as a white solid. LCMS: (ESI): m/z calcd. for C$_{23}$H$_{23}$N$_6$O$_2$ 417.2 [M+H]$^+$, found 417.3.

A mixture of 48-7 (48 mg, 0.115 mmol, 1 eq.) and PtO$_2$ (250 mg, 1.10 mmol, 9.55 eq.) in THF (10 mL) was hydrogenated under H$_2$ (1 atm) at rt for 12 h. The mixture was filtered through a pad of Celite. The filtrate was concentrated under reduced pressure to give a residue, which was purified by prep-HPLC (column: Phenomenex Gemini-NX 80*40 mm*3 um; mobile phase: [water (0.05% NH$_3$H$_2$O+10 mM NH$_4$HCO$_3$)-ACN]; B %: 24%-38%, 8 min) to give 48 (10 mg, 0.0236 mmol, 20.5% yield, 98.88% purity) as a white solid. LCMS: (ESI): m/z calcd. for C$_{23}$H$_{27}$N$_6$O$_2$ 419.21 [M+H]$^+$, found 419.3. $^1$H NMR (400 MHz, CD$_3$OD) δ: 7.90 (d, J=8.8 Hz, 1H), 7.75 (s, 1H), 7.56 (d, J=8.3 Hz, 1H), 7.35 (s, 1H), 7.12 (dd, J=1.5, 8.0 Hz, 1H), 6.84 (d, J=4.5 Hz, 1H), 6.76 (d, J=8.8 Hz, 1H), 6.55 (d, J=4.5 Hz, 1H), 4.46-4.41 (m, 1H), 3.86 (d, J=6.0 Hz, 1H), 3.78-3.70 (m, 1H), 2.88-2.69 (m, 2H), 2.08-2.01 (m, 1H), 1.89-1.66 (m, 3H), 1.23 (s, 3H).

Example 44

Compound 49

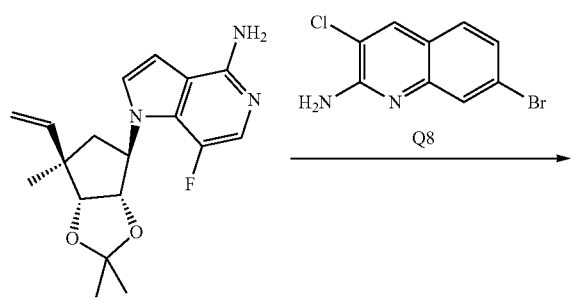

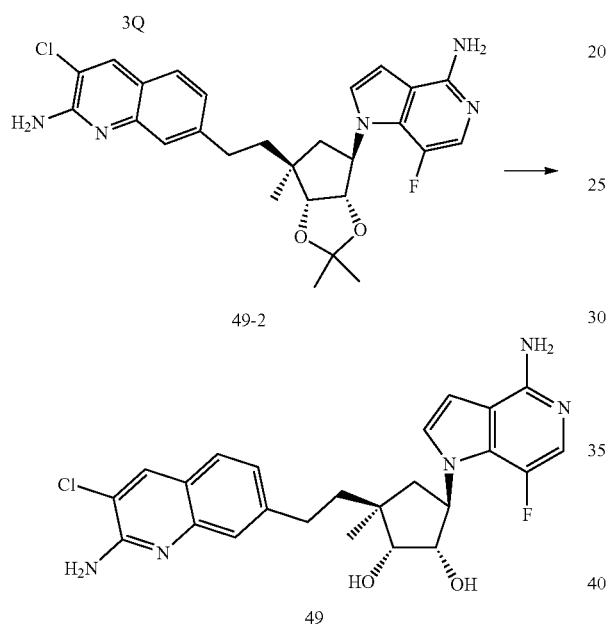

To a mixture of 3Q (100 mg, 0.302 mmol, 1 eq.) in THF (5 mL) was added 9-BBN dimer (160.7 mg, 0.664 mmol, 2.2 eq.). The mixture was stirred at 50° C. for 1 h and then cooled to rt. A solution of K₃PO₄ (320.3 mg, 1.51 mmol, 5 eq.) in H₂O (0.5 mL) was added, and the mixture was stirred at rt for 0.2 h. 7-bromo-3-chloro-quinolin-2-amine Q8 (93.3 mg, 0.362 mmol, 1.2 eq.) and Pd(dppf)Cl₂ (22.08 mg, 0.030 mmol, 0.1 eq.) were then added. The mixture was stirred at 60° C. for 8 h. Upon completion, the mixture was diluted with brine (10 mL) and extracted with EA (3×20 mL). The separated organic layers were combined, dried over anhydrous Na₂SO₄ and concentrated to give a residue. The residue was purified by prep-HPLC (40 g C-18 column: chromatography (0%~65% CH₃CN/H₂O (1 mL NH₃.H₂O in 2 L H₂O) @ 40 mL/min) to afford 49-2 (55 mg, 0.105 mmol, 35% yield, 97.4% purity) as a brown solid. LCMS: (ESI): m/z calcd. for $C_{27}H_{30}ClFN_5O_2$ 510.20 [M+H]$^+$, found 510.3.

To a solution of 49-2 (55 mg, 0.105 mmol, 1 eq.) in THF (3 mL) was added HCl (4 M, 2 mL). The mixture was stirred at rt for 6 h. Upon completion, the mixture was concentrated under reduced pressure to afford a residue, which was purified by prep-HPLC twice (column: Phenomenex Gemini-NX 80*40 mm*3 um; mobile phase: [water (0.05% NH₃H₂O+10 mM NH₄HCO₃)-ACN]; B %: 32%-52%, 8 min) to give 49 (28 mg, 0.0593 mmol, 56% yield, 99.49% purity) as a white solid. LCMS: (ESI): m/z calcd. for $C_{24}H_{26}ClFN_5O_2$ 470.17 [M+H]$^+$, found 470.1. $^1$H NMR (400 MHz, CD₃OD) δ: 8.06 (s, 1H), 7.56 (d, J=8.3 Hz, 1H), 7.42 (d, J=5.0 Hz, 1H), 7.40 (s, 1H), 7.35 (d, J=3.3 Hz, 1H), 7.17 (dd, J=1.5, 8.3 Hz, 1H), 6.73-6.68 (m, 1H), 5.11-5.00 (m, 1H), 4.46-4.38 (m, 1H), 3.91 (d, J=6.5 Hz, 1H), 2.90-2.69 (m, 2H), 2.11 (dd, J=8.3, 12.8 Hz, 1H), 1.93-1.73 (m, 3H), 1.22 (s, 3H).

Example 45

Compound 50

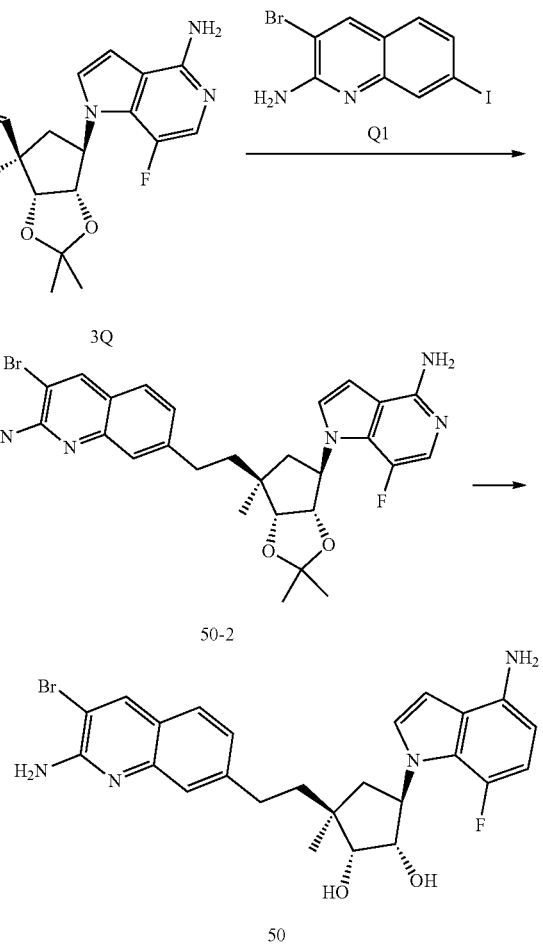

To a solution of 3Q (100 mg, 0.302 mmol, 1 eq.) in THF (5 mL) was added 9-BBN dimmer (160.7 mg, 0.664 mmol, 2.2 eq.). The mixture was stirred at 50° C. for 1 h and cooled to rt. A solution of K₃PO₄ (320.3 mg, 1.51 mmol, 5 eq.) in H₂O (0.5 mL) was added, and the mixture was stirred at rt for 0.2 h. 3-bromo-7-iodo-quinolin-2-amine (Q1) (126.4 mg, 0.362 mmol, 1.2 eq.) and Pd(dppf)Cl₂ (22.1 mg, 0.030 mmol, 0.1 eq.) were then added. The mixture was stirred at 50° C. for 3 h. Upon completion, the mixture was diluted with brine (10 mL) and extracted with EA (3×20 mL). The separated organic layers were combined, dried over anhydrous Na₂SO₄ and concentrated to give a residue, which was purified by column chromatography (100-200 mesh, SiO₂, CH$_2$C$_{12}$/MeOH (100:1 to 10:1), eluted 1 L) to provide 50-2 (160 mg, 0.212 mmol, 73.4% purity, 70% yield) as a brown solid. LCMS: (ESI): m/z calcd. for C$_{27}$H$_{30}$BrFN$_5$O$_2$ 554.15 [M+H]$^+$, found 556.1.

To a solution of 50-2 (160 mg, 0.212 mmol, 1 eq.) in THF (4 mL) was added HCl (4 M, 2 mL). The mixture was stirred at rt for 8 h. Upon completion, the mixture was concentrated under reduced pressure to afford a residue. The residue was purified by prep-HPLC (acidic condition, column: Agela ASB 150*25 mm*5 um; mobile phase: [water (0.05% HCl)-ACN]; B %: 12%-42%, 9 min), and then (basic condition, column: Phenomenex Gemini-NX 80*40 mm*3 um; mobile phase: [water (0.05% NH$_3$H$_2$O+10 mM NH$_4$HCO$_3$)-ACN]; B %: 30%-60%, 8 min) to give 50 (25 mg, 0.0484 mmol, 23% yield, 99.66% purity) as a white solid. LCMS: (ESI): m/z calcd. for C$_{24}$H$_{26}$BrFN$_5$O$_2$ 516.12 [M+H]$^+$, found 516.1. $^1$H NMR (400 MHz, CD$_3$OD) δ: 8.25 (s, 1H), 7.55 (d, J=8.3 Hz, 1H), 7.42 (d, J=5.0 Hz, 1H), 7.39 (s, 1H), 7.35 (d, J=3.3 Hz, 1H), 7.17 (dd, J=1.5, 8.3 Hz, 1H), 6.73-6.67 (m, 1H), 5.12-5.01 (m, 1H), 4.45-4.39 (m, 1H), 3.91 (d, J=6.3 Hz, 1H), 2.90-2.69 (m, 2H), 2.11 (dd, J=8.8, 12.5 Hz, 1H), 1.93-1.72 (m, 3H), 1.22 (s, 3H). $^{19}$F NMR (376 MHz, CD$_3$OD) δ: −161.68 (br s, 1F).

Example 46

Compound 51

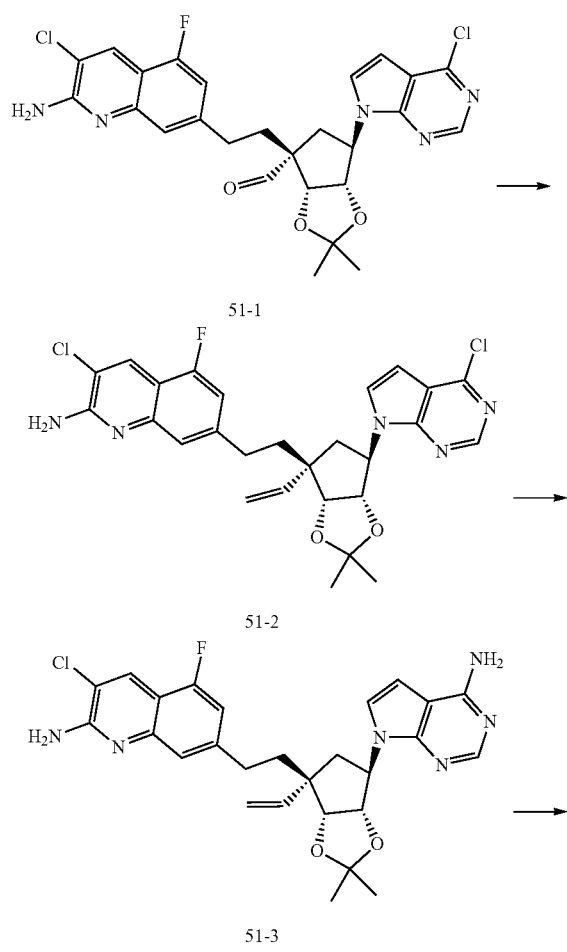

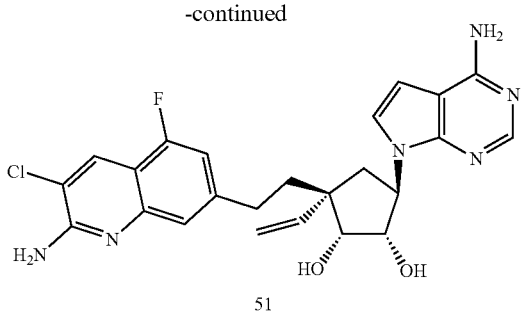

To a mixture of PPh$_3$CH$_3$Br (255.91 mg, 716.38 μmol, 5.2 eq.) in THF (3 mL) was added t-BuOK (77.29 mg, 688.83 μmol, 5 eq.) at 0° C., and the mixture was stirred at 25° C. for 0.5 h. Compound 51-1 (75 mg, 137.77 μmol, 1 eq.) was added, and the mixture was stirred at 25° C. for 1.5 h. Upon completion, the reaction was quenched by the addition of NH$_4$Cl (10 mL) at 0° C. The mixture was then extracted with EtOAc (3×20 mL). The combined organic layers were washed with brine (3×20 mL), dried over anhydrous Na$_2$SO$_4$, filtered and concentrated under reduced pressure to give a residue. The residue was purified by flash silica gel chromatography (ISCO®; 20 g SepaFlash® Silica Flash Column, Eluent of 0~1.9% MeOH/DCM @ 30 mL/min) to afford 51-2 (38 mg, 64.45 μmol, 46.78% yield, 88% purity) as a colorless oil. LCMS: (ESI): m/z calcd. for C$_{27}$H$_{27}$Cl$_2$FN$_5$O$_2$ 542.1. [M+H]$^+$, found 542.1.

A solution of 51-2 (38 mg, 70.05 μmol, 1 eq.) in dioxane (1 mL) and NH$_3$.H$_2$O (4.55 g, 32.46 mmol, 5 mL, 25% aq., 206.74 eq.) was stirred in a 30 mL of sealed tube at 110° C. for 24 h. Upon completion, the reaction was quenched by the addition of NaHCO$_3$ (sat. aq., 5 mL). The mixture was extracted with EtOAc (3×20 mL). The combined organic layers were washed with brine (3×20 mL), dried over anhydrous Na$_2$SO$_4$, filtered and concentrated under reduced pressure to give a residue. The residue was purified by flash silica gel chromatography (ISCO®; 25 g SepaFlash® Silica Flash Column, Eluent of 0~3.1% MeOH/DCM gradient @ 30 mL/min) to afford 51-3 (26 mg, 46.73 μmol, 66.71% yield, 94% purity) as a white solid. LCMS: (ESI): m/z calcd. for C$_{27}$H$_{29}$ClFN$_6$O$_2$ 523.2 [M+H]+, found 523.1.

To a solution of 51-3 (26 mg, 49.71 μmol, 1 eq.) in THF (1 mL) was added HCl (4M, aq., 1 mL), and the mixture was stirred at 25° C. for 12 h. Upon completion, the mixture was concentrated under reduced pressure to give a residue. The residue was purified by prep-HPLC (column: Phenomenex Gemini-NX 80*40 mm*3 um; mobile phase: [water (0.05% NH$_3$H$_2$+10 mM NH$_4$HCO$_3$)-ACN]; B %: 21%-45%, 8 min) to afford 51 (15 mg, 31.06 μmol, 62.48% yield, 100% purity) as a white solid. LCMS: (ESI): m/z calcd. for C$_{24}$H$_{25}$ClFN$_6$O$_2$ 483.2. [M+H]$^+$, found 483.3. $^1$H NMR (400 MHz, CD$_3$OD) δ: 8.18 (s, 1H), 8.09 (s, 1H), 7.23 (d, J=3.5 Hz, 1H), 7.21 (s, 1H), 6.89 (d, J=10.8 Hz, 1H), 6.59 (d, J=3.5 Hz, 1H), 6.13 (dd, J=11.0, 17.8 Hz, 1H), 5.42-5.22 (m, 2H), 5.03-4.92 (m, 1H), 4.60 (d, J=6.5 Hz, 1H), 4.02 (d, J=6.0 Hz, 1H), 2.81-2.61 (m, 2H), 2.57 (dd, J=9.0, 13.3 Hz, 1H), 2.11-1.92 (m, 3H). $^{19}$F NMR (376 MHz, CD$_3$OD) δ: −125.86 (s, 1F).

Example 47

Compound 52

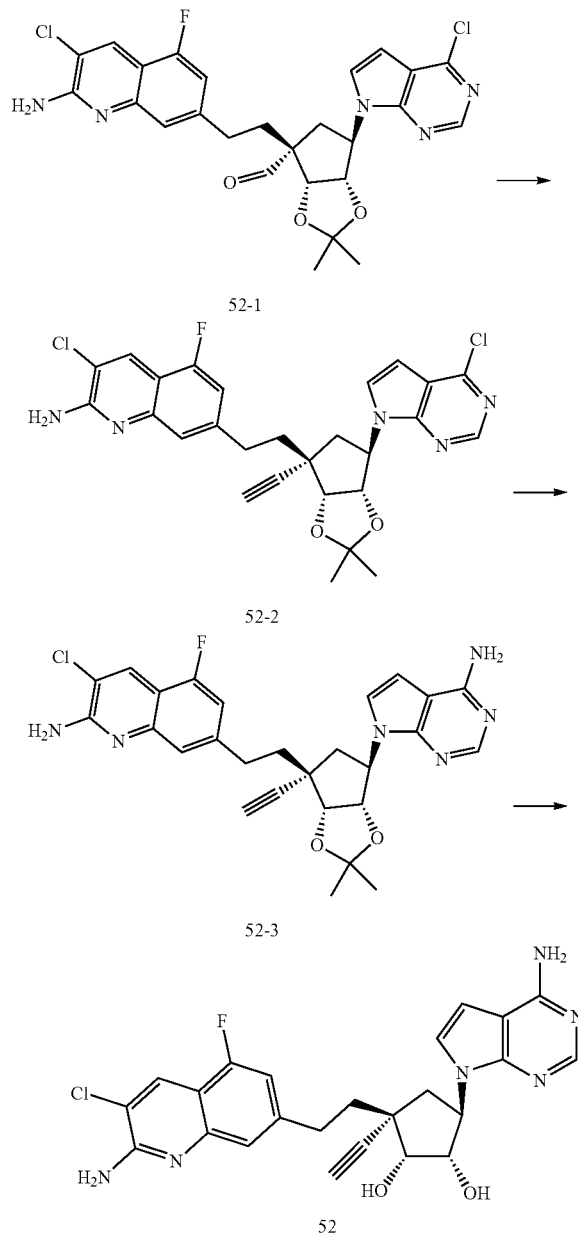

To a solution of 52-1 (75 mg, 137.77 µmol, 1 eq.) in CH₃CN (3 mL) were added K₂CO₃ (38.08 mg, 275.53 µmol, 2 eq.) and 1-diazo-1-dimethoxyphosphoryl-propan-2-one (52.93 mg, 275.53 µmol, 2 eq.). The mixture was stirred at 25° C. for 12 h. Upon completion, the reaction was quenched by the addition of NH₄Cl (sat. aq., 10 mL). The mixture was extracted with EtOAc (3×20 mL). The combined organic layers were washed with brine (3×20 mL), dried over anhydrous Na₂SO₄, filtered and concentrated under reduced pressure to give a residue. The residue was purified by flash silica gel chromatography (ISCO®; 20 g SepaFlash® Silica Flash Column, Eluent of 0~2.1% MeOH/DCM @ 30 mL/min) to afford 52-2 (41 mg, 72.07 µmol, 52.32% yield, 95% purity) as a colorless oil. LCMS: (ESI): m/z calcd. for $C_{27}H_{25}Cl_2FN_5O_2$ 540.1. [M+H]⁺, found 540.0.

A solution of 52-2 (40 mg, 74.02 µmol, 1 eq.) in dioxane (4 mL) and NH₃.H₂O (3.64 g, 25.97 mmol, 4 mL, 25% purity, 206.74 eq.) was stirred in a 30 mL sealed tube at 110° C. for 24 h. Upon completion, the reaction was quenched by the addition of NaHCO₃ (sat. aq., 5 mL). The mixture was extracted with EtOAc (3×20 mL). The combined organic layers were washed with brine (3×20 mL), dried over anhydrous Na₂SO₄, filtered and concentrated under reduced pressure to give a residue. The residue was purified by flash silica gel chromatography (ISCO®; 25 g SepaFlash® Silica Flash Column, Eluent of 0~2.8% MeOH/DCM gradient @ 30 mL/min) to afford 52-3 (10 mg, 18.43 µmol, 24.90% yield, 96% purity) as a white solid. LCMS: (ESI): m/z calcd. for $C_{27}H_{27}ClFN_6O_2$, 521.2 [M+H]⁺, found 521.2.

A solution of 52-3 (10 mg, 18.50 µmol, 1 eq.) in HCl (4M aq., 1 mL) and THF (1 mL) was stirred at 25° C. for 12 h. Upon completion, the mixture was concentrated under reduced pressure to give a residue. The residue was purified by prep-HPLC (column: Phenomenex Gemini-NX 80*40 mm*3 um; mobile phase: [water (0.05% NH₃H₂O+10 mM NH₄HCO₃)-ACN]; B %: 21%-45%, 8 min) to afford 52 (5 mg, 10.40 µmol, 56.19% yield, 100% purity) as a white solid. LCMS: (ESI): m/z calcd. for $C_{24}H_{23}ClFN_6O_2$ 481.2. [M+H]⁺, found 481.2. ¹H NMR (400 MHz, CD₃OD) δ: 8.19 (s, 1H), 8.08 (s, 1H), 7.26 (s, 1H), 7.21 (d, J=3.8 Hz, 1H), 6.93 (d, J=10.0 Hz, 1H), 6.59 (d, J=3.5 Hz, 1H), 5.17-5.04 (m, 1H), 4.55 (t, J=6.8 Hz, 1H), 4.00 (d, J=6.8 Hz, 1H), 3.17-3.01 (m, 1H), 2.93 (dt, J=4.8, 12.7 Hz, 1H), 2.81 (s, 1H), 2.46 (dd, J=8.3, 12.8 Hz, 1H), 2.23-2.09 (m, 2H), 2.08-1.97 (m, 1H). ¹⁹F NMR (376 MHz, CD₃OD) δ: −125.74 (s, 1F).

Example 48

Compound 53

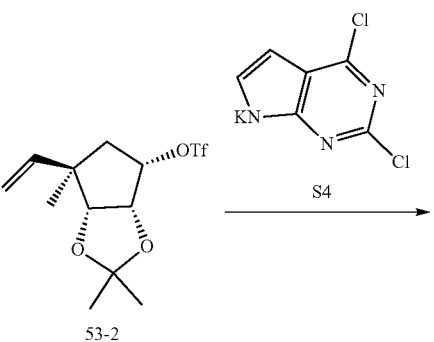

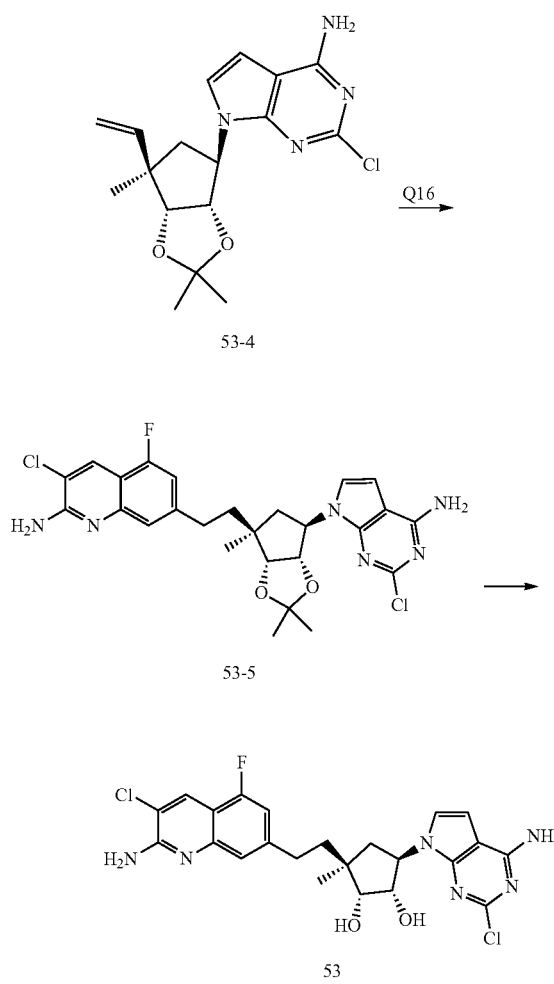

To a solution of 53-1 (1 g, 5.04 mmol, 1 eq.) in DCM (10 mL) were added Tf₂O (2.13 g, 7.57 mmol, 1.25 mL, 1.5 eq.) and pyridine (1.60 g, 20.18 mmol, 1.63 mL, 4 eq.). The mixture was stirred at 0° C. for 1 h. Upon completion, the reaction was quenched with H₂O (10 mL) at 0° C., then extracted with DCM (10 mL). The aqueous phase was extracted with DCM (3×20 mL). The combined organic layers were washed with brine (30 mL), dried over anhydrous Na₂SO₄, filtered and concentrated under reduced pressure to give 53-2 (1.8 g, crude) as a brown oil, which is used for the next step without further purification.

To a solution of 2,4-dichloro-7H-pyrrolo[2,3-d]pyrimidine (S4) (1.5 g, 7.98 mmol, 1.46 eq.) in DMF (5 mL) was added t-BuOK (832.57 mg, 7.42 mmol, 1.36 eq.). The mixture was stirred at 15° C. for 1 h. Compound 53-2 (1.8 g, 5.45 mmol, 1 eq.) was added at 0° C., and the mixture was stirred at 15° C. for 48 h under N₂. Upon completion, the reaction was partitioned between DCM (20 mL) and brine (20 mL). The aqueous phase was extracted with DCM (3×30 mL). The organic layers were combined, dried over Na₂SO₄, filtered and concentrated under reduced pressure to give a residue. The residue was purified by flash silica gel chromatography (ISCO®; 40 g SepaFlash® Silica Flash Column, Eluent of 0~12% Ethyl acetate/Petroleum ether gradient @ 35 mL/min) to give 53-3 (0.51 g, 1.29 mmol, 25.6% yield, 93.173% purity) was obtained as colorless oil. LCMS: (ESI): m/z calcd. for $C_{17}H_{20}Cl_2N_3O_2$ 368.09 $[M+H]^+$, found 369.9.

A solution of 53-3 (510 mg, 1.38 mmol, 1 eq.) in dioxane (10 mL) with sat. NH₃.H₂O (9.10 g, 64.91 mmol, 10 mL, 25% purity, 46.95 eq.) was stirred at 100° C. for 48 h in a 100 mL of sealed tube. Upon completion, the reaction was partitioned between EA (30 mL) and brine (30 mL). The organic phase was separated, and the aqueous phase was extracted with EA (3×30 mL). The organic layers were combined and dried over Na₂SO₄, filtered and concentrated under reduced pressure to give crude 53-4 (470 mg, 1.29 mmol, 93.5% yield, 95.419% purity) as a yellow oil, which was directly used for the next step without further purification. LCMS: (ESI): m/z calcd. for $C_{17}H_{22}ClN_4O_2$ 349.14 $[M+H]^+$, found 349.1.

To the mixture of 53-4 (157.20 mg, 0.430 mmol, 1 eq.) in THF (4 mL) was added 9-BBN dimer (228.95 mg, 0.946 mmol, 2.2 eq.). The mixture was stirred at 50° C. for 1 h, and then cooled to 10° C. A solution of K₃PO₄ (456.39 mg, 2.15 mmol, 5 eq.) in H₂O (0.5 mL) was added, and the mixture was stirred at 10° C. for 0.2 h. Q16 (142.16 mg, 0.516 mmol, 1.2 eq.) and Pd(dppf)Cl₂ (31.46 mg, 0.043 mmol, 0.1 eq.) were added, and the mixture was stirred at 55° C. for 2 h under Ar. The mixture was partitioned between EA (20 mL) and water (10 mL). The aqueous phase was extracted with EA (3×20 mL). The organic layers were combined and washed with brine (30 mL), dried over anhydrous Na₂SO₄, filtered and concentrated under reduced pressure to give a residue. The residue was purified by column chromatography (SiO₂, Petroleum ether/Ethyl acetate (1:1) then DCM: MeOH (20:1)) to afford 53-5 (300 mg, 0.350 mmol, 77% yield, 63.729% purity) as a yellow solid. LCMS: (ESI): m/z calcd. for $C_{26}H_{28}Cl_2FN_6O_2$ 545.16 $[M+H]^+$, found 545.1.

To a solution of 53-5 (300 mg, 0.350 mmol, 63.729% purity, 1 eq.) in THF (4 mL) was added HCl (4 M aq, 2 mL, 22.82 eq.). The mixture was stirred at 15° C. for 4 h, and then concentrated under reduced pressure to afford a residue. The residue was purified by prep-HPLC (column: Phenomenex Gemini-NX 80*40 mm*3 um; mobile phase: [water (0.05% NH₃H₂O+10 mM NH₄HCO₃)-ACN]; B %: 34%-59%, 8 min) to give 53 (77 mg, 0.150 mmol, 42.88% yield, 98.64% purity) as an off-white solid. LCMS: (ESI): m/z calcd. $C_{23}H_{24}Cl_2FN_6O_2$ 527.12 $[M+Na]^+$, found 527.1. ¹H NMR (400 MHz, CD₃OD) δ: 8.19 (s, 1H), 7.24 (s, 1H), 7.18 (d, J=3.7 Hz, 1H), 6.94 (dd, J=1.1, 10.9 Hz, 1H), 6.56 (d, J=3.6 Hz, 1H), 4.97-4.91 (m, 1H), 4.58-4.48 (m, 1H), 3.93 (d, J=6.3 Hz, 1H), 2.92-2.71 (m, 2H), 2.09-1.96 (m, 2H), 1.93-1.79 (m, 2H), 1.23 (s, 3H). ¹⁹F NMR (400 MHz, CD₃OD) δ: −125.87.

Example 49

Compound 54

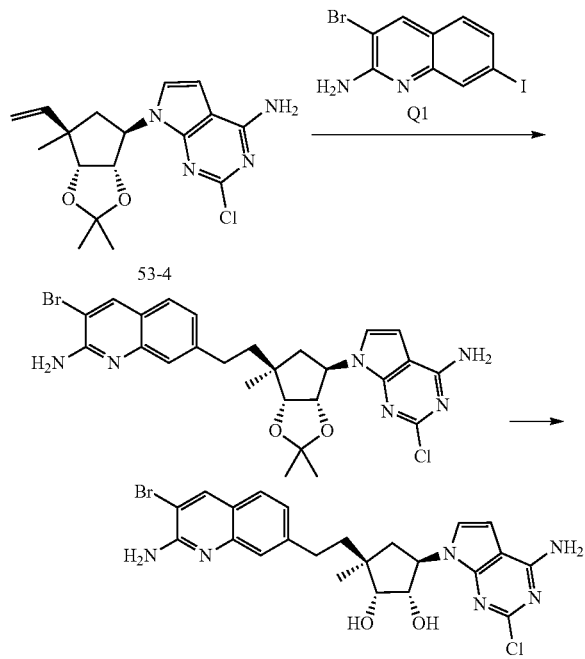

To a mixture of 53-4 (142 mg, 0.388 mmol, 1 eq.) in THF (4 mL) was added 9-BBN dimer (206.82 mg, 0.855 mmol, 2.2 eq.). The mixture was stirred at 50° C. for 1 h, and then cooled to 10° C. A solution of $K_3PO_4$ (412.26 mg, 1.94 mmol, 5 eq.) in $H_2O$ (0.5 mL) was added, and the mixture was stirred at 10° C. for 0.2 h. Q1 (162.66 mg, 0.466 mmol, 1.2 eq.) and Pd(dppf)Cl$_2$ (28.42 mg, 0.0388 mmol, 0.1 eq.) were added, and the mixture was stirred at 55° C. for 2 h under Ar. The mixture was partitioned between EA (20 mL) and water (10 mL). The aqueous phase was extracted with EA (3×20 mL). The organic layers were combined, washed with brine (30 mL), dried over anhydrous $Na_2SO_4$, filtered and concentrated under reduced pressure to give a residue. The residue was purified by column chromatography (SiO$_2$, Petroleum ether/Ethyl acetate (2:1) then DCM:MeOH (20:1)) to afford 54-1 (270 mg, 0.307 mmol, 79% yield, 65% purity) as a yellow solid. LCMS: (ESI): m/z calcd. for $C_{26}H_{29}BrClN_6O_2$ 571.11 [M+H]$^+$, found 573.0.

To a solution of 54-1 (270 mg, 0.307 mmol, 65% purity, 1 eq.) in THF (4 mL) was added HCl (4 M aq., 2 mL, 22.82 eq.), and the mixture was stirred at 15° C. for 4 h. The mixture was concentrated under reduced pressure to afford a residue. The residue was purified by prep-HPLC (column: Phenomenex Gemini-NX 80*40 mm*3 um; mobile phase: [water (0.05% NH$_3$H$_2$O+10 mM NH$_4$HCO$_3$)-ACN]; B %: 32%-56%, 8 min) to give 54 (70 mg, 0.132 mmol, 43% yield, 100% purity) as a white solid. LCMS: (ESI): m/z calcd. for $C_{23}H_{25}BrClN_6O_2$ 531.08 [M+H]$^+$, found 533.1. $^1$H NMR (400 MHz, CD$_3$OD) δ: 8.26 (s, 1H), 7.55 (d, J=8.2 Hz, 1H), 7.40 (s, 1H), 7.20 (d, J=8.2 Hz, 1H), 7.17 (d, J=3.6 Hz, 1H), 6.56 (d, J=3.6 Hz, 1H), 4.98-4.91 (m, 1H), 4.52 (t, J=6.9 Hz, 1H), 3.93 (d, J=6.2 Hz, 1H), 2.93-2.70 (m, 2H), 2.11-1.93 (m, 2H), 1.92-1.79 (m, 2H), 1.23 (s, 3H).

Example 50

Compound 55

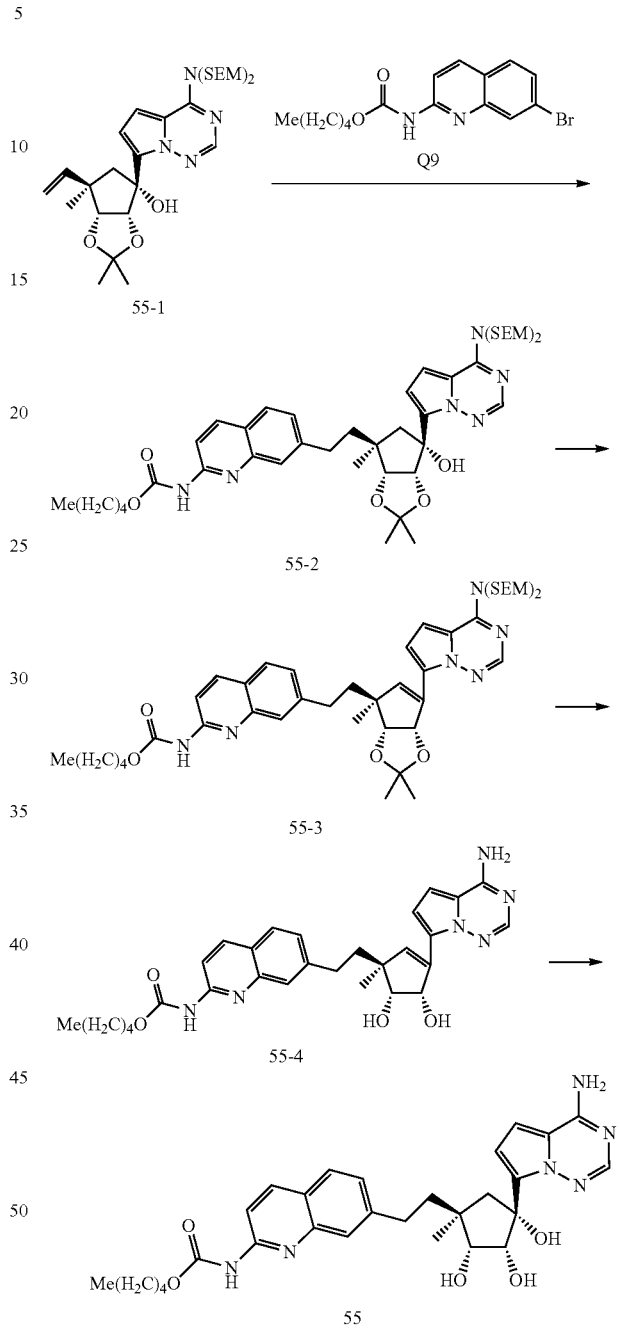

A mixture of 55-1 (613 mg, 1.04 mmol, 1 eq.) and 9-BBN dimer (627 mg, 2.59 mmol, 2.5 eq.) in THF (10 mL) was stirred at 50° C. for 2 h under Ar, and the cooled to rt. A solution of $K_3PO_4$ (1.10 g, 5.19 mmol, 5 eq.) in $H_2O$ (1 mL) was added, and the mixture was stirred for 0.5 h. Q9 (419 mg, 1.24 mmol, 1.2 eq.) and Pd(dppf)Cl$_2$ (76 mg, 0.103 mmol, 0.1 eq.) were added, and the mixture was purged with Ar (3×) and then stirred at 70° C. for 12 h under Ar. The reaction was quenched by the addition of water (50 mL) and extracted with EA (3×100 mL). The combined organic layers were washed with brine (100 mL), dried over Na₂SO₄, filtered and concentrated under reduced pressure to give a residue. The residue was purified by column chromatography (SiO₂, Petroleum ether:Ethyl acetate=30:1 to 5:1) to afford 55-2 (550 mg, 608.80 μmol, 59% yield, 94% purity) as a white solid. LCMS: (ESI): m/z calcd. for C₄₄H₆₉N₆O₇Si₂ 849.47 [M+H]⁺, found 849.4.

To a solution of 55-2 (550 mg, 647.66 μmol, 1 eq.) in DCM (10 mL) was added DAST (1.04 g, 6.48 mmol, 855.70 μL, 10 eq.) at 0° C., and the mixture was stirred at 0° C. for 2 h. The reaction was quenched by addition of water (50 mL) and extracted with EA (3×100 mL). The combined organic layers were washed with brine (100 mL), dried over Na₂SO₄, filtered and concentrated under reduced pressure to give a residue. The residue was purified by column chromatography (SiO₂, Petroleum ether:Ethyl acetate=30:1 to 5:1) to afford 55-3 (450 mg, 498.08 μmol, 76.90% yield, 92% purity) as a white solid. LCMS: (ESI): m/z calcd. for C₄₄H₆₆N₆O₆Si₂Na 853.46 [M+Na]⁺, found 853.4.

To a solution of 55-3 (440 mg, 529.36 μmol, 1 eq.) in THF (8 mL) was added HCl (4 M, 4 mL), and the mixture was stirred at 25° C. for 5 h. Upon completion, the mixture was concentrated under reduced pressure to give a residue. The residue was dissolved in a mixed solvent of t-BuOH (8 mL) and H₂O (4 mL), and PPTS (664.15 mg, 2.64 mmol, 5 eq.) was added. The mixture was stirred at 50° C. for 3 h. The mixture was concentrated under reduced pressure to give a residue. The residue was purified by prep-HPLC (column: Phenomenex Gemini-NX 80*40 mm*3 um; mobile phase: [water (0.05% NH₃H₂O+10 mM NH₄HCO₃)-ACN]; B %: 17%-47%, 8 min) to afford 55-4 (200 mg, 373.15 μmol, 71% yield, 99% purity) as a white solid. LCMS: (ESI): m/z calcd. for C₂₉H₃₅N₆O₄ 531.26 [M+H]⁺, found 531.4.

To a solution of 55-4 (175 mg, 329.80 μmol, 1 eq.) in THF (30 mL) was added PtO₂ (875 mg, 3.85 mmol, 11.68 eq.), and the mixture was stirred under H₂ (15 psi) atmosphere at 25° C. for 18 h. The mixture was filtered through a pad of Celite to remove PtO₂. The filtrate was concentrated under reduced pressure to afford a residue. The residue was purified by SEC (column: Chiralcel OJ-3 100¡Á4.6 mm I.D., 3 um; Mobile phase: A: CO₂ B: ethanol (0.05% DEA); Isocratic: 40% B; Flow rate: 2.8 mL/min; Column temp.: 35° C.; ABPR: 1500 psi; to afford 55 (70 mg, 128.79 μmol, 39% yield, 98% purity) as a white solid. LCMS: (ESI): m/z calcd. for C₂₉H₃₇N₆O₄ 533.28 [M+H]⁺, found 533.4. ¹H NMR (400 MHz, DMSO) δ: 10.33 (s, 1H), 8.24 (d, J=9.0 Hz, 1H), 7.99 (d, J=8.8 Hz, 1H), 7.81-7.75 (m, 2H), 7.53 (s, 3H), 7.32 (br d, J=8.2 Hz, 1H), 6.81 (d, J=4.4 Hz, 1H), 6.51 (d, J=4.2 Hz, 1H), 4.69 (br d, J=5.7 Hz, 1H), 4.41 (br d, J=5.3 Hz, 1H), 4.29 (br d, J=6.8 Hz, 1H), 4.11 (t, J=6.6 Hz, 2H), 3.72 (br t, J=5.5 Hz, 1H), 3.61 (br d, J=9.3 Hz, 1H), 2.80 (br dd, J=4.4, 12.3 Hz, 1H), 2.75-2.67 (m, 1H), 1.93 (br dd, J=8.7, 12.7 Hz, 1H), 1.80-1.71 (m, 1H), 1.68-1.56 (m, 3H), 1.50 (br t, J=11.8 Hz, 1H), 1.38-1.31 (m, 4H), 1.12 (s, 3H), 0.92-0.87 (m, 3H).

Example 51

Compound 56

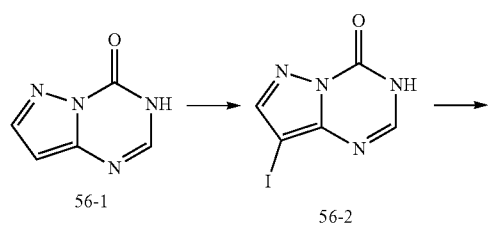

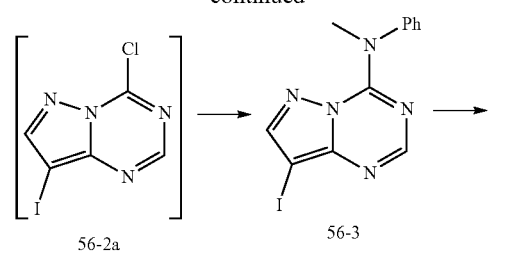

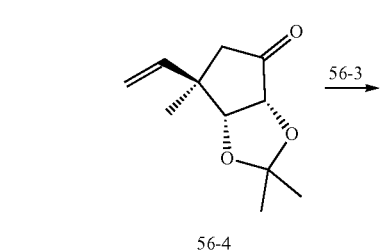

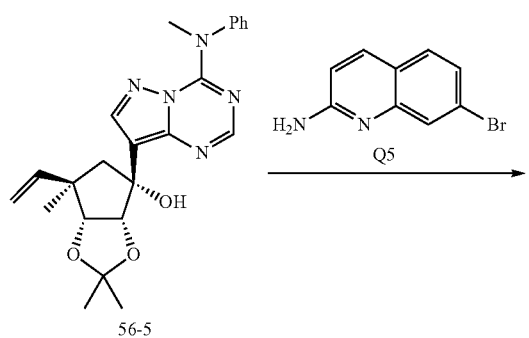

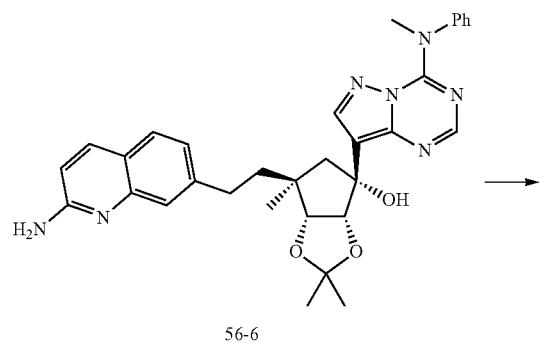

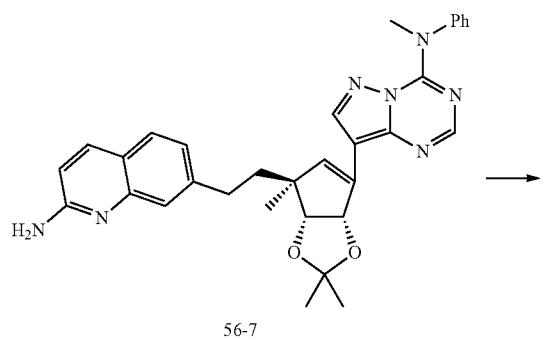

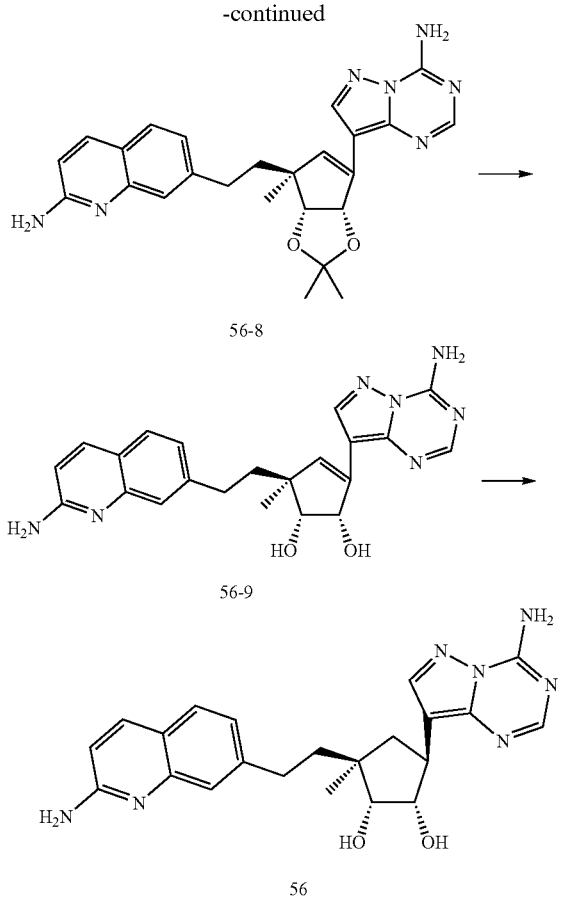

To a solution of 56-1 (5 g, 36.73 mmol, 1 eq.) in DMF (50 mL) was added NIS (10.74 g, 47.76 mmol, 1.3 eq.), and the mixture was stirred at 40° C. for 3.5 h. The mixture was poured into water (200 mL) and filtered to give a residue. The residue was triturated with water (50 mL×2) to give 56-2 (6.49 g, 23.78 mmol, 64% yield, 96% purity) as a brown solid. LCMS: (ESI): m/z calcd. for $C_5H_4IN_4O$ 262.94 [M+H]$^+$, found 262.9.

A solution of 56-2 (6.49 g, 24.77 mmol, 1 eq.), POCl$_3$ (83.73 g, 546.07 mmol, 50.75 mL, 22.05 eq.), and DMAP (9.08 g, 74.31 mmol, 3 eq.) was stirred at 105° C. for 2 h. The mixture was concentrated under reduced pressure to give 56-2a (15 g, crude) as a brown solid. To a solution of 56-2a (7.5 g, 26.74 mmol, 1 eq.) in DCM (80 mL) was added N-methylaniline (11.46 g, 106.97 mmol, 11.61 mL, 4 eq.) dropwise at 0° C., followed by addition of TEA (16.24 g, 160.45 mmol, 22.33 mL, 6 eq.). The mixture was stirred at 25° C. for 12 h. The mixture was diluted with H$_2$O (50 mL) and extracted with DCM (2×50 mL). The combined organic layers were washed with brine (50 mL), dried over anhydrous Na$_2$SO$_4$, filtered and concentrated under reduced pressure to give a residue. The residue was purified by flash silica gel chromatography (ISCO®; 120 g SepaFlash® Silica Flash Column, Eluent of 0~20% Ethyl acetate/Petroleum ether gradient @ 50 mL/min) to give 56-3 (6.68 g, 18.83 mmol, 76% yield, 99% purity) as a white solid (Note: two parallel reactions from 56-2a were carried out, then combined for purification). LCMS: (ESI): m/z calcd. for $C_{12}H_{11}IN_5$ 352.0 [M+H]$^+$, found 351.9.

To a solution of 56-3 (5.37 g, 15.29 mmol, 3 eq.) in THF (15 mL) was added i-PrMgCl.LiCl (1.3 M, 12.94 mL, 3.3 eq.) dropwise. The mixture was stirred at −20° C. for 10 min, warmed to 0° C. and then stirred at 0° C. for 1 h. A solution of 56-4 (1 g, 5.10 mmol, 1 eq.) in THF (10 mL) was added dropwise to the mixture at −20° C., and then stirred at 0° C. for 1 h 20 min. The reaction was quenched with NH$_4$Cl solution (30 mL) and extracted with EA (2×30 mL). The combined organic layers were washed with brine (50 mL), dried over anhydrous Na$_2$SO$_4$, filtered and concentrated under reduced pressure to give a residue. The residue was purified by flash C-18 column chromatography (40 g, 0%~60% MeCN, 0.5 mL NH$_3$.H$_2$O in 1 L H$_2$O, 30 mL/min) to give 56-5 (1.01 g, 2.30 mmol, 45% yield) as a white solid. LCMS: (ESI): m/z calcd. for $C_{23}H_{28}N_5O_3$ 422.21 [M+H]$^+$, found 422.1.

To a solution of 56-5 (1.01 g, 2.40 mmol, 1 eq.) in THF (25 mL) was added 9-BBN dimer (1.45 g, 5.99 mmol, 2.5 eq.). The mixture was stirred at 50° C. for 2 h under N$_2$ and then cooled to rt. A solution of K$_3$PO$_4$ (2.54 g, 11.98 mmol, 5 eq.) in H$_2$O (2.5 mL) was added, and the mixture was stirred at rt for 0.5 h. 7-bromoquinolin-2-amine Q5 (694.89 mg, 3.12 mmol, 1.3 eq.) and Pd(dppf)Cl$_2$ (175.34 mg, 0.239 mmol, 0.1 eq.) were added, and the mixture was stirred at 60° C. for 12 h. The mixture was diluted with H$_2$O (20 mL) and extracted with EA (2×20 mL). The combined organic layers were washed with brine (50 mL), dried over anhydrous Na$_2$SO$_4$, filtered and concentrated under reduced pressure to give a residue. The residue was purified by column chromatography (SiO$_2$, Petroleum ether:Ethyl acetate=2:1 to 1:1 to DCM:MeOH=100:1 to 20:1) to give 56-6 (1 g, 1.71 mmol, 71% yield) as a yellow solid. LCMS: (ESI): m/z calcd. for $C_{32}H_{36}N_7O_3$ 566.28 [M+H]$^+$, found 566.2.

To a solution of 56-6 (0.95 g, 1.68 mmol, 1 eq.) in DCM (15 mL) was added DAST (1.35 g, 8.40 mmol, 1.11 mL, 5 eq.) at 0° C., and the mixture was stirred at 0° C. for 0.5 h. reaction was quenched by addition of NaHCO$_3$ solution (10 mL), diluted with DCM (5 mL) and extracted with DCM (2×10 mL). The combined organic layers were washed with brine (20 mL), dried over anhydrous Na$_2$SO$_4$, filtered and concentrated under reduced pressure to give a residue. The residue was purified by column chromatography (SiO$_2$, DCM:MeOH=100:1 to 20:1) to give 56-7 (708 mg, 1.27 mmol, 75% yield, 98% purity) as a yellow solid. LCMS: (ESI): m/z calcd. for $C_{32}H_{34}N_7O_2$ 548.27 [M+H]$^+$, found 548.1.

To a solution of 56-7 (708 mg, 1.29 mmol, 1 eq.) in dioxane (15 mL) was added NH$_3$.H$_2$O (13.65 g, 97.37 mmol, 15 mL, 25% purity), and the mixture was stirred at 100° C. for 24 h. The mixture was concentrated under reduced pressure to give a residue. The residue was purified by column chromatography (SiO$_2$, DCM:MeOH=50:1 to 12:1) to give 56-8 (238 mg, 483.78 μmol, 37% yield, 93% purity) as a white solid. LCMS: (ESI): m/z calcd. for $C_{25}H_{28}N_7O_2$ 458.22 [M+H]$^+$, found 458.3.

To a solution of 56-8 (228 mg, 498.33 μmol, 1 eq.) in THF (4 mL) was added HCl (4 M aq., 2.00 mL), and the mixture was stirred at 25° C. for 12 h. The mixture was concentrated under reduced pressure to give a residue. The residue was purified by prep-HPLC (column: Phenomenex Gemini-NX 80*40 mm*3 um; mobile phase: [water (0.05% NH$_3$H$_2$O+ 10 mM NH$_4$HCO$_3$)-ACN]; B %: 40%-60%, 8 min) to give 56-9 (160 mg, 375.60 μmol, 75% yield, 98% purity) as a white solid. LCMS: (ESI): m/z calcd. for $C_{22}H_{24}N_7O_2$ 418.19 [M+H]$^+$, found 418.1.

To a solution of 56-9 (30 mg, 71.86 μmol, 1 eq.) in a mixed solvent of THF (7.5 mL) and MeOH (1.5 mL) was added PtO$_2$ (150 mg, 660.57 μmol, 9.19 eq.). The suspension was degassed/purged with H$_2$ (3×) and stirred under H$_2$ (15 Psi) atmosphere at 25° C. for 4 h. The mixture was filtered through a pad of Celite to remove PtO$_2$. The filtrate was concentrated under reduced pressure to give a white solid (30 mg, crude product). The crude product was combined with another batch (25 mg scale) for prep-HPLC (column: Phenomenex Gemini-NX 80*40 mm*3 um; mobile phase: [water (0.05% NH$_3$H$_2$O+10 mM NH$_4$HCO$_3$)-ACN]; B %: 12%-42%, 8 min) to give 56 (impure, 10 mg, 23.39 μmol, 98.1% purity by HPLC, NMR shows an impurity) as a white solid, which was confirmed by LCMS, HPLC and $^1$H NMR. LCMS: (ESI): m/z calcd. for C$_{22}$H$_{26}$N$_7$O$_2$ 420.2 [M+H]$^+$, found 420.3. $^1$H NMR (400 MHz, CD$_3$OD) δ: 8.28 (d, J=9.3 Hz, 1H), 8.01 (d, J=9.8 Hz, 2H), 7.79 (d, J=8.3 Hz, 1H), 7.50 (s, 1H), 7.42 (d, J=8.5 Hz, 1H), 6.99 (d, J=9.3 Hz, 1H), 4.30 (dd, J=6.3, 8.0 Hz, 1H), 3.86 (d, J=6.0 Hz, 1H), 3.44-3.36 (m, 1H), 2.97-2.80 (m, 2H), 2.03-1.94 (m, 1H), 1.89-1.74 (m, 3H), 1.22 (s, 3H).

Impure 56 was further purified by SFC (column: DAICEL CHIRALPAK AD (250 mm*30 mm, 10 um); mobile phase: [0.1% NH$_3$H$_2$O ETOH]; B %: 60%-60%, min) to give 56 (2 mg, 4.57 μmol, 19% yield, 95.9% purity) as a white solid, which was confirmed by LCMS, HPLC and $^1$H NMR. LCMS: (ESI): m/z calcd. for C$_{22}$H$_{26}$N$_7$O$_2$ 420.2 [M+H]$^+$, found 420.3. $^1$H NMR (400 MHz, CD$_3$OD) δ: 8.01 (s, s, 2H), 7.93 (d, J=9.0 Hz, 1H), 7.58 (d, J=8.2 Hz, 1H), 7.37 (s, 1H), 7.16 (dd, J=1.5, 8.1 Hz, 1H), 6.78 (d, J=8.9 Hz, 1H), 4.30 (dd, J=6.1, 8.2 Hz, 1H), 3.85 (d, J=6.1 Hz, 1H), 3.40 (td, J=8.4, 11.1 Hz, 1H), 2.90-2.71 (m, 2H), 1.99 (m, 1H), 1.87-1.72 (m, 3H), 1.21 (s, 3H).

Examples 52

Compound 57

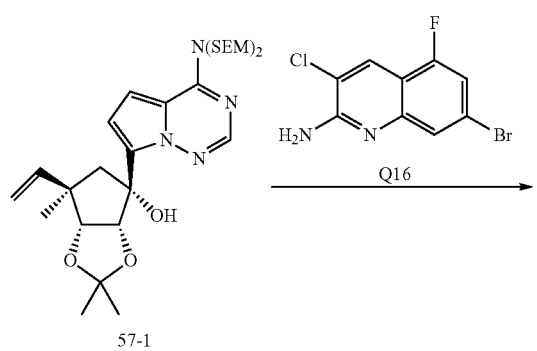

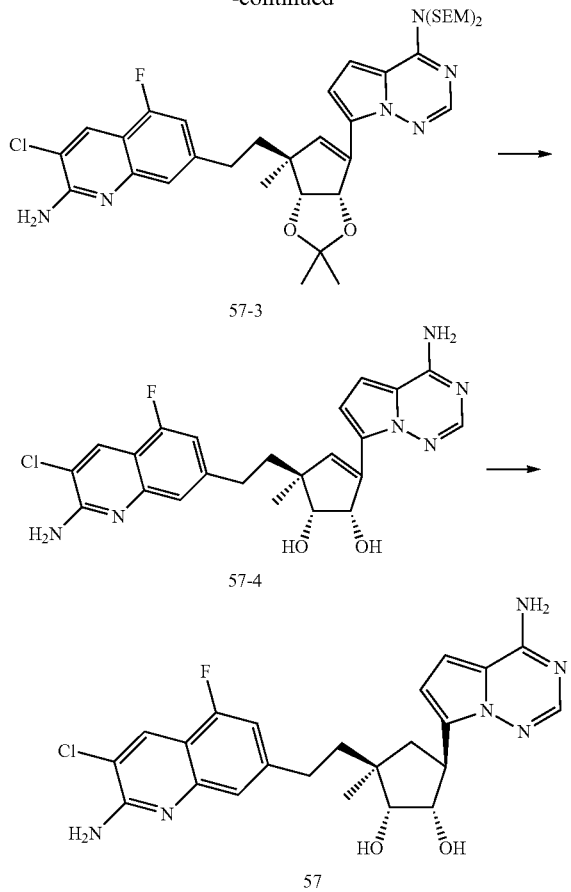

To a mixture of 57-1 (500 mg, 846.17 μmol, 1 eq.) in THF (10 mL) was added 9-BBN dimer (512 mg, 2.12 mmol, 2.5 eq.). The mixture was stirred at 50° C. for 2 h under N$_2$, and then cooled to 25° C. A solution of K$_3$PO$_4$ (898 mg, 4.23 mmol, 5 eq.) in H$_2$O (1 mL) was added, and the mixture was stirred for 0.5 h. Q16 (280 mg, 1.02 mmol, 1.2 eq.) and Pd(dppf)Cl$_2$ (62 mg, 0.084 mmol, 0.1 eq.) were added, and the mixture was purged with N$_2$ (3X). The mixture was stirred at 60° C. for 12 h. The mixture was diluted with water (5 mL) and extracted with EA (2×5 mL). The combined organic layers were washed with brine (10 mL), dried over Na$_2$SO$_4$, filtered and concentrated under reduced pressure to give a residue. The residue was purified by flash silica gel chromatography (ISCO®; 40 g SepaFlash® Silica Flash Column, Eluent of 5~20% Ethyl acetate/Petroleum ether gradient @ 30 mL/min) to afford 57-2 (415 mg, 519.60 μmol, 61% yield, 98.6% purity) as a yellow solid. LCMS: (ESI): m/z calcd. for C$_{38}$H$_{57}$ClFN$_6$O$_5$Si$_2$ 787.35 [M+H]$^+$, found 787.1.

To a solution of 57-2 (415 mg, 526.98 μmol, 1 eq.) in DCM (7 mL) was added DAST (424.72 mg, 2.63 mmol, 348.13 μL, 5 eq.) at 0° C. The mixture was stirred at 0° C. for 1 h. The mixture was diluted with water (10 mL) and extracted with DCM (2×5 mL). The combined organic layers were washed with brine (10 mL), dried over Na$_2$SO$_4$, filtered and concentrated under reduced pressure to give a residue. The residue was purified by flash silica gel chromatography (ISCO®; 40 g SepaFlash® Silica Flash Column, Eluent of 0~20% Ethyl acetate/Petroleum ether gradient @ 30 mL/min) to afford 57-3 (274 mg, 341.84 μmol, 64% yield, 96% purity) as a white solid. LCMS: (ESI): m/z calcd. for $C_{38}CH_{54}ClFN_6O_4Si_2Na$ 791.34 $[M+Na]^+$, found 791.2.

To a solution of 57-3 (207 mg, 0.269 mmol, 1 eq.) in THF (4 mL) was added HCl (aq., 4 M, 2 mL). The mixture was stirred at 25° C. for 6 h. The mixture was concentrated under reduced pressure to give a residue. The residue was dissolved in t-BuOH (10 mL) and $H_2O$ (5 mL), and PPTS (352.57 mg, 1.40 mmol, 5 eq.) was added. The mixture was stirred at 50° C. for 12 h. The mixture was concentrated under reduced pressure to give a residue. The residue was purified by reverse-phase flash column (40 g C-18 column, 0%~60% MeCN in water (0.5 mL $NH_3.H_2O$ in 1 L $H_2O$)@ 35 mL/min) to afford 57-4 (85 mg, 0.171 mmol, 63% yield, 94.8% purity) as a white solid. LCMS: (ESI): m/z calcd. for $C_{23}H_{23}ClFN_6O_2$ 469.15 $[M+H]^+$, found 469.1.

To a solution of 57-4 (30 mg, 0.063 mmol, 1 eq.) in MeOH (12 mL) was added Crabtree's catalyst (180.00 mg, 223.63 μmol, 3.5 eq.). The suspension was degassed and purged with $H_2$ (3×). The mixture was stirred under $H_2$ (15 Psi) at 25° C. for 5 h. mixture was treated with TMT (1,3,5-triazine-2,4,6-trithiol) and then kept overnight. The resulting suspension was filtered and concentrated under reduced pressure to give a residue. The residue was purified by prep-TLC ($SiO_2$, DCM:MeOH=7:1) to give a syrup (10 mg), which was further purified by SFC (column: DAICEL CHIRALPAK IG (250 mm*30 mm, 10 um); mobile phase: [0.1% $NH_3H_2O$ IPA]; B %: 60%-60%, min) to give impure 57 (8 mg, 16.87 μmol, 26% yield, 99.29% purity, contains some grease) as a yellow solid. It was combined with another batch (7 mg of impure product) and triturated with EA (2×0.5 mL) and isopropyl ether (0.5 mL) to afford 57 (10 mg, 21.06 μmol, 99.18% purity) as a white solid. LCMS: (ESI): m/z calcd. for $C_{23}H_{25}ClFN_6O_2$ 471.16 $[M+H]^+$, found 471.2. $^1$H NMR (400 MHz, $CD_3OD$) δ: 8.17 (s, 1H), 7.76 (s, 1H), 7.21 (s, 1H), 6.87 (dd, J=1.3, 10.9 Hz, 1H), 6.84 (d, J=4.4 Hz, 1H), 6.54 (d, J=4.4 Hz, 1H), 4.44 (dd, J=6.3, 7.2 Hz, 1H), 3.85 (d, J=6.1 Hz, 1H), 3.78-3.67 (m, 1H), 2.87-2.67 (m, 2H), 2.03 (dd, J=8.9, 12.9 Hz, 1H), 1.87-1.68 (m, 3H), 1.21 (s, 3H).

Example 53

Compound 58

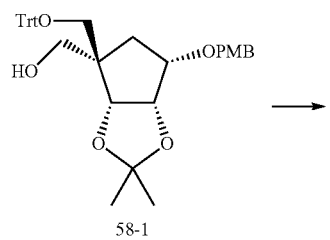

58-1

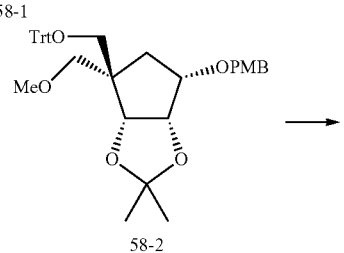

58-2

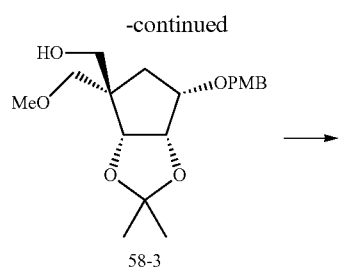

58-3

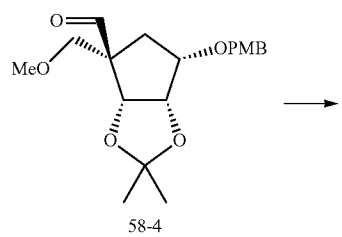

58-4

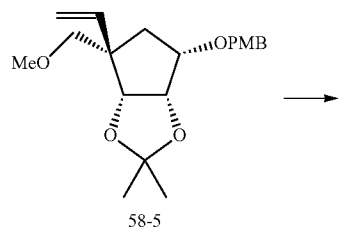

58-5

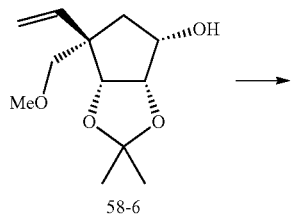

58-6

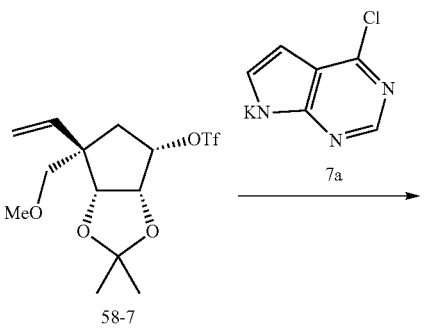

58-7

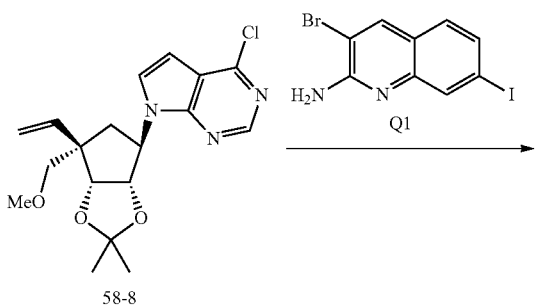

58-8

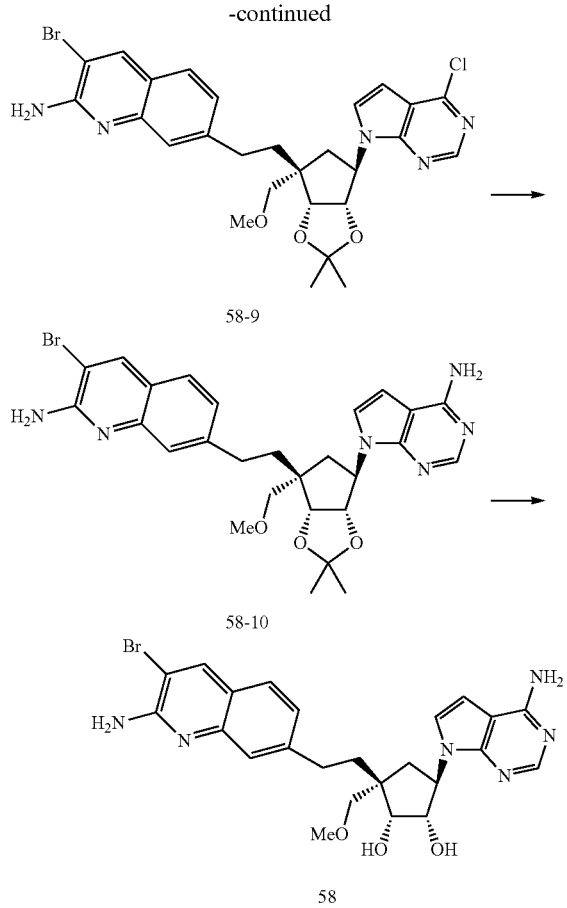

58

To a solution of 58-1 (2 g, 3.44 mmol, 1 eq.) in THF (20 mL) was added NaH (826.50 mg, 20.66 mmol, 60% purity, 6 eq.) in portions at 0° C. under $N_2$. The mixture was stirred at 0° C. for 0.5 h. MeI (8.18 g, 57.63 mmol, 3.59 mL, 16.73 eq.) was added dropwise at 0° C. The mixture was stirred at 15° C. for 12 h under $N_2$. The reaction was quenched by dropwise addition of $NH_4Cl$ (sat., aq., 50 mL) at 0° C. and extracted with EA (3×30 mL). The combined organic layer was washed with brine (30 mL), dried over $Na_2SO_4$, filtered and concentrated in vacuum. The residue was purified by a silica gel column (PE:EA=100:0 to 5:1) to give 58-2 (1.1 g, 1.63 mmol, 47% yield, 88% purity) as a colorless oil. LCMS: (ESI): m/z calcd. for $C_{38}H_{42}O_6Na$, 617.30 [M+Na]+, found 617.1.

To a solution of 58-2 (0.8 g, 1.18 mmol, 88% purity, 1 eq.) and $Et_3SiH$ (1.38 g, 11.84 mmol, 1.89 mL, 10 eq.) in DCM (20 mL) was added TEA (539.89 mg, 4.73 mmol, 350.58 μL, 4 eq.) at 0° C. The mixture was stirred at 0° C. for 0.5 h. The reaction was quenched with sat. $NaHCO_3$ solution (30 mL) and extracted with EA (3×30 mL). The combined organic layers were washed with brine (90 mL), dried over anhydrous $Na_2SO_4$, filtered and concentrated under reduced pressure to give a residue. The residue was purified by flash silica gel chromatography (ISCO®; 12 g CombiFlash® Silica Flash Column, Eluent of 0~50% Ethyl acetate/Petroleum ether gradient @ 35 mL/min) to afford 58-3 (0.31 g, 0.859 mmol, 97% purity, 74% yield) as a colorless syrup. LCMS: (ESI): m/z calcd. for $C_{19}H_{28}O_6Na$ 375.2, [M+Na]+, found 375.2.

To a solution of 58-3 (0.31 g, 0.859 mmol, 1 eq.) in $CH_3CN$ (60 mL) was added IBX (738.93 mg, 2.64 mmol, 3 eq.). The mixture was stirred at 60° C. for 3 h. The mixture was cooled to 10° C. and diluted with EA (100 mL). The precipitation was filtered to move insoluble matters, and the filtrate was concentrated to afford 58-4 (0.34 g, crude) as a yellow gum. LCMS: (ESI): m/z calcd. for $C_{19}H_{30}O_6N$ 368.2, [M+$NH_4$]+, found 368.3.

To a solution of $MePPh_3Br$ (980.18 mg, 2.74 mmol, 5 eq.) in THF (20 mL) was added t-BuOK (1 M in THF, 2.20 mL, 4 eq.), and the mixture was stirred at 10° C. for 0.5 h. A solution of 58-4 (0.34 g, 0.549 mmol, 56.557% purity, 1 eq.) in THF (10 mL) was added. The mixture was stirred at 10° C. for 1 h. The reaction was quenched with sat. $NH_4Cl$ (30 mL). The mixture was extracted with EA (3×30 mL) and washed with brine (60 mL). The separated organic layer was dried over anhydrous $Na_2SO_4$, filtered and concentrated to afford a residue. The residue was purified by flash silica gel chromatography (ISCO®; 25 g CombiFlash® Silica Flash Column, Eluent of 0~20% Ethyl acetate/Petroleum ether gradient @ 35 mL/min) to afford 58-5 (210 mg, 0.557 mmol, 92.4% purity, 63% yield over 2 steps) as a colorless gum. LCMS: (ESI): m/z calcd. for $C_{20}H_{32}O_5N$ 366.2, [M+$NH_4$]+ found 366.3.

To a solution of 58-5 (160 mg, 0.424 mmol, 92.4% purity, 1 eq.) in a mixed solvent of DCM (6 mL) and $H_2O$ (0.6 mL) was added DDQ (192.64 mg, 0.849 mmol, 2 eq.). The mixture was stirred at 10° C. for 18 h. The reaction was quenched with sat. $NaHCO_3$ solution (20 mL), and then extracted with EA (3×20 mL). The combined organic layers were washed with brine (60 mL), dried over anhydrous $Na_2SO_4$, filtered and concentrated under reduced pressure to give a crude. The residue was purified by flash silica gel chromatography (ISCO®; 25 g CombiFlash® Silica Flash Column, Eluent of 0~25% Ethyl acetate/Petroleum ether gradient @ 35 mL/min) to afford 58-6 (90 mg, 0.394 mmol, 93% yield) as a light yellow gum. $^1$H NMR (400 MHz, $CDCl_3$) δ: 5.83 (dd, J=11.0, 17.8 Hz, 1H), 5.20 (d, J=11.0 Hz, 1H), 5.09 (d, J=18.1 Hz, 1H), 4.54 (dd, J=0.9, 5.4 Hz, 1H), 4.50-4.44 (m, 1H), 4.05 (ddd, J=4.4, 6.0, 10.4 Hz, 1H), 3.58 (d, J=8.8 Hz, 1H), 3.34 (s, 3H), 3.29 (d, J=8.8 Hz, 1H), 2.42 (d, J=10.0 Hz, 1H), 1.99 (dd, J=6.4, 12.2 Hz, 1H), 1.52 (s, 3H), 1.47 (d, J=12.0 Hz, 1H), 1.38 (s, 3H).

To a solution of 58-6 (100 mg, 0.438 mmol, 1 eq.) and pyridine (138.6 mg, 1.75 mmol, 0.141 mL, 4 eq.) in DCM (5 mL) was added $Tf_2O$ (185.3 mg, 0.657 mmol, 0.108 mL, 1.5 eq.) dropwise at 0° C. The mixture was stirred at 0° C. for 2 h. The reaction was quenched with $H_2O$ (10 mL), and then extracted with DCM (3×20 mL). The combined organic layers were washed with brine (60 mL), dried over anhydrous $Na_2SO_4$, filtered and concentrated under reduced pressure to afford 58-7 (160 mg, crude, 0.444 mmol) as a brown oil. $^1$H NMR (400 MHz, $CDCl_3$) δ: 5.84 (dd, J=11.2, 17.9 Hz, 1H), 5.27 (d, J=11.0 Hz, 1H), 5.13 (d, =17.8 Hz, 1H), 4.96 (td, J=6.3, 10.8 Hz, 1H), 4.64 (t, J=5.4 Hz, 1H), 4.53 (d, J=5.0 Hz, 1H), 3.59 (d, J=8.8 Hz, 1H), 3.38-3.36 (m, 1H), 3.35 (s, 3H), 2.21 (dd, J=6.8, 12.3 Hz, 1H), 2.13-1.99 (m, 1H), 1.54 (s, 3H), 1.37 (s, 3H).

To a solution of 7a (127.7 mg, 666 μmol, 1.5 eq.) in DMF (2 mL) was added a solution of 58-7 (160 mg, 0.444 mmol, 1 eq.) in DMF (2 mL). The mixture was stirred at 10° C. for 48 h. The mixture was added $H_2O$ (10 mL), and then extracted with EA (3×10 mL). The combined organic layers were washed with brine (30 mL), dried over anhydrous $Na_2SO_4$, filtered and concentrated under reduced pressure to give a residue. The residue was purified by flash silica gel chromatography (ISCO®; 12 g CombiFlash® Silica Flash Column, Eluent of 0~10% Ethyl acetate/Petroleum ether gradient @ 30 mL/min) to afford 58-8 (90 mg, 0.242 mmol, 97.9% purity, 55% yield over 2 steps) as a colorless gum. LCMS: (ESI): m/z calcd. for $C_{18}H_{23}O_3N_3Cl$ 364.1, [M+H]$^+$, found 364.2.

To a solution of 58-8 (46 mg, 0.124 mmol, 97.953% purity, 1 eq.) in THF (3 mL) was added 9-BBN dimer (65.94 mg, 0.272 mmol, 2.2 eq.). The mixture was stirred at 50° C. for 1.5 h, and then cooled to 10° C. A solution of $K_3PO_4$ (131.44 mg, 0.619 mmol, 5 eq.) in $H_2O$ (0.3 mL) was added, and the mixture was stirred at 10° C. for 0.5 h. Q1 (51.86 mg, 0.149 mmol, 1.2 eq.) and Pd(dppf)Cl$_2$ (9.06 mg, 0.012 mmol, 0.1 eq.) were added. The mixture was degassed with $N_2$ (3×) and stirred at 50° C. for 2 h. The mixture was diluted with brine (10 mL), and then extracted with EA (3×10 mL). The combined organic layers were washed with brine (30 mL), dried over anhydrous $Na_2SO_4$, filtered and concentrated under reduced pressure to give a residue. The residue was purified by flash silica gel chromatography (ISCO®; 12 g CombiFlash® Silica Flash Column, Eluent of 0~50% Ethyl acetate/Petroleum ether gradient @ 30 mL/min) to afford 58-9 (36 mg, 0.058 mmol, 47% yield, 94.2% purity) as a yellow gum. LCMS: (ESI): m/z calcd. for $C_{27}H_{30}BrClN_5O_3$ 586.1, [M+2+H]$^+$, found 588.1.

To a solution of 58-9 (36 mg, 0.058 mmol, 94% purity, 1 eq.) in dioxane (5 mL) was added $NH_3H_2O$ (4.55 g, 32.46 mmol, 5 mL, 25% purity, 561.78 eq.). The mixture was stirred at 100° C. for 48 h in a 30 mL sealed tube. The mixture was treated with brine (10 mL) and extracted with EA (3×20 mL). The combined organic layers were washed with brine (50 mL), dried over anhydrous $Na_2SO_4$, filtered and concentrated under reduced pressure to afford 58-10 (34 mg, 0.050 mmol, 87% yield, 84% purity) as a brown syrup. LCMS: (ESI): m/z calcd. for $C_{27}H_{32}O_3N_6Br$ 567.2, [M+H]$^+$, found 567.2.

To a solution of 58-10 (34 mg, 0.050 mmol, 83.799% purity, 1 eq.) in THF (4 mL) was added HCl (4 M aq., 2 mL, 159.34 eq.). The mixture was stirred at 10° C. for 3 h. The mixture was concentrated to give the residue. The residue was purified by prep-HPLC (basic condition; column: Phenomenex Gemini-NX 80*40 mm*3 um; mobile phase: [water (0.05% $NH_3.H_2O$+10 mM $NH_4HCO_3$)-ACN]; B %: 23%-49%, 8 min) to afford 58 (17 mg, 0.032 mmol, 64% yield, 99.1% purity) as a white solid. LCMS: (ESI): m/z calcd. for $C_{24}H_{28}O_3N_6Br$ 527.1, [M+2+H]$^+$, found 529.2. $^1$H NMR (400 MHz, CD$_3$OD) δ: 8.27 (s, 1H), 8.08 (s, 1H), 7.57 (d, J=8.3 Hz, 1H), 7.43 (s, 1H), 7.23 (d, J=3.8 Hz, 1H), 7.20 (d, J=8.3 Hz, 1H), 6.59 (d, J=3.5 Hz, 1H), 5.00 (q, J=9.5 Hz, 1H), 4.62 (dd, J=5.4, 8.9 Hz, 1 H), 3.99 (d, J=5.3 Hz, 1H), 3.70 (d, J=9.0 Hz, 1H), 3.51 (d, J=9.3 Hz, 1H), 3.43 (s, 3H), 2.92-2.70 (m, 2H), 2.17 (dd, J=9.3, 13.6 Hz, 1H), 1.99 (br t, J=8.4 Hz, 2H), 1.88 (dd, J=10.0, 13.6 Hz, 1H).

Example 54

Compound 59

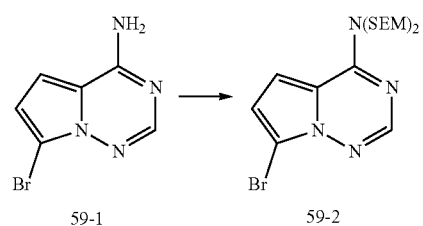

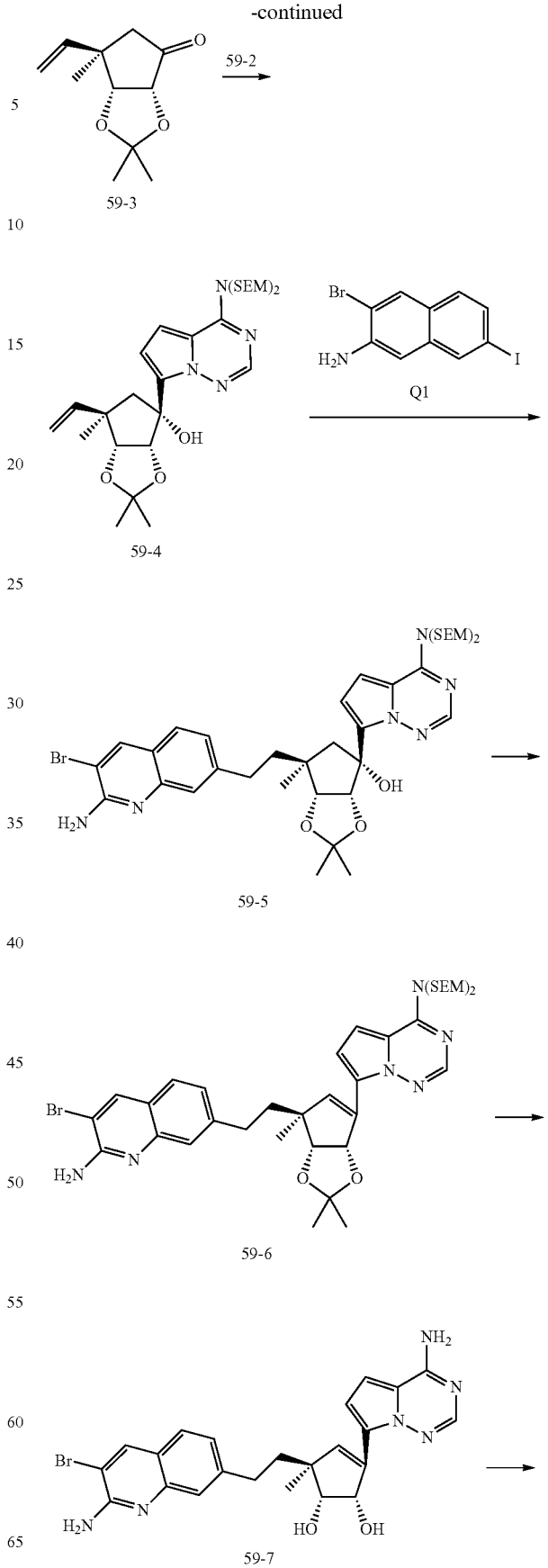

-continued

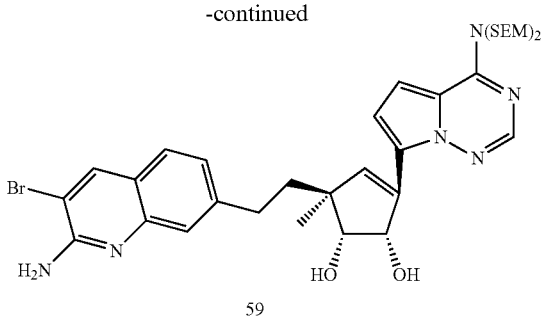

59

To a solution of 59-1 (2 g, 9.39 mmol, 1 eq.) in DMF (20 mL) was added NaH (938.7 mg, 23.47 mmol, 60% purity, 2.5 eq.) at 0° C., and the mixture was stirred at 0° C. for 0.5 h. SEM-Cl (3.29 g, 19.72 mmol, 3.49 mL, 2.1 eq.) was added at 0° C., and the mixture was stirred at 20° C. for 4 h. The reaction was quenched by the addition of $H_2O$ (60 mL) at 20° C., and then extracted with EA (2×50 mL). The combined organic layers were washed with brine (20 mL), dried over $Na_2SO_4$, filtered, and concentrated under reduced pressure to give a residue. The residue was purified by flash silica gel chromatography (ISCO®; 40 g SepaFlash® Silica Flash Column, Eluent of 0~4% Ethyl acetate/Petroleum ether gradient @ 45 mL/min) to afford 59-2 (2.64 g, 5.35 mmol, 57% yield, 96% purity) as a colorless oil. LCMS: (ESI): m/z calcd. for $C_{18}H_{34}BrN_4O_2Si_2$ 475.13 $[M+2+H]^+$, found 475.0.

To a solution of 59-2 (3.62 g, 7.64 mmol, 3 eq.) in THF (15 mL) at −15° C. was added iPrMgBr.LiCl (1.3 M in THF, 5.88 mL, 3 eq.) dropwise. The mixture was stirred at −15° C. for 10 min, then allowed to warm to 0° C., and stirred at 0° C. for 1 h. A solution of 59-3 (500 mg, 2.55 mmol, 1 eq.) in THF (5 mL) was added dropwise at −15° C., and the mixture was stirred at 0° C. for 10 min. The reaction was quenched by the addition of $NH_4Cl$ (sat. aq., 10 mL), diluted with $H_2O$ (40 mL) and extracted with EA (2×50 mL). The combined organic layers were washed with brine (30 mL), dried over $Na_2SO_4$, filtered and concentrated under reduced pressure to give a residue. The residue was purified by flash silica gel chromatography (ISCO®; 40 g SepaFlash® Silica Flash Column, Eluent of 0~8% Ethyl acetate/Petroleum ether gradient @ 45 mL/min) to afford 59-4 (1.28 g, 2.08 mmol, 82% yield, 96% purity) as a colorless oil. LCMS: (ESI): m/z calcd. for $C_{29}H_{51}N_4O_5Si_2$ 591.33 $[M+H]^+$, found 591.3.

A mixture of 59-4 (680 mg, 1.10 mmol, 96% purity, 1.0 eq.) and 9-BBN dimer (668.43 mg, 2.76 mmol, 2.5 eq.) in THF (15 mL) was stirred at 50° C. for 1.5 h under $N_2$, and then cooled to 20° C. A solution of $K_3PO_4$ (1.17 g, 5.52 mmol, 5 eq.) in $H_2O$ (3 mL) was added, and the mixture was stirred for 0.5 h. Q1 (462.6 mg, 1.33 mmol, 1.2 eq.) and Pd(dppf)Cl$_2$ (80.8 mg, 0.11 mmol, 0.1 eq.) were added. The mixture was purged with $N_2$ (3×) and stirred at 60° C. for 2 h. The mixture was diluted with $H_2O$ (30 mL) and extracted with EA (2×50 mL). The combined organic layers were washed with brine (20 mL), dried over $Na_2SO_4$, filtered, and concentrated under reduced pressure to give a residue. The residue was purified by flash silica gel chromatography (ISCO®; 40 g SepaFlash® Silica Flash Column, Eluent of 0~31% Ethyl acetate/Petroleum ether gradient @ 45 mL/min) to afford 59-5 (663 mg, 773.8 μmol, 70% yield, 95% purity) as a colorless oil. LCMS: (ESI): m/z calcd. for $C_{38}H_{58}BrN_6O_5Si_2$ 815.31 $[M+2+H]^+$, found 815.3.

To a solution of 59-5 (663.0 mg, 773.80 μmol, 95% purity, 1 eq.) in DCM (10 mL) was added DAST (623.64 mg, 3.87 mmol, 511.18 μL, 5 eq.) at 0° C., and the mixture was stirred at 0° C. for 1 h. The reaction was quenched by addition sat. $NaHCO_3$ (2 mL), diluted with $H_2O$ (20 mL) and extracted with EA (2×50 mL). The combined organic layers were washed with brine (10 mL), dried over $Na_2SO_4$, filtered and concentrated under reduced pressure to give a residue. The residue was purified by flash silica gel chromatography (ISCO®; 40 g SepaFlash® Silica Flash Column, Eluent of 0~27% Ethyl acetate/Petroleum ether gradient @ 45 mL/min) to afford 59-6 (249 mg, 303.45 μmol, 39% yield, 97% purity) as a white solid. LCMS: (ESI): m/z calcd. for $C_{38}H_{56}BrN_6O_4Si_2$ 797.30 $[M+2+H]^+$, found 797.3.

To a solution of 59-6 (249 mg, 303.45 μmol, 97% purity, 1 eq.) in THF (6 mL) was added HCl (4 M, 2.91 mL, 38.36 eq.) at 20° C. under $N_2$, and the mixture was stirred at 20° C. for 5 h. The mixture was concentrated under reduced pressure to give a residue. The residue was dissolved in a mixed solvent of $H_2O$ (12 mL) and t-BuOH (12 mL). PPTS (762.57 mg, 3.03 mmol, 10 eq.) was added at 20° C. The mixture was stirred at 50° C. for 12 h, and concentrated under reduced pressure to give a residue. The residue was purified by flash column (C18 column, 0.5% $NH_3.H_2O$-ACN), and then triturated with EA (2 mL) at 20° C. for 2 h. The solid was collected by filtration and dried under reduced pressure to afford 59-7 (80 mg, 142.12 μmol, 47% yield, 88% purity) as an off-white solid. LCMS: (ESI): m/z calcd. for $C_{23}H_{24}BrN_6O_2$ 497.11 $[M+2+H]^+$, found 497.2.

To a solution of 59-7 (50 mg, 88.8 μmol, 88% purity, 1 eq.) in MeOH (20 mL) was added Crabtree's catalyst (600 mg, 745.44 μmol, 8.39 eq.). The mixture was degassed under vacuum and purged with $H_2$ several times, and stirred under $H_2$ (15 psi) at 20° C. for 24 h. TMT (1, 3, 5-triazine-2, 4, 6-trithiol) was added, and the mixture was stirred at 20° C. for 15 min. The insoluble materials were removed by filtration. The filtrate was concentrated under reduced pressure to give a residue. The residue was purified by prep-TLC (SiO$_2$, DCM:MeOH=10:1) to afford the impure product (13 mg, 23.52 μmol, 26% yield, 90% purity) as a yellow solid, which was combined with other batches to give 19 mg of the impure product. The impure product (19 mg) was purified by prep-HPLC (basic condition, column: Phenomenex Gemini-NX 80*40 mm*3 um; mobile phase: [water (0.05% $NH_3H_2O$+10 mM $NH_4HCO_3$)-ACN]; B %: 30%-50%, 8 min) to give 59 (9 mg, 21.06 μmol, 98% purity) as a white solid. TLCMS: (ESI): m/z calcd. for $C_{23}H_{26}BrN_6O_2$ 499.12 $[M+2+H]^+$, found 499.2. $^1H$ NMR (400 MHz, CD$_3$OD) δ: 8.25 (s, 1H), 7.76 (s, 1H), 7.55 (d, J=8.3 Hz, 1H), 7.38 (s, 1H), 7.15 (d, J=8.3 Hz, 1H), 6.84 (d, J=4.3 Hz, 1H), 6.54 (d, J=4.3 Hz, 1H), 4.44 (t, J=6.8 Hz, 1H), 3.86 (d, J=6.3 Hz, 1H), 3.69-3.78 (m, 1H), 2.70-2.88 (m, 2H), 2.00-2.09 (m, 2H), 1.72-1.79 (m, 2H), 1.23 (s, 3H).

Example 55

Compound 60

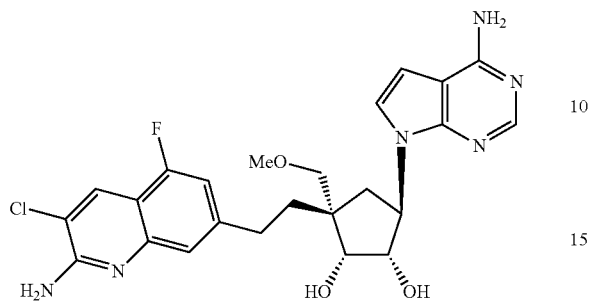

Compound 60 was prepared similarly as described for 58, using 58-8, and using Q16 instead of Q1. $^1$H NMR (400 MHz, CD$_3$OD) δ: 8.21 (s, 1H), 8.19-8.05 (m, 1H), 7.28 (s, 1H), 7.25 (d, J=3.5 Hz, 1H), 6.96 (d, J=11.3 Hz, 1H), 6.61 (d, J=3.5 Hz, 1H), 5.06-4.96 (m, 1H), 4.66 (dd, J=5.3, 9.0 Hz, 1H), 3.99 (d, J=5.3 Hz, 1H), 3.71 (d, J=9.5 Hz, 1H), 3.51 (d, J=9.3 Hz, 1H), 3.45 (s, 3H), 2.91-2.70 (m, 2H), 2.17 (dd, J=9.4, 13.7 Hz, 1H), 2.00 (t, J=8.5 Hz, 2H), 1.91 (dd, J=9.8, 13.6 Hz, 1H); $^{19}$F NMR (376 MHz, CD$_3$OD) δ: −125.91 (s, 1F)

Example 56

Description of LCMS Conditions

| Method Code | Instrument | Column | Mobile Phase | Gradient | Flow mL/min | Run time (min) |
|---|---|---|---|---|---|---|
| 1 | A | Xbridge Shield RP-18.5 um, 2.1 * 50 mm | A: water(4L) + NH$_3$•H$_2$O(0.8 mL) B: acetonitrile | 0%-60% (solvent B) over 6 minutes and holding at 60% for 0.5 minutes | 0.8 | 7 |
| 2 | A | Xtimate C18 2.1 * 30 mm, 3 um | A: water(4L) + TFA (1.5 mL) B: acetonitrile (4L) + TFA(0.75 mL) | 0%-30% (solvent B) over 3 minutes and holding at 30% for 0.5 minutes | 0.8 | 4 |
| 3 | B | Xtimate C18 2.1 * 30 mm, 3 um | A: water(4L) + TFA(1.5mL) B: acetonitrile 4L) + TFA(0.75 mL) | 0%-60% (solvent B) over 0.9 minutes and holding at 60% for 0.6 minutes | 1.2 | 2 |
| 4 | A | Xtimate C18 2.1 * 30 mm, 3 um | A: water(4L) + TFA(1.5 mL) B: acetonitrile | 0%-30% (solvent B) over 0.9 minutes and holding at 30% for 0.6 minutes | 1.2 | 2 |
| 5 | A | Xbridge Shield RP-18.5 um, 2.1 * 50 mm | A: water(4L) + NH$_3$•H$_2$O(0.8 mL) B: acetonitrile | 0%-30% (solvent B) over 2 minutes and holding at 30% for 0.48 minutes | 1 | 3 |
| 6 | A | Xtimate C18 2.1 * 30 mm, 3 um | A: water(4L) + TFA(1.5 mL) B: acetonitrile (4L) + TFA(0.7 5 mL) | 0%-60% (solvent B) over 6 minutes and holding at 60% for 0.5 minutes | 0.8 | 7 |
| 7 | A | Xbridge Shield RP-18.5 um, 2.1 * 50 mm | A: water(4L) + NH$_3$•H$_2$O(0.8 mL) B: acetonitrile | 10%-80% (solvent B) over 6 minutes and holding at 80% for 0.5 minutes | 0.8 | 7 |
| 8 | A | Xbridge Shield RP-18.5 um, 2.1 * 50 mm | A: water(4L) + NH$_3$•H$_2$O(0.8 mL) B: acetonitrile | 10%-80% (solvent B) over 2 minutes and holding at 80% for 0.48 minutes | 1 | 3 |
| 9 | A | Xtimate C18 2.1 * 30 mm, 3 um | A: water(4L) + TFA(1.5 mL) B: acetonitrile 4L) + TFA(0.75 mL) | 0%-30% (solvent B) over 6 minutes and holding at 30% for 0.5 minutes | 0.8 | 7 |

| Method Code | Instrument | Column | Mobile Phase | Gradient | Flow mL/min | Run time (min) |
|---|---|---|---|---|---|---|
| 10 | A | Xbridge Shield RP-18.5um, 2.1 * 50 mm | A: water(4L) + NH₃•H₂O(0.8 mL) B: acetonitrile | 0%-60% (solvent B) over 2 minutes and holding at 60% for 0.48 minutes | 1 | 3 |
| 11 | A | Xtimate C18 2.1 * 30 mm, 3um | A: water(4L) + TFA(1.5 mL) B: acetonitrile | 0%-60% (solvent B) over 6 minutes and holding at 60% for 0.5 minutes | 0.8 | 7 |
| 12 | A | Xtimate C18 2.1 * 30 mm, 3 um | A: water(4L)+ TFA(1.5mL) B: acetonitrile | 0%-30% (solvent B) over 6 minutes and holding at 30% for 0.5 minutes | 0.8 | 7 |

A = SHIMADZU LC20-MS2020; B = Agilent LC1200-MS6110; Column Temp. = 50° C.

| Compound | Rt (min) | [M + H]⁺ | Method code |
|---|---|---|---|
| 1 | 4.125 | 499.1 | 1 |
| 2 | 2.663 | 517.2 [M + Na]⁺ | 2 |
| 3 | 1.177 | 516.1 | 3 |
| 4 | 1.299 | 495.2 | 4 |
| 5 | 2.546 | 419.2 | 5 |
| 6 | 2.498 | 419.2 | 5 |
| 7 | 4.160 | 421.0 | 1 |
| 8 | 4.209 | 421.1 | 1 |
| 9 | 4.051 | 503.1 | 1 |
| 10 | 4.114 | 433.3 | 1 |
| 11 | 4.364 | 487.1 | 1 |
| 12 | 2.604 | 419.3 | 7 |
| 13 | 3.681 | 417.2 | 1 |
| 14 | 4.448 | 459.2 | 1 |
| 15 | 1.548 | 497.1 | 8 |
| 16 | 3.260 | 407.2 | 1 |
| 17 | 2.022 | 499.1 | 1 |
| 18 | 4.048 | 453.3 | 9 |
| 19 | 4.187 | 451.2 | 1 |
| 20 | 2.040 | 533.5 | 8 |
| 20A | 4.163 | 533.3 | 7 |
| 21 | 2.596 | 436.2 | 6 |
| 21A | 2.610 | 436.3 | 6 |
| 22 | 1.705 | 418.2 | 10 |
| 23 | 2.045 | 469.2 | 10 |
| 24 | 3.333 | 420.3 | 1 |
| 25A | 4.064 | 557.3 | 7 |
| 26 | 4.241 | 559.5 | 7 |
| 26-A | 4.168 | 559.3 | 7 |
| 27 | 1.946 | 444.2 | 10 |
| 28 | 1.664 | 467.2 | 8 |
| 29 | 1.760 | 450.2 | 10 |
| 30 | 4.450 | 471.2 | 9 |
| 31 | 1.939 | 475.2 | 10 |
| 32 | 2.892 | 470.3 | 6 |
| 33 | 4.180 | 567.2 | 7 |
| 34 | 1.794 | 488.4 | 8 |
| 35 | 1.764 | 423.2 | 10 |
| 36 | 4.249 | 475.1 | 1 |
| 37 | 3.764 | 437.2 | 9 |
| 38 | 2.561 | 418.3 | 2 |
| 39 | 2.905 | 470.2 | 2 |
| 40 | 3.457 | 487.3 | 9 |
| 41 | 2.912 | 455.2 | 11 |
| 42 | 4.523 | 454.1 | 12 |
| 43 | 3.710 | 488.2 | 7 |
| 44 | 4.259 | 482.2 | 1 |
| 45 | 3.745 | 500.2 | 1 |
| 46 | 4.207 | 431.2 | 1 |
| 47 | 3.688 | 397.3 | 1 |
| 48 | 4.037 | 419.3 | 1 |
| 49 | 3.176 | 470.1 | 6 |
| 50 | 3.275 | 516.1 | 6 |
| 51 | 1.724 | 483.3 | 8 |
| 52 | 3.197 | 481.2 | 7 |
| 53 | 3.593 | 527.1* | 6 |
| 54 | 3.342 | 533.1** | 6 |
| 55 | 4.501 | 533.4 | 7 |
| 56 | 3.760 | 420.3 | 1 |
| 57 | 4.527 | 471.16 | 1 |
| 58 | 3.106 | 529.2 | 7 |
| 59 | 4.311 | 499.2** | 1 |
| 60 | 3.299 | 501.2 | 7 |

*[M + Na]⁺ **[M + 2 + H]⁺

Example 57

Additional Compounds

The foregoing syntheses are exemplary and can be used as a starting point to prepare a large number of additional compounds. Examples of compounds of Formula (I), and pharmaceutically acceptable salts thereof, that can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

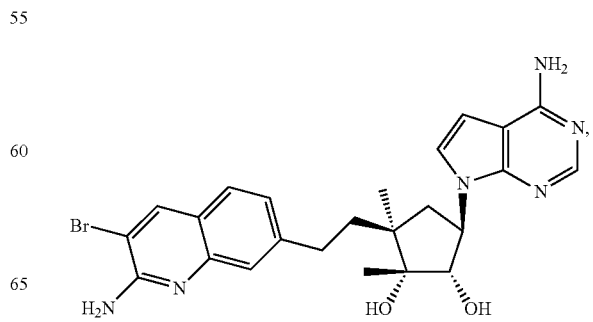

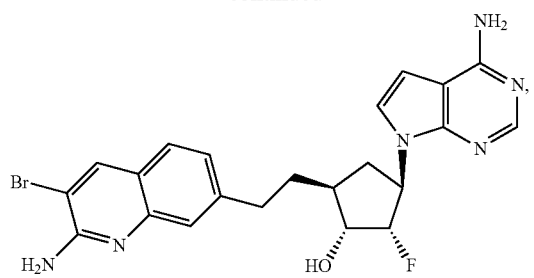
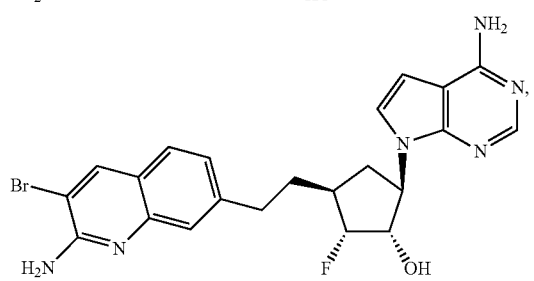
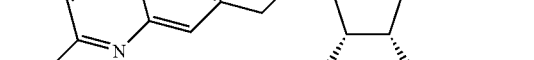
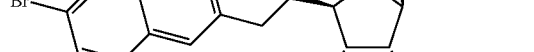
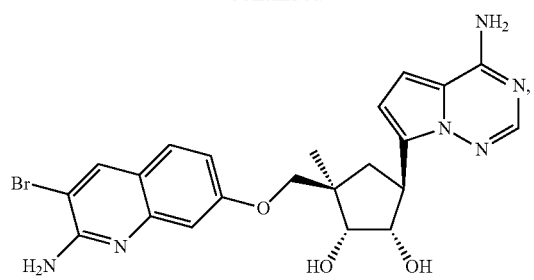
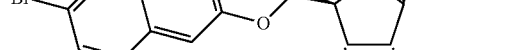

269
-continued
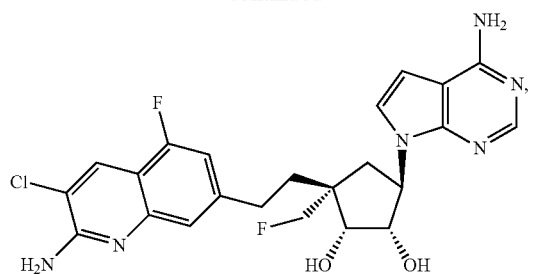
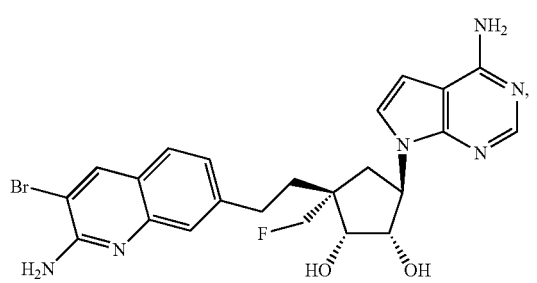
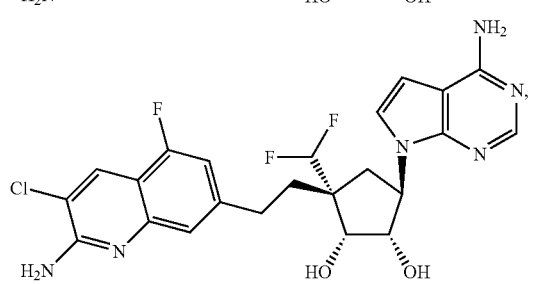
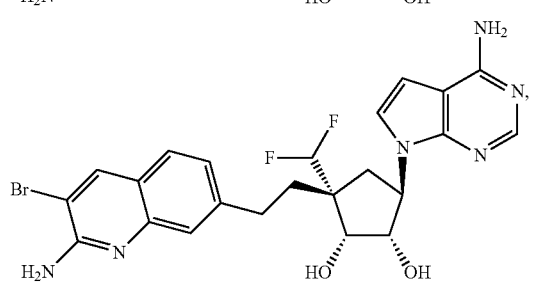
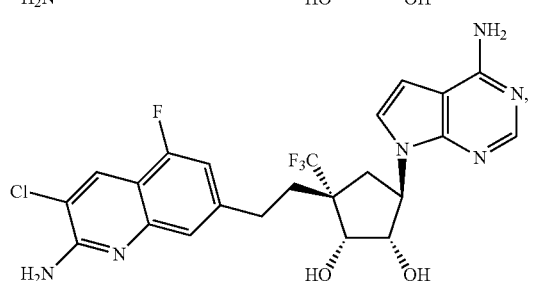
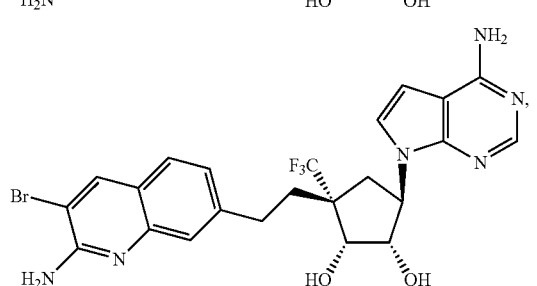
270
-continued
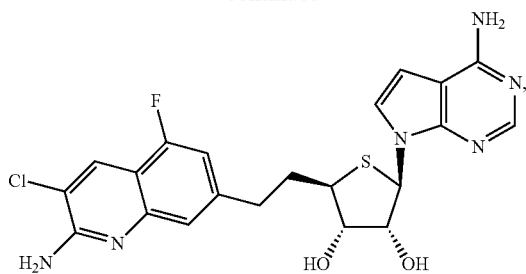
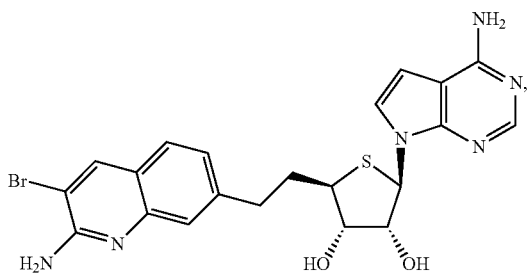
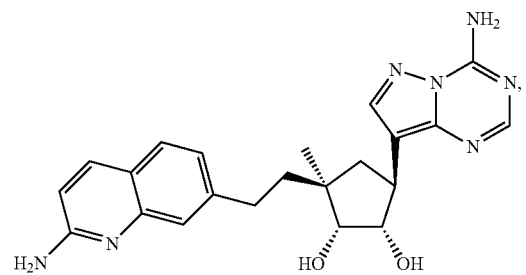
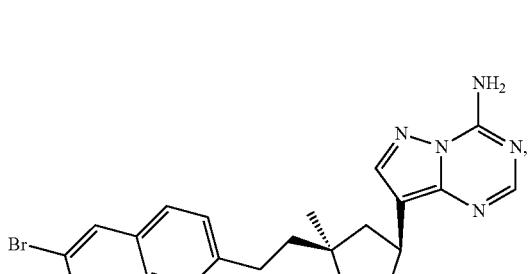
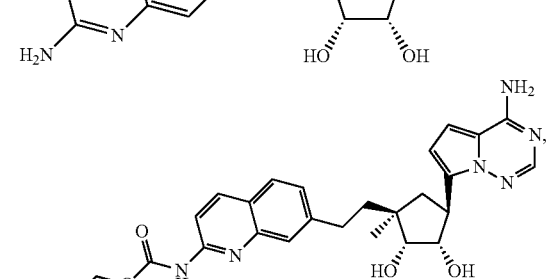
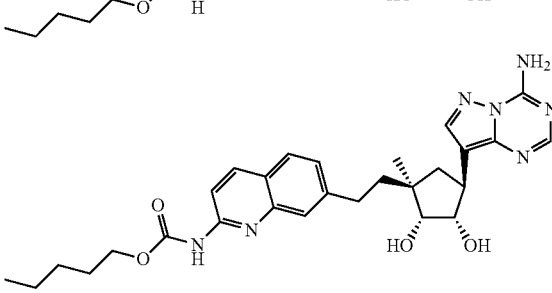

-continued
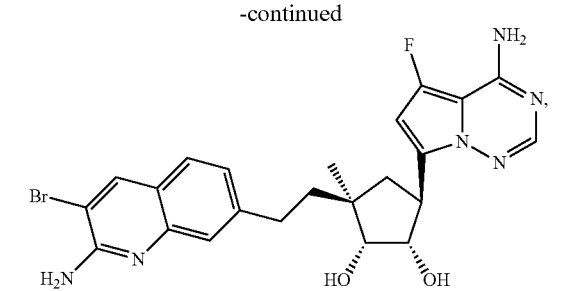
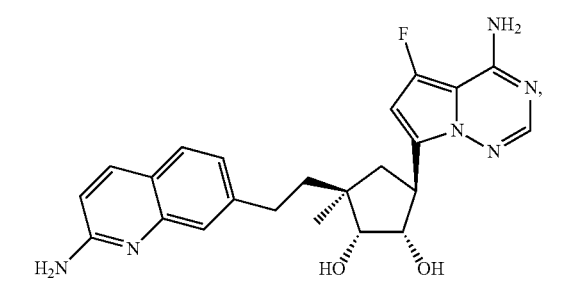
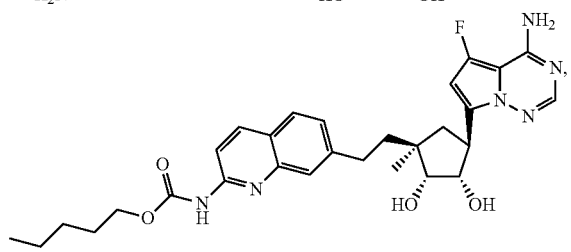
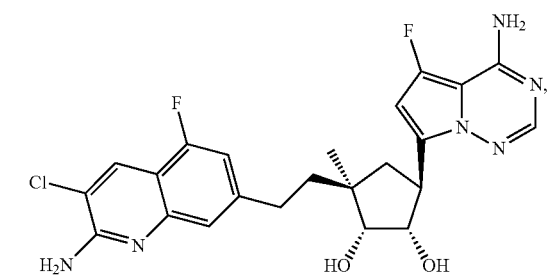
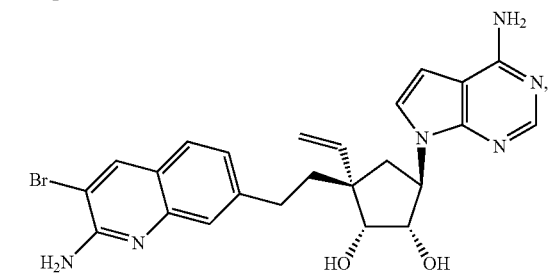
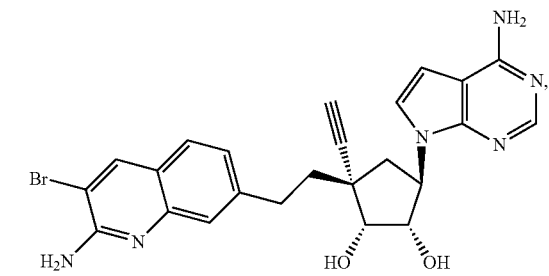
-continued
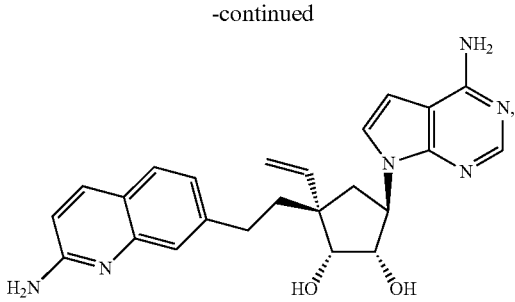
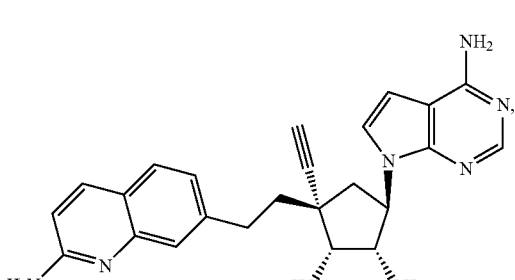
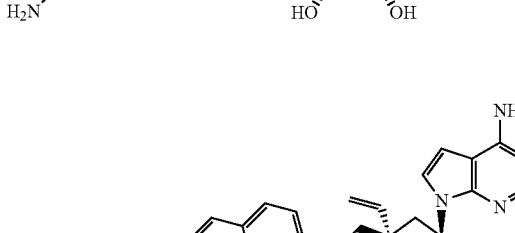
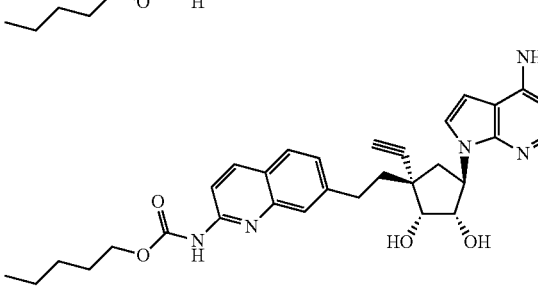
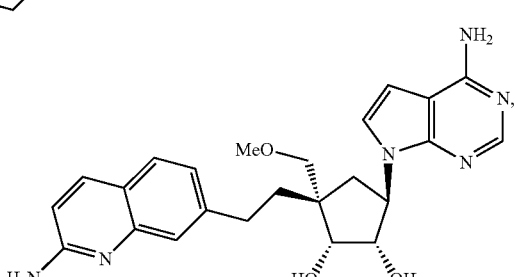
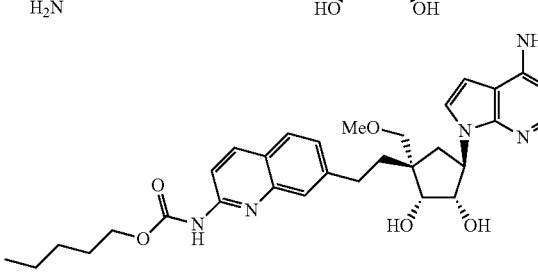

273
-continued
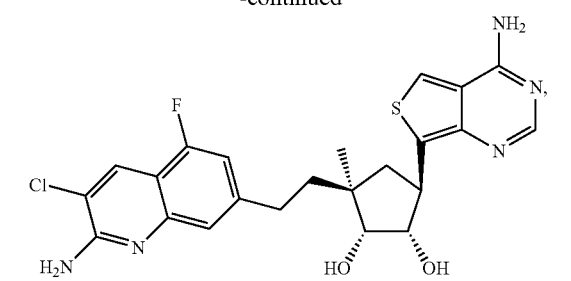
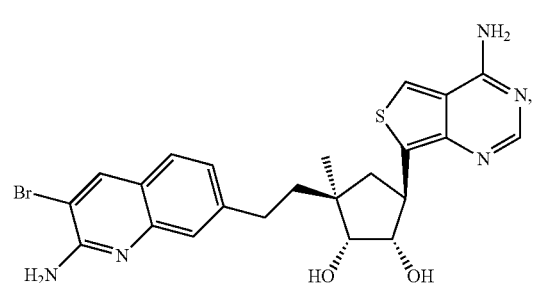
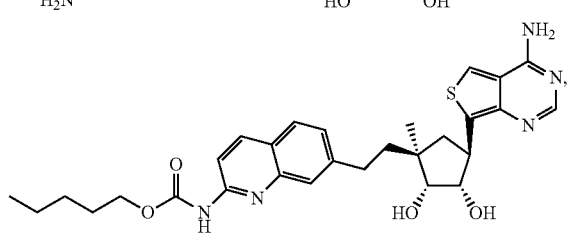
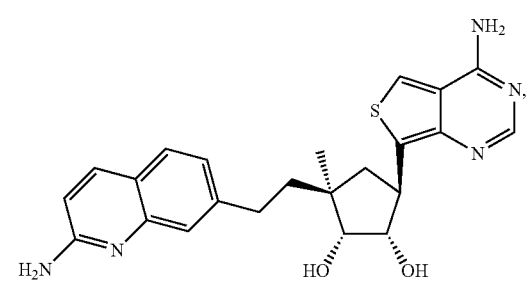
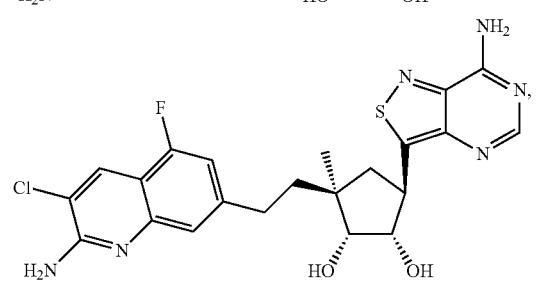
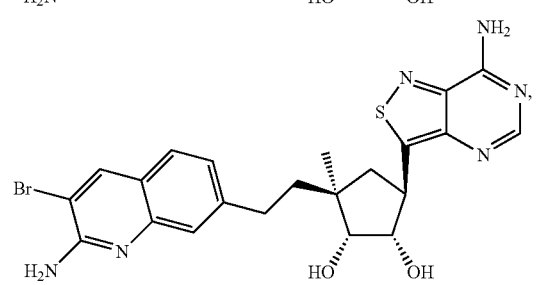
274
-continued
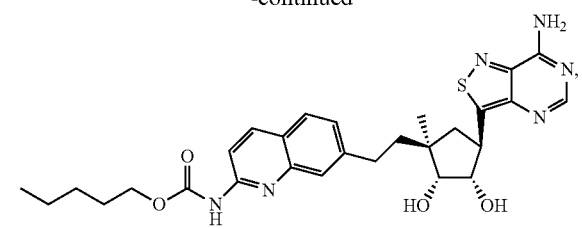
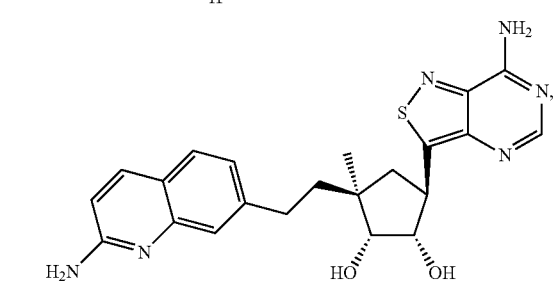
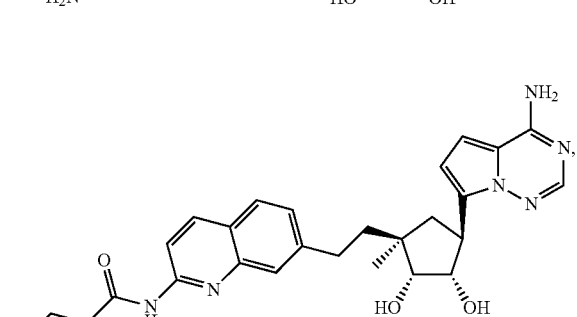
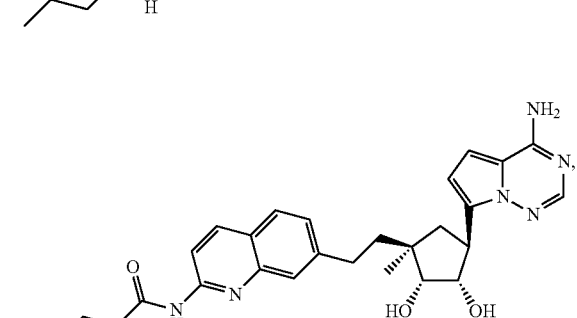
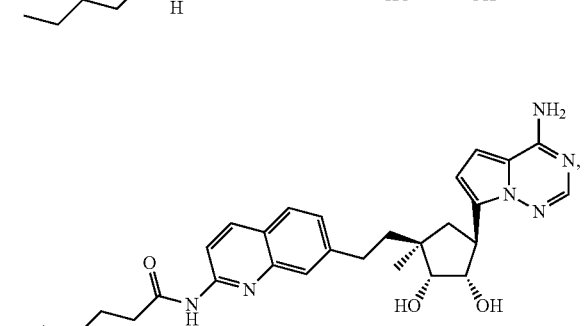
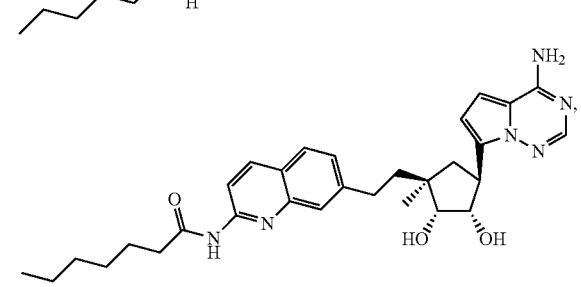

-continued

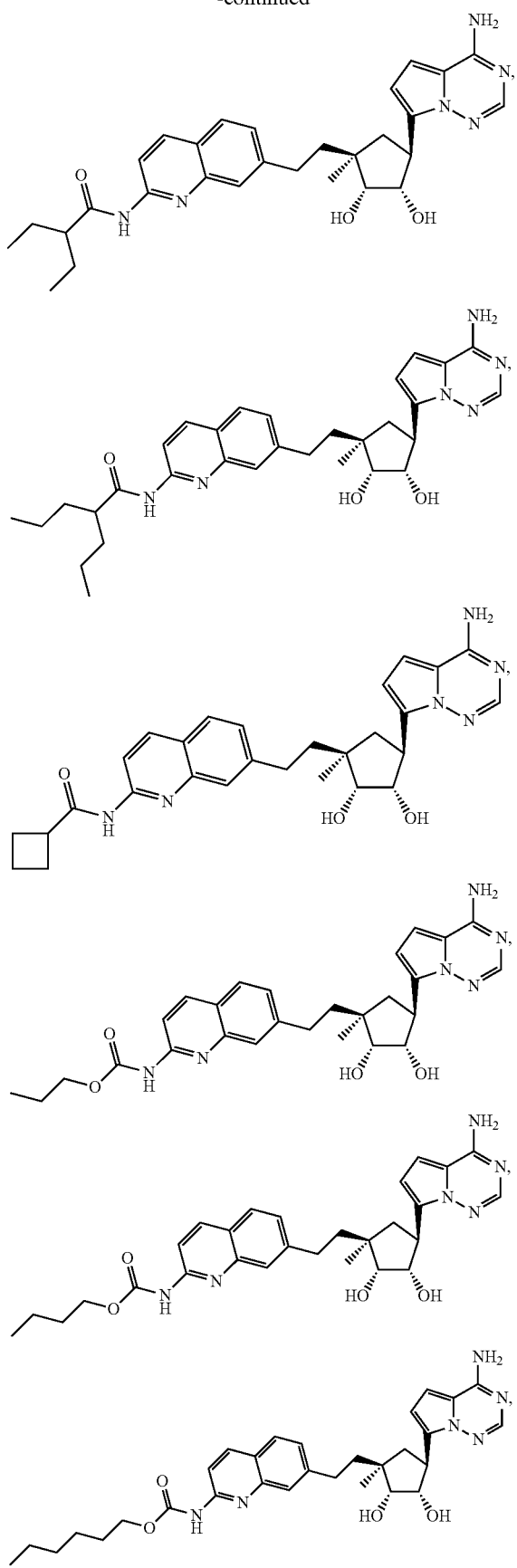

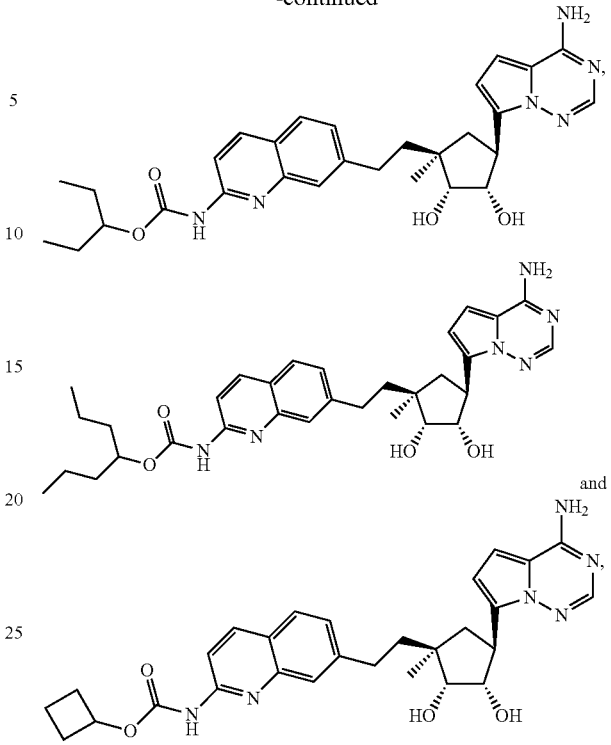

including pharmaceutically acceptable salts of any of the foregoing).

Example A

PRMT5/MEP50 Enzyme Inhibition Assay

Assay 1

Compounds were tested for inhibition of methyltransferase activity in a radioisotope filter binding assay, similar to previously described in A selective inhibitor of PRMT5 with in vivo and in vitro potency in MCL models. Chan-Penebre et al., Nat Chem Biol. (2015) 11(6):432-7. In the standard PRMT5/MEP50 enzyme inhibition assay, compounds were tested in a 10-dose $IC_{50}$ mode with 3- or 5-fold serial dilution, in singlet, starting at 1, 10, or 100 μM. Control compound, SAH (S-(5'-Adenosyl)-L-homocysteine), was tested in 10-dose $IC_{50}$ mode with 3-fold serial dilution starting at 100 μM. Reactions were carried out at 1 μM 3H-SAM (PerkinElmer) and 5 μM histone H2A as substrates for methyl transfer. Following a 60 min incubation at 30° C., the reaction was stopped with 20% TCA. Each reaction was spotted on a filter plate (Multiscreen FB Filter plate, Millipore) and washed 5 times in PBS, after which scintillation fluid was added and signal was detected in a scintillation counter. Percent enzyme activity was calculated based on no inhibitor DMSO control as 100% activity. $EC_{50}$ values were determined in GraphPad Prism 8 using the [inhibitor] vs. response—Variable slope (four parameters) function.

Assay 2

Compounds were tested for inhibition of methyltransferase activity in 384-well plate assay format using mass spectrometry technology. In this enzyme inhibition assay, compounds were tested in a 11-dose $IC_{50}$ mode with 3-serial dilution, in duplicate, starting at 1, 10, or 100 μM. Reactions were carried out at 1 μM SAM and 0.1 μM histone H4 1-21 peptide as substrates for methyl transfer. Following an 18-hour incubation at rt, the reaction was stopped with 0.5% formic acid. Products of the reaction were captured while unreacted substrates were washed away, prior to MALDI mass spectrometry detection and analysis. Percent enzyme activity was calculated based on no inhibitor DMSO control as 100% activity. $EC_{50}$ values were determined in GraphPad Prism 8 using the [inhibitor] vs. response—Variable slope (four parameters) function.

The $IC_{50}$ values were derived from the procedure as described herein and are shown in Table 1. Compounds of Formula (I) show activity in this assay. A value of 'A' in the table below indicates an $IC_{50}$ of <1 nM, a value of 'B' indicates an $IC_{50} \geq 1$ nM to $\leq 100$ nM, and a value of 'C' indicates an $IC_{50}$ value of >100 nM.

TABLE 1

| Compound: | Assay 1 $IC_{50}$ | Assay 2 $IC_{50}$ |
|---|---|---|
| 1 | A | A |
| 2 | A | A |
| 3 | C | C |
| 4 | A | A |
| 5 | A | A |
| 6 | B | B |
| 7 | A | B |
| 8 | B | C |
| 9 | A | A |
| 10 | A | A |
| 11 | C | B |
| 12 | A | A |
| 13 | A | A |
| 14 | A | A |
| 15 | — | A |
| 16 | — | A |
| 17 | — | C |
| 18 | — | A |
| 19 | — | A |
| 20 | — | B |
| 20-A | — | C |
| 21 | — | A |
| 21-A | — | B |
| 22 | — | A |
| 23 | — | A |
| 24 | — | A |
| 25-A | — | C |
| 26 | — | C |
| 26-A | — | C |
| 27 | — | A |
| 28 | — | A |
| 29 | — | A |
| 30 | — | A |
| 31 | — | A |
| 36 | — | A |
| 37 | — | A |
| 38 | — | A |
| 39 | — | A |
| 40 | — | A |
| 41 | — | A |
| 42 | — | A |
| 43 | — | A |
| 44 | — | A |
| 45 | — | A |
| 46 | — | A |
| 47 | — | A |
| 48 | — | A |
| 49 | — | A |
| 50 | — | A |
| 51 | — | A |
| 52 | — | A |
| 53 | — | A |
| 54 | — | A |
| 55 | | C |
| 56 | | A |
| 57 | | A |

TABLE 1-continued

| Compound: | Assay 1 $IC_{50}$ | Assay 2 $IC_{50}$ |
|---|---|---|
| 58 | | A |
| 59 | | A |

Example B

Cell Proliferation Assays

HepG2 hepatoma cells (ATCC, HB-8065) were maintained in DMEM with high glucose (Lonza, 12-914F) supplemented with 10% fetal bovine serum (FBS; Biowest, S181B-500) and 2 mM L-glutamine (Biowest, X0551-100) at 37° C. and 5% $CO_2$. A549 lung carcinoma cells (ATCC, CCL-185) were maintained in F-12K medium (ThermoFisher 21127030) supplemented with 10% FBS at 37° C. and 5% $CO_2$. Exponentially growing HepG2 or A549 were plated in white, clear-bottom 96-well plates (Corning, 3903) at a cell density of 2000 (HepG2) or 350 (A549) cells per well in 199 µL of HepG2 medium. Next, 1 µL of a 5-fold 9-point dilution series of test compound in DMSO was added to the different wells. Cells were incubated at 37° C. 5% $CO_2$ for 7 days. Cell viability was assessed on day 7 with the CellTiter-Glo 2.0 Cell Viability assay kit (Promega, G9243) to quantify the intracellular amounts of ATP: first, 100 µL of cell culture medium was removed from each well, next 100 µL of CellTiter-Glo® 2.0 Reagent was added and plates were shaken for 2 minutes on an orbital shaker. After 10 minutes stabilization at room temperature, read-out was performed on a ThermoFisher VarioSkan Lux plate reader. Counts were normalized to DMSO control (0% inhibition) and the cytotoxic control (100% inhibition) and $EC_{50}$ values were determined in GraphPad Prism 8 using the [Agonist] vs. response—Variable slope (four parameters) function.

The $EC_{50}$ values were derived from the procedure as described herein and are shown in Table 2. As shown by the data of Table 2, compounds of Formula (I) have activity in this assay. A value of 'A' in the table below indicates an $EC_{50}$ of <20 nM, a value of 'B' indicates an $EC_{50} \geq 20$ nM to <100 nM, a value of 'C' indicates an $EC_{50}$ value of $EC_{50} \geq 100$ nM to <1000 nM and a value of 'D' indicates an $EC_{50} \geq 1000$ nM

TABLE 2

| HepG2 and A549 | | |
|---|---|---|
| Compound | $EC_{50}$ HepG2 | $EC_{50}$ A549 |
| 1 | A | A |
| 2 | A | A |
| 3 | C | C |
| 4 | A | A |
| 5 | C | C |
| 6 | D | D |
| 7 | C | C |
| 8 | C | D |
| 9 | B | B |
| 10 | A | A |
| 11 | C | D |
| 12 | A | A |
| 13 | A | A |
| 14 | A | A |
| 15 | C | C |
| 16 | D | D |
| 17 | D | D |
| 18 | A | A |
| 19 | A | A |

TABLE 2-continued

| Compound | EC$_{50}$ HepG2 | EC$_{50}$ A549 |
|---|---|---|
| 20 | A | B |
| 20-A | C | C |
| 21 | A | A |
| 21-A | D | D |
| 22 | C | C |
| 23 | A | A |
| 24 | B | B |
| 25-A | D | D |
| 26 | B | C |
| 26-A | D | D |
| 27 | B | B |
| 28 | B | C |
| 29 | A | B |
| 30 | A | A |
| 31 | C | D |
| 32 | A | A |
| 33 | A | A |
| 34 | A | A |
| 35 | A | A |
| 36 | A | A |
| 37 | A | A |
| 38 | A | A |
| 39 | B | B |
| 40 | A | A |
| 41 | A | A |
| 42 | A | A |
| 43 | B | A |
| 44 | C | B |
| 45 | C | C |
| 46 | C | C |
| 47 | C | B |
| 48 | A | A |
| 49 | A | A |
| 50 | A | A |
| 51 | A | A |
| 52 | A | A |
| 53 | A | A |
| 54 | A | A |
| 55 | B | B |
| 56 | A | A |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

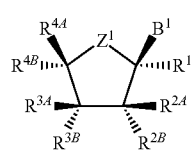

(I)

wherein:
B$^1$ is an optionally substituted

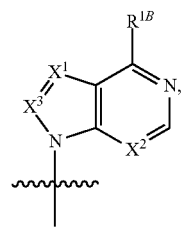

an optionally substituted

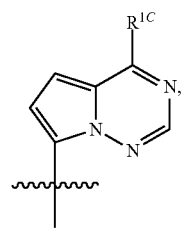

an optionally substituted

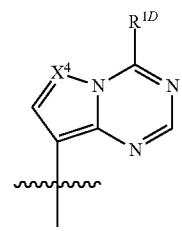

or an optionally substituted

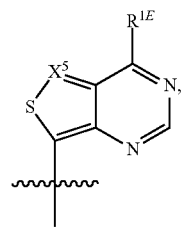

wherein X$^1$ is N or CR$^{C1}$; X$^2$ is N or CR$^{C2}$; X$^3$ is N or CR$^{C3}$; X$^4$ is N or CR$^{C4}$; X$^5$ is N or CR$^{C5}$; and R$^{C1}$, R$^{C2}$, R$^{C3}$, R$^{C4}$ and R$^{C5}$ are independently hydrogen, halogen or an unsubstituted C$_{1-4}$ alkyl;

R$^{1B}$, R$^{1C}$, R$^{1D}$ and R$^{1E}$ are independently hydrogen, halogen, hydroxy, an unsubstituted C$_{1-4}$ alkyl, an unsubstituted C$_{2-4}$ alkenyl, an unsubstituted C$_3$-C$_6$ cycloalkyl, an unsubstituted C$_{1-4}$ alkoxy or NR$^{A1}$R$^{A2}$; and R$^{A1}$ and R$^{A2}$ are independently selected from the group consisting of hydrogen, hydroxy, an unsubstituted C$_{1-4}$ alkyl, an unsubstituted C$_{1-4}$ alkoxy and —C(=O)R$^{C6}$, wherein R$^{C6}$ is hydrogen, an unsubstituted C$_{1-4}$ alkyl or an unsubstituted C$_{3-4}$ monocyclic cycloalkyl;

281

$R^1$ is hydrogen;
$R^{2A}$ is hydrogen or an unsubstituted $C_{1-4}$ alkyl;
$R^{2B}$ is halogen, OH, —O—C(=O)—$C_{1-4}$ alkyl or —O—C(=O)—CH($R^{1'}$)—$NH_2$, wherein $R^{1'}$ is H, —$CH_3$, —CH($CH_3$)$_2$, —$CH_2$—CH($CH_3$)$_2$ or —CH($CH_3$)—CH($CH_3$)$_2$;
$R^{3A}$ is hydrogen, an unsubstituted or a substituted $C_{1-4}$ alkyl, an unsubstituted or a substituted $C_{2-4}$ alkenyl or an unsubstituted or a substituted $C_{2-4}$ alkynyl, wherein when the $C_{1-4}$ alkyl, the $C_{2-4}$ alkenyl and the $C_{2-4}$ alkynyl are substituted, each is independently substituted with 1 or more fluoros;
$R^{3B}$ is halogen, OH, —O—C(=O)—$C_{1-4}$ alkyl or —O—C(=O)—CH($R^{1'''}$)—$NH_2$, wherein $R^{1'''}$ is H, —$CH_3$, —CH($CH_3$)$_2$, —$CH_2$—CH($CH_3$)$_2$ or —CH($CH_3$)—CH($CH_3$)$_2$;
$R^{4A}$ is —($CR^{D1}R^{E1}$)($CR^{D2}R^{E2}$)n-$R^{F1}$, —($CR^{G1}R^{H1}$)—O—$R^{J1}$, —O—($CR^{K1}R^{L1}$)—$R^{M1}$ or —($CR^{N1}R^{O1}$)p-$R^{P1}$;
  wherein $R^{D1}$, $R^{E1}$, $R^{D2}$ and $R^{E2}$ are independently selected from the group consisting of hydrogen, halogen, hydroxy and an unsubstituted $C_{1-3}$ alkyl; n is 0 or 1; and $R^{F1}$ is an unsubstituted or a substituted aryl, an unsubstituted or a substituted heteroaryl or an unsubstituted or a substituted heterocyclyl; or
  $R^{D1}$ and $R^{E1}$ are taken together with the carbon to which $R^{D1}$ and $R^{E1}$ are attached to form an unsubstituted cyclopropyl ring; and $R^{D2}$ and $R^{E2}$ are independently selected from the group consisting of hydrogen, halogen, hydroxy and an unsubstituted $C_{1-3}$ alkyl; n is 1; and $R^{F1}$ is an unsubstituted or a substituted aryl, an unsubstituted or a substituted heteroaryl or an unsubstituted or a substituted heterocyclyl; or
  $R^{D1}$ and $R^{E2}$ are independently selected from the group consisting of hydrogen, halogen, hydroxy and an unsubstituted $C_{1-3}$ alkyl; $R^{E1}$ and $R^{D2}$ are taken together with the carbon to which $R^{E1}$ and $R^{D2}$ are attached to form an unsubstituted cyclopropyl ring; n is 1; and $R^{F1}$ is an unsubstituted or a substituted aryl, an unsubstituted or a substituted heteroaryl or an unsubstituted or a substituted heterocyclyl;
  $R^{D1}$ and $R^{E2}$ are independently selected from the group consisting of hydrogen, halogen and hydroxy; $R^{E1}$ and $R^{D2}$ together form a double bond; n is 1; and $R^{F1}$ is an unsubstituted or a substituted aryl, an unsubstituted or a substituted heteroaryl or an unsubstituted or a substituted heterocyclyl;
  $R^{G1}$, $R^{H1}$, $R^{K1}$, $R^{L1}$, $R^{N1}$ and $R^{O1}$ are independently selected from the group consisting of hydrogen, halogen, hydroxy and an unsubstituted $C_{1-3}$ alkyl; $R^{J1}$ and $R^{M1}$ are independently an unsubstituted or a substituted aryl, an unsubstituted or a substituted heteroaryl or an unsubstituted or a substituted heterocyclyl; $R^{P1}$ is an unsubstituted or a substituted heteroaryl; and p is 3 or 4;
$R^{4B}$ is $C_{1-4}$ alkyl substituted with $OCH_3$, an unsubstituted $C_{2-4}$ alkenyl or an unsubstituted $C_{2-4}$ alkynyl,
$Z^1$ is $CR^{5A}R^{5B}$, O, S or N (an unsubstituted $C_{1-4}$ alkyl);
$R^{5A}$ and $R^{5B}$ are independently hydrogen, halogen, cyano or an unsubstituted or a substituted $C_{1-4}$ alkyl, wherein when the $C_{1-4}$ alkyl is substituted, the $C_{1-4}$ alkyl is substituted with 1 or more substituents independently selected from the group consisting of fluoro and hydroxy; or
$R^{5A}$ and $R^{5B}$ together with the carbon $R^{5A}$ and $R^{5B}$ are attached form a double bond optionally substituted

282 with one or two halogen, $R^{5A}$ and $R^{5B}$ together with the carbon $R^{5A}$ and $R^{5B}$ are attached form an unsubstituted cyclopropyl or $R^{5A}$ and $R^{5B}$ together with the carbon $R^{5A}$ and $R^{5B}$ are attached form an unsubstituted or a substituted oxetane, wherein when the oxetane is substituted, the oxetane is substituted independently with 1 or 2 halogens; or $R^{2A}$ and $R^{2B}$ together with the carbon $R^{2A}$ and $R^{2B}$ are attached form a 3, 4 or 5 membered monocyclic cycloalkyl or a 3, 4 or 5 membered monocyclic heterocyclyl; or $R^{3A}$ and $R^{3B}$ together with the carbon $R^{3A}$ and $R^{3B}$ are attached form a 3, 4 or 5 membered monocyclic cycloalkyl or a 3, 4 or 5 membered monocyclic heterocyclyl; or $R^1$ and $R^{5B}$ together with the carbon $R^1$ and $R^{5B}$ are attached form an unsubstituted cyclopropyl.

2. The compound of claim 1, wherein $Z^1$ is $CR^{5A}R^{5B}$; and $R^{5A}$ and $R^{5B}$ are each hydrogen.

3. The compound of claim 1, wherein $R^{2A}$ is hydrogen; and $R^{3A}$ is hydrogen.

4. The compound of claim 1, wherein $R^{2B}$ is OH; and $R^{3B}$ is OH.

5. The compound of claim 1, wherein $R^{2B}$ is —O—C(=O)—$C_{1-4}$ alkyl; and $R^{3B}$ is —O—C(=O)—$C_{1-4}$ alkyl.

6. The compound of claim 1, wherein $R^{4A}$ is —($CR^{D1}R^{E1}$)($CR^{D2}R^{E2}$)n-$R^{F1}$; n is 0; and $R^{D1}$ and $R^{E1}$ are each hydrogen.

7. The compound of claim 1, wherein $R^{4A}$ is —($CR^{D1}R^{E1}$)($CR^{D2}R^{E2}$)n-$R^{F1}$; n is 1; and $R^{D1}$, $R^{E1}$, $R^{D2}$ and $R^{E2}$ are each hydrogen.

8. The compound of claim 6, wherein $R^{F1}$ is an unsubstituted or a substituted heteroaryl.

9. The compound of claim 7, wherein $R^{F1}$ is selected from the group consisting of:

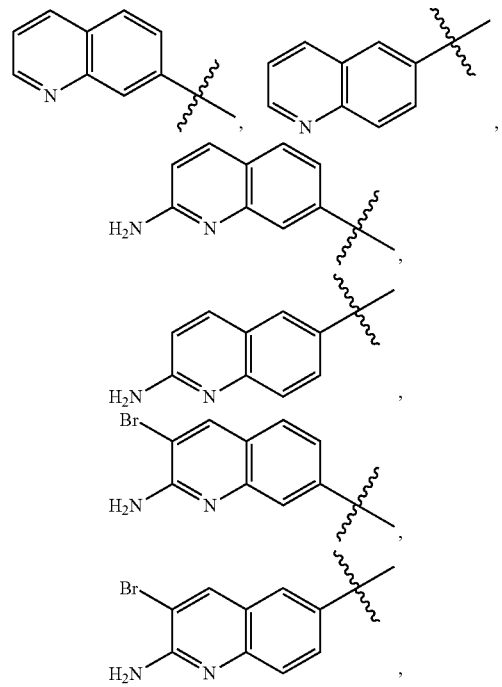

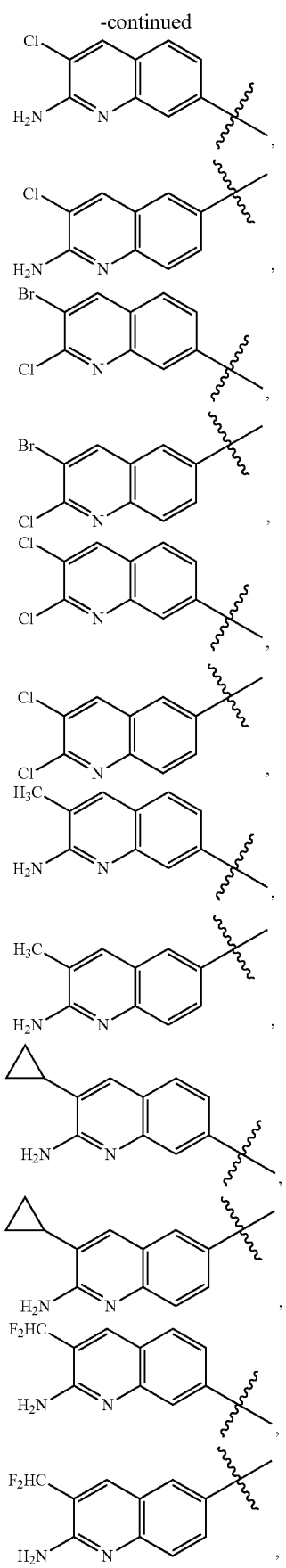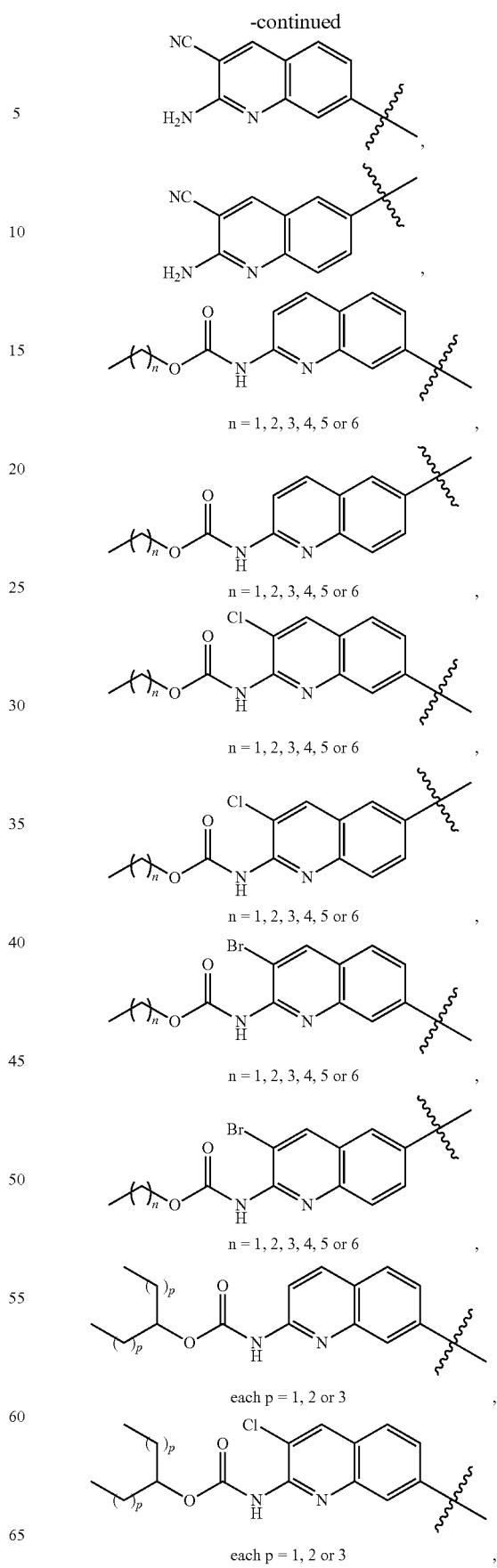

-continued
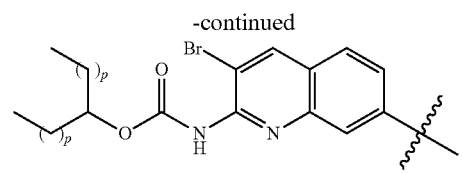
each p = 1, 2 or 3 ,
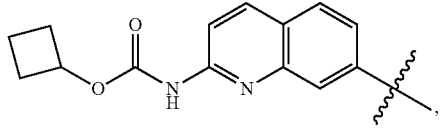
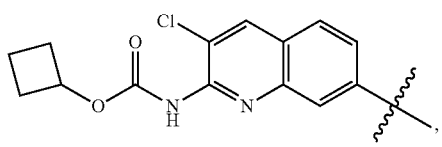
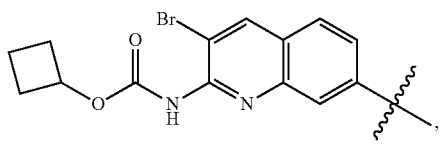
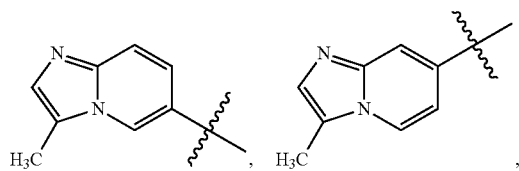
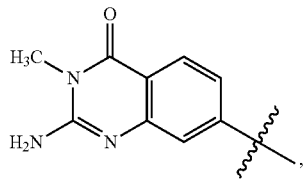
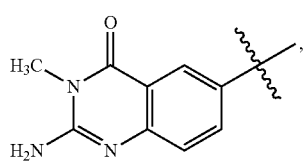
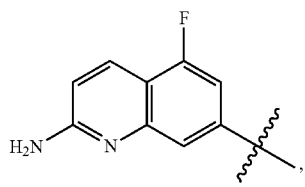
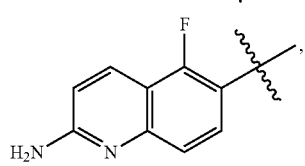
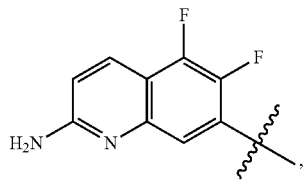
-continued
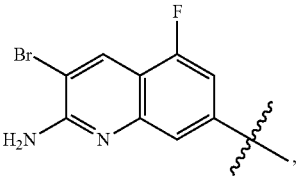
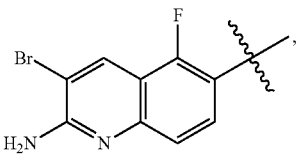
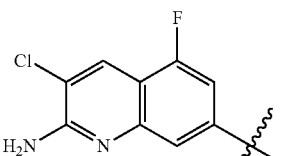
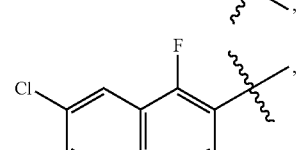
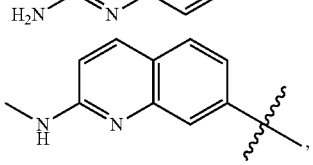
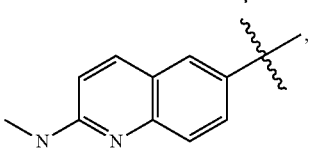
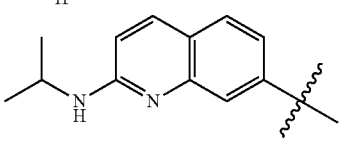
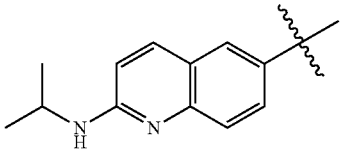
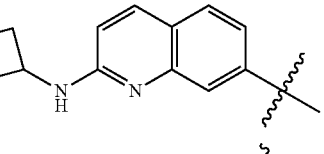
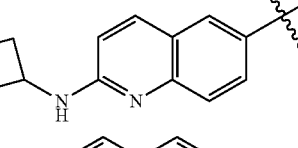
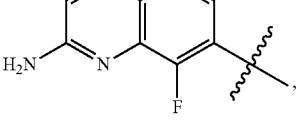

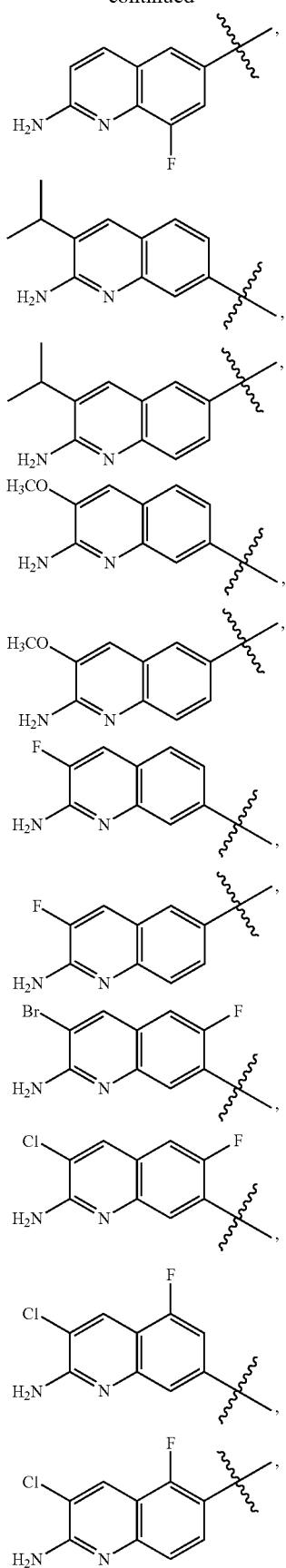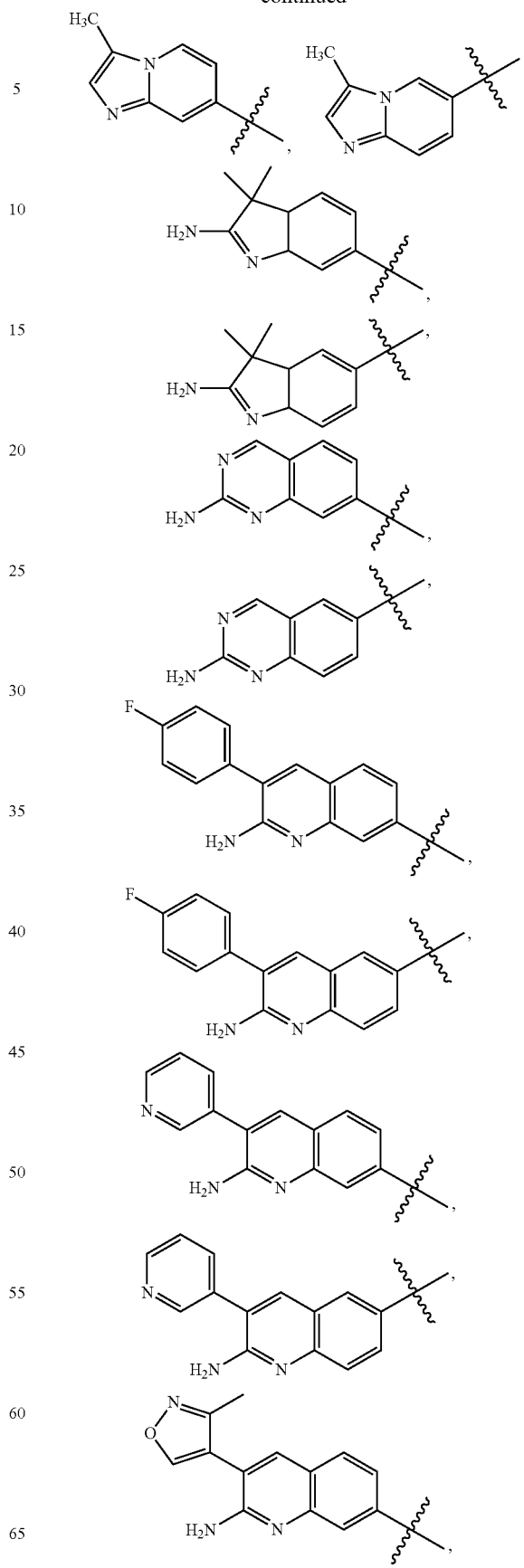

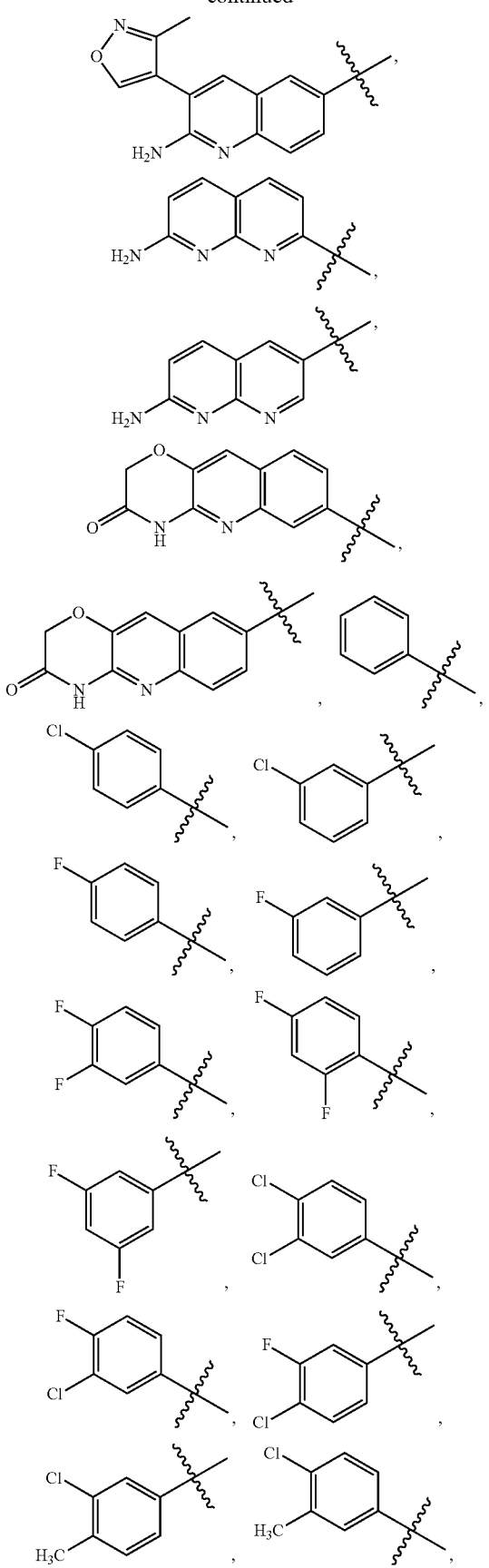
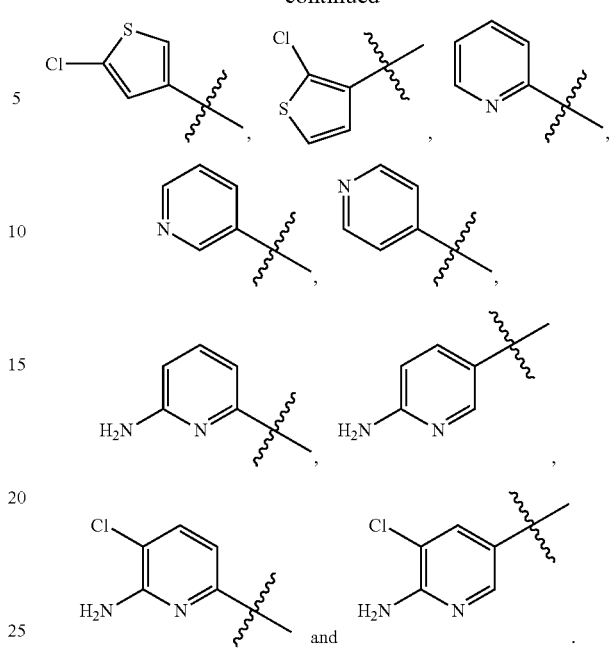
10. The compound of claim 1, wherein $R^{4A}$ is $-(CR^{G1}R^{H1})-O-R^{J1}$, $-O-(CR^{K1}R^{L1})-R^{M1}$ or $-(CR^{N1}R^{O1})p-R^{P1}$.
11. The compound of claim 1, wherein $R^{4B}$ is a $C_1$ alkyl substituted with $OCH_3$.
12. The compound of claim 1, wherein $R^{4B}$ is an unsubstituted $C_{2-4}$ alkenyl.
13. The compound of claim 1, wherein $B^1$ is selected from the group consisting of:
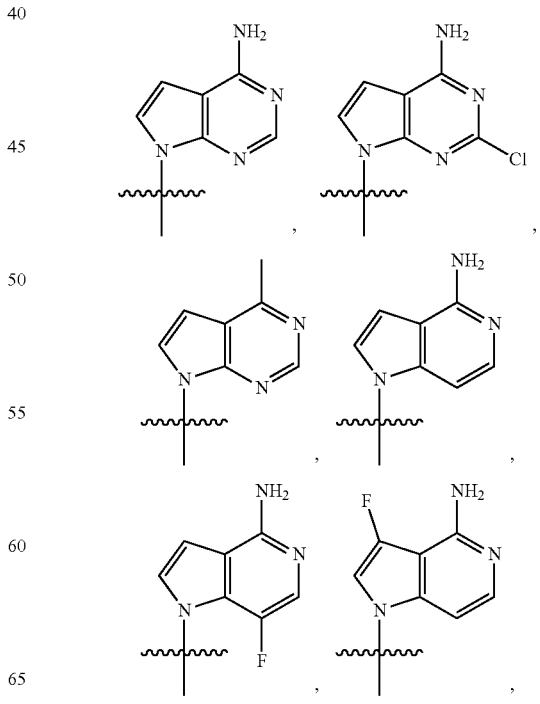

-continued
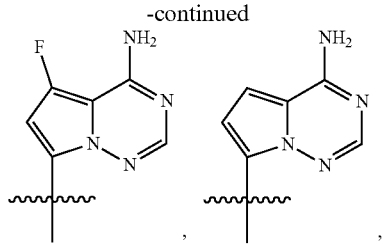
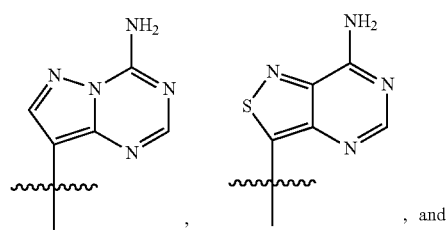
, and
-continued
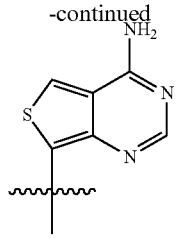
14. The compound of claim 1, wherein the compound is
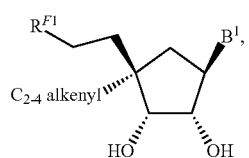
or a pharmaceutically acceptable salt thereof.
15. The compound of claim 1, wherein the compound is selected from the group consisting of:
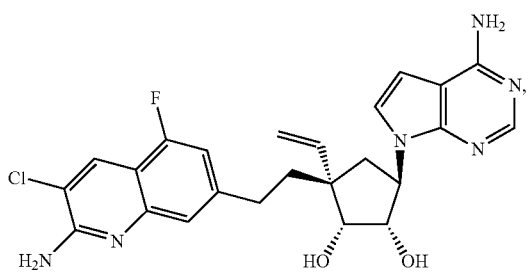
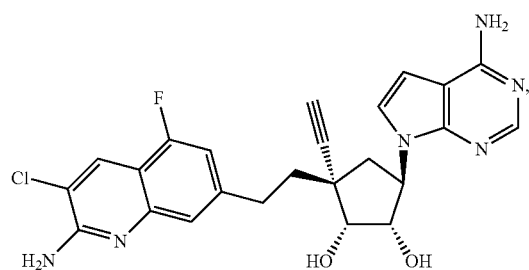
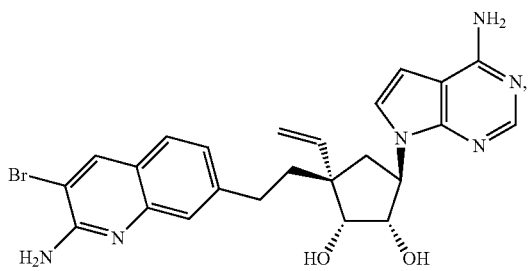
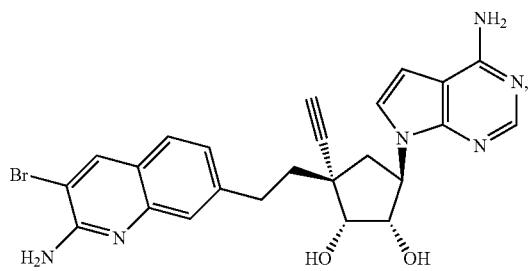
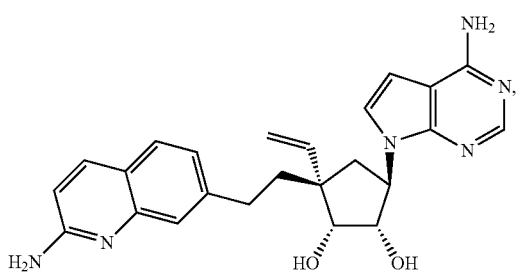
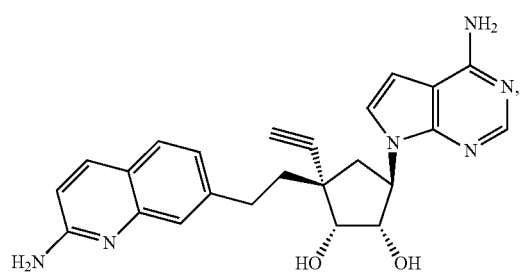

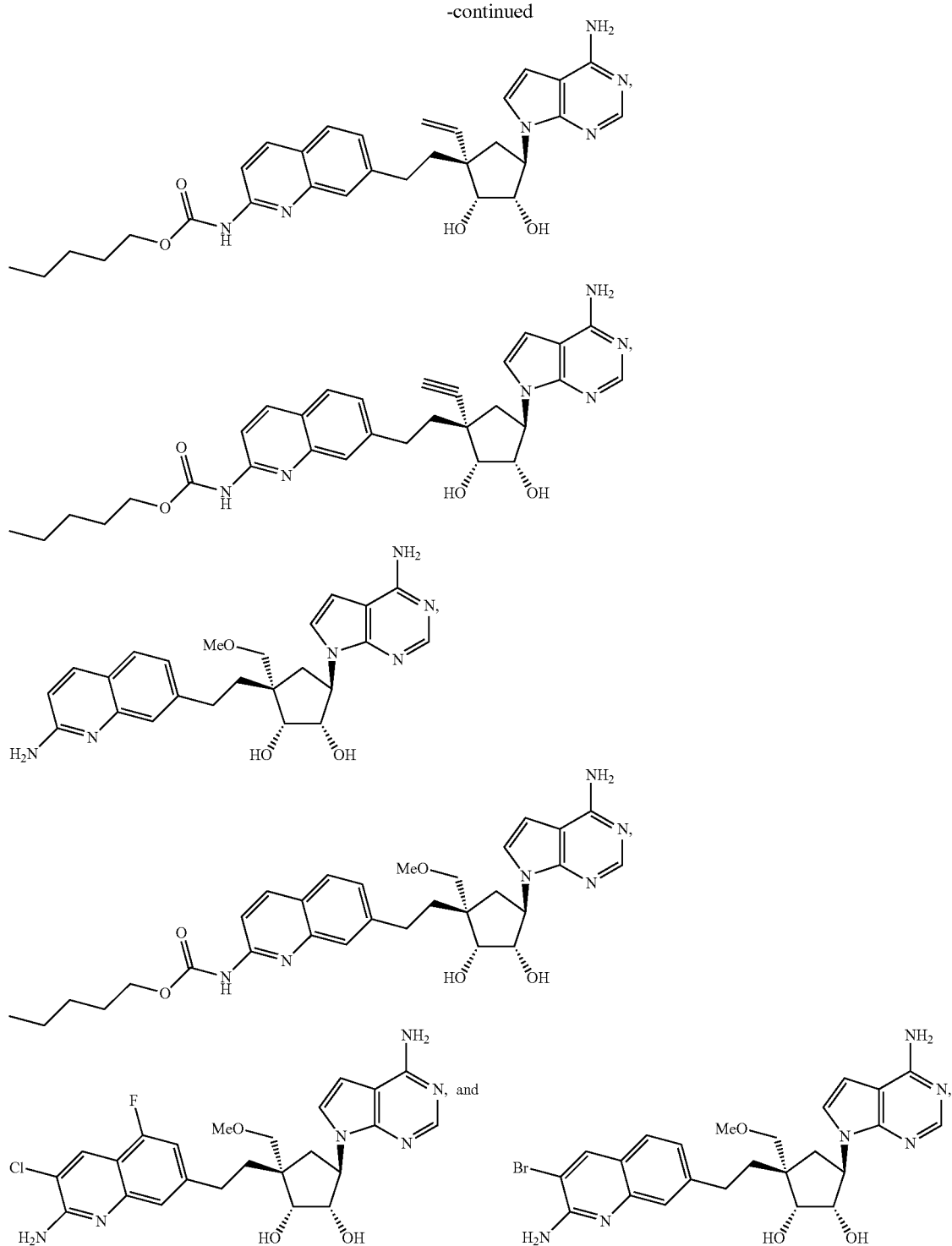

or a pharmaceutically acceptable salt of any of the foregoing.

16. A pharmaceutical composition comprising an effective amount of a compound of claim 1, or a pharmaceutically acceptable salt thereof, and excipient.

17. A method for treating a cancer comprising administering an effective amount of a compound of claim 1, or a pharmaceutically acceptable salt thereof, to a subject in need thereof.

18. A method for modulating PRMT5 comprising contacting the PRMT5 enzyme with an effective amount of a compound of claim 1, or a pharmaceutically acceptable salt thereof.

19. A method for inhibiting PRMT5 comprising contacting the PRMT5 enzyme with a compound of claim 1, or a pharmaceutically acceptable salt thereof.

20. The method of claim 17, further comprises the use of an additional agent selected from the group consisting of a kinase inhibitor, a checkpoint inhibitor/modulator and an anti-VEGF antibody.

21. The compound of claim 1, wherein $R^{4B}$ is an unsubstituted $C_{2-4}$ alkynyl.

22. The compound of claim 1, wherein:
$B^1$ is an optionally substituted

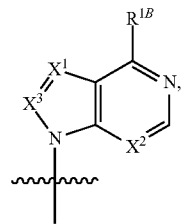

an optionally substituted

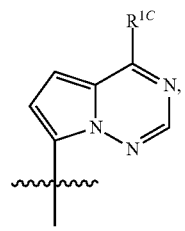

an optionally substituted

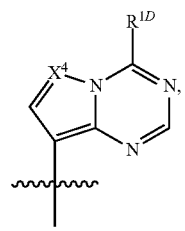

or an optionally substituted

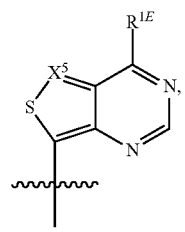

wherein $X^1$ is N or $CR^{C1}$; $X^2$ is N or $CR^{C2}$; $X^3$ is N or $CR^{C3}$; $X^4$ is N or $CR^{C4}$; $X^5$ is N or $CR^{C5}$; and $R^{C1}$, $R^{C2}$, $R^{C3}$, $R^{C4}$ and $R^{C5}$ are independently hydrogen, halogen or an unsubstituted $C_{1-4}$ alkyl;

$R^{1B}$, $R^{1C}$, $R^{1D}$ and $R^{1E}$ are independently hydrogen, halogen, hydroxy, an unsubstituted $C_{1-4}$ alkyl, an unsubstituted $C_{2-4}$ alkenyl, an unsubstituted $C_3$-$C_6$ cycloalkyl, an unsubstituted $C_{1-4}$ alkoxy or $NR^{A1}R^{A2}$; and $R^{A1}$ and $R^{A2}$ are independently selected from the group consisting of hydrogen, hydroxy, an unsubstituted $C_{1-4}$ alkyl, an unsubstituted $C_{1-4}$ alkoxy and —C(=O)$R^{C6}$, wherein $R^{C6}$ is hydrogen, an unsubstituted $C_{1-4}$ alkyl or an unsubstituted $C_{3-4}$ monocyclic cycloalkyl;

$R^1$ is hydrogen;

$R^{2A}$ is hydrogen;

$R^{2B}$ is halogen, OH, —O—C(=O)—$C_{1-4}$ alkyl or —O—C(=O)—CH($R^{1"}$)—NH$_2$, wherein $R^{1"}$ is H, —CH$_3$, —CH(CH$_3$)$_2$, —CH$_2$—CH(CH$_3$)$_2$ or —CH(CH$_3$)—CH(CH$_3$)$_2$;

$R^{3A}$ is hydrogen, an unsubstituted or a substituted $C_{1-4}$ alkyl, an unsubstituted or a substituted $C_{2-4}$ alkenyl or an unsubstituted or a substituted $C_{2-4}$ alkynyl, wherein when the $C_{1-4}$ alkyl, the $C_{2-4}$ alkenyl and the $C_{2-4}$ alkynyl are substituted, each is independently substituted with 1 or more fluoros;

$R^{3B}$ is halogen, OH, —O—C(=O)—$C_{1-4}$ alkyl or —O—C(=O)—CH($R^{1'''}$)—NH$_2$, wherein $R^{1'''}$ is H, —CH$_3$, —CH(CH$_3$)$_2$, —CH$_2$—CH(CH$_3$)$_2$ or —CH(CH$_3$)—CH(CH$_3$)$_2$;

$R^{4A}$ is —(CR$^{D1}$R$^{E1}$)(CR$^{D2}$R$^{E2}$)n-R$^{F1}$;

wherein $R^{D1}$, $R^{E1}$, $R^{D2}$ and $R^{E2}$ are independently selected from the group consisting of hydrogen, halogen, hydroxy and an unsubstituted $C_{1-3}$ alkyl; n is 0 or 1; and $R^{F1}$ is an unsubstituted or a substituted aryl, an unsubstituted or a substituted heteroaryl or an unsubstituted or a substituted heterocyclyl; or $R^{D1}$ and $R^{E1}$ are taken together with the carbon to which $R^{D1}$ and $R^{E1}$ are attached to form an unsubstituted cyclopropyl ring; and $R^{D2}$ and $R^{E2}$ are independently selected from the group consisting of hydrogen, halogen, hydroxy and an unsubstituted $C_{1-3}$ alkyl; n is 1; and $R^{F1}$ is an unsubstituted or a substituted aryl, an unsubstituted or a substituted heteroaryl or an unsubstituted or a substituted heterocyclyl; or $R^{D1}$ and $R^{E2}$ are independently selected from the group consisting of hydrogen, halogen, hydroxy and an unsubstituted $C_{1-3}$ alkyl; $R^{E1}$ and $R^{D2}$ are taken together with the carbon to which $R^{E1}$ and $R^{D2}$ are attached to form an unsubstituted cyclopropyl ring; n is 1; and $R^{F1}$ is an unsubstituted or a substituted aryl, an unsubstituted or a substituted heteroaryl or an unsubstituted or a substituted heterocyclyl; or $R^{D1}$ and $R^{E2}$ are independently selected from the group consisting of hydrogen, halogen and hydroxy; $R^{E1}$ and $R^{D2}$ together form a double bond; n is 1; and $R^{F1}$ is an unsubstituted or a substituted aryl, an unsubstituted or a substituted heteroaryl or an unsubstituted or a substituted heterocyclyl;

$R^{G1}$, $R^{H1}$, $R^{K1}$, $R^{L1}$, $R^{N1}$ and $R^{O1}$ are independently selected from the group consisting of hydrogen, halogen, hydroxy and an unsubstituted $C_{1-3}$ alkyl; $R^{J1}$ and $R^{M1}$ are independently an unsubstituted or a substituted aryl, an unsubstituted or a substituted heteroaryl or an unsubstituted or a substituted heterocyclyl; $R^{P1}$ is an unsubstituted or a substituted heteroaryl; and p is 3 or 4;

$R^{4B}$ is a substituted $C_{1-4}$ alkyl substituted with OCH$_3$, an unsubstituted $C_{2-4}$ alkenyl or an unsubstituted $C_{2-4}$ alkynyl, $Z^1$ is $CR^{5A}R^{5B}$; and $R^{5A}$ and $R^{5B}$ are each hydrogen.

23. The compound of claim 1, wherein the compound is

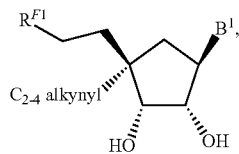

or a pharmaceutically acceptable salt thereof.

24. The compound of claim 1, wherein the compound is

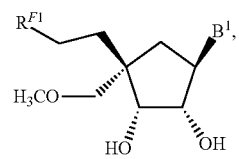

or a pharmaceutically acceptable salt thereof.

25. The compound of claim 1, wherein the compound is

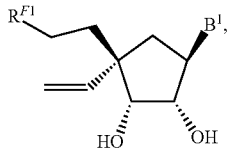

or a pharmaceutically acceptable salt thereof.

26. The compound of claim 1, wherein the compound is

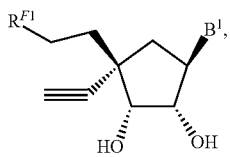

or a pharmaceutically acceptable salt thereof.

* * * * *